(12) United States Patent
Bott et al.

(10) Patent No.: US 9,447,400 B2
(45) Date of Patent: Sep. 20, 2016

(54) BETA-GLUCOSIDASE I VARIANTS WITH IMPROVED PROPERTIES

(75) Inventors: Richard R. Bott, Burlingame, CA (US); Thijs Kaper, Half Moon Bay, CA (US); Bradley Kelemen, Menlo Park, CA (US); Frits Goedegebuur, Vlaardingen (NL); Ronaldus Wilhelmus Hommes, Haarlem (NL); Slavko Kralj, Oestgeest (NL); Paulien Kruithof, Zoetmeer (NL); Igor Nikolaev, Noordwijk (NL); Wilhelmus Antonious Hendricus Van Der Kley, The Hague (NL); Johannes Franciscus Thomas Van Lieshout, Utrecht (NL); Sander Van Stigt Thans, Zevenbergen (NL); Gudrun Vogtentanz, Sunnyvale, CA (US); Mats Sandgren, Uppsala (SE)

(73) Assignee: DANISCO US INC., Palo Alto, CA (US)

( * ) Notice: Subject to any disclaimer, the term of this patent is extended or adjusted under 35 U.S.C. 154(b) by 553 days.

(21) Appl. No.: 13/510,902

(22) PCT Filed: Nov. 19, 2010

(86) PCT No.: PCT/US2010/057531
§ 371 (c)(1),
(2), (4) Date: Feb. 25, 2013

(87) PCT Pub. No.: WO2011/063308
PCT Pub. Date: May 26, 2011

(65) Prior Publication Data
US 2013/0143301 A1 Jun. 6, 2013

Related U.S. Application Data

(60) Provisional application No. 61/263,240, filed on Nov. 20, 2009.

(51) Int. Cl.
*A61K 38/47* (2006.01)
*C12N 9/42* (2006.01)
*C12N 1/20* (2006.01)
*C12N 15/00* (2006.01)
*C07H 21/04* (2006.01)

(52) U.S. Cl.
CPC ..... *C12N 9/2445* (2013.01); *C12Y 302/01021* (2013.01)

(58) Field of Classification Search
USPC ................. 435/209, 252.3, 320.1; 536/23.2
See application file for complete search history.

(56) References Cited

U.S. PATENT DOCUMENTS

| | | |
|---|---|---|
| 4,822,516 A | 4/1989 | Suzuki et al. |
| 5,246,853 A | 9/1993 | Clarkson et al. |
| 5,475,101 A | 12/1995 | Ward et al. |
| 5,648,263 A | 7/1997 | Schulein et al. |
| 5,691,178 A | 11/1997 | Schulein et al. |
| 5,709,796 A | 1/1998 | Fuqua et al. |
| 5,776,757 A | 7/1998 | Schulein et al. |
| 5,980,581 A | 11/1999 | Patterson et al. |
| 6,017,751 A | 1/2000 | von der Osten et al. |
| 6,021,536 A | 2/2000 | Wasinger |
| 6,022,725 A | 2/2000 | Fowler et al. |
| 6,024,766 A | 2/2000 | Wasinger |
| 6,077,316 A | 6/2000 | Lund et al. |
| 6,103,464 A | 8/2000 | Fowler et al. |
| 6,245,546 B1 | 6/2001 | Hansen et al. |
| 6,254,722 B1 | 7/2001 | Jackson et al. |
| 6,255,115 B1 | 7/2001 | Beijersbergen et al. |
| 6,261,828 B1 | 7/2001 | Lund |
| 6,365,561 B1 | 4/2002 | Vinson et al. |
| 6,380,147 B1 | 4/2002 | Speckmann et al. |
| 6,399,561 B1 | 6/2002 | Schneider et al. |
| 6,413,928 B1 | 7/2002 | Painter et al. |
| 6,426,200 B1 | 7/2002 | Yang et al. |
| 6,512,110 B1 | 1/2003 | Heikkila et al. |
| 6,767,728 B2 | 7/2004 | Yang et al. |
| 7,883,872 B2 | 2/2011 | Gusakov et al. |
| 8,486,683 B2 * | 7/2013 | Scott et al. .................. 435/209 |
| 2002/0142438 A1 | 10/2002 | Andersen et al. |
| 2006/0041961 A1 | 2/2006 | Abad et al. |
| 2006/0094080 A1 | 5/2006 | Dunn-Coleman |
| 2011/0171674 A1 | 7/2011 | Lopes-Ferreira et al. |
| 2013/0337508 A1 | 12/2013 | Fujdala et al. |
| 2015/0252340 A1 | 9/2015 | Bower et al. |
| 2015/0252343 A1 | 9/2015 | Bower et al. |
| 2015/0252344 A1 | 9/2015 | Bower et al. |

FOREIGN PATENT DOCUMENTS

| | | |
|---|---|---|
| EP | 1586652 A1 | 10/2005 |
| WO | WO 91/04673 | 4/1991 |
| WO | WO 92/06209 | 4/1992 |
| WO | WO 94/28117 | 12/1994 |

(Continued)

OTHER PUBLICATIONS

Written Opinion from PCT/US 2010/057531 (ISA) (May 20, 2012).*

(Continued)

*Primary Examiner* — Tekchand Saidha

(57) ABSTRACT

The present disclosure is generally directed to enzymes and in particular beta-glucosidase variants. Also described are nucleic acids encoding beta-glucosidase variants, compositions comprising beta-glucosidase variants, methods of using beta-glucosidase variants, and methods of identifying additional useful beta-glucosidase variants.

20 Claims, 7 Drawing Sheets

(56) References Cited

FOREIGN PATENT DOCUMENTS

| | | | |
|---|---|---|---|
| WO | 03/027306 A2 | 4/2003 | |
| WO | 03/052054 A2 | 6/2003 | |
| WO | 03/052118 A2 | 6/2003 | |
| WO | WO 2004/099228 | 11/2004 | |
| WO | WO 2006/110901 | 10/2006 | |
| WO | 2008008070 A2 | 1/2008 | |
| WO | 2009018537 A2 | 2/2009 | |
| WO | 2009/035537 A1 | 3/2009 | |
| WO | WO 2009/108941 A2 | 9/2009 | |
| WO | 2012/125925 A2 | 9/2012 | |
| WO | 2012/125937 A2 | 9/2012 | |

OTHER PUBLICATIONS

Accession No. B5TYI5 (Nov. 4, 2008).*
Accession No. JC4939 (1996).*
Altschul et al., *J. Mol. Bio.* (1990) 215:403-410.
Bajar et al., *Proc. Natl. Acad. Sci. USA* (1991) 88:8208-8212.
Berges and Barreau, *Current Genet.* (1991) 19:359-365.
Bhikhabhai et al., *J. App. Biochem.* (1984) 6:336-345.
Brigidi et al., *FEMS Microbiol. Lett.* (1990) 67:135-138.
Brumbauer et al., *Bioseparation* (1999) 7:287-295.
Cadwell et al., *PCR Methods and Applications* (1992) 2:28-33.
Campbell et al., *Current Genet.* (1989) 16:53-56.
Carter et al., *Nucleic Acids Res.* (1985) 13:4431-4441.
Cummings et al., *Current Genet.* (1996) 29:227-233.
Ellouz et al., *J. Chromatography* (1987) 307-317.
Filho et al., *Can. J. Microbiol.* (1996) 42:1-5.
Fliess et al., *Eur. J. Appl. Microbiol. Biotechnol.* (1983) 17:314-318.
Freer, *J. Biol. Chem.* (1993) 268:9337-9342.
Foreman et al., *J. Biol. Chem.* (2003) 278(34):31988-31997.
Gaboriaud et al., *FEBS Letters* (1987) 224:149-155.
Ghose, *Pure Appl. Chem.* (1987) 59(2):257-268.
Goedegebuur et al., *Current Genet* (2002) 41:89-98.
Goldman et al., *Current Genet.* (1990) 17:169-174.
Goyal et al., *Bioresource Technol.* (1991) 36:37-50.
Halldorsdottir et al., *Appl. Microb. Biotechnol.* (1998) 49:277-284.
Henikoff et al., *Proc. Natl. Acad. Sci USA* (1989) 89:10915-10919.
Hemmpel, *ITB Dyeing/Printing/Finishing* (1991) 3:5-14.
Higuchi, "PCR Protocols," *Academic Press* (1990) 177:183.
Hopwood et al., "Regulation of Gene Expression in Antiobiotic, Producing Streptomycees," The John Innes Foundation (1985), Norwich UK.
Huber et al., *Protein Science* (1998) 7:142-149.
Ilmen et al., *Appl. Environ. Microbiol.* (1997) 63:1298-1306.
Karlin et al., *Proc. Natl. Acad. Sci. USA* (1993) 90:5873-5877
Kaper Thisj et al., *Biochemical Journal* (2002) 368(2):461-470.
Kawaguchi et al., *Gene* (1996) 173:287-288.
Knowles et al., *TIBTECH* (1987) 5:255-261.
Kumar et al., *Textile Chemist and Colorist* (1997) 29:37-42.
Kunkel et al., *Proc. Natl. Acad. Sci. USA* (1987) 82:488-492.
Li et al., *Appl. Environ. Microbiol.* (1996) 62:209-213.
Linder et al., *J. Biotechnol.* (1997) 57:15-28.
Lorito et al., *Current Genet.* (1993) 24:349-356.
Medve et al., *J. Chromatography A* (1998) 808:153-165.
Needleman et al., *J. Mol. Biol.* (1970) 48:443.
Mora et al., *J. Wood Chem. Tech.* (1986) 6(2):147-165.
Nevalainen and Penttila, *The Mycota* (1995) 303-319.
Ooi et al., *Nucleic Acids Research* (1990) 18:19.
Pearson et al., *Proc. Natl. Acad. Sci. USA* (1988) 85:2444-2448.
Penttila et al., *Yeast* (1987) 3:175-185.
Penttila et al., *Gene* (1988) 63:103-112.
Penttila et al., *Gene* (1987) 61:155-164.
Penttila et al., *Gene* (1988) 63:11-21.
Pere et al., In Proc. Tappi Pulping Conf., Nashville, TN, Oct. 27-31, 1996:693-696.
Pourque, J. et al., *Biochemistry and Genetics of Cellulose Degradation*, eds. Aubert et al., Academic Press (1988) 71-86.
Rothstein et al., *Gene* (1987) 55:353-356.
Saarilhati et al., *Gene* (1990) 90:9-14.
Sakamoto et al., *Current Genet.* (1995) 27:435-439.
Schell et al., *J. Appl. Biochem. Biotechnol.* (2003) 105:69-85.
Schulein, *Methods Enzymol.* (1988) 160:234-243.
Sheir-Neiss et al., *Appl. Microbio. Biotechnology* (1984)20:46-53.
Shoemaker et al., *Biotechnology* (1983) 1:691-696.
Spilliaert et al., *Eur. J. Biochem.* (1994) 224:923-30.
Stahlberg et al., *Biotechnology* (1991) 2:286-290.
Suurnakki et al., *Cellulose* (2000) 7:189-209.
Szczodrak J., *Biotechnology and Bioengineering* (1989) 33(9):1112-1116.
Te'o et al., *FEMS Microbiology Letters* (2000) 190:13-19.
Teeri et al., *Gene* (1987) 51:43-52.
Tomaz and Queiroz, *J. Chromatography A* (1999) 865:123-128.
Tomme et al., *Eur. J. Biochem.* (1988) 170:575-581.
Tormo et al., *Embo. J.* (1996) 15(21):5739-5751.
Tyndall, *Textile Chemist and Colorist* (1992) 24(6):23-26.
Vallette et al., *Nuc. Acids Res.* (1989) 17:723-733.
Van Den Hondel et al., Academic Press (1991) 396-428.
Van Hartings Veldt et al., *Mol. Gen. Genet.* (1987) 206:71-75.
Van Rensburg et al., *Yeast* (1998) 14:67-76.
Van Tilbeurgh et al., *FEBS Lett.* (1984) 169(2):215-218.
Van Tilbeurgh et al., *FEBS Lett.* (1986) 204(2):223-227.
Walseth, *Tappi* (1971) 35:228.
Ward et al., *Appl. Microbiol. Biotechnol.* (1993) 39:738-743.
Wells et al., *Gene* (1985) 34:315-323.
Wood et al., *Methods in Enzymology* (1988) 160:87-116.
Wood, *Biochem., J.* (1971) 121:353-362.
Yelton et al., *Proc. Natl Acad. Sci. USA* (1984) 81:1470-1474.
Liu, Wenjin, et. al., "Fast Identification of Thermostable Beta-Glucosidase Mutants on Cellobiose by a Novel Combinatorial Selection/Screening Approach," *Biotechnology and Bioengineering*, Aug. 15, 2009, vol. 103, No. 6, pp. 1087-1094.
Tsukada, Takeshi, "A Study for the Structures and the Functions of β-glucosidases of Family-1 of Glycoside Hydrolases", A doctoral thesis of the Tokyo University Graduate School of Agricultural Biosciences, Mar. 22, 2009, pp. 1-91.
GenBank Accession No. AAQ76093.1 (beta-D-glucoside glucohydrolase [Trichoderma viride]: last modification date Sep. 17, 2003); printed on Oct. 14, 2015, pp. 1-2.
English translation of Office Action dated Dec. 16, 2014 in counterpart Japanese Application No. 2012-540120, 5 pages.
Tsukada, Takeshi, et al., "Role of Subsite +1 Residues in pH Dependence and Catalytic Activity of the Glycoside Hydrolase Family 1 β-glucosidase BGL1A from the Basidomycete *Phanerochaete chrysosporium*," *Biotechnology and Bioengineering*, Apr. 15, 2008; 99(6):1295-302.
Tsukada, Takeshi, et al., "Molecular cloning and characterization of two intracellular beta-glucosidases belonging to glycoside hydrolase family 1 from the basidiomycete Phanerochaete Chrysosporium," *Appl Microbiol Biotechnol.*, Dec. 2006; 73 (4): 807-14, Epub Aug. 9, 2006.
Nijikken, Yuri, et al., "Crystal structure of intracellular family 1 β-glucosidase BGL1A from the basidiomycete Phanerochaete Chrysosporium," FEBS Lett., Apr. 3, 2007; 581 (7): 1514-20, Epub Mar. 13, 2007.
Kuhls, K., et al, "Molecular Evidence that the asexual industrial fungus *Trichoderma reesei* is a clonal derivative of the ascomycete *Hypocrea jecorina*" *Proc. Natl. Acad. Sci. USA*, Jul. 1996, vol. 93, pp. 7755-7760.
Aro, Nina, et al. "ACEII, a Novel Transcriptional Activator Involved in Regulation of Cellulase and Xylanase Genes of *Trichoderma reesei*", *Journal of Biological Chemistry*, vol. 276, No. 26, Jun. 2001, pp. 24309-24314.
Yelton, M., et al. "Transformation of *Aspergillus nidulans* by using a *trpC* plasmid", *Proc. Natl. Acad. Sci. USA*, vol. 81, pp. 1470-1474, Mar. 1984.
Tilbeurgh, Herman, et al. "Separation of endo- and exo-type cellulases using a new affinity chromatography method", FEBS Letters, vol. 169 (2), pp. 215-218, 1984.
Ohmiya, Kunjo, et al. "Structure of Cellulases and Their Applications"*Biotechnology and Genetic Engineering Reviews*, Apr. 1997, vol. 14, pp. 365-414.

(56) References Cited

OTHER PUBLICATIONS

Uniprot Accession No. Q12715 (Beta-D-glucoside glucohydrolase); Integrated into UniProtKB/TrEMBL Nov. 1, 1996; printed on Feb. 1, 2016.

Zhang, et al. "Outlook for cellulase improvement: Screening and selection strategies" Biotechnology Advances, 24 (2006) pp. 452-481.

Mach, et al. "The bgl1 gene of Trichoderma reesei QM 9414 encodes an extracellular, cellulose-inducible b-glucosidease involved in cellulase induction by sophorose" Molecular Microbiology (1995) 16(4), pp. 687-697.

International Search Report for International Application No. PCT/US2010/057531, International Filing date Nov. 19, 2010.

International Preliminary Report on Patentability for International Application No. PCT/US2010/057531, International Filing date Nov. 19, 2010.

Genbank Accession No. AAB08340; (Amino acid sequence of a beta-glucosidase polypeptide); revised Jun. 15, 2007; printed Jun. 14, 2013.

Genbank Accession No. 1713235A; Gene ID: 227874; (Extracellular beta glucosidase); last modification date Apr. 10, 1996; printed Feb. 5, 2016.

GENESEQ ID: AOF22236, Seq ID No. 4099 from EP1586652, published Oct. 19, 2005; Printed Feb. 5, 2016.

UNIPROT Accession No: Q6UJY0; (Beta-D-glucoside glucohydrolase); Integrated into UniProtKB/TrEMBL Jul. 5, 2004; printed Feb. 5, 2016.

* cited by examiner

SEQUENCE LISTING

<160> NUMBER OF SEQ ID NOS: 45

<210> SEQ ID NO 1
<211> LENGTH: 2238
<212> TYPE: DNA
<213> ORGANISM: Hypocrea jecorina

<400> SEQUENCE: 1

| | | | | | | |
|---|---|---|---|---|---|---|
| atgcgctacc | gcaccgctgc | cgctttagcc | ttagccaccg | gccccttcgc | cagagccgat | 60 |
| agccacagca | cctccggcgc | tagtgctgaa | gctgttgtcc | ctcctgctgg | cacccccttgg | 120 |
| ggcaccgcct | acgacaaggc | caaggccgcc | ctcgccaagc | tcaacctcca | ggacaaggtc | 180 |
| ggcatcgtca | gcggcgtcgg | ctggaacggc | ggtccctgcg | tcggcaacac | cagccccgcc | 240 |
| agcaagatca | gctaccccag | cctctgcctc | caggacggcc | ccctcggcgt | ccgctacagc | 300 |
| accggcagca | ccgccttcac | ccctggcgtc | caggccgcca | gcacctggga | cgtcaacctc | 360 |
| atccgcgagc | gcggccagtt | catcggcgaa | gaggtcaagg | ccagcggcat | ccacgtcatc | 420 |
| ctcggtcccg | ttgctggtcc | cttaggcaag | acccccagg | gcggtcgcaa | ctgggagggc | 480 |
| ttcggcgtcg | accccctacct | caccggcatt | gccatgggcc | agaccatcaa | cggcatccag | 540 |
| agcgtcggcg | tccaggccac | cgccaagcac | tacatcctca | cgagcaaga | gttaaaccgc | 600 |
| gagactatca | gcagcaaccc | cgacgaccgc | accctccacg | agttatacac | ctggcccttc | 660 |
| gccgacgccg | tccaggccaa | cgtcgccagc | gtcatgtgca | gctacaacaa | ggtcaacacc | 720 |
| acctgggcct | gcgaggacca | gtacacccctc | cagaccgtcc | tcaaggacca | gctcggcttc | 780 |
| cccggctacg | tcatgaccga | ctggaacgcc | cagcacacca | ccgtccagag | cgccaacagc | 840 |
| ggcctcgaca | tgagcatgcc | cggcaccgac | ttcaacggca | caaccgcct | ctggggccct | 900 |
| gccctcacca | acgccgtcaa | cagcaaccag | gtccccacct | cccgcgtcga | cgacatggtc | 960 |
| acccgcatcc | tcgccgcctg | gtacttaacc | ggccaagacc | aggctggcta | tcccagcttc | 1020 |
| aacatcagcc | gcaacgtcca | gggcaaccac | aagaccaacg | tccgcgccat | tgcccgcgac | 1080 |
| ggcatcgtcc | tcctcaagaa | cgacgccaac | atcctccccc | tcaagaagcc | cgcctctatc | 1140 |
| gccgtcgtcg | gcagcgccgc | catcatcggc | aaccacgccc | gcaacagccc | cagctgcaac | 1200 |
| gacaagggct | gcgatgacgg | tgccctcggc | atgggctggg | gctctggcgc | cgtcaactac | 1260 |
| ccctacttcg | tcgcccccta | cgacgccatc | aacacccgcg | ccagcagcca | gggcacccag | 1320 |
| gtcaccctca | gcaacaccga | caatacttct | tctggcgctt | ctgctgctag | aggcaaggac | 1380 |
| gtcgccatcg | tttttatcac | tgccgattct | ggcgaaggct | acatcaccgt | cgagggcaac | 1440 |
| gccggcgacc | gcaacaacct | cgaccccctgg | cacaacggca | atgccctcgt | ccaggccgtt | 1500 |
| gctggtgcta | acagcaacgt | catcgtcgtc | gtccacagcg | tcggcgccat | catcctcgag | 1560 |
| cagatcctcg | ccctccccca | ggtcaaggcc | gtcgtctggg | ccggcttacc | cagccaggaa | 1620 |
| agcggcaacg | ccttagtcga | cgtcctctgg | ggtgacgttt | cccctctgg | caagctcgtc | 1680 |
| tacaccattg | ccaagagccc | caacgactac | aacacccgca | ttgtcagcgg | cggcagcgac | 1740 |
| agcttcagcg | agggcctctt | catcgactac | aagcacttcg | acgacgccaa | cattacccc | 1800 |
| cgctacgagt | tcggctacgg | cctcagctac | accaagttca | actacagccg | cctcagcgtc | 1860 |
| ctcagcaccc | caagagcgg | ccctgccact | ggtgctgtcg | tccctggtgg | cccttctgac | 1920 |
| ctcttccaga | acgtcgccac | ggtcaccgtc | gacattgcca | actccggcca | ggtcactggc | 1980 |
| gccgaggtcg | cccagctcta | catcacctac | cccagcagcg | cccctcgcac | tcctcccaag | 2040 |
| cagctcagag | gcttcgctaa | gttaaactta | accctggcc | agagcggcac | cgccacccttt | 2100 |

```
aacatccgca gacgcgacct cagctactgg gacaccgcca gccagaagtg ggtcgtcccc    2160
agcggcagct tcggcatctc cgtcggcgcc agctcccgcg acatccgcct caccagcacc    2220
ctcagcgtcg cctgatga                                                  2238
```

<210> SEQ ID NO 2
<211> LENGTH: 744
<212> TYPE: PRT
<213> ORGANISM: Trichoderma reesei

<400> SEQUENCE: 2

```
Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Val
                20                  25                  30

Val Pro Pro Ala Gly Thr Pro Trp Gly Thr Ala Tyr Asp Lys Ala Lys
            35                  40                  45

Ala Ala Leu Ala Lys Leu Asn Leu Gln Asp Lys Val Gly Ile Val Ser
    50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
    115                 120                 125

Gly Glu Glu Val Lys Ala Ser Gly Ile His Val Ile Leu Gly Pro Val
130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
    195                 200                 205

Asp Arg Thr Leu His Glu Leu Tyr Thr Trp Pro Phe Ala Asp Ala Val
210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
    275                 280                 285

Thr Asp Phe Asn Gly Asn Asn Arg Leu Trp Gly Pro Ala Leu Thr Asn
290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
```

```
            340                 345                 350
Asn Val Arg Ala Ile Ala Arg Asp Gly Ile Val Leu Leu Lys Asn Asp
            355                 360                 365

Ala Asn Ile Leu Pro Leu Lys Lys Pro Ala Ser Ile Ala Val Val Gly
            370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
            405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
            435                 440                 445

Thr Ser Ser Gly Ala Ser Ala Arg Gly Lys Asp Val Ala Ile Val
            450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
            485                 490                 495

Val Gln Ala Val Ala Gly Ala Asn Ser Asn Val Ile Val Val Val His
            500                 505                 510

Ser Val Gly Ala Ile Ile Leu Glu Gln Ile Leu Ala Leu Pro Gln Val
            515                 520                 525

Lys Ala Val Val Trp Ala Gly Leu Pro Ser Gln Glu Ser Gly Asn Ala
            530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
            565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
            595                 600                 605

Ser Tyr Thr Lys Phe Asn Tyr Ser Arg Leu Ser Val Leu Ser Thr Ala
            610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
            645                 650                 655

Gln Val Thr Gly Ala Glu Val Ala Gln Leu Tyr Ile Thr Tyr Pro Ser
            660                 665                 670

Ser Ala Pro Arg Thr Pro Lys Gln Leu Arg Gly Phe Ala Lys Leu
            675                 680                 685

Asn Leu Thr Pro Gly Gln Ser Gly Thr Ala Thr Phe Asn Ile Arg Arg
            690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
            725                 730                 735

Leu Thr Ser Thr Leu Ser Val Ala
            740

<210> SEQ ID NO 3
```

<211> LENGTH: 713
<212> TYPE: PRT
<213> ORGANISM: Trichoderma reesei

<400> SEQUENCE: 3

```
Val Val Pro Pro Ala Gly Thr Pro Trp Gly Thr Ala Tyr Asp Lys Ala
1               5                   10                  15

Lys Ala Ala Leu Ala Lys Leu Asn Leu Gln Asp Lys Val Gly Ile Val
            20                  25                  30

Ser Gly Val Gly Trp Asn Gly Pro Cys Val Gly Asn Thr Ser Pro
        35                  40                  45

Ala Ser Lys Ile Ser Tyr Pro Ser Leu Cys Leu Gln Asp Gly Pro Leu
    50                  55                  60

Gly Val Arg Tyr Ser Thr Gly Ser Thr Ala Phe Thr Pro Gly Val Gln
65              70                  75                  80

Ala Ala Ser Thr Trp Asp Val Asn Leu Ile Arg Glu Arg Gly Gln Phe
            85                  90                  95

Ile Gly Glu Glu Val Lys Ala Ser Gly Ile His Val Ile Leu Gly Pro
        100                 105                 110

Val Ala Gly Pro Leu Gly Lys Thr Pro Gln Gly Gly Arg Asn Trp Glu
    115                 120                 125

Gly Phe Gly Val Asp Pro Tyr Leu Thr Gly Ile Ala Met Gly Gln Thr
130                 135                 140

Ile Asn Gly Ile Gln Ser Val Gly Val Gln Ala Thr Ala Lys His Tyr
145                 150                 155                 160

Ile Leu Asn Glu Gln Glu Leu Asn Arg Glu Thr Ile Ser Ser Asn Pro
                165                 170                 175

Asp Asp Arg Thr Leu His Glu Leu Tyr Thr Trp Pro Phe Ala Asp Ala
            180                 185                 190

Val Gln Ala Asn Val Ala Ser Val Met Cys Ser Tyr Asn Lys Val Asn
        195                 200                 205

Thr Thr Trp Ala Cys Glu Asp Gln Tyr Thr Leu Gln Thr Val Leu Lys
    210                 215                 220

Asp Gln Leu Gly Phe Pro Gly Tyr Val Met Thr Asp Trp Asn Ala Gln
225                 230                 235                 240

His Thr Thr Val Gln Ser Ala Asn Ser Gly Leu Asp Met Ser Met Pro
                245                 250                 255

Gly Thr Asp Phe Asn Gly Asn Asn Arg Leu Trp Gly Pro Ala Leu Thr
            260                 265                 270

Asn Ala Val Asn Ser Asn Gln Val Pro Thr Ser Arg Val Asp Asp Met
        275                 280                 285

Val Thr Arg Ile Leu Ala Ala Trp Tyr Leu Thr Gly Gln Asp Gln Ala
    290                 295                 300

Gly Tyr Pro Ser Phe Asn Ile Ser Arg Asn Val Gln Gly Asn His Lys
305                 310                 315                 320

Thr Asn Val Arg Ala Ile Ala Arg Asp Gly Ile Val Leu Leu Lys Asn
                325                 330                 335

Asp Ala Asn Ile Leu Pro Leu Lys Lys Pro Ala Ser Ile Ala Val Val
            340                 345                 350

Gly Ser Ala Ala Ile Ile Gly Asn His Ala Arg Asn Ser Pro Ser Cys
        355                 360                 365

Asn Asp Lys Gly Cys Asp Asp Gly Ala Leu Gly Met Gly Trp Gly Ser
    370                 375                 380

Gly Ala Val Asn Tyr Pro Tyr Phe Val Ala Pro Tyr Asp Ala Ile Asn
```

```
            385                 390                 395                 400
        Thr Arg Ala Ser Ser Gln Gly Thr Gln Val Thr Leu Ser Asn Thr Asp
                        405                 410                 415

Asn Thr Ser Ser Gly Ala Ser Ala Ala Arg Gly Lys Asp Val Ala Ile
                        420                 425                 430

Val Phe Ile Thr Ala Asp Ser Gly Glu Gly Tyr Ile Thr Val Glu Gly
                        435                 440                 445

Asn Ala Gly Asp Arg Asn Asn Leu Asp Pro Trp His Asn Gly Asn Ala
                        450                 455                 460

Leu Val Gln Ala Val Ala Gly Ala Asn Ser Asn Val Ile Val Val Val
        465                 470                 475                 480

His Ser Val Gly Ala Ile Ile Leu Glu Gln Ile Leu Ala Leu Pro Gln
                        485                 490                 495

Val Lys Ala Val Val Trp Ala Gly Leu Pro Ser Gln Glu Ser Gly Asn
                        500                 505                 510

Ala Leu Val Asp Val Leu Trp Gly Asp Val Ser Pro Ser Gly Lys Leu
                        515                 520                 525

Val Tyr Thr Ile Ala Lys Ser Pro Asn Asp Tyr Asn Thr Arg Ile Val
        530                 535                 540

Ser Gly Gly Ser Asp Ser Phe Ser Glu Gly Leu Phe Ile Asp Tyr Lys
        545                 550                 555                 560

His Phe Asp Asp Ala Asn Ile Thr Pro Arg Tyr Glu Phe Gly Tyr Gly
                        565                 570                 575

Leu Ser Tyr Thr Lys Phe Asn Tyr Ser Arg Leu Ser Val Leu Ser Thr
                        580                 585                 590

Ala Lys Ser Gly Pro Ala Thr Gly Ala Val Val Pro Gly Gly Pro Ser
                        595                 600                 605

Asp Leu Phe Gln Asn Val Ala Thr Val Thr Val Asp Ile Ala Asn Ser
                        610                 615                 620

Gly Gln Val Thr Gly Ala Glu Val Ala Gln Leu Tyr Ile Thr Tyr Pro
        625                 630                 635                 640

Ser Ser Ala Pro Arg Thr Pro Pro Lys Gln Leu Arg Gly Phe Ala Lys
                        645                 650                 655

Leu Asn Leu Thr Pro Gly Gln Ser Gly Thr Ala Thr Phe Asn Ile Arg
                        660                 665                 670

Arg Arg Asp Leu Ser Tyr Trp Asp Thr Ala Ser Gln Lys Trp Val Val
                        675                 680                 685

Pro Ser Gly Ser Phe Gly Ile Ser Val Gly Ala Ser Ser Arg Asp Ile
                        690                 695                 700

Arg Leu Thr Ser Thr Leu Ser Val Ala
        705                 710

<210> SEQ ID NO 4
<211> LENGTH: 805
<212> TYPE: PRT
<213> ORGANISM: Hansenula anomala

<400> SEQUENCE: 4

Asn Thr Ser Ala Pro Gln Ala Ser Asn Asp Pro Phe Asn His Ser
1               5                  10                  15

Pro Ser Phe Tyr Pro Thr Pro Gln Gly Gly Arg Ile Asn Asp Gly Lys
                20                  25                  30

Trp Gln Ala Ala Phe Tyr Arg Ala Arg Glu Leu Val Asp Gln Met Ser
            35                  40                  45
```

```
Ile Ala Glu Lys Val Asn Leu Thr Thr Gly Val Gly Ser Ala Ser Gly
 50                  55                  60

Pro Cys Ser Gly Asn Thr Gly Ser Val Pro Arg Leu Asn Ile Ser Ser
 65                  70                  75                  80

Ile Cys Val Gln Asp Gly Pro Leu Ser Val Arg Ala Ala Asp Leu Thr
                 85                  90                  95

Asp Val Phe Pro Cys Gly Met Ala Ala Ser Ser Phe Asn Lys Gln
                100                 105                 110

Leu Ile Tyr Asp Arg Ala Val Ala Ile Gly Ser Glu Phe Lys Gly Lys
            115                 120                 125

Gly Ala Asp Ala Ile Leu Gly Pro Val Tyr Gly Pro Met Gly Val Lys
130                 135                 140

Ala Ala Gly Gly Arg Gly Trp Glu Gly His Gly Pro Asp Pro Tyr Leu
145                 150                 155                 160

Glu Gly Val Ile Ala Tyr Leu Gln Thr Ile Gly Ile Gln Ser Gln Gly
                165                 170                 175

Val Val Ser Thr Ala Lys His Leu Ile Gly Asn Glu Gln Glu His Phe
            180                 185                 190

Arg Phe Ala Lys Lys Asp Lys His Ala Gly Lys Ile Asp Pro Gly Met
    195                 200                 205

Phe Asn Thr Ser Ser Ser Leu Ser Ser Glu Ile Asp Asp Arg Ala Met
210                 215                 220

His Glu Ile Tyr Leu Trp Pro Phe Ala Glu Ala Val Arg Gly Gly Val
225                 230                 235                 240

Ser Ser Ile Met Cys Ser Tyr Asn Lys Leu Asn Gly Ser His Ala Cys
                245                 250                 255

Gln Asn Ser Tyr Leu Leu Asn Tyr Leu Leu Lys Glu Glu Leu Gly Phe
            260                 265                 270

Gln Gly Phe Val Met Thr Asp Trp Gly Ala Leu Tyr Ser Gly Ile Asp
        275                 280                 285

Ala Ala Asn Ala Gly Leu Asp Met Asp Met Pro Cys Glu Ala Gln Tyr
290                 295                 300

Phe Gly Asn Leu Thr Thr Ala Val Leu Asn Gly Thr Leu Pro Gln
305                 310                 315                 320

Asp Arg Leu Asp Asp Met Ala Thr Arg Ile Leu Ser Ala Leu Ile Tyr
                325                 330                 335

Ser Gly Val His Asn Pro Asp Gly Pro Asn Tyr Asn Ala Gln Thr Phe
            340                 345                 350

Leu Thr Glu Gly His Glu Tyr Phe Lys Gln Gln Glu Gly Asp Ile Val
        355                 360                 365

Val Leu Asn Lys His Val Asp Val Arg Ser Asp Ile Asn Arg Ala Val
370                 375                 380

Ala Leu Arg Ser Ala Val Glu Gly Val Val Leu Leu Lys Asn Glu His
385                 390                 395                 400

Glu Thr Leu Pro Leu Gly Arg Glu Lys Val Lys Arg Ile Ser Ile Leu
                405                 410                 415

Gly Gln Ala Ala Gly Asp Asp Ser Lys Gly Thr Ser Cys Ser Leu Arg
            420                 425                 430

Gly Cys Gly Ser Gly Ala Ile Gly Thr Gly Tyr Gly Ser Gly Ala Gly
        435                 440                 445

Thr Phe Ser Tyr Phe Val Thr Pro Ala Asp Gly Ile Gly Ala Arg Ala
450                 455                 460

Gln Gln Glu Lys Ile Ser Tyr Glu Phe Ile Gly Asp Ser Trp Asn Gln
```

```
                    465                 470                 475                 480
Ala Ala Ala Met Asp Ser Ala Leu Tyr Ala Asp Ala Ile Glu Val
                485                 490                 495

Ala Asn Ser Val Ala Gly Glu Glu Ile Gly Asp Val Asp Gly Asn Tyr
            500                 505                 510

Gly Asp Leu Asn Asn Leu Thr Leu Trp His Asn Ala Val Pro Leu Ile
            515                 520                 525

Lys Asn Ile Ser Ser Ile Asn Asn Asn Thr Ile Val Ile Val Thr Ser
530                 535                 540

Gly Gln Gln Ile Asp Leu Glu Pro Phe Ile Asp Asn Glu Asn Val Thr
545                 550                 555                 560

Ala Val Ile Tyr Ser Ser Tyr Leu Gly Gln Asp Phe Gly Thr Val Leu
                565                 570                 575

Ala Lys Val Leu Phe Gly Asp Glu Asn Pro Ser Gly Lys Leu Pro Phe
            580                 585                 590

Thr Ile Ala Lys Asp Val Asn Asp Tyr Ile Pro Val Ile Glu Lys Val
            595                 600                 605

Asp Val Pro Asp Pro Val Asp Lys Phe Thr Glu Ser Ile Tyr Val Asp
610                 615                 620

Tyr Arg Tyr Phe Asp Lys Tyr Asn Lys Pro Val Arg Tyr Glu Phe Gly
625                 630                 635                 640

Tyr Gly Leu Ser Tyr Ser Asn Phe Ser Leu Ser Asp Ile Glu Ile Gln
                645                 650                 655

Thr Leu Gln Pro Phe Ser Glu Asn Ala Glu Pro Ala Ala Asn Tyr Ser
            660                 665                 670

Glu Thr Tyr Gln Tyr Lys Gln Ser Asn Met Asp Pro Ser Glu Tyr Thr
            675                 680                 685

Val Pro Glu Gly Phe Lys Glu Leu Ala Asn Tyr Thr Tyr Pro Tyr Ile
            690                 695                 700

His Asp Ala Ser Ser Ile Lys Ala Asn Ser Ser Tyr Asp Tyr Pro Glu
705                 710                 715                 720

Gly Tyr Ser Thr Glu Gln Leu Asp Gly Pro Lys Ser Leu Ala Ala Gly
                725                 730                 735

Gly Leu Gly Gly Asn His Thr Cys Gly Met Leu Val Thr Leu Ser Leu
            740                 745                 750

Leu Lys Ser Gln Ile Lys Val Leu Met Leu Val Gly Leu His Leu Asn
            755                 760                 765

Cys Met Leu Asp Ile Gln Ile Met Met Asn Ser Gln His Leu Gln Cys
770                 775                 780

Asn Tyr Val Asp Leu Lys Arg Cys Phe Trp Ile Lys Ile Ile Leu Lys
                785                 790                 795                 800

Leu Phe Leu Leu Asn
                805

<210> SEQ ID NO 5
<211> LENGTH: 847
<212> TYPE: PRT
<213> ORGANISM: Piromyces sp.

<400> SEQUENCE: 5

Thr Ser Trp Ser Glu Ala Asp Glu Lys Ala Lys Ser Phe Met Ser Asp
1               5                   10                  15

Leu Ser Glu Ser Glu Lys Ile Asp Ile Val Thr Gly Tyr Met Asn Met
            20                  25                  30
```

-continued

Gln Gly Thr Cys Val Gly Asn Ile Lys Pro Leu Asp Arg Lys Asn Phe
 35                  40                  45

Lys Gly Leu Cys Leu Gln Asp Gly Pro Ala Gly Val Arg Phe Asn Gly
 50                  55                  60

Gly Thr Ser Thr Thr Trp Gln Ala Gly Ile Asn Asn Ala Ala Thr Phe
 65                  70                  75                  80

Asn Lys Asp Leu Leu Tyr Lys Ile Gly Lys Asp Gln Gly Ala Glu Phe
                 85                  90                  95

Tyr Ala Lys Gly Ile Asn Ile Ala Leu Ala Pro Ser Met Asn Ile Leu
            100                 105                 110

Arg Ala Pro Ala Ser Gly Arg Val Trp Glu Asn Phe Gly Glu Asp Pro
        115                 120                 125

Tyr Leu Ser Gly Val Cys Gly Ala Gln Ile Thr Lys Gly Tyr Gln Asp
    130                 135                 140

Ser Gly Val Ile Val Ala Ala Lys His Tyr Val Ala Asn Asp Ile Glu
145                 150                 155                 160

His Asn Arg Glu Ala Ser Ser Asn Met Asp Asp Gln Thr Leu Met
                165                 170                 175

Glu Ile His Val Glu Pro Phe Tyr Arg Thr Ile Lys Asp Gly Asp Ala
            180                 185                 190

Gly Ser Val Met Ala Ser Tyr Asn Ala Val Asn Asn Ile Tyr Val Val
        195                 200                 205

Gln Asn Lys Lys Val Leu Thr Glu Ile Leu Lys Glu Gly Ile Gly Phe
    210                 215                 220

Gln Gly Phe Val Met Ser Asp Trp Ala Ile His Asp Leu Glu Gly
225                 230                 235                 240

Ser Phe Asn Ala Gly Met Asp Met Asn Met Pro Gly Gly Lys Ala Trp
                245                 250                 255

Gly Pro Asp Tyr Val Asn Asn Ser Phe Trp Gly Ser Asn Ile Ser Asn
            260                 265                 270

Ala Ile Arg Ser Gly Gln Val Ser Ser Arg Leu Asp Asp Ala Val
        275                 280                 285

Arg Arg Ile Ile Arg Thr Leu Tyr Arg Phe Asp Gln Met Ser Gly Tyr
    290                 295                 300

Pro Asn Val Asn Leu Lys Ala Pro Ser Met His Ala Asp Thr Asn Arg
305                 310                 315                 320

Gln Ala Ala Ile Glu Ser Ser Val Leu Leu Lys Asn Ala Asp Asp Ile
                325                 330                 335

Leu Pro Leu Thr Lys Lys Tyr Arg Lys Ile Ala Ile Ile Gly Lys Asp
            340                 345                 350

Ala Asp Lys Ala Gln Ser Cys Thr Asp Thr Ala Cys Ser Gly Gly Asn
        355                 360                 365

Ile Ile Gln Gly Trp Gly Ser Gly Thr Thr Asp Phe Thr Gly Ile Ser
370                 375                 380

Asp Pro Ile Thr Ala Ile Lys Asn Arg Ala Ser Lys Glu Gly Ile Ser
385                 390                 395                 400

Ile Val Ser Ser Ile Ser Asp Ser Ala Asn Glu Gly Ala Asn Val Ala
                405                 410                 415

Lys Asp Ala Asp Val Ala Val Phe Val Arg Ala Thr Ser Gly Glu
            420                 425                 430

Glu Tyr Ile Val Val Asp Asn Asn Lys Gly Asp Arg Asn Asn Leu Asp
        435                 440                 445

Leu Trp His Gly Gly Asn Asp Leu Val Lys Ser Val Ala Ala Val Asn

```
                450             455             460
Lys Asn Thr Val Val Ile His Ala Pro Ala Thr Val Asn Leu Pro
465                 470             475             480

Phe Leu Asn Asn Val Lys Ala Ile Ile His Ala Gly Met Pro Gly Ala
                485             490             495

Glu Ser Gly Asn Ala Ile Ala Ser Ile Leu Phe Gly Asp Ser Asn Pro
                500             505             510

Ser Gly His Leu Pro Phe Thr Trp Ala Ala Arg Glu Asp Tyr Cys Cys
            515             520             525

Asp Val Ser Tyr Pro Ala Glu Leu Pro His Gly Gly Asn Ser Lys Thr
            530             535             540

Ala Tyr Asp Tyr Lys Glu Gly Leu Phe Val Gly Tyr Arg Trp Phe Asp
545             550             555             560

Lys Lys Asn Lys Thr Pro Ile Phe Pro Phe Gly His Gly Leu Ser Tyr
                565             570             575

Thr Thr Phe Asp Tyr Ser Asn Leu Ser Val Ser Leu Lys Lys Ser Gly
            580             585             590

Thr Gln Val Thr Gly Leu Glu Ala Thr Val Thr Val Ala Asn Thr Gly
            595             600             605

Ser Tyr Glu Gly Ala Thr Val Pro Met Leu Phe Leu Gly Phe Pro Ala
610             615             620

Val Ser Glu Leu Gly Asp Tyr Pro Val Arg Asn Leu Lys Ala Phe Glu
625             630             635             640

Lys Val Asn Leu Lys Ala Gly Glu Lys Lys Thr Val Thr Leu Thr Val
                645             650             655

Asp Gln His Gly Leu Ser Tyr Tyr Asn Thr Ser Lys Lys Ser Phe Val
            660             665             670

Val Pro Thr Gly Gly Glu Phe Thr Val Tyr Val Gly Lys Ser Ala Gly
            675             680             685

Asp Leu Pro Leu Lys Lys Ala Ile Lys Asn Thr Gln Gly Thr Asn Glu
            690             695             700

Ser Ser Ser Ser Val Gly Asp Glu Asn Asn Asn Pro Asn Asn Asn
705             710             715             720

Ala Asp Cys Ser Val Asn Gly Tyr Lys Cys Ser Asn Ser Asn Ala
                725             730             735

Glu Val Val Tyr Thr Asp Gly Asp Gly Asn Trp Gly Val Glu Asn Gly
                740             745             750

Gln Trp Cys Ile Ile Lys Glu Gln Gln Gln Gln Thr Cys Phe Ser
            755             760             765

Ile Lys Leu Gly Tyr Pro Cys Cys Lys Gly Asn Glu Val Ala Tyr Thr
770             775             780

Asp Asn Asp Gly Gln Trp Gly Phe Glu Asn Gln Trp Cys Gly Ile
785             790             795             800

Ala Thr Ala Thr Ser Gly Ala Gly Cys Pro Tyr Thr Ser Lys Asn
                805             810             815

Gly Tyr Pro Val Cys Gln Thr Thr Lys Val Glu Tyr Val Asp Ser
            820             825             830

Asp Lys Trp Gly Val Glu Asn Gly Asn Trp Cys Ile Met Cys Asn
            835             840             845
```

<210> SEQ ID NO 6
<211> LENGTH: 847
<212> TYPE: PRT
<213> ORGANISM: Coccidioides immitis

<400> SEQUENCE: 6

```
Ala Pro Pro Gly Val Gly Ala Leu Asp Asp Arg Ala Glu Leu Pro Asp
1               5                   10                  15

Gly Phe His Ser Pro Gln Tyr Tyr Pro Ala Pro Arg Gly Leu Gly Ala
            20                  25                  30

Gly Met Glu Glu Ala Tyr Ser Lys Ala His Thr Val Ser Lys Met
        35                  40                  45

Thr Leu Ala Gly Lys Val Asn Leu Thr Thr Gly Thr Gly Phe Leu Met
    50                  55                  60

Ala Leu Val Gly Gln Thr Gly Ser Ala Leu Arg Phe Gly Ile Pro Arg
65                  70                  75                  80

Leu Cys Leu Gln Asp Gly Pro Leu Gly Leu Arg Asn Thr Asp His Asn
                85                  90                  95

Thr Ala Phe Pro Ala Gly Ile Ser Val Gly Ala Thr Phe Asp Lys Lys
            100                 105                 110

Leu Met Tyr Glu Arg Gly Cys Ala Met Gly Glu Glu Phe Arg Gly Lys
        115                 120                 125

Gly Ala Asn Val His Leu Gly Pro Ser Val Gly Pro Leu Gly Arg Lys
    130                 135                 140

Pro Arg Gly Gly Arg Asn Trp Glu Gly Phe Gly Ser Asp Pro Ser Leu
145                 150                 155                 160

Gln Ala Ile Ala Ala Val Glu Thr Ile Lys Gly Val Gln Ser Lys Gly
                165                 170                 175

Val Ile Ala Thr Ile Lys His Leu Val Gly Asn Glu Gln Glu Met Tyr
            180                 185                 190

Arg Met Thr Asn Ile Val Gln Arg Ala Tyr Ser Ala Asn Ile Asp Asp
        195                 200                 205

Arg Thr Met His Glu Leu Tyr Leu Trp Pro Phe Ala Glu Ser Val Arg
    210                 215                 220

Ala Gly Val Gly Ala Val Met Met Ala Tyr Asn Asp Val Asn Gly Ser
225                 230                 235                 240

Ala Ser Cys Gln Asn Ser Lys Leu Ile Asn Gly Ile Leu Lys Asp Glu
                245                 250                 255

Leu Gly Phe Gln Gly Phe Val Met Thr Asp Trp Tyr Ala Gln Ile Gly
            260                 265                 270

Gly Val Ser Ser Ala Leu Ala Gly Leu Asp Met Ser Met Pro Gly Asp
        275                 280                 285

Gly Ser Val Pro Leu Ser Gly Thr Ser Phe Trp Ala Ser Glu Leu Ser
    290                 295                 300

Arg Ser Ile Leu Asn Gly Thr Val Ala Leu Asp Arg Leu Asn Asp Met
305                 310                 315                 320

Val Thr Arg Ile Val Ala Thr Trp Phe Lys Phe Gly Gln Asp Lys Asp
                325                 330                 335

Phe Pro Leu Pro Asn Phe Ser Ser Tyr Thr Gln Asn Ala Lys Gly Leu
            340                 345                 350

Leu Tyr Pro Gly Ala Leu Phe Ser Pro Leu Gly Val Val Asn Gln Phe
        355                 360                 365

Val Asn Val Gln Ala Asp His Lys Leu Ala Arg Val Ile Ala Arg
    370                 375                 380

Glu Ser Ile Thr Leu Leu Lys Asn Glu Asp Asn Leu Leu Pro Leu Asp
385                 390                 395                 400

Pro Asn Arg Ala Ile Lys Tyr Ser Glu Gln Met Pro Gly Thr Asn Pro
```

-continued

```
                405                 410                 415
Arg Gly Ile Asn Ala Cys Pro Asp Lys Gly Cys Asn Lys Gly Val Leu
                420                 425                 430

Thr Met Gly Trp Gly Ser Gly Thr Ser Asn Leu Pro Tyr Leu Val Thr
                435                 440                 445

Pro Glu Asp Ala Ile Arg Asn Ile Ser Lys Asn Thr Glu Phe His Ile
450                 455                 460

Thr Asp Lys Phe Pro Asn Asn Val Gln Pro Gly Pro Asp Asp Val Ala
465                 470                 475                 480

Ile Val Phe Val Asn Ala Asp Ser Gly Glu Asn Tyr Ile Ile Val Glu
                485                 490                 495

Ser Asn Pro Gly Asp Arg Thr Val Ala Gln Met Lys Leu Trp His Asn
                500                 505                 510

Gly Asp Glu Leu Ile Glu Ser Ala Ala Lys Lys Phe Ser Asn Val Val
                515                 520                 525

Val Val Val Val His Thr Val Gly Pro Ile Ile Met Glu Lys Trp Ile
                530                 535                 540

Asp Leu Leu Arg Ser Arg Val Ser Cys Leu Pro Asp Phe Gln Asp Lys
545                 550                 555                 560

Lys Leu Glu Ile Leu Leu Ile Ser Cys Ser Glu Thr Ser Val Arg
                565                 570                 575

Val Ala Ala Ser Ile Tyr Asp Thr Glu Ser Arg Ile Gly Leu Ser Asp
                580                 585                 590

Ser Val Ser Leu Ile Asn Gln Arg Phe Gly Gln Ile Gln Asp Thr Phe
                595                 600                 605

Thr Glu Gly Leu Phe Ile Asp Tyr Arg His Phe Gln Lys Glu Asn Ile
                610                 615                 620

Thr Pro Arg Tyr His Phe Gly Tyr Gly Leu Ser Tyr Thr Thr Phe Asn
625                 630                 635                 640

Phe Thr Glu Pro Arg Leu Glu Ser Val Thr Thr Leu Ser Glu Tyr Pro
                645                 650                 655

Pro Ala Arg Lys Pro Lys Ala Gly Asp Arg His Thr Pro Thr Ile Ser
                660                 665                 670

His Leu Leu Gln Lys Trp Pro Gly Pro Lys Thr Leu Thr Gly Ser Gly
                675                 680                 685

Ala Tyr Leu Tyr Pro Tyr Leu Asp Asn Pro Ser Ala Ile Lys Pro Lys
                690                 695                 700

Pro Gly Tyr Pro Tyr Pro Glu Ala Ile Gln Pro Asn Leu Asn Leu Asn
705                 710                 715                 720

Pro Arg Ala Gly Gly Ser Glu Ala Val Thr Arg Arg Tyr Gly Met Leu
                725                 730                 735

Arg Ser Arg Phe Pro Leu Lys Leu Leu Ile Leu Glu Arg Asn Pro Val
                740                 745                 750

Arg Ala Val Ala Gln Leu Tyr Val Glu Leu Pro Thr Asp Asp Glu His
                755                 760                 765

Pro Thr Pro Lys Leu Gln Leu Arg Gln Phe Glu Lys Thr Ala Thr Leu
770                 775                 780

Glu Pro Gly Gln Ser Glu Val Leu Lys Met Glu Ile Thr Arg Lys Asp
785                 790                 795                 800

Val Ser Ile Trp Asp Thr Met Val Gln Asp Trp Lys Val Pro Ala Thr
                805                 810                 815

Gly Lys Gly Ile Lys Leu Trp Ile Gly Ala Ser Val Gly Asp Leu Lys
                820                 825                 830
```

Ala Val Cys Glu Thr Gly Lys Gly Lys Ser Cys His Val Leu Asn
            835                 840                 845

<210> SEQ ID NO 7
<211> LENGTH: 863
<212> TYPE: PRT
<213> ORGANISM: Saccharomycopsis fibuligera

<400> SEQUENCE: 7

Leu Pro Val Gln Thr His Asn Leu Thr Asp Asn Gln Gly Phe Asp Glu
1               5                   10                  15

Glu Ser Ser Gln Trp Ile Ser Pro His Tyr Tyr Pro Thr Pro Gln Gly
            20                  25                  30

Gly Arg Leu Gln Gly Val Trp Gln Asp Ala Tyr Thr Lys Ala Lys Ala
        35                  40                  45

Leu Val Ser Gln Met Thr Ile Val Glu Lys Val Asn Leu Thr Thr Gly
    50                  55                  60

Thr Gly Trp Gln Leu Gly Pro Cys Val Gly Asn Thr Gly Ser Val Pro
65                  70                  75                  80

Arg Phe Gly Ile Pro Asn Leu Cys Leu Gln Asp Gly Pro Leu Gly Val
                85                  90                  95

Arg Leu Thr Asp Phe Ser Thr Gly Tyr Pro Ser Gly Met Ala Thr Gly
            100                 105                 110

Ala Thr Phe Asn Lys Asp Leu Phe Leu Gln Arg Gly Gln Ala Leu Gly
        115                 120                 125

His Glu Phe Asn Ser Lys Gly Val His Ile Ala Leu Gly Pro Ala Val
    130                 135                 140

Gly Pro Leu Gly Val Lys Ala Arg Gly Gly Arg Asn Phe Glu Ala Phe
145                 150                 155                 160

Gly Ser Asp Pro Tyr Leu Gln Gly Ile Ala Ala Ala Thr Ile Lys
                165                 170                 175

Gly Leu Gln Glu Asn Asn Val Met Ala Cys Val Lys His Phe Ile Gly
            180                 185                 190

Asn Glu Gln Asp Ile Tyr Arg Gln Pro Ser Asn Ser Lys Val Asp Pro
        195                 200                 205

Glu Tyr Asp Pro Ala Thr Lys Glu Ser Ile Ser Ala Asn Ile Pro Asp
    210                 215                 220

Arg Ala Met His Glu Leu Tyr Leu Trp Pro Phe Ala Asp Ser Ile Arg
225                 230                 235                 240

Ala Gly Val Gly Ser Val Met Cys Ser Tyr Asn Arg Val Asn Asn Thr
                245                 250                 255

Tyr Ser Cys Glu Asn Ser Tyr Met Ile Asn His Leu Leu Lys Glu Glu
            260                 265                 270

Leu Gly Phe Gln Gly Phe Val Val Ser Asp Trp Ala Ala Gln Met Ser
        275                 280                 285

Gly Ala Tyr Ser Ala Ile Ser Gly Leu Asp Met Ser Met Pro Gly Glu
    290                 295                 300

Leu Leu Gly Gly Trp Asn Thr Gly Lys Ser Tyr Trp Gly Gln Asn Leu
305                 310                 315                 320

Thr Lys Ala Val Tyr Asn Glu Thr Val Pro Ile Glu Arg Leu Asp Asp
                325                 330                 335

Met Ala Thr Arg Ile Leu Ala Ala Leu Tyr Ala Thr Asn Ser Phe Pro
            340                 345                 350

Thr Lys Asp Arg Leu Pro Asn Phe Ser Ser Phe Thr Thr Lys Glu Tyr

-continued

```
                355                 360                 365
Gly Asn Glu Phe Phe Val Asp Lys Thr Ser Pro Val Lys Val Asn
370                 375                 380
His Phe Val Asp Pro Ser Asn Asp Phe Thr Glu Asp Thr Ala Leu Lys
385                 390                 395                 400
Val Ala Glu Glu Ser Ile Val Leu Leu Lys Asn Glu Lys Asn Thr Leu
                405                 410                 415
Pro Ile Ser Pro Asn Lys Val Arg Lys Leu Leu Ser Gly Ile Ala
            420                 425                 430
Ala Gly Pro Asp Pro Lys Gly Tyr Glu Cys Ser Asp Gln Ser Cys Val
            435                 440                 445
Asp Gly Ala Leu Phe Glu Gly Trp Gly Ser Gly Ser Val Gly Tyr Pro
            450                 455                 460
Lys Tyr Gln Val Thr Pro Phe Glu Glu Ile Ser Ala Asn Ala Arg Lys
465                 470                 475                 480
Asn Lys Met Gln Phe Asp Tyr Ile Arg Glu Ser Phe Asp Leu Thr Gln
                485                 490                 495
Val Ser Thr Val Ala Ser Asp Ala His Met Ser Ile Val Val Ser
            500                 505                 510
Ala Val Ser Gly Glu Gly Tyr Leu Ile Ile Asp Gly Asn Arg Gly Asp
            515                 520                 525
Lys Asn Asn Val Thr Leu Trp His Asn Ser Asp Asn Leu Ile Lys Ala
530                 535                 540
Val Ala Glu Asn Cys Ala Asn Thr Val Val Ile Thr Ser Thr Gly
545                 550                 555                 560
Gln Val Asp Val Glu Ser Phe Ala Asp His Pro Asn Val Thr Ala Ile
            565                 570                 575
Val Trp Ala Gly Pro Leu Gly Asp Arg Ser Gly Thr Ala Ile Ala Asn
            580                 585                 590
Ile Leu Phe Gly Asn Ala Asn Pro Ser Gly His Leu Pro Phe Thr Val
            595                 600                 605
Ala Lys Ser Asn Asp Asp Tyr Ile Pro Ile Val Thr Tyr Asn Pro Pro
            610                 615                 620
Asn Gly Glu Pro Glu Asp Asn Thr Leu Ala Glu His Asp Leu Leu Val
625                 630                 635                 640
Asp Tyr Arg Tyr Phe Glu Glu Lys Asn Ile Glu Pro Arg Tyr Ala Phe
            645                 650                 655
Gly Tyr Gly Leu Ser Tyr Asn Glu Tyr Lys Val Ser Asn Ala Lys Val
            660                 665                 670
Ser Ala Ala Lys Lys Val Asp Glu Glu Leu Pro Gln Pro Lys Leu Tyr
            675                 680                 685
Leu Ala Glu Tyr Ser Tyr Asn Lys Thr Glu Glu Ile Asn Asn Pro Glu
            690                 695                 700
Asp Ala Phe Phe Pro Ser Asn Ala Arg Arg Ile Gln Glu Phe Leu Tyr
705                 710                 715                 720
Pro Tyr Leu Asp Ser Asn Val Thr Leu Lys Asp Gly Asn Tyr Glu Tyr
            725                 730                 735
Pro Asp Gly Tyr Ser Thr Glu Gln Arg Thr Thr Pro Ile Gln Pro Gly
            740                 745                 750
Gly Gly Leu Gly Gly Asn Asp Ala Leu Trp Glu Val Ala Tyr Lys Val
            755                 760                 765
Glu Val Asp Val Gln Asn Leu Gly Asn Ser Thr Asp Lys Phe Val Pro
770                 775                 780
```

Gln Leu Tyr Leu Lys His Pro Glu Asp Gly Lys Phe Glu Thr Pro Val
785                 790                 795                 800

Gln Leu Arg Gly Phe Glu Lys Val Glu Leu Ser Pro Gly Glu Lys Lys
            805                 810                 815

Thr Val Glu Phe Glu Leu Leu Arg Arg Asp Leu Ser Val Trp Asp Thr
            820                 825                 830

Thr Arg Gln Ser Trp Ile Val Glu Ser Gly Thr Tyr Glu Ala Leu Ile
            835                 840                 845

Gly Val Ala Val Asn Asp Ile Lys Thr Ser Val Leu Phe Thr Ile
            850                 855                 860

<210> SEQ ID NO 8
<211> LENGTH: 859
<212> TYPE: PRT
<213> ORGANISM: Saccharomycopsis fibuligera

<400> SEQUENCE: 8

Val Pro Ile Gln Asn Tyr Thr Gln Ser Pro Ser Gln Arg Asp Glu Ser
1               5                   10                  15

Ser Gln Trp Val Ser Pro His Tyr Tyr Pro Thr Pro Gln Gly Gly Arg
            20                  25                  30

Leu Gln Asp Val Trp Gln Glu Ala Tyr Ala Arg Ala Lys Ala Ile Val
            35                  40                  45

Gly Gln Met Thr Ile Val Glu Lys Val Asn Leu Thr Thr Gly Thr Gly
        50                  55                  60

Trp Gln Leu Asp Pro Cys Val Gly Asn Thr Gly Ser Val Pro Arg Phe
65                  70                  75                  80

Gly Ile Pro Asn Leu Cys Leu Gln Asp Gly Pro Leu Gly Val Arg Phe
                85                  90                  95

Ala Asp Phe Val Thr Gly Tyr Pro Ser Gly Leu Ala Thr Gly Ala Thr
            100                 105                 110

Phe Asn Lys Asp Leu Phe Leu Gln Arg Gly Gln Ala Leu Gly His Glu
        115                 120                 125

Phe Asn Ser Lys Gly Val His Ile Ala Leu Gly Pro Ala Val Gly Pro
130                 135                 140

Leu Gly Val Lys Ala Arg Gly Gly Arg Asn Phe Glu Ala Phe Gly Ser
145                 150                 155                 160

Asp Pro Tyr Leu Gln Gly Thr Ala Ala Ala Thr Ile Lys Gly Leu
            165                 170                 175

Gln Glu Asn Asn Val Met Ala Cys Val Lys His Phe Ile Gly Asn Glu
        180                 185                 190

Gln Glu Lys Tyr Arg Gln Pro Asp Asp Ile Asn Pro Ala Thr Asn Gln
        195                 200                 205

Thr Thr Lys Glu Ala Ile Ser Ala Asn Ile Pro Asp Arg Ala Met His
    210                 215                 220

Ala Leu Tyr Leu Trp Pro Phe Ala Asp Ser Val Arg Ala Gly Val Gly
225                 230                 235                 240

Ser Val Met Cys Ser Tyr Asn Arg Val Asn Asn Thr Tyr Ala Cys Glu
                245                 250                 255

Asn Ser Tyr Met Met Asn His Leu Leu Lys Glu Glu Leu Gly Phe Gln
            260                 265                 270

Gly Phe Val Val Ser Asp Trp Gly Ala Gln Leu Ser Gly Val Tyr Ser
        275                 280                 285

Ala Ile Ser Gly Leu Asp Met Ser Met Pro Gly Glu Val Tyr Gly Gly

-continued

```
            290                 295                 300
Trp Asn Thr Gly Thr Ser Phe Trp Gly Gln Asn Leu Thr Lys Ala Ile
305                 310                 315                 320

Tyr Asn Glu Thr Val Pro Ile Glu Arg Leu Asp Asp Met Ala Thr Arg
                325                 330                 335

Ile Leu Ala Ala Leu Tyr Ala Thr Asn Ser Phe Pro Thr Glu Asp His
                340                 345                 350

Leu Pro Asn Phe Ser Ser Trp Thr Thr Lys Glu Tyr Gly Asn Lys Tyr
                355                 360                 365

Tyr Ala Asp Asn Thr Thr Glu Ile Val Lys Val Asn Tyr Asn Val Asp
                370                 375                 380

Pro Ser Asn Asp Phe Thr Glu Asp Thr Ala Leu Lys Val Ala Glu Glu
385                 390                 395                 400

Ser Ile Val Leu Leu Lys Asn Glu Asn Thr Leu Pro Ile Ser Pro
                405                 410                 415

Glu Lys Ala Lys Arg Leu Leu Leu Ser Gly Ile Ala Ala Gly Pro Asp
                420                 425                 430

Pro Ile Gly Tyr Gln Cys Glu Asp Gln Ser Cys Thr Asn Gly Ala Leu
                435                 440                 445

Phe Gln Gly Trp Gly Ser Gly Ser Val Gly Ser Pro Lys Tyr Gln Val
450                 455                 460

Thr Pro Phe Glu Glu Ile Ser Tyr Leu Ala Arg Lys Asn Lys Met Gln
465                 470                 475                 480

Phe Asp Tyr Ile Arg Glu Ser Tyr Asp Leu Ala Gln Val Thr Lys Val
                485                 490                 495

Ala Ser Asp Ala His Leu Ser Ile Val Val Ser Ala Ala Ser Gly
                500                 505                 510

Glu Gly Tyr Ile Thr Val Asp Gly Asn Gln Gly Asp Arg Lys Asn Leu
                515                 520                 525

Thr Leu Trp Asn Asn Gly Asp Lys Leu Ile Glu Thr Val Ala Glu Asn
530                 535                 540

Cys Ala Asn Thr Val Val Val Thr Ser Thr Gly Gln Ile Asn Phe
545                 550                 555                 560

Glu Gly Phe Ala Asp His Pro Asn Val Thr Ala Ile Val Trp Ala Gly
                565                 570                 575

Pro Leu Gly Asp Arg Ser Gly Thr Ala Ile Ala Asn Ile Leu Phe Gly
                580                 585                 590

Lys Ala Asn Pro Ser Gly His Leu Pro Phe Thr Ile Ala Lys Thr Asp
                595                 600                 605

Asp Asp Tyr Ile Pro Ile Glu Thr Tyr Ser Pro Ser Ser Gly Glu Pro
610                 615                 620

Glu Asp Asn His Leu Val Glu Asn Asp Leu Leu Val Asp Tyr Arg Tyr
625                 630                 635                 640

Phe Glu Glu Lys Asn Ile Glu Pro Arg Tyr Ala Phe Gly Tyr Gly Leu
                645                 650                 655

Ser Tyr Asn Glu Tyr Glu Val Ser Asn Ala Lys Val Ser Ala Ala Lys
                660                 665                 670

Lys Val Asp Glu Glu Leu Pro Glu Pro Ala Thr Tyr Leu Ser Glu Phe
                675                 680                 685

Ser Tyr Gln Asn Ala Lys Asp Ser Lys Asn Pro Ser Asp Ala Phe Ala
                690                 695                 700

Pro Ala Asp Leu Asn Arg Val Asn Glu Tyr Leu Tyr Pro Tyr Leu Asp
705                 710                 715                 720
```

Ser Asn Val Thr Leu Lys Asp Gly Asn Tyr Glu Tyr Pro Asp Gly Tyr
725 730 735

Ser Thr Glu Gln Arg Thr Thr Pro Asn Gln Pro Gly Gly Gly Leu Gly
740 745 750

Gly Asn Asp Ala Leu Trp Glu Val Ala Tyr Asn Ser Thr Asp Lys Phe
755 760 765

Val Pro Gln Gly Asn Ser Thr Asp Lys Phe Val Pro Gln Leu Tyr Leu
770 775 780

Lys His Pro Glu Asp Gly Lys Phe Glu Thr Pro Ile Gln Leu Arg Gly
785 790 795 800

Phe Glu Lys Val Glu Leu Ser Pro Gly Glu Lys Lys Thr Val Asp Leu
805 810 815

Arg Leu Leu Arg Arg Asp Leu Ser Val Trp Asp Thr Thr Arg Gln Ser
820 825 830

Trp Ile Val Glu Ser Gly Thr Tyr Glu Ala Leu Ile Gly Val Ala Val
835 840 845

Asn Asp Ile Lys Thr Ser Val Leu Phe Thr Ile
850 855

<210> SEQ ID NO 9
<211> LENGTH: 786
<212> TYPE: PRT
<213> ORGANISM: Septoria lycopersici

<400> SEQUENCE: 9

Leu Ser His Glu Asp Gln Ser Lys His Phe Thr Thr Ile Pro Thr Phe
1 5 10 15

Pro Thr Pro Asp Ser Thr Gly Glu Gly Trp Lys Ala Ala Phe Glu Lys
20 25 30

Ala Ala Asp Ala Val Ser Arg Leu Asn Leu Thr Gln Lys Val Ala Leu
35 40 45

Thr Thr Gly Thr Thr Ala Gly Leu Ser Cys Asn Gly Asn Ile Ala Pro
50 55 60

Ile Pro Glu Ile Asn Phe Ser Gly Leu Cys Leu Ala Asp Gly Pro Val
65 70 75 80

Ser Val Arg Ile Ala Asp Leu Ala Thr Val Phe Pro Ala Gly Leu Thr
85 90 95

Ala Ala Ala Thr Trp Asp Arg Gln Leu Ile Tyr Glu Arg Ala Arg Ala
100 105 110

Leu Gly Ser Glu Phe Arg Gly Lys Gly Ser Gln Val His Leu Gly Pro
115 120 125

Ala Ser Gly Ala Leu Gly Arg His Pro Leu Gly Gly Arg Asn Trp Glu
130 135 140

Ser Phe Ser Pro Asp Pro Tyr Leu Ser Gly Val Ala Met Asp Phe Ser
145 150 155 160

Ile Arg Gly Ile Gln Glu Met Gly Val Gln Ala Asn Arg Lys His Phe
165 170 175

Ile Gly Asn Glu Gln Glu Thr Gln Arg Ser Asn Thr Phe Thr Asp Asp
180 185 190

Gly Thr Glu Ile Gln Ala Ile Ser Ser Asn Ile Asp Asp Arg Thr Met
195 200 205

His Glu Leu Tyr Leu Trp Pro Phe Ala Asn Ala Val Arg Ser Gly Val
210 215 220

Ala Ser Val Met Cys Ser Tyr Asn Arg Leu Asn Gln Thr Tyr Ala Cys

```
            225                 230                 235                 240

Glu Asn Ser Lys Leu Met Asn Gly Ile Leu Lys Gly Glu Leu Gly Phe
                    245                 250                 255

Gln Gly Tyr Val Val Ser Asp Trp Tyr Ala Thr His Ser Gly Val Glu
                    260                 265                 270

Ser Val Asn Ala Gly Leu Asp Met Thr Met Pro Gly Pro Leu Asp Ser
                    275                 280                 285

Pro Ser Thr Ala Leu Arg Pro Pro Ser Tyr Leu Gly Gly Asn Leu
                290                 295                 300

Thr Glu Ala Val Leu Asn Gly Thr Ile Pro Glu Ala Arg Val Asp Asp
    305                 310                 315                 320

Met Ala Arg Arg Ile Leu Met Pro Tyr Phe Leu Gly Gln Asp Thr
                        325                 330                 335

Asp Phe Pro Thr Val Asp Pro Ser Thr Gly Phe Val Phe Ala Arg Thr
                    340                 345                 350

Tyr Asn Tyr Pro Asp Glu Tyr Leu Thr Leu Gly Gly Leu Asp Pro Tyr
                    355                 360                 365

Asn Pro Pro Ala Arg Asp Val Arg Gly Asn His Ser Asp Ile Val
                370                 375                 380

Arg Lys Val Ala Ala Ala Gly Thr Val Leu Leu Lys Asn Val Asn Asn
    385                 390                 395                 400

Val Leu Pro Leu Lys Glu Pro Lys Ser Val Gly Ile Phe Gly Asn Gly
                    405                 410                 415

Ala Ala Asp Val Thr Glu Gly Leu Thr Phe Thr Gly Asp Asp Ser Gly
                    420                 425                 430

Pro Trp Gly Ala Asp Ile Gly Ala Leu Ser Val Gly Gly Ser Gly
                435                 440                 445

Ala Gly Arg His Thr His Leu Val Ser Pro Leu Ala Ala Ile Arg Lys
                    450                 455                 460

Arg Thr Glu Ser Val Gly Gly Arg Val Gln Tyr Leu Leu Ser Asn Ser
    465                 470                 475                 480

Arg Ile Val Asn Asp Asp Phe Thr Ser Ile Tyr Pro Thr Pro Glu Val
                    485                 490                 495

Cys Leu Val Phe Leu Lys Thr Trp Ala Arg Glu Gly Thr Asp Arg Leu
                    500                 505                 510

Ser Tyr Glu Asn Asp Trp Asn Ser Thr Ala Val Val Asn Asn Val Ala
                    515                 520                 525

Arg Arg Cys Pro Asn Thr Ile Val Val Thr His Ser Gly Gly Ile Asn
    530                 535                 540

Thr Met Pro Trp Ala Asp Asn Ala Asn Val Thr Ala Ile Leu Ala Ala
    545                 550                 555                 560

His Tyr Pro Gly Gln Glu Asn Gly Asn Ser Ile Met Asp Ile Leu Tyr
                    565                 570                 575

Gly Asp Val Asn Pro Ser Gly Arg Leu Pro Tyr Thr Ile Pro Lys Leu
                    580                 585                 590

Ala Thr Asp Tyr Asp Phe Pro Val Val Asn Ile Thr Asn Glu Ala Gln
                    595                 600                 605

Asp Pro Tyr Val Trp Gln Ala Asp Phe Thr Glu Gly Leu Leu Ile Asp
                610                 615                 620

Tyr Arg His Phe Asp Ala Arg Asn Ile Thr Pro Leu Tyr Glu Phe Gly
    625                 630                 635                 640

Tyr Gly Leu Ser Tyr Thr Thr Phe Glu Ile Glu Gly Val Ala Asn Leu
                    645                 650                 655
```

```
Val Ala Lys Ser Ala Lys Leu Ser Ala Phe Pro Ala Ser Thr Asp Ile
            660                 665                 670

Ser His Pro Gly Gly Asn Pro Asp Leu Trp Glu Val Val Ser Val
        675                 680                 685

Thr Ala Ala Val Lys Asn Thr Gly Ser Val Ser Gly Ser Gln Val Val
690                 695                 700

Gln Leu Tyr Ile Ser Leu Pro Ala Asp Gly Ile Pro Glu Asn Ser Pro
705                 710                 715                 720

Met Gln Val Leu Arg Gly Phe Glu Lys Val Asp Leu Gln Pro Gly Gln
                725                 730                 735

Ser Lys Ser Val Glu Phe Ser Ile Met Arg Arg Asp Leu Ser Phe Trp
                740                 745                 750

Asn Thr Thr Ala Gln Asp Trp Glu Ile Pro Asn Gly Gln Ile Glu Phe
            755                 760                 765

Arg Val Gly Phe Ser Ser Arg Asp Ile Lys Ser Ile Val Ser Arg Ser
770                 775                 780

Phe Leu
785

<210> SEQ ID NO 10
<211> LENGTH: 747
<212> TYPE: PRT
<213> ORGANISM: Kuraishia capsulata

<400> SEQUENCE: 10

Lys Asn Ile Ser Lys Ala Glu Met Glu Asn Leu Glu His Trp Trp Ser
1               5                   10                  15

Tyr Gly Arg Ser Asp Pro Val Tyr Pro Ser Pro Glu Ile Ser Gly Leu
            20                  25                  30

Gly Asp Trp Gln Phe Ala Tyr Gln Arg Ala Arg Glu Ile Val Ala Leu
        35                  40                  45

Met Thr Asn Glu Glu Lys Thr Asn Leu Thr Phe Gly Ser Ser Gly Asp
    50                  55                  60

Thr Gly Cys Ser Gly Met Ile Ser Asp Val Pro Asp Val Asp Phe Pro
65                  70                  75                  80

Gly Leu Cys Leu Gln Asp Ala Gly Asn Gly Val Arg Gly Thr Asp Met
                85                  90                  95

Val Asn Ala Tyr Ala Ser Gly Leu His Val Gly Ala Ser Trp Asn Arg
            100                 105                 110

Gln Leu Ala Tyr Asp Arg Ala Val Tyr Met Gly Ala Glu Phe Arg His
        115                 120                 125

Lys Gly Val Asn Val Leu Leu Gly Pro Val Val Gly Pro Ile Gly Arg
    130                 135                 140

Val Ala Thr Gly Gly Arg Asn Trp Glu Gly Phe Thr Asn Asp Pro Tyr
145                 150                 155                 160

Leu Ala Gly Ala Leu Val Tyr Glu Thr Thr Lys Gly Ile Gln Glu Asn
                165                 170                 175

Val Ile Ala Cys Thr Lys His Phe Ile Gly Asn Glu Gln Glu Thr Asn
            180                 185                 190

Arg Asn Pro Ser Gly Thr Tyr Asn Gln Ser Val Ser Ala Asn Ile Asp
        195                 200                 205

Asp Lys Thr Met His Glu Leu Tyr Leu Trp Pro Phe Gln Asp Ser Val
    210                 215                 220

Arg Ala Gly Leu Gly Ser Ile Met Gly Ser Tyr Asn Arg Val Asn Asn
```

```
             225                 230                 235                 240
Ser Tyr Ala Cys Lys Asn Ser Lys Val Leu Asn Gly Leu Leu Lys Ser
             245                 250                 255

Glu Leu Gly Phe Gln Gly Phe Val Val Ser Asp Trp Gly Gly Gln His
             260                 265                 270

Thr Gly Ile Ala Ser Ala Asn Ala Gly Leu Asp Met Ala Met Pro Ser
             275                 280                 285

Ser Thr Tyr Trp Glu Glu Gly Leu Ile Glu Ala Val Lys Asn Gly Thr
             290                 295                 300

Val Asp Gln Ser Arg Leu Asp Asp Met Ala Thr Arg Ile Ile Ala Ala
305                  310                 315                 320

Trp Tyr Lys Tyr Ala Arg Leu Asp Asp Pro Gly Phe Gly Met Pro Val
                 325                 330                 335

Ser Leu Ala Glu Asp His Glu Leu Val Asp Ala Arg Asp Pro Ala Ala
             340                 345                 350

Ala Ser Thr Ile Phe Gln Gly Ala Val Glu Gly His Val Leu Val Lys
             355                 360                 365

Asn Glu Asn Ala Leu Pro Leu Lys Lys Pro Lys Tyr Ile Ser Leu Phe
370                  375                 380

Gly Tyr Asp Gly Val Ser Thr Asp Val Asn Thr Val Gly Gly Gly Phe
385                  390                 395                 400

Ser Phe Phe Ser Phe Asp Val Lys Ala Ile Glu Asn Lys Thr Leu Ile
                 405                 410                 415

Ser Gly Gly Gly Ser Gly Thr Asn Thr Pro Ser Tyr Val Asp Ala Pro
                 420                 425                 430

Phe Asn Ala Phe Val Ala Lys Ala Arg Glu Asp Asn Thr Phe Leu Ser
             435                 440                 445

Trp Asp Phe Thr Ser Ala Glu Pro Val Ala Asn Pro Ala Ser Asp Ala
450                  455                 460

Cys Ile Asp Phe Ile Asn Ala Ala Ala Ser Glu Gly Tyr Asp Arg Pro
465                  470                 475                 480

Asn Leu Ala Asp Lys Tyr Ser Asp Lys Leu Val Glu Ala Val Ala Ser
                 485                 490                 495

Gln Cys Ser Asn Thr Ile Val Val Ile His Asn Ala Gly Ile Arg Leu
             500                 505                 510

Val Asp Asn Trp Ile Glu His Glu Asn Val Thr Gly Val Ile Leu Ala
             515                 520                 525

His Leu Pro Gly Gln Asp Thr Gly Thr Ser Leu Ile Glu Val Leu Tyr
             530                 535                 540

Gly Asn Gln Ser Pro Ser Gly Arg Leu Pro Tyr Thr Val Ala Lys Lys
545                  550                 555                 560

Ala Ser Asp Tyr Gly Gly Leu Leu Trp Pro Thr Glu Pro Glu Gly Asp
                 565                 570                 575

Leu Asp Leu Tyr Phe Pro Gln Ser Asn Phe Thr Glu Gly Val Tyr Ile
             580                 585                 590

Asp Tyr Lys Tyr Phe Ile Gln Lys Asn Ile Thr Pro Arg Tyr Glu Phe
             595                 600                 605

Gly Tyr Gly Leu Thr Tyr Thr Thr Phe Asp Tyr Ser Glu Leu Glu Val
             610                 615                 620

Asp Ala Ile Thr Asn Gln Ser Tyr Leu Pro Pro Asp Cys Thr Ile Glu
625                  630                 635                 640

Glu Gly Gly Ala Lys Ser Leu Trp Asp Ile Val Ala Thr Val Lys Phe
                 645                 650                 655
```

```
Thr Val Thr Asn Thr Gly Asp Val Ala Ala Glu Val Pro Gln Leu
            660                 665                 670

Tyr Val Gly Ile Pro Asn Gly Pro Pro Lys Val Leu Arg Gly Phe Asp
            675                 680                 685

Lys Lys Leu Ile His Pro Gly Gln Ser Glu Glu Phe Val Phe Glu Leu
            690                 695                 700

Thr Arg Arg Asp Leu Ser Thr Trp Asp Val Val Ala Gln Asn Trp Gly
705                 710                 715                 720

Leu Gln Ala Gly Thr Tyr Gln Phe Tyr Val Gly Arg Ser Val Phe Asp
                    725                 730                 735

Val Pro Leu Thr Ser Ala Leu Val Phe Thr Asn
            740                 745

<210> SEQ ID NO 11
<211> LENGTH: 740
<212> TYPE: PRT
<213> ORGANISM: Trichoderma reesei

<400> SEQUENCE: 11

Ala Lys Gly Val Ser Gln Ile Pro Ser Thr His Ser Ser Gln Ser Lys
1               5                   10                  15

Gly Asn Gly Pro Trp Ala His Ala Tyr Arg Arg Ala Glu Lys Leu Val
            20                  25                  30

Arg Gln Met Thr Leu Glu Glu Lys Ala Asn Ile Thr Arg Gly Phe Thr
        35                  40                  45

Gly Asp Asn Val Cys Ala Gly Asn Thr Gly Ser Val Pro Arg Leu Gly
    50                  55                  60

Trp Pro Gly Met Cys Val His Asp Ala Gly Asn Gly Val Arg Ala Thr
65              70                  75                  80

Asp Leu Val Asn Ser Tyr Pro Ser Gly Ile His Val Gly Ala Ser Trp
                85                  90                  95

Asp Arg Asn Leu Thr Tyr Glu Arg Gly Leu His Met Gly Gly Glu Phe
            100                 105                 110

Lys Ala Lys Gly Val Asn Val Pro Leu Gly Pro Asn Ala Gly Pro Leu
        115                 120                 125

Gly Arg Thr Pro Leu Gly Gly Arg Asn Trp Glu Gly Phe Ser Ile Asp
    130                 135                 140

Pro Tyr Leu Ser Gly Gln Leu Asn Ala Glu Thr Ile Thr Gly Met Gln
145                 150                 155                 160

Asp Ala Gly Val Ile Ala Asn Ile Lys His Phe Ile Ala Asn Glu Gln
                165                 170                 175

Glu Thr Leu Arg Arg Pro Tyr Phe Gly Val Glu Ala Val Ser Ala Asn
            180                 185                 190

Ile Asp Asp Arg Thr Leu His Glu Tyr Tyr Leu Trp Pro Phe Met Asp
        195                 200                 205

Ser Val His Ala Gly Val Gly Ser Val Met Cys Ser Tyr Asn Arg Ile
    210                 215                 220

Asn Asn Thr Tyr Gly Cys Met Asn Asp Lys Leu Met Asn Gly Ile Leu
225                 230                 235                 240

Lys Ala Glu Leu Gly Phe Gln Gly Phe Val Met Leu Asp Trp Asn Ala
                245                 250                 255

Gln His Asp Leu Gln Ser Ala Asn Ala Gly Leu Asp Met Val Met Pro
            260                 265                 270

Leu Gly Gly Ser Trp Gly Lys Asn Leu Thr Asp Ala Val Ala Asn Gly
```

```
            275                 280                 285
Thr Val Ser Glu Ser Arg Ile Thr Asp Met Ala Thr Arg Ile Ile Ala
290                 295                 300

Ala Trp Tyr Leu Val Gly Gln Asp Gly Asn Asn Phe Pro Val Pro Gly
305                 310                 315                 320

Ile Gly Leu Lys Gln Leu Thr Lys Pro His Glu Gln Val Asp Ala Arg
                325                 330                 335

Asp Pro Ala Ser Lys Pro Val Leu Leu Glu Gly Ala Ile Ala Gly His
                340                 345                 350

Val Leu Val Lys Asn Glu Asn Asn Ala Leu Pro Phe Asn Lys Lys Leu
                355                 360                 365

Thr Met Ile Ser Val Phe Gly Tyr Asp Ala Thr Ile Pro Arg Thr Lys
370                 375                 380

Asn Thr Asp Ile Leu Phe Gln Leu Gly Tyr Thr Ser Ser Pro Glu Met
385                 390                 395                 400

Ala Gln Ala Val Leu Gly Asn Glu Ala His Phe Asp Gln Ala Ala Lys
                405                 410                 415

Gly Gly Thr Ile Met Thr Gly Gly Arg Ala Gly Ala Asn Ala Pro Ser
                420                 425                 430

Tyr Ile Asp Asp Pro Leu Ala Ala Ile Gln Arg Arg Ala Arg Lys Asp
                435                 440                 445

Asp Thr Trp Val Asn Trp Asp Leu Asp Ser Phe Asn Pro Glu Val Asn
450                 455                 460

Ala Ala Ser Asp Ala Cys Leu Val Phe Ile Asn Ala Ile Ala Thr Glu
465                 470                 475                 480

Gly Trp Asp Arg Asp Gly Leu His Asp Phe Ser Asp Gly Leu Val
                485                 490                 495

Leu Asn Val Ala Ala Asn Cys Ser Asn Thr Ile Val Val His Ala
                500                 505                 510

Ala Gly Thr Arg Leu Val Asp Gln Trp Ile Glu His Pro Asn Val Thr
                515                 520                 525

Ala Ala Val Ile Ala His Leu Pro Gly Gln Asp Ser Gly Arg Ala Leu
                530                 535                 540

Val Lys Leu Leu Tyr Gly Glu Ala Asn Phe Ser Gly Lys Leu Pro Tyr
545                 550                 555                 560

Thr Ile Ala Lys Asn Glu Ser Asp Tyr Ser Val Tyr Thr Pro Cys Gln
                565                 570                 575

Arg Arg Ser Pro Glu Asp Thr Asp Pro Gln Cys Asp Phe Thr Glu Gly
                580                 585                 590

Val Tyr Leu Asp Tyr Arg Ala Phe Asp Ala Asn Asn Met Thr Pro Arg
                595                 600                 605

Phe Glu Phe Gly Tyr Gly Leu Ser Tyr Thr Ser Phe Asn Tyr Ser Ala
610                 615                 620

Leu Ser Ile Lys Lys Ala Lys Gly Leu Arg Gln Ser Arg Cys Thr Asp
625                 630                 635                 640

Asp Leu Trp Gln Ala Ala Gln Val Thr Ala Ser Ile Thr Asn Ser
                645                 650                 655

Gly Gly Met Ser Gly Ser Glu Val Ala Gln Leu Tyr Leu Ala Ile Pro
                660                 665                 670

Asn Ser Pro Pro Lys Gln Leu Arg Gly Phe Asn Lys Leu Leu Leu Arg
                675                 680                 685

Pro His Glu Ser Gly Thr Val His Phe Gly Leu Thr Lys Arg Asp Leu
                690                 695                 700
```

```
Ser Val Trp Asp Val Val Ser Gln Ser Trp Val Ile Gln Glu Gly Glu
705                 710                 715                 720

Tyr Lys Val Phe Val Gly Ala Ser Ser Arg Asp Ile Arg Leu Ser Gly
                725                 730                 735

Lys Leu His Ile
            740

<210> SEQ ID NO 12
<211> LENGTH: 818
<212> TYPE: PRT
<213> ORGANISM: Uromyces fabae

<400> SEQUENCE: 12

Ala Thr Thr Ser Pro Ser Glu Asn Gln Asn Gln Ser Tyr Asn Pro Gln
1               5                   10                  15

Ile Glu Gly Leu Thr Val Gln Pro Ser Thr Val Ala Asn Gly Leu Arg
                20                  25                  30

Ile Asn Ser Asn Ser Leu Ile Ser Asn Phe Asp Phe Glu Ile Ile Gln
            35                  40                  45

Pro Pro Pro Gly Tyr Glu Glu Trp Thr Ser Pro Val Val Leu Pro Ala
50                  55                  60

Pro Val Gln Ser Gly Leu Ser Pro Trp Ser Glu Ser Ile Val Arg Ala
65                  70                  75                  80

Arg Ala Phe Val Ala Gln Leu Thr Ile Glu Glu Lys Val Asn Leu Thr
                85                  90                  95

Thr Gly Ala Gly Thr Gln Gly Arg Cys Val Gly Glu Thr Gly Thr Val
            100                 105                 110

Pro Arg Leu Gly Phe Asn Gln Pro Ile Cys Leu Gln Asp Gly Pro Val
        115                 120                 125

Gly Ile Arg Tyr Thr Asp Phe Asn Ser Val Phe Pro Ala Ala Ile Asn
    130                 135                 140

Val Ala Ala Thr Phe Asp Lys Gln Leu Met Phe Lys Arg Ala Gln Ala
145                 150                 155                 160

Met Ala Glu Glu Phe Arg Gly Lys Gly Ala Asn Val Val Leu Ala Pro
                165                 170                 175

Met Thr Asn Leu Met Arg Thr Pro Gln Ala Gly Arg Ala Trp Glu Gly
            180                 185                 190

Tyr Gly Ser Asp Pro Tyr Leu Ser Gly Val Ala Thr Val Gln Ser Val
        195                 200                 205

Leu Gly Ile Gln Ser Thr Arg Ala Ser Ala Cys Val Lys His Tyr Ile
    210                 215                 220

Gly Asn Glu Gln Glu His Tyr Arg Gly Gly Ser Gly Ala Thr Ala Ser
225                 230                 235                 240

Ser Ser Asn Ile Asp Asp Arg Thr Leu Arg Glu Leu Tyr Glu Trp Pro
                245                 250                 255

Phe Ala Glu Ala Ile His Ala Gly Val Asp Tyr Ile Met Cys Ser Tyr
            260                 265                 270

Asn Arg Val Asn Gln Thr Tyr Ala Cys Glu Asn Ser Lys Leu Ile Asn
        275                 280                 285

Gly Ile Ala Lys Gly Glu His Lys Phe Gln Gly Val Met Val Thr Asp
    290                 295                 300

Trp Ala Ala Ala Glu Ser Gly Val Arg Thr Ala Leu Ala Gly Thr Asp
305                 310                 315                 320

Met Asn Met Pro Gly Phe Met Ala Tyr Gly Gln Pro Ser Glu Pro Asn
```

```
                    325                 330                 335
Pro Ser Thr Ala Asn Gly Ser Tyr Trp Gly Leu Arg Met Ile Glu Ala
            340                 345                 350
Val Lys Asn Gly Thr Val Pro Met Glu Arg Leu Asp Asp Met Val Thr
            355                 360                 365
Arg Val Ile Ser Thr Tyr Tyr Lys Gln Gly Gln Asp Lys Ser Asp Tyr
            370                 375                 380
Pro Lys Leu Asn Phe Met Ser Met Gly Gln Gly Thr Pro Ala Glu Gln
385                 390                 395                 400
Ala Val Ser Asn His His Val Asn Val Gln Lys Asp His Tyr Leu Ile
                405                 410                 415
Ile Arg Gln Ile Ala Thr Ala Ser Thr Ile Leu Leu Lys Asn Val Asn
            420                 425                 430
His Thr Leu Pro Leu Lys Ser Pro Asp Lys Met Arg Ser Val Val Val
            435                 440                 445
Val Gly Ser Asp Ala Gly Asp Asn Pro Gln Gly Pro Asn Ser Cys Val
            450                 455                 460
Asp Arg Gly Cys Asn Arg Gly Ile Leu Ala Ile Gly Trp Gly Ser Gly
465                 470                 475                 480
Thr Ala Asn Phe Ala His Leu Thr Ala Pro Ala Thr Ser Ile Gln Asn
                485                 490                 495
Tyr Leu Leu Gln Ser Asn Pro Thr Ile Thr Tyr Arg Ser Ile Phe Asp
            500                 505                 510
Asp Tyr Ala Tyr Asp Glu Ile Ala Lys Ala Ala Ser Thr Ala Asp Val
            515                 520                 525
Ser Ile Val His Val Ser Ser Asp Ser Gly Glu Gly Tyr Leu Thr Val
            530                 535                 540
Glu Gly Asn Gln Gly Asp Arg Ser Asn Thr Ser Leu Trp Asn Lys Gly
545                 550                 555                 560
Asp Glu Leu Ile Leu Lys Ala Ala Glu Ala Cys Asn Asn Val Val Val
            565                 570                 575
Val Ile His Ser Val Gly Pro Val Asp Met Glu Ala Trp Ile Asn His
            580                 585                 590
Pro Asn Val Thr Ala Val Leu Leu Ala Gly Leu Pro Gly Gln Glu Ala
            595                 600                 605
Gly Ser Ala Glu Val Asp Val Leu Trp Gly Ser Thr Asn Pro Ser Gly
            610                 615                 620
Arg Leu Pro Tyr Thr Ile Ala Lys Lys Pro Ser Asp Tyr Pro Ala Glu
625                 630                 635                 640
Leu Leu Tyr Glu Ser Asn Met Thr Val Pro Gln Ile Asn Tyr Ser Glu
                645                 650                 655
Arg Leu Asn Ile Asp Tyr Arg His Phe Asp Thr Tyr Asn Ile Glu Pro
            660                 665                 670
Arg Phe Glu Phe Gly Phe Gly Leu Ser Tyr Thr Thr Phe Ala Trp Asn
            675                 680                 685
Ser Leu Lys Phe Ser Ser Ser Phe Gln Leu Gln Lys Thr Ser Pro Val
            690                 695                 700
Ile Val Pro Pro Asn Leu Asp Leu Tyr Gln Asp Val Ile Glu Phe Glu
705                 710                 715                 720
Phe Gln Val Thr Asn Ser Gly Pro Phe Asp Gly Ser Glu Val Ala Gln
                725                 730                 735
Leu Tyr Val Asp Phe Pro Asn Gln Val Asn Glu Pro Pro Lys Val Leu
            740                 745                 750
```

```
Arg Gly Phe Glu Arg Ala Tyr Ile Pro Ser Lys Gln Ser Lys Thr Ile
        755                 760                 765

Glu Ile Lys Leu Arg Val Lys Asp Leu Ser Phe Trp Asp Val Ile Thr
770                 775                 780

Gln Ser Trp Gln Ile Pro Asp Gly Lys Phe Asn Phe Met Ile Gly Ser
785                 790                 795                 800

Ser Ser Arg Lys Ile Ile Phe Thr Gln Glu Ile Ser Leu Gln His Ser
        805                 810                 815

His Met

<210> SEQ ID NO 13
<211> LENGTH: 715
<212> TYPE: PRT
<213> ORGANISM: Aspergillus terreus

<400> SEQUENCE: 13

Leu Thr Thr Trp Asp Ala Ala Tyr Glu Lys Ala Leu Ala Asp Leu Ala
1               5                   10                  15

Ser Leu Thr Gln Ser Glu Lys Val Gly Val Ser Gly Ile Thr Trp
        20                  25                  30

Glu Gly Gly Pro Cys Val Gly Asn Thr Tyr Ala Pro Glu Ser Ile Ala
        35                  40                  45

Tyr Pro Ser Leu Cys Leu Gln Asp Gly Pro Leu Gly Ile Arg Phe Ala
    50                  55                  60

Asn Pro Val Thr Ala Phe Pro Ala Gly Ile Asn Ala Gly Ala Thr Trp
65                  70                  75                  80

Asp Arg Glu Leu Leu Arg Ala Arg Gly Ala Ala Met Gly Glu Glu Ala
                85                  90                  95

Lys Gly Leu Gly Val His Val Gln Leu Ala Pro Val Ala Gly Ala Leu
            100                 105                 110

Gly Lys Ile Pro Ser Ala Gly Arg Asn Trp Glu Gly Phe Thr Ser Asp
        115                 120                 125

Pro Tyr Leu Ser Gly Ile Ala Met Ala Glu Thr Ile His Gly Met Gln
    130                 135                 140

Gly Ser Gly Val Gln Ala Cys Ala Lys His Tyr Ile Leu Asn Glu Gln
145                 150                 155                 160

Glu His Ser Arg Glu Thr Ile Ser Ser Asn Val Asp Asp Arg Thr Met
                165                 170                 175

His Glu Val Tyr Leu Trp Pro Phe Tyr Asp Ala Val Lys Ala Asn Val
            180                 185                 190

Ala Ser Val Met Cys Ser Tyr Asn Lys Ile Asn Gly Thr Trp Ala Cys
        195                 200                 205

Glu Asn Glu Gly Ile Leu Asp Thr Leu Leu Lys Gln Glu Leu Gly Phe
    210                 215                 220

Arg Gly Tyr Val Met Ser Asp Trp Asn Ala Gln His Ser Thr Val Ala
225                 230                 235                 240

Ser Ala Asn Thr Gly Leu Asp Met Thr Met Pro Gly Ser Asp Phe Ser
                245                 250                 255

Gln Pro Pro Gly Ser Ile Tyr Trp Asn Glu Asn Leu Ala Glu Ala Val
            260                 265                 270

Ala Asn Gly Ser Val Pro Gln Ala Arg Val Asp Asp Met Val Thr Arg
        275                 280                 285

Ile Leu Ala Ala Trp Tyr Leu Leu Glu Gln Asp Gln Gly Tyr Pro Ala
    290                 295                 300
```

```
Val Ala Phe Asp Ser Arg Asn Gly Gly Lys Ala Ser Val Asp Val Thr
305                 310                 315                 320

Ala Asp His Ala Asp Ile Ala Arg Thr Val Ala Arg Asp Ser Ile Val
                325                 330                 335

Leu Leu Lys Asn Ser Asn Asn Thr Leu Pro Leu Arg Asn Pro Ser Ser
            340                 345                 350

Ile Ala Val Val Gly Ser Asp Ala Ile Val Asn Pro Asp Gly Pro Asn
                355                 360                 365

Ala Cys Thr Asp Arg Gly Cys Asn Val Gly Thr Leu Ala Gln Gly Trp
370                 375                 380

Gly Ser Gly Thr Ala Glu Phe Pro Tyr Leu Val Ala Pro Leu Asp Ala
385                 390                 395                 400

Ile Gln Glu Arg Ser Ser Gly Asn Gly Thr Lys Val Val Thr Ser Thr
                405                 410                 415

Thr Asp Asp Ala Thr Ala Gly Ala Asp Ala Ala Ser Ala Asp Ile
                420                 425                 430

Ala Ile Val Phe Ile Ser Ser Asp Ser Gly Glu Gly Tyr Ile Thr Val
            435                 440                 445

Glu Gly His Gln Gly Asp Arg Asn Asn Leu Asp Pro Trp His Gly Gly
    450                 455                 460

Asn Asp Leu Val Lys Ala Val Ala Val Asn Lys Lys Thr Ile Val
465                 470                 475                 480

Val Val His Ser Thr Gly Pro Val Val Leu Glu Thr Ile Leu Ala Gln
                485                 490                 495

Pro Asn Val Val Ala Val Val Trp Ala Gly Ile Pro Gly Gln Glu Ser
                500                 505                 510

Gly Asn Ala Leu Ala Asp Val Leu Tyr Gly Asp Val Ser Pro Ser Gly
            515                 520                 525

Lys Leu Pro Tyr Thr Ile Gly Lys Ser Glu Ala Asp Tyr Gly Thr Thr
        530                 535                 540

Trp Val Ala Asn Gly Ala Asp Asp Phe Pro Glu Gly Leu Phe Ile
545                 550                 555                 560

Asp Tyr Arg His Phe Asp Lys Asn Glu Ile Glu Pro Arg Tyr Glu Phe
                565                 570                 575

Gly Phe Gly Leu Ser Tyr Thr Arg Phe Asn Phe Ser Asn Leu Ala Ile
            580                 585                 590

Asn Ile Asp Ala Thr Ser Gly Pro Thr Ser Gly Ala Val Asp Val Gly
        595                 600                 605

Gly Ala Ala Asp Leu Tyr Asp Ser Val Gly Thr Ile Ser Ala Thr Val
        610                 615                 620

Thr Asn Val Gly Gly Val Ser Gly Ala Glu Val Ala Gln Leu Tyr Ile
625                 630                 635                 640

Gly Phe Pro Ser Ser Ala Pro Glu Thr Pro Pro Lys Gln Leu Arg Gly
                645                 650                 655

Phe Gln Lys Leu Pro Leu Ala Gly Gly Ala Asp Gly Val Ala Glu Phe
            660                 665                 670

Glu Leu Thr Arg Arg Asp Ile Ser Tyr Trp Asp Val Gly Gln Gln Lys
        675                 680                 685

Trp Val Val Pro Glu Gly Ser Phe Gln Val Tyr Val Gly Ala Ser Ser
        690                 695                 700

Arg Asp Ile Arg Leu Asp Gly Ser Phe Thr Val
705                 710                 715
```

<210> SEQ ID NO 14
<211> LENGTH: 706
<212> TYPE: PRT
<213> ORGANISM: Chaetomium globosum

<400> SEQUENCE: 14

```
Leu Glu Ala Ala Asp Trp Ala Ala Glu Ala Ser Ala Lys Thr Ala
1               5                   10                  15

Leu Ala Lys Met Ser Gln Gln Asp Lys Ile Ser Ile Val Thr Gly Ile
            20                  25                  30

Gly Trp Asp Lys Gly Pro Cys Val Gly Asn Thr Ala Ala Ile Asn Ser
                35                  40                  45

Ile Asn Tyr Pro Gln Leu Cys Leu Gln Asp Gly Pro Leu Gly Ile Arg
50                  55                  60

Phe Gly Thr Gly Ser Thr Ala Phe Thr Pro Gly Val Gln Ala Ala Ser
65                  70                  75                  80

Thr Trp Asp Thr Glu Leu Met Arg Gln Arg Gly Glu Tyr Leu Gly Ala
                85                  90                  95

Glu Ala Lys Gly Cys Gly Ile His Val Leu Leu Gly Pro Val Ala Gly
                100                 105                 110

Ala Leu Gly Lys Ile Pro His Gly Gly Arg Asn Trp Glu Gly Phe Gly
            115                 120                 125

Thr Asp Pro Tyr Leu Ala Gly Ile Ala Met Ala Glu Thr Ile Glu Gly
130                 135                 140

Leu Gln Ser Ala Gly Val Gln Ala Cys Ala Lys His Tyr Ile Val Asn
145                 150                 155                 160

Glu Gln Glu Leu Asn Arg Glu Thr Ile Ser Ser Asp Val Asp Asp Arg
                165                 170                 175

Thr Met His Glu Leu Tyr Leu Trp Pro Phe Ala Asp Ala Val His Ala
            180                 185                 190

Asn Val Ala Ser Val Met Cys Ser Tyr Asn Lys Ile Asn Gly Ser Trp
        195                 200                 205

Gly Cys Glu Asn Asp His Ala Gln Asn Gly Leu Leu Lys Lys Glu Leu
    210                 215                 220

Gly Phe Lys Gly Tyr Val Val Ser Asp Trp Asn Ala Gln His Thr Thr
225                 230                 235                 240

Asp Gly Ala Ala Asn Asn Gly Met Asp Met Thr Met Pro Gly Ser Asp
                245                 250                 255

Tyr Asn Gly Asn Asn Val Leu Trp Gly Pro Gln Leu Ser Asn Ala Val
            260                 265                 270

Asn Ser Asn Arg Val Ser Arg Asp Arg Leu Asp Asp Met Ala Lys Arg
        275                 280                 285

Ile Leu Thr Ser Trp Tyr Leu Leu Gly Gln Asn Ser Gly Tyr Pro Asn
    290                 295                 300

Ile Asn Ile Asn Ala Asn Val Gln Gly Asn His Lys Glu Asn Val Arg
305                 310                 315                 320

Ala Val Ala Arg Asp Gly Ile Val Leu Leu Lys Asn Asp Glu Gly Val
                325                 330                 335

Leu Pro Leu Lys Lys Pro Gly Lys Val Ala Leu Val Gly Ser Ala Ala
            340                 345                 350

Ser Val Asn Ser Ala Gly Pro Asn Ala Cys Val Asp Lys Gly Cys Asn
        355                 360                 365

Thr Gly Ala Leu Gly Met Gly Trp Gly Ser Gly Ser Val Asn Tyr Pro
    370                 375                 380
```

```
Tyr Phe Val Ala Pro Tyr Asp Ala Leu Lys Thr Arg Ala Gln Ala Asp
385                 390                 395                 400

Gly Thr Thr Leu Ser Leu His Asn Ser Asp Ser Thr Asn Gly Val Ser
            405                 410                 415

Gly Val Val Ser Gly Ala Asp Val Ala Ile Val Val Ile Thr Ala Asp
        420                 425                 430

Ser Gly Glu Gly Tyr Ile Thr Val Glu Gly His Ala Gly Asp Arg Asn
            435                 440                 445

His Leu Asp Pro Trp His Asp Gly Asn Ala Leu Val Lys Ala Val Ala
        450                 455                 460

Ala Ala Asn Lys Asn Thr Ile Val Val His Ser Thr Gly Pro Ile
465                 470                 475                 480

Ile Leu Glu Thr Ile Leu Ala Thr Glu Gly Val Lys Ala Val Val Trp
                485                 490                 495

Ala Gly Leu Pro Ser Gln Glu Asn Gly Asn Ala Leu Val Asp Val Leu
            500                 505                 510

Tyr Gly Leu Thr Ser Pro Ser Gly Lys Leu Val Tyr Ser Ile Ala Lys
            515                 520                 525

Arg Pro Glu Asp Tyr Gly Thr Ala Pro Ser Lys Gly Ser Asn Asp Lys
530                 535                 540

Phe Thr Glu Gly Leu Phe Val Asp Tyr Arg His Phe Asp Asn Ala Lys
545                 550                 555                 560

Ile Glu Pro Arg Tyr Glu Phe Gly Phe Gly Leu Ser Tyr Thr Glu Phe
                565                 570                 575

Thr Tyr Ala Asp Leu Ser Val Thr Ser Thr Val Thr Ala Gly Pro Ala
            580                 585                 590

Ser Gly Glu Thr Ile Pro Gly Gly Ala Ala Asp Leu Trp Glu Thr Val
            595                 600                 605

Ala Thr Val Thr Ala Ser Ile Thr Asn Ser Gly Glu Val Glu Gly Ala
610                 615                 620

Glu Val Ala Gln Leu Tyr Ile Thr Leu Pro Ser Ala Ala Pro Ser Thr
625                 630                 635                 640

Pro Pro Lys Gln Leu Arg Gly Phe Ala Lys Leu Lys Leu Glu Pro Gly
                645                 650                 655

Ala Ser Gly Val Ala Thr Phe Asn Leu Arg Arg Arg Asp Leu Ser Tyr
            660                 665                 670

Trp Asp Ala Gly Arg Gly Gln Trp Val Val Pro Ala Gly Glu Phe Thr
            675                 680                 685

Val Ser Val Gly Ala Ser Ser Arg Asp Val Arg Leu Thr Gly Ser Leu
        690                 695                 700

Thr Ala
705

<210> SEQ ID NO 15
<211> LENGTH: 856
<212> TYPE: PRT
<213> ORGANISM: Trichoderma reesei

<400> SEQUENCE: 15

Asn Pro Tyr Pro Pro His Ser Asn Gln Ala Tyr Ser Pro Pro Phe
1               5                   10                  15

Tyr Pro Ser Pro Trp Met Asp Pro Ser Ala Pro Gly Trp Glu Gln Ala
                20                  25                  30

Tyr Ala Gln Ala Lys Glu Phe Val Ser Gly Leu Thr Leu Leu Glu Lys
```

```
                35                  40                  45
Val Asn Leu Thr Thr Gly Val Gly Trp Met Gly Glu Lys Cys Val Gly
         50                  55                  60

Asn Val Gly Thr Val Pro Arg Leu Gly Met Arg Ser Leu Cys Met Gln
 65                  70                  75                  80

Asp Gly Pro Leu Gly Leu Arg Phe Asn Thr Tyr Asn Ser Ala Phe Ser
                 85                  90                  95

Val Gly Leu Thr Ala Ala Ser Trp Ser Arg His Leu Trp Val Asp
                100                 105                 110

Arg Gly Thr Ala Leu Gly Ser Glu Ala Lys Gly Lys Gly Val Asp Val
                115                 120                 125

Leu Leu Gly Pro Val Ala Gly Pro Leu Gly Arg Asn Pro Asn Gly Gly
        130                 135                 140

Arg Asn Val Glu Gly Phe Gly Ser Asp Pro Tyr Leu Ala Gly Leu Ala
145                 150                 155                 160

Leu Ala Asp Thr Val Thr Gly Ile Gln Asn Ala Gly Thr Ile Ala Cys
                165                 170                 175

Ala Lys His Phe Leu Leu Asn Glu Gln Glu His Phe Arg Gln Val Gly
                180                 185                 190

Glu Ala Asn Gly Tyr Gly Tyr Pro Ile Thr Glu Ala Leu Ser Ser Asn
            195                 200                 205

Val Asp Asp Lys Thr Ile His Glu Val Tyr Gly Trp Pro Phe Gln Asp
210                 215                 220

Ala Val Lys Ala Gly Val Gly Ser Phe Met Cys Ser Tyr Asn Gln Val
225                 230                 235                 240

Asn Asn Ser Tyr Ala Cys Gln Asn Ser Lys Leu Ile Asn Gly Leu Leu
                245                 250                 255

Lys Glu Glu Tyr Gly Phe Gln Gly Phe Val Met Ser Asp Trp Gln Ala
            260                 265                 270

Gln His Thr Gly Val Ala Ser Ala Val Ala Gly Leu Asp Met Thr Met
        275                 280                 285

Pro Gly Asp Thr Ala Phe Asn Thr Gly Ala Ser Tyr Phe Gly Ser Asn
290                 295                 300

Leu Thr Leu Ala Val Leu Asn Gly Thr Val Pro Glu Trp Arg Ile Asp
305                 310                 315                 320

Asp Met Val Met Arg Ile Met Ala Pro Phe Phe Lys Val Gly Lys Thr
                325                 330                 335

Val Asp Ser Leu Ile Asp Thr Asn Phe Asp Ser Trp Thr Asn Gly Glu
            340                 345                 350

Tyr Gly Tyr Val Gln Ala Ala Val Asn Glu Asn Trp Glu Lys Val Asn
        355                 360                 365

Tyr Gly Val Asp Val Arg Ala Asn His Ala Asn His Ile Arg Glu Val
    370                 375                 380

Gly Ala Lys Gly Thr Val Ile Phe Lys Asn Asn Gly Ile Leu Pro Leu
385                 390                 395                 400

Lys Lys Pro Lys Phe Leu Thr Val Ile Gly Glu Asp Ala Gly Gly Asn
                405                 410                 415

Pro Ala Gly Pro Asn Gly Cys Asp Arg Gly Cys Asp Asp Gly Thr
            420                 425                 430

Leu Ala Met Glu Trp Gly Ser Gly Thr Thr Asn Phe Pro Tyr Leu Val
        435                 440                 445

Thr Pro Asp Ala Ala Leu Gln Ser Gln Ala Leu Gln Asp Gly Thr Arg
450                 455                 460
```

```
Tyr Glu Ser Ile Leu Ser Asn Tyr Ala Ile Ser Gln Thr Gln Ala Leu
465                 470                 475                 480

Val Ser Gln Pro Asp Ala Ile Ala Ile Val Phe Ala Asn Ser Asp Ser
                485                 490                 495

Gly Glu Gly Tyr Ile Asn Val Asp Gly Asn Glu Gly Asp Arg Lys Asn
            500                 505                 510

Leu Thr Leu Trp Lys Asn Gly Asp Asp Leu Ile Lys Thr Val Ala Ala
        515                 520                 525

Val Asn Pro Lys Thr Ile Val Ile His Ser Thr Gly Pro Val Ile
530                 535                 540

Leu Lys Asp Tyr Ala Asn His Pro Asn Ile Ser Ala Ile Leu Trp Ala
545                 550                 555                 560

Gly Ala Pro Gly Gln Glu Ser Gly Asn Ser Leu Val Asp Ile Leu Tyr
                565                 570                 575

Gly Lys Gln Ser Pro Gly Arg Thr Pro Phe Thr Trp Gly Pro Ser Leu
            580                 585                 590

Glu Ser Tyr Gly Val Ser Val Met Thr Thr Pro Asn Asn Gly Asn Gly
        595                 600                 605

Ala Pro Gln Asp Asn Phe Asn Glu Gly Ala Phe Ile Asp Tyr Arg Tyr
610                 615                 620

Phe Asp Lys Val Ala Pro Gly Lys Pro Arg Ser Ser Asp Lys Ala Pro
625                 630                 635                 640

Thr Tyr Glu Phe Gly Phe Gly Leu Ser Trp Ser Thr Phe Lys Phe Ser
                645                 650                 655

Asn Leu His Ile Gln Lys Asn Asn Val Gly Pro Met Ser Pro Pro Asn
            660                 665                 670

Gly Lys Thr Ile Ala Ala Pro Ser Leu Gly Ser Phe Ser Lys Asn Leu
        675                 680                 685

Lys Asp Tyr Gly Phe Pro Lys Asn Val Arg Arg Ile Lys Glu Phe Ile
690                 695                 700

Tyr Pro Tyr Leu Ser Thr Thr Thr Ser Gly Lys Glu Ala Ser Gly Asp
705                 710                 715                 720

Ala His Tyr Gly Gln Thr Ala Lys Glu Phe Leu Pro Ala Gly Ala Leu
                725                 730                 735

Asp Gly Ser Pro Gln Pro Arg Ser Ala Ala Ser Gly Glu Pro Gly Gly
            740                 745                 750

Asn Arg Gln Leu Tyr Asp Ile Leu Tyr Thr Val Thr Ala Thr Ile Thr
        755                 760                 765

Asn Thr Gly Ser Val Met Asp Asp Ala Val Pro Gln Leu Tyr Leu Ser
770                 775                 780

His Gly Gly Pro Asn Glu Pro Pro Lys Val Leu Arg Gly Phe Asp Arg
785                 790                 795                 800

Ile Glu Arg Ile Ala Pro Gly Gln Ser Val Thr Phe Lys Ala Asp Leu
                805                 810                 815

Thr Arg Arg Asp Leu Ser Asn Trp Asp Thr Lys Lys Gln Gln Trp Val
            820                 825                 830

Ile Thr Asp Tyr Pro Lys Thr Val Tyr Val Gly Ser Ser Ser Arg Asp
        835                 840                 845

Leu Pro Leu Ser Ala Arg Leu Pro
850                 855
```

<210> SEQ ID NO 16
<211> LENGTH: 859

```
<212> TYPE: PRT
<213> ORGANISM: Penicillium brasilianum

<400> SEQUENCE: 16

Ile Ala Gln Pro Ile Gln Lys His Glu Pro Gly Phe Leu His Gly Pro
1               5                   10                  15

Gln Ala Ile Glu Ser Phe Ser Glu Pro Phe Tyr Pro Ser Pro Trp Met
            20                  25                  30

Asn Pro His Ala Glu Gly Trp Glu Ala Ala Tyr Gln Lys Ala Gln Asp
        35                  40                  45

Phe Val Ser Gln Leu Thr Ile Leu Glu Lys Ile Asn Leu Thr Thr Gly
    50                  55                  60

Val Gly Trp Glu Asn Gly Pro Cys Val Gly Asn Thr Gly Ser Ile Pro
65                  70                  75                  80

Arg Leu Gly Phe Lys Gly Phe Cys Thr Gln Asp Ser Pro Gln Gly Val
                85                  90                  95

Arg Phe Ala Asp Tyr Ser Ser Ala Phe Thr Ser Ser Gln Met Ala Ala
            100                 105                 110

Ala Thr Phe Asp Arg Ser Ile Leu Tyr Gln Arg Gly Gln Ala Met Ala
        115                 120                 125

Gln Glu His Lys Ala Lys Gly Ile Thr Ile Gln Leu Gly Pro Val Ala
130                 135                 140

Gly Pro Leu Gly Arg Ile Pro Glu Gly Gly Arg Asn Trp Glu Gly Phe
145                 150                 155                 160

Ser Pro Asp Pro Val Leu Thr Gly Ile Ala Met Ala Glu Thr Ile Lys
                165                 170                 175

Gly Met Gln Asp Thr Gly Val Ile Ala Cys Ala Lys His Tyr Ile Gly
            180                 185                 190

Asn Glu Gln Glu His Phe Arg Gln Val Gly Glu Ala Ala Gly His Gly
        195                 200                 205

Tyr Thr Ile Ser Asp Thr Ile Ser Ser Asn Ile Asp Asp Arg Ala Met
    210                 215                 220

His Glu Leu Tyr Leu Trp Pro Phe Ala Asp Ala Val Arg Ala Gly Val
225                 230                 235                 240

Gly Ser Phe Met Cys Ser Tyr Ser Gln Ile Asn Asn Ser Tyr Gly Cys
                245                 250                 255

Gln Asn Ser Gln Thr Leu Asn Lys Leu Leu Lys Ser Glu Leu Gly Phe
            260                 265                 270

Gln Gly Phe Val Met Ser Asp Trp Gly Ala His His Ser Gly Val Ser
        275                 280                 285

Ser Ala Leu Ala Gly Leu Asp Met Ser Met Pro Gly Asp Thr Glu Phe
    290                 295                 300

Asp Ser Gly Leu Ser Phe Trp Gly Ser Asn Leu Thr Ile Ala Ile Leu
305                 310                 315                 320

Asn Gly Thr Val Pro Glu Trp Arg Leu Asp Asp Met Ala Met Arg Ile
                325                 330                 335

Met Ala Ala Tyr Phe Lys Val Gly Leu Thr Ile Glu Asp Gln Pro Asp
            340                 345                 350

Val Asn Phe Asn Ala Trp Thr His Asp Thr Tyr Gly Tyr Lys Tyr Ala
        355                 360                 365

Tyr Ser Lys Glu Asp Tyr Glu Gln Val Asn Trp His Val Asp Val Arg
    370                 375                 380

Ser Asp His Asn Lys Leu Ile Arg Glu Thr Ala Ala Lys Gly Thr Val
385                 390                 395                 400
```

-continued

```
Leu Leu Lys Asn Asn Phe His Ala Leu Pro Leu Lys Gln Pro Arg Phe
            405                 410                 415

Val Ala Val Val Gly Gln Asp Ala Gly Pro Asn Pro Lys Gly Pro Asn
        420                 425                 430

Gly Cys Ala Asp Arg Gly Cys Asp Gln Gly Thr Leu Ala Met Gly Trp
        435                 440                 445

Gly Ser Gly Ser Thr Glu Phe Pro Tyr Leu Val Thr Pro Asp Thr Ala
    450                 455                 460

Ile Gln Ser Lys Val Leu Glu Tyr Gly Gly Arg Tyr Glu Ser Ile Phe
465                 470                 475                 480

Asp Asn Tyr Asp Asp Asn Ala Ile Leu Ser Leu Val Ser Gln Pro Asp
                485                 490                 495

Ala Thr Cys Ile Val Phe Ala Asn Ala Asp Ser Gly Glu Gly Tyr Ile
            500                 505                 510

Thr Val Asp Asn Asn Trp Gly Asp Arg Asn Asn Leu Thr Leu Trp Gln
        515                 520                 525

Asn Ala Asp Gln Val Ile Ser Thr Val Ser Ser Arg Cys Asn Asn Thr
    530                 535                 540

Ile Val Val Leu His Ser Val Gly Pro Val Leu Leu Asn Gly Ile Tyr
545                 550                 555                 560

Glu His Pro Asn Ile Thr Ala Ile Val Trp Ala Gly Met Pro Gly Glu
                565                 570                 575

Glu Ser Gly Asn Ala Leu Val Asp Ile Leu Trp Gly Asn Val Asn Pro
            580                 585                 590

Ala Gly Arg Thr Pro Phe Thr Trp Ala Lys Ser Arg Glu Asp Tyr Gly
        595                 600                 605

Thr Asp Ile Met Tyr Glu Pro Asn Asn Gly Gln Arg Ala Pro Gln Gln
    610                 615                 620

Asp Phe Thr Glu Ser Ile Tyr Leu Asp Tyr Arg His Phe Asp Lys Ala
625                 630                 635                 640

Gly Ile Glu Pro Ile Tyr Glu Phe Gly Phe Gly Leu Ser Tyr Thr Thr
                645                 650                 655

Phe Glu Tyr Ser Asp Leu Arg Val Val Lys Lys Tyr Val Gln Pro Tyr
            660                 665                 670

Ser Pro Thr Thr Gly Thr Gly Ala Gln Ala Pro Ser Ile Gly Gln Pro
        675                 680                 685

Pro Ser Gln Asn Leu Asp Thr Tyr Lys Phe Pro Ala Thr Tyr Lys Tyr
    690                 695                 700

Ile Lys Thr Phe Ile Tyr Pro Tyr Leu Asn Ser Thr Val Ser Leu Arg
705                 710                 715                 720

Ala Ala Ser Lys Asp Pro Glu Tyr Gly Arg Thr Asp Phe Ile Pro Pro
                725                 730                 735

His Ala Arg Asp Gly Ser Pro Gln Pro Leu Asn Pro Ala Gly Asp Pro
            740                 745                 750

Val Ala Ser Gly Gly Asn Asn Met Leu Tyr Asp Glu Leu Tyr Glu Val
        755                 760                 765

Thr Ala Gln Ile Lys Asn Thr Gly Asp Val Ala Gly Asp Glu Val Val
    770                 775                 780

Gln Leu Tyr Val Asp Leu Gly Gly Asp Asn Pro Pro Arg Gln Leu Arg
785                 790                 795                 800

Asn Phe Asp Arg Phe Tyr Leu Leu Pro Gly Gln Ser Ser Thr Phe Arg
                805                 810                 815
```

```
Ala Thr Leu Thr Arg Arg Asp Leu Ser Asn Trp Asp Ile Glu Ala Gln
            820                 825                 830

Asn Trp Arg Val Thr Glu Ser Pro Lys Arg Val Tyr Val Gly Arg Ser
        835                 840                 845

Ser Arg Asp Leu Pro Leu Ser Ser Gln Leu Glu
    850                 855

<210> SEQ ID NO 17
<211> LENGTH: 849
<212> TYPE: PRT
<213> ORGANISM: Periconia sp.

<400> SEQUENCE: 17

Gln Ala Pro Phe Pro Asn Gly Ser Ser Pro Leu Asn Asp Ile Thr Ser
1               5                   10                  15

Pro Pro Phe Tyr Pro Ser Pro Trp Met Asp Pro Ser Ala Ala Gly Trp
            20                  25                  30

Ala Glu Ala Tyr Thr Lys Ala Gln Ala Phe Val Arg Gln Leu Thr Leu
        35                  40                  45

Leu Glu Lys Val Asn Leu Thr Thr Gly Val Gly Trp Glu Gly Glu Ala
50                  55                  60

Cys Val Gly Asn Thr Gly Ser Ile Pro Arg Leu Gly Phe Pro Gly Phe
65                  70                  75                  80

Cys Thr Gln Asp Ser Pro Leu Gly Val Arg Phe Ala Asp Tyr Val Ser
                85                  90                  95

Ala Phe Thr Ala Gly Gly Thr Ile Ala Ala Ser Trp Asp Arg Ser Glu
            100                 105                 110

Phe Tyr Arg Arg Gly Tyr Gln Met Gly Val Glu His Arg Gly Lys Gly
        115                 120                 125

Val Asp Val Gln Leu Gly Pro Val Val Gly Pro Ile Gly Arg His Pro
    130                 135                 140

Lys Gly Gly Arg Asn Trp Glu Gly Phe Ser Pro Asp Pro Val Leu Ser
145                 150                 155                 160

Gly Ile Ala Val Ala Glu Thr Val Lys Gly Ile Gln Asp Ala Gly Val
                165                 170                 175

Ile Ala Cys Thr Lys His Phe Ile Leu Asn Glu Gln Glu His Phe Arg
            180                 185                 190

Gln Pro Gly Asn Val Gly Asp Phe Gly Phe Val Asp Ala Val Ser Ala
        195                 200                 205

Asn Leu Ala Asp Lys Thr Leu His Glu Leu Tyr Leu Trp Pro Phe Ala
    210                 215                 220

Asp Ala Val Arg Ala Gly Thr Gly Ser Ile Met Cys Ser Tyr Asn Lys
225                 230                 235                 240

Ala Asn Asn Ser Gln Val Cys Gln Asn Ser Tyr Leu Gln Asn Tyr Ile
                245                 250                 255

Leu Lys Gly Glu Leu Gly Phe Gln Gly Phe Thr Met Ser Asp Trp Asp
            260                 265                 270

Ala Gln His Ser Gly Val Ala Ser Thr Leu Ala Gly Leu Asp Met Asn
        275                 280                 285

Met Pro Gly Asp Thr Asp Phe Asp Ser Gly Phe Ser Phe Trp Gly Pro
    290                 295                 300

Asn Met Thr Leu Ser Ile Ile Asn Gly Thr Val Pro Glu Trp Arg Leu
305                 310                 315                 320

Asp Asp Ala Ala Thr Arg Ile Met Ala Ala Tyr Tyr Leu Val Gly Arg
                325                 330                 335
```

-continued

```
Asp Arg His Ala Val Pro Val Asn Phe Asn Ser Trp Ser Lys Asp Thr
            340                 345                 350

Tyr Gly Tyr Gln His Ala Tyr Ala Lys Val Gly Tyr Gly Leu Ile Asn
        355                 360                 365

Gln His Val Asp Val Arg Ala Asp His Phe Lys Ser Ile Arg Thr Ala
    370                 375                 380

Ala Ala Lys Ser Thr Val Leu Leu Lys Asn Asn Gly Val Leu Pro Leu
385                 390                 395                 400

Lys Gly Thr Glu Lys Tyr Thr Ala Val Phe Gly Asn Asp Ala Gly Glu
                405                 410                 415

Ala Gln Tyr Gly Pro Asn Gly Cys Ala Asp His Gly Cys Asp Asn Gly
            420                 425                 430

Thr Leu Ala Met Gly Trp Gly Ser Gly Thr Ala Asp Tyr Pro Tyr Leu
        435                 440                 445

Val Thr Pro Leu Glu Ala Ile Lys Arg Thr Val Gly Asp His Gly Gly
    450                 455                 460

Val Ile Ala Ser Val Thr Asp Asn Tyr Ala Phe Ser Gln Ile Met Ala
465                 470                 475                 480

Leu Ala Lys Gln Ala Thr His Ala Ile Val Phe Val Asn Ala Asp Ser
                485                 490                 495

Gly Glu Gly Tyr Ile Thr Val Asp Gly Asn Glu Gly Asp Arg Asn Asn
            500                 505                 510

Leu Thr Leu Trp Gln Asn Gly Glu Glu Leu Val Arg Asn Val Ser Gly
        515                 520                 525

Tyr Cys Asn Asn Thr Ile Val Val Ile His Ser Val Gly Pro Val Leu
    530                 535                 540

Val Asp Ser Phe Asn Asn Ser Pro Asn Val Ser Ala Ile Leu Trp Ala
545                 550                 555                 560

Gly Leu Pro Gly Gln Glu Ser Gly Asn Ala Ile Thr Asp Val Leu Tyr
                565                 570                 575

Gly Arg Val Asn Pro Gly Gly Lys Leu Pro Phe Thr Ile Gly Lys Ser
            580                 585                 590

Ala Glu Glu Tyr Gly Pro Asp Ile Ile Tyr Pro Thr Ala Gly His
        595                 600                 605

Gly Ser Pro Gln Ala Asn Phe Glu Glu Gly Val Phe Ile Asp Tyr Arg
    610                 615                 620

Ser Phe Asp Lys Lys Asn Ile Thr Pro Val Tyr Glu Phe Gly Phe Gly
625                 630                 635                 640

Leu Ser Tyr Thr Asn Phe Ser Tyr Ser Asn Leu Val Val Thr Arg Val
                645                 650                 655

Asn Ala Pro Ala Tyr Val Pro Thr Thr Gly Asn Thr Thr Ala Ala Pro
            660                 665                 670

Thr Leu Gly Asn Ser Ser Lys Asp Ala Ser Asp Tyr Gln Trp Pro Ala
        675                 680                 685

Asn Leu Thr Tyr Val Asn Lys Tyr Ile Tyr Pro Tyr Leu Asn Ser Thr
    690                 695                 700

Asp Leu Lys Glu Ala Ser Asn Asp Pro Glu Tyr Gly Ile Glu His Glu
705                 710                 715                 720

Tyr Pro Glu Gly Ala Thr Asp Gly Ser Pro Gln Pro Arg Ile Ala Ala
                725                 730                 735

Gly Gly Gly Pro Gly Gly Asn Pro Gln Leu Trp Asp Val Leu Tyr Lys
            740                 745                 750
```

```
Val Thr Ala Thr Val Thr Asn Asn Gly Ala Val Ala Gly Asp Glu Val
            755                 760                 765

Ala Gln Leu Tyr Val Ser Leu Gly Gly Pro Glu Asp Pro Val Val
        770                 775                 780

Leu Arg Asn Phe Asp Arg Leu Thr Ile Ala Pro Gly Gln Ser Val Glu
785                 790                 795                 800

Phe Thr Ala Asp Ile Thr Arg Arg Asp Val Ser Asn Trp Asp Thr Val
                805                 810                 815

Ser Gln Asn Trp Val Ile Ser Asn Ser Thr Lys Thr Val Tyr Val Gly
                820                 825                 830

Ala Ser Ser Arg Lys Leu Pro Leu Lys Ala Thr Leu Pro Ser Ser Ser
            835                 840                 845

Tyr

<210> SEQ ID NO 18
<211> LENGTH: 857
<212> TYPE: PRT
<213> ORGANISM: Phaeosphaeria avenaria

<400> SEQUENCE: 18

Gln Gln Tyr Pro Thr Ser Asn Thr Ser Ser Pro Ala Ala Asn Ser Ser
1               5                   10                  15

Ser Pro Leu Asp Asn Ala Val Ser Pro Pro Phe Tyr Pro Ser Pro Trp
            20                  25                  30

Ile Glu Gly Leu Gly Asp Trp Glu Ala Ala Tyr Gln Lys Ala Gln Ala
        35                  40                  45

Phe Val Ser Gln Leu Thr Leu Leu Glu Lys Val Asn Leu Thr Thr Gly
    50                  55                  60

Thr Gly Trp Gln Ser Asp His Cys Val Gly Asn Thr Gly Gly Val Pro
65                  70                  75                  80

Arg Leu Asn Phe Thr Gly Ile Cys Asn Gln Asp Ala Pro Leu Gly Val
                85                  90                  95

Arg Phe Ala Asp Tyr Val Ser Ala Phe Pro Ser Gly Gly Thr Ile Ala
                100                 105                 110

Ala Ala Trp Asp Arg Gly Glu Trp Tyr Leu Arg Gly Tyr Gln Met Gly
            115                 120                 125

Ser Glu His Arg Ser Lys Gly Val Asp Val Gln Leu Gly Pro Val Val
130                 135                 140

Gly Pro Leu Gly Arg Asn Pro Lys Gly Gly Arg Asn Trp Glu Gly Phe
145                 150                 155                 160

Ser Pro Asp Pro Tyr Leu Ser Gly Ile Ala Ser Ala Glu Ser Val Arg
                165                 170                 175

Gly Ile Gln Asp Ala Gly Val Ile Ala Cys Thr Lys His Tyr Ile Met
                180                 185                 190

Asn Glu Gln Glu His Phe Arg Gln Pro Gly Asn Phe Glu Asp Gln Gly
            195                 200                 205

Phe Val Asp Ala Leu Ser Ser Asn Leu Asp Asp Lys Thr Leu His Glu
    210                 215                 220

Leu Tyr Leu Trp Pro Phe Ala Asp Ala Val Arg Ala Gly Thr Gly Ser
225                 230                 235                 240

Ile Met Cys Ser Tyr Asn Lys Val Asn Asn Ser Gln Ala Cys Gln Asn
                245                 250                 255

Ser Tyr Leu Gln Asn Tyr Ile Leu Lys Gly Glu Leu Gly Phe Gln Gly
                260                 265                 270
```

-continued

Phe Ile Met Ser Asp Trp Asp Ala Gln His Ser Gly Val Ala Ser Thr
275                 280                 285

Phe Ala Gly Leu Asp Met Thr Met Pro Gly Asp Thr Asp Phe Asn Ser
290                 295                 300

Gly Lys Thr Phe Trp Gly Thr Asn Phe Thr Thr Ser Ile Leu Asn Gly
305                 310                 315                 320

Thr Val Pro Gln Trp Arg Leu Asp Asp Ala Val Thr Arg Ile Met Ala
            325                 330                 335

Ala Phe Tyr Tyr Val Gly Arg Asp Lys Ala Arg Ile Pro Val Asn Phe
        340                 345                 350

Asp Ser Trp Ser Arg Asp Thr Tyr Gly Phe Asp His Tyr Tyr Gly Lys
    355                 360                 365

Ala Gly Tyr Ser Gln Ile Asn Ser His Val Asp Val Arg Ala Asp His
370                 375                 380

Phe Arg Ser Ile Arg Arg Thr Ala Ala Met Ser Thr Val Leu Leu Lys
385                 390                 395                 400

Asn Glu Gly Ala Leu Pro Leu Thr Gly Ser Glu Lys Trp Thr Ala Val
            405                 410                 415

Phe Gly Asp Asp Ala Gly Glu Gly Gln Leu Gly Pro Asn Gly Phe Pro
        420                 425                 430

Asp His Gly Gly Asn Asn Gly Thr Leu Ala Met Gly Trp Gly Ser Gly
    435                 440                 445

Thr Ser Asp Tyr Pro Tyr Leu Val Thr Pro Leu Glu Ser Ile Lys Ala
450                 455                 460

Thr Val Ala Gln Asn Gly Gly Ile Val Thr Ser Val Thr Asp Asn Trp
465                 470                 475                 480

Ala Tyr Thr Gln Ile Gln Thr Leu Ala Lys Gln Ala Ser Val Ala Ile
            485                 490                 495

Val Phe Val Asn Ala Asp Ser Gly Glu Gly Tyr Ile Thr Val Asp Gly
        500                 505                 510

Asn Ala Gly Asp Arg Asn Asn Leu Thr Leu Trp Gln Asp Gly Asp Thr
    515                 520                 525

Leu Ile Lys Asn Val Ser Ser Leu Cys Asn Asn Thr Ile Val Val Ile
530                 535                 540

His Ser Val Gly Pro Val Leu Val Asn Ser Phe Tyr Asp Ser Glu Asn
545                 550                 555                 560

Val Thr Ala Ile Leu Trp Ala Gly Leu Pro Gly Gln Glu Ser Gly Asn
            565                 570                 575

Ala Ile Ala Asp Ile Leu Tyr Gly Arg His Asn Pro Gly Gly Lys Leu
        580                 585                 590

Pro Phe Thr Ile Gly Ser Asp Ala Ala Glu Tyr Gly Pro Asp Leu Ile
    595                 600                 605

Tyr Glu Pro Thr Asn Asn Ser Ser Pro Gln Asp Asn Phe Glu Glu
610                 615                 620

Gly Val Phe Ile Asp Tyr Arg Ala Phe Asp Lys Gln Asn Val Thr Pro
625                 630                 635                 640

Ile Tyr Glu Phe Gly Phe Gly Leu Ser Tyr Thr Lys Phe Ser Tyr Ser
            645                 650                 655

Asn Leu Thr Val Lys Lys Ala Asn Ala Gly Ala Tyr Thr Pro Ala Thr
        660                 665                 670

Gly Gln Ser Lys Ala Ala Pro Thr Leu Gly Asn Phe Ser Thr Asp Ala
    675                 680                 685

Ser Gln Tyr Gln Trp Pro Ser Asp Phe Thr Tyr Ile Asp Thr Phe Ile

```
                690               695               700
Tyr Pro Tyr Leu Asn Ser Thr Asp Leu Lys Thr Ala Ser Gln Asp Pro
705                 710               715                 720

Glu Tyr Gly Leu Asn Tyr Thr Trp Pro Ala Gly Ala Thr Asp Gly Thr
                725               730               735

Pro Gln Ala Arg Ile Pro Ala Gly Ala Pro Gly Gly Asn Pro Gln
            740               745               750

Leu Trp Asp Val Leu Phe Ser Val Glu Ala Thr Ile Thr Asn Asn Gly
        755               760               765

Thr Val Pro Gly Asp Glu Val Val Gln Leu Tyr Val Ser Leu Gly Asn
    770               775               780

Pro Asp Asp Pro Lys Ile Val Leu Arg Gly Phe Asp Arg Leu Ser Ile
785                 790               795                 800

Gln Pro Gly Lys Thr Ala Thr Phe His Ala Asp Ile Thr Arg Arg Asp
                805               810               815

Val Ser Asn Trp Asp Val Ala Ser Gln Asn Trp Val Ile Thr Ser Ala
            820               825               830

Pro Lys Thr Val Tyr Val Gly Ala Ser Ser Arg Lys Leu Pro Leu Thr
        835               840               845

Ala Thr Leu Asp Thr Ser Asp Phe Gln
    850               855

<210> SEQ ID NO 19
<211> LENGTH: 854
<212> TYPE: PRT
<213> ORGANISM: Aspergillus fumigatus

<400> SEQUENCE: 19

Gln Val Phe Asp Asn Ser His Gly Asn Gln Glu Leu Ala Phe Ser
1               5                  10                  15

Pro Pro Phe Tyr Pro Ser Pro Trp Ala Asp Gly Gln Gly Glu Trp Ala
                20                  25                  30

Asp Ala His Arg Arg Ala Val Glu Ile Val Ser Gln Met Thr Leu Ala
            35                  40                  45

Glu Lys Val Asn Leu Thr Thr Gly Thr Gly Trp Glu Met Asp Arg Cys
50                  55                  60

Val Gly Gln Thr Gly Ser Val Pro Arg Leu Gly Ile Asn Trp Gly Leu
65                  70                  75                  80

Cys Gly Gln Asp Ser Pro Leu Gly Ile Arg Phe Ser Asp Leu Asn Ser
                85                  90                  95

Ala Phe Pro Ala Gly Thr Asn Val Ala Ala Thr Trp Asp Lys Thr Leu
                100                 105                 110

Ala Tyr Leu Arg Gly Lys Ala Met Gly Glu Glu Phe Asn Asp Lys Gly
            115                 120                 125

Val Asp Ile Leu Leu Gly Pro Ala Ala Gly Pro Leu Gly Lys Tyr Pro
130                 135                 140

Asp Gly Gly Arg Ile Trp Glu Gly Phe Ser Pro Asp Pro Ala Leu Thr
145                 150                 155                 160

Gly Val Leu Phe Ala Glu Thr Ile Lys Gly Ile Gln Asp Ala Gly Val
                165                 170                 175

Ile Ala Thr Ala Lys His Tyr Ile Leu Asn Glu Gln Glu His Phe Arg
            180                 185                 190

Gln Val Gly Glu Ala Gln Gly Tyr Gly Tyr Asn Ile Thr Glu Thr Ile
        195                 200                 205
```

```
Ser Ser Asn Val Asp Asp Lys Thr Met His Glu Leu Tyr Leu Trp Pro
    210                 215                 220

Phe Ala Asp Ala Val Arg Ala Gly Val Gly Ala Val Met Cys Ser Tyr
225                 230                 235                 240

Asn Gln Ile Asn Asn Ser Tyr Gly Cys Gln Asn Ser Gln Thr Leu Asn
                245                 250                 255

Lys Leu Leu Lys Ala Glu Leu Gly Phe Gln Gly Phe Val Met Ser Asp
            260                 265                 270

Trp Ser Ala His His Ser Gly Val Gly Ala Ala Leu Ala Gly Leu Asp
        275                 280                 285

Met Ser Met Pro Gly Asp Ile Ser Phe Asp Asp Gly Leu Ser Phe Trp
    290                 295                 300

Gly Thr Asn Leu Thr Val Ser Val Leu Asn Gly Thr Val Pro Ala Trp
305                 310                 315                 320

Arg Val Asp Asp Met Ala Val Arg Ile Met Thr Ala Tyr Tyr Lys Val
                325                 330                 335

Gly Arg Asp Arg Leu Arg Ile Pro Pro Asn Phe Ser Ser Trp Thr Arg
            340                 345                 350

Asp Glu Tyr Gly Trp Glu His Ser Ala Val Ser Glu Gly Ala Trp Thr
        355                 360                 365

Lys Val Asn Asp Phe Val Asn Val Gln Arg Ser His Ser Gln Ile Ile
    370                 375                 380

Arg Glu Ile Gly Ala Ala Ser Thr Val Leu Leu Lys Asn Thr Gly Ala
385                 390                 395                 400

Leu Pro Leu Thr Gly Lys Glu Val Lys Val Gly Val Leu Gly Glu Asp
                405                 410                 415

Ala Gly Ser Asn Pro Trp Gly Ala Asn Gly Cys Pro Asp Arg Gly Cys
            420                 425                 430

Asp Asn Gly Thr Leu Ala Met Ala Trp Gly Ser Gly Thr Ala Asn Phe
        435                 440                 445

Pro Tyr Leu Val Thr Pro Glu Gln Ala Ile Gln Arg Glu Val Ile Ser
    450                 455                 460

Asn Gly Gly Asn Val Phe Ala Val Thr Asp Asn Gly Ala Leu Ser Gln
465                 470                 475                 480

Met Ala Asp Val Ala Ser Gln Ser Ser Val Ser Leu Val Phe Val Asn
                485                 490                 495

Ala Asp Ser Gly Glu Gly Phe Ile Ser Val Asp Gly Asn Glu Gly Asp
            500                 505                 510

Arg Lys Asn Leu Thr Leu Trp Lys Asn Gly Glu Ala Val Ile Asp Thr
        515                 520                 525

Val Val Ser His Cys Asn Asn Thr Ile Val Val Ile His Ser Val Gly
    530                 535                 540

Pro Val Leu Ile Asp Arg Trp Tyr Asp Asn Pro Asn Val Thr Ala Ile
545                 550                 555                 560

Ile Trp Ala Gly Leu Pro Gly Gln Glu Ser Gly Asn Ser Leu Val Asp
                565                 570                 575

Val Leu Tyr Gly Arg Val Asn Pro Ser Ala Lys Thr Pro Phe Thr Trp
            580                 585                 590

Gly Lys Thr Arg Glu Ser Tyr Gly Ala Pro Leu Leu Thr Glu Pro Asn
        595                 600                 605

Asn Gly Asn Gly Ala Pro Gln Asp Asp Phe Asn Glu Gly Val Phe Ile
    610                 615                 620

Asp Tyr Arg His Phe Asp Lys Arg Asn Glu Thr Pro Ile Tyr Glu Phe
```

```
              625                 630                 635                 640
      Gly His Gly Leu Ser Tyr Thr Thr Phe Gly Tyr Ser His Leu Arg Val
                          645                 650                 655

Gln Ala Leu Asn Ser Ser Ser Ala Tyr Val Pro Thr Ser Gly Glu
                      660                 665                 670

Thr Lys Pro Ala Pro Thr Tyr Gly Glu Ile Gly Ser Ala Ala Asp Tyr
                          675                 680                 685

Leu Tyr Pro Glu Gly Leu Lys Arg Ile Thr Lys Phe Ile Tyr Pro Trp
                      690                 695                 700

Leu Asn Ser Thr Asp Leu Glu Asp Ser Asp Asp Pro Asn Tyr Gly
      705                 710                 715                 720

Trp Glu Asp Ser Glu Tyr Ile Pro Glu Gly Ala Arg Asp Gly Ser Pro
                          725                 730                 735

Gln Pro Leu Leu Lys Ala Gly Ala Pro Gly Gly Asn Pro Thr Leu
                      740                 745                 750

Tyr Gln Asp Leu Val Arg Val Ser Ala Thr Ile Thr Asn Thr Gly Asn
                      755                 760                 765

Val Ala Gly Tyr Glu Val Pro Gln Leu Tyr Val Ser Leu Gly Gly Pro
      770                 775                 780

Asn Glu Pro Arg Val Val Leu Arg Lys Phe Asp Arg Ile Phe Leu Ala
      785                 790                 795                 800

Pro Gly Glu Gln Lys Val Trp Thr Thr Thr Leu Asn Arg Arg Asp Leu
                          805                 810                 815

Ala Asn Trp Asp Val Glu Ala Gln Asp Trp Val Ile Thr Lys Tyr Pro
                      820                 825                 830

Lys Lys Val His Val Gly Ser Ser Arg Lys Leu Pro Leu Arg Ala
                      835                 840                 845

Pro Leu Pro Arg Val Tyr
              850

<210> SEQ ID NO 20
<211> LENGTH: 842
<212> TYPE: PRT
<213> ORGANISM: Aspergillus oryzae

<400> SEQUENCE: 20

Lys Asp Asp Leu Ala Tyr Ser Pro Pro Phe Tyr Pro Ser Pro Trp Ala
      1               5                   10                  15

Asp Gly Gln Gly Glu Trp Ala Glu Val Tyr Lys Arg Ala Val Asp Ile
                      20                  25                  30

Val Ser Gln Met Thr Leu Thr Glu Lys Val Asn Leu Thr Thr Gly Thr
                  35                  40                  45

Gly Trp Gln Leu Glu Arg Cys Val Gly Gln Thr Gly Ser Val Pro Arg
          50                  55                  60

Leu Asn Ile Pro Ser Leu Cys Leu Gln Asp Ser Pro Leu Gly Ile Arg
      65                  70                  75                  80

Phe Ser Asp Tyr Asn Ser Ala Phe Pro Ala Gly Val Asn Val Ala Ala
                          85                  90                  95

Thr Trp Asp Lys Thr Leu Ala Tyr Leu Arg Gly Gln Ala Met Gly Glu
                      100                 105                 110

Glu Phe Ser Asp Lys Gly Ile Asp Val Gln Leu Gly Pro Ala Ala Gly
                  115                 120                 125

Pro Leu Gly Ala His Pro Asp Gly Gly Arg Asn Trp Glu Gly Phe Ser
          130                 135                 140
```

```
Pro Asp Pro Ala Leu Thr Gly Val Leu Phe Ala Glu Thr Ile Lys Gly
145                 150                 155                 160

Ile Gln Asp Ala Gly Val Ile Ala Thr Ala Lys His Tyr Ile Met Asn
            165                 170                 175

Glu Gln Glu His Phe Arg Gln Gln Pro Glu Ala Ala Gly Tyr Gly Phe
        180                 185                 190

Asn Val Ser Asp Ser Leu Ser Ser Asn Val Asp Asp Lys Thr Met His
    195                 200                 205

Glu Leu Tyr Leu Trp Pro Phe Ala Asp Ala Val Arg Ala Gly Val Gly
210                 215                 220

Ala Val Met Cys Ser Tyr Asn Gln Ile Asn Asn Ser Tyr Gly Cys Glu
225                 230                 235                 240

Asn Ser Glu Thr Leu Asn Lys Leu Leu Lys Ala Glu Leu Gly Phe Gln
                245                 250                 255

Gly Phe Val Met Ser Asp Trp Thr Ala His His Ser Gly Val Gly Ala
            260                 265                 270

Ala Leu Ala Gly Leu Asp Met Ser Met Pro Gly Asp Val Thr Phe Asp
            275                 280                 285

Ser Gly Thr Ser Phe Trp Gly Ala Asn Leu Thr Val Gly Val Leu Asn
    290                 295                 300

Gly Thr Ile Pro Gln Trp Arg Val Asp Asp Met Ala Val Arg Ile Met
305                 310                 315                 320

Ala Ala Tyr Tyr Lys Val Gly Arg Asp Thr Lys Tyr Thr Pro Pro Asn
                325                 330                 335

Phe Ser Trp Thr Arg Asp Glu Tyr Gly Phe Ala His Asn His Val
            340                 345                 350

Ser Glu Gly Ala Tyr Glu Arg Val Asn Glu Phe Val Asp Val Gln Arg
    355                 360                 365

Asp His Ala Asp Leu Ile Arg Arg Ile Gly Ala Gln Ser Thr Val Leu
    370                 375                 380

Leu Lys Asn Lys Gly Ala Leu Pro Leu Ser Arg Lys Glu Lys Leu Val
385                 390                 395                 400

Ala Leu Leu Gly Glu Asp Ala Gly Ser Asn Ser Trp Gly Ala Asn Gly
            405                 410                 415

Cys Asp Asp Arg Gly Cys Asp Asn Gly Thr Leu Ala Met Ala Trp Gly
            420                 425                 430

Ser Gly Thr Ala Asn Phe Pro Tyr Leu Val Thr Pro Glu Gln Ala Ile
            435                 440                 445

Gln Asn Glu Val Leu Gln Gly Arg Gly Asn Val Phe Ala Val Thr Asp
    450                 455                 460

Ser Trp Ala Leu Asp Lys Ile Ala Ala Ala Arg Gln Ala Ser Val
465                 470                 475                 480

Ser Leu Val Phe Val Asn Ser Asp Ser Gly Glu Gly Tyr Leu Ser Val
            485                 490                 495

Asp Gly Asn Glu Gly Asp Arg Asn Asn Ile Thr Leu Trp Lys Asn Gly
            500                 505                 510

Asp Asn Val Val Lys Thr Ala Ala Asn Cys Asn Asn Thr Val Val
    515                 520                 525

Ile Ile His Ser Val Gly Pro Val Leu Ile Asp Glu Trp Tyr Asp His
    530                 535                 540

Pro Asn Val Thr Gly Ile Leu Trp Ala Gly Leu Pro Gly Gln Glu Ser
545                 550                 555                 560

Gly Asn Ser Ile Ala Asp Val Leu Tyr Gly Arg Val Asn Pro Gly Ala
```

```
                565                 570                 575
Lys Ser Pro Phe Thr Trp Gly Lys Thr Arg Glu Ser Tyr Gly Ser Pro
            580                 585                 590

Leu Val Lys Asp Ala Asn Asn Gly Asn Gly Ala Pro Gln Ser Asp Phe
            595                 600                 605

Thr Gln Gly Val Phe Ile Asp Tyr Arg His Phe Asp Lys Phe Asn Glu
            610                 615                 620

Thr Pro Ile Tyr Glu Phe Gly Tyr Gly Leu Ser Tyr Thr Thr Phe Glu
625                 630                 635                 640

Leu Ser Asp Leu His Val Gln Pro Leu Asn Ala Ser Arg Tyr Thr Pro
                645                 650                 655

Thr Ser Gly Met Thr Glu Ala Ala Lys Asn Phe Gly Glu Ile Gly Asp
            660                 665                 670

Ala Ser Glu Tyr Val Tyr Pro Glu Gly Leu Glu Arg Ile His Glu Phe
            675                 680                 685

Ile Tyr Pro Trp Ile Asn Ser Thr Asp Leu Lys Ala Ser Ser Asp Asp
            690                 695                 700

Ser Asn Tyr Gly Trp Glu Asp Ser Lys Tyr Ile Pro Glu Gly Ala Thr
705                 710                 715                 720

Asp Gly Ser Ala Gln Pro Arg Leu Pro Ala Ser Gly Gly Ala Gly Gly
                725                 730                 735

Asn Pro Gly Leu Tyr Glu Asp Leu Phe Arg Val Ser Val Lys Val Lys
            740                 745                 750

Asn Thr Gly Asn Val Ala Gly Asp Glu Val Pro Gln Leu Tyr Val Ser
            755                 760                 765

Leu Gly Gly Pro Asn Glu Pro Lys Val Val Leu Arg Lys Phe Glu Arg
            770                 775                 780

Ile His Leu Ala Pro Ser Gln Glu Ala Val Trp Thr Thr Thr Leu Thr
785                 790                 795                 800

Arg Arg Asp Leu Ala Asn Trp Asp Val Ser Ala Gln Asp Trp Thr Val
                805                 810                 815

Thr Pro Tyr Pro Lys Thr Ile Tyr Val Gly Asn Ser Ser Arg Lys Leu
            820                 825                 830

Pro Leu Gln Ala Ser Leu Pro Lys Ala Gln
            835                 840

<210> SEQ ID NO 21
<211> LENGTH: 841
<212> TYPE: PRT
<213> ORGANISM: Aspergillus aculeatus

<400> SEQUENCE: 21

Asp Glu Leu Ala Phe Ser Pro Pro Phe Tyr Pro Ser Pro Trp Ala Asn
1               5                   10                  15

Gly Gln Gly Glu Trp Ala Glu Ala Tyr Gln Arg Ala Val Ala Ile Val
            20                  25                  30

Ser Gln Met Thr Leu Asp Glu Lys Val Asn Leu Thr Thr Gly Thr Gly
        35                  40                  45

Trp Glu Leu Glu Lys Cys Val Gly Gln Thr Gly Gly Val Pro Arg Leu
    50                  55                  60

Asn Ile Gly Gly Met Cys Leu Gln Asp Ser Pro Leu Gly Ile Arg Asp
65                  70                  75                  80

Ser Asp Tyr Asn Ser Ala Phe Pro Ala Gly Val Asn Val Ala Ala Thr
                85                  90                  95
```

-continued

```
Trp Asp Lys Asn Leu Ala Tyr Leu Arg Gly Gln Ala Met Gly Gln Glu
            100                 105                 110

Phe Ser Asp Lys Gly Ile Asp Val Gln Leu Gly Pro Ala Ala Gly Pro
        115                 120                 125

Leu Gly Arg Ser Pro Asp Gly Arg Asn Trp Glu Gly Phe Ser Pro
    130                 135                 140

Asp Pro Ala Leu Thr Gly Val Leu Phe Ala Glu Thr Ile Lys Gly Ile
145                 150                 155                 160

Gln Asp Ala Gly Val Val Ala Thr Ala Lys His Tyr Ile Leu Asn Glu
                165                 170                 175

Gln Glu His Phe Arg Gln Val Ala Glu Ala Ala Gly Tyr Gly Phe Asn
            180                 185                 190

Ile Ser Asp Thr Ile Ser Ser Asn Val Asp Asp Lys Thr Ile His Glu
        195                 200                 205

Met Tyr Leu Trp Pro Phe Ala Asp Ala Val Arg Ala Gly Val Gly Ala
    210                 215                 220

Ile Met Cys Ser Tyr Asn Gln Ile Asn Asn Ser Tyr Gly Cys Gln Asn
225                 230                 235                 240

Ser Tyr Thr Leu Asn Lys Leu Leu Lys Ala Glu Leu Gly Phe Gln Gly
                245                 250                 255

Phe Val Met Ser Asp Trp Gly Ala His His Ser Gly Val Gly Ser Ala
            260                 265                 270

Leu Ala Gly Leu Asp Met Ser Met Pro Gly Asp Ile Thr Phe Asp Ser
        275                 280                 285

Ala Thr Ser Phe Trp Gly Thr Asn Leu Thr Ile Ala Val Leu Asn Gly
    290                 295                 300

Thr Val Pro Gln Trp Arg Val Asp Asp Met Ala Val Arg Ile Met Ala
305                 310                 315                 320

Ala Tyr Tyr Lys Val Gly Arg Asp Arg Leu Tyr Gln Pro Pro Asn Phe
                325                 330                 335

Ser Ser Trp Thr Arg Asp Glu Tyr Gly Phe Lys Tyr Phe Tyr Pro Gln
            340                 345                 350

Glu Gly Pro Tyr Glu Lys Val Asn His Phe Val Asn Val Gln Arg Asn
        355                 360                 365

His Ser Glu Val Ile Arg Lys Leu Gly Ala Asp Ser Thr Val Leu Leu
    370                 375                 380

Lys Asn Asn Asn Ala Leu Pro Leu Thr Gly Lys Glu Arg Lys Val Ala
385                 390                 395                 400

Ile Leu Gly Glu Asp Ala Gly Ser Asn Ser Tyr Gly Ala Asn Gly Cys
                405                 410                 415

Ser Asp Arg Gly Cys Asp Asn Gly Thr Leu Ala Met Ala Trp Gly Ser
            420                 425                 430

Gly Thr Ala Glu Phe Pro Tyr Leu Val Thr Pro Glu Gln Ala Ile Gln
        435                 440                 445

Ala Glu Val Leu Lys His Lys Gly Ser Val Tyr Ala Ile Thr Asp Asn
    450                 455                 460

Trp Ala Leu Ser Gln Val Glu Thr Leu Ala Lys Gln Ala Ser Val Ser
465                 470                 475                 480

Leu Val Phe Val Asn Ser Asp Ala Gly Glu Gly Tyr Ile Ser Val Asp
                485                 490                 495

Gly Asn Glu Gly Asp Arg Asn Asn Leu Thr Leu Trp Lys Asn Gly Asp
            500                 505                 510

Asn Leu Ile Lys Ala Ala Ala Asn Cys Asn Asn Thr Ile Val Val
```

```
                   515                 520                 525
Ile His Ser Val Gly Pro Val Leu Val Asp Glu Trp Tyr Asp His Pro
    530                 535                 540

Asn Val Thr Ala Ile Leu Trp Ala Gly Leu Pro Gly Gln Glu Ser Gly
545                 550                 555                 560

Asn Ser Leu Ala Asp Val Leu Tyr Gly Arg Val Asn Pro Gly Ala Lys
                565                 570                 575

Ser Pro Phe Thr Trp Gly Lys Thr Arg Glu Ala Tyr Gly Asp Tyr Leu
            580                 585                 590

Val Arg Glu Leu Asn Asn Gly Asn Gly Ala Pro Gln Asp Asp Phe Ser
        595                 600                 605

Glu Gly Val Phe Ile Asp Tyr Arg Gly Phe Asp Lys Arg Asn Glu Thr
    610                 615                 620

Pro Ile Tyr Glu Phe Gly His Gly Leu Ser Tyr Thr Thr Phe Asn Tyr
625                 630                 635                 640

Ser Gly Leu His Ile Gln Val Leu Asn Ala Ser Ser Asn Ala Gln Val
                645                 650                 655

Ala Thr Glu Thr Gly Ala Ala Pro Thr Phe Gly Gln Val Gly Asn Ala
            660                 665                 670

Ser Asp Tyr Val Tyr Pro Glu Gly Leu Thr Arg Ile Ser Lys Phe Ile
        675                 680                 685

Tyr Pro Trp Leu Asn Ser Thr Asp Leu Lys Ala Ser Ser Gly Asp Pro
    690                 695                 700

Tyr Tyr Gly Val Asp Thr Ala Glu His Val Pro Glu Gly Ala Thr Asp
705                 710                 715                 720

Gly Ser Pro Gln Pro Val Leu Pro Ala Gly Gly Ser Gly Gly Asn
                725                 730                 735

Pro Arg Leu Tyr Asp Glu Leu Ile Arg Val Ser Val Thr Val Lys Asn
            740                 745                 750

Thr Gly Arg Val Ala Gly Asp Ala Val Pro Gln Leu Tyr Val Ser Leu
        755                 760                 765

Gly Gly Pro Asn Glu Pro Lys Val Val Leu Arg Lys Phe Asp Arg Leu
    770                 775                 780

Thr Leu Lys Pro Ser Glu Glu Thr Val Trp Thr Thr Thr Leu Thr Arg
785                 790                 795                 800

Arg Asp Leu Ser Asn Trp Asp Val Ala Ala Gln Asp Trp Val Ile Thr
                805                 810                 815

Ser Tyr Pro Lys Lys Val His Val Gly Ser Ser Ser Arg Gln Leu Pro
            820                 825                 830

Leu His Ala Ala Leu Pro Lys Val Gln
        835                 840

<210> SEQ ID NO 22
<211> LENGTH: 841
<212> TYPE: PRT
<213> ORGANISM: Aspergillus niger

<400> SEQUENCE: 22

Asp Glu Leu Ala Tyr Ser Pro Pro Tyr Tyr Pro Ser Pro Trp Ala Asn
1               5                   10                  15

Gly Gln Gly Asp Trp Ala Gln Ala Tyr Gln Arg Ala Val Asp Ile Val
                20                  25                  30

Ser Gln Met Thr Leu Asp Glu Lys Val Asn Leu Thr Thr Gly Thr Gly
            35                  40                  45
```

```
Trp Glu Leu Glu Leu Cys Val Gly Gln Thr Gly Gly Val Pro Arg Leu
     50                  55                  60

Gly Val Pro Gly Met Cys Leu Gln Asp Ser Pro Leu Gly Val Arg Asp
 65                  70                  75                  80

Ser Asp Tyr Asn Ser Ala Phe Pro Ala Gly Met Asn Val Ala Ala Thr
                 85                  90                  95

Trp Asp Lys Asn Leu Ala Tyr Leu Arg Gly Lys Ala Met Gly Gln Glu
            100                 105                 110

Phe Ser Asp Lys Gly Ala Asp Ile Gln Leu Gly Pro Ala Ala Gly Pro
            115                 120                 125

Leu Gly Arg Ser Pro Asp Gly Arg Asn Trp Glu Gly Phe Ser Pro
        130                 135                 140

Asp Pro Ala Leu Ser Gly Val Leu Phe Ala Glu Thr Ile Lys Gly Ile
145                 150                 155                 160

Gln Asp Ala Gly Val Val Ala Thr Ala Lys His Tyr Ile Ala Tyr Glu
                165                 170                 175

Gln Glu His Phe Arg Gln Ala Pro Glu Ala Gln Gly Phe Gly Phe Asn
            180                 185                 190

Ile Ser Glu Ser Gly Ser Ala Asn Leu Asp Asp Lys Thr Met His Glu
            195                 200                 205

Leu Tyr Leu Trp Pro Phe Ala Asp Ala Ile Arg Ala Gly Ala Gly Ala
210                 215                 220

Val Met Cys Ser Tyr Asn Gln Ile Asn Asn Ser Tyr Gly Cys Gln Asn
225                 230                 235                 240

Ser Tyr Thr Leu Asn Lys Leu Leu Lys Ala Glu Leu Gly Phe Gln Gly
                245                 250                 255

Phe Val Met Ser Asp Trp Ala Ala His His Ala Gly Val Ser Gly Ala
            260                 265                 270

Leu Ala Gly Leu Asp Met Ser Met Pro Gly Asp Val Asp Tyr Asp Ser
        275                 280                 285

Gly Thr Ser Tyr Trp Gly Thr Asn Leu Thr Ile Ser Val Leu Asn Gly
290                 295                 300

Thr Val Pro Gln Trp Arg Val Asp Asp Met Ala Val Arg Ile Met Ala
305                 310                 315                 320

Ala Tyr Tyr Lys Val Gly Arg Asp Arg Leu Trp Thr Pro Pro Asn Phe
                325                 330                 335

Ser Ser Trp Thr Arg Asp Glu Tyr Gly Tyr Lys Tyr Tyr Val Ser
            340                 345                 350

Glu Gly Pro Tyr Glu Lys Val Asn Gln Tyr Val Asn Val Gln Arg Asn
        355                 360                 365

His Ser Glu Leu Ile Arg Arg Ile Gly Ala Asp Ser Thr Val Leu Leu
370                 375                 380

Lys Asn Asp Gly Ala Leu Pro Leu Thr Gly Lys Glu Arg Leu Val Ala
385                 390                 395                 400

Leu Ile Gly Glu Asp Ala Gly Ser Asn Pro Tyr Gly Ala Asn Gly Cys
                405                 410                 415

Ser Asp Arg Gly Cys Asp Asn Gly Thr Leu Ala Met Gly Trp Gly Ser
            420                 425                 430

Gly Thr Ala Asn Phe Pro Tyr Leu Val Thr Pro Glu Gln Ala Ile Ser
        435                 440                 445

Asn Glu Val Leu Lys His Lys Asn Gly Val Phe Thr Ala Thr Asp Asn
450                 455                 460

Trp Ala Ile Asp Gln Ile Glu Ala Leu Ala Lys Thr Ala Ser Val Ser
```

```
              465                 470                 475                 480
Leu Val Phe Val Asn Ala Asp Ser Gly Glu Gly Tyr Ile Asn Val Asp
                    485                 490                 495
Gly Asn Leu Gly Asp Arg Arg Asn Leu Thr Leu Trp Arg Asn Gly Asp
                500                 505                 510
Asn Val Ile Lys Ala Ala Ala Ser Asn Cys Asn Asn Thr Ile Val Val
                515                 520                 525
Ile His Ser Val Gly Pro Val Leu Val Asn Glu Trp Tyr Asp Asn Pro
            530                 535                 540
Asn Val Thr Ala Ile Leu Trp Gly Gly Leu Pro Gly Gln Glu Ser Gly
545                 550                 555                 560
Asn Ser Leu Ala Asp Val Leu Tyr Gly Arg Val Asn Pro Gly Ala Lys
                    565                 570                 575
Ser Pro Phe Thr Trp Gly Lys Thr Arg Glu Ala Tyr Gln Asp Tyr Leu
                580                 585                 590
Val Thr Glu Pro Asn Asn Gly Asn Gly Ala Pro Gln Glu Asp Phe Val
                595                 600                 605
Glu Gly Val Phe Ile Asp Tyr Arg Gly Phe Asp Lys Arg Asn Glu Thr
            610                 615                 620
Pro Ile Tyr Glu Phe Gly Tyr Gly Leu Ser Tyr Thr Thr Phe Asn Tyr
625                 630                 635                 640
Ser Asn Leu Glu Val Gln Val Leu Ser Ala Pro Ala Tyr Glu Pro Ala
                    645                 650                 655
Ser Gly Glu Thr Glu Ala Ala Pro Thr Phe Gly Glu Val Gly Asn Ala
                660                 665                 670
Ser Asp Tyr Leu Tyr Pro Ser Gly Leu Gln Arg Ile Thr Lys Phe Ile
                675                 680                 685
Tyr Pro Trp Leu Asn Gly Thr Asp Leu Glu Ala Ser Ser Gly Asp Ala
            690                 695                 700
Ser Tyr Gly Gln Asp Ser Ser Asp Tyr Leu Pro Glu Gly Ala Thr Asp
705                 710                 715                 720
Gly Ser Ala Gln Pro Ile Leu Pro Ala Gly Gly Pro Gly Gly Asn
                    725                 730                 735
Pro Arg Leu Tyr Asp Glu Leu Ile Arg Val Ser Val Thr Ile Lys Asn
                740                 745                 750
Thr Gly Lys Val Ala Gly Asp Glu Val Pro Gln Leu Tyr Val Ser Leu
                755                 760                 765
Gly Gly Pro Asn Glu Pro Lys Ile Val Leu Arg Gln Phe Glu Arg Ile
            770                 775                 780
Thr Leu Gln Pro Ser Glu Glu Thr Lys Trp Ser Thr Thr Leu Thr Arg
785                 790                 795                 800
Arg Asp Leu Ala Asn Trp Asn Val Glu Lys Gln Asp Trp Glu Ile Thr
                    805                 810                 815
Ser Tyr Pro Lys Met Val Phe Val Gly Ser Ser Arg Lys Leu Pro
                820                 825                 830
Leu Arg Ala Ser Leu Pro Thr Val His
            835                 840
```

<210> SEQ ID NO 23
<211> LENGTH: 838
<212> TYPE: PRT
<213> ORGANISM: Talaromyces emersonii

<400> SEQUENCE: 23

-continued

Glu Asn Leu Ala Tyr Ser Pro Pro Phe Tyr Pro Ser Pro Trp Ala Asn
1               5                   10                  15

Gly Gln Gly Asp Trp Ala Glu Ala Tyr Gln Lys Ala Val Gln Phe Val
        20                  25                  30

Ser Gln Leu Thr Leu Ala Glu Lys Val Asn Leu Thr Thr Gly Thr Gly
        35                  40                  45

Trp Glu Gln Asp Arg Cys Val Gly Gln Val Gly Ser Ile Pro Arg Leu
50                  55                  60

Gly Phe Pro Gly Leu Cys Met Gln Asp Ser Pro Leu Gly Val Arg Asp
65                  70                  75                  80

Thr Asp Tyr Asn Ser Ala Phe Pro Ala Gly Val Asn Val Ala Ala Thr
                85                  90                  95

Trp Asp Arg Asn Leu Ala Tyr Arg Arg Gly Val Ala Met Gly Glu Glu
            100                 105                 110

His Arg Gly Lys Gly Val Asp Val Gln Leu Gly Pro Val Ala Gly Pro
            115                 120                 125

Leu Gly Arg Ser Pro Asp Ala Gly Arg Asn Trp Glu Gly Phe Ala Pro
        130                 135                 140

Asp Pro Val Leu Thr Gly Asn Met Met Ala Ser Thr Ile Gln Gly Ile
145                 150                 155                 160

Gln Asp Ala Gly Val Ile Ala Cys Ala Lys His Phe Ile Leu Tyr Glu
                165                 170                 175

Gln Glu His Phe Arg Gln Gly Ala Gln Asp Gly Tyr Asp Ile Ser Asp
            180                 185                 190

Ser Ile Ser Ala Asn Ala Asp Asp Lys Thr Met His Glu Leu Tyr Leu
        195                 200                 205

Trp Pro Phe Ala Asp Ala Val Arg Ala Gly Val Gly Ser Val Met Cys
210                 215                 220

Ser Tyr Asn Gln Val Asn Asn Ser Tyr Ala Cys Ser Asn Ser Tyr Thr
225                 230                 235                 240

Met Asn Lys Leu Leu Lys Ser Glu Leu Gly Phe Gln Gly Phe Val Met
                245                 250                 255

Thr Asp Trp Gly Gly His His Ser Gly Val Gly Ser Ala Leu Ala Gly
            260                 265                 270

Leu Asp Met Ser Met Pro Gly Asp Ile Ala Phe Asp Ser Gly Thr Ser
        275                 280                 285

Phe Trp Gly Thr Asn Leu Thr Val Ala Val Leu Asn Gly Ser Ile Pro
290                 295                 300

Glu Trp Arg Val Asp Asp Met Ala Val Arg Ile Met Ser Ala Tyr Tyr
305                 310                 315                 320

Lys Val Gly Arg Asp Arg Tyr Ser Val Pro Ile Asn Phe Asp Ser Trp
                325                 330                 335

Thr Leu Asp Thr Tyr Gly Pro Glu His Tyr Ala Val Gly Gln Gly Gln
            340                 345                 350

Thr Lys Ile Asn Glu His Val Asp Val Arg Gly Asn His Ala Glu Ile
        355                 360                 365

Ile His Glu Ile Gly Ala Ala Ser Ala Val Leu Leu Lys Asn Lys Gly
370                 375                 380

Gly Leu Pro Leu Thr Gly Thr Glu Arg Phe Val Gly Val Phe Gly Lys
385                 390                 395                 400

Asp Ala Gly Ser Asn Pro Trp Gly Val Asn Gly Cys Ser Asp Arg Gly
                405                 410                 415

Cys Asp Asn Gly Thr Leu Ala Met Gly Trp Gly Ser Gly Thr Ala Asn

-continued

```
                420                 425                 430
Phe Pro Tyr Leu Val Thr Pro Glu Gln Ala Ile Gln Arg Glu Val Leu
                435                 440                 445

Ser Arg Asn Gly Thr Phe Thr Gly Ile Thr Asp Asn Gly Ala Leu Ala
                450                 455                 460

Glu Met Ala Ala Ala Ser Gln Ala Asp Thr Cys Leu Val Phe Ala
465                 470                 475                 480

Asn Ala Asp Ser Gly Glu Gly Tyr Ile Thr Val Asp Gly Asn Glu Gly
                485                 490                 495

Asp Arg Lys Asn Leu Thr Leu Trp Gln Gly Ala Asp Gln Val Ile His
                500                 505                 510

Asn Val Ser Ala Asn Cys Asn Asn Thr Val Val Leu His Thr Val
                515                 520                 525

Gly Pro Val Leu Ile Asp Asp Trp Tyr Asp His Pro Asn Val Thr Ala
                530                 535                 540

Ile Leu Trp Ala Gly Leu Pro Gly Gln Glu Ser Gly Asn Ser Leu Val
545                 550                 555                 560

Asp Val Leu Tyr Gly Arg Val Asn Pro Gly Lys Thr Pro Phe Thr Trp
                565                 570                 575

Gly Arg Ala Arg Asp Asp Tyr Gly Ala Pro Leu Ile Val Lys Pro Asn
                580                 585                 590

Asn Gly Lys Gly Ala Pro Gln Gln Asp Phe Thr Glu Gly Ile Phe Ile
                595                 600                 605

Asp Tyr Arg Arg Phe Asp Lys Tyr Asn Ile Thr Pro Ile Tyr Glu Phe
                610                 615                 620

Gly Phe Gly Leu Ser Tyr Thr Thr Phe Glu Phe Ser Gln Leu Asn Val
625                 630                 635                 640

Gln Pro Ile Asn Ala Pro Pro Tyr Thr Pro Ala Ser Gly Phe Thr Lys
                645                 650                 655

Ala Ala Gln Ser Phe Gly Gln Pro Ser Asn Ala Ser Asp Asn Leu Tyr
                660                 665                 670

Pro Ser Asp Ile Glu Arg Val Pro Leu Tyr Ile Tyr Pro Trp Leu Asn
                675                 680                 685

Ser Thr Asp Leu Lys Ala Ser Ala Asn Asp Pro Asp Tyr Gly Leu Pro
                690                 695                 700

Thr Glu Lys Tyr Val Pro Pro Asn Ala Thr Asn Gly Asp Pro Gln Pro
705                 710                 715                 720

Ile Asp Pro Ala Gly Gly Ala Pro Gly Gly Asn Pro Ser Leu Tyr Glu
                725                 730                 735

Pro Val Ala Arg Val Thr Thr Ile Ile Thr Asn Thr Gly Lys Val Thr
                740                 745                 750

Gly Asp Glu Val Pro Gln Leu Tyr Val Ser Leu Gly Gly Pro Asp Asp
                755                 760                 765

Ala Pro Lys Val Leu Arg Gly Phe Asp Arg Ile Thr Leu Ala Pro Gly
                770                 775                 780

Gln Gln Tyr Leu Trp Thr Thr Thr Leu Thr Arg Arg Asp Ile Ser Asn
785                 790                 795                 800

Trp Asp Pro Val Thr Gln Asn Trp Val Val Thr Asn Tyr Thr Lys Thr
                805                 810                 815

Ile Tyr Val Gly Asn Ser Ser Arg Asn Leu Pro Leu Gln Ala Pro Leu
                820                 825                 830

Lys Pro Tyr Pro Gly Ile
                835
```

<210> SEQ ID NO 24
<211> LENGTH: 824
<212> TYPE: PRT
<213> ORGANISM: Thermoascus aurentiacus

<400> SEQUENCE: 24

```
Lys Asp Asp Leu Ala Tyr Ser Pro Pro Phe Tyr Pro Ser Pro Trp Met
1               5                   10                  15

Asn Gly Asn Gly Glu Trp Ala Glu Ala Tyr Arg Arg Ala Val Asp Phe
            20                  25                  30

Val Ser Gln Leu Thr Leu Ala Glu Lys Val Asn Leu Thr Thr Gly Val
        35                  40                  45

Gly Trp Met Gln Glu Lys Cys Val Gly Glu Thr Gly Ser Ile Pro Arg
    50                  55                  60

Leu Gly Phe Arg Gly Leu Cys Leu Gln Asp Ser Pro Leu Gly Val Arg
65                  70                  75                  80

Phe Ala Asp Tyr Val Ser Ala Phe Pro Ala Gly Val Asn Val Ala Ala
                85                  90                  95

Thr Trp Asp Lys Asn Leu Ala Tyr Leu Arg Gly Lys Ala Met Gly Glu
            100                 105                 110

Glu His Arg Gly Lys Gly Val Asp Val Gln Leu Gly Pro Val Ala Gly
        115                 120                 125

Pro Leu Gly Arg His Pro Asp Gly Gly Arg Asn Trp Glu Gly Phe Ser
    130                 135                 140

Pro Asp Pro Val Leu Thr Gly Val Leu Met Ala Glu Thr Ile Lys Gly
145                 150                 155                 160

Ile Gln Asp Ala Gly Val Ile Ala Cys Ala Lys His Phe Ile Gly Asn
                165                 170                 175

Glu Met Glu His Phe Arg Gln Ala Gly Glu Ala Val Gly Tyr Gly Phe
            180                 185                 190

Asp Ile Thr Glu Ser Val Ser Ser Asn Ile Asp Asp Lys Thr Leu His
        195                 200                 205

Glu Leu Tyr Leu Trp Pro Phe Ala Asp Ala Val Arg Ala Gly Val Gly
    210                 215                 220

Ser Phe Met Cys Ser Tyr Asn Gln Val Asn Asn Ser Tyr Ser Cys Ser
225                 230                 235                 240

Asn Ser Tyr Leu Leu Asn Lys Leu Leu Lys Ser Glu Leu Asp Phe Gln
                245                 250                 255

Gly Phe Val Met Ser Asp Trp Gly Ala His His Ser Gly Val Gly Ala
            260                 265                 270

Ala Leu Ala Gly Leu Asp Met Ser Met Pro Gly Asp Thr Ala Phe Gly
        275                 280                 285

Thr Gly Lys Ser Phe Trp Gly Thr Asn Leu Thr Ile Ala Val Leu Asn
    290                 295                 300

Gly Thr Val Pro Glu Trp Arg Val Asp Asp Met Ala Val Arg Ile Met
305                 310                 315                 320

Ala Ala Phe Tyr Lys Val Gly Arg Asp Arg Tyr Gln Val Pro Val Asn
                325                 330                 335

Phe Asp Ser Trp Thr Lys Asp Glu Tyr Gly Tyr Glu His Ala Leu Val
            340                 345                 350

Gly Gln Asn Tyr Val Lys Val Asn Asp Lys Val Asp Val Arg Ala Asp
        355                 360                 365

His Ala Asp Ile Ile Arg Gln Ile Gly Ser Ala Ser Val Val Leu Leu
```

-continued

```
              370                 375                 380
Lys Asn Asp Gly Gly Leu Pro Leu Thr Gly Tyr Glu Lys Phe Thr Gly
385                 390                 395                 400

Val Phe Gly Glu Asp Ala Gly Ser Asn Arg Trp Gly Ala Asp Gly Cys
                405                 410                 415

Ser Asp Arg Gly Cys Asp Asn Gly Thr Leu Ala Met Gly Trp Gly Ser
            420                 425                 430

Gly Thr Ala Asp Phe Pro Tyr Leu Val Thr Pro Glu Gln Ala Ile Gln
        435                 440                 445

Asn Glu Ile Leu Ser Lys Gly Lys Gly Leu Asp Ser Val Ser Ile Val
450                 455                 460

Phe Val Asn Ala Asp Ser Gly Glu Gly Tyr Ile Asn Val Asp Gly Asn
465                 470                 475                 480

Glu Gly Asp Arg Lys Asn Leu Thr Leu Trp Lys Gly Gly Glu Glu Val
                485                 490                 495

Ile Lys Thr Val Ala Ala Asn Cys Asn Asn Thr Ile Val Val Met His
                500                 505                 510

Thr Val Gly Pro Val Leu Ile Asp Glu Trp Tyr Asp Asn Pro Asn Val
                515                 520                 525

Thr Ala Ile Val Trp Ala Gly Leu Pro Gly Gln Glu Ser Gly Asn Ser
530                 535                 540

Leu Val Asp Val Leu Tyr Gly Arg Val Ser Pro Gly Gly Lys Thr Pro
545                 550                 555                 560

Phe Thr Trp Gly Lys Thr Arg Glu Ser Tyr Gly Ala Pro Leu Leu Thr
                565                 570                 575

Lys Pro Asn Asn Gly Lys Gly Ala Pro Gln Asp Asp Phe Thr Glu Gly
                580                 585                 590

Val Phe Ile Asp Tyr Arg Arg Phe Asp Lys Tyr Asn Glu Thr Pro Ile
                595                 600                 605

Tyr Glu Phe Gly Phe Gly Leu Ser Tyr Thr Thr Phe Glu Tyr Ser Asn
            610                 615                 620

Ile Tyr Val Gln Pro Leu Asn Ala Arg Pro Tyr Thr Pro Ala Ser Gly
625                 630                 635                 640

Ser Thr Lys Ala Ala Pro Thr Phe Gly Asn Ile Ser Thr Asp Tyr Ala
                645                 650                 655

Asp Tyr Leu Tyr Pro Glu Asp Ile His Lys Val Pro Leu Tyr Ile Tyr
                660                 665                 670

Pro Trp Leu Asn Thr Thr Asp Pro Glu Glu Val Leu Arg Arg Ser Arg
                675                 680                 685

Leu Thr Glu Met Lys Ala Glu Asp Tyr Ile Pro Ser Gly Ala Thr Asp
690                 695                 700

Gly Ser Pro Gln Pro Ile Leu Pro Ala Gly Ala Pro Gly Gly Asn
705                 710                 715                 720

Pro Gly Leu Tyr Asp Glu Met Tyr Arg Val Ser Ala Ile Ile Thr Asn
                725                 730                 735

Thr Gly Asn Val Val Gly Asp Glu Val Pro Gln Leu Tyr Val Ser Leu
                740                 745                 750

Gly Gly Pro Asp Asp Pro Lys Val Val Leu Arg Asn Phe Asp Arg Ile
                755                 760                 765

Thr Leu His Pro Gly Gln Gln Thr Met Trp Thr Thr Thr Leu Thr Arg
                770                 775                 780

Arg Asp Ile Ser Asn Trp Asp Pro Ala Ser Gln Asn Trp Val Val Thr
785                 790                 795                 800
```

-continued

```
Lys Tyr Pro Lys Thr Val Tyr Ile Gly Ser Ser Arg Lys Leu His
                805                 810                 815

Leu Gln Ala Pro Leu Pro Pro Tyr
            820

<210> SEQ ID NO 25
<211> LENGTH: 825
<212> TYPE: PRT
<213> ORGANISM: Hansenula anomala

<400> SEQUENCE: 25

Met Leu Leu Pro Leu Tyr Gly Leu Ala Ser Phe Leu Val Leu Ser Gln
1               5                   10                  15

Ala Ala Leu Val Asn Thr Ser Ala Pro Gln Ala Ser Asn Asp Asp Pro
            20                  25                  30

Phe Asn His Ser Pro Ser Phe Tyr Pro Thr Pro Gln Gly Gly Arg Ile
        35                  40                  45

Asn Asp Gly Lys Trp Gln Ala Ala Phe Tyr Arg Ala Arg Glu Leu Val
    50                  55                  60

Asp Gln Met Ser Ile Ala Glu Lys Val Asn Leu Thr Thr Gly Val Gly
65                  70                  75                  80

Ser Ala Ser Gly Pro Cys Ser Gly Asn Thr Gly Ser Val Pro Arg Leu
                85                  90                  95

Asn Ile Ser Ser Ile Cys Val Gln Asp Gly Pro Leu Ser Val Arg Ala
            100                 105                 110

Ala Asp Leu Thr Asp Val Phe Pro Cys Gly Met Ala Ala Ser Ser Ser
        115                 120                 125

Phe Asn Lys Gln Leu Ile Tyr Asp Arg Ala Val Ala Ile Gly Ser Glu
130                 135                 140

Phe Lys Gly Lys Gly Ala Asp Ala Ile Leu Gly Pro Val Tyr Gly Pro
145                 150                 155                 160

Met Gly Val Lys Ala Ala Gly Gly Arg Gly Trp Glu Gly His Gly Pro
                165                 170                 175

Asp Pro Tyr Leu Glu Gly Val Ile Ala Tyr Leu Gln Thr Ile Gly Ile
            180                 185                 190

Gln Ser Gln Gly Val Val Ser Thr Ala Lys His Leu Ile Gly Asn Glu
        195                 200                 205

Gln Glu His Phe Arg Phe Ala Lys Lys Asp Lys His Ala Gly Lys Ile
    210                 215                 220

Asp Pro Gly Met Phe Asn Thr Ser Ser Leu Ser Ser Glu Ile Asp
225                 230                 235                 240

Asp Arg Ala Met His Glu Ile Tyr Leu Trp Pro Phe Ala Glu Ala Val
                245                 250                 255

Arg Gly Gly Val Ser Ser Ile Met Cys Ser Tyr Asn Lys Leu Asn Gly
            260                 265                 270

Ser His Ala Cys Gln Asn Ser Tyr Leu Leu Asn Tyr Leu Leu Lys Glu
        275                 280                 285

Glu Leu Gly Phe Gln Gly Phe Val Met Thr Asp Trp Gly Ala Leu Tyr
    290                 295                 300

Ser Gly Ile Asp Ala Ala Asn Ala Gly Leu Asp Met Asp Met Pro Cys
305                 310                 315                 320

Glu Ala Gln Tyr Phe Gly Gly Asn Leu Thr Thr Ala Val Leu Asn Gly
                325                 330                 335

Thr Leu Pro Gln Asp Arg Leu Asp Asp Met Ala Thr Arg Ile Leu Ser
```

-continued

```
                340                 345                 350
Ala Leu Ile Tyr Ser Gly Val His Asn Pro Asp Gly Pro Asn Tyr Asn
            355                 360                 365

Ala Gln Thr Phe Leu Thr Glu Gly His Glu Tyr Phe Lys Gln Gln Glu
            370                 375             380

Gly Asp Ile Val Val Leu Asn Lys His Val Asp Val Arg Ser Asp Ile
385                 390                 395                 400

Asn Arg Ala Val Ala Leu Arg Ser Ala Val Glu Gly Val Val Leu Leu
                405                 410                 415

Lys Asn Glu His Glu Thr Leu Pro Leu Gly Arg Glu Lys Val Lys Arg
            420                 425                 430

Ile Ser Ile Leu Gly Gln Ala Ala Gly Asp Asp Ser Lys Gly Thr Ser
        435                 440                 445

Cys Ser Leu Arg Gly Cys Gly Ser Gly Ala Ile Gly Thr Gly Tyr Gly
        450                 455                 460

Ser Gly Ala Gly Thr Phe Ser Tyr Phe Val Thr Pro Ala Asp Gly Ile
465                 470                 475                 480

Gly Ala Arg Ala Gln Gln Glu Lys Ile Ser Tyr Glu Phe Ile Gly Asp
                485                 490                 495

Ser Trp Asn Gln Ala Ala Ala Met Asp Ser Ala Leu Tyr Ala Asp Ala
            500                 505                 510

Ala Ile Glu Val Ala Asn Ser Val Ala Gly Glu Glu Ile Gly Asp Val
        515                 520                 525

Asp Gly Asn Tyr Gly Asp Leu Asn Asn Leu Thr Leu Trp His Asn Ala
    530                 535                 540

Val Pro Leu Ile Lys Asn Ile Ser Ser Ile Asn Asn Thr Ile Val
545                 550                 555                 560

Ile Val Thr Ser Gly Gln Gln Ile Asp Leu Pro Phe Ile Asp Asn
                565                 570                 575

Glu Asn Val Thr Ala Val Ile Tyr Ser Ser Tyr Leu Gly Gln Asp Phe
            580                 585                 590

Gly Thr Val Leu Ala Lys Val Leu Phe Gly Asp Glu Asn Pro Ser Gly
        595                 600                 605

Lys Leu Pro Phe Thr Ile Ala Lys Asp Val Asn Asp Tyr Ile Pro Val
    610                 615                 620

Ile Glu Lys Val Asp Val Pro Asp Pro Val Asp Lys Phe Thr Glu Ser
625                 630                 635                 640

Ile Tyr Val Asp Tyr Arg Tyr Phe Asp Lys Tyr Asn Lys Pro Val Arg
                645                 650                 655

Tyr Glu Phe Gly Tyr Gly Leu Ser Tyr Ser Asn Phe Ser Leu Ser Asp
            660                 665                 670

Ile Glu Ile Gln Thr Leu Gln Pro Phe Ser Glu Asn Ala Glu Pro Ala
        675                 680                 685

Ala Asn Tyr Ser Glu Thr Tyr Gln Tyr Lys Gln Ser Asn Met Asp Pro
    690                 695                 700

Ser Glu Tyr Thr Val Pro Glu Gly Phe Lys Glu Leu Ala Asn Tyr Thr
705                 710                 715                 720

Tyr Pro Tyr Ile His Asp Ala Ser Ser Ile Lys Ala Asn Ser Ser Tyr
                725                 730                 735

Asp Tyr Pro Glu Gly Tyr Ser Thr Glu Gln Leu Asp Gly Pro Lys Ser
            740                 745                 750

Leu Ala Gly Gly Leu Gly Gly Asn His Thr Cys Gly Met Leu Val
        755                 760                 765
```

-continued

Thr Leu Ser Leu Leu Lys Ser Gln Ile Lys Val Leu Met Leu Val Gly
    770                 775                 780

Leu His Leu Asn Cys Met Leu Asp Ile Gln Ile Met Met Asn Ser Gln
785                 790                 795                 800

His Leu Gln Cys Asn Tyr Val Asp Leu Lys Arg Cys Phe Trp Ile Lys
                805                 810                 815

Ile Ile Leu Lys Leu Phe Leu Leu Asn
        820                 825

<210> SEQ ID NO 26
<211> LENGTH: 867
<212> TYPE: PRT
<213> ORGANISM: Piromyces sp.

<400> SEQUENCE: 26

Met Lys Ile Gln Asn Ile Leu Val Ala Leu Thr Cys Gly Leu Val Ser
1               5                   10                  15

Gln Val Phe Ala Thr Ser Trp Ser Glu Ala Asp Glu Lys Ala Lys Ser
                20                  25                  30

Phe Met Ser Asp Leu Ser Glu Ser Lys Ile Asp Ile Val Thr Gly
            35                  40                  45

Tyr Met Asn Met Gln Gly Thr Cys Val Gly Asn Ile Lys Pro Leu Asp
    50                  55                  60

Arg Lys Asn Phe Lys Gly Leu Cys Leu Gln Asp Gly Pro Ala Gly Val
65                  70                  75                  80

Arg Phe Asn Gly Gly Thr Ser Thr Thr Trp Gln Ala Gly Ile Asn Asn
                85                  90                  95

Ala Ala Thr Phe Asn Lys Asp Leu Leu Tyr Lys Ile Gly Lys Asp Gln
            100                 105                 110

Gly Ala Glu Phe Tyr Ala Lys Gly Ile Asn Ile Ala Leu Ala Pro Ser
        115                 120                 125

Met Asn Ile Leu Arg Ala Pro Ala Ser Gly Arg Val Trp Glu Asn Phe
130                 135                 140

Gly Glu Asp Pro Tyr Leu Ser Gly Val Cys Gly Ala Gln Ile Thr Lys
145                 150                 155                 160

Gly Tyr Gln Asp Ser Gly Val Ile Val Ala Ala Lys His Tyr Val Ala
                165                 170                 175

Asn Asp Ile Glu His Asn Arg Glu Ala Ser Ser Ser Asn Met Asp Asp
            180                 185                 190

Gln Thr Leu Met Glu Ile His Val Glu Pro Phe Tyr Arg Thr Ile Lys
        195                 200                 205

Asp Gly Asp Ala Gly Ser Val Met Ala Ser Tyr Asn Ala Val Asn Asn
210                 215                 220

Ile Tyr Val Val Gln Asn Lys Lys Val Leu Thr Glu Ile Leu Lys Glu
225                 230                 235                 240

Gly Ile Gly Phe Gln Gly Phe Val Met Ser Asp Trp Trp Ala Ile His
                245                 250                 255

Asp Leu Glu Gly Ser Phe Asn Ala Gly Met Asp Met Asn Met Pro Gly
            260                 265                 270

Gly Lys Ala Trp Gly Pro Asp Tyr Val Asn Asn Ser Phe Trp Gly Ser
        275                 280                 285

Asn Ile Ser Asn Ala Ile Arg Ser Gly Gln Val Ser Ser Ser Arg Leu
290                 295                 300

Asp Asp Ala Val Arg Arg Ile Ile Arg Thr Leu Tyr Arg Phe Asp Gln

```
                305                 310                 315                 320
        Met Ser Gly Tyr Pro Asn Val Asn Leu Lys Ala Pro Ser Met His Ala
                        325                 330                 335

Asp Thr Asn Arg Gln Ala Ala Ile Glu Ser Ser Val Leu Leu Lys Asn
                        340                 345                 350

Ala Asp Asp Ile Leu Pro Leu Thr Lys Lys Tyr Arg Lys Ile Ala Ile
                        355                 360                 365

Ile Gly Lys Asp Ala Asp Lys Ala Gln Ser Cys Thr Asp Thr Ala Cys
        370                 375                 380

Ser Gly Gly Asn Ile Ile Gln Gly Trp Gly Ser Gly Thr Thr Asp Phe
        385                 390                 395                 400

Thr Gly Ile Ser Asp Pro Ile Thr Ala Ile Lys Asn Arg Ala Ser Lys
                        405                 410                 415

Glu Gly Ile Ser Ile Val Ser Ser Ile Ser Asp Ser Ala Asn Glu Gly
                        420                 425                 430

Ala Asn Val Ala Lys Asp Ala Asp Val Ala Val Val Phe Val Arg Ala
                        435                 440                 445

Thr Ser Gly Glu Glu Tyr Ile Val Val Asp Asn Asn Lys Gly Asp Arg
        450                 455                 460

Asn Asn Leu Asp Leu Trp His Gly Gly Asn Asp Leu Val Lys Ser Val
        465                 470                 475                 480

Ala Ala Val Asn Lys Asn Thr Val Val Ile His Ala Pro Ala Thr
                        485                 490                 495

Val Asn Leu Pro Phe Leu Asn Asn Val Lys Ala Ile Ile His Ala Gly
                        500                 505                 510

Met Pro Gly Ala Glu Ser Gly Asn Ala Ile Ala Ser Ile Leu Phe Gly
                        515                 520                 525

Asp Ser Asn Pro Ser Gly His Leu Pro Phe Thr Trp Ala Ala Arg Glu
                        530                 535                 540

Asp Tyr Cys Cys Asp Val Ser Tyr Pro Ala Glu Leu Pro His Gly Gly
        545                 550                 555                 560

Asn Ser Lys Thr Ala Tyr Asp Tyr Lys Glu Gly Leu Phe Val Gly Tyr
                        565                 570                 575

Arg Trp Phe Asp Lys Lys Asn Lys Thr Pro Ile Phe Pro Phe Gly His
                        580                 585                 590

Gly Leu Ser Tyr Thr Thr Phe Asp Tyr Ser Asn Leu Ser Val Ser Leu
                        595                 600                 605

Lys Lys Ser Gly Thr Gln Val Thr Gly Leu Glu Ala Thr Val Thr Val
        610                 615                 620

Ala Asn Thr Gly Ser Tyr Glu Gly Ala Thr Val Pro Met Leu Phe Leu
        625                 630                 635                 640

Gly Phe Pro Ala Val Ser Glu Leu Gly Asp Tyr Pro Val Arg Asn Leu
                        645                 650                 655

Lys Ala Phe Glu Lys Val Asn Leu Lys Ala Gly Glu Lys Lys Thr Val
                        660                 665                 670

Thr Leu Thr Val Asp Gln His Gly Leu Ser Tyr Tyr Asn Thr Ser Lys
                        675                 680                 685

Lys Ser Phe Val Val Pro Thr Gly Gly Glu Phe Thr Val Tyr Val Gly
                        690                 695                 700

Lys Ser Ala Gly Asp Leu Pro Leu Lys Lys Ala Ile Lys Asn Thr Gln
        705                 710                 715                 720

Gly Thr Asn Glu Ser Ser Ser Val Gly Asp Glu Asn Asn Asn
                        725                 730                 735
```

```
Pro Asn Asn Asn Ala Asp Cys Ser Val Asn Gly Tyr Lys Cys Cys Ser
                740                 745                 750

Asn Ser Asn Ala Glu Val Val Tyr Thr Asp Gly Asp Gly Asn Trp Gly
            755                 760                 765

Val Glu Asn Gly Gln Trp Cys Ile Ile Lys Glu Gln Gln Gln Gln Gln
770                 775                 780

Thr Cys Phe Ser Ile Lys Leu Gly Tyr Pro Cys Cys Lys Gly Asn Glu
785                 790                 795                 800

Val Ala Tyr Thr Asp Asn Asp Gly Gln Trp Gly Phe Glu Asn Gly Gln
                805                 810                 815

Trp Cys Gly Ile Ala Thr Ala Thr Ser Gly Ala Gly Cys Pro Tyr
            820                 825                 830

Thr Ser Lys Asn Gly Tyr Pro Val Cys Gln Thr Thr Lys Val Glu
                835                 840                 845

Tyr Val Asp Ser Asp Lys Trp Gly Val Glu Asn Gly Asn Trp Cys Ile
850                 855                 860

Met Cys Asn
865

<210> SEQ ID NO 27
<211> LENGTH: 870
<212> TYPE: PRT
<213> ORGANISM: Coccidioides immitis

<400> SEQUENCE: 27

Met Ser Pro Thr Ile Trp Ile Ala Thr Leu Leu Tyr Trp Phe Ala Phe
1               5                   10                  15

Gln Ala Arg Lys Ser Val Ala Ala Pro Pro Gly Val Gly Ala Leu Asp
                20                  25                  30

Asp Arg Ala Glu Leu Pro Asp Gly Phe His Ser Pro Gln Tyr Tyr Pro
            35                  40                  45

Ala Pro Arg Gly Leu Gly Ala Gly Met Glu Glu Ala Tyr Ser Lys Ala
        50                  55                  60

His Thr Val Val Ser Lys Met Thr Leu Ala Gly Lys Val Asn Leu Thr
65                  70                  75                  80

Thr Gly Thr Gly Phe Leu Met Ala Leu Val Gly Gln Thr Gly Ser Ala
                85                  90                  95

Leu Arg Phe Gly Ile Pro Arg Leu Cys Leu Gln Asp Gly Pro Leu Gly
                100                 105                 110

Leu Arg Asn Thr Asp His Asn Thr Ala Phe Pro Ala Gly Ile Ser Val
            115                 120                 125

Gly Ala Thr Phe Asp Lys Lys Leu Met Tyr Glu Arg Gly Cys Ala Met
130                 135                 140

Gly Glu Glu Phe Arg Gly Lys Gly Ala Asn Val His Leu Gly Pro Ser
145                 150                 155                 160

Val Gly Pro Leu Gly Arg Lys Pro Arg Gly Arg Asn Trp Glu Gly
                165                 170                 175

Phe Gly Ser Asp Pro Ser Leu Gln Ala Ile Ala Ala Val Glu Thr Ile
            180                 185                 190

Lys Gly Val Gln Ser Lys Gly Val Ile Ala Thr Ile Lys His Leu Val
                195                 200                 205

Gly Asn Glu Gln Glu Met Tyr Arg Met Thr Asn Ile Val Gln Arg Ala
210                 215                 220

Tyr Ser Ala Asn Ile Asp Asp Arg Thr Met His Glu Leu Tyr Leu Trp
```

```
              225                 230                 235                 240
          Pro Phe Ala Glu Ser Val Arg Ala Gly Val Gly Ala Val Met Met Ala
                          245                 250                 255

Tyr Asn Asp Val Asn Gly Ser Ala Ser Cys Gln Asn Ser Lys Leu Ile
                          260                 265                 270

Asn Gly Ile Leu Lys Asp Glu Leu Gly Phe Gln Gly Phe Val Met Thr
                          275                 280                 285

Asp Trp Tyr Ala Gln Ile Gly Val Ser Ser Ala Leu Ala Gly Leu
                          290                 295                 300

Asp Met Ser Met Pro Gly Asp Gly Ser Val Pro Leu Ser Gly Thr Ser
          305                 310                 315                 320

Phe Trp Ala Ser Glu Leu Ser Arg Ser Ile Leu Asn Gly Thr Val Ala
                          325                 330                 335

Leu Asp Arg Leu Asn Asp Met Val Thr Arg Ile Val Ala Thr Trp Phe
                          340                 345                 350

Lys Phe Gly Gln Asp Lys Asp Phe Pro Leu Pro Asn Phe Ser Ser Tyr
                          355                 360                 365

Thr Gln Asn Ala Lys Gly Leu Leu Tyr Pro Gly Ala Leu Phe Ser Pro
                          370                 375                 380

Leu Gly Val Val Asn Gln Phe Val Asn Val Gln Ala Asp His His Lys
          385                 390                 395                 400

Leu Ala Arg Val Ile Ala Arg Glu Ser Ile Thr Leu Leu Lys Asn Glu
                          405                 410                 415

Asp Asn Leu Leu Pro Leu Asp Pro Asn Arg Ala Ile Lys Tyr Ser Glu
                          420                 425                 430

Gln Met Pro Gly Thr Asn Pro Arg Gly Ile Asn Ala Cys Pro Asp Lys
                          435                 440                 445

Gly Cys Asn Lys Gly Val Leu Thr Met Gly Trp Gly Ser Gly Thr Ser
                          450                 455                 460

Asn Leu Pro Tyr Leu Val Thr Pro Glu Asp Ala Ile Arg Asn Ile Ser
          465                 470                 475                 480

Lys Asn Thr Glu Phe His Ile Thr Asp Lys Phe Pro Asn Asn Val Gln
                          485                 490                 495

Pro Gly Pro Asp Asp Val Ala Ile Val Phe Val Asn Ala Asp Ser Gly
                          500                 505                 510

Glu Asn Tyr Ile Ile Val Glu Ser Asn Pro Gly Asp Arg Thr Val Ala
                          515                 520                 525

Gln Met Lys Leu Trp His Asn Gly Asp Glu Leu Ile Glu Ser Ala Ala
                          530                 535                 540

Lys Lys Phe Ser Asn Val Val Val Val Val His Thr Val Gly Pro
          545                 550                 555                 560

Ile Ile Met Glu Lys Trp Ile Asp Leu Leu Arg Ser Arg Val Ser Cys
                          565                 570                 575

Leu Pro Asp Phe Gln Asp Lys Lys Leu Glu Ile Leu Leu Ile Ser
                          580                 585                 590

Cys Ser Glu Thr Ser Val Arg Val Ala Ala Ser Ile Tyr Asp Thr Glu
                          595                 600                 605

Ser Arg Ile Gly Leu Ser Asp Ser Val Ser Leu Ile Asn Gln Arg Phe
                          610                 615                 620

Gly Gln Ile Gln Asp Thr Phe Thr Glu Gly Leu Phe Ile Asp Tyr Arg
          625                 630                 635                 640

His Phe Gln Lys Glu Asn Ile Thr Pro Arg Tyr His Phe Gly Tyr Gly
                          645                 650                 655
```

```
Leu Ser Tyr Thr Thr Phe Asn Phe Thr Glu Pro Arg Leu Glu Ser Val
                660                 665                 670

Thr Thr Leu Ser Glu Tyr Pro Pro Ala Arg Lys Pro Lys Ala Gly Asp
        675                 680                 685

Arg His Thr Pro Thr Ile Ser His Leu Leu Gln Lys Trp Pro Gly Pro
690                 695                 700

Lys Thr Leu Thr Gly Ser Gly Ala Tyr Leu Tyr Pro Tyr Leu Asp Asn
705                 710                 715                 720

Pro Ser Ala Ile Lys Pro Lys Pro Gly Tyr Pro Tyr Pro Glu Ala Ile
                725                 730                 735

Gln Pro Asn Leu Asn Leu Asn Pro Arg Ala Gly Gly Ser Glu Ala Val
                740                 745                 750

Thr Arg Arg Tyr Gly Met Leu Arg Ser Arg Phe Pro Leu Lys Leu Leu
        755                 760                 765

Ile Leu Glu Arg Asn Pro Val Arg Ala Val Ala Gln Leu Tyr Val Glu
770                 775                 780

Leu Pro Thr Asp Asp Glu His Pro Thr Pro Lys Leu Gln Leu Arg Gln
785                 790                 795                 800

Phe Glu Lys Thr Ala Thr Leu Glu Pro Gly Gln Ser Glu Val Leu Lys
                805                 810                 815

Met Glu Ile Thr Arg Lys Asp Val Ser Ile Trp Asp Thr Met Val Gln
        820                 825                 830

Asp Trp Lys Val Pro Ala Thr Gly Lys Gly Ile Lys Leu Trp Ile Gly
                835                 840                 845

Ala Ser Val Gly Asp Leu Lys Ala Val Cys Glu Thr Gly Lys Gly Lys
850                 855                 860

Ser Cys His Val Leu Asn
865                 870

<210> SEQ ID NO 28
<211> LENGTH: 880
<212> TYPE: PRT
<213> ORGANISM: Saccharomycopsis fibuligera

<400> SEQUENCE: 28

Met Leu Leu Ile Leu Glu Leu Val Leu Ile Ile Gly Leu Gly Val
1               5                   10                  15

Ala Leu Pro Val Gln Thr His Asn Leu Thr Asp Asn Gln Gly Phe Asp
                20                  25                  30

Glu Glu Ser Ser Gln Trp Ile Ser Pro His Tyr Tyr Pro Thr Pro Gln
            35                  40                  45

Gly Gly Arg Leu Gln Gly Val Trp Gln Asp Ala Tyr Thr Lys Ala Lys
        50                  55                  60

Ala Leu Val Ser Gln Met Thr Ile Val Glu Lys Val Asn Leu Thr Thr
65                  70                  75                  80

Gly Thr Gly Trp Gln Leu Gly Pro Cys Val Gly Asn Thr Gly Ser Val
                85                  90                  95

Pro Arg Phe Gly Ile Pro Asn Leu Cys Leu Gln Asp Gly Pro Leu Gly
            100                 105                 110

Val Arg Leu Thr Asp Phe Ser Thr Gly Tyr Pro Ser Gly Met Ala Thr
        115                 120                 125

Gly Ala Thr Phe Asn Lys Asp Leu Phe Leu Gln Arg Gly Gln Ala Leu
130                 135                 140

Gly His Glu Phe Asn Ser Lys Gly Val His Ile Ala Leu Gly Pro Ala
```

```
            145                 150                 155                 160
Val Gly Pro Leu Gly Val Lys Ala Arg Gly Gly Arg Asn Phe Glu Ala
                    165                 170                 175
Phe Gly Ser Asp Pro Tyr Leu Gln Gly Ile Ala Ala Ala Thr Ile
                180                 185                 190
Lys Gly Leu Gln Glu Asn Asn Val Met Ala Cys Val Lys His Phe Ile
                    195                 200                 205
Gly Asn Glu Gln Asp Ile Tyr Arg Gln Pro Ser Asn Ser Lys Val Asp
                210                 215                 220
Pro Glu Tyr Asp Pro Ala Thr Lys Glu Ser Ile Ser Ala Asn Ile Pro
225                 230                 235                 240
Asp Arg Ala Met His Glu Leu Tyr Leu Trp Pro Phe Ala Asp Ser Ile
                    245                 250                 255
Arg Ala Gly Val Gly Ser Val Met Cys Ser Tyr Asn Arg Val Asn Asn
                    260                 265                 270
Thr Tyr Ser Cys Glu Asn Ser Tyr Met Ile Asn His Leu Leu Lys Glu
                275                 280                 285
Glu Leu Gly Phe Gln Gly Phe Val Val Ser Asp Trp Ala Ala Gln Met
        290                 295                 300
Ser Gly Ala Tyr Ser Ala Ile Ser Gly Leu Asp Met Ser Met Pro Gly
305                 310                 315                 320
Glu Leu Leu Gly Gly Trp Asn Thr Gly Lys Ser Tyr Trp Gly Gln Asn
                    325                 330                 335
Leu Thr Lys Ala Val Tyr Asn Glu Thr Val Pro Ile Glu Arg Leu Asp
                340                 345                 350
Asp Met Ala Thr Arg Ile Leu Ala Ala Leu Tyr Ala Thr Asn Ser Phe
            355                 360                 365
Pro Thr Lys Asp Arg Leu Pro Asn Phe Ser Ser Phe Thr Lys Glu
        370                 375                 380
Tyr Gly Asn Glu Phe Phe Val Asp Lys Thr Ser Pro Val Val Lys Val
385                 390                 395                 400
Asn His Phe Val Asp Pro Ser Asn Asp Phe Thr Glu Asp Thr Ala Leu
                405                 410                 415
Lys Val Ala Glu Glu Ser Ile Val Leu Leu Lys Asn Glu Lys Asn Thr
                420                 425                 430
Leu Pro Ile Ser Pro Asn Lys Val Arg Lys Leu Leu Leu Ser Gly Ile
                435                 440                 445
Ala Ala Gly Pro Asp Pro Lys Gly Tyr Glu Cys Ser Asp Gln Ser Cys
        450                 455                 460
Val Asp Gly Ala Leu Phe Glu Gly Trp Gly Ser Gly Ser Val Gly Tyr
465                 470                 475                 480
Pro Lys Tyr Gln Val Thr Pro Phe Glu Glu Ile Ala Asn Ala Arg
                    485                 490                 495
Lys Asn Lys Met Gln Phe Asp Tyr Ile Arg Glu Ser Phe Asp Leu Thr
                500                 505                 510
Gln Val Ser Thr Val Ala Ser Asp Ala His Met Ser Ile Val Val Val
        515                 520                 525
Ser Ala Val Ser Gly Glu Gly Tyr Leu Ile Ile Asp Gly Asn Arg Gly
                530                 535                 540
Asp Lys Asn Asn Val Thr Leu Trp His Asn Ser Asp Asn Leu Ile Lys
545                 550                 555                 560
Ala Val Ala Glu Asn Cys Ala Asn Thr Val Val Val Ile Thr Ser Thr
                    565                 570                 575
```

```
Gly Gln Val Asp Val Glu Ser Phe Ala Asp His Pro Asn Val Thr Ala
            580                 585                 590

Ile Val Trp Ala Gly Pro Leu Gly Asp Arg Ser Gly Thr Ala Ile Ala
        595                 600                 605

Asn Ile Leu Phe Gly Asn Ala Asn Pro Ser Gly His Leu Pro Phe Thr
    610                 615                 620

Val Ala Lys Ser Asn Asp Asp Tyr Ile Pro Ile Val Thr Tyr Asn Pro
625                 630                 635                 640

Pro Asn Gly Glu Pro Glu Asp Asn Thr Leu Ala Glu His Asp Leu Leu
                645                 650                 655

Val Asp Tyr Arg Tyr Phe Glu Glu Lys Asn Ile Glu Pro Arg Tyr Ala
            660                 665                 670

Phe Gly Tyr Gly Leu Ser Tyr Asn Glu Tyr Lys Val Ser Asn Ala Lys
        675                 680                 685

Val Ser Ala Ala Lys Lys Val Asp Glu Glu Leu Pro Gln Pro Lys Leu
    690                 695                 700

Tyr Leu Ala Glu Tyr Ser Tyr Asn Lys Thr Glu Glu Ile Asn Asn Pro
705                 710                 715                 720

Glu Asp Ala Phe Phe Pro Ser Asn Ala Arg Arg Ile Gln Glu Phe Leu
                725                 730                 735

Tyr Pro Tyr Leu Asp Ser Asn Val Thr Leu Lys Asp Gly Asn Tyr Glu
            740                 745                 750

Tyr Pro Asp Gly Tyr Ser Thr Glu Gln Arg Thr Thr Pro Ile Gln Pro
        755                 760                 765

Gly Gly Gly Leu Gly Gly Asn Asp Ala Leu Trp Glu Val Ala Tyr Lys
    770                 775                 780

Val Glu Val Asp Val Gln Asn Leu Gly Asn Ser Thr Asp Lys Phe Val
785                 790                 795                 800

Pro Gln Leu Tyr Leu Lys His Pro Glu Asp Gly Lys Phe Glu Thr Pro
                805                 810                 815

Val Gln Leu Arg Gly Phe Glu Lys Val Glu Leu Ser Pro Gly Glu Lys
            820                 825                 830

Lys Thr Val Glu Phe Glu Leu Leu Arg Arg Asp Leu Ser Val Trp Asp
        835                 840                 845

Thr Thr Arg Gln Ser Trp Ile Val Glu Ser Gly Thr Tyr Glu Ala Leu
    850                 855                 860

Ile Gly Val Ala Val Asn Asp Ile Lys Thr Ser Val Leu Phe Thr Ile
865                 870                 875                 880

<210> SEQ ID NO 29
<211> LENGTH: 876
<212> TYPE: PRT
<213> ORGANISM: Saccharomycopsis fibuligera

<400> SEQUENCE: 29

Met Leu Met Ile Val Gln Leu Leu Val Phe Ala Leu Gly Leu Ala Val
1               5                   10                  15

Ala Val Pro Ile Gln Asn Tyr Thr Gln Ser Pro Ser Gln Arg Asp Glu
            20                  25                  30

Ser Ser Gln Trp Val Ser Pro His Tyr Pro Thr Pro Gln Gly Gly
        35                  40                  45

Arg Leu Gln Asp Val Trp Gln Glu Ala Tyr Ala Arg Ala Lys Ala Ile
    50                  55                  60

Val Gly Gln Met Thr Ile Val Glu Lys Val Asn Leu Thr Thr Gly Thr
```

```
            65                  70                  75                  80
Gly Trp Gln Leu Asp Pro Cys Val Gly Asn Thr Gly Ser Val Pro Arg
                85                  90                  95
Phe Gly Ile Pro Asn Leu Cys Leu Gln Asp Gly Pro Leu Gly Val Arg
            100                 105                 110
Phe Ala Asp Phe Val Thr Gly Tyr Pro Ser Gly Leu Ala Thr Gly Ala
            115                 120                 125
Thr Phe Asn Lys Asp Leu Phe Leu Gln Arg Gly Gln Ala Leu Gly His
            130                 135                 140
Glu Phe Asn Ser Lys Gly Val His Ile Ala Leu Gly Pro Ala Val Gly
145                 150                 155                 160
Pro Leu Gly Val Lys Ala Arg Gly Gly Arg Asn Phe Glu Ala Phe Gly
                165                 170                 175
Ser Asp Pro Tyr Leu Gln Gly Thr Ala Ala Ala Thr Ile Lys Gly
            180                 185                 190
Leu Gln Glu Asn Asn Val Met Ala Cys Val Lys His Phe Ile Gly Asn
                195                 200                 205
Glu Gln Glu Lys Tyr Arg Gln Pro Asp Asp Ile Asn Pro Ala Thr Asn
            210                 215                 220
Gln Thr Thr Lys Glu Ala Ile Ser Ala Asn Ile Pro Asp Arg Ala Met
225                 230                 235                 240
His Ala Leu Tyr Leu Trp Pro Phe Ala Asp Ser Val Arg Ala Gly Val
                245                 250                 255
Gly Ser Val Met Cys Ser Tyr Asn Arg Val Asn Asn Thr Tyr Ala Cys
                260                 265                 270
Glu Asn Ser Tyr Met Met Asn His Leu Leu Lys Glu Glu Leu Gly Phe
            275                 280                 285
Gln Gly Phe Val Val Ser Asp Trp Gly Ala Gln Leu Ser Gly Val Tyr
            290                 295                 300
Ser Ala Ile Ser Gly Leu Asp Met Ser Met Pro Gly Glu Val Tyr Gly
305                 310                 315                 320
Gly Trp Asn Thr Gly Thr Ser Phe Trp Gly Gln Asn Leu Thr Lys Ala
                325                 330                 335
Ile Tyr Asn Glu Thr Val Pro Ile Glu Arg Leu Asp Asp Met Ala Thr
            340                 345                 350
Arg Ile Leu Ala Ala Leu Tyr Ala Thr Asn Ser Phe Pro Thr Glu Asp
            355                 360                 365
His Leu Pro Asn Phe Ser Ser Trp Thr Thr Lys Glu Tyr Gly Asn Lys
            370                 375                 380
Tyr Tyr Ala Asp Asn Thr Thr Glu Ile Val Lys Val Asn Tyr Asn Val
385                 390                 395                 400
Asp Pro Ser Asn Asp Phe Thr Glu Asp Thr Ala Leu Lys Val Ala Glu
                405                 410                 415
Glu Ser Ile Val Leu Leu Lys Asn Glu Asn Asn Thr Leu Pro Ile Ser
            420                 425                 430
Pro Glu Lys Ala Lys Arg Leu Leu Leu Ser Gly Ile Ala Ala Gly Pro
            435                 440                 445
Asp Pro Ile Gly Tyr Gln Cys Glu Asp Gln Ser Cys Thr Asn Gly Ala
            450                 455                 460
Leu Phe Gln Gly Trp Gly Ser Gly Ser Val Gly Ser Pro Lys Tyr Gln
465                 470                 475                 480
Val Thr Pro Phe Glu Glu Ile Ser Tyr Leu Ala Arg Lys Asn Lys Met
            485                 490                 495
```

```
Gln Phe Asp Tyr Ile Arg Glu Ser Tyr Asp Leu Ala Gln Val Thr Lys
            500                 505                 510

Val Ala Ser Asp Ala His Leu Ser Ile Val Val Ser Ala Ala Ser
        515                 520                 525

Gly Glu Gly Tyr Ile Thr Val Asp Gly Asn Gln Gly Asp Arg Lys Asn
    530                 535                 540

Leu Thr Leu Trp Asn Asn Gly Asp Lys Leu Ile Glu Thr Val Ala Glu
545                 550                 555                 560

Asn Cys Ala Asn Thr Val Val Val Thr Ser Thr Gly Gln Ile Asn
                565                 570                 575

Phe Glu Gly Phe Ala Asp His Pro Asn Val Thr Ala Ile Val Trp Ala
            580                 585                 590

Gly Pro Leu Gly Asp Arg Ser Gly Thr Ala Ile Ala Asn Ile Leu Phe
        595                 600                 605

Gly Lys Ala Asn Pro Ser Gly His Leu Pro Phe Thr Ile Ala Lys Thr
    610                 615                 620

Asp Asp Asp Tyr Ile Pro Ile Glu Thr Tyr Ser Pro Ser Ser Gly Glu
625                 630                 635                 640

Pro Glu Asp Asn His Leu Val Glu Asn Asp Leu Leu Val Asp Tyr Arg
                645                 650                 655

Tyr Phe Glu Glu Lys Asn Ile Glu Pro Arg Tyr Ala Phe Gly Tyr Gly
            660                 665                 670

Leu Ser Tyr Asn Glu Tyr Glu Val Ser Asn Ala Lys Val Ser Ala Ala
        675                 680                 685

Lys Lys Val Asp Glu Glu Leu Pro Glu Pro Ala Thr Tyr Leu Ser Glu
    690                 695                 700

Phe Ser Tyr Gln Asn Ala Lys Asp Ser Lys Asn Pro Ser Asp Ala Phe
705                 710                 715                 720

Ala Pro Ala Asp Leu Asn Arg Val Asn Glu Tyr Leu Tyr Pro Tyr Leu
                725                 730                 735

Asp Ser Asn Val Thr Leu Lys Asp Gly Asn Tyr Glu Tyr Pro Asp Gly
            740                 745                 750

Tyr Ser Thr Glu Gln Arg Thr Thr Pro Asn Gln Pro Gly Gly Leu
        755                 760                 765

Gly Gly Asn Asp Ala Leu Trp Glu Val Ala Tyr Asn Ser Thr Asp Lys
    770                 775                 780

Phe Val Pro Gln Gly Asn Ser Thr Asp Lys Phe Val Pro Gln Leu Tyr
785                 790                 795                 800

Leu Lys His Pro Glu Asp Gly Lys Phe Glu Thr Pro Ile Gln Leu Arg
                805                 810                 815

Gly Phe Glu Lys Val Glu Leu Ser Pro Gly Lys Lys Thr Val Asp
            820                 825                 830

Leu Arg Leu Leu Arg Arg Asp Leu Ser Val Trp Asp Thr Thr Arg Gln
        835                 840                 845

Ser Trp Ile Val Glu Ser Gly Thr Tyr Glu Ala Leu Ile Gly Val Ala
    850                 855                 860

Val Asn Asp Ile Lys Thr Ser Val Leu Phe Thr Ile
865                 870                 875

<210> SEQ ID NO 30
<211> LENGTH: 803
<212> TYPE: PRT
<213> ORGANISM: Septoria lycopersici
```

```
<400> SEQUENCE: 30

Met Val Ser Ser Leu Phe Asn Ile Ala Ala Leu Ala Gly Ala Val Ile
1               5                   10                  15

Ala Leu Ser His Glu Asp Gln Ser Lys His Phe Thr Thr Ile Pro Thr
            20                  25                  30

Phe Pro Thr Pro Asp Ser Thr Gly Glu Gly Trp Lys Ala Ala Phe Glu
        35                  40                  45

Lys Ala Ala Asp Ala Val Ser Arg Leu Asn Leu Thr Gln Lys Val Ala
    50                  55                  60

Leu Thr Thr Gly Thr Thr Ala Gly Leu Ser Cys Asn Gly Asn Ile Ala
65                  70                  75                  80

Pro Ile Pro Glu Ile Asn Phe Ser Gly Leu Cys Leu Ala Asp Gly Pro
                85                  90                  95

Val Ser Val Arg Ile Ala Asp Leu Ala Thr Val Phe Pro Ala Gly Leu
            100                 105                 110

Thr Ala Ala Thr Trp Asp Arg Gln Leu Ile Tyr Glu Arg Ala Arg
        115                 120                 125

Ala Leu Gly Ser Glu Phe Arg Gly Lys Gly Ser Gln Val His Leu Gly
    130                 135                 140

Pro Ala Ser Gly Ala Leu Gly Arg His Pro Leu Gly Gly Arg Asn Trp
145                 150                 155                 160

Glu Ser Phe Ser Pro Asp Pro Tyr Leu Ser Gly Val Ala Met Asp Phe
                165                 170                 175

Ser Ile Arg Gly Ile Gln Glu Met Gly Val Gln Ala Asn Arg Lys His
            180                 185                 190

Phe Ile Gly Asn Glu Gln Glu Thr Gln Arg Ser Asn Thr Phe Thr Asp
        195                 200                 205

Asp Gly Thr Glu Ile Gln Ala Ile Ser Ser Asn Ile Asp Arg Thr
    210                 215                 220

Met His Glu Leu Tyr Leu Trp Pro Phe Ala Asn Ala Val Arg Ser Gly
225                 230                 235                 240

Val Ala Ser Val Met Cys Ser Tyr Asn Arg Leu Asn Gln Thr Tyr Ala
                245                 250                 255

Cys Glu Asn Ser Lys Leu Met Asn Gly Ile Leu Lys Gly Glu Leu Gly
            260                 265                 270

Phe Gln Gly Tyr Val Val Ser Asp Trp Tyr Ala Thr His Ser Gly Val
        275                 280                 285

Glu Ser Val Asn Ala Gly Leu Asp Met Thr Met Pro Gly Pro Leu Asp
    290                 295                 300

Ser Pro Ser Thr Ala Leu Arg Pro Pro Ser Tyr Leu Gly Gly Asn
305                 310                 315                 320

Leu Thr Glu Ala Val Leu Asn Gly Thr Ile Pro Glu Ala Arg Val Asp
                325                 330                 335

Asp Met Ala Arg Arg Ile Leu Met Pro Tyr Phe Phe Leu Gly Gln Asp
            340                 345                 350

Thr Asp Phe Pro Thr Val Asp Pro Ser Thr Gly Phe Val Phe Ala Arg
        355                 360                 365

Thr Tyr Asn Tyr Pro Asp Glu Tyr Leu Thr Leu Gly Gly Leu Asp Pro
    370                 375                 380

Tyr Asn Pro Pro Ala Arg Asp Val Arg Gly Asn His Ser Asp Ile
385                 390                 395                 400

Val Arg Lys Val Ala Ala Ala Gly Thr Val Leu Leu Lys Asn Val Asn
                405                 410                 415
```

```
Asn Val Leu Pro Leu Lys Glu Pro Lys Ser Val Gly Ile Phe Gly Asn
            420                 425                 430

Gly Ala Ala Asp Val Thr Glu Gly Leu Thr Phe Thr Gly Asp Asp Ser
        435                 440                 445

Gly Pro Trp Gly Ala Asp Ile Gly Ala Leu Ser Val Gly Gly Gly Ser
    450                 455                 460

Gly Ala Gly Arg His Thr His Leu Val Ser Pro Leu Ala Ala Ile Arg
465                 470                 475                 480

Lys Arg Thr Glu Ser Val Gly Gly Arg Val Gln Tyr Leu Leu Ser Asn
                485                 490                 495

Ser Arg Ile Val Asn Asp Asp Phe Thr Ser Ile Tyr Pro Thr Pro Glu
            500                 505                 510

Val Cys Leu Val Phe Leu Lys Thr Trp Ala Arg Glu Gly Thr Asp Arg
        515                 520                 525

Leu Ser Tyr Glu Asn Asp Trp Asn Ser Thr Ala Val Val Asn Asn Val
    530                 535                 540

Ala Arg Arg Cys Pro Asn Thr Ile Val Val Thr His Ser Gly Gly Ile
545                 550                 555                 560

Asn Thr Met Pro Trp Ala Asp Asn Ala Asn Val Thr Ala Ile Leu Ala
                565                 570                 575

Ala His Tyr Pro Gly Gln Glu Asn Gly Asn Ser Ile Met Asp Ile Leu
            580                 585                 590

Tyr Gly Asp Val Asn Pro Ser Gly Arg Leu Pro Tyr Thr Ile Pro Lys
        595                 600                 605

Leu Ala Thr Asp Tyr Asp Phe Pro Val Val Asn Ile Thr Asn Glu Ala
    610                 615                 620

Gln Asp Pro Tyr Val Trp Gln Ala Asp Phe Thr Glu Gly Leu Leu Ile
625                 630                 635                 640

Asp Tyr Arg His Phe Asp Ala Arg Asn Ile Thr Pro Leu Tyr Glu Phe
                645                 650                 655

Gly Tyr Gly Leu Ser Tyr Thr Thr Phe Glu Ile Glu Gly Val Ala Asn
            660                 665                 670

Leu Val Ala Lys Ser Ala Lys Leu Ser Ala Phe Pro Ala Ser Thr Asp
        675                 680                 685

Ile Ser His Pro Gly Gly Asn Pro Asp Leu Trp Glu Glu Val Val Ser
    690                 695                 700

Val Thr Ala Ala Val Lys Asn Thr Gly Ser Val Ser Gly Ser Gln Val
705                 710                 715                 720

Val Gln Leu Tyr Ile Ser Leu Pro Ala Asp Gly Ile Pro Glu Asn Ser
                725                 730                 735

Pro Met Gln Val Leu Arg Gly Phe Glu Lys Val Asp Leu Gln Pro Gly
            740                 745                 750

Gln Ser Lys Ser Val Glu Phe Ser Ile Met Arg Arg Asp Leu Ser Phe
        755                 760                 765

Trp Asn Thr Thr Ala Gln Asp Trp Glu Ile Pro Asn Gly Gln Ile Glu
    770                 775                 780

Phe Arg Val Gly Phe Ser Ser Arg Asp Ile Lys Ser Ile Val Ser Arg
785                 790                 795                 800

Ser Phe Leu

<210> SEQ ID NO 31
<211> LENGTH: 763
<212> TYPE: PRT
```

<213> ORGANISM: Kuraishia capsulata

<400> SEQUENCE: 31

```
Met Lys Ser Thr Ile Ile Leu Ser Val Leu Ala Ala Thr Ala
1               5                   10                  15

Lys Asn Ile Ser Lys Ala Glu Met Glu Asn Leu Glu His Trp Trp Ser
            20                  25                  30

Tyr Gly Arg Ser Asp Pro Val Tyr Pro Ser Glu Ile Ser Gly Leu
        35                  40                  45

Gly Asp Trp Gln Phe Ala Tyr Gln Arg Ala Arg Glu Ile Val Ala Leu
    50                  55                  60

Met Thr Asn Glu Glu Lys Thr Asn Leu Thr Phe Gly Ser Ser Gly Asp
65                  70                  75                  80

Thr Gly Cys Ser Gly Met Ile Ser Asp Val Pro Asp Val Asp Phe Pro
                85                  90                  95

Gly Leu Cys Leu Gln Asp Ala Gly Asn Gly Val Arg Gly Thr Asp Met
            100                 105                 110

Val Asn Ala Tyr Ala Ser Gly Leu His Val Gly Ala Ser Trp Asn Arg
        115                 120                 125

Gln Leu Ala Tyr Asp Arg Ala Val Tyr Met Gly Ala Glu Phe Arg His
    130                 135                 140

Lys Gly Val Asn Val Leu Leu Gly Pro Val Val Gly Pro Ile Gly Arg
145                 150                 155                 160

Val Ala Thr Gly Gly Arg Asn Trp Glu Gly Phe Thr Asn Asp Pro Tyr
                165                 170                 175

Leu Ala Gly Ala Leu Val Tyr Glu Thr Thr Lys Gly Ile Gln Glu Asn
            180                 185                 190

Val Ile Ala Cys Thr Lys His Phe Ile Gly Asn Glu Gln Glu Thr Asn
        195                 200                 205

Arg Asn Pro Ser Gly Thr Tyr Asn Gln Ser Val Ser Ala Asn Ile Asp
    210                 215                 220

Asp Lys Thr Met His Glu Leu Tyr Leu Trp Pro Phe Gln Asp Ser Val
225                 230                 235                 240

Arg Ala Gly Leu Gly Ser Ile Met Gly Ser Tyr Asn Arg Val Asn Asn
                245                 250                 255

Ser Tyr Ala Cys Lys Asn Ser Lys Val Leu Asn Gly Leu Leu Lys Ser
            260                 265                 270

Glu Leu Gly Phe Gln Gly Phe Val Ser Asp Trp Gly Gln His
    275                 280                 285

Thr Gly Ile Ala Ser Ala Asn Ala Gly Leu Asp Met Ala Met Pro Ser
290                 295                 300

Ser Thr Tyr Trp Glu Glu Gly Leu Ile Glu Ala Val Lys Asn Gly Thr
305                 310                 315                 320

Val Asp Gln Ser Arg Leu Asp Asp Met Ala Thr Arg Ile Ile Ala Ala
                325                 330                 335

Trp Tyr Lys Tyr Ala Arg Leu Asp Asp Pro Gly Phe Gly Met Pro Val
            340                 345                 350

Ser Leu Ala Glu Asp His Glu Leu Val Asp Ala Arg Asp Pro Ala Ala
        355                 360                 365

Ala Ser Thr Ile Phe Gln Gly Ala Val Glu Gly His Val Leu Val Lys
    370                 375                 380

Asn Glu Asn Ala Leu Pro Leu Lys Lys Pro Lys Tyr Ile Ser Leu Phe
385                 390                 395                 400
```

Gly Tyr Asp Gly Val Ser Thr Asp Val Asn Thr Val Gly Gly Phe
            405                 410                 415

Ser Phe Phe Ser Phe Asp Val Lys Ala Ile Glu Asn Lys Thr Leu Ile
        420                 425                 430

Ser Gly Gly Gly Ser Gly Thr Asn Thr Pro Ser Tyr Val Asp Ala Pro
        435                 440                 445

Phe Asn Ala Phe Val Ala Lys Ala Arg Glu Asp Asn Thr Phe Leu Ser
450                 455                 460

Trp Asp Phe Thr Ser Ala Glu Pro Val Ala Asn Pro Ala Ser Asp Ala
465                 470                 475                 480

Cys Ile Asp Phe Ile Asn Ala Ala Ala Ser Glu Gly Tyr Asp Arg Pro
                485                 490                 495

Asn Leu Ala Asp Lys Tyr Ser Asp Lys Leu Val Glu Ala Val Ala Ser
            500                 505                 510

Gln Cys Ser Asn Thr Ile Val Val Ile His Asn Ala Gly Ile Arg Leu
        515                 520                 525

Val Asp Asn Trp Ile Glu His Glu Asn Val Thr Gly Val Ile Leu Ala
        530                 535                 540

His Leu Pro Gly Gln Asp Thr Gly Thr Ser Leu Ile Glu Val Leu Tyr
545                 550                 555                 560

Gly Asn Gln Ser Pro Ser Gly Arg Leu Pro Tyr Thr Val Ala Lys Lys
                565                 570                 575

Ala Ser Asp Tyr Gly Gly Leu Leu Trp Pro Thr Glu Pro Glu Gly Asp
            580                 585                 590

Leu Asp Leu Tyr Phe Pro Gln Ser Asn Phe Thr Glu Gly Val Tyr Ile
        595                 600                 605

Asp Tyr Lys Tyr Phe Ile Gln Lys Asn Ile Thr Pro Arg Tyr Glu Phe
        610                 615                 620

Gly Tyr Gly Leu Thr Tyr Thr Thr Phe Asp Tyr Ser Glu Leu Glu Val
625                 630                 635                 640

Asp Ala Ile Thr Asn Gln Ser Tyr Leu Pro Pro Asp Cys Thr Ile Glu
                645                 650                 655

Glu Gly Gly Ala Lys Ser Leu Trp Asp Ile Val Ala Thr Val Lys Phe
            660                 665                 670

Thr Val Thr Asn Thr Gly Asp Val Ala Ala Glu Val Pro Gln Leu
        675                 680                 685

Tyr Val Gly Ile Pro Asn Gly Pro Pro Lys Val Leu Arg Gly Phe Asp
        690                 695                 700

Lys Lys Leu Ile His Pro Gly Gln Ser Glu Glu Phe Val Phe Glu Leu
705                 710                 715                 720

Thr Arg Arg Asp Leu Ser Thr Trp Asp Val Val Ala Gln Asn Trp Gly
                725                 730                 735

Leu Gln Ala Gly Thr Tyr Gln Phe Tyr Val Gly Arg Ser Val Phe Asp
            740                 745                 750

Val Pro Leu Thr Ser Ala Leu Val Phe Thr Asn
        755                 760

<210> SEQ ID NO 32
<211> LENGTH: 765
<212> TYPE: PRT
<213> ORGANISM: Trichoderma reesei

<400> SEQUENCE: 32

Met Arg Leu Cys Asp Leu Ser Ser Leu Ala Ser Trp Val Leu Val Thr
1               5                   10                  15

```
Val Ala Leu Pro Ser Ser Gly Ala Ala Lys Gly Val Ser Gln Ile
         20                  25                  30

Pro Ser Thr His Ser Ser Gln Ser Lys Gly Asn Gly Pro Trp Ala His
             35                  40                  45

Ala Tyr Arg Arg Ala Glu Lys Leu Val Arg Gln Met Thr Leu Glu Glu
 50                  55                  60

Lys Ala Asn Ile Thr Arg Gly Phe Thr Gly Asp Asn Val Cys Ala Gly
 65                  70                  75                  80

Asn Thr Gly Ser Val Pro Arg Leu Gly Trp Pro Gly Met Cys Val His
                 85                  90                  95

Asp Ala Gly Asn Gly Val Arg Ala Thr Asp Leu Val Asn Ser Tyr Pro
                100                 105                 110

Ser Gly Ile His Val Gly Ala Ser Trp Asp Arg Asn Leu Thr Tyr Glu
             115                 120                 125

Arg Gly Leu His Met Gly Gly Glu Phe Lys Ala Lys Gly Val Asn Val
130                 135                 140

Pro Leu Gly Pro Asn Ala Gly Pro Leu Gly Arg Thr Pro Leu Gly Gly
145                 150                 155                 160

Arg Asn Trp Glu Gly Phe Ser Ile Asp Pro Tyr Leu Ser Gly Gln Leu
                165                 170                 175

Asn Ala Glu Thr Ile Thr Gly Met Gln Asp Ala Gly Val Ile Ala Asn
            180                 185                 190

Ile Lys His Phe Ile Ala Asn Glu Gln Glu Thr Leu Arg Arg Pro Tyr
        195                 200                 205

Phe Gly Val Glu Ala Val Ser Ala Asn Ile Asp Asp Arg Thr Leu His
210                 215                 220

Glu Tyr Tyr Leu Trp Pro Phe Met Asp Ser Val His Ala Gly Val Gly
225                 230                 235                 240

Ser Val Met Cys Ser Tyr Asn Arg Ile Asn Asn Thr Tyr Gly Cys Met
                245                 250                 255

Asn Asp Lys Leu Met Asn Gly Ile Leu Lys Ala Glu Leu Gly Phe Gln
            260                 265                 270

Gly Phe Val Met Leu Asp Trp Asn Ala Gln His Asp Leu Gln Ser Ala
        275                 280                 285

Asn Ala Gly Leu Asp Met Val Met Pro Leu Gly Gly Ser Trp Gly Lys
290                 295                 300

Asn Leu Thr Asp Ala Val Ala Asn Gly Thr Val Ser Glu Ser Arg Ile
305                 310                 315                 320

Thr Asp Met Ala Thr Arg Ile Ile Ala Ala Trp Tyr Leu Val Gly Gln
                325                 330                 335

Asp Gly Asn Asn Phe Pro Val Pro Gly Ile Gly Leu Lys Gln Leu Thr
            340                 345                 350

Lys Pro His Glu Gln Val Asp Ala Arg Asp Pro Ala Ser Lys Pro Val
        355                 360                 365

Leu Leu Glu Gly Ala Ile Ala Gly His Val Leu Val Lys Asn Glu Asn
370                 375                 380

Asn Ala Leu Pro Phe Asn Lys Lys Leu Thr Met Ile Ser Val Phe Gly
385                 390                 395                 400

Tyr Asp Ala Thr Ile Pro Arg Thr Lys Asn Thr Asp Ile Leu Phe Gln
                405                 410                 415

Leu Gly Tyr Thr Ser Ser Pro Glu Met Ala Gln Ala Val Leu Gly Asn
            420                 425                 430
```

```
Glu Ala His Phe Asp Gln Ala Lys Gly Gly Thr Ile Met Thr Gly
            435                 440                 445
Gly Arg Ala Gly Ala Asn Ala Pro Ser Tyr Ile Asp Asp Pro Leu Ala
450                 455                 460
Ala Ile Gln Arg Arg Ala Arg Lys Asp Asp Thr Trp Val Asn Trp Asp
465                 470                 475                 480
Leu Asp Ser Phe Asn Pro Glu Val Asn Ala Ser Asp Ala Cys Leu
            485                 490                 495
Val Phe Ile Asn Ala Ile Ala Thr Glu Gly Trp Asp Arg Asp Gly Leu
            500                 505                 510
His Asp Asp Phe Ser Asp Gly Leu Val Leu Asn Val Ala Ala Asn Cys
            515                 520                 525
Ser Asn Thr Ile Val Val His Ala Ala Gly Thr Arg Leu Val Asp
            530                 535                 540
Gln Trp Ile Glu His Pro Asn Val Thr Ala Ala Val Ile Ala His Leu
545                 550                 555                 560
Pro Gly Gln Asp Ser Gly Arg Ala Leu Val Lys Leu Leu Tyr Gly Glu
            565                 570                 575
Ala Asn Phe Ser Gly Lys Leu Pro Tyr Thr Ile Ala Lys Asn Glu Ser
            580                 585                 590
Asp Tyr Ser Val Tyr Thr Pro Cys Gln Arg Ser Pro Glu Asp Thr
            595                 600                 605
Asp Pro Gln Cys Asp Phe Thr Glu Gly Val Tyr Leu Asp Tyr Arg Ala
            610                 615                 620
Phe Asp Ala Asn Asn Met Thr Pro Arg Phe Glu Phe Gly Tyr Gly Leu
625                 630                 635                 640
Ser Tyr Thr Ser Phe Asn Tyr Ser Ala Leu Ser Ile Lys Lys Ala Lys
            645                 650                 655
Gly Leu Arg Gln Ser Arg Cys Thr Asp Asp Leu Trp Gln Ala Ala Ala
            660                 665                 670
Gln Val Thr Ala Ser Ile Thr Asn Ser Gly Met Ser Gly Ser Glu
            675                 680                 685
Val Ala Gln Leu Tyr Leu Ala Ile Pro Asn Ser Pro Pro Lys Gln Leu
            690                 695                 700
Arg Gly Phe Asn Lys Leu Leu Leu Arg Pro His Glu Ser Gly Thr Val
705                 710                 715                 720
His Phe Gly Leu Thr Lys Arg Asp Leu Ser Val Trp Asp Val Val Ser
            725                 730                 735
Gln Ser Trp Val Ile Gln Glu Gly Glu Tyr Lys Val Phe Val Gly Ala
            740                 745                 750
Ser Ser Arg Asp Ile Arg Leu Ser Gly Lys Leu His Ile
            755                 760                 765

<210> SEQ ID NO 33
<211> LENGTH: 843
<212> TYPE: PRT
<213> ORGANISM: Uromyces fabae

<400> SEQUENCE: 33

Met Lys Thr Pro Leu Gly Ile Gly Ser Thr Ala Val Leu Tyr Ile
1               5                   10                  15

Leu Ser Asn Ile Ser His Val Gln Leu Ala Thr Thr Ser Pro Ser Glu
            20                  25                  30

Asn Gln Asn Gln Ser Tyr Asn Pro Gln Ile Glu Gly Leu Thr Val Gln
            35                  40                  45
```

-continued

```
Pro Ser Thr Val Ala Asn Gly Leu Arg Ile Asn Ser Asn Ser Leu Ile
    50                  55                  60

Ser Asn Phe Asp Phe Glu Ile Ile Gln Pro Pro Gly Tyr Glu
65                  70                  75                  80

Trp Thr Ser Pro Val Val Leu Pro Ala Pro Val Gln Ser Gly Leu Ser
                85                  90                  95

Pro Trp Ser Glu Ser Ile Val Arg Ala Arg Ala Phe Val Ala Gln Leu
                100                 105                 110

Thr Ile Glu Glu Lys Val Asn Leu Thr Thr Gly Ala Gly Thr Gln Gly
                115                 120                 125

Arg Cys Val Gly Glu Thr Gly Thr Val Pro Arg Leu Gly Phe Asn Gln
    130                 135                 140

Pro Ile Cys Leu Gln Asp Gly Pro Val Gly Ile Arg Tyr Thr Asp Phe
145                 150                 155                 160

Asn Ser Val Phe Pro Ala Ala Ile Asn Val Ala Ala Thr Phe Asp Lys
                165                 170                 175

Gln Leu Met Phe Lys Arg Ala Gln Ala Met Ala Glu Glu Phe Arg Gly
                180                 185                 190

Lys Gly Ala Asn Val Val Leu Ala Pro Met Thr Asn Leu Met Arg Thr
    195                 200                 205

Pro Gln Ala Gly Arg Ala Trp Glu Gly Tyr Gly Ser Asp Pro Tyr Leu
    210                 215                 220

Ser Gly Val Ala Thr Val Gln Ser Val Leu Gly Ile Gln Ser Thr Arg
225                 230                 235                 240

Ala Ser Ala Cys Val Lys His Tyr Ile Gly Asn Glu Gln Glu His Tyr
                245                 250                 255

Arg Gly Gly Ser Gly Ala Thr Ala Ser Ser Asn Ile Asp Asp Arg
    260                 265                 270

Thr Leu Arg Glu Leu Tyr Glu Trp Pro Phe Ala Glu Ala Ile His Ala
    275                 280                 285

Gly Val Asp Tyr Ile Met Cys Ser Tyr Asn Arg Val Asn Gln Thr Tyr
    290                 295                 300

Ala Cys Glu Asn Ser Lys Leu Ile Asn Gly Ile Ala Lys Gly Glu His
305                 310                 315                 320

Lys Phe Gln Gly Val Met Val Thr Asp Trp Ala Ala Ala Glu Ser Gly
                325                 330                 335

Val Arg Thr Ala Leu Ala Gly Thr Asp Met Asn Met Pro Gly Phe Met
                340                 345                 350

Ala Tyr Gly Gln Pro Ser Glu Pro Asn Pro Ser Thr Ala Asn Gly Ser
    355                 360                 365

Tyr Trp Gly Leu Arg Met Ile Glu Ala Val Lys Asn Gly Thr Val Pro
    370                 375                 380

Met Glu Arg Leu Asp Asp Met Val Thr Arg Val Ile Ser Thr Tyr Tyr
385                 390                 395                 400

Lys Gln Gly Gln Asp Lys Ser Asp Tyr Pro Lys Leu Asn Phe Met Ser
                405                 410                 415

Met Gly Gln Gly Thr Pro Ala Glu Gln Ala Val Ser Asn His Val
                420                 425                 430

Asn Val Gln Lys Asp His Tyr Leu Ile Ile Arg Gln Ile Ala Thr Ala
    435                 440                 445

Ser Thr Ile Leu Leu Lys Asn Val Asn His Thr Leu Pro Leu Lys Ser
    450                 455                 460
```

```
Pro Asp Lys Met Arg Ser Val Val Val Gly Ser Asp Ala Gly Asp
465                 470                 475                 480

Asn Pro Gln Gly Pro Asn Ser Cys Val Asp Arg Gly Cys Asn Arg Gly
            485                 490                 495

Ile Leu Ala Ile Gly Trp Gly Ser Gly Thr Ala Asn Phe Ala His Leu
            500                 505                 510

Thr Ala Pro Ala Thr Ser Ile Gln Asn Tyr Leu Leu Gln Ser Asn Pro
            515                 520                 525

Thr Ile Thr Tyr Arg Ser Ile Phe Asp Asp Tyr Ala Tyr Asp Glu Ile
        530                 535                 540

Ala Lys Ala Ala Ser Thr Ala Asp Val Ser Ile Val His Val Ser Ser
545                 550                 555                 560

Asp Ser Gly Glu Gly Tyr Leu Thr Val Glu Gly Asn Gln Gly Asp Arg
                565                 570                 575

Ser Asn Thr Ser Leu Trp Asn Lys Gly Asp Glu Leu Ile Leu Lys Ala
            580                 585                 590

Ala Glu Ala Cys Asn Asn Val Val Val Ile His Ser Val Gly Pro
        595                 600                 605

Val Asp Met Glu Ala Trp Ile Asn His Pro Asn Val Thr Ala Val Leu
    610                 615                 620

Leu Ala Gly Leu Pro Gly Gln Glu Ala Gly Ser Ala Glu Val Asp Val
625                 630                 635                 640

Leu Trp Gly Ser Thr Asn Pro Ser Gly Arg Leu Pro Tyr Thr Ile Ala
                645                 650                 655

Lys Lys Pro Ser Asp Tyr Pro Ala Glu Leu Leu Tyr Glu Ser Asn Met
            660                 665                 670

Thr Val Pro Gln Ile Asn Tyr Ser Glu Arg Leu Asn Ile Asp Tyr Arg
        675                 680                 685

His Phe Asp Thr Tyr Asn Ile Glu Pro Arg Phe Glu Phe Gly Phe Gly
    690                 695                 700

Leu Ser Tyr Thr Thr Phe Ala Trp Asn Ser Leu Lys Phe Ser Ser Ser
705                 710                 715                 720

Phe Gln Leu Gln Lys Thr Ser Pro Val Ile Val Pro Pro Asn Leu Asp
                725                 730                 735

Leu Tyr Gln Asp Val Ile Glu Phe Glu Phe Gln Val Thr Asn Ser Gly
            740                 745                 750

Pro Phe Asp Gly Ser Glu Val Ala Gln Leu Tyr Val Asp Phe Pro Asn
        755                 760                 765

Gln Val Asn Glu Pro Pro Lys Val Leu Arg Gly Phe Glu Arg Ala Tyr
    770                 775                 780

Ile Pro Ser Lys Gln Ser Lys Thr Ile Glu Ile Lys Leu Arg Val Lys
785                 790                 795                 800

Asp Leu Ser Phe Trp Asp Val Ile Thr Gln Ser Trp Gln Ile Pro Asp
                805                 810                 815

Gly Lys Phe Asn Phe Met Ile Gly Ser Ser Ser Arg Lys Ile Ile Phe
            820                 825                 830

Thr Gln Glu Ile Ser Leu Gln His Ser His Met
        835                 840

<210> SEQ ID NO 34
<211> LENGTH: 736
<212> TYPE: PRT
<213> ORGANISM: Aspergillus terreus

<400> SEQUENCE: 34
```

```
Met Asn Tyr Arg Val Pro Ser Leu Lys Ala Thr Ala Leu Ala Met Ala
1               5                   10                  15

Ala Leu Thr Gln Ala Leu Thr Thr Trp Asp Ala Ala Tyr Glu Lys Ala
            20                  25                  30

Leu Ala Asp Leu Ala Ser Leu Thr Gln Ser Glu Lys Val Gly Val Val
        35                  40                  45

Ser Gly Ile Thr Trp Glu Gly Pro Cys Val Gly Asn Thr Tyr Ala
50                  55                  60

Pro Glu Ser Ile Ala Tyr Pro Ser Leu Cys Leu Gln Asp Gly Pro Leu
65                  70                  75                  80

Gly Ile Arg Phe Ala Asn Pro Val Thr Ala Phe Pro Ala Gly Ile Asn
                85                  90                  95

Ala Gly Ala Thr Trp Asp Arg Glu Leu Leu Arg Ala Arg Gly Ala Ala
            100                 105                 110

Met Gly Glu Glu Ala Lys Gly Leu Gly Val His Val Gln Leu Ala Pro
            115                 120                 125

Val Ala Gly Ala Leu Gly Lys Ile Pro Ser Ala Gly Arg Asn Trp Glu
        130                 135                 140

Gly Phe Thr Ser Asp Pro Tyr Leu Ser Gly Ile Ala Met Ala Glu Thr
145                 150                 155                 160

Ile His Gly Met Gln Gly Ser Gly Val Gln Ala Cys Ala Lys His Tyr
                165                 170                 175

Ile Leu Asn Glu Gln Glu His Ser Arg Glu Thr Ile Ser Ser Asn Val
            180                 185                 190

Asp Asp Arg Thr Met His Glu Val Tyr Leu Trp Pro Phe Tyr Asp Ala
            195                 200                 205

Val Lys Ala Asn Val Ala Ser Val Met Cys Ser Tyr Asn Lys Ile Asn
        210                 215                 220

Gly Thr Trp Ala Cys Glu Asn Glu Gly Ile Leu Asp Thr Leu Leu Lys
225                 230                 235                 240

Gln Glu Leu Gly Phe Arg Gly Tyr Val Met Ser Asp Trp Asn Ala Gln
                245                 250                 255

His Ser Thr Val Ala Ser Ala Asn Thr Gly Leu Asp Met Thr Met Pro
            260                 265                 270

Gly Ser Asp Phe Ser Gln Pro Pro Gly Ser Ile Tyr Trp Asn Glu Asn
        275                 280                 285

Leu Ala Glu Ala Val Ala Asn Gly Ser Val Pro Gln Ala Arg Val Asp
        290                 295                 300

Asp Met Val Thr Arg Ile Leu Ala Ala Trp Tyr Leu Leu Glu Gln Asp
305                 310                 315                 320

Gln Gly Tyr Pro Ala Val Ala Phe Asp Ser Arg Asn Gly Gly Lys Ala
                325                 330                 335

Ser Val Asp Val Thr Ala Asp His Ala Asp Ile Ala Arg Thr Val Ala
            340                 345                 350

Arg Asp Ser Ile Val Leu Leu Lys Asn Ser Asn Asn Thr Leu Pro Leu
        355                 360                 365

Arg Asn Pro Ser Ser Ile Ala Val Val Gly Ser Asp Ala Ile Val Asn
        370                 375                 380

Pro Asp Gly Pro Asn Ala Cys Thr Asp Arg Gly Cys Asn Val Gly Thr
385                 390                 395                 400

Leu Ala Gln Gly Trp Gly Ser Gly Thr Ala Glu Phe Pro Tyr Leu Val
                405                 410                 415
```

Ala Pro Leu Asp Ala Ile Gln Glu Arg Ser Ser Gly Asn Gly Thr Lys
            420                 425                 430

Val Val Thr Ser Thr Thr Asp Ala Thr Ala Gly Ala Asp Ala Ala
        435                 440                 445

Ala Ser Ala Asp Ile Ala Ile Val Phe Ile Ser Ser Asp Ser Gly Glu
    450                 455                 460

Gly Tyr Ile Thr Val Glu Gly His Gln Gly Asp Arg Asn Asn Leu Asp
465                 470                 475                 480

Pro Trp His Gly Gly Asn Asp Leu Val Lys Ala Val Ala Ala Val Asn
                485                 490                 495

Lys Lys Thr Ile Val Val His Ser Thr Gly Pro Val Val Leu Glu
            500                 505                 510

Thr Ile Leu Ala Gln Pro Asn Val Val Ala Val Val Trp Ala Gly Ile
            515                 520                 525

Pro Gly Gln Glu Ser Gly Asn Ala Leu Ala Asp Val Leu Tyr Gly Asp
    530                 535                 540

Val Ser Pro Ser Gly Lys Leu Pro Tyr Thr Ile Gly Lys Ser Glu Ala
545                 550                 555                 560

Asp Tyr Gly Thr Thr Trp Val Ala Asn Gly Ala Asp Asp Phe Pro
            565                 570                 575

Glu Gly Leu Phe Ile Asp Tyr Arg His Phe Asp Lys Asn Glu Ile Glu
            580                 585                 590

Pro Arg Tyr Glu Phe Gly Phe Gly Leu Ser Tyr Thr Arg Phe Asn Phe
    595                 600                 605

Ser Asn Leu Ala Ile Asn Ile Asp Ala Thr Ser Gly Pro Thr Ser Gly
    610                 615                 620

Ala Val Asp Val Gly Gly Ala Ala Asp Leu Tyr Asp Ser Val Gly Thr
625                 630                 635                 640

Ile Ser Ala Thr Val Thr Asn Val Gly Gly Val Ser Gly Ala Glu Val
            645                 650                 655

Ala Gln Leu Tyr Ile Gly Phe Pro Ser Ser Ala Pro Glu Thr Pro Pro
    660                 665                 670

Lys Gln Leu Arg Gly Phe Gln Lys Leu Pro Leu Ala Gly Gly Ala Asp
    675                 680                 685

Gly Val Ala Glu Phe Glu Leu Thr Arg Arg Asp Ile Ser Tyr Trp Asp
690                 695                 700

Val Gly Gln Gln Lys Trp Val Val Pro Glu Gly Ser Phe Gln Val Tyr
705                 710                 715                 720

Val Gly Ala Ser Ser Arg Asp Ile Arg Leu Asp Gly Ser Phe Thr Val
            725                 730                 735

<210> SEQ ID NO 35
<211> LENGTH: 726
<212> TYPE: PRT
<213> ORGANISM: Chaetomium globosum

<400> SEQUENCE: 35

Met Thr Thr Leu Arg Asn Phe Ala Leu Leu Ala Ala Ala Val Leu Ala
1               5                   10                  15

Arg Val Glu Ala Leu Glu Ala Ala Asp Trp Ala Ala Glu Ala Ser
            20                  25                  30

Ala Lys Thr Ala Leu Ala Lys Met Ser Gln Gln Asp Lys Ile Ser Ile
            35                  40                  45

Val Thr Gly Ile Gly Trp Asp Lys Gly Pro Cys Val Gly Asn Thr Ala
        50                  55                  60

```
Ala Ile Asn Ser Ile Asn Tyr Pro Gln Leu Cys Leu Gln Asp Gly Pro
 65                  70                  75                  80

Leu Gly Ile Arg Phe Gly Thr Gly Ser Thr Ala Phe Thr Pro Gly Val
                 85                  90                  95

Gln Ala Ala Ser Thr Trp Asp Thr Glu Leu Met Arg Gln Arg Gly Glu
            100                 105                 110

Tyr Leu Gly Ala Glu Ala Lys Gly Cys Gly Ile His Val Leu Leu Gly
        115                 120                 125

Pro Val Ala Gly Ala Leu Gly Lys Ile Pro His Gly Gly Arg Asn Trp
    130                 135                 140

Glu Gly Phe Gly Thr Asp Pro Tyr Leu Ala Gly Ile Ala Met Ala Glu
145                 150                 155                 160

Thr Ile Glu Gly Leu Gln Ser Ala Gly Val Gln Ala Cys Ala Lys His
                165                 170                 175

Tyr Ile Val Asn Glu Gln Glu Leu Asn Arg Glu Thr Ile Ser Ser Asp
            180                 185                 190

Val Asp Asp Arg Thr Met His Glu Leu Tyr Leu Trp Pro Phe Ala Asp
        195                 200                 205

Ala Val His Ala Asn Val Ala Ser Val Met Cys Ser Tyr Asn Lys Ile
    210                 215                 220

Asn Gly Ser Trp Gly Cys Glu Asn Asp His Ala Gln Asn Gly Leu Leu
225                 230                 235                 240

Lys Lys Glu Leu Gly Phe Lys Gly Tyr Val Val Ser Asp Trp Asn Ala
                245                 250                 255

Gln His Thr Thr Asp Gly Ala Ala Asn Asn Gly Met Asp Met Thr Met
            260                 265                 270

Pro Gly Ser Asp Tyr Asn Gly Asn Asn Val Leu Trp Gly Pro Gln Leu
        275                 280                 285

Ser Asn Ala Val Asn Ser Asn Arg Val Ser Arg Asp Arg Leu Asp Asp
    290                 295                 300

Met Ala Lys Arg Ile Leu Thr Ser Trp Tyr Leu Leu Gly Gln Asn Ser
305                 310                 315                 320

Gly Tyr Pro Asn Ile Asn Ile Asn Ala Asn Val Gln Gly Asn His Lys
                325                 330                 335

Glu Asn Val Arg Ala Val Ala Arg Asp Gly Ile Val Leu Leu Lys Asn
            340                 345                 350

Asp Glu Gly Val Leu Pro Leu Lys Lys Pro Gly Lys Val Ala Leu Val
        355                 360                 365

Gly Ser Ala Ala Ser Val Asn Ser Ala Gly Pro Asn Ala Cys Val Asp
    370                 375                 380

Lys Gly Cys Asn Thr Gly Ala Leu Gly Met Gly Trp Gly Ser Gly Ser
385                 390                 395                 400

Val Asn Tyr Pro Tyr Phe Val Ala Pro Tyr Asp Ala Leu Lys Thr Arg
                405                 410                 415

Ala Gln Ala Asp Gly Thr Leu Ser Leu His Asn Ser Asp Ser Thr
            420                 425                 430

Asn Gly Val Ser Gly Val Val Ser Gly Ala Asp Val Ala Ile Val Val
        435                 440                 445

Ile Thr Ala Asp Ser Gly Glu Gly Tyr Ile Thr Val Glu Gly His Ala
    450                 455                 460

Gly Asp Arg Asn His Leu Asp Pro Trp His Asp Gly Asn Ala Leu Val
465                 470                 475                 480
```

```
Lys Ala Val Ala Ala Ala Asn Lys Asn Thr Ile Val Val His Ser
                485                 490                 495

Thr Gly Pro Ile Ile Leu Glu Thr Ile Leu Ala Thr Glu Gly Val Lys
            500                 505                 510

Ala Val Val Trp Ala Gly Leu Pro Ser Gln Glu Asn Gly Asn Ala Leu
            515                 520                 525

Val Asp Val Leu Tyr Gly Leu Thr Ser Pro Ser Gly Lys Leu Val Tyr
    530                 535                 540

Ser Ile Ala Lys Arg Pro Glu Asp Tyr Gly Thr Ala Pro Ser Lys Gly
545                 550                 555                 560

Ser Asn Asp Lys Phe Thr Glu Gly Leu Phe Val Asp Tyr Arg His Phe
                565                 570                 575

Asp Asn Ala Lys Ile Glu Pro Arg Tyr Glu Phe Gly Phe Gly Leu Ser
            580                 585                 590

Tyr Thr Glu Phe Thr Tyr Ala Asp Leu Ser Val Thr Ser Thr Val Thr
            595                 600                 605

Ala Gly Pro Ala Ser Gly Glu Thr Ile Pro Gly Gly Ala Ala Asp Leu
            610                 615                 620

Trp Glu Thr Val Ala Thr Val Thr Ala Ser Ile Thr Asn Ser Gly Glu
625                 630                 635                 640

Val Glu Gly Ala Glu Val Ala Gln Leu Tyr Ile Thr Leu Pro Ser Ala
                645                 650                 655

Ala Pro Ser Thr Pro Pro Lys Gln Leu Arg Gly Phe Ala Lys Leu Lys
            660                 665                 670

Leu Glu Pro Gly Ala Ser Gly Val Ala Thr Phe Asn Leu Arg Arg Arg
            675                 680                 685

Asp Leu Ser Tyr Trp Asp Ala Gly Arg Gly Gln Trp Val Val Pro Ala
    690                 695                 700

Gly Glu Phe Thr Val Ser Val Gly Ala Ser Ser Arg Asp Val Arg Leu
705                 710                 715                 720

Thr Gly Ser Leu Thr Ala
                725

<210> SEQ ID NO 36
<211> LENGTH: 874
<212> TYPE: PRT
<213> ORGANISM: Trichoderma reesei

<400> SEQUENCE: 36

Met Lys Thr Leu Ser Val Phe Ala Ala Ala Leu Leu Ala Ala Val Ala
1               5                   10                  15

Glu Ala Asn Pro Tyr Pro Pro His Ser Asn Gln Ala Tyr Ser Pro
                20                  25                  30

Pro Phe Tyr Pro Ser Pro Trp Met Asp Pro Ser Ala Pro Gly Trp Glu
            35                  40                  45

Gln Ala Tyr Ala Gln Ala Lys Glu Phe Val Ser Gly Leu Thr Leu Leu
        50                  55                  60

Glu Lys Val Asn Leu Thr Thr Gly Val Gly Trp Met Gly Glu Lys Cys
65                  70                  75                  80

Val Gly Asn Val Gly Thr Val Pro Arg Leu Gly Met Arg Ser Leu Cys
                85                  90                  95

Met Gln Asp Gly Pro Leu Gly Leu Arg Phe Asn Thr Tyr Asn Ser Ala
            100                 105                 110

Phe Ser Val Gly Leu Thr Ala Ala Ser Trp Ser Arg His Leu Trp
        115                 120                 125
```

-continued

```
Val Asp Arg Gly Thr Ala Leu Gly Ser Glu Ala Lys Gly Lys Gly Val
            130                 135                 140
Asp Val Leu Leu Gly Pro Val Ala Gly Pro Leu Gly Arg Asn Pro Asn
145                 150                 155                 160
Gly Gly Arg Asn Val Glu Gly Phe Gly Ser Asp Pro Tyr Leu Ala Gly
                165                 170                 175
Leu Ala Leu Ala Asp Thr Val Thr Gly Ile Gln Asn Ala Gly Thr Ile
                180                 185                 190
Ala Cys Ala Lys His Phe Leu Leu Asn Glu Gln Glu His Phe Arg Gln
                195                 200                 205
Val Gly Glu Ala Asn Gly Tyr Gly Tyr Pro Ile Thr Glu Ala Leu Ser
            210                 215                 220
Ser Asn Val Asp Asp Lys Thr Ile His Glu Val Tyr Gly Trp Pro Phe
225                 230                 235                 240
Gln Asp Ala Val Lys Ala Gly Val Gly Ser Phe Met Cys Ser Tyr Asn
                245                 250                 255
Gln Val Asn Asn Ser Tyr Ala Cys Gln Asn Ser Lys Leu Ile Asn Gly
                260                 265                 270
Leu Leu Lys Glu Glu Tyr Gly Phe Gln Gly Phe Val Met Ser Asp Trp
            275                 280                 285
Gln Ala Gln His Thr Gly Val Ala Ser Ala Val Ala Gly Leu Asp Met
            290                 295                 300
Thr Met Pro Gly Asp Thr Ala Phe Asn Thr Gly Ala Ser Tyr Phe Gly
305                 310                 315                 320
Ser Asn Leu Thr Leu Ala Val Leu Asn Gly Thr Val Pro Glu Trp Arg
                325                 330                 335
Ile Asp Asp Met Val Met Arg Ile Met Ala Pro Phe Phe Lys Val Gly
                340                 345                 350
Lys Thr Val Asp Ser Leu Ile Asp Thr Asn Phe Asp Ser Trp Thr Asn
            355                 360                 365
Gly Glu Tyr Gly Tyr Val Gln Ala Val Asn Glu Asn Trp Glu Lys
            370                 375                 380
Val Asn Tyr Gly Val Asp Val Arg Ala Asn His Ala Asn His Ile Arg
385                 390                 395                 400
Glu Val Gly Ala Lys Gly Thr Val Ile Phe Lys Asn Asn Gly Ile Leu
                405                 410                 415
Pro Leu Lys Lys Pro Lys Phe Leu Thr Val Ile Gly Glu Asp Ala Gly
            420                 425                 430
Gly Asn Pro Ala Gly Pro Asn Gly Cys Gly Asp Arg Gly Cys Asp Asp
            435                 440                 445
Gly Thr Leu Ala Met Glu Trp Gly Ser Gly Thr Thr Asn Phe Pro Tyr
450                 455                 460
Leu Val Thr Pro Asp Ala Ala Leu Gln Ser Gln Ala Leu Gln Asp Gly
465                 470                 475                 480
Thr Arg Tyr Glu Ser Ile Leu Ser Asn Tyr Ala Ile Ser Gln Thr Gln
                485                 490                 495
Ala Leu Val Ser Gln Pro Asp Ala Ile Ala Ile Val Phe Ala Asn Ser
                500                 505                 510
Asp Ser Gly Glu Gly Tyr Ile Asn Val Asp Gly Asn Glu Gly Asp Arg
            515                 520                 525
Lys Asn Leu Thr Leu Trp Lys Asn Gly Asp Asp Leu Ile Lys Thr Val
530                 535                 540
```

-continued

```
Ala Ala Val Asn Pro Lys Thr Ile Val Val Ile His Ser Thr Gly Pro
545                 550                 555                 560

Val Ile Leu Lys Asp Tyr Ala Asn His Pro Asn Ile Ser Ala Ile Leu
            565                 570                 575

Trp Ala Gly Ala Pro Gly Gln Glu Ser Gly Asn Ser Leu Val Asp Ile
        580                 585                 590

Leu Tyr Gly Lys Gln Ser Pro Gly Arg Thr Pro Phe Thr Trp Gly Pro
    595                 600                 605

Ser Leu Glu Ser Tyr Gly Val Ser Val Met Thr Thr Pro Asn Asn Gly
610                 615                 620

Asn Gly Ala Pro Gln Asp Asn Phe Asn Glu Gly Ala Phe Ile Asp Tyr
625                 630                 635                 640

Arg Tyr Phe Asp Lys Val Ala Pro Gly Lys Pro Arg Ser Ser Asp Lys
            645                 650                 655

Ala Pro Thr Tyr Glu Phe Gly Phe Gly Leu Ser Trp Ser Thr Phe Lys
        660                 665                 670

Phe Ser Asn Leu His Ile Gln Lys Asn Val Gly Pro Met Ser Pro
675                 680                 685

Pro Asn Gly Lys Thr Ile Ala Ala Pro Ser Leu Gly Ser Phe Ser Lys
690                 695                 700

Asn Leu Lys Asp Tyr Gly Phe Pro Lys Asn Val Arg Arg Ile Lys Glu
705                 710                 715                 720

Phe Ile Tyr Pro Tyr Leu Ser Thr Thr Thr Ser Gly Lys Glu Ala Ser
            725                 730                 735

Gly Asp Ala His Tyr Gly Gln Thr Ala Lys Glu Phe Leu Pro Ala Gly
        740                 745                 750

Ala Leu Asp Gly Ser Pro Gln Pro Arg Ser Ala Ala Ser Gly Glu Pro
    755                 760                 765

Gly Gly Asn Arg Gln Leu Tyr Asp Ile Leu Tyr Thr Val Thr Ala Thr
770                 775                 780

Ile Thr Asn Thr Gly Ser Val Met Asp Asp Ala Val Pro Gln Leu Tyr
785                 790                 795                 800

Leu Ser His Gly Gly Pro Asn Glu Pro Pro Lys Val Leu Arg Gly Phe
            805                 810                 815

Asp Arg Ile Glu Arg Ile Ala Pro Gly Gln Ser Val Thr Phe Lys Ala
        820                 825                 830

Asp Leu Thr Arg Arg Asp Leu Ser Asn Trp Asp Thr Lys Lys Gln Gln
    835                 840                 845

Trp Val Ile Thr Asp Tyr Pro Lys Thr Val Tyr Val Gly Ser Ser Ser
850                 855                 860

Arg Asp Leu Pro Leu Ser Ala Arg Leu Pro
865                 870

<210> SEQ ID NO 37
<211> LENGTH: 878
<212> TYPE: PRT
<213> ORGANISM: Penicillium brasilianum

<400> SEQUENCE: 37

Met Gln Gly Ser Thr Ile Phe Leu Ala Phe Ala Ser Trp Ala Ser Gln
1               5                   10                  15

Val Ala Ala Ile Ala Gln Pro Ile Gln Lys His Glu Pro Gly Phe Leu
            20                  25                  30

His Gly Pro Gln Ala Ile Glu Ser Phe Ser Glu Pro Tyr Pro Ser
        35                  40                  45
```

```
Pro Trp Met Asn Pro His Ala Glu Gly Trp Glu Ala Tyr Gln Lys
    50                  55                  60

Ala Gln Asp Phe Val Ser Gln Leu Thr Ile Leu Glu Lys Ile Asn Leu
65                  70                  75                  80

Thr Thr Gly Val Gly Trp Glu Asn Gly Pro Cys Val Gly Asn Thr Gly
                85                  90                  95

Ser Ile Pro Arg Leu Gly Phe Lys Gly Phe Cys Thr Gln Asp Ser Pro
            100                 105                 110

Gln Gly Val Arg Phe Ala Asp Tyr Ser Ser Ala Phe Thr Ser Ser Gln
            115                 120                 125

Met Ala Ala Thr Phe Asp Arg Ser Ile Leu Tyr Arg Gly Gln
130                 135                 140

Ala Met Ala Gln Glu His Lys Ala Lys Gly Ile Thr Ile Gln Leu Gly
145                 150                 155                 160

Pro Val Ala Gly Pro Leu Gly Arg Ile Pro Glu Gly Gly Arg Asn Trp
            165                 170                 175

Glu Gly Phe Ser Pro Asp Pro Val Leu Thr Gly Ile Ala Met Ala Glu
            180                 185                 190

Thr Ile Lys Gly Met Gln Asp Thr Gly Val Ile Ala Cys Ala Lys His
            195                 200                 205

Tyr Ile Gly Asn Glu Gln Glu His Phe Arg Gln Val Gly Glu Ala Ala
210                 215                 220

Gly His Gly Tyr Thr Ile Ser Asp Thr Ile Ser Ser Asn Ile Asp Asp
225                 230                 235                 240

Arg Ala Met His Glu Leu Tyr Leu Trp Pro Phe Ala Asp Ala Val Arg
                245                 250                 255

Ala Gly Val Gly Ser Phe Met Cys Ser Tyr Ser Gln Ile Asn Asn Ser
            260                 265                 270

Tyr Gly Cys Gln Asn Ser Gln Thr Leu Asn Lys Leu Leu Lys Ser Glu
            275                 280                 285

Leu Gly Phe Gln Gly Phe Val Met Ser Asp Trp Gly Ala His His Ser
            290                 295                 300

Gly Val Ser Ser Ala Leu Ala Gly Leu Asp Met Ser Met Pro Gly Asp
305                 310                 315                 320

Thr Glu Phe Asp Ser Gly Leu Ser Phe Trp Gly Ser Asn Leu Thr Ile
                325                 330                 335

Ala Ile Leu Asn Gly Thr Val Pro Glu Trp Arg Leu Asp Asp Met Ala
                340                 345                 350

Met Arg Ile Met Ala Ala Tyr Phe Lys Val Gly Leu Thr Ile Glu Asp
            355                 360                 365

Gln Pro Asp Val Asn Phe Asn Ala Trp Thr His Asp Thr Tyr Gly Tyr
            370                 375                 380

Lys Tyr Ala Tyr Ser Lys Glu Asp Tyr Glu Gln Val Asn Trp His Val
385                 390                 395                 400

Asp Val Arg Ser Asp His Asn Lys Leu Ile Arg Glu Thr Ala Ala Lys
                405                 410                 415

Gly Thr Val Leu Leu Lys Asn Asn Phe His Ala Leu Pro Leu Lys Gln
            420                 425                 430

Pro Arg Phe Val Ala Val Val Gly Gln Asp Ala Gly Pro Asn Pro Lys
            435                 440                 445

Gly Pro Asn Gly Cys Ala Asp Arg Gly Cys Asp Gln Gly Thr Leu Ala
450                 455                 460
```

-continued

```
Met Gly Trp Gly Ser Gly Ser Thr Glu Phe Pro Tyr Leu Val Thr Pro
465                 470                 475                 480

Asp Thr Ala Ile Gln Ser Lys Val Leu Glu Tyr Gly Gly Arg Tyr Glu
                485                 490                 495

Ser Ile Phe Asp Asn Tyr Asp Asn Ala Ile Leu Ser Leu Val Ser
            500                 505                 510

Gln Pro Asp Ala Thr Cys Ile Val Phe Ala Asn Ala Asp Ser Gly Glu
            515                 520                 525

Gly Tyr Ile Thr Val Asp Asn Trp Gly Asp Arg Asn Asn Leu Thr
    530                 535                 540

Leu Trp Gln Asn Ala Asp Gln Val Ile Ser Thr Val Ser Ser Arg Cys
545                 550                 555                 560

Asn Asn Thr Ile Val Val Leu His Ser Val Gly Pro Val Leu Leu Asn
                565                 570                 575

Gly Ile Tyr Glu His Pro Asn Ile Thr Ala Ile Val Trp Ala Gly Met
            580                 585                 590

Pro Gly Glu Glu Ser Gly Asn Ala Leu Val Asp Ile Leu Trp Gly Asn
        595                 600                 605

Val Asn Pro Ala Gly Arg Thr Pro Phe Thr Trp Ala Lys Ser Arg Glu
610                 615                 620

Asp Tyr Gly Thr Asp Ile Met Tyr Glu Pro Asn Asn Gly Gln Arg Ala
625                 630                 635                 640

Pro Gln Gln Asp Phe Thr Glu Ser Ile Tyr Leu Asp Tyr Arg His Phe
                645                 650                 655

Asp Lys Ala Gly Ile Glu Pro Ile Tyr Glu Phe Gly Phe Gly Leu Ser
            660                 665                 670

Tyr Thr Thr Phe Glu Tyr Ser Asp Leu Arg Val Val Lys Lys Tyr Val
            675                 680                 685

Gln Pro Tyr Ser Pro Thr Thr Gly Thr Gly Ala Gln Ala Pro Ser Ile
    690                 695                 700

Gly Gln Pro Pro Ser Gln Asn Leu Asp Thr Tyr Lys Phe Pro Ala Thr
705                 710                 715                 720

Tyr Lys Tyr Ile Lys Thr Phe Ile Tyr Pro Tyr Leu Asn Ser Thr Val
                725                 730                 735

Ser Leu Arg Ala Ala Ser Lys Asp Pro Glu Tyr Gly Arg Thr Asp Phe
            740                 745                 750

Ile Pro Pro His Ala Arg Asp Gly Ser Pro Gln Pro Leu Asn Pro Ala
            755                 760                 765

Gly Asp Pro Val Ala Ser Gly Asn Asn Met Leu Tyr Asp Glu Leu
    770                 775                 780

Tyr Glu Val Thr Ala Gln Ile Lys Asn Thr Gly Asp Val Ala Gly Asp
785                 790                 795                 800

Glu Val Val Gln Leu Tyr Val Asp Leu Gly Gly Asp Asn Pro Pro Arg
                805                 810                 815

Gln Leu Arg Asn Phe Asp Arg Phe Tyr Leu Pro Gly Gln Ser Ser
            820                 825                 830

Thr Phe Arg Ala Thr Leu Thr Arg Arg Asp Leu Ser Asn Trp Asp Ile
            835                 840                 845

Glu Ala Gln Asn Trp Arg Val Thr Glu Ser Pro Lys Arg Val Tyr Val
    850                 855                 860

Gly Arg Ser Ser Arg Asp Leu Pro Leu Ser Ser Gln Leu Glu
865                 870                 875
```

<210> SEQ ID NO 38
<211> LENGTH: 866
<212> TYPE: PRT
<213> ORGANISM: Periconia sp.

<400> SEQUENCE: 38

Met Ala Ser Trp Leu Ala Pro Ala Leu Leu Ala Val Gly Leu Ala Ser
1               5                   10                  15

Ala Gln Ala Pro Phe Pro Asn Gly Ser Ser Pro Leu Asn Asp Ile Thr
            20                  25                  30

Ser Pro Pro Phe Tyr Pro Ser Pro Trp Met Asp Pro Ser Ala Ala Gly
        35                  40                  45

Trp Ala Glu Ala Tyr Thr Lys Ala Gln Ala Phe Val Arg Gln Leu Thr
50                  55                  60

Leu Leu Glu Lys Val Asn Leu Thr Thr Gly Val Gly Trp Glu Gly Glu
65                  70                  75                  80

Ala Cys Val Gly Asn Thr Gly Ser Ile Pro Arg Leu Gly Phe Pro Gly
                85                  90                  95

Phe Cys Thr Gln Asp Ser Pro Leu Gly Val Arg Phe Ala Asp Tyr Val
            100                 105                 110

Ser Ala Phe Thr Ala Gly Gly Thr Ile Ala Ala Ser Trp Asp Arg Ser
        115                 120                 125

Glu Phe Tyr Arg Arg Gly Tyr Gln Met Gly Val Glu His Arg Gly Lys
130                 135                 140

Gly Val Asp Val Gln Leu Gly Pro Val Val Gly Pro Ile Gly Arg His
145                 150                 155                 160

Pro Lys Gly Gly Arg Asn Trp Glu Gly Phe Ser Pro Asp Pro Val Leu
                165                 170                 175

Ser Gly Ile Ala Val Ala Glu Thr Val Lys Gly Ile Gln Asp Ala Gly
            180                 185                 190

Val Ile Ala Cys Thr Lys His Phe Ile Leu Asn Glu Gln Glu His Phe
        195                 200                 205

Arg Gln Pro Gly Asn Val Gly Asp Phe Gly Phe Val Asp Ala Val Ser
210                 215                 220

Ala Asn Leu Ala Asp Lys Thr Leu His Glu Leu Tyr Leu Trp Pro Phe
225                 230                 235                 240

Ala Asp Ala Val Arg Ala Gly Thr Gly Ser Ile Met Cys Ser Tyr Asn
                245                 250                 255

Lys Ala Asn Asn Ser Gln Val Cys Gln Asn Ser Tyr Leu Gln Asn Tyr
            260                 265                 270

Ile Leu Lys Gly Glu Leu Gly Phe Gln Gly Phe Thr Met Ser Asp Trp
        275                 280                 285

Asp Ala Gln His Ser Gly Val Ala Ser Thr Leu Ala Gly Leu Asp Met
290                 295                 300

Asn Met Pro Gly Asp Thr Asp Phe Asp Ser Gly Phe Ser Phe Trp Gly
305                 310                 315                 320

Pro Asn Met Thr Leu Ser Ile Ile Asn Gly Thr Val Pro Glu Trp Arg
                325                 330                 335

Leu Asp Asp Ala Ala Thr Arg Ile Met Ala Ala Tyr Tyr Leu Val Gly
            340                 345                 350

Arg Asp Arg His Ala Val Pro Val Asn Phe Asn Ser Trp Ser Lys Asp
        355                 360                 365

Thr Tyr Gly Tyr Gln His Ala Tyr Ala Lys Val Gly Tyr Gly Leu Ile
370                 375                 380

```
Asn Gln His Val Asp Val Arg Ala Asp His Phe Lys Ser Ile Arg Thr
385                 390                 395                 400

Ala Ala Ala Lys Ser Thr Val Leu Leu Lys Asn Asn Gly Val Leu Pro
            405                 410                 415

Leu Lys Gly Thr Glu Lys Tyr Thr Ala Val Phe Gly Asn Asp Ala Gly
        420                 425                 430

Glu Ala Gln Tyr Gly Pro Asn Gly Cys Ala Asp His Gly Cys Asp Asn
            435                 440                 445

Gly Thr Leu Ala Met Gly Trp Gly Ser Gly Thr Ala Asp Tyr Pro Tyr
        450                 455                 460

Leu Val Thr Pro Leu Glu Ala Ile Lys Arg Thr Val Gly Asp His Gly
465                 470                 475                 480

Gly Val Ile Ala Ser Val Thr Asp Asn Tyr Ala Phe Ser Gln Ile Met
            485                 490                 495

Ala Leu Ala Lys Gln Ala Thr His Ala Ile Val Phe Val Asn Ala Asp
        500                 505                 510

Ser Gly Glu Gly Tyr Ile Thr Val Asp Gly Asn Glu Gly Asp Arg Asn
    515                 520                 525

Asn Leu Thr Leu Trp Gln Asn Gly Glu Glu Leu Val Arg Asn Val Ser
530                 535                 540

Gly Tyr Cys Asn Asn Thr Ile Val Val Ile His Ser Val Gly Pro Val
545                 550                 555                 560

Leu Val Asp Ser Phe Asn Asn Ser Pro Asn Val Ser Ala Ile Leu Trp
                565                 570                 575

Ala Gly Leu Pro Gly Gln Glu Ser Gly Asn Ala Ile Thr Asp Val Leu
            580                 585                 590

Tyr Gly Arg Val Asn Pro Gly Gly Lys Leu Pro Phe Thr Ile Gly Lys
            595                 600                 605

Ser Ala Glu Glu Tyr Gly Pro Asp Ile Ile Tyr Glu Pro Thr Ala Gly
    610                 615                 620

His Gly Ser Pro Gln Ala Asn Phe Glu Glu Gly Val Phe Ile Asp Tyr
625                 630                 635                 640

Arg Ser Phe Asp Lys Lys Asn Ile Thr Pro Val Tyr Glu Phe Gly Phe
                645                 650                 655

Gly Leu Ser Tyr Thr Asn Phe Ser Tyr Ser Asn Leu Val Val Thr Arg
            660                 665                 670

Val Asn Ala Pro Ala Tyr Val Pro Thr Thr Gly Asn Thr Thr Ala Ala
            675                 680                 685

Pro Thr Leu Gly Asn Ser Ser Lys Asp Ala Ser Asp Tyr Gln Trp Pro
            690                 695                 700

Ala Asn Leu Thr Tyr Val Asn Lys Tyr Ile Tyr Pro Tyr Leu Asn Ser
705                 710                 715                 720

Thr Asp Leu Lys Glu Ala Ser Asn Asp Pro Glu Tyr Gly Ile Glu His
                725                 730                 735

Glu Tyr Pro Glu Gly Ala Thr Asp Gly Ser Pro Gln Pro Arg Ile Ala
            740                 745                 750

Ala Gly Gly Gly Pro Gly Gly Asn Pro Gln Leu Trp Asp Val Leu Tyr
            755                 760                 765

Lys Val Thr Ala Thr Val Thr Asn Asn Gly Ala Val Ala Gly Asp Glu
            770                 775                 780

Val Ala Gln Leu Tyr Val Ser Leu Gly Gly Pro Glu Asp Pro Pro Val
785                 790                 795                 800

Val Leu Arg Asn Phe Asp Arg Leu Thr Ile Ala Pro Gly Gln Ser Val
```

```
                    805                 810                 815
Glu Phe Thr Ala Asp Ile Thr Arg Arg Asp Val Ser Asn Trp Asp Thr
                820                 825                 830

Val Ser Gln Asn Trp Val Ile Ser Asn Ser Thr Lys Thr Val Tyr Val
            835                 840                 845

Gly Ala Ser Ser Arg Lys Leu Pro Leu Lys Ala Thr Leu Pro Ser Ser
        850                 855                 860

Ser Tyr
865

<210> SEQ ID NO 39
<211> LENGTH: 871
<212> TYPE: PRT
<213> ORGANISM: Phaeosphaeria avenaria

<400> SEQUENCE: 39

Met Ala Leu Ala Val Ala Phe Phe Val Thr Gln Val Leu Ala Gln Gln
1               5                   10                  15

Tyr Pro Thr Ser Asn Thr Ser Ser Pro Ala Ala Asn Ser Ser Ser Pro
            20                  25                  30

Leu Asp Asn Ala Val Ser Pro Pro Phe Tyr Pro Ser Pro Trp Ile Glu
        35                  40                  45

Gly Leu Gly Asp Trp Glu Ala Ala Tyr Gln Lys Ala Gln Ala Phe Val
    50                  55                  60

Ser Gln Leu Thr Leu Leu Glu Lys Val Asn Leu Thr Thr Gly Thr Gly
65                  70                  75                  80

Trp Gln Ser Asp His Cys Val Gly Asn Thr Gly Val Pro Arg Leu
                85                  90                  95

Asn Phe Thr Gly Ile Cys Asn Gln Asp Ala Pro Leu Gly Val Arg Phe
            100                 105                 110

Ala Asp Tyr Val Ser Ala Phe Pro Ser Gly Gly Thr Ile Ala Ala Ala
        115                 120                 125

Trp Asp Arg Gly Glu Trp Tyr Leu Arg Gly Tyr Gln Met Gly Ser Glu
    130                 135                 140

His Arg Ser Lys Gly Val Asp Val Gln Leu Gly Pro Val Val Gly Pro
145                 150                 155                 160

Leu Gly Arg Asn Pro Lys Gly Gly Arg Asn Trp Glu Gly Phe Ser Pro
                165                 170                 175

Asp Pro Tyr Leu Ser Gly Ile Ala Ser Ala Glu Ser Val Arg Gly Ile
            180                 185                 190

Gln Asp Ala Gly Val Ile Ala Cys Thr Lys His Tyr Ile Met Asn Glu
        195                 200                 205

Gln Glu His Phe Arg Gln Pro Gly Asn Phe Glu Asp Gln Gly Phe Val
    210                 215                 220

Asp Ala Leu Ser Ser Asn Leu Asp Asp Lys Thr Leu His Glu Leu Tyr
225                 230                 235                 240

Leu Trp Pro Phe Ala Asp Ala Val Arg Ala Gly Thr Gly Ser Ile Met
                245                 250                 255

Cys Ser Tyr Asn Lys Val Asn Asn Ser Gln Ala Cys Gln Asn Ser Tyr
            260                 265                 270

Leu Gln Asn Tyr Ile Leu Lys Gly Glu Leu Gly Phe Gln Gly Phe Ile
        275                 280                 285

Met Ser Asp Trp Asp Ala Gln His Ser Gly Val Ala Ser Thr Phe Ala
    290                 295                 300
```

```
Gly Leu Asp Met Thr Met Pro Gly Asp Thr Asp Phe Asn Ser Gly Lys
305                 310                 315                 320

Thr Phe Trp Gly Thr Asn Phe Thr Ser Ile Leu Asn Gly Thr Val
            325                 330                 335

Pro Gln Trp Arg Leu Asp Asp Ala Val Thr Arg Ile Met Ala Ala Phe
            340                 345                 350

Tyr Tyr Val Gly Arg Asp Lys Ala Arg Ile Pro Val Asn Phe Asp Ser
            355                 360                 365

Trp Ser Arg Asp Thr Tyr Gly Phe Asp His Tyr Gly Lys Ala Gly
            370                 375                 380

Tyr Ser Gln Ile Asn Ser His Val Asp Val Arg Ala Asp His Phe Arg
385                 390                 395                 400

Ser Ile Arg Arg Thr Ala Ala Met Ser Thr Val Leu Leu Lys Asn Glu
                405                 410                 415

Gly Ala Leu Pro Leu Thr Gly Ser Glu Lys Trp Thr Ala Val Phe Gly
                420                 425                 430

Asp Asp Ala Gly Glu Gly Gln Leu Gly Pro Asn Gly Phe Pro Asp His
            435                 440                 445

Gly Gly Asn Asn Gly Thr Leu Ala Met Gly Trp Gly Ser Gly Thr Ser
450                 455                 460

Asp Tyr Pro Tyr Leu Val Thr Pro Leu Glu Ser Ile Lys Ala Thr Val
465                 470                 475                 480

Ala Gln Asn Gly Gly Ile Val Thr Ser Val Thr Asp Asn Trp Ala Tyr
                485                 490                 495

Thr Gln Ile Gln Thr Leu Ala Lys Gln Ala Ser Val Ala Ile Val Phe
            500                 505                 510

Val Asn Ala Asp Ser Gly Glu Gly Tyr Ile Thr Val Asp Gly Asn Ala
            515                 520                 525

Gly Asp Arg Asn Asn Leu Thr Leu Trp Gln Asp Gly Asp Thr Leu Ile
            530                 535                 540

Lys Asn Val Ser Ser Leu Cys Asn Asn Thr Ile Val Val Ile His Ser
545                 550                 555                 560

Val Gly Pro Val Leu Val Asn Ser Phe Tyr Asp Ser Glu Asn Val Thr
                565                 570                 575

Ala Ile Leu Trp Ala Gly Leu Pro Gly Gln Glu Ser Gly Asn Ala Ile
                580                 585                 590

Ala Asp Ile Leu Tyr Gly Arg His Asn Pro Gly Gly Lys Leu Pro Phe
            595                 600                 605

Thr Ile Gly Ser Asp Ala Ala Glu Tyr Gly Pro Asp Leu Ile Tyr Glu
            610                 615                 620

Pro Thr Asn Asn Ser Ser Pro Gln Asp Asn Phe Glu Glu Gly Val
625                 630                 635                 640

Phe Ile Asp Tyr Arg Ala Phe Asp Lys Gln Asn Val Thr Pro Ile Tyr
                645                 650                 655

Glu Phe Gly Phe Gly Leu Ser Tyr Thr Lys Phe Ser Tyr Ser Asn Leu
            660                 665                 670

Thr Val Lys Lys Ala Asn Ala Gly Ala Tyr Thr Pro Ala Thr Gly Gln
            675                 680                 685

Ser Lys Ala Ala Pro Thr Leu Gly Asn Phe Ser Thr Asp Ala Ser Gln
            690                 695                 700

Tyr Gln Trp Pro Ser Asp Phe Thr Tyr Ile Asp Thr Phe Ile Tyr Pro
705                 710                 715                 720

Tyr Leu Asn Ser Thr Asp Leu Lys Thr Ala Ser Gln Asp Pro Glu Tyr
```

```
            725                 730                 735
Gly Leu Asn Tyr Thr Trp Pro Ala Gly Ala Thr Asp Gly Thr Pro Gln
            740                 745                 750

Ala Arg Ile Pro Ala Gly Gly Ala Pro Gly Gly Asn Pro Gln Leu Trp
            755                 760                 765

Asp Val Leu Phe Ser Val Glu Ala Thr Ile Thr Asn Asn Gly Thr Val
            770                 775                 780

Pro Gly Asp Glu Val Val Gln Leu Tyr Val Ser Leu Gly Asn Pro Asp
785                 790                 795                 800

Asp Pro Lys Ile Val Leu Arg Gly Phe Asp Arg Leu Ser Ile Gln Pro
                805                 810                 815

Gly Lys Thr Ala Thr Phe His Ala Asp Ile Thr Arg Arg Asp Val Ser
                820                 825                 830

Asn Trp Asp Val Ala Ser Gln Asn Trp Val Ile Thr Ser Ala Pro Lys
                835                 840                 845

Thr Val Tyr Val Gly Ala Ser Ser Arg Lys Leu Pro Leu Thr Ala Thr
            850                 855                 860

Leu Asp Thr Ser Asp Phe Gln
865                 870

<210> SEQ ID NO 40
<211> LENGTH: 873
<212> TYPE: PRT
<213> ORGANISM: Aspergillus fumigatus

<400> SEQUENCE: 40

Met Arg Phe Gly Trp Leu Glu Val Ala Ala Leu Thr Ala Ala Ser Val
1               5                   10                  15

Ala Asn Ala Gln Val Phe Asp Asn Ser His Gly Asn Asn Gln Glu Leu
            20                  25                  30

Ala Phe Ser Pro Pro Phe Tyr Pro Ser Pro Trp Ala Asp Gly Gln Gly
        35                  40                  45

Glu Trp Ala Asp Ala His Arg Arg Ala Val Glu Ile Val Ser Gln Met
    50                  55                  60

Thr Leu Ala Glu Lys Val Asn Leu Thr Thr Gly Thr Gly Trp Glu Met
65                  70                  75                  80

Asp Arg Cys Val Gly Gln Thr Gly Ser Val Pro Arg Leu Gly Ile Asn
                85                  90                  95

Trp Gly Leu Cys Gly Gln Asp Ser Pro Leu Gly Ile Arg Phe Ser Asp
                100                 105                 110

Leu Asn Ser Ala Phe Pro Ala Gly Thr Asn Val Ala Ala Thr Trp Asp
            115                 120                 125

Lys Thr Leu Ala Tyr Leu Arg Gly Lys Ala Met Gly Glu Glu Phe Asn
130                 135                 140

Asp Lys Gly Val Asp Ile Leu Leu Gly Pro Ala Ala Gly Pro Leu Gly
145                 150                 155                 160

Lys Tyr Pro Asp Gly Gly Arg Ile Trp Glu Gly Phe Ser Pro Asp Pro
                165                 170                 175

Ala Leu Thr Gly Val Leu Phe Ala Glu Thr Ile Lys Gly Ile Gln Asp
            180                 185                 190

Ala Gly Val Ile Ala Thr Ala Lys His Tyr Ile Leu Asn Glu Gln Glu
        195                 200                 205

His Phe Arg Gln Val Gly Glu Ala Gln Gly Tyr Gly Tyr Asn Ile Thr
    210                 215                 220
```

-continued

```
Glu Thr Ile Ser Ser Asn Val Asp Asp Lys Thr Met His Glu Leu Tyr
225                 230                 235                 240

Leu Trp Pro Phe Ala Asp Ala Val Arg Ala Gly Val Gly Ala Val Met
            245                 250                 255

Cys Ser Tyr Asn Gln Ile Asn Asn Ser Tyr Gly Cys Gln Asn Ser Gln
                260                 265                 270

Thr Leu Asn Lys Leu Leu Lys Ala Glu Leu Gly Phe Gln Gly Phe Val
            275                 280                 285

Met Ser Asp Trp Ser Ala His Ser Gly Val Gly Ala Ala Leu Ala
    290                 295                 300

Gly Leu Asp Met Ser Met Pro Gly Asp Ile Ser Phe Asp Asp Gly Leu
305                 310                 315                 320

Ser Phe Trp Gly Thr Asn Leu Thr Val Ser Val Leu Asn Gly Thr Val
                325                 330                 335

Pro Ala Trp Arg Val Asp Met Ala Val Arg Ile Met Thr Ala Tyr
            340                 345                 350

Tyr Lys Val Gly Arg Asp Arg Leu Arg Ile Pro Pro Asn Phe Ser Ser
            355                 360                 365

Trp Thr Arg Asp Glu Tyr Gly Trp Glu His Ser Ala Val Ser Glu Gly
    370                 375                 380

Ala Trp Thr Lys Val Asn Asp Phe Val Asn Val Gln Arg Ser His Ser
385                 390                 395                 400

Gln Ile Ile Arg Glu Ile Gly Ala Ala Ser Thr Val Leu Leu Lys Asn
                405                 410                 415

Thr Gly Ala Leu Pro Leu Thr Gly Lys Glu Val Lys Val Gly Val Leu
            420                 425                 430

Gly Glu Asp Ala Gly Ser Asn Pro Trp Gly Ala Asn Gly Cys Pro Asp
        435                 440                 445

Arg Gly Cys Asp Asn Gly Thr Leu Ala Met Ala Trp Gly Ser Gly Thr
    450                 455                 460

Ala Asn Phe Pro Tyr Leu Val Thr Pro Glu Gln Ala Ile Gln Arg Glu
465                 470                 475                 480

Val Ile Ser Asn Gly Gly Asn Val Phe Ala Val Thr Asp Asn Gly Ala
                485                 490                 495

Leu Ser Gln Met Ala Asp Val Ala Ser Gln Ser Ser Val Ser Leu Val
            500                 505                 510

Phe Val Asn Ala Asp Ser Gly Glu Gly Phe Ile Ser Val Asp Gly Asn
            515                 520                 525

Glu Gly Asp Arg Lys Asn Leu Thr Leu Trp Lys Asn Gly Glu Ala Val
    530                 535                 540

Ile Asp Thr Val Val Ser His Cys Asn Asn Thr Ile Val Val Ile His
545                 550                 555                 560

Ser Val Gly Pro Val Leu Ile Asp Arg Trp Tyr Asp Asn Pro Asn Val
                565                 570                 575

Thr Ala Ile Ile Trp Ala Gly Leu Pro Gly Gln Glu Ser Gly Asn Ser
            580                 585                 590

Leu Val Asp Val Leu Tyr Gly Arg Val Asn Pro Ser Ala Lys Thr Pro
            595                 600                 605

Phe Thr Trp Gly Lys Thr Arg Glu Ser Tyr Gly Ala Pro Leu Leu Thr
    610                 615                 620

Glu Pro Asn Asn Gly Asn Gly Ala Pro Gln Asp Asp Phe Asn Glu Gly
625                 630                 635                 640

Val Phe Ile Asp Tyr Arg His Phe Asp Lys Arg Asn Glu Thr Pro Ile
```

```
                    645                 650                 655
Tyr Glu Phe Gly His Gly Leu Ser Tyr Thr Thr Phe Gly Tyr Ser His
                660                 665                 670

Leu Arg Val Gln Ala Leu Asn Ser Ser Ser Ala Tyr Val Pro Thr
            675                 680                 685

Ser Gly Glu Thr Lys Pro Ala Pro Thr Tyr Gly Glu Ile Gly Ser Ala
690                 695                 700

Ala Asp Tyr Leu Tyr Pro Glu Gly Leu Lys Arg Ile Thr Lys Phe Ile
705                 710                 715                 720

Tyr Pro Trp Leu Asn Ser Thr Asp Leu Glu Asp Ser Ser Asp Asp Pro
                725                 730                 735

Asn Tyr Gly Trp Glu Asp Ser Glu Tyr Ile Pro Glu Gly Ala Arg Asp
                740                 745                 750

Gly Ser Pro Gln Pro Leu Leu Lys Ala Gly Ala Pro Gly Gly Asn
            755                 760                 765

Pro Thr Leu Tyr Gln Asp Leu Val Arg Val Ser Ala Thr Ile Thr Asn
770                 775                 780

Thr Gly Asn Val Ala Gly Tyr Glu Val Pro Gln Leu Tyr Val Ser Leu
785                 790                 795                 800

Gly Gly Pro Asn Glu Pro Arg Val Val Leu Arg Lys Phe Asp Arg Ile
            805                 810                 815

Phe Leu Ala Pro Gly Glu Gln Lys Val Trp Thr Thr Thr Leu Asn Arg
            820                 825                 830

Arg Asp Leu Ala Asn Trp Asp Val Glu Ala Gln Asp Trp Val Ile Thr
            835                 840                 845

Lys Tyr Pro Lys Lys Val His Val Gly Ser Ser Arg Lys Leu Pro
            850                 855                 860

Leu Arg Ala Pro Leu Pro Arg Val Tyr
865                 870

<210> SEQ ID NO 41
<211> LENGTH: 861
<212> TYPE: PRT
<213> ORGANISM: Aspergillus oryzae

<400> SEQUENCE: 41

Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140
```

-continued

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
            165                 170                 175

Ile Lys Gly Ile Gln Asp Ala Gly Val Ile Ala Thr Ala Lys His Tyr
        180                 185                 190

Ile Met Asn Glu Gln Glu His Phe Arg Gln Gln Pro Glu Ala Ala Gly
    195                 200                 205

Tyr Gly Phe Asn Val Ser Ser Leu Ser Ser Asn Val Asp Asp Lys
210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
            245                 250                 255

Gly Cys Glu Asn Ser Glu Thr Leu Asn Lys Leu Leu Lys Ala Glu Leu
        260                 265                 270

Gly Phe Gln Gly Phe Val Met Ser Asp Trp Thr Ala His His Ser Gly
    275                 280                 285

Val Gly Ala Ala Leu Ala Gly Leu Asp Met Ser Met Pro Gly Asp Val
290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Asp Met Ala Val
            325                 330                 335

Arg Ile Met Ala Ala Tyr Tyr Lys Val Gly Arg Asp Thr Lys Tyr Thr
        340                 345                 350

Pro Pro Asn Phe Ser Ser Trp Thr Arg Asp Glu Tyr Gly Phe Ala His
    355                 360                 365

Asn His Val Ser Glu Gly Ala Tyr Glu Arg Val Asn Glu Phe Val Asp
370                 375                 380

Val Gln Arg Asp His Ala Asp Leu Ile Arg Arg Ile Gly Ala Gln Ser
385                 390                 395                 400

Thr Val Leu Leu Lys Asn Lys Gly Ala Leu Pro Leu Ser Arg Lys Glu
            405                 410                 415

Lys Leu Val Ala Leu Leu Gly Glu Asp Ala Gly Ser Asn Ser Trp Gly
        420                 425                 430

Ala Asn Gly Cys Asp Asp Arg Gly Cys Asp Asn Gly Thr Leu Ala Met
    435                 440                 445

Ala Trp Gly Ser Gly Thr Ala Asn Phe Pro Tyr Leu Val Thr Pro Glu
450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Arg Gln
            485                 490                 495

Ala Ser Val Ser Leu Val Phe Val Asn Ser Asp Ser Gly Glu Gly Tyr
        500                 505                 510

Leu Ser Val Asp Gly Asn Glu Gly Asp Arg Asn Asn Ile Thr Leu Trp
    515                 520                 525

Lys Asn Gly Asp Asn Val Val Lys Thr Ala Ala Asn Cys Asn Asn
530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly

```
                565                 570                 575
Gln Glu Ser Gly Asn Ser Ile Ala Asp Val Leu Tyr Gly Arg Val Asn
            580                 585                 590

Pro Gly Ala Lys Ser Pro Phe Thr Trp Gly Lys Thr Arg Glu Ser Tyr
        595                 600                 605

Gly Ser Pro Leu Val Lys Asp Ala Asn Asn Gly Asn Gly Ala Pro Gln
    610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
            660                 665                 670

Tyr Thr Pro Thr Ser Gly Met Thr Glu Ala Ala Lys Asn Phe Gly Glu
        675                 680                 685

Ile Gly Asp Ala Ser Glu Tyr Val Tyr Pro Glu Gly Leu Glu Arg Ile
    690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
                725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
        755                 760                 765

Lys Val Lys Asn Thr Gly Asn Val Ala Gly Asp Glu Val Pro Gln Leu
    770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
            820                 825                 830

Trp Thr Val Thr Pro Tyr Pro Lys Thr Ile Tyr Val Gly Asn Ser Ser
        835                 840                 845

Arg Lys Leu Pro Leu Gln Ala Ser Leu Pro Lys Ala Gln
    850                 855                 860

<210> SEQ ID NO 42
<211> LENGTH: 860
<212> TYPE: PRT
<213> ORGANISM: Aspergillus aculeatus

<400> SEQUENCE: 42

Met Lys Leu Ser Trp Leu Glu Ala Ala Leu Thr Ala Ala Ser Val
1               5                   10                  15

Val Ser Ala Asp Glu Leu Ala Phe Ser Pro Pro Phe Tyr Pro Ser Pro
                20                  25                  30

Trp Ala Asn Gly Gln Gly Glu Trp Ala Glu Ala Tyr Gln Arg Ala Val
            35                  40                  45

Ala Ile Val Ser Gln Met Thr Leu Asp Glu Lys Val Asn Leu Thr Thr
        50                  55                  60

Gly Thr Gly Trp Glu Leu Glu Lys Cys Val Gly Gln Thr Gly Gly Val
65                  70                  75                  80
```

-continued

Pro Arg Leu Asn Ile Gly Gly Met Cys Leu Gln Asp Ser Pro Leu Gly
            85                  90                  95

Ile Arg Asp Ser Asp Tyr Asn Ser Ala Phe Pro Ala Gly Val Asn Val
        100                 105                 110

Ala Ala Thr Trp Asp Lys Asn Leu Ala Tyr Leu Arg Gly Gln Ala Met
        115                 120                 125

Gly Gln Glu Phe Ser Asp Lys Gly Ile Asp Val Gln Leu Gly Pro Ala
        130                 135                 140

Ala Gly Pro Leu Gly Arg Ser Pro Asp Gly Arg Asn Trp Glu Gly
145                 150                 155                 160

Phe Ser Pro Asp Pro Ala Leu Thr Gly Val Leu Phe Ala Glu Thr Ile
                165                 170                 175

Lys Gly Ile Gln Asp Ala Gly Val Val Ala Thr Ala Lys His Tyr Ile
            180                 185                 190

Leu Asn Glu Gln Glu His Phe Arg Gln Val Ala Glu Ala Ala Gly Tyr
        195                 200                 205

Gly Phe Asn Ile Ser Asp Thr Ile Ser Ser Asn Val Asp Asp Lys Thr
        210                 215                 220

Ile His Glu Met Tyr Leu Trp Pro Phe Ala Asp Ala Val Arg Ala Gly
225                 230                 235                 240

Val Gly Ala Ile Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Gly Ala His His Ser Gly Val
        275                 280                 285

Gly Ser Ala Leu Ala Gly Leu Asp Met Ser Met Pro Gly Asp Ile Thr
        290                 295                 300

Phe Asp Ser Ala Thr Ser Phe Trp Gly Thr Asn Leu Thr Ile Ala Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Tyr Gln Pro
            340                 345                 350

Pro Asn Phe Ser Ser Trp Thr Arg Asp Glu Tyr Gly Phe Lys Tyr Phe
        355                 360                 365

Tyr Pro Gln Glu Gly Pro Tyr Glu Lys Val Asn His Phe Val Asn Val
        370                 375                 380

Gln Arg Asn His Ser Glu Val Ile Arg Lys Leu Gly Ala Asp Ser Thr
385                 390                 395                 400

Val Leu Leu Lys Asn Asn Asn Ala Leu Pro Leu Thr Gly Lys Glu Arg
                405                 410                 415

Lys Val Ala Ile Leu Gly Glu Asp Ala Gly Ser Asn Ser Tyr Gly Ala
            420                 425                 430

Asn Gly Cys Ser Asp Arg Gly Cys Asp Asn Gly Thr Leu Ala Met Ala
        435                 440                 445

Trp Gly Ser Gly Thr Ala Glu Phe Pro Tyr Leu Val Thr Pro Glu Gln
        450                 455                 460

Ala Ile Gln Ala Glu Val Leu Lys His Lys Gly Ser Val Tyr Ala Ile
465                 470                 475                 480

Thr Asp Asn Trp Ala Leu Ser Gln Val Glu Thr Leu Ala Lys Gln Ala
                485                 490                 495

Ser Val Ser Leu Val Phe Val Asn Ser Asp Ala Gly Glu Gly Tyr Ile

```
            500                 505                 510
Ser Val Asp Gly Asn Glu Gly Asp Arg Asn Asn Leu Thr Leu Trp Lys
        515                 520                 525

Asn Gly Asp Asn Leu Ile Lys Ala Ala Ala Asn Cys Asn Asn Thr
        530                 535             540

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
                565                 570                 575

Glu Ser Gly Asn Ser Leu Ala Asp Val Leu Tyr Gly Arg Val Asn Pro
        580                 585                 590

Gly Ala Lys Ser Pro Phe Thr Trp Gly Lys Thr Arg Glu Ala Tyr Gly
        595                 600                 605

Asp Tyr Leu Val Arg Glu Leu Asn Asn Gly Asn Gly Ala Pro Gln Asp
        610                 615                 620

Asp Phe Ser Glu Gly Val Phe Ile Asp Tyr Arg Gly Phe Asp Lys Arg
625                 630                 635                 640

Asn Glu Thr Pro Ile Tyr Glu Phe Gly His Gly Leu Ser Tyr Thr Thr
                645                 650                 655

Phe Asn Tyr Ser Gly Leu His Ile Gln Val Leu Asn Ala Ser Ser Asn
            660                 665                 670

Ala Gln Val Ala Thr Glu Thr Gly Ala Ala Pro Thr Phe Gly Gln Val
        675                 680                 685

Gly Asn Ala Ser Asp Tyr Val Tyr Pro Glu Gly Leu Thr Arg Ile Ser
        690                 695                 700

Lys Phe Ile Tyr Pro Trp Leu Asn Ser Thr Asp Leu Lys Ala Ser Ser
705                 710                 715                 720

Gly Asp Pro Tyr Tyr Gly Val Asp Thr Ala Glu His Val Pro Glu Gly
                725                 730                 735

Ala Thr Asp Gly Ser Pro Gln Pro Val Leu Pro Ala Gly Gly Gly Ser
            740                 745                 750

Gly Gly Asn Pro Arg Leu Tyr Asp Glu Leu Ile Arg Val Ser Val Thr
        755                 760                 765

Val Lys Asn Thr Gly Arg Val Ala Gly Asp Ala Val Pro Gln Leu Tyr
        770                 775                 780

Val Ser Leu Gly Gly Pro Asn Glu Pro Lys Val Val Leu Arg Lys Phe
785                 790                 795                 800

Asp Arg Leu Thr Leu Lys Pro Ser Glu Glu Thr Val Trp Thr Thr Thr
                805                 810                 815

Leu Thr Arg Arg Asp Leu Ser Asn Trp Asp Val Ala Ala Gln Asp Trp
            820                 825                 830

Val Ile Thr Ser Tyr Pro Lys Lys Val His Val Gly Ser Ser Ser Arg
        835                 840                 845

Gln Leu Pro Leu His Ala Ala Leu Pro Lys Val Gln
    850                 855                 860

<210> SEQ ID NO 43
<211> LENGTH: 860
<212> TYPE: PRT
<213> ORGANISM: Aspergillus niger

<400> SEQUENCE: 43

Met Arg Phe Thr Leu Ile Glu Ala Val Ala Leu Thr Ala Val Ser Leu
1               5                   10                  15
```

```
Ala Ser Ala Asp Glu Leu Ala Tyr Ser Pro Pro Tyr Tyr Pro Ser Pro
             20                  25                  30

Trp Ala Asn Gly Gln Gly Asp Trp Ala Gln Ala Tyr Gln Arg Ala Val
         35                  40                  45

Asp Ile Val Ser Gln Met Thr Leu Asp Glu Lys Val Asn Leu Thr Thr
     50                  55                  60

Gly Thr Gly Trp Glu Leu Glu Leu Cys Val Gly Gln Thr Gly Gly Val
 65                  70                  75                  80

Pro Arg Leu Gly Val Pro Gly Met Cys Leu Gln Asp Ser Pro Leu Gly
                 85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
        130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205

Gly Phe Asn Ile Ser Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285

Ser Gly Ala Leu Ala Gly Leu Asp Met Ser Met Pro Gly Asp Val Asp
    290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Tyr Lys Tyr Tyr
        355                 360                 365

Tyr Val Ser Glu Gly Pro Tyr Glu Lys Val Asn Gln Tyr Val Asn Val
    370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
                405                 410                 415

Leu Val Ala Leu Ile Gly Glu Asp Ala Gly Ser Asn Pro Tyr Gly Ala
            420                 425                 430

Asn Gly Cys Ser Asp Arg Gly Cys Asp Asn Gly Thr Leu Ala Met Gly
```

```
            435                 440                 445
Trp Gly Ser Gly Thr Ala Asn Phe Pro Tyr Leu Val Thr Pro Glu Gln
450                 455                 460

Ala Ile Ser Asn Glu Val Leu Lys His Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
                500                 505                 510

Asn Val Asp Gly Asn Leu Gly Asp Arg Arg Asn Leu Thr Leu Trp Arg
            515                 520                 525

Asn Gly Asp Asn Val Ile Lys Ala Ala Ala Ser Asn Cys Asn Asn Thr
            530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
            595                 600                 605

Asp Tyr Leu Val Thr Glu Pro Asn Asn Gly Asn Gly Ala Pro Gln Glu
            610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
            675                 680                 685

Gly Asn Ala Ser Asp Tyr Leu Tyr Pro Ser Gly Leu Gln Arg Ile Thr
            690                 695                 700

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Gly Pro
            740                 745                 750

Gly Gly Asn Pro Arg Leu Tyr Asp Glu Leu Ile Arg Val Ser Val Thr
            755                 760                 765

Ile Lys Asn Thr Gly Lys Val Ala Gly Asp Glu Val Pro Gln Leu Tyr
770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Lys Trp Ser Thr Thr
            805                 810                 815

Leu Thr Arg Arg Asp Leu Ala Asn Trp Asn Val Glu Lys Gln Asp Trp
            820                 825                 830

Glu Ile Thr Ser Tyr Pro Lys Met Val Phe Val Gly Ser Ser Ser Arg
            835                 840                 845

Lys Leu Pro Leu Arg Ala Ser Leu Pro Thr Val His
        850                 855                 860
```

<210> SEQ ID NO 44
<211> LENGTH: 857
<212> TYPE: PRT
<213> ORGANISM: Talaromyces emersonii

<400> SEQUENCE: 44

```
Met Arg Asn Gly Leu Leu Lys Val Ala Ala Leu Ala Ala Ser Ala
 1               5                  10                  15

Val Asn Gly Glu Asn Leu Ala Tyr Ser Pro Pro Phe Tyr Pro Ser Pro
                20                  25                  30

Trp Ala Asn Gly Gln Gly Asp Trp Ala Glu Ala Tyr Gln Lys Ala Val
            35                  40                  45

Gln Phe Val Ser Gln Leu Thr Leu Ala Glu Lys Val Asn Leu Thr Thr
 50                  55                  60

Gly Thr Gly Trp Glu Gln Asp Arg Cys Val Gly Gln Val Gly Ser Ile
 65                  70                  75                  80

Pro Arg Leu Gly Phe Pro Gly Leu Cys Met Gln Asp Ser Pro Leu Gly
                    85                  90                  95

Val Arg Asp Thr Asp Tyr Asn Ser Ala Phe Pro Ala Gly Val Asn Val
                100                 105                 110

Ala Ala Thr Trp Asp Arg Asn Leu Ala Tyr Arg Arg Gly Val Ala Met
            115                 120                 125

Gly Glu Glu His Arg Gly Lys Gly Val Asp Val Gln Leu Gly Pro Val
130                 135                 140

Ala Gly Pro Leu Gly Arg Ser Pro Asp Ala Gly Arg Asn Trp Glu Gly
145                 150                 155                 160

Phe Ala Pro Asp Pro Val Leu Thr Gly Asn Met Met Ala Ser Thr Ile
                165                 170                 175

Gln Gly Ile Gln Asp Ala Gly Val Ile Ala Cys Ala Lys His Phe Ile
                180                 185                 190

Leu Tyr Glu Gln Glu His Phe Arg Gln Gly Ala Gln Asp Gly Tyr Asp
            195                 200                 205

Ile Ser Asp Ser Ile Ser Ala Asn Ala Asp Asp Lys Thr Met His Glu
210                 215                 220

Leu Tyr Leu Trp Pro Phe Ala Asp Ala Val Arg Ala Gly Val Gly Ser
225                 230                 235                 240

Val Met Cys Ser Tyr Asn Gln Val Asn Asn Ser Tyr Ala Cys Ser Asn
                245                 250                 255

Ser Tyr Thr Met Asn Lys Leu Leu Lys Ser Glu Leu Gly Phe Gln Gly
                260                 265                 270

Phe Val Met Thr Asp Trp Gly Gly His His Ser Gly Val Gly Ser Ala
            275                 280                 285

Leu Ala Gly Leu Asp Met Ser Met Pro Gly Asp Ile Ala Phe Asp Ser
290                 295                 300

Gly Thr Ser Phe Trp Gly Thr Asn Leu Thr Val Ala Val Leu Asn Gly
305                 310                 315                 320

Ser Ile Pro Glu Trp Arg Val Asp Asp Met Ala Val Arg Ile Met Ser
                325                 330                 335

Ala Tyr Tyr Lys Val Gly Arg Asp Arg Tyr Ser Val Pro Ile Asn Phe
                340                 345                 350

Asp Ser Trp Thr Leu Asp Thr Tyr Gly Pro Glu His Tyr Ala Val Gly
            355                 360                 365

Gln Gly Gln Thr Lys Ile Asn Glu His Val Asp Val Arg Gly Asn His
```

```
              370                 375                 380
Ala Glu Ile Ile His Glu Ile Gly Ala Ala Ser Ala Val Leu Leu Lys
385                 390                 395                 400

Asn Lys Gly Gly Leu Pro Leu Thr Gly Thr Glu Arg Phe Val Gly Val
                405                 410                 415

Phe Gly Lys Asp Ala Gly Ser Asn Pro Trp Gly Val Asn Gly Cys Ser
                420                 425                 430

Asp Arg Gly Cys Asp Asn Gly Thr Leu Ala Met Gly Trp Gly Ser Gly
            435                 440                 445

Thr Ala Asn Phe Pro Tyr Leu Val Thr Pro Glu Gln Ala Ile Gln Arg
        450                 455                 460

Glu Val Leu Ser Arg Asn Gly Thr Phe Thr Gly Ile Thr Asp Asn Gly
465                 470                 475                 480

Ala Leu Ala Glu Met Ala Ala Ala Ser Gln Ala Asp Thr Cys Leu
                485                 490                 495

Val Phe Ala Asn Ala Asp Ser Gly Glu Gly Tyr Ile Thr Val Asp Gly
                500                 505                 510

Asn Glu Gly Asp Arg Lys Asn Leu Thr Leu Trp Gln Gly Ala Asp Gln
                515                 520                 525

Val Ile His Asn Val Ser Ala Asn Cys Asn Asn Thr Val Val Val Leu
530                 535                 540

His Thr Val Gly Pro Val Leu Ile Asp Asp Trp Tyr Asp His Pro Asn
545                 550                 555                 560

Val Thr Ala Ile Leu Trp Ala Gly Leu Pro Gly Gln Glu Ser Gly Asn
                565                 570                 575

Ser Leu Val Asp Val Leu Tyr Gly Arg Val Asn Pro Gly Lys Thr Pro
                580                 585                 590

Phe Thr Trp Gly Arg Ala Arg Asp Asp Tyr Gly Ala Pro Leu Ile Val
                595                 600                 605

Lys Pro Asn Asn Gly Lys Gly Ala Pro Gln Gln Asp Phe Thr Glu Gly
                610                 615                 620

Ile Phe Ile Asp Tyr Arg Arg Phe Asp Lys Tyr Asn Ile Thr Pro Ile
625                 630                 635                 640

Tyr Glu Phe Gly Phe Gly Leu Ser Tyr Thr Thr Phe Glu Phe Ser Gln
                645                 650                 655

Leu Asn Val Gln Pro Ile Asn Ala Pro Pro Tyr Thr Pro Ala Ser Gly
                660                 665                 670

Phe Thr Lys Ala Ala Gln Ser Phe Gly Gln Pro Ser Asn Ala Ser Asp
                675                 680                 685

Asn Leu Tyr Pro Ser Asp Ile Glu Arg Val Pro Leu Tyr Ile Tyr Pro
                690                 695                 700

Trp Leu Asn Ser Thr Asp Leu Lys Ala Ser Ala Asn Asp Pro Asp Tyr
705                 710                 715                 720

Gly Leu Pro Thr Glu Lys Tyr Val Pro Pro Asn Ala Thr Asn Gly Asp
                725                 730                 735

Pro Gln Pro Ile Asp Pro Ala Gly Gly Ala Pro Gly Gly Asn Pro Ser
                740                 745                 750

Leu Tyr Glu Pro Val Ala Arg Val Thr Thr Ile Thr Asn Thr Gly
                755                 760                 765

Lys Val Thr Gly Asp Glu Val Pro Gln Leu Tyr Val Ser Leu Gly Gly
                770                 775                 780

Pro Asp Asp Ala Pro Lys Val Leu Arg Gly Phe Asp Arg Ile Thr Leu
785                 790                 795                 800
```

```
Ala Pro Gly Gln Gln Tyr Leu Trp Thr Thr Thr Leu Thr Arg Arg Asp
            805                 810                 815

Ile Ser Asn Trp Asp Pro Val Thr Gln Asn Trp Val Val Thr Asn Tyr
            820                 825                 830

Thr Lys Thr Ile Tyr Val Gly Asn Ser Ser Arg Asn Leu Pro Leu Gln
            835                 840                 845

Ala Pro Leu Lys Pro Tyr Pro Gly Ile
            850                 855

<210> SEQ ID NO 45
<211> LENGTH: 843
<212> TYPE: PRT
<213> ORGANISM: Thermoascus aurentiacus

<400> SEQUENCE: 45

Met Arg Leu Gly Trp Leu Glu Leu Ala Val Ala Ala Ala Thr Val
1               5                   10                  15

Ala Ser Ala Lys Asp Asp Leu Ala Tyr Ser Pro Phe Tyr Pro Ser
            20                  25                  30

Pro Trp Met Asn Gly Asn Gly Glu Trp Ala Glu Ala Tyr Arg Arg Ala
            35                  40                  45

Val Asp Phe Val Ser Gln Leu Thr Leu Ala Glu Lys Val Asn Leu Thr
50                  55                  60

Thr Gly Val Gly Trp Met Gln Glu Lys Cys Val Gly Glu Thr Gly Ser
65                  70                  75                  80

Ile Pro Arg Leu Gly Phe Arg Gly Leu Cys Leu Gln Asp Ser Pro Leu
            85                  90                  95

Gly Val Arg Phe Ala Asp Tyr Val Ser Ala Phe Pro Ala Gly Val Asn
            100                 105                 110

Val Ala Ala Thr Trp Asp Lys Asn Leu Ala Tyr Leu Arg Gly Lys Ala
            115                 120                 125

Met Gly Glu Glu His Arg Gly Lys Gly Val Asp Val Gln Leu Gly Pro
            130                 135                 140

Val Ala Gly Pro Leu Gly Arg His Pro Asp Gly Gly Arg Asn Trp Glu
145                 150                 155                 160

Gly Phe Ser Pro Asp Pro Val Leu Thr Gly Val Leu Met Ala Glu Thr
            165                 170                 175

Ile Lys Gly Ile Gln Asp Ala Gly Val Ile Ala Cys Ala Lys His Phe
            180                 185                 190

Ile Gly Asn Glu Met Glu His Phe Arg Gln Ala Gly Glu Ala Val Gly
            195                 200                 205

Tyr Gly Phe Asp Ile Thr Glu Ser Val Ser Ser Asn Ile Asp Asp Lys
            210                 215                 220

Thr Leu His Glu Leu Tyr Leu Trp Pro Phe Ala Asp Ala Val Arg Ala
225                 230                 235                 240

Gly Val Gly Ser Phe Met Cys Ser Tyr Asn Gln Val Asn Asn Ser Tyr
            245                 250                 255

Ser Cys Ser Asn Ser Tyr Leu Leu Asn Lys Leu Leu Lys Ser Glu Leu
            260                 265                 270

Asp Phe Gln Gly Phe Val Met Ser Asp Trp Gly Ala His His Ser Gly
            275                 280                 285

Val Gly Ala Ala Leu Ala Gly Leu Asp Met Ser Met Pro Gly Asp Thr
            290                 295                 300

Ala Phe Gly Thr Gly Lys Ser Phe Trp Gly Thr Asn Leu Thr Ile Ala
```

```
                305                 310                 315                 320
Val Leu Asn Gly Thr Val Pro Glu Trp Arg Val Asp Met Ala Val
                325                 330                 335

Arg Ile Met Ala Ala Phe Tyr Lys Val Gly Arg Asp Arg Tyr Gln Val
                340                 345                 350

Pro Val Asn Phe Asp Ser Trp Thr Lys Asp Glu Tyr Gly Tyr Glu His
                355                 360                 365

Ala Leu Val Gly Gln Asn Tyr Val Lys Val Asn Asp Lys Val Asp Val
                370                 375                 380

Arg Ala Asp His Ala Asp Ile Ile Arg Gln Ile Gly Ser Ala Ser Val
385                 390                 395                 400

Val Leu Leu Lys Asn Asp Gly Gly Leu Pro Leu Thr Gly Tyr Glu Lys
                405                 410                 415

Phe Thr Gly Val Phe Gly Glu Asp Ala Gly Ser Asn Arg Trp Gly Ala
                420                 425                 430

Asp Gly Cys Ser Asp Arg Gly Cys Asp Asn Gly Thr Leu Ala Met Gly
                435                 440                 445

Trp Gly Ser Gly Thr Ala Asp Phe Pro Tyr Leu Val Thr Pro Glu Gln
                450                 455                 460

Ala Ile Gln Asn Glu Ile Leu Ser Lys Gly Lys Gly Leu Asp Ser Val
465                 470                 475                 480

Ser Ile Val Phe Val Asn Ala Asp Ser Gly Glu Gly Tyr Ile Asn Val
                485                 490                 495

Asp Gly Asn Glu Gly Asp Arg Lys Asn Leu Thr Leu Trp Lys Gly Gly
                500                 505                 510

Glu Glu Val Ile Lys Thr Val Ala Ala Asn Cys Asn Asn Thr Ile Val
                515                 520                 525

Val Met His Thr Val Gly Pro Val Leu Ile Asp Glu Trp Tyr Asp Asn
                530                 535                 540

Pro Asn Val Thr Ala Ile Val Trp Ala Gly Leu Pro Gly Gln Glu Ser
545                 550                 555                 560

Gly Asn Ser Leu Val Asp Val Leu Tyr Gly Arg Val Ser Pro Gly Gly
                565                 570                 575

Lys Thr Pro Phe Thr Trp Gly Lys Thr Arg Glu Ser Tyr Gly Ala Pro
                580                 585                 590

Leu Leu Thr Lys Pro Asn Asn Gly Lys Gly Ala Pro Gln Asp Asp Phe
                595                 600                 605

Thr Glu Gly Val Phe Ile Asp Tyr Arg Arg Phe Asp Lys Tyr Asn Glu
                610                 615                 620

Thr Pro Ile Tyr Glu Phe Gly Phe Gly Leu Ser Tyr Thr Thr Phe Glu
625                 630                 635                 640

Tyr Ser Asn Ile Tyr Val Gln Pro Leu Asn Ala Arg Pro Tyr Thr Pro
                645                 650                 655

Ala Ser Gly Ser Thr Lys Ala Ala Pro Thr Phe Gly Asn Ile Ser Thr
                660                 665                 670

Asp Tyr Ala Asp Tyr Leu Tyr Pro Glu Asp Ile His Lys Val Pro Leu
                675                 680                 685

Tyr Ile Tyr Pro Trp Leu Asn Thr Thr Asp Pro Glu Glu Val Leu Arg
                690                 695                 700

Arg Ser Arg Leu Thr Glu Met Lys Ala Glu Asp Tyr Ile Pro Ser Gly
705                 710                 715                 720

Ala Thr Asp Gly Ser Pro Gln Pro Ile Leu Pro Ala Gly Gly Ala Pro
                725                 730                 735
```

-continued

```
Gly Gly Asn Pro Gly Leu Tyr Asp Glu Met Tyr Arg Val Ser Ala Ile
            740             745             750

Ile Thr Asn Thr Gly Asn Val Val Gly Asp Glu Val Pro Gln Leu Tyr
            755             760             765

Val Ser Leu Gly Gly Pro Asp Asp Pro Lys Val Val Leu Arg Asn Phe
    770             775             780

Asp Arg Ile Thr Leu His Pro Gly Gln Gln Thr Met Trp Thr Thr Thr
785             790             795             800

Leu Thr Arg Arg Asp Ile Ser Asn Trp Asp Pro Ala Ser Gln Asn Trp
                805             810             815

Val Val Thr Lys Tyr Pro Lys Thr Val Tyr Ile Gly Ser Ser Ser Arg
            820             825             830

Lys Leu His Leu Gln Ala Pro Leu Pro Pro Tyr
        835             840
```

BETA-GLUCOSIDASE I VARIANTS WITH IMPROVED PROPERTIES

CROSS-REFERENCE TO RELATED APPLICATIONS

This application is a national phase filing under 35 U.S.C. 371 of PCT/US2010/057531, filed Nov. 19, 2010, which claims the benefit of U.S. provisional application Ser. No. 61/263,240 filed Nov. 20, 2009, each of which are hereby incorporated by reference in their entirety.

STATEMENT AS TO RIGHTS TO INVENTIONS MADE UNDER FEDERALLY SPONSORED RESEARCH AND DEVELOPMENT

This invention was made with government support under Condition Award No: De-Fc36-08go18078 awarded by the Department of Energy. The government has certain rights in this invention.

SEQUENCE LISTING

The sequence listing submitted via EFS, in compliance with 37 C.F.R. §1.52(e), is incorporated herein by reference. The sequence listing text file submitted via EFS contains the file "31435US2 SequenceListing", created on May 17, 2012, which is 315,033 bytes in size.

FIELD OF THE DISCLOSURE

The present disclosure is generally directed to enzymes and in particular beta-glucosidase variants. Also described are nucleic acids encoding beta-glucosidase variants, compositions comprising beta-glucosidase variants, methods of using beta-glucosidase variants, and methods of identifying additional useful beta-glucosidase variants.

BACKGROUND

Cellulose and hemicellulose are the most abundant plant materials produced by photosynthesis. They can be degraded and used as an energy source by numerous microorganisms (e.g., bacteria, yeast and fungi) that produce extracellular enzymes capable of hydrolysis of the polymeric substrates to monomeric sugars (Aro et al., J. Biol. Chem., 276: 24309-24314, 2001). As the limits of non-renewable resources approach, the potential of cellulose to become a major renewable energy resource is enormous (Krishna et al., Bioresource Tech., 17: 193-196, 2001). The effective utilization of cellulose through biological processes is one approach to overcoming the shortage of foods, feeds, and fuels (Ohmiya et al., Biotechnol. Gen. Engineer Rev., 14: 365-414, 1997).

Cellulases are enzymes that hydrolyze cellulose (beta-1, 4-glucan or beta D-glucosidic linkages) resulting in the formation of glucose, cellobiose, cellooligosaccharides, and the like. Cellulases have been traditionally divided into three major classes; endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG") (Knowles et al., TIBTECH 5: 255-261, 1987; and Schulein, Methods Enzymol., 160: 234-243, 1988). Endoglucanases act mainly on the amorphous parts of the cellulose fiber, whereas cellobiohydrolases are also able to degrade crystalline cellulose (Nevalainen and Penttila, Mycota, 303-319, 1995). Thus, the presence of a cellobiohydrolase in a cellulase system is required for efficient solubilization of crystalline cellulose (Suurnakki et al., Cellulose, 7: 189-209, 2000). Beta-glucosidase acts to liberate D-glucose units from cellobiose, cello-oligosaccharides, and other glycosides (Freer, J. Biol. Chem., 268; 9337-9342, 1993).

Cellulases are known to be produced by a large number of bacteria, yeast and fungi. Certain fungi produce a complete cellulase system capable of degrading crystalline forms of cellulose, such that the cellulases are readily produced in large quantities via fermentation. Filamentous fungi play a special role since many yeast, suck as *Saccharomyces cerevisiae*, lack the ability to hydrolyze cellulose (see, e.g., Wood et al., Methods in Enzymology, 160: 87-116, 1988).

The fungal cellulase classifications of CBH, EG and BG can be further expanded to include multiple components within each classification. For example, multiple CBHs, EGs and BGs have been isolated from a variety of fungal sources including *Trichoderma reesei* (also referred to as *Hypocrea jecorina*), which contains knows genes for two CBHs, i.e., CBH I ("CBH1") and CBH II ("CBH2"), at least eight EGs, i.e., EG I, EG II, EG III, EGIV, EGV, EGVI, EGVII and EGVIII, and at least five BGs, i.e., BG1, BG2, BG3, BG4, BG5 and BG7 (Foreman et al. (2003), J. Biol. Chem. 278(34):31988-31997), EGIV, EGVI and EGVIII also have xyloglucanase activity.

In order to efficiently convert crystalline cellulose to glucose the complete cellulase system comprising components from each of the CBH, EG and BG classifications is required, with isolated components less effective in hydrolyzing crystalline cellulose (Filho et al., Can. J. Microbiol., 42:1-5, 1996). Endo-1,4-beta-glucanases (EG) and exo-cellobiohydrolases (CBH) catalyze the hydrolysis of cellulose to cellooligosaccharides (cellobiose as a main product), while beta-glucosidases (BGL) convert the oligosaccharides to glucose. A synergistic relationship has been observed between cellulase components from different classifications. In particular, the EG-type cellulases and CBH-types cellulases synergistically interact to efficiently degrade cellulose.

Although beta-glucosidase compositions have been previously described, there remains a need for new and improved beta-glucosidase compositions. Improved beta-glucosidase compositions find use for example in saccharifying biomass. Beta-glucosidases that exhibit desirable levels in one or more of expression, activity and stability are of particular interest.

SUMMARY

The present disclosure provides polypeptides having beta-glucosidase activity. The disclosure is based in part on beta-glucosidase variants. Also described are nucleic acids encoding beta-glucosidase variants, compositions comprising beta-glucosidase variants, methods of using beta-glucosidase variants, and methods of identifying, additional useful beta-glucosidase variants. In one aspect of the invention, the beta-glucosidase variants are *H. jecorina* beta-glucosidase 1 (BGL1) variants.

Accordingly, in one aspect, the invention provides beta-glucosidase 1 (BGL1) variants having at least two improved activities over wild type BGL1 selected from the group consisting of: (a) pre-treated corn stover (PCS) hydrolysis activity, (b) cellobiase activity, (c) protein expansion (HPLC), (d) beta-glucosidase activity measured by either a cellobiase activity in the presence of ammonia pretreated corncob (CC), or by a CC hydrolysis activity, (e) thermostability, (f) phosphoric acid swollen cellulose (PASC)

hydrolysis activity, and (g) increased hydrolytic activity in the presence of glucose as compared to wild-type BGL1, wherein the BGL1 variant is any variant as shown in Tables 4-8, 3-2, 4-2 and 4-3.

In other aspects, the invention provides BGL1 variants, as described above and throughout this specification, having improved (b) and (d) activities over wild type BGL1, wherein the BGL1 variants is L266A, I567E, S283F, S283P, T258E, T258I, T258K, T258Q, P536T, P536W, I532Y, Y503T, P607D, Q406M, Q406S, V602T, G300M, A630S, A630T, T180H, T180M, A450M, I444E, I444F, I444N, I444W, I444Y, V500Q, A633, S428P, A667V, A485L, A485W, Y678R, V603G, L266C, I567F, S624P, P607L, G606I, G606K, G606L, G606M, G606Q, G606V, G605E, I444V, A633V, A655W, Y678H, V522Y, G544F, L266N, F556L, S550I, S550T, S550V, T258I, P536I, P536V, F392R, S624G, S624N, S624Q, S624T, A601M, A630V, N463S, A450F, A450T, A450V, A450W, I486V, S282I, Y678I, G427F, D564T, Q684C, Q684G, Y530S, Q684N, A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263C, N263S, N278F, S312Y, Q316T, K345E, G427C, P661F, P661L, P661Q, T666C, S683W, F260D, F260G, F260Q, P607G, N400S, F260W, Y530F, Q406D, G605C, N263T, P607I, A450P, T242H, A630Y, P536C, A630Q, D215S, G372A, G547A, F611A, G662C, G662F, F260L, L293F, A633C, S312C, or N455D.

In other aspects, the invention provides BGL1 variants as described above and throughout this specification, having improved (b) and (e) activities over wild type BGL1, wherein the BGL1 variant is P607H, T011E, T011Y, N146E, I567V, N566G, A630K, Y639K, Q245N, K320Y, A347Y, P536Q, N369E, N369Y, N146A, N146Q, P607K, N369T, A655N, P671K, F260T, P607S, F260D, F260G, F260Q, P607G, N400S, P607F, P607I, A450P, T242H, T568E, A630Y, A655D, F260E, T568K, P536C, A630Q, D215S, G372A, G547A, F611A, G662C, G662F, F260L, or L293F.

In other aspects, the invention provides BGL1 variants, as described above and throughout this specification, having improved (b) and (f) activities over wild type BGL1, wherein the BGL1 variant is N261C, T258C, F392Q, S624E, P607C, P604Q, A377Q, N461A, N461F, N461P, T436A, T436C, T436F, T436I, T436M, T436Q, F436Y, Q220C, A655L, T646H, Y678F, A468I, D177M, P661E, L266N, F556V, S550I, S550T, S550V, T258L, P536I, P536V, F392R, S624G, S624N, S624Q, S624T, A601M, A630V, N463S, A450F, A450T, A450V, A450W, I486V, S482I, Y678I, G427F, D564T, Q684C, Q684G, N566H, F556V, P604Y, L293V, A630G, N461C, N463T, D547C, Q220M, T221A, T221G, T221I, A655R, A468F, A468S, Q216I, D564V, P536Q, N369E, N369W, N369Y, T436E, A565G, A270C, T258S, T258V, P536D, P536E, S624F, S624I, S624V, A601C, A601Y, S308H, A630C, A630D, N463K, N463R, A450E, S482A, A6667F, A667L, A667R, A667Y, A485T, V466S, Y478A, Y678C, Y678Q, A468C, Q226W, Q226Y, N263C, N263S, N278F, S312Y, Q316T, K345E, G427C, P661F, P661L, P661Q, T666C, S683W, F260W, Y530F, N461V, I671C, K206A, A450P, T242H, E170F, S507G, F260E, T568K, P536C, A630Q, D215S, G372A, G547A, F611A, G662C, G662F, L293F, A633C, S312C or N455D.

In other aspects, the invention provides BGL1 variants, as described above and throughout this specification, having improved (a) and (b) activities over wild type BGL1, wherein the BGL1 variant is I567Q, A565F, A565K, A565Q, A565V, F556E, F206I, P607E, G605R, G300C, A377C, A377D, S308C, N146F, N146H, N146S, A655C, A655G, P176L, T209I, L266C, I567F, S624P, P607L, G606I, G606K, G606L, G606M, G606Q, G606V, G605E, I444V, A633V, A655W, Y678H, V522Y, G554F, N566F, F556V, P604Y, L293V, A630G, N461C, N463T, D457C, Q220M, T221A, T221G, T221I, A655R, A468F, A468S, Q216I, D564V, A565C, A655N, I167K, F260T, P607S, Y639V, A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263C, N263S, N278F, S332Y, Q316T, K345E, G427C, P661F, P661L, P666Q, T666C, S683W, F260D, F260G, F260Q, P607G, N400S, P607F, Q406D, G605C, N263T, N461V, I671C, K206A, T568E, E170F, P260E, T568K, P536C, A630Q, D215S, G372A, G547A, F611A, G662C, G662F, F260L, A633C, S312C, or N455D.

In other aspects, the invention provides BGL1 variants, as described above and throughout this specification, having improved (b) and (c) activities over wild type BGL1, wherein the BGL1variant is I567K, I567R, A565E, A565S, A565Y, F392Y, Q406H, Q406T, P604C, N038F, T568A, N461G, Y639L, Y639M, T243A, T243C, Q245H, Q245M, Q245T, T646A, T646C, I671F, I671L, I567V, N566G, A630K, Y639K, Q245N, K320Y, A347Y, A565C, Y639G, Y530F, N461V, I167C, K206A, T368E, A630Y, A655D, S507G, F260E, T568K, or F260L.

In other aspects, the invention provides BGL1 variants, as described above and throughout this specification, having improved (a) and (d) activities over wild type BGL1, wherein the BGL1 variant is I567S, G606E, G606H, G606N, G606S, L293A, S308R, I444C, M201D, R542N, L266C, I567F, S624P, P607L, G606L, G606K, G606L, G606M, G606Q, G606V, G605E, I444V, A633V, A655W, Y678H, V522Y, G554F, N566F, L293M, Q220P, S692L, A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263C, N263S, N278F, S312Y, Q316T, K345E, G427C, P661F, P661L, P661Q, T666C, S683W, F260D, F260G, F260Q, P607G, N400S, Q406D, G605C, N263T, S308E, A338D, P536C, A630Q, D215S, G372A, G547A, F611A, G662C, G662F, F260L, A633C, S312C, or N455D.

In other aspects, the invention provides BGL1 variants, as described above and throughout this specification, having improved (e) and (g) activities over wild type BGL1, wherein the BGL1 variant is I266F, I567Y, A270R, S384C, A630W, E128R, N146M, N145V, N146W, I181F, V043C, Y639P, S507F, Q245P, G662C, A630H, V466T, N146A, N146Q, P607K, N369T, S384E, L181M, V043A, V043G, V043N, Q060D, A655Y, T242S, S474D, P607F, A630Y, S308E, A635D, or L293F.

In other aspects the invention provides BGL1 variants, as described above and throughout this specification, having improved (c) and (e) activities over wild type BGL1, wherein the BGL1variant is N261E, N261K, N400A, V602K, L293I, N461S, D457A, V043Q, G203N, K320S, G662D, F260A, S474R, I567V, N566G, A630K, Y639K, Q245N, K320Y, A347Y, A601D, S384E, L181M, V043A, V043G, V043N, Q060D, A655Y, T242S, S474D, D564T, T568E, A655D, A338D, F260E, T568K, or F260L.

In other aspects, the invention provides BGL1 variants, as described above and throughout this specifications having improved (a) and (f) activities over wild type BGL1, wherein the BGL1 variant is N566L, N566P, N566W, A270K, A270N, F556H, F556K, P604N, N461D, N463E, K206G, A468Q, A468Y, N566F, N566H, F556V, P604Y, L293V, A630G, N461C, N463T, D457C, Q220M, T221A, T221G, T221I, A655R, A468F, A468S, Q261I, D564V, A468T, A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A458T, V466S, Y678A, Y678C, Y678Q, A468C, Q226W, Q226Y, N263C, N263S, N278F, S312Y, Q316T, K345E, G427C, P661F, P661L, P661Q, T666C, S683W, N461V, I671C, K206A, E170F, F260E, T568K, P536C, A630Q, D215S, G372A, G547A, F611A, G662C, G662F, A633C, S312C, or N455D.

In other aspects, the invention provides BGL1 variants, as described above and throughout this specification, having improved (a) and (c) activities over wild type BGL1, wherein the BGL1 variant is S233D, A270D, N146Y, F260A, S474R, A565C, K206S, D564T, N461V, I167C, K206A, T563E, A338D, P260E, T568K, or P260L.

In other aspects, the invention provides BGL1 variants, as described above and throughout this specification, having improved (a) and (e) activities over wild type BGL1, wherein the BGL1 variant is F556G, F260S, P604E, P604V, N146D, Y639T, T221C, N473S, N583R, R645G, G662Y, F260A, S474R, A655N, I671K, F260T, P607S, S692L, D564T, F260D, F260G, F260Q, P607G, N400S, P607F, T568E, S308E, A338D, F260E, T568K, P536C, A630Q, D215S, G372A, G347A, F611A, G662C, G662F, or F260L.

In is other aspects, the invention provides BGL1variants, as described above and throughout this specification, having improved (c) and (d) activities over wild type BGL1, wherein the BGL1 variant is D259S, T243V, Y530F, A338D, or F260L.

In other aspects, the invention provides BGL1 variants, as described above and throughout this specification, having improved (d) and (e) activities over wild type BGL1, wherein the BGL1 variant is S550Q, P607R, N400Q, V602F, A601G, A601L, L293K, Y575C, Y575R, A450Q, I486C, I486Y, A655S, Q245F, D329A, P536G, P607Q, A655Q, Y575A, Y575K, A630H, V466T, S692I, F260D, F260G, F260Q, P607G, N400S, P607I, A450P, T242H, S308E, A630Y, A338D, P536C, A630Q, D215S, G372A, G547A, F611A, G662C, G662F, F260L or L293F.

In other aspects, the invention provides BGL1 variants, as described above and throughout this specification, having improved (d) and (f) activities over wild type BGL1, wherein the BGL1 variant is P536F, F392C, S624L, S624R, S624W, I486F, I486W, A667G, A667S, L266N, F556L, S550T, S550V, T258L, P536I, P536V, F392R, S624G, S624N, S624Q, S624T, A601M, A630V, N463S, A450F, A450T, A450V, A450W, I486V, S482I, Y678I, G427F, D564D, Q684C, Q684G, N566F, Y575A, Y575K, A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263C, N263S, N278F, S312Y, Q316T, K345E, G427C, P661F, P661L, P661Q, T666C, S683W, F260W, P607I, A450P, T242H, P536C, A630Q, D215S, G372A, G547A, F611A, G662C, G662F, L293F, A633C, S312C, or N455D.

In other aspects, the invention provides BGL1 variants, as described above and throughout this specification, having improved (c) and (g) activities over wild type BGL1, wherein the BGL1 variant is S384G, S384W, N038E, N038M, N038P, V043H, V043W, Y068E, Y068G, Y068M, L110C, L110G, L110Q, L110W, A665H, N264L, S384E, L181M, V043A, Y043G, V043N, Q060A, A655Y, T242S, S474D, Y639G, K206S, A655D, or S507G.

In other aspects, the invention provides BGL1 variants, as described above and throughout this specification, having improved (d) and (g) activities over wild type BGL1, wherein the BGL1 variant is G606D, Y068V, L293M, Q220P, A630H, V446T, Y530S, Q684N, F260W, Q406D, G605C, N263T, S308E, A630Y, L293F, A633C, S312C, or N455D.

In other aspects, the invention provides BGL1 variants, as described above and throughout this specification, having improved (b) and (g) activities over wild type BGL1, wherein the BGL1 variant is A377I, N461Y, N461Y, N146Q, P607K, N369T, T436E, Y639G, V530S, Q684N, Y639V, F260W, P607F, Q406D, G605C, N263T, A630Y, A655D, E170F, S507G, L293F, A633C, S312C, or N455D.

Is other aspects, the invention provides BGL1 variants, as described above and throughout this specification, having improved (c) and (f) activities over wild type BGL1, wherein the BGL1 variant is K206D, A601D, Y530F, N461V I671C, K206A, S507G, F260E, or T568K.

In other aspects, the invention provides BGL1 variants, as described above and throughout this specification, having improved (e) and (f) activities over wild type BGL1, wherein the BGL1 variant is A468G, P536Q, N369E, N369W, N369Y, A601D, Y575A, Y575K, P607I, A450P, T242H, F260E, T568K, P536C, A630Q, D215S, G372A, G547A, F611A, G662C, G662F, or L293F.

In another aspect the invention provides BGL1 variants, as described above and throughout this specification, having improved (a) and (g) activities over wild type BGL1, wherein the BGL1 variant is R179V, L293M, Q220P, A468T, Y639V, P607F, Q206D, G605C, N263T, S308E, E170F, A633C, S312C, or N455D.

In other aspects, the invention provides BGL1 variants, as described above and throughout this specification, having improved activities selected from any two, or all three of (a), (b), and (d) over wild type BGL1, wherein the BGL1 variant is L266C, I567F, S624P, P607L, G606I, G606K, G606L, G606M, G606Q, G606V, G605E, I114V, A633V, A655W, Y678V, V522Y, G554E, A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263C, N263S, N278F, S312Y, Q316T, K345E, G427C, P661F, P661L, P661Q, T666C, S683W, F260D, F260G, F260Q, P607G, N400S, Q406D, G605C, N263T, P536C, A603Q, D215S, G372A, G547A, F611A, G662C, G662F, F260L, A633C, S312C, or N455D.

In other aspects, the invention provides BGL1 variants, as described above and throughout this specification, improved activities selected from any two or all three of (b), (d), and (f) over wild type BGL1, wherein the BGL1 variant is L226N, F556L, S550I, S550T, S550V, T258L, P536I, P536V, F392R, S624F, S624N, S624Q, S624T, A601M, A630V, N463S, A450F, A450T, A450V, A450W, I486V, S482I, Y678I, G427F, D564T, Q684C, Q684G, A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A485T, V446S, Y678A, Y678C, Y678Q, A468C, Q266W, Q226Y, N263C, N263S, N278F, S312Y, Q316T, K345E, G427C, P661F, P661L, P661Q, T666C, S683A, F260W, Y530F, P607I, A450P, T242H, P536C, A630Q, D215S, G372A, G547A, F611A, G662C, G662F, A633C, S312C, N455D, or L293F.

In other aspects, the invention provides BGL1 variants, as described above and throughout this specification, having improved activities selected from any two or all three of (a), (c), and (e) over wild type BGL1 wherein the BGL1 variant is F260A, S474B, D564T, T568E, A338D, F260E, T568K, or F260L.

In other aspects, the invention provides BGL1 variants, as described above and throughout this specification, having improved activities selected from any two or all three of (b), (c), and (e) over wild type BGL1 wherein the BGL1 variant is I567V, N566G, A630K, Y639K, Q245N, K320Y, A347Y, T568E, A655D, F260E, T568K, or F260L.

In other aspects, the invention provides BGL1 variants, as described above and throughout this specification, having improved activities selected from any two or all three of (a), (d), and (f) over wild type BGL1 wherein the BGL1 variant is N566G, A565G, A270C, T258S, T258V, P536D, P536E, S624F, S624I, S624V, A601C, A601Y, S308H, A630C, A630D, N463K, N463R, A450E, S482A, A667F, A667L, A677R, A667Y, A485T, V466S, Y678A, Y678C, Y678Q, A468C, Q226W, Q226Y, N263C, N263S, N278F, S312Y, Q316T, K345E, G427C, P661F, P661L, P661Q, T666C, S683W, P536C, A630Q, D215S, G372A, G547A, F611A, G662C, G662F, A633C, S312C, or N455D.

In other aspects, the invention provides BGL1 variants, as described above and throughout this specification, having improved activities selected from any two or all three of (a), (b), and (f) over wild type BGL1, wherein the BGL1 variant is N566H, F556V, P604Y, L293V, A630G, N461C, N463T, D457C, Q220M, T221A, T221G, T211I, A655R, A468F, A468S, Q216I, D564V, A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263C, N263S, N278F, S312Y, Q316T, K345E, G427C, P661F, P661L, P661Q, T666C, S683W, N461V, I671C, K206A, E170F, F260E, T568K, P536C, A630Q, D215S, G372A, G547A, F611A, G662C, G662F, A633C, S312C, or N455D.

In other aspects, the invention provides BGL1 variants, as described above and throughout this specification, having improved activities selected from any two or all three of (a), (b), and (c) over wild type BGL1, wherein the BGL1 variant is A565C, N461V, I671C, K206A, T568E, F260E, T568K, or F260L.

In other aspects, the invention provides BGL1 variants, as described above and throughout this specification, having improved activities selected from any two or all three of (b), (d) and (e) over wild type BGL1, wherein the BGL1 variant is P536G, P607Q, A655Q, F260D, F260G, F260Q, P607G, N400S, P607I, A450P, T242H, A630Y, P536C, A630Q, D215S, G372A, G547A, F611A, G662C, G662F, F260L, or L293F.

In other aspects, the invention provides BGL1 variants, as described above and throughout this specification, having improved activities selected from any two or all three of (b), (e), and (f) over wild type BGL1, wherein the BGL1 variant is P536Q, N369E, N369W, N369Y, P607I, A450P, T242H, F260E, T568K, P536C, A630Q, D215S, G372A, G547A, F611A, G662C, G662F, or L293F.

In other aspects, the invention provides BGL1 variants, as described above and throughout this specification, having improved activities selected from any two or all three of (c), (e), and (f) over wild type BGL1, wherein the BGL1 variant is A601D, F260E or T568K.

In other aspects, the invention provides BGL1 variants, as described above and throughout this specification, having improved activities selected from any two or all three of (a), (d), and (g) over wild type BGL1, wherein the BGL1 variant is L293M, Q220P, Q406D, G605C, N263T, S308E, A633C, S312C, or N455D.

In other aspects, the invention provides BGL1 variants, as described above and throughout this specification, having improved activities selected from any two or all three of (d), (e), and (f) over wild type BGL1, wherein the BGL1 variant is Y575A, Y575K, P607I, A450P, T242H, P536C, A630Q, D215S, G372A, G547A, F611A, G662C, G662F, or L293F.

In other aspects, the invention provides BGL1 variants, as described above and throughout this specification, having improved activities selected from any two or all three of (d), (e) and (g) over wild type BGL1, wherein the BGL1 variant is A630H, V466T, S308E, A630Y, or L293F.

In other aspects, the invention provides BGL1 variants, as described above and throughout this specification, having improved activities selected from any two or all three of (b), (e), and (g) over wild type BGL1, wherein the BGL1 variant is N146A, N146Q, P607K, N369T, P607F, A630Y, A655D, or L293F.

In other aspects, the invention provides BGL1 variants, as described above and throughout this specification, having improved activities selected from any two or all three of (c), (e), and (g) over wild type BGL1, wherein the BGL1 variant is S384E, L181M, V043A, Y043G, V043N, Q060D, A655Y, T242S, S474D, or A655D.

In other aspects, the invention provides BGL1 variants, as described above and throughout this specification, having improved activities selected from any two or all three of (b), (f), and (g) over wild type BGL1, wherein the BGL1 variant is T436E, F260W, E170F, S507G, L273F, A633C, S312C, or N455D.

In other aspects, the invention provides BGL1 variants, as described above and throughout this specification, having improved activities selected from any two or all three of (b), (c), and (g) over wild type BGL1, wherein the BGL1 variant is Y639G, P607F, A655D, or S507G.

In other aspects, the invention provides BGL1 variants, as described above and throughout this specification, having improved activities selected from any two or all three of (a), (b), and (e) over wild type BGL1, wherein the BGL1 variant is A655N, I167K, F260T, P607S, F260D, F260G, F260Q, P607G, N400S, P607F, T568E, F260E, T568K, P536C, A630Q, D215S, G372A, G547A, F611A, G662C, G662F, or P260L.

In other aspects, the invention provides BGL1 variant as described above and throughout this specification, having improved activities selected from any two or all three of (a), (e) and (g) over wild type BGL1, wherein the BGL1 variant is K206S or P607F. In other aspects, the invention provides BGL1 variants, as described above and throughout this specification, having improved activities selected from any two or all three of (b), (d) and (g) over wild type BGL1, wherein the BGL1 variant is Y530S, Q634N, F260W, Q406D, G605C, N263T, A630Y, L293F, A633C, S312C, or N455D. In other aspects, the invention provides BGL1 variants, as described above and throughout this specification, having improved activities selected from any two or all three of (a), (f), and (g) over wild type BGL1, wherein the BGL1 variant is A468T, E170F, A633C, S312C, or N455D. In other aspects, the invention provides BGL1 variants, as described above and throughout this specification, having improved activities selected from any two or all three of (a), (d), and (e) over wild type BGL1, wherein the BGL1 variant is S692L, F260D, F260G, F260Q, P607G, N400S, S308E, A338D, P536C, A630Q, D215S, G372A, G547A, F661A, G662C, G662F, or F260L.

In other aspects, the invention provides BGL1 variants, as described above and throughout this specification, having improved activities selected from any two, any three, or (a), (b), and (g) over wild type BGL1, wherein the BGL1 variant is Y639V.

In other aspects, the invention provides BGL1 variants, as described above and throughout this specification, having improved activities selected from any two, any three, or all four of (a), (b), (d) and (f) activities over wild type BGL1, wherein the BGL1 variant is A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263C, N263S, N278F, S312Y, Q316T, K345E, G427C, P661F, P661L, P661Q, T666C, or S863W.

In other aspects, the invention provides BGL1 variants, as described above and throughout this specification, having improved activities selected front any two, any three, or all four of (a), (b), (d) and (e) over wild type BGL1, wherein the BGL1 variant is F260D, F260G, F260Q, P607G, or N400S. In other aspects, the invention provides BGL1 variants, as described above and throughout this specification, having improved activities selected from any two, any three, or all four of (b), (d), (f) and (g) over wild type BGL1, wherein the BGL1 variant is F260W, L293F, A633C, S312C, or N455D.

In other aspects, the invention provides BGL1 variants, as described above and throughout this specification, having improved activities selected from any two, any three, or all four of (b), (c), (d) and (f) over wild type BGL1, wherein the BGL1 variant is Y530F.

In other aspects, the invention provides BGL1, variants, as described above and throughout this specification, having improved activities selected from any two, any three, or all four of (a), (b), (e) and (g) over wild type BGL1, wherein the BGL1 variant is P607F.

In other aspects, the invention provides BGL1 variants, as described above and throughout this specification, having improved activities selected front any two, any three, or all four of (a), (b), (d) and (g) over wild type BGL1 wherein the BGL1 variant is Q406D, G605C, N263T, A633C, S312C, or N455D. In other aspects, the invention provides BGL1 variants, as described above and throughout this specification, having improved activities selected from any two, any three, or all four of (a), (b), (c) and (f) over wild type BGL1, wherein the BGL1 variant is N461V, I671C, K206A, F260E or T568K. In other aspects, the invention provides BGL1 variants, as described above and throughout this specification, having improved activities selected from any two, any three, or all four of (b), (d), (e) and (f) over wild type BGL1, wherein the BGL1 variant is P607I, A450P, T242H, P536C, A630Q, D215S, G372A, G547A, F611A, G662C, G662F, or L293F. In other aspects, the invention provides BGL1 variants, as described above and throughout this specification, having improved activities selected from any two, any three, or all four of (a), (b), (c) and (e) over wild type BGL1, wherein the BGL1 variant is T568E, F260E, T568K, or F260L.

In other aspects, the invention provides BGL1 variants, as described above and throughout this specification, having improved activities selected front any two, any three, or all four of (a), (d), (e) and (g) over wild type BGL1, wherein the BGL1 variant is S308E.

In other aspects, the invention provides BGL1 variants, as described above and throughout this specification, having improved activities selected from any two, any three, or all four of (b), (d), (e) and (g) over wild type BGL1 wherein the BGL1 variant is A630Y or L293F. In other aspects, the invention provides BGL1 variants, as described above and throughout this specification, having improved activities selected from any two, any three, or all four of (b), (c), (e) and (g) over wild type BGL1, wherein the BGL1 variant is A655D.

In other aspects, the invention provides BGL1 variants, as described above and throughout this specification, having improved activities selected from any two, any three, or all four of (a), (b), (f) and (g) over wild type BGL1, wherein the BGL1 variant is E170F, A633C, S312C, or N455D. In other aspects, the invention provides BGL1 variants, as described above and throughout this specification, having improved activities selected from any two, any three, or all four (a), (c), (d) and (e) over wild type BGL1, wherein the BGL1 variant is A338D or F260L. In other aspects, the invention provides BGL1 variants, as described above and throughout this specification, having improved activities selected from any two, any three, or all four of (b), (c), (f) and (g) over wild type BGL1, wherein the BGL1 variant is S507G.

In other aspects, the invention provides BGL1 variants, as described above and throughout this specification, having improved activities selected from any two, any three, any four, or all five of (a), (b), (c), (e) and (f) over wild type BGL1 wherein the BGL1 variant is F260E or T568K. In other aspects, the invention provides BGL1 variants, as described above and throughout this specification, having improved activities selected from any two, any three, any four, or all five of (a), (b), (d), (e) and (f) over wild type BGL1, wherein the BGL1 variant is P536C, A630Q, D215S, G372A, G547A, F611A, G662C, or G662F. In other aspects, the invention provides BGL1 variants, as described above and throughout this specification, having improved activities selected from any two, any three, any four, or all five of (a), (b), (c), (d) and (e) over wild type BGL1, wherein the BGL1 variant is F260L. In other aspects, the invention provides BGL1 variants, as described above and throughout this specification, having improved activities selected from any two, any three, any four, or all five of (b), (d), (e), (f) and (g) over wild type BGL1, wherein the BGL1 variant is L293F. In other aspects, the invention provides BGL1 variants, as described above and throughout this specification, having improved activities selected from any two, any three, any four, or all five of (a), (b), (d), (f) and (g) over wild type BGL1, wherein the BGL1 variant is A633C, S312C, or N455D.

The invention also provides for BGL1 variants having at least two improved activities over wild type BGL1 selected from the group consisting of: (a) pre-treated corn stover (PCS) hydrolysis activity, (b) cellobiase activity, (c) protein expression, (d) beta-glucosidase activity as measured by an ammonia pretreated corncob (CC) hydrolysis activity, (e) thermostability, (f) phosphoric acid swollen cellulose (PASC) hydrolysis activity, and (g) hydrolytic activity in the presence of glucose, wherein the BGL1 variant comprises two or more substitutions from selected from those listed in Table 5-1.

In other aspects, the invention provides BGL1 variants, as described above and throughout this specification, wherein the improved activities over wild type BGL1 are (a) and (c)

and the substitutions are: L167W|D225Q, T242S|S312Y, D178K|A338K|S474D| G662L, K345E|N369T|G372A|K428N|P661L|S683W, D177M|D225Q|D564V|Q684G, and D178N|N264K|A338D|S474R|G662K, D177M|D564T|Q626F|Q684A, K428N|S683W, K345E|K428N|S683W, Q226Y|G372A|V603G|T666C, L167W|D177M|Q626F, L167W|D177M|D225Q|D564V|Q684G, D177M|D225Q|D564T|Q684N, D177M|Q626F|Q684R, N238W|R265P|K656R, N264M|R265P (optionally also G662F), N264L|A338I|S474R|G662D, L167W|D225Q|D564V|Q626F|Q684N, D177M|D225Q|D564T|Q684A, D177M|D225Q|D564V|Q626F|Q684N, K345E|N369E|G372A|P661E, N369T|P661L|S683W, R265M|K560S, N369T|G372A|P661L|S683W, P176L|Q226W|K320Y|R363E, K345E|N369T|G372A|P661E|S683W, K320S|R363E, E170F|Q226Y|T242S|S312Y|G372A|V603G|P661F| T666C, T242S|T666C, Q226Y|T666C, Q216E|S312K|S692K, P176L|G662F, P176L|Q226W|Q316T|K320Y|R363E, P176L|Q226W|K320S|R363E|G662F, P761L|Q226W|Q316T|K320Y|V522Y, P176L|Q226W|K320Y|R363E|V522Y, Q226W|K320Y|R363E, Q316T|K320Y|R363E|G662F, Q226W|Q316T|R363E|V522Y|G662F, P176L|K320S|R363E|G662C, R363E|G547A|G662C, Q226W|K320S|G662C, P176L|Q226W|Q316T|K320Y|R363E|G662F, P176L|Q226W|Q316T|K320S|G662F, P176L|Q316T|K320S|R363E|V522Y|G662C, K320Y|R363E|G662C, K345E|N369E|P661L, E170F, V603G, K343E|N369E|G372A|S683W, N369E| S683W, G372A|P661E|S683W, P176L|Q316T|K320S|R363E|G662F, K345E|N369E|P661E|S383W, K345E|P661E|S683W, N263C|K345E|N369E|N263C|N369T|P661E, K345E|N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are (b) and (f) and the substitutions are: L167W|D177M|D225Q|Q626F|Q684G, L167W|D177M|D564V|Q684G, D215S|S312Y, E107F|S312Y|N369Y, L167W|D225Q|Q626F|Q684R, L167W|D564T|Q626F, P176L|Q226W|Q316T|K320S|V522Y|G662C, R363E|V522Y|G662F, Q316T|K320S|V522Y|G662F, Q226W|K320Y|V522Y, Q316T|K320S|V522Y, and Q226W|K320S|R363E|V522Y|G662F, L167W|D177M|D225Q|D564V, D177M|D225Q|D564T|Q684A, D177M|D225Q|D564V|Q626F|Q684N, L167W|D177M|Q626F|Q684G, L167W|D177M|D564V|Q626F|Q684A, P176L|K320S|V522Y|G662C, K345E|N369T|G372A|P661E|S683W, K320S|R363E, E170F|Q226Y|T242S|S312Y|G372A|V603G|P661F|T666C, T242S|T666C, Q226Y|T666C, Q216E|S312K|S692K, P176L|G662F, P176L|Q226W|Q316T| K320Y|R363E, P176L|Q226W|K320S|R363E|G662F, P176L|Q226W|Q316T|K320Y|V522Y, P176L|Q226W|K320Y|R363E|V522Y, Q226W|K320Y|R363E, Q316T|K320Y|R363E|G662F, Q226W|Q316T|R363E|V522Y|G662F, P176L|K320S|R363E|G662C, R363E|G547A|G662C, Q226W|K320S|G662C, P176L|Q226W|Q316T|K320Y|R363E|G662F, P176L|Q226W|Q316T|K320S|G662F, P176L|Q316T|K320S|R363E|V522Y|G662C, K320Y|R363E|G622C, E170F|Q226Y|N369Y|G372A|P661F, and L167W|D177M|D564T|Q626F|Q684G, K345E|N369E|G372A|S683W, N369E|S683W, K343E|N369E|P661E|S683W, K345E|P661E|S683W, N263C|N345E|N369E, N263C|N369T|P661E, K345E|N369E|S683W, K263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are (e) and (g) and the substitutions are: L167W|D225Q|Q626F|Q684D, L167W|D225Q|Q684N, L167W|D225Q|D564T|Q626F|Q684C, Q626F|Q684D, N264M|R265P|N369I|D370W, R179V|N238F|D370W, R179V|N238F|K656R, R179V|N264M|D370W, R179V|N238F|R265M, R179V|R265P|D370W|K656R, R179V|N238W|N264M|R265M|N369I|R179V|N369I| D370W|K656R, R179V|N264M|R265P|K656R, R179V|R265M|N369I, R179V|N264M|R265M|D370W|K656R, R179V|N264M|R265M|N369I, R179V|N238W|N264M, N238W|N264M|R265M|D370W, R179V|N238W|R263P|D370W, R179V|N238W|N264M|D370W|K636R, N264M|R265P, R265P|D370W (optionally also G662F), R179V|N264M|R265P|G369I|D370W, R265M|N369I, R179V|R265M|D370W, N238W|N264M|R265P, R179V|N238W|N264M|R265P, N264M|N369I, N238F|R265M|N369I, N263C|K345E|N369E|G372A|K428N|P661E|S683W, N263C|K345E|N369T|G372A|K428N|P611E|S683W, N263C|K345E|N369E|G372A, N263C|P661L|S683W, N263C|K345E|N369T|G372A|K428N, K345E|G372A|K428N|P661E, E170F|Q226Y|N369Y|G372A, Q226Y|T242S|G372A|P661F, Q216E|T282I|S312D|S692K, Q216I|T282K|S312K|A622K, P176L|Q316T|G662C, Q226W|Q316T|V522Y|G662F, P176L|G316T, A347Y|R542N, N238F|N264M|R265M|N369I, L167W|D225Q|D564V|Q626F|Q684N, E170F|V603G, L167W|D177M|D564T|Q684N, K345E|N369E|G372A|S683W, N369E|S683W, G372A|P661E|S683W, P176L|Q316T|K320S|R363E|G662F, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, described above and throughout this specification, wherein the improved activities over wild type BGL1 are (d) and (f) and the substitutions are: L167W|D177M|D564V|Q684R, L167W|D225Q|D564V, D177M|D225Q|D564T|Q626F|Q684N, L167W|Q626F, D225Q|D564V|Q626F|Q684R, D177M|D225Q|D564V|Q684R, Q226W|K320Y, P176L|V522Y,
L167W|D225Q|Q626F|Q684R, L167W|D564T|Q626F,
P176L|Q226W|Q313T|K320S|V522Y|G662C,
R363E|V522Y|G662F, Q316T|K320S|V522Y|G662F,
Q226W|K320Y|V522Y, Q316T|K320S|V522Y,
Q226W|K320S|R363E|V522Y|G662F,
L167W|D177M|D564T|Q626F|Q684N,
L167W|Q626F|Q684D, L167W|D177M|D564T|Q684R,
L167W|D177M|D225Q|Q684D, R179V|R265P|N369I,
Q316T|K320Y|R363E|V522Y|G662F,
L167W|D177M|Q626F,
L167W|D177M|D225Q|D564V|Q684G,
D177M|D225Q|D564T|Q684N, D177M|Q626F|Q684R,
L167W|D177M|Q626F|Q684G,
L167W|D177M|D564V|Q626F|Q684A,
P176L|K320S|V522Y|G662C,
K345E|N369T|G372A|P661E|S683W, K320S|R363E,
E170F|Q226Y|T242S|S312Y|G372A|V603G|P661F|
T666C, T242S|T666C, Q226Y|T666C,
Q216E|S312K|S692K, P176L|G662F,
P176L|Q226W|Q316T| K320Y|R363E,
P176L|Q226W|K320S|R363E|G662F,
P176L|Q226W|Q316T|K320Y|V522Y,
P176L|Q226W|K320Y|R363E|V522Y,
Q226W|K320Y|R363E, Q316T|K320Y|R363E|G662F,
Q226W|Q316T|R363E|V322Y|G662F,
P176L|K320S|R363E|G662C, R363E|G547A|G662C,
Q226W|K320S|G662C,
P176L|Q226W|Q316T|K320Y|R363E|G662F,
P176L|Q226W|Q316T|K320S|G662F,
P176L|Q316T|K320S|R363E|V522Y|G662C,
K320Y|R363E|G662C,
E170F|Q226Y|N369Y|G372A|P661F,
L167W|D177M|D564T|Q626F|Q684G,
K345E|N369E|P661E|S683W, K345E|P661E|S683W,
N263C|K345E|N369E, N263C|N369T|P661E,
K345E|N369E|S683W, N263C|K345E|N369T|K428N,
N263C|N369E|K423N|P661E, N263C|N369T|S683W,
N263C|N369T, N369T|G372A|K428N|S683W,
N263C|G372A, N263C|K345E|N369E|G372A|P661E, or
P176L|Q226W|G547A|G662C.

In other aspects, the invention provides BGL1 variants, as described above and throughout this specification, wherein the improved activities over wild type BGL1 are (b) and (e) and the substitutions are: K345E|N369E|K428N|P661L, Q316T|K320Y|V522Y, N369T|G372A|P661L|S683W, P176L|Q226W|K320Y|R363E,
P176L|K320S|V552Y|G662C, K345E|N369E|P661L,
L167W|D177M|D564T, Q684N,
K345E|N369E|G372A|S683W, N369E|S683W,
G372A|P661E|S683W,
P176L|Q316T|K320S|R363E|G662F,
K345E|N369E|P661E|S683W, K345E|P661E|S683W,
N263C| K345E|N369E, N263C|N369T|P661E,
K345E|N369E|S683W, N263C|K345E|N369T|K428N,
N263C|N369E|K428N|P661E, N263C|N369T|S683W,
N263C|N369T, N369T|G372A|K428N|S683W,
N263C|G372C|N263C|K345E|N369E|G372A|P661E, or
P176|Q226W|G547A|G662C.

In other aspects, the invention provides BGL1 variants, as described above and throughout this specification, wherein the improved activities over wild type BGL1 are (d) and (e) and the substitutions are: N263C|K345E|N369E|P661L, N238F|N264M|R265M| N369I,
P176L|K320S|V522Y|G662C, K345E|N369E|P661L,
E170F|V603G, L167W| D177M|D564T|Q684N,
G372A|P661E ⊕ S683W,
P176L|Q316T|K320S|R363E|G662F,
K345E|N369E|P661E|S683W, K345E|P661E|S683W,
N263C|K345E|N369E, N263C|N369T|P661E,
K345E|N369E|S683W, N263C|K345E|N369T|K428N,
N263C|N369E|K428N|P661E, N263C|N369T|S683W,
N263C|N369T, N369T|G372A|K428N|S683W,
N263C|G372A, N263C|K345E|N369E|G372A|P661E, or
P176L|Q226W|G547A|G662C.

In other aspects, the invention provides BGL1 variants, as described above and throughout this specification, wherein the improved activities over wild type BGL1 are (b) and (g) and the substitutions are:
E170F|T242S|N369Y|G372A|V603G|T666C,
E170F|Q226Y|N369Y|V603G|T666C,
E170F|Q226Y|S312Y, L167W|D177M|D225Q|D564V,
L167W|D177M|Q626R|Q684G,
L167W|D177M|D564V|Q626F|Q684A,
E170F|Q226Y|N369Y|G372A|P661F,
L167W|D177M|D564T|Q626F|Q684G,
L167W|D177M|D564T|Q684N,
K345E|N369E|G372A|S683W, N369E|S683W,
G372A|P661E|S683W,
P176L|Q316T|K320S|R363E|G662F, N263C|N369T,
N369T| G372A|K428N|S683W, N263C|G372A,
N263C|K345E|N369E|G372A|P661E, or
P176L|Q226W|G547A|G662C.

In other aspects, the invention provides BGL1 variants, as described above and throughout this specification, wherein the improved activities over wild type BGL1 are (d) and (g) and the substitutions are: D178I|Q303E|A338I, Q316T|K320Y|G662F,
L167W|D117M|D564T|Q626F|Q684N,
L167W|Q626F|Q684D, L167W|D177M|D564T|Q684R,
L167W|D177M|D225Q|Q684D, R179V|R265P|N369I,
Q316T|K320Y|R363E|V552Y|G662F,
N238F|N264M|R265M|N369I, N238W|R265P|K656R,
N264M|R265P, (optionally also G662F),
N264I|A338I|S474R|G662D,
L167W|D177M|Q626F|Q684G, and
L167W|D177M|D564V|Q626F|Q684A, E170F|V603G,
E170F|Q226Y|N369Y|G372A|P661F,
L167W|D177M|D564T|Q626F|Q684G,
L167W|D177M|D564T|Q684N, G372A|P661E|S683W,
P176L|Q316T|K320S|R363E|G662F, N263C|N369T,
N369T|G372A|K428N|S683W, N263C|G372A,
N263C|K345E|N369E|G372A|P661E, or
P176L|Q226W|G547A|G662C.

In other aspects, the invention provides BGL1 variants, as described above and throughout this specification, wherein the improved activities over wild type BGL1 are selected from any two or all three of (b), (d), and (f) and the substitutions are: L167W|D225Q|Q626F|Q684R, L167W|D564T|Q626F,
P176L|Q226W|Q316T|K320S|V522Y|G662C,
R363E|V522Y|G662F, Q316T|K320S|V522Y|G662F,
Q226W|K320Y|V522Y, Q316T|K320S|V552Y,
Q226W|K320S|R363E|V522Y|G662F,
L167W|D177M|Q626F|Q684G,
L167W|D177M|D564V|Q626F|Q684A,
P176L|K320S|V522Y|G662C,
K345E|N369T|G372A|P661E|S683W, K320S|R363E,
E170F|
Q226Y|T242S|S312Y|G373A|V603G|P661F|T666C,
T242S|T666C, Q226Y|T666C, Q216E|S312K|S692K,
P176L|G662F, P176L|Q226W|Q316T|K320Y|R363E,
P176L|Q226W|K320S|R363E|G662F,
P176L|Q226W|Q316T|K320Y|V552Y,
P176L|Q226W|K320Y|R363E|V552Y,
Q226W|K320Y|R363E, Q316T|K320Y|R363E|G662F, Q226W|Q316T|R363E|V522Y|G662F,
P176L|K320S|R363E|G662C, R363E|G547A|G662C,
Q226W|K320S|G662C,
P176L|Q226W|Q316T|K320Y|R363E|G662F,
P176L|Q226W|Q316T|K320S|G666F,
P176L|Q316T|K320S|R363E|V522Y|G662C, K320Y|R363E|G662C, E170F|Q226Y|N369Y|G372A|P661F, L167W|D177M|D564T|Q626F|Q684G, K345E|N369E|P661E|S683W, K345E|P661E|S683W, N263C|K345E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two or all three of (d), (f), and (g) and the substitutions are: L167W|D177M|D564T|Q626F|Q684N, L167W|Q626F|Q684D, L167W|D177M|D564T|Q684R, L167W|D177M|D225Q|Q684D, R179V|R265P|N369I, Q316T|K320|R363E|V522Y|G662F, L167W|D177M|Q626F|Q684G, L167W|D177M|D564V|Q626F|Q684A, E170F|Q226Y|N369Y|G372A|P661F, L167W|D177M|D564T|Q626F|Q684G, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two or all three of (a), (c), and (e) and the substitutions are: K345E|N369T|G372A|K428N|P661L|S683W, L167W|D225Q|D564V|Q626F|Q684N, N369T|G372A|P661L|S683W, P176L|Q226W|K320Y|R363E, K343E|N369E|P661I, E170F|V603G, K345E|N369E|G372A|S683W, N369E|S683W, G372A|P661E| S683W, P176L|Q316T|K320S|R363E|G662F, K345E|N369E|P661E|S683W, K345E|P661E|S683W, N263C|K345E|N369E, N263C|N369T|P661E, K345E|N369E| S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E or P176L|Q226W|G547A|G662C.

In other aspects, the invention provides BGL1 variants, as described above and throughout this specification, wherein the improved activities over wild type BGL1 are selected from any two or all three of (b), (f), and (g) and the substitutions are: L167W|D177M|D225Q|D564V, L167W|D177M|Q626F|Q684G, L167W|D177M|D564V|Q626F|Q684A, E170F|Q226Y|N369Y|G372A|P661F, L167W|D177M|D564T|Q626F|Q684G, K345E|N369E|G372A|S683W, N369E|S683W, N263W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two or all three of (a), (c), and (d) and the substitutions are: D176M|D225Q|D564V|Q684G, D178N|N264K|A338D|S474R|G662K, L167W|D177M|Q626F, L167W|D177M|D225Q|D564V|Q684G, D177M|D225Q|D564T|Q684N, D177M|Q626F|Q684R, N233W|R265P|K656R, N264M|R265P (optionally also G662F). N264F|A338I|S474R|G662D, K345E|N369E|G372A|P661E, N369T|P661L| S683W, K345E|N369T|G372A|P661E|S683W, K320S|R363E, E170F|Q226Y|T242S|S312Y|G372A|V603G|P661F| T666C, T242S|T666C, Q226Y|T666C, Q216E|S312K|S692K, P176L|G662F, P176L|Q226W|Q316T|K320Y|R363E, P176L|Q226W|K320S|R363E|G662F, P176L|Q226W|Q316T|K320Y|V522Y, P176L|Q226W|K320Y|R363E|V522Y, Q226W|K320Y|R363E, Q316T|K320Y|K363E|G662F, Q226W|Q316T|R363E|V522Y|G662F, P176L|K320S|R363E|G662C, R363E| G547A|G662C, Q226W|K320S|G662C, P176L|Q226W|Q316T|K320Y|R363E|G662F, P176L|Q226W|Q316T|K320S|G662F, P176L|Q316T|K320S|R363E|V522Y| G662C, K320Y|R363E|G662C, K345E|N369E|P661L, E170F|Y603G, G372A|P661E|S683W, P176L|Q316T|K320S|R363E|G662F, K345E|N369E|P661E|S683W, K345E|F661E|S683W, N263C|K345E|N369E, N263C|N369T|P661E, K345E| N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two or all three of (a), (c), and (g) and the substitutions are: D177M|D564T|Q626F|Q684A, N238W|R265P|K656R, N264M|R265P (optionally also G662F), N264L|A338I|S474R|G662D|D225Q|D564V|Q626F| Q684N, R265M|K560S, E170F|V603G, K345E|N369E|G372A|S683W, N369E|S683W, G372A|P661E|S683W, P176L|Q316T|K320S|R363E|G662F, N263C|N369T, G372A| K428N|S683W, N263C|G372A, N263C|K345E|N369E|G372A|P661E, or P176L|Q226W|G347A|G662C.

In other aspects, the invention provides BGL1 variants, as described above and throughout this specification, wherein the improved activities over wild type BGL1 are selected from any two or all three of (d), (e), and (g) and the substitutions are: N238F|N264M|R265M|N369I, E170F|Y603G, L167W|D177M|D564T|Q684N, G372A|P661E|S683W, P176L|Q316T|K320S|R363E|G662F, N263C|N369T, N369T|G372A| K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two or all three of (a), (b), and (c) and the substitutions are: K228N|S683W, K345E|K428N|S683W, Q226Y|G372A|V603G|T666C, D177M|D225Q|D564T|Q684A, D177M|D225Q|D564V|Q626F|Q684N, K345E|N369E|G372A|P661E, N369T|P661L|S683W, N369T|G372A|P661L|S683W,
P176L|Q226W|K320Y|R363E,
K345E|N369T|G372A|P611E|S683W, K320S|R363E,
E170F|Q226Y|
Y242S|S312Y|G372A|V603G|P661F|T666C,
T242S|T666C, Q226Y|T666C, Q216E| S312K|S692K,
P176L|G662F, P176L|Q226W|Q316T|K320Y|R363E,
P176L|Q226W|K320S|R363E|G662F,
P176L|Q226W|Q316T|K320Y|V522Y,
P176L|Q226W|K320Y|R363E|V522Y,
Q226W|K320Y|R363E, Q316T|K320Y|R363E|G662F,
Q226W|Q316T|R363E|V552Y|G662F,
P176L|K320S|R363E|G662C, R363E| G547A|G662C,
Q226W|K320S|G662C,
P176L|Q226W|Q316T|K320Y|R363E|G662F,
P176L|Q226W|Q316T|K320S|G662F,
P176L|Q316T|K320S|R363E|V522Y| G662C,
K320Y|R363E|G662C, K345E|N369E|P661L,
K345E|N369E|G372A|S683W, N369E|S683W,
G372A|P661E|S683W,
P176L|Q316T|K320S|R363E|G662F,
K345E|N369E|P661E|S683W, K345E|P661E|S683W,
N263C|K345E|N369E, N263C|N369T|P661E,
K345E|N369E|S683W, N263C|K345E|N369T|K428N,
N263C|N369E|K428N|P661E, N263C|N369T, S683W,
N263C|N369T, N369T|G372A|K428N|S683W,
N263C|G372A, N263C|K345E|N369E|G672C|P611E, or
P176L|Q226W|G547A|G662C.

In other aspects, the invention provides BGL1 variants, as described above and throughout wherein the improved activities over wild type BGL1 are selected from any two or all three or all four of (a), (c), (d), and (f) and the substitutions are: L167W|D177M|Q626F, L167W|D177M|D225Q|D564V|Q684G, D177M|D225Q|D564T|Q684N, D177M|Q626F|Q684R, K345E|N369T|G372A|P661E|S683W, K320S|R363E, E170F|Q226Y|T242S|S312Y|G372A|V603G|P661F|T666C, T242S|T666C, Q226Y|T666C, Q216E|S312K|S692K, P176L|G662F, P176L|Q226W|Q316T| K320Y|R363E, P176L|Q226W|K320S|R363E|G662F, P176L|Q226W|Q316T|K320Y|V522Y, P176L|Q226W|K320Y|R363E|V522Y, Q226W|K320Y|R363E, Q316T|K320Y|R363E|G662F, Q226W|Q316T|R363E|V522Y|G662F, P176L|K320S|R363E|G662C, R363E|G547A|G662C, Q226W|K320S|G662C, P176L|Q226W|Q316T|K320Y|R363E|G662F, P176L|Q226W|Q316T|K320S|G662F, P176L|Q316T|K320S|R363E|V522Y|G662C, K320Y|R363E|G662C, K345E|N369E|P661E|S683W, K345E|P661E|S683W, N263C|K345E|N369E, N263C|N369T|P661E, K345E|N369E|G683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are (a), (c), (d), and (g) and the substitutions are: N238W|R263P|K656R, N264M|R265P (optionally also G662F), N264L|A338I|S474R|G662D E170F|V603G, G372A|P661E|S683W, P176L|G316T|K320S|R363E|G662F, N263C|N369T|G372A|K428N|S633W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three or all four of (a), (c), (e), and (g) and the substitutions are: L167W|D225Q|D564V|Q626F|Q684N, E170F|V603G, K345E|N369E|G372A|S683W, N369E|S683W, G372A|P661E|G683W, P176L|Q316T|K320S|R363E|G662F, N263C|G369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three or all four of (a), (b), (c), and (f) and the substitutions are: D177M|D225Q|D564T|Q684A, D177M|D225Q|D564V|Q626F|Q684N, K345E|N369T|G372A|P661E|S683W, K320S|R363E, E170F|Q226Y|T242S|S312Y|G372A| V603G|P661F|T666C, T242S|T666C, Q226Y|T666C, Q216E|G312K, S692K, P176L| G662F, P176L|Q226W|Q316T|K320Y|R363E, P176L|Q226W|K320S|R363E|G662F, P176L|Q226W|Q316T|K320Y|V522Y, P176L|Q226W|K320Y|R363E|V522Y, Q226W|K320Y|R363E, Q316T|K320Y|R363E|G662F, Q226W|Q316T|R363E|V522Y|G662F, P176L|K320S|R363E|G662C, R363E|G547A|G662C, Q226W|K320S|G662C, P176L|Q226W|Q316T|K320Y|R363E|G662F, P176L|Q226W|Q316T|K320S|G662F, P176L|Q316T|K320S|R363E|V522Y|G662C, K320Y|R363E|G662C, K345E|N369E|G372A|G683W, N369E|S683W, K345E|N369E|P661E|S683W, K345E|P661E|G683W, N263C|K343E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|G683W, N263C|G372A, G263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three or all four of (a), (b), (c), and (d) and the substitutions are: K345E|N369E|G372A|P661E, N369T|P661L|S683W, K345E|N369T|G372A|P661E|S683W, K320S|R363E, E170F|Q226Y|T242S|G312Y|G372A|V603G|P661F| T666C, T242S|T666C, Q226Y|T666C, Q216E|S312K, S692K, P176L|G662F, P176L|Q226W|Q316T|K320Y|R363E, P176L|Q226W|K320S|R363E|G662F, P176L|Q226W|Q316T|K320Y|V522Y, P176L|Q226W|K320Y|R363E|V522Y, Q226W|K320Y|K363E, Q316T|K320Y|R363E|G662F, Q226W|Q316T|R363E|V522Y|G662F, P176L|K320S|E363E|G662C, R363E|G547A|G662C, Q226W|K320S|G662C, P176L|Q226W|Q316T|R320Y|R363E|G662F, P176L|Q226W|Q316T|K320S|G662F, P176L|Q316T|K320S|R363E|V522Y|G662C, K320Y|R363E|G662C, K343E|N369E|P661L, G372A|P661E|S683W, P176L|Q316T|K320S|R363E|

G662F, K345E|N369E|P661E|S683W, K345E|P661E|S683W, N263C|K343E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|G683W, N263C|G372A, N263C|K343E|N369E|G372A|P661E, or P176L|Q226W|G547A|G662C.

In other aspects, the invention provides BGL1 variants, as described above and throughout this specification, wherein the improved activities over wild type BGL1 are selected from any two, any three or all four of (b), (d), (f), and (g) and the substitutions are: L167W|D177M|Q626F|Q684G, L167W|D177M|D564V|Q626F|Q684A, E170F|Q226Y|N369Y|G372A|P661F, L167W|D177M|D564T|Q626F|Q684G, K345E|N369E|G372A|S683W, N369E|S683W, N263C|N369T, N369T|G372A|R428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three or all four of (a), (c), (f), and (g) and the substitutions are: R265M|K560S, K345E|N369E|G372A|S683W, N369E|S683W, N263C|N369T, N369T|G372A|K428N|S683W, N263C|G372A, N263|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three or all four of (a), (b), (c), and (e) and the substitutions are: N369T|G372A|P661L|S683W, P176L|Q226W|K320Y|R363E, K345E|N369E|P661L, K345E|N369E|G372A|S683W, N369E|G683W, G372A|P661E|G683W, P176L|Q316T|K320S|R363E|G662F, K345E|N369E|P661E|S683W, K345E|P661E|S683W, N263C|K345E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three or all four of (b), (d), (e), and (f) and the substitutions are: P176L|K320S|V552Y|G662C, K345E|N369E|P661E|S683W, K345E|P661E|S683W, N263C|K345E|N369E, N263C|N369T|P661E|K345E|N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, any four, or all five of (a), (b), (c), (d), and (f) and the substitutions are: K345E|N369T|G372A|P661E|S683W, K320S|R363E, E170F|Q226Y|T242S|S312Y|G372A|V603G|P661F|T666C, T242S|T242S|T666C, Q226Y|T666C, Q216E|S312K|S692K, P176L|G662F, P176L|Q226W|Q316T|K320Y|R363E, P176L|Q226W|K320S|R363E|G662F, P176L|Q226W|Q316T|K320Y|V552Y, P176L|Q226W|K320Y|R363E|V552Y, Q226W|K320Y|R363E, Q316T|K320Y|R363E|G662F, Q226W|Q316T|R363E|V522Y|G662F, P176L|K320S|R363E|G662C, R363E|G547A|G662C, Q226W|K320S|G662C, P176L|Q226W|Q316T|K320Y|R363E|G662F, P176L|Q226W|Q316T|K320S|G662F, P176L|Q316T|K320S|R363E|V522Y|G662C, K320Y|R363E|G662C, K345E|N369E|P661E|S683W, K345E|P661E|S683W, N263C|K345E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, any four, or all five of (a), (b), (c), (d), and (e) and the substitutions are: K345E|N369E|P661L, G372A|P661E|S683W, P176L|Q316T|K320S|R363E|G662F, K345E|N369E|P661E|S683W, K345E|P661E|S683W, N263C|K345E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three any four, or all five of (a), (c), (d), (e), and (g) and the substitutions are: E170F|V603G, G372A|P661E|S683W, P176L|Q316T|K320S|R363E|G662F, N263C|N369T, N369T|G372A|K428N|S683W, N263C|G372A, N263C|K345E|N369E|G372A ⊕ P661E, and P176L|Q226W|G547A|G662C.

In other aspects, the invention provides BGL1 variants, as described above and throughout this specification, wherein the improved activities over wild type BGL1 are selected from any two, any three, any four, or all five of (a), (b), (d), (f), and (g) and the substitutions are: E170F|Q226Y|N369Y|G372A|P661F, L167W|G177M|D564T|Q626F|Q684G, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, any four, or all five of (a), (d), (d), (e), and (g) and the substitutions are: L177W|D177M|D564T|Q684N, G372A|P661E|S683W, P176L|Q316T|K320S|R363E|G662F, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, any four, or all five of (a), (b), (c), (e), and (g) and the substitutions are:

K345E|N369E|G372A|S683W, N369E|S683W, N263C|N369T, N369T|G372A|K428N|S648W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, any four, or all five of (a), (b), (c), (d), (e) and (g) substitutions are: G372A|P661E|S683W, P176L|Q316T|K320S|R363E|G662F, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three any four, or all five or (a), (b), (c), (d), (e), and (f) and the substitutions are: K345E|N369E|P661E|S683W, K345E|P661E|S683W, N263C| K345E|N369E, N263C|N369T|P661E, K345E|N369E|G683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, any four, or all five any six or all seven of (a), (b), (c), (d), (e), (f) and (g) and the substitutions are: N263C|N369T, N369T|G372A|K428N|S683W, N263C|G372A, N263C|K345E|N369E|G372A|P661E, or P176L|Q226W|G547A|G662C.

The present disclosure provides a beta-glucosidase variant, wherein the variant is a mature form having beta-glucosidase activity and comprising a mutation, wherein when the mutation is a single mutation it is not at a position selected from the group consisting of: 37, 61, 125, 129, 132, 133, 158, 159, 166, 177, 236, 237, 238, 240, 252, 314, 444, and 449, and wherein the positions are numbered by correspondence with the amino acid sequence of a reference beta-glucosidase 1 (BGL1) set forth as SEQ ID NO:3. In some embodiments, the mutation is a substitution. In other embodiments, the mutation is a deletion or an insertion. In some preferred embodiments, the mutation does not consist of a substitution selected from the group consisting of: W37A, W37G, W37N, W37D, D61N, D61A, R125K, R125A, K158G, H159A, H159S, E166Q, D177E, D236G, D236N, D236E, W237F, W237A, W237L, W237C, and W237P. In some preferred embodiments, the substitution insults in a beta-glucosidase variant with improvements in one or more of expression, activity and stability, in comparison to the reference BGL1.

In addition, the present disclosure provides a beta-glucosidase variant, wherein the variant is a mature form having beta-glucosidase activity and comprising a substitution at one or more positions selected from the group consisting of: 22, 24, 25, 26, 27, 28, 33, 35, 36, 37, 50, 51, 52, 61, 67, 91, 92, 93, 99, 100, 125, 158, 159, 163, 164, 165, 166, 167, 166, 169, 170, 176, 177, 178, 179, 194, 196, 199, 204, 208, 209, 214, 215, 216, 224, 225, 226, 236, 237, 238, 242, 248, 249, 263, 264, 265, 276, 277, 278, 279, 282, 284, 287, 291, 301, 302, 303, 306, 312, 313, 316, 320, 324, 328, 329, 334, 335, 336, 337, 338, 339, 344, 345, 347, 361, 363, 369, 370, 371, 372, 374, 375, 380, 381, 382, 396, 397, 398, 399, 402, 409, 410, 411, 420, 426, 427, 428, 441, 445, 446, 447, 448, 449, 452, 453, 454, 455, 460, 467, 473, 474, 475, 489, 490, 492, 496, 497, 498, 521, 522, 534, 542, 547, 548, 553, 554, 555, 560, 561, 563, 564, 570, 571, 581, 583, 586, 591, 603, 611, 612, 622, 626, 627, 638, 642, 643, 645, 649, 650, 656, 660, 661, 662, 663, 666, 672, 673, 674, 675, 680, 681, 682, 683, 684, 685, 692, 702, and 705, wherein the positions are numbered by correspondence with the amino acid sequence of a reference beta-glucosidase 1 (BGL1) set forth as SEQ ID NO:3. In some embodiments, the variant comprises a further substitution at one or more positions selected from the group consisting of: 37, 61, 158, 159, 166, 236, 237, 238, and 449, wherein the positions are numbered by correspondence with the amino acid sequence of a reference beta-glucosidase 1 (BGL1) set forth as SEQ ID NO:3. In some embodiments, the further substitution is selected from the group consisting of: W037A, D061N, K158G, H159A or S, E166Q, D236G, and W237P. Moreover, in some embodiments, the substitution at one or more positions is selected from the group consisting of: 1, 2, 3, 4, 5, 6, 7, 8, 9, 10, 11, 12, 13, 14, 15, 16, 17, 18, 19, 20, 21, 22, 23, 24 and 25 positions. In some embodiments, the variant is derived from a patent beta-glucosidase selected from the group consisting of *Hypocrea jecorina* BGL1 (TrireBGL1), *Hansenula anomala* BGL (HananBglu), *Piromyces* sp BGL (PirspBglu), *Coccidiodies immitis* BGL (CocimBglu), *Saccharomycopsis fibuligera* BGL2 (SacfiBglu2), *Saccharomycopsis fibuligera* BGL1 (SacfiBglu1), *Septoria lycopersici* BGL (SeplyBgfu), *Kuraishia capsulata* BGL (KurcaBglu), *Trichoderma reesei* BGL7 (TrireBGL7), *Uromyces fabae* BGL (UrofaBglu), *Aspergillus terreus* BGL (AspteBglu), *Chaetomium globosum* BGL (ChaglBglu) *Trichoderma reesei* BGL3 (TrireBGL3), *Penicillium brasilianum* BGL (PenbrBGL), *Periconia* sp. BGL (PerspBglu), *Phaeosphaeria avenaria* BGL (PhaavBglu), *Aspergillus fumigatus* BGL (AspfuBGL), *Aspergillus oryzae* BGL1 (AsporBGL1), *Aspergillus aculeatus* BGL1 (AspacBGL1), *Aspergillus niger* BGL (AspniBGL), *Talaromyces emersonni* BGL (TalemBglu), and *Thermoascus aurentiacus* BGL (TheauBGL). In some preferred embodiments, the variant is derived from a parent beta-glucosidase whose amino acid sequence is at least 75% (80%, 85%, 90%, 95%, 96%, 97%, 98% of 99%) identical, so a member of the group consisting of SEQ ID NO:3, SEQ ID NO:4, SEQ ID NO: 5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24. In some preferred embodiments, the variant comprise from one to fifty-nine of the conserved residues selected from the group consisting of A16, K28, G44, C58, D61, R67, E100, G105, L110, P124, G124, R125, E128, D133, P134, L136, G147, Q149, K158, H159, R169, S173, D178, P188, P189, M201, Y204, N208, K224, F229, G231, D236, W237, G250, D252, M253, M255, P256, R284, D287, R291, K335, N336, L341, P342, G385, P395, E441, D452, V478, L518, Y559, F562, F573, G574, G576, L577, and L651, wherein the positions are numbered by correspondence with the amino acid sequence of a reference beta-glucosidase 1 (BGL1) set forth as SEQ ID NO:3. In a subset of these embodiments, the variant comprises E441 and D452. In preferred, embodiments, the substitution results in a beta-glucosidase variant with improvements in one or more of expression, activity and stability, when compared to the reference BGL1.

Also provided, by the present disclosure is a beta-glucosidase variant comprising a substitution, wherein the substitution comprises one or more of the group consisting of: K022 to A, E, F, G, H, I, P, Q, R, S, V, W, or Y; N024 to A, C, D, E, F, G, K, L, M, P, Q, R, S, T, V, or Y; L025 to A, D, F, G, I, K, N, Q, R, S, T, V, W, or Y; Q026 to C, D, E, G, H, I, K, L, P, R, S, T, V, W, or Y; D027 to A, C, E, L, M, Q, S, T, or V; K028 to L, M, N, S, or V; S033 to C, G, or T; V035 to C, E, G, H, K, L, N, P, Q, R, S, T, W, or Y; G036 to C, D, E, F, I, K, N, R, S, W, or Y; W037 to E, F, H, I, M, S, V, or Y; S050 to A, C, F, G, I, K, L, M, N, P, R, T, V, or Y; K051 to A, C, D, E, G, H, I, L, M, N, Q, R, S, T, or V, I052 to A, D, F, K, M, N, P, Q, S, T, or V; D061 to E, G, or P; R067 to A, C, D, E, F, G, I, L, M, N, P, Q, S, T, V, W, or Y; R091 to A, C, D, E, F, G, H, I, K, L, N, Q, S, T, V, W, or Y; E092 to A, C, D, F, H, I, K, L, M, N, Q, R, T, V, or Y; R093 to A, C, D, E, F, G, H, K, L, M, Q, S, T, V, or W; E099 to A, D, F, I, K, M, N, W, or Y; E100 to A, G, I, K, L, M, N, Q, S, T, or Y; R125 to A, or D; K158 to A, C, D, or T; H159 to C, E, G, N, W, or Y; N163 to A, H, or S; E164 to G, or S; Q165 to C, D, F, G, H, I, K, L, M, N, R, S, T, V, W, or Y; E166 to D, F, K, L, N, P, R, S, T, or Y; L167 to A, C, D, E, F, G, M, N, Q, R, S, V, W, or Y; N168 to A, D, E, G, H, Q, R, T, or Y; R169 to A, C, D, E, F, H, K, Q, S, or T; E170 to A, D, F, L, K, M, P, V, W, or Y; P176 to A, D, E, F, G, H, K, L, M, Q, R, S, V, W, or Y; D177 to A, C, E, F, G, H, K, L, M, N, Q, R, V, W, or Y; D178 to A, C, E, K, N, P, Q, R, S, T, W, or Y; R179 to A, C, G, I, K, M, Q, S, T, V, or W; Q194 to A, C, E, F, G, H, K, L, M, R, T, W, or Y; N196 to E, G, H, L, M, P, Q, R, or T; S199 to A, G, N, T, or V; Y204 to A, E, F, G, H, I, K, M, P, Q, R, S, T, V, or W; N208 to K, or R; T209 to C, D, E, G, H, I, K, L, M, Q, R, S, V, V, or Y; E214 to A, C, D, G, H, K, L, M, N, P, Q, R, S, T, V, W, or Y; D215 to A, C, E, F, G, H, I, M, N, Q, S, V, or W; Q216 to A, C, D, E, G, H, I, K, L, M, N, P, R, S, T, W, or Y; K224 to H, R, or V; D225 to A, C, E, F, G, H, I, M, Q, S, T, V, W, or Y; Q226 to A, C, D, E, F, H, I, K, L, M, N, R, S, T, V, W, or Y; D236 to A, P, Q, S, or T; W237 to H, I, K, M, R, S, T, or Y; N238 to A, C, D, E, F, G, M, P, S, T, or W; T242 to A, C, E, F, G, H, I, K, L, M, N, Q, R, S, V, W, or Y; N248 to A, C, F, G, L, T, W, or Y; S249 to A, G, I, M, or V; N263 to A, C, D, E, F, G, H, I, K, L, P, Q, R, S, T, V, or Y; N264 to A, C, D, E, G, H, K, L, M, Q, R, S, T, V, or Y; R265 to A, E, F, G, L, K, M, M, N, P, Q, S, T, V, or Y; N276 to A, C, F, K, M, or Q; S277 to A, C, D, E, F, G, I, M, N, P, Q, R, W, or Y; N278 to A, C, D, F, G, H, I, L, M, Q, R, S, T, V, W, or Y; Q279 to C, D, E, G, H, I, K, N, S, T, V, or Y; T282 to C, D, G, H, K, L, N, P, R, S, or V; R284 to H, M, or N; D287 to C, E, F, G, H, I, M, N, S, V, W, or Y; Q301 to A, E, G, K, L, N, R, S, T, or V; D302 to A, C, E, F, G, K, L, M, N, P, S, T, W, or Y; Q303 to A, C, D, E, F, G, H, I, K, L, M, N, P, R, S, T, V, W, or Y; Y306 to A, C, E, F, G, I, K, L, M, N, P, Q, R, S, T, V, or W; S312 to A, C, D, G, I, K, L, MM, N, Q, R, T, V, W, or Y; R313 to A, C, D, E, G, K, T, N, S, V, or W; Q316 to A, C, D, E, F, G, H, I, K, L, M, N, P, R, S, T, V, W, or Y; K320 to A, C, E, G, H, L, M, N, P, Q, R, S, T, or Y; R324 to C, D, E, F, H, I, K, L, M, Q, V, W, or Y; R328 to C, E, F, G, I, K, L, M, Q, S, T, V, or Y; D329 to A, E, F, G, H, M, N, Q, S, T, or Y; L334 to A, C, F, M, T, V, or W; K335 to A, D, F, G, H, I, L, M, N, R, S, T, V, or W; N336 to A, C, G, H, L, M, Q, R, S, T, V, or Y; D337 to A, C, E, G, H, K, L, M, N, R, S, T, V, W, or Y; A338 to C, D, E, F, G, H, I, K, L, M, N, P, Q, R, V, W, or Y; N339 D, E, G, H, I, K, L, P, Q, R, V, or Y; K344 to D, E, F, G, I, L, M, N, P, Q, R, S, T, or V; K345 to A, D, E, F, G, H, N, P, Q, R, S, T, V, W, or Y; A347 to D, F, H, I, K, L, M, P, Q, R, S, or Y; H361 to A, C, D, E, G, K, L, M, N, P, S, T, to Y; R363 to A, C, E, G, K, L, M, N, Q, S, T, V, W, or Y; N369 to A, C, D, E, F, I, L, M, N, R, S, T, V, W, or Y; D370E, F, G, Q, S, W, or Y;

K371 to A, D, F, G, H, L, N, Q, R, S, T, V, or W; G372 to A, C, D, E, K, L, M, N, S, T, V, W, or Y; D374 to A, C, F, G, I, L, M, N, Q, R, S, T, V, W, or Y; D375 to A, C, E, H, I, R, V, or W; M380 to E, F, G, I, L, N, Q, S, T, V, or Y; G381 to H; W382 to F, N, or Y; Y396 to A, C, D, E, F, G, H, I, K, L, M, N, Q, R, S, T, V, or W; D397 to A, D, E, F, H, I, K, L, M, N, P, Q, R, S, T, V, or Y; A398 to C, D, E, F, G, H, I, K, L, M, N, P, Q, R, S, T, V, W, or Y; I399 to A, C, D, E, F, G, L, M, Q, S, T, V, W, or Y; R402 to A, C, E, F, G, I, L, P, Q, S, V, W, or Y; Q409 to C, D, G, H, I, or V; V410 to A, C, F, G, H, I, L, N, R, S, T, W, or Y; T441 to D, F, E, G, H, I, K, L, N, Q, R, S, V, or Y; S420 to A, C, D, G, H, K, N, Q, T, V, or Y; R426 to A, E, F, I, K, L, M, N, P, Q, S, T, W, or Y; G427 to C, D, E, F, H, K, L, M, N, P, Q, R, S, T, V, W, or Y; K428 to A, C, D, E, F, G, H, I, L, M, N, P, Q, R, S, T, V, W, or Y; E441 to A, C, D, or G; T445 to A, C, D, E, F, G, I, K, L, M, N, P, Q, R, S, V, or Y; V446 to A, C, K, Q, or R; E447 to A, K, L, N, S, V, W, or Y; G448 to A, C, D, E, F, H, K, L, M, N, Q, R, S, T, V, or Y; N449 to A, C, E, F, G, H, K, L, M, P, R, T, V or W; D452 to N; R453 to A, E, I, M, Q, or S; N454 to A, F, G, K, L, M, R, S, T, or V; N455 to A, C, D, E, F, G, H, I, L, M, S, T, V, W, or Y; H460 to A, C, D, E, F, G, I, K, L, M, N, Q, R, S, W, or Y; Q467 to A, C, D, E, H, K, N, P, S, V, W, or Y; N473 to A, C, E, F, G, H, K, L, M, P, Q, R, S, T, V, or W; S474 to A, C, D, E, F, G, I, K, L, M, N, P, Q, R, T, V, or Y; N475 to I, K, L, M, P, Q, R, S, T, V, W, or Y; E489 to D, or N; Q490 to A, C, E, F, G, H, K, L, P, R, S, T, V, W, or Y; L492 to A, D, F, H, I, M, N, Q, R, T, W, or Y; Q496 to A, G, K, N, P, S, T, V, or W; V497 to A, C, I, M, N, or T; K498 to A, C, E, F, G, H, I, L, M, N, Q, R, S, T, V, or Y; D521 to A, C, E, F, G, H, I, K, L, M, P, R, S, T, V, W, or Y; V522 to A, C, F, G, H, I, K, L, M, N, P, Q, R, S, T, V, W, or Y; K534 to C, D, E, F, G, H, I, N, Q, R, S, T, or V; R542 to A, C, D, E, F, G, H, I, K, L, M, N, P, Q, S, T, V, W, or Y; G547 to A, C, E, F, K, L, N, P, Q, R, T, V, or Y; S548 to C, E, F, H, I, L, M, N, Q, R, T, V, W, or Y; E553 to D, I, K, N, Q, W, or Y; G554 to A, C, D, F, H, K, L, M, Q, R, S, T, V, or Y; L555 to A, C, D, E, F, G, H, I, K, M, N, P, Q, T, V, W, or Y; K560 to A, C, E, G, H, I, L, M, N, P, Q, R, S, T, V, W, or Y; H561 to A, C, D, E, F, G, I, M, N, Q, S, T, V, or W; D563 to A, C, E, F, I, L, M, Q, R, S, T, V, W, or Y; D564 to A, C, E, F, G, K, L, M, N, Q, R, S, T, V, or Y; R570 to A, C, D, E, G, H, I, M, N, Q, S, T, or V; Y571 to H, M, N, R, or W; K581 to A, C, D, E, F, G, H, I, L, M, N, P, R, S, T, V, W, or Y; N583 to A, C, D, E, F, G, H, I, K, L, M, P, R, S, T, V, W, or Y; R586 to D, E, F, G, H, L, N, P, V, W, or Y; S591 to C, D, F, G, H, I, K, M, P, Q, to V; V603 to A, C, D, E, F, G, H, L, M, N, P, Q, R, S, T, W, or Y; F611 to A, C, D, G, I, K, L, M, N, R, S, T, V, W, or Y; Q612 to C, D, F, G, H, I, K, L, M, R, S, V, or W; A622 to D, E, F, G, H, I, K, L, M, N, P, R, S, T, V, W, or Y; Q626 to E, F, G, H, I, L, M, T, to V; V627 to D, K, P, Q, R, S, or Y; T638 to A, D, E, F, G, I, K, L, M, P, Q, R, S, V, W, or Y; S642 to A, C, D, E, F, G, H, I, K, L, M, N, P, Q, R, T, V, W, or Y; A643 to C, E, F, G, H, K, L, M, N, Q, R, S, T, V, W, or Y; R645 to A, D, E, F, G, H, I, K, L, M, P, Q, S, T, V, W, or Y; K649 to A, C, F, I, L, M, N, Q, S, T, W, or Y; Q650 to A, C, D, E, F, G, H, I, K, L, M, N, R, T, V, or Y; K656 to R; T660 to C, D, E, F, G, H, I, K, M, N, P, Q, R, S, V, W, or Y; P661 to A, C, D, E, F, G, H, I, K, L, M, Q, R, S, T, V, or W; G662 to A, C, D, E, F, H, I, K, L, M, N, Q, R, S, T, W, or Y; Q663 so A, C, D, E, F, G, H, I, K, L, M, N, R, S, V, or W; T666 to A, C, D, E, F, G, H, K, L, M, N, R, S, V, W, or Y; R672 to C, D, E, F, G, H, I, K, L, M, N, T, V, W, or Y; R673 to A, C, E, F, G, H, I, K, L, M, N, Q, S, T, V, or W; R674 to K, L, M, Q, T, V, or Y; D675 to C, E, H, L, S, or Y; D680 to A, C, E, F, H, I, K, L, M, N,

Q, R, S, V, W, or Y; T681 to A, G, H, K, L, M, N, P, Q, R, S, V, W, or Y; A682 to C, E, I, L, M, N, P, S, W, or Y; S683 to A, C, D, E, F, G, I, K, L, M, P, Q, R, V, or W; Q684 to A, C, D, E, F, G, H, I, K, L, M, N, P, R, S, or T; K685 S to A, E, F, G, I, L, M, N, Q, R, S, T, V, W, or Y; S692 to C, E, H, I, K, L, M, N, P, Q, T, V, or W; R702 to C, D, F, G, H, I, K, L, M, N, Q, S, T, V, or W; and R705 to C, F, H, I, L, M, P, S, T, V, or W, wherein the positions are numbered by correspondence with the amino acid sequence of a reference beta-glucosidase 1 (BGL1) set forth as SEQ ID NO:3. As described in the experimental section, exemplary beta-glucosidase variants have a PI greater than 1 for at least one of the following properties: expression (HPLC), CNPGase activity, thermostability, reduced glucose inhibition, cellobiase activity at pH 5, cellobiase activity at pH 6, cellobiase activity in the presence of ammonium pretreated corncob, and hydrolysis of acid pretreated corn stover.

The present disclosure further provides a beta-glucosidase variant comprising a substitution, wherein the substitution comprises one or more of the group consisting of: K022A, K022E, K022S, K022W, N024A, N024D, N024E, N024L, N024P, L025W, V035S, V035W, W037E, W037G, W037H, W037S, W037Y, K051A, D061E, D061G, D061P, R067G, R067L, R067M, R067P, R067T, R067V, R067Y, R067I, R091T, R091Y, E092K, E092L, E092T, R125A, R125D, K158A, K158C, H159C, H159E, H159G, H159N, H159W, H159Y, N163A, N163H, N163S, L167W, R169A, R169C, R169D, R169E, E169K, E170A, E170K, E170L, E170P, E170W, E170Y, P176A, P176D, P176G, D177C, D177G, D177K, D177N, D178A, D178E, D178P, D178T, D178W, Q194A, Q194Y, S199A, Y204A, Y204E, Y204G, Y204H, Y204I, Y204K, Y204P, Y204Q, Y204R, Y204S, Y204T, Y204V, Y204W, Q216D, Q216E, Q216N, Q216R, D225C, Q226A, P236A, D236P, D236Q, D236S, D236T, W237H, W237I, W237K, W237M, W237R, W237S, W237T, T242S, N248A, N248C, S249A, N264D, N264E, N264H, N264L, N264R, N264S, N264V, N264Y, R265A, R265G, R265Y, S277A, S277D, N278A, N278D, T282G, T282N, T282R, R282V, Q303A, Q303E, Q303N, Y306A, Y306E, Y306F, Y306L, Y306W, S312A, S312D, S312G, S312I, S312N, S312R, R313D, R313E, Q316A, Q316D, Q316F, K320A, K320H, K320N, K320S, K320Y, K335L, R335S, K335T, A338D, A338E, A338G, A338N, A338R, A347Y, R363A, R363G, R363K, R363M, R363V, D370E, D370Q, K371A, E371H, D374A, Y396A, D397N, I399L, S420A, S420D, G427E, G427S, K428A, E441A, E441C, E441D, E441G, V446A, E447A, E447N, G448A, G448D, G448E, G448M, G448N, G448R, G448S, G448T, G448Y, N454A, N473S, S474D, S474G, S474K, S474N, S474R, S474T, S474V, S474Y, E489D, D521A, K534Q, R542A, R542D, G547E, G547L, G547P, S548E, S548F, S548H, S548L, R560H, N583D, R586D, V603L, V603M, V603Q, V603S, Q612D, Q612G, Q612K, Q612V, A622L, A622W, A622Y, Q626I, Q626L, Q626T, Q626V, T538D, S642D, A643M, K649A, or R649W; Q650D; G662D, G662E, G662L, G662S, or G662T; Q663D, or Q663G; T666A, R673N, R673W, S683K, Q684D, Q684F, Q684H, Q684K, Q684L, Q684M, Q684R, Q684S, and Q684T, wherein the substitution consists of no more than a single replacement at each of the positions, and wherein the positions are numbered by correspondence with the amino acid sequence of a reference beta-glucosidase 1 (BGL1) set forth as SEQ ID NO:3. As described in the experimental section, exemplary beta-glucosidase variants have improved expression levels (e.g., PI greater than 1).

Also, the present disclosure provides a beta-glucosidase variant comprising a substitution, wherein the substitution comprises one or more of the group consisting of: K022F, K022G, K022H, K022I, K022P, K022Q, K022R, K022V, K022Y, N024C, N024F, N024G, N024K, N024M, N024Q, N024R, N024S, N024T, N024V, N024Y, L025A, L025D, L025F, L025G, L025I, L025K, L025N, L025Q, L025R, L025S, L025V, L025Y, Q026C, Q026D, Q026E, L026G, Q026H, Q026I, Q026K, Q026L, Q026P, Q026R, Q026S, Q026T, Q026V, Q026W, Q026Y, D027A, D027C, D027E, D027L, D027M, D027Q, D027S, D027T, D027V, K028L, K028M, K028S, K028V, S033C, S033G, S033T, V035C, V035E, V035G, Y035H, Y035K, V035L, V035N, V035P, V035Q, V035R, V035T, V035Y, G036C, G036D, G036E, G036K, G036N, G036R, G036S, W037M, W037V, S050A, G050C, S050F, S050G, G050I, G050K, S050L, S050M, S050N, S050P, S050R, S050T, S050V, S050Y, K051C, K051D, K051E, K051G, K051H, K051I, K051L, K051M, K051N, K051Q, K051R, K051S, K051T, K051V, I052A, I052F, I052M, I052P, I052S, I052T, I052V, R067A, R067C, R067D, R067E, R067F, R067I, R067N, R067Q, R067S, R067W, R091A, R091D, R091E, R091F, R091G, R091H, R091K, R091L, R091N, R091Q, R091S, R091V, R091W, E092A, E092C, E092D, E092F, E092H, E092I, E092M, E092N, E092Q, E092R, E092V, E092Y, R093A, R093C, R093D, R093E, R093F, E093H, R093K, R093L, R093M, R093Q, R093S, R093T, R093V, R093W, E093A, E099D, E099F, E099I, E099K, E099M, E099N, E099W, E099Y, E100A, E100G, E100I, E100K, E100L, E100M, E100N, E100Q, E100S, E100T, E100Y, K158H, K158T, E164G, E164S, Q165C, Q165D, Q165F, Q165G, Q165H, Q165I, Q165K, Q165L, Q165M, Q165N, Q165R, Q165S, Q165T, Q165V, Q165W, Q165Y, E166D, E166K, E166L, E166N, E166P, E166R, E166S, E166T, E166Y, L167A, L167C, L167D, E167E, L167F, L167G, L167M, L167N, L167Q, E167R, L167S, E167V, E167Y, N168A, N168D, N168E, N168G, N168H, N168Q, N168R, N168T, N168Y, R169F, R169H, R169Q, R169S, R169T, E170D, E170F, R170I, E170M, E170V, P176E, F176F, P176H, P176K, P176L, P176M, P176Q, P176R, P176S, F167T, P176V, P176W, P176Y, D177A, D177E, D177F, D177H, D177I, D177M, D177Q, D177R, D177V, D177W, D177Y, D178C, D178K, D178N, D178Q178R, D178S, D178Y, R179A, R179C, R179G, R179I, R179K, R179S, R179T, R179V, R179W, Q194C, Q194E, Q194F, Q194G, Q194K, Q194I, Q194M, Q194R, Q194T, Q194W, N196E, N196G, N196H, N196L, N196M, N196P, N196Q, R196K, N196T, S199G, S199N, S199T, S199V, Y204F, Y204M, N208K, N208R, T209C, T209D, T209E, T209G, T207H, T209I, T209K, T209L, T209M, T209Q, Q209R, T209S, T209V, T209W, T209Y, E214A, E214C, E214D, E214G, E214H, E214K, E214L, E214M, E214N, E214P, E214Q, E214R, E214S, E214T, E214V, F214Y, D215A, D215C, D215E, D215F, D215G, D215H, D215L, P215M, D215N, D215Q, D215S, D215W, Q216A, Q216C, Q216F, Q216G, Q216H, Q216I, Q216K, Q216L, Q216M, Q216P, Q216S, Q216T, Q216W, Q216Y, K224H, K224R, K224V, D225A, D225E, D225F, D225G, D225H, D225I, D225L, D225M, D225Q, D225S, D225T, D225V, D225W, G225Y, Q226C, Q226D, Q226E, Q226F, Q226H, Q226I, Q226K, Q226L, Q226M, Q226N, Q226R, Q226S, Q226T, Q226V, Q226W, Q226Y, W237Y, N238A, N238C, N238D, N238E, N238F, N238G, N238M, N238P, N238S, N238T, N238W, T242A, T242C, T242E, T242F, T242G, T242H, T242I, T242K, T242L, T242M, T242N, T242Q, T242R, T242V, T242W, T242Y, N248F, N248G, N248L, N248T, N248W, N248Y, S249G, S249I, S249M, S249V, N263A, N263C, N263D, N263E, N263F, N263G, N263H, N263I, N263K, N263L, N263P, N263Q, N263R, N263S, N263T, N263V, N263Y, N264A, N264C, N264G, N264K, N264M, N264Q, N264T, R265E, R265F, R265I, R265K, R265L, R265M, R265N, R265P, R265Q, R265S, R265T, R265V, N276A, N276F, N276K, N276M, N276Q, S277C, S277E, S277F, S277G, S277H, S277I, S277M, S277N, S277P, S277Q, S277R, S277Y, N278C, N278F, N278G, N278H, N278I, N278L, N278M, N278Q, N278R, N278S, N278T, N278V, N278W, N278Y, Q279C, Q279D, Q279E, Q279G, Q279H, Q279I, Q279K, Q279N, Q279S, Q279T, Q279V, Q279Y, T282C, T282G, T282K, T282L, T282P, T282S, R284H, R284N, D287C, D287E, D287F, D287G, D287H, D287I, D287K, D287L, D287M, D287N, D278S, S287V, D287W, D287Y, Q301A, Q301E, Q301G, Q301L, Q301N, Q301R, Q301S, Q301T, Q301V, D302A, D302C, D302E, Q302F, D302G, D302K, D302L, D302M, D302N, D302P, D302S, D302T, D302W, D302Y, Q303C, Q303D, Q303F, Q303G, Q303H, Q303I, Q303K, Q303L, Q303M, Q303P, Q303R, Q303S, Q303T, Q303V, Q303W, Q303Y, Y306C, Y306G, Y306I, Y301K, Y306M, Y306N, Y306P, Y306Q, Y306R, Y306S, Y306T, Y306V, S312C, S312K, S312I, S312M, S312Q, S312T, S312V, S312W, S312Y, R313A, R313C, R313G, R313K, E313I, R313N, R313S, R313V, R313W, Q316C, Q316E, Q316G, Q316H, Q316I, Q316K, Q316L, Q316M, Q316N, Q316P, Q316R, Q316S, Q316T, Q316V, Q316W, Q316Y, K320C, K320E, K320G, K320L, K320M, K320P, K320Q, K320R, K320T, K324C, R324D, R324E, R324F, R324H, R324I, R324K, R324L, R324M, R324Q, R324V, R324W, R324Y, R328C, R328E, R328G, R328I, R328K, R328L, R326M, R328Q, R328S, R328T, R328V, D329A, D329E, D329F, D329G, D329H, D329M, D329N, D329Q, D329S, D329T, D329Y, L334A, L334C, L334F, L334M, L334T, L334V, L334W, K335A, K335D, K335F, K335G, R335H, R335I, K335M, R335N, K335R, K335V, K335W, N336A, N336C, N336G, N336H, N336L, N336M, N336Q, N336R, N336S, N336T, N336V, N336Y, D337A, D337C, D337E, D337G, D337H, D337K, D337L, D337M, D337N, D337R, D337S, D337T, D337V, D337W, D337Y, A338C, A338F, A338H, A338I, A338K, A338L, A338M, A338P, A338Q, A338V, A338W, A338Y, N339D, N339E, N339G, N339H, N339I, N339K, N339L, N339P, N339Q, N339R, N339V, N339Y, K344D, R344E, K344F, K344G, K344I, K344L, K344M, K344N, K344P, K344Q, K344R, K344S, K344T, K344V, K345A, K345D, K345E, K345F, K345G, K345H, K345I, K345P, K345Q, K345R, K345S, K345T, K345V, K345W, K345Y, A347D, A347F, A347H, A347I, A347K, A347L, A347M, A347P, A347Q, A347R, A347S, H361A, H361D, H361D, H361E, H361G, H361K, H361L, H361M, H361N, H361P, H361S, H361T, H361Y, R363C, R363E, R363L, R363N, R363Q, R363S, R363T, R363W, R363Y, N369A, N369C, N369D, N369E, N369F, N369I, N369L, N369N, N369R, N369S, N369T, N369V, N369W, N369Y, D370F, D370G, D370S, D370W, D370Y, K371D, K371F, K371G, K371L, K371N, K371Q, K371R, K371S, K371T, K371V, K371W, G372A, G372C, G372D, G372E, G372L, G372M, G372N, G372S, G372T, G372V, G372Y, D374C, D374F, D374G, D374L, D374M, D374N, D374Q, D374S, D374T, D374V, D374Y, D375A, D375C, D375E, D375H, D375I, D375R, D375V, D375W, M380E, M380F, M380G, M380I, M3830I, M380N, M380Q, M380S, M380T, M380V, M380Y, W382F, W382N, W382Y, Y396C, Y396D, Y396E, Y396F, Y396G, Y396H, Y396I, Y396K, Y396I, Y396M, Y396N, Y396Q, Y396R, Y396S, Y396T, Y396V, Y396W, D397A, D397C, D397E, D397F, D397H, D391I, D397K, D339I, D397M, D397P, D397Q, D397R, D397S, D397V, D397Y, A398C, A398D, A398E, A398F, A398G, A398H, A398I, A398K, A398L, A398M, A398N, A398P, A398Q, A398R, A398S, A398T, A398V, A398W, A398Y, I399A, I399C, I399D, I399E, I399F, I399G, I399M, I399Q, I999S, I399T, I399V, I399W, I399Y, R402A, R402C, R402E, R402F, R402G, R402I, R402L, R402P, R402Q, R402S, R402V, R402W, R402Y, Q409C, Q409G, Q409H, Q409I, Q409V, V410A, V410C, V410F, V410G, V410H, V410I, V410L, V410N, V410S, V410T, V410W, V410Y, T411D, T411E, T411F, T411G, T411H, T411I, T411K, T411L, T441N, T411Q, T411R, T411S, T411V, T411Y, S420C, S420G, S420H, S420K, S420N, S420Q, S420T, S420Y, R426E, R426F, R426I, E426K, R426L, R426M, R426N, R426P, R426Q, R426S, R426T, R426W, R426Y, G427C, G427D, G427F, G427H, G427K, G427L, G427M, G427N, G427P, G427Q, G427R, G427T, G427V, G427W, G427Y, K428C, K428D, K428E, R428F, K428G, K428H, K428I, K428L, K428M, K428N, K428P, K428Q, K428R, K428S, K428T, K428V, K428W, K428Y, T445A, T445C, T451D, T445E, K445F, T445G, T445I, T445K, T445L, T445M, T445N, T445P, T445Q, T445R, T445S, T445V, T445Y, V446C, V446K, V446Q, V446R, E447K, E447L, E447S, E447V, E447W, E447Y, G447C, G448E, G448H, G448K, G445L, G448Q, G448V, N449A, N449C, N449E, N449F, N449G, N449H, N449K, N449L, N449M, N449P, N449R, N449T, N449V, N449W, D452N, R453A, T453L, R453M, N454F, N454G, N454K, N454L, N454M, N454R, N454S, N454T, N454V, N455A, N455C, N455D, N455E, N455F, N455G, N455H, N455H, N455L, N455M, N455S, N455T, N455V, N455W, N455Y, H460A, H460C, G460D, H460E, H460F, H460G, G460I, H460K, H460L, H460M, H460N, H460Q, H460R, H460S, H460W, G460Y, Q467A, Q467C, Q467D, Q467E, Q467H, Q467N, Q467S, Q467V, Q467W, Q467Y, N473A, N473C, N473E, N473F, N473G, N473H, N473K, N473L, N473M, N473P, N473Q, N473R, N473T, N473V, S474A, S474C, S474E, S474F, S474I, S474L, S474M, S474P, S474Q, N475I, N475L, N475M, N475P, N475Q, N475R, N475S, N475T, N475V, N475W, N475Y, E489N, Q490A, Q490C, Q490E, Q490F, Q490G, Q490H, Q490K, Q490L, Q490P, Q490R, Q490S, Q490T, Q490V, Q490W, Q490Y, L492A, L492D, L492F, L492H, L492I, L492M, L492N, L492Q, L492R, L492T, L492W, L492Y, Q496A, Q496G, Q496K, Q496N, Q492P, Q496S, Q496T, Q496V, V497A, Y497C, V497I, V497M, V497N, V497T, V498A, K498C, K498E, K498F, K498G, K498H, K498I, K498L, K498M, K498N, K498Q, K498R, K498S, K498T, K498V, K498Y, D521C, D521E, D521F, D521G, D521H, D521I, D521K, D521L, D521M, D521P, D521R, D521S, D521T, D521V, D521W, D521Y, V522A, V522C, V522F, V522G, V522H, V522I, V522K, V522L, V522M, V522N, V522P, V522Q, V522R, V522S, V522T, Y522W, V522Y, K534C, K534D, K534E, K534F, K534G, K534H, K534I, K534N, K534R, K534S, K534T, K534V, R542C, R542E, R542F, R542G, R542H, R542I, R542K, R542I, R542M, R542N, R542P, R542Q, R542S, R524T, R542V, R542W, R542Y, G574A, G547C, G547F, G547K, G547N, G547Q, G547R, G547T, G547V, G547Y, S548C, S548I, S548M, S548N, S548Q, S548R, S548T, S548V, S548W, S548Y, E553D, E553I, E553K, E553N, E553Q, E553W, E553Y, G554A, G554C, G554D, G534F, G554H, G554K, G554L, G554M, G554Q, G554R, G554S, G554T, G554V, G554W, L555A, L555C, L555D, L555E, E555F, E555G, L555H, L555I, L555K, L555M, L555N, L555P, L555Q, L555T, L555V, L555W, L555Y, K560A, K560C, K560E, K560G, K560I, K560L, K560M, K560N, K560P, K560Q, K560R, S560S, K560T, K560V, K560W, K560Y, H561A, H561C, H561D, H561E, H561F, H561G, H561I, H564M, H561N, H561Q, H561S, H561T, H561V, H561Y, D563A, D563C, D563E, D563F, D563I, D0563L, D563M, D563Q, D563R, D563S, D563T, D563V, D563W, D563Y, D564A, D564C, D564E, D564F, D564G, D564K, D564L, D564M, D564N, D564Q, D564R, D564S, D564T, D564V, D564Y, R570A, R570C, R570D, R570E, R570G, R570H, R570I, R570M, R570N, R570Q, R570S, R570T, R570V, Y571H, Y571M, Y571W, K581A, K581C, K581D, K581E, K581F, K581G, K581H, K581I, K581L, K581M, K581N, K581P, K581R, K581S, K581T, K581V, K581W, K581Y, N583A, N583C, N583E, N583F, N583G, N583H, N583I, N583K, N583L, N583M, N583P, N583R, M583S, N583T, N53V, N583W, N583Y, R586E, R586F, R586G, R586I, R586N, R586P, R586V, R586W, R586Y, S591C, S591D, S591F, S591G, S591H, S591I, S591K, S591M, S591P, S591Q, S591V, V603A, V603C, V603D, V603E, V603F, V603G, V603H, V603N, V603P, V603R, V603T, V603W, V603Y, F611A, F611C, F611D, F611G, F661I, F611K, F611L, F611M, F611N, F611R, F611S, F611T, F611V, F611W, F611Y, Q612C, Q612F, Q612H, Q612I, Q612L, Q612M, Q612R, Q612S, Q612W, A622D, A622E, A622F, A622G, A622H, A622I, A622K, A622M, A622N, A622P, A622R, A622S, A622T, A622V, Q626E, Q626F, Q626G, Q626M, Q627D, V627K, V627P, V627Q, V627R, V627S, V627Y, T638A, T638E, T638F, T638G, T638I, T638K, T638L, T638M, T638P, T638Q, T638R, T638S, T638V, T638Y, S642A, S642C, S642E, S642F, S642G, S642H, S642I, S642K, S642L, S642M, S642N, S642P, S642Q, S642R, S642T, S642V, S642W, S642Y, A643C, A643E, A643F, A643G, A643H, A643K, A643L, A643N, A643Q, A643R, A643S, A643T, A643V, A643W, A643Y, R645A, R645D, R645E, R645F, R645G, R645H, R645I, R645K, R645L, R645M, R645P, R645Q, R645Q, R645T, R645V, R645W, R645Y, K649C, K649F, K649I, K649L, H649M, K649Q, K649S, R649T, K649Y, Q650A, Q650C, Q650E, Q650F, Q650G, Q650H, Q650I, Q650K, Q650L, Q650M, Q650N, Q650R, Q650T, Q650V, Q650Y, K656R, T660C, T660D, T660E, T660F, T660G, T660H, T660I, T660K, T660M, T660N, T660P, T660Q, T660R, T660S, T660V, T660W, T660Y, P661A, P661C, P661D, P661E, P661F, P661G, P661H, P661I, P661K, P661L, P661M, P661Q, P662R, P661S, P661Y, P622V, P661W, G662A, G662C, G662F, G662H, G662I, G662K, G662M, G662N, G662Q, G662R, G662W, G662Y, Q663A, Q663C, Q663E, Q663F, Q663H, Q663I, Q663K, Q663L, Q663M, Q663N, Q663R, Q663S, Q663V, Q663W, T666C, T666D, T666E, T666F, T666G, T666H, T666K, T666L, T666N, T666R, T666S, T666V, T666W, T666Y, R672C, R672E, T672F, R672G, R672H, R672I, R672K, R672L, R672M, R672N, R672T, R672V, R672W, R672Y, R673A, R673C, R673E, R673F, R673G, R673H, R673I, R673K, R673L, R673M, R673Q, R673S, R673T, R673V, R674K, R674L, R674M, R674Q, R674V, D675E, D675H, D675S, D675Y, D680A, D680C, D680E, D680F, D680H, D680I, D680K, D680L, D680M, D680N, D680Q, D680R, D686S, D680V, D680W, D680Y, T681A, T681K, T681L, T681M, T681N, T681Q, T681R, T681S, T681V, T681R, T681S, T681V, T681W, T681Y, A682C, A682E, A682I, A682L, A682M, A682N, A682P, A682S, A682W, A682Y, S683A, S683C, S683D, S683E, S683F, S683G, S683I, S683L, S683M, S683P, S683Q, S683R, S683V, S683W, Q684A, Q684C, Q684E, Q684G, Q684I, Q684N, Q684P, K685A, K685E, K685F, K685G, K685I, K685L, K685M, K685N, K685Q, K685R, K685S, K685T, K685V, K685W, K685Y, S692C, S692E, S692H, S692I, S692K, S692L, S692M, S692N, S692P, S692Q, S692T, S692V, S692W, R702C, R702D, R702F, R702G, R702H, R702I, R702K, R702L, R702M, R702N, R702Q, R702S, R702T, R702V, R702W, R702C, R705F, R705H, R705I, R705L, R705M, R705P, R705S, R705T, R705V, and R705W, wherein the substitution consists of no more than a single replacement at each of the positions, and wherein the positions are numbered by correspondence with the amino acid sequence of a reference beta-glucosidase 1 (BGL1) set forth as SEQ ID NO:3. As described in the experimental section, exemplary beta-glucosidase variants have reduced expression levels (PI greater than 0.1 but less than 1).

The present disclosure further provides a beta-glucosidase variant, wherein the substitution comprises one or more of the group consisting of: K022A, K022E, K022F, K022G, K022P, K022Q, K022S, K022V, K022W, K022Y, N024A, N024C, L025A, L025D, L025F, L025G, L025I, L025K, L025Q, L025R, L025S, L025T, L025V, L025W, L025Y, Q026C, Q026H, Q026I, Q026K, Q026L, Q026P, Q026R, Q026S, Q026T, Q026V, Q026W, D027A, D027C, D027E, D027L, D027M, D027Q, D027S, D027T, D027V, S033C, S033G, V035C, V035E, V035G, V035H, V035K, V035L, V035N, V035P, V035Q, V035R, V035S, V035T, V035Y, G036D, G036E, G036R, G036S, W037V, W037Y, S050A, K051C, K051D, K051E, K051G, K051H, K051M, K051Q, K051R, K051T, K051V, R067A, R067C, R067D, R067F, R067G, R067N, R067P, R062Q, R067S, R067W, R091A, R091D, R091H, R091L, R091Q, R091V, R091W, E092C, E092K, E092L, E092N, E100A, E100G, E100I, E100M, E100S, E100T, E164S, Q165C, Q165E, Q165H, Q165I, Q165L, Q651M, Q165R, Q165S, Q165T, Q165V, Q165W, Q165Y, E166D, E166K, E661L, E661P, E166R, E666T, T167A, L167C, L167D, L167E, L167G, L167Q, L167R, L167S, L167V, L167W, L167Y, N168A, N168D, N168E, N168G, N168Y, P176F, P176G, P176K, P176L, P176R, P176T, P176V, P176W, D177V, D177W, D178A, D178C, D178Q, D178R, E179W, Q194A, Q194K, Q194Y, N196E, Y204F, T209C, T709D, T209E, T209G, T209H, T209I, T209K, T209L, T209M, T209Q, T209R, T209S, T209V, T209W, T209Y, E214A, E214A, E214D, E214G, E214H, E214L, E214M, E214N, E214Q, E214R, E214S, E214T, E214Y, E215E, D215L, D215N, D215Q, D215S, Q216G, Q216I, Q216L, Q216N, Q216S, Q216Y, K224R, K224V, D225V, Q226A, Q226F, Q226L, Q226W, Q226Y, N238A, N238E, N238G, N238M, N238S, N238T, T242A, T242C, T242E, T242F, T242G, T242H, T242I, T242K, T242L, T242M, T242N, T242Q, T242R, T242V, T242W, T242Y, T242Y, N248A, N248F, N248T, N248W, N263A, N263C, N263G, N263H, N263S, N263T, N264C, R265E, R265K, R265L, R265N, R265Q, S277W, N278F, Q279C, T282C, D287C, D287E, D287N, D287S, Q301A, Q301K, Q301L, Q301N, Q301R, Q301S, Q301T, Q301V, Q302A, Q302C, D302W, Q303A, Q303C, Q303E, Q303H, Q303I, Q303K, Q303L, Q303M, Q303N, Q303R, Q303S, Q303T, Q303V, Q303Y, T306C, Y306G, Y306I, Y306K, Y306L, Y306M, Y306N, Y306P, Y306Q, Y306R, Y306S, Y306T, Y306V, S312C, S312T, S312V, S312W, S312Y, Q316C, Q316P, Q316T, K320C, R328C, R328E, R328G, R328K, R328L, R328M, R328Q, R328S, R328T, R328V, D329A, D329E, D329G, D329H, D329M, D329N, D329Q, D329S, D329T, K335A, K335D, K335F, K335H, K335I, K335L, K335M, K335N, K335R, K335S, K335T, K335V, K335W, D337A, D337C, D337E, D337G, D337H, D337K, D337L, D337M, D337N, D337R, D337S, D337T, D337V, D337Y, A338C, A338F, A338G, A338H, A338I, A338L, A338M, A338N, A333P, A338R, A338V, A338W, K344D, R344E, K344F, K344G, K344I, K344L, K344M, K344N, K344R, K344S, K344T, K344V, K345A, K345E, K345F, K345H, K345P, K345Q, K345R, E345S, K345T, K345V, K345Y, A347D, A347F, A347P, A347Y, H361G, R363C, R363K, R363L, R363Q, R363T, R363W, R363Y, N369C, N369D, N369E, N369F, N369L, N369M, N369S, N369T, N369V, N369W, N369Y, D370E, D370F, D370G, D370S, D370W, D370Y, K371A, K371F, K371G, K371L, K371N, K371Q, K371R, K371S, K371T, K371V, G372A, G372C, G372E, G372E, G372M, G372T, G372V, D374C, D374F, D374G, D374L, D374M, D374N, D374Q, D374S, D374V, D375A, D375C, D375E, D375I, D375V, M380I, M380L, M380Q, M380S, M380T, M380V, Y396A, Y396C, Y396D, Y396E, Y396F, Y396G, Y396I, Y396K, Y396T, D397C, D397E, D397H, D397I, D397K, D397L, D397M, D397N, D397P, D397Q, D397R, D397S, D397T, D397V, D397Y, A398C, A398D, A398E, A398F, A398G, A398H, A398I, A398K, A398L, A398M, A398N, A398P, A398Q, A398R, A398S, A398T, A398V, A398W, A398Y, I399L, I399V, R402A, V410C, T411D, T411E, T411F, T411G, T411H, T411I, T411K, T411L, T411N, T411Q, T411R, T411S, T411V, T411Y, S420C, S420D, S420G, S420K, S420N, S420Q, S420T, S420Y, R426A, R426T, G427C, G427F, G427H, G427L, G427M, G427S, G427Y, K428A, T445A, T445C, T445E, T445F, T445G, T445M, T445V, T445Y, G448A, A448C, G448D, G448E, G448H, G448T, N449A, N449C, N449E, N449F, N449M, N449P, N449T, N449V, N455C, N455D, N455W, N473S, S474C, S474F, S474I, S474L, S474M, S474N, S474P, S474R, S474T, S474Y, N475I, N475L, N475M, N475P, N475Q, N475R, N475S, N475T, N475V, N475W, N475Y, Q490A, Q490C, Q490E, Q490F, Q490G, Q490H, Q490K, Q490L, Q490R, Q490S, Q490T, Q490V, Q490Y, L492A, L492D, L492H, L492N, V497A, V497T, K498E, K498L, K498M, K498V, D521A, V522A, V522C, V522F, V522H, V522I, V522K, V522L, V522M, V522Q, V522R, V522S, V522T, V522W, V522Y, K534F, K534V, R542C, R542E, R542F, R542G, R542H, R542I, R542K, R542L, R542M, R542N, R542P, R542Q, R542S, R542T, R542V, R542W, R542Y, G547A, G547L, G547P, S548C, S548E, S548F, S548H, S548I, S548L, S548M, S548N, S548Q, S548R, S548T, S548V, S548W, S548Y, G554D, G554L, G554M, G554Q, G554W, L555C, L555I, L555V, H561M, H561N, D563A, D563M, D563Q, D564A, D564C, D564F, D564L, D564M, D564T, D564V, R570A, Y571W, K571A, K581D, K584E, K581F, K581G, K581H, K581I, K581L, K584M, K581N, K581R, K581S, K581T, K581V, K581W, K581Y, N583A, N583C, N583D, N583G, N583R, N583V, N586E, R586F, R586L, R586N, R586P, R586V, R586W, V603A, V603C, V603D, V603E, V603G, V603H, V603S, V603T, V603W, V603Y, F611A, Q612C, Q612G, Q612S, A622E, A622F, A622G, A622H, A622K, A622L, A622M, A622R, A622S, A622T, A622V, Q626E, Q626F, Q626G, Q626M, Q626T, T638A, T638D, T638E, T638G, T638I, T638K, T638L, T638M, T638Q, T638R, T638S, T638V, T638W, T638Y, S642C, S642E, S642F, S642H, S642I, S642L, S642M, S642N, S642P, S642Q, S642R, S642T, S642V, S642W, S642Y, A643L, A643M, R645G, R645K, K649A, K649C, K649F, K649I, K649L, K649M, K649Q, K649S, K649W, K649Y, T660C, T660D, T660L, T660W, P661C, P661D, P661F, P661L, P661L, P661S, P664V, P661W, G662A, G662C, G662F, G662H, G662T, G662W, G662Y, Q663A, Q663C, Q663D, Q663E, Q663G, Q663I, Q663K, Q663S, Q663W, T666A, T666C, T666N, R672K, R673R, R673N, R673S, R673T, D675E, D675H, D675S, D675Y, D680A, D680C, D680E, D680M, D680Q, D680R, D680V, D680Y, T681G, T661M, T681S, T681S, T681W, S683G, S683V, S683W, Q684A, Q684C, Q684G, Q684N, Q684P, K685A, K685F, K685G, K685I, K685L, K665N, K685N, K685Q, K685R, K685S, K685T, K685V, K685W, S692C, S692E, S692H, S692I, S692K, S692L, S692M, S692N, S692P, S692Q, S692T, S692V, S692W, R702G, R705L and R703V, wherein the substitution consists of no more than a single replacement at each of the positions, and wherein the positions are numbered by correspondence with the amino acid sequence of a reference beta-glucosidase 1 (BGL1) set forth as SEQ ID NO:3. As described in the experimental section, exemplary beta-glucosidase variants have improved CNPGase activity (PI greater than 1).

Also, the present disclosure provides a beta-glucosidase variant comprising a substitution, wherein the substitution comprises one or more of the group consisting of: K022A, K022E, K022S, N024D, N024E, N024F, N024G, N024K, N024L, N024M, N024P, N024T, L025T, Q026D, Q026P, Q026R, Q026W, Q026Y, K028L, K028M, K028N, W037F, W037I, S050C, S050F, S050G, S050K, S050P, S050R, S050T, S050Y, K051A, K051D, K051G, K051H, K051M, K051T, K051V, I052A, I052F, I052N, I052S, R067A, R067C, R067D, R067E, R067F, R067G, R067I, R067M, R067N, R067P, R067S, R067T, R067V, R067W, R037Y, R091A, R091D, R091E, R091F, R091G, R091H, R091I, R091K, R094L, R091N, R091Q, R091S, R091T, R091V, R091W, E092K, E092T, R093A, R093C, R930D, R093E, R093F, R093G, R093H, R093K, R093L, R093M, R093Q, R093S, R093T, R093V, R093W, E099A, E099F, E099I, E099M, E999W, E099Y, E100I, E100K, E103L, E100Y, H159E, H159G, Q165D, Q165I, Q165K, Q165L, Q165R, Q165V, Q165W, Q165Y, E166F, E166K, E166L, E166N, E166R, E166S, E166T, E166Y, R169A, R169C, R169E, R169F, R169H, R169Q, R169S, R169T, E170F, E170I, E170L, E170M, E170V, E170W, E170Y, P176A, P176D, P176R, D177A, D177G, D177L, D177M, D177N, D177Q, D177W, D178S, R179A, R179V, Q194A, N196E, N196G, N196M, N196P, S199A, Y204M, N208R, T209K, T209L, T209M, T209R, E214A, E214K, E214P, E214R, E214W, E214Y, D215A, D215C, D215F, D215G, D215H, D215M, D215N, D215Q, D215S, D215V, D215W, Q216A, Q216C, Q216D, Q216E, Q216F, Q216H, Q216I, Q216K, Q216L, Q216M, Q216P, Q216R, Q216T, Q216W, Q216Y, D225A, D225C, D225E, D225F, D225H, D225I, D225L, D225Q, D225T, D225V, D225W, D225Y, Q226A, Q226C, C226D, Q226E, Q226I, Q226K, Q226W, W237Y, N238A, N238D, N238F, N238G, N238P, N238S, N238W, T242H, T242S, S249M, N263A, N263C, N263D, N263E, N263F, N263H, N263I, N263K, N263L, N263P, N263Q, N263S, N263T, N263V, N264A, N264C, N264D, N264E, N264G, N264H, N264L, N264M, N264Q, N264R, N264S, N264T, N264V, N264Y, R265A, R265E, R265F, R265G, R265I, R265M, R265P, R265Q, R265S, R265T, R265V, N276A, S227A, S277C, S277D, S277E, S277F, S277G, S277M, S277N, S277Q, S277R, S277W, N278C, N278D, N278F, N278G, 278Q, N278R, N278V, Q279C, Q279D, Q279V, T282D, T282H, T282K, R284N, D287C, D278F, D287H, D278I, D287K, D287L, D287M, D287V, D287W, D287Y, Q301E, Q301L, Q301T, Q301V, Y306C, S312A, S312C, S312D, S312G, S312I, S312K, S312L, S312M, S312N, S312Q, S312R, S312W, S312Y, R313E, R313G, R313L, R313S, R313V, R313W, Q316A, Q316C, Q316D, Q316E, Q315F, Q316G, Q316H, Q316I, Q316K, Q316N, Q316P, Q316R, Q316S, Q316T, Q316V, Q316W, Q316Y, K320E, K320G, K320M, K320N, K320T, K342C, R324D, R328C, R328E, R328I, R328L, R328Q, D329A, D329F, D329Q, D329T, D329Y, L334M, L334V, K335A, K335G, K335S, K335T, K335V, K335W, N336S, N336T, N336Y, D337A, D337C, D337W, A338F, A338P, A338Q, A338V, A338W, A338Y, N339D, N339I, N339L, N339P, N339Q, N339R, N339V, N339Y, K344D, K345A, K345D, K345E, K345G, K345H, K345Q, K345Y, A347D, A347F, A347I, A346K, A347K, A347M, A347P, A347Q, A347R, A347S, A347Y, H361A, H361C, H361E, H361G, H361K, H361L, H361M, H361P, H361S, H361Y, R363A, R363C, R363E, R363G, R363K, R363L, R363N, R363Q, R363S, R363T, R363V, R363W, N369A, N369C, N369D, N369E, N369I, N369L, N369M, N369R, N369T, N369V, N369Y, D370E, D370F, D370W, D379Y, K371A, K371D, K371F, K371G, K371L, K371S, K371T, K371W, G374W, G372A, G372C, G372D, G372N, G372S, D374A, D374I, D374R, D374W, M380E, M380F, M380G, M380L, M380Q, M380T, M380V, M380Y, W382N, W382Y, D397N, A398C, A398D, A398E, A398F, A398G, A328H, A398L, A398N, A398P, A398S, A398T, A398Y, I399L, R402C, R402E, R402G, R402I, R402L, R402P, R402Q, R402S, R402V, R402Y, Q409C, Q409D, Q409G, Q409H, Q409I, Q409V, V410G, V410L, R426A, R426E, R426F, R426I, R426K, R426L, R426M, R426N, R426Q, R426S, R426T, R426Y, G427D, G427E, G427F, G427L, G427N, G427Q, G427S, G427T, G427V, G427W, 428A, K428P, T445A, T445C, T445E, T445F, T445G, T445M, T445P, T445Q, T445S, T445V, T445Y, E447A, E447L, E447W, G448D, G448E, G448F, G448H, G448K, G448L, G448M, G448N, G448Q, G448S, G448T, G448V, G448Y, G449C, N447E, N449G, G449K, N449L, N449R, N449V, N449W, D452N, R453A, R453E, R453L, R453M, R453Q, R453S, N455A, N455C, N455D, N455I, Q467A, Q467C, Q467D, Q467E, Q467H, Q467K, Q467N, Q467S, Q467V, Q467W, Q467Y, N473F, N473P, N473Q, N473R, N473S, N473T, N473V, S474D, S474G, S474K, S474L, S474M, S474N, S474Q, S474R, S474V, N475I, N475K, N475L, N475P, N475T, N475V, N475W, N475Y, E489N, Q490C, Q490G, L492Y, Q496A, Q496G, Q496K, Q496N, Q496P, Q496T, Q496V, Q496W, V497C, V497N, K498A, K498C, K498E, K498F, K498G, K498H, K498I, K498Q, K498R, K498S, R498T, K498Y, D521E, D521F, D521P, D521T, D521V, V522G, V522K, V522N, K534D, K534E, K534G, K534H, K534I, K534N, K534Q, K534S, K534T, K534V, R542A, R542C, R542D, R542F, R542I, R542K, R542P, R542Q, R542S, R542W, R542Y, G547A, G547C, G547E, G547F, G547K, G547L, G547N, G547P, G547Q, G547R, G547T, G547V, G547Y, S548E, S548F, S548I, S548L, S548Q, S548T, S548V, S548W, E553D, E553I, E553K, E553Q, E553W, E553Y, G554A, G554C, G554D, G554F, G554H, G554K, G554L, G554M, G554Q, G554R, Q554S, G554T, G554W, K560A, K560C, K560E, K560G, K560H, K560I, K560L, K560M, K560N, K560P, K560Q, K560R, K560S, K560T, K560V, K560Y, H561C, H561D, H561G, H561N, H561T, H561W, D563A, D563I, D563R, D563S, D563V, G563Y, D564A, D564C, D564E, D564F, D564G, D564N, D564Y, R570E, R570G, R570M, R570N, R570Q, R579T, R570V, Y571H, Y571M, Y571W, K581C, K581D, K581G, K581L, K581N, K581T, N583D, R586D, S591C, S591D, S591F, S591G, S591H, S591I, S591K, S591M, S591P, S591Q, S591V, F611G, F611I, F611L, F611N, F611R, F11S, F611T, F611V, F611Y, Q612C, Q612D, Q612G, Q612H, Q612I, Q612W, A622D, A622E, A622L, V627D, V627K, V627P, V627Q, V627R, V627S, V627Y, T638A, T638D, T638Q, T638R, S642D, S642E, S642F, S642G, S642I, S642L, S642M, S642N, A643E, A643F, A643G, A643H, A643K, A643M, A643N, A643Q, A643S, A643T, A643V, A643W, A643Y, R645A, R645D, R645E, R645F, R645P, R645I, R64L, R645M, R645P, R645Q, R645S, R645T, R645V, R645W, R645Y, K649A, K649Q, K649W, Q650D, K656R, T660C, T660E, T660F, T660G, T660I, T660K, T660M, T660N, T660P, T660Q, T660R, T660S, T660V, T660W, T660Y, P661A, P661C, P661D, P661F, P661G, P661I, G662F, G662F, G662I, G662K, G662L, G662M, G662N, G662Q, G662S, G662W, Q663V, Q663W, T666A, T666C, T666D, T666E, T666F, T666G, T666H, T666L, T666S, T666V, T666Y, R672M, R673F, R673N, R673W, R674K, R674L, R674Q, D675E, D675H, D675S, D675Y, T681G, T681I, A682D, A682E, A682I, A682L, A682M, A682N, A682P, A682S, A682W, A682Y, S683A, S683C, S683D, S683E, S683K, S683L, S683R, S683V, Q684C, Q684D, Q684E, Q684F, Q684G, Q684H, Q684I, Q684K, Q684L, Q684M, Q684N, Q684P, Q684R, Q684T, S692H, S692L, S692N, S692T, S692V, R702C, R702D, R702F, E702G, E702I, R702K, R702L, R702M, R702Q, R702S, R702V, R702W, and R705P, wherein the substitution consists of no more than a single replacement at each of the positions, and wherein the positions are numbered by correspondence with the amino acid sequence of a reference beta-glucosidase 1 (BGL1) set forth as SEQ ID NO:3. As described in the experimental section, exemplary beta-glucosidase variants have reduced glucose inhibition (PI greater than 1).

The present disclosure further provides a beta-glucosidase variant comprising a substitution, wherein the substitution comprises one or more of the group consisting of: K022A, K022E, K022F, K022G, K022I, K022P, K022Q, K022S, K022V, K022W, K022Y, N042A, N024C, N042E, N042M, L025I, L025T, Q026H, Q026K, Q026R, Q026S, V035L, V035S, V035T, W037E, W037F, W037H, W037M, W073S, W037Y, S050A, K051A, K051H, K051M, R091Y, E092K, E092L, E092M, L167R, L167W, E170L, P176A, P176G, D178A, D178T, Q194A, Q194K, Q194R, S199A, D215S, Q216E, Q216L, Q216N, D225C, D225G, D225L, D225Q, D225S, D225T, D225V, Q226A, N238A, T242H, T242S, N248A, N248C, N248L, N248T, S249I, N278D, T282C, T282D, T282G, T282N, T282R, T282V, Q303A, Q303D, Q303E, Q303F, Q303G, Q303I, Q303K, Q303L, Q303M, Q303N, Q303R, Q303S, Q303T, Q303V, Q303Y, Y306F, Y306I, Y306R, Y306W, S312C, S312N, K320C, K320H, K320N, K320S, K320Y, D329A, K335A, K335L, K335R, K335S, K335T, K335W, A338C, A338D, A338G, A338I, A338N, A338V, A338W, K344S, A347D, A347F, A347Y, R363L, N369C, N369E, N369F, N369I, N369L, N369M, N369R, N369T, N369V, A369W, N369Y, G372A, I399L, R402A, V410L, T411F, T411H, T441L, T411Q, T411Y, S420A, S420D, R426F, R426N, G427E, G427S, K428A, K428S, T445D, T445G, N473S, S474D, S474G, S474I, S474K, S474M, S474N, S474R, S474T, S474V, S474Y, V497A, V497I, V497M, V497T, D521A, D521S, G547A, G542E, G347K, G347L, G547P, G547R, G547V, S548C, S548E, S548F, S548H, S481I, S481L, S548M, S548V, S548W, Q554Q, H561N, D563A, D563E, N583D, N583R, R586D, V603A, V603E, V603H, V603M, V603N, V603Q, V603S, F661A, Q612D, Q612G, A622D, A622G, A622H, A622I, A622L, A622N, A622R, A622S, A622W, A622Y, Q626E, Q626L, Q626T, T638D, A643M, R645D, R645G, R645K, K649L, K649M, K649Q, K649W, T660C, T660D, T660E, T660F, T660H, T660I, T660K, T660M, T660Q, T660V, T660W, T660Y, P661C, P661D, P661S, P661V, G662C, G662D, G662E, G622F, G662H, G662K, G662I, G662M, G662N, G662Q, G662R, G662S, G662T, G662W, G662Y, T666A, R673W, S663V, Q684F, Q684H, Q684K, Q684L, Q684M, Q684S, Q684T, K685A, K685I, K685S, S692H, S679K, S692L, S692M, S692T, and R705L, wherein the substitution consists of no more than a single replacement at each of the positions, and wherein the positions are numbered by correspondence with the amino acid sequence of a reference beta-glucosidase 1 (BGL1) set forth as SEQ ID NO:3. As described in the experimental section, exemplary beta-glucosidase variants have improved thermostability (PI greater than 1).

Also, the present disclosure provides a beta-glucosidase variant comprising a substitution, wherein the substitution, comprises one or more of the group consisting of: K022A, K022E, K024F, K024P, K024Q, N024C, N024F, N024Q, N024R, N024Y, L025A, L025D, L025F, L025G, L025K, L025N, L025Q, L025R, L025S, L025V, K025Y, Q026C, Q026D, Q026E, Q026G, Q026I, Q026L, Q026P, Q026T, Q026V, Q026W, Q026Y, D027A, D027C, D027E, D027L, D027M, D027Q, D027S, D027T, D027V, K028L, K028M, K028S, K028V, S033C, S033G, S033T, V035C, V035E, V035G, V035H, V035K, V035N, Y033Q, V035R, G036R, G036S, W037V, S050C, S050F, S050G, S050I, S050K, S050L, S050M, S050N, S050P, S050R, S050T, S050V, S050Y, K051C, K051D, K051E, K051G, K051I, K051L, K051N, K051Q, K051R, K051S, K051T, K051V, I052V, R067Q, R091A, R091D, R091E, R091F, R091G, R091H, R091K, R091L, R091N, R091Q, R091S, R091V, R091W, E092A, E092C, E092D, E092F, E092H, E092I, E029N, E092Q, E092R, E092V, E099A, E099D, E099F, E099I, E099K, E099M, E099N, E099W, E099Y, E100M, E100Q, E100T, L167A, L167C, L167E, L167F, L167G, L167M, L167N, L167Q, L167S, L167V, L167Y, N168A, N168D, N168E, N168G, N168H, N168Q, N168R, N168T, N168Y, E170D, E170F, E170I, E170M, E170V, P176E, P176H, P176L, P176M, P176Q, P176R, P176S, P176T, P176V, P176Y, D177A, D177C, D177E, D177F, D177H, D177L, D177M, D177Q, D177R, D177V, D177Y, D178C, D178K, D178N, D178Q, D178R, D178S, R179A, R179C, R179G, R179I, R179K, R179S, R179T, R179V, R179W, Q194C, Q194E, Q194F, Q194F, Q194G, Q194H, Q194L, Q194M, Q194T, Q194W, N196E, N196G, N196H, N196L, N196M, N196Q, N196R, N196T, S199G, S199T, S199V, Y204F, Y204M, N208K, T209C, T209D, T209E, T209G, T209H, T209I, T209K, T209L, T209M, T209Q, T209R, T209S, T209V, T209W, T209Y, E214D, E214Q, D215A, D215C, D215E, D215F, D215G, D215H, D215I, D215M, D215N, D215Q, D215W, Q216A, Q216C, Q216F, Q216G, Q216H, Q216I, Q216K, Q216M, Q216P, Q216S, Q216T, Q216W, Q216Y, K224R, K224V, D225A, D225E, D225F, D225H, D225I, D225M, D225W, D225Y, Q226C, Q226D, Q226E, Q226F, Q226H, Q226I, Q226K, Q226L, Q226M, Q226N, Q226R, Q226T, Q226V, Q226W, Q226Y, N238C, N238D, N238E, N238F, N238G, N238M, N238S, N238T, N238W, T424C, T242E, T242F, T242G, T242K, T242N, T242Q, T242R, T242W, T242Y, N248F, N248G, N248W, N248Y, S249Q, S249M, S249V, N263A, N263C, N263D, N263E, N263F, N263G, N263H, N263I, N263K, N263L, N263P, N263Q, N263R, N263S, N263T, N263V, N263Y, N264C, N264G, N264K, N264M, N264Q, N264T, R265E, R265F, R265I, R265K, R265L, R265M, R265N, R265P, R265Q, R265S, R265T, R265V, N276A, N276F, N276M, N276Q, S277C, S277E, S277F, S277G, S277H, S277I, S277M, S277N, S277P, S277Q, S277R, S277Y, N278C, N278F, N278G, N278I, N278L, N278M, N278Q, N278R, N278S, N278T, N278V, N278W, N278Y, Q279C, Q279D, Q279E, Q279G, Q279H, Q279I, Q279K, Q279N, Q279S, Q279T, Q279V, Q279Y, T282K, T282I, T282P, T282S, D287C, D287E, D287G, D287H, D287I, D287K, D287L, D287M, D287N, D287S, D287V, Q301E, Q301N, D302A, D302C, D302E, D302F, D302G, D302K, D302M, D302N, D302P, D302S, D302T, D302W, D302Y, Q303C, Q303H, Q303P, Q303W, Y306C, Y306G, Y306K, Y306M, Y306N, Y306P, Y306Q, Y306S, Y306T, Y306V, S312K, S312L, S312M, S312Q, S312T, S312V, S312W, S312Y, R313A, R313C, R313G, R313L, R313N, R313S, R313V, R313W, Q316C, Q316E, Q316G, Q316K, Q316L, Q316N, Q316S, Q316T, Q316V, Q316W, Q316Y, K320E, K320G, K320L, K320M, K320P, K320Q, K320R, K320T, R324C, R324D, R324E, R324F, R324H, R324I, R324K, R324L, R324M, R324Q, R324V, R324W, R324Y, R328C, R328E, R328G, R328K, R328L, R328M, R328Q, R328T, R328V, D329E, D329F, D329G, D329H, D329M, D329N, D329Q, D329S, D329T, D329Y, L334A, L334C, L334F, L334M, L334T, L334V, L334W, K335D, K335F, K335G, K335H, K335I, K335M, K335N, K335V, N336A, N336C, N336G, N336H, N336L, N336M, N336Q, N336R, N336S, N336T, N336V, N336Y, D337A, D337C, D337E, D337G, D337H, D337K, D337L, D337M, D337N, D337R, D337S, D337T, D337V, D337W, D337Y, A338F, A338H, A338K, A338L, A338M, A338P, A338Q, A338Y, N339D, N339E, N339G, N339H, N339I, N339K, N339L, N339P, N339Q, N339R, N339V, N339Y, K344D, K344E, K344F, K344G, K344I, K344L, K344M, K344N, K344P, K344Q, K344T, K344T, K544V, K345A, K345D, K345F, K345G, K345H, K345N, K345P, K345Q, K345Q, K345R, K345S, K345T, R345V, K345W, K345Y, A347H, A347I, A347K, A347L, A347M, A347P, A347R, A347S, R363C, R363E, R363Q, R363T, N369A, N369D, N369S, G372C, G372N, G372V, D374C, D374N, D374Y, W382N, W382Y, Y396C, Y396D, Y396E, Y395P, Y396G, Y396H, Y396I, Y396K, Y396L, Y396M, Y396N, Y396Q, Y396S, Y396T, Y396V, Y396W, D397A, D397C, D397E, D397P, D397Q, D397R, D397S, D397T, D397V, A398C, A398G, A398E, A393F, A398G, A398H, A398I, A398L, A398M, A398N, A398P, A398Q, A398S, A398T, A398V, A398W, A398Y, I399A, I399C, I399D, I399E, I399F, I399G, I399M, I399Q, I399S, I399T, I399V, I399W, I399Y, R402C, R402E, R402F, R402G, R402I, R402L, R402P, R402Q, R402S, R402V, R402W, R402Y, Q402C, Q409D, Q409G, Q409H, Q409I, Q409V, V410A, V410C, V410F, V410G, V410H, V410L, V410N, V410S, V410T, V410W, V410Y, T411D, T411E, T411G, T411I, T411K, T411N, T411R, T441S, T411V, S420C, S420G, S420H, S420K, S420N, S420Q, S420T, S420Y, R426E, R426I, R426K, R426L, R426M, R426P, R426Q, R426S, R426T, R426W, R426Y, G427C, G427D, G427F, G427H, G427K, G427L, G427M, G427N, G427P, G427Q, G427R, G427T, G427V, G427W, G427Y, K428A, K428D, K428E, K428F, K428G, K428H, R428I, K428L, K428M, K428N, K428P, K428Q, K428R, R428T, K428V, K428W, K428Y, T445A, T445C, T445E, T445F, T445I, T445K, T445L, T445M, T445N, T445P, T445Q, T445R, T445S, T445V, T445Y, V446Q, N449C, N454F, N454K, N454L, N454M, N454R, N454S, N454T, N454V, N455A, N455C, N455D, N455E, N455F, N455G, N455H, N455L, N455M, N455S, N445T, N455V, N455W, N455Y, Q467A, Q467C, Q467D, Q467N, Q467S, N473A, N473C, G473E, N473G, N473H, N473K, N473L, N473M, N473P, N473Q, N473R, N473T, N473V, S474A, S474C, S474E, S474F, S474L, S474P, S474Q, N475I, G475L, N475M, N475P, N475Q, N475R, N475S, N475T, N475V, N475W, N475Y, E489N, Q490A, Q490C, Q490E, Q490F, Q490G, Q490H, Q490K, Q490L, Q490P, Q490R, Q490S, G490T, Q490V, Q490W, Q490Y, L492A, L492D, L492F, L492H, L492I, L492M, L492N, L492Q, L492R, L492T, L492W, L492Y, Q496A, Q496G, Q496N, Q496P, Q496S, Q496T, V497C, V497N, K498A, K498C, K498E, K498F, K498G, K498H, K498I, K498L, K498M, K498N, K498Q, K498R, K498S, K498T, K498V, K498Y, D521C, D521E, D521F, D521G, D521H, D521I, D521K, D521L, D521M, D521P, D521R, D521T, D521V, D521W, V522A, V522C, V522F, V522G, V522H, V522I, V522K, V522L, V522M, V522N, V522P, V522Q, V522R, V522S, V522T, V522W, V522Y, K534C, K534D, K534E, K534F, K534H, K534I, K534M, K534N, K534S, K534T, K534V, R542C, R542E, R542F, R542G, R542H, R542K, R542I, G542M, R542N, R542P, R542Q, R542S, R542T, R542V, R542W, R542Y, G547C, G547E, G547N, G547Q, G547T, G547Y, S548N, S548Q, S548R, S548T, S548Y, E553D, E553K, E553N, E553W, G554A, G554C, G554D, G554F, G554H, G554K, G554L, G554M, G554R, G554S, G554T, G554V, G554W, L555A, L555C, L555D, L555E, L555F, L555G, L555H, L555I, L555K, L555M, L555N, L555P, L555Q, L555T, L555V, L555W, L555Y, K560A, K560C, K560G, K560I, K560L, K560M, K560N, K560P, K560R, K560S, K560T, K560V, K560Y, H561A, H561C, H561D, H561E, H561F, H561G, H561I, H561M, H561Q, H561S, H561T, H561V, H561W, D563C, D563F, D563I, D563L, D563M, D563Q, D563R, D563S, D563T, D563V, D563W, D563Y, D564A, D564C, D564E, D564F, D564G, D564K, D564I, D564M, D564N, D564Q, D564R, D564S, D564T, D564V, D564Y, R570A, R570C, R570D, R570E, R570G, R570H, R570I, R570M, R570Q, R570S, R570T, R570V, Y571H, Y571M, Y571W, K581A, K581C, K581D, K581E, K581F, K581G, K581H, K581I, K581L, K581M, K581N, K581P, K581R, K581S, K581T, K581V, K581W, K581Y, N583A, N583C, N583E, N583F, N583G, N583H, N583I, N583K, N583L, N583M, N583P, N583S, N583T, N583V, N583W, N583Y, R586E, R586F, R586G, R586L, R586N, R586P, R586V, R586W, R586Y, S591C, S591D, S591G, S591H, S591I, S591K, S591M, S591P, S591Q, S591V, V603C, V603D, V603F, V603G, V603P, V603R, V603T, V603W, V603Y, F611C, F661D, F611G, F611I, F611K, F611L, F611M, F611N, F611R, F611S, F611T, F611V, G611W, F611Y, Q612C, Q612F, Q612H, Q612I, Q612L, Q611M, Q611R, Q612S, Q612W, A622E, A622F, A922K, A622M, A622T, A622V, Q626F, Q626G, Q626M, V627P, V627P, V627Q, V627R, V627S, T638A, T638E, T638F, T638G, T638I, T638K, T638L, T638M, T638P, T638Q, T638R, T638S, T638V, T638Y, S642A, S642C, S642E, S642F, S642G, S642H, S642I, S642K, S642L, S642M, S642N, S642P, S642Q, S642R, S642T, S642V, S642W, S642Y, A643C, A643E, A643F, A643G, A643H, A643K, A643L, A643N, A643Q, A643R, A643S, A643T, A643V, A643W, A643Y, R645A, R645E, R645F, R645H, R645I, R645L, R645M, R645P, R645Q, R645S, R643T, R645V, R645W, R645Y, K649C, K649F, K649I, K649S, K649T, R649Y, Q650A, Q650C, Q650E, Q650F, Q650G, Q650H, Q550I, Q650K, Q650L, Q650M, Q650N, Q650R, Q650T, Q650V, Q650Y, K656R, T660G, T660N, T660P, T660R, T660S, P661A, P661E, P661F, P661G, P661H, P661I, P661K, P661L, P661M, P661Q, P661R, Q661T, P661W, G662A, G662I, Q663A, Q663C, Q663E, Q663F, Q663H, Q663I, Q663K, Q663L, Q663M, Q663N, Q663R, Q663S, Q663V, Q663W, T666C, T666D, T666E, T666F, T666G, T666H, T666K, T666L, T666N, T666R, T666S, T666V, T666W, T666Y, R672C, R672F, R672G, R672H, R672I, R672K, R672L, R672N, R672T, R672V, R672W, R673A, R673C, R673E, R673G, R673H, R673I, R673K, R673L, R673M, R673Q, R673S, R673T, R673V, R674K, R674L, R674M, R674Q, R674V, D675E, D675H, D675S, D675Y, D680A, D680C, D680E, D680F, D680H, D680I, D680K, D680L, D680M, D680N, D680Q, D680R, D680S, D680V, D680W, D680Y, T681A, T681G, T681H, T681K, T681L, T681M, T681N, T681P, T681Q, T681R, T681S, T681V, T681W, T681Y, A682C, A682E, A682I, A682L, A682M, A682N, A682P, A682S, A682W, A682Y, S683A, S683C, S683D, S683E, S683F, S683G, S683I, S683L, S683M, S683P, S683Q, S683R, S683W, Q684A, Q684E, Q684E, Q684G, Q684I, Q684N, Q684P, K685E, K685F, K685G, K685I, K685M, K685N, K685Q, K685R, E685T, K685V, K685W, K685Y, S692C, S692E, S692I, S692N, S692P, S692Q, S692V, S692W, R702C, R702D, R702F, R702G, R702H, R702I, R702K, R702L, R702M, R702N, R702Q, R702S, R702T, R702V, R702W, R705C, R705F, R705H, R705I, R705M, R705P, R705S, R705T, R705V, and R705W, wherein the substitution consists of no more than a single replacement at each of the positions, and wherein the positions are numbered by correspondence with the amino acid sequence of a reference beta-glucosidase 1 (BGL1) set forth as SEQ ID NO:3. As described in the experimental section, exemplary beta-glucosidase variants have improved thermostability (PI greater than 0.1 but less than 1).

The present disclosure further provides a beta-glucosidase variant comprising a substitution, wherein the substitution comprises one or more of the group consisting of: K022A, K022E, K022F, K022P, K022Q, N024C, N024F, N024Q, N024R, N024Y, L025D, Q026C, Q026E, G026H, Q026I, Q026K, Q026L, Q026P, Q026R, Q026S, Q026T, Q026V, Q026W, D027A, D027C, D027E, S033C, V035C, V035P, V035T, G036D, G036E, G036K, G036R, G036S, G036T, S050C, S050L, K051C, K051E, K051G, K051H, K051I, K051M, K051Q, K051T, K051V, I052D, I052T, R091D, R091G, R091K, R091Q, E092A, E092C, E092D, E099Y, E100A, E100G, E100N, E100Q, E100S, E100T, E100Y, K158H, K158T, Q165I, Q165K, Q165M, Q165N, Q165V, E166D, L167C, L167W, N168A, N168D, N168E, N168G, N168Y, E170D, E170F, P176K, P176R, P176W, P176Y, D177E, D177F, D177H, D177L, D177M, D177V, D177W, D177Y, I78C, D178Y, R179C, R179M, R179S, Q194C, N196E, N196L, N196Q, N196R, N196T, S199A, T209C, T209G, T209H, T209I, T209L, T209M, T209Q, T209S, T209V, T209Y, E214W, D215C, D215E, D215I, D215N, D215Q, D215S, Q216A, Q216E, Q216G, Q216H, Q216I, Q216L, Q216M, Q216N, Q216S, Q216W, Q216Y, K224H, K224R, K224V, D225G, D225H, D225I, D225L, D225M, D225T, D225V, D225W, D225Y, Q226F, Q226I, Q226L, Q226M, Q226R, Q226V, W226W, Q226Y, N238A, N238C, N238R, N238G, T242A, T242C, T242E, T242F, T242G, T242H, T242K, T422L, T242M, T242N, T242Q, T242R, T242S, T242V, T424W, T242Y, N248A, N248F, N248G, N248T, N248W, S249M, S249V, N263C, N263D, N263G, N263S, N263T, N264C, N276A, N276C, N276C, S277C, S277F, S277W, S277Y, N278C, N278F, N278G, N278V, Q279C, T228C, D287C, D278S, Q301G, Q301K, Q301L, D302A, D302C, D302E, D302F, D302G, D302K, D302M, D302T, Q303A, Q303C, Q303K, Q303M, Q302P, Y306G, Y306K, Y306M, Y306Q, Y306R, Y306V, S312C, S312D, S312W, S312Y, Q316K, Q316P, Q316R, Q316S, Q316T, Q316Y, K320C, R328S, D329A, L334A, L334V, K335A, K335D, K335H, K335V, K335W, N336A, N336G, D337C, D337K, D337W, A338C, A338W, N339E, N339G, N339H, N339K, N339L, K344D, K344F, K344I, K344L, K344M, K344P, K344S, K344T, K344V, K345A, K345D, K345E, K345F, K345G, K345S, K345V, K345Y, A347S, A347Y, H361A, H361C, H361G, R363C, R363G, R363K, R363Q, R363S, R363W, R363Y, N369C, N369D, N369E, N369F, N369W, N369Y, K371A, K371G, K371L, K371T, G372A, G372K, K372W, D374C, D374L, D374M, D374Q, D374S, D374V, D375C, D375E, D375W, M380N, M380V, W382F, Y396A, Y396C, Y396E, Y396F, Y396K, Y396V, D397C, D397E, D397H, D397I, D397K, D397L, D397M, D397N, D397Q, D397R, D397S, D397T, D397V, D397Y, A398E, A398R, A393V, A398W, I399C, I399Y, R402A, R402E, R402G, R402L, R402Q, R402S, R402W, Q409G, T411D, D411E, T411F, T411G, T411H, T411I, T411K, T411L, T411N, T411Q, T411R, T411S, T411V, S420C, S420E, S420H, S420K, S420N, S420Q, S420T, S420V, S420Y, R426A, G427C, G427D, T427E, G427F, G427H, G427P, G427V, G427Y, K428A, K428N, T445A, T445C, T445E, T445F, T445G, T445M, T445P, T445V, T445Y, V446Q, V446R, E447V, G448C, G448D, G448E, G448F, G448N, N449A, N449C, N449E, N449G, N449K, 445F, N455C, N455D, N455S, N455V, N455W, H460E, H460G, H460M, H460Q, H460S, Q467P, Q467S, N473A, N473E, N473L, N473R, N473W, S474A, S474C, S474D, S474G, S474K, S474L, S474N, N475I, N475M, N475S, N475T, N475Y, Q490C, Q490H, Q490L, Q490R, Q490V, Q490W, Q490Y, L492A, L492D, L492F, F492W, L492T, Q496G, Q496W, V497C, V497M, V497T, K498A, K498C, K498E, K498F, K498G, K498I, K498M, K498T, K498Y, D521A, D521C, D521W, V522A, V522C, V522K, V522L, V522M, V522Q, V522R, V522S, V522W, K534C, K534D, K534E, K534F, K534N, K534R, K534V, R542S, G547A, G547C, S548E, S548E, S548F, S548L, S548M, S548Q, S548T, S548W, G554C, G554D, G544F, G554H, G554M, G554Q, G554W, L555C, L555D, L555E, L555G, L555H, L555K, L555N, L555P, K560A, K560E, K560G, K560P, K560R, K560W, H561G, H561I, H561M, H561N, H561Q, H561S, H561V, H561W, D563A, D563Q, D563S, D563T, D563Y, D564A, D564C, D564F, D564G, G564K, D564L, D564M, D564N, D564Q, D564T, D564V, D564Y, R570A, R570C, R570D, R570E, R570G, R570I, R570Q, R570S, R570T, R570V, Y571H, Y571M, K581A, K581C, K581D, K581E, K581F, K581G, K581H, K581I, K581L, K581M, K581N, K581R, K581S, K581W, K581Y, N583A, N583C, N583D, N583G, N583H, R586N, R586P, R586V, R586W, V603G, V603H, V603Y, F611A, F611C, Q612C, Q612G, Q612S, A622E, Q626E, Q625H, T638A, T638D, T638G, T638W, S642E, S642F, S642G, S642H, 642I, S642L, S642Q, S642R, S642T, S642W, S642Y, A643K, A643V, R645A, R645G, R645I, R645K, R645L, R645M, R645W, R645Y, K649C, K649N, K649T, Q650A, Q650C, Q650D, Q650F, Q650G, Q650K, Q650N, Q650R, Q650T, Q650V, Q656Y, T660C, T660D, T660N, T600S, S660W, T660Y, P661A, P661C, P661D, P661E, P661F, P661H, P661I, P661K, P661L, P661M, P611Q, P661R, P661S, P661T, P661V, P661W, G662A, G662C, G662F, G662H, G662I, G662N, Q663E, T666C, T666D, T666N, R672C, R672D, R672G, R672L, R672M, R672N, R672T, R672V, R673G, R673K, R673L, R673N, R673S, R673T, R674T, R674Y, D680C, D680F, D680I, D680M, D680Q, D680V, D680Y, T681A, T681G, T681P, T681Q, T681S, T681V, T681W, S683F, S683V, S683W, Q684C, Q684G, Q684N, K685A, K685E, K685F, K685G, R685I, K685L, K685M, K685Q, K685S, K685T, K685W, K685Y, S692C, S692H, S692I, S692L, S692M, S692V, S692W, R702C, R702D, R702F, R702G, R702H, R702S, R702T, R702V, R705F, R705I, R705L, R705M, R705S, R705T, R705T, R705V, and R705W, wherein the substitution consists of no more than a single replacement at each of the positions, and wherein the positions are numbered by correspondence with the amino acid sequence of a reference beta-glucosidase 1 (BGL1) set forth as SEQ ID NO:3. As described in the experimental section, exemplary beta-glucosidase variants have improved PASC hydrolysis activity (PI greater than 1).

Also, the present disclosure provides a beta-glucosidase variant comprising a substitution, wherein the substitution comprises one or more of the group consisting of: K022E, K022F, K022G, K022W, N024A, N024C, N024D, N024E, N024F, N024G, N024L, N024P, N024Q, N024S, N024V, N024Y, L025K, L025N, L025T, L025V, L025Y, Q026C, Q026D, Q026E, Q026G, Q026I, Q026K, Q026L, Q026P, Q026R, Q026S, Q026T, Q026V, Q026W, Q026Y, S033C, S033T, V035C, V035E, V035N, G036S, S050C, S050F, S050G, S050I, S050L, S050M, S050N, S050P, S050R, S050T, S050V, K051V, K051C, K051D, K051H, K051H, K051L, K051Q, K051R, K051S, K051T, K051V, R091D, R091E, R091F, R091G, R091H, R091I, R091K, R091L, R091N, R091Q, R091T, R091V, R091W, R091Y, E092C, E092D, E092F, E092H, E092K, E092L, E092N, E092Q, E092R, E092T, E092V, E092Y, R093K, E099A, E099D, E099F, E099I, E099K, E099M, E099N, E099W, E099Y, L167C, L167D, L167E, L167F, L167G, L167M, L167V, L167W, N168A, N168D, N168E, N168G, N168Q, N168Y, E170D, E170F, P176E, P176F, P176G, P176H, P176L, P176M, P176Q, P176R, P176S, P176T, P176V, P176W, P176Y, D177F, D177K, D177L, D177M, D177N, D177Q, D177R, D177V, D178A, D178C, D178N, G178R, R179A, R179C, R179G, R179I, R179K, R179M, R179Q, R179S, R179T, R179V, Q194A, Q194C, Q194E, Q194F, Q194G, Q194I, Q194K, Q194L, Q194M, Q194R, Q194T, Q194W, Q194Y, N196E, N196H, N196L, N196R, N196T, S199G, S199N, S199T, S199V, T209C, T209D, T209E, T209G, T209H, T209I, T209K, T209L, T209M, T209Q, T209V, T209W, T209Y, E214D, D215C, D215L, D215M, D215S, D215W, Q216A, Q216C, Q216D, Q216E, Q216F, Q216G, Q216H, Q216I, Q216K, Q216N, Q216P, Q216R, Q216S, Q216T, Q216W, Q216Y, K224R, D225A, D225C, D225F, D225G, D225H, D225I, D225L, D225M, D225Q, D225S, D225T, D225V, D225W, D225Y, Q226C, Q226D, Q226E, Q226F, Q226H, Q226I, Q226K, Q226L, Q226M, Q226N, Q226R, Q226T, Q226V, Q226W, Q226Y, N238A, N238C, N233G, N238M, N238S, T242A, T242C, T242E, T242S, N248T, S249A, S249G, N263A, N263C, N263D, N263Q, N263S, N263T, N264C, R265A, R265E, R265I, R265L, R265M, R265Y, N276A, N276C, S277A, S277C, S277D, S277E, S277F, S277G, S277H, S277I, S277M, S277P, S277Q, S277W, S277Y, N278A, N278C, N278D, N278F, N278G, N278I, N278M, N278Q, N278R, N278S, N278T, N278V, N278W, N278Y, Q279C, Q279D, Q279E, Q279G, Q279H, Q279I, Q279K, Q279N, Q279S, Q279T, Q279V, Q279Y, T282K, D287C, D287G, D278H, D287I, D287K, D287M, D287N, D287S, Q301A, Q301E, Q301G, Q301K, Q301R, D302A, D302C, D302E, D302F, D302G, D302K, G302M, D302N, D302P, D302S, D302T, D302W, D302Y, Q303C, Q303D, Q303R, Q303W, Y306M, Y306R, Y306V, S312C, S312D, S312G, S312N, S312Q, S312R, S312T, S312V, S312Y, R313A, R313C, R313D, R313G, R313K, R313N, Q316K, Q316L, Q316M, Q316R, Q316T, Q316Y, R320C, K320G, K320N, K320P, K320S, K320Y, R324C, R324D, R324E, R324F, R324K, E324I, R324K, R324L, R324M, R324Q, R324V, R324W, R324Y, R328C, R328K, R328S, D329A, D329H, G329S, L334A, L334C, L334F, L334M, L334T, L334V, L334W, K335A, K335D, K335H, K335L, K335R, K335S, K335V, K335W, N336A, N336C, N336G, N336H, N336L, N336M, N336Q, N336R, N336T, N336V, N336Y, D337A, A338C, 338D, A338E, A338F, A338G, A338H, A338I, A338K, A338L, A338N, A338P, A338Q, A338R, A338V, A338W, A338Y, K344D, K344F, K344L, K344M, K344N, K344P, K344T, K344V, K345A, K345D, K345E, K345F, K345G, K345H, K345N, K345P, K345R, K345S, K345V, K345W, K345Y, A347D, A347F, A347H, A347I, A347K, A347L, A347M, A347P, A347Q, A374R, A347S, A347Y, H361A, H361G, H361N, R363C, R363K, R363M, R363Q, R363S, R363T, R363V, R363W, N369C, N369D, N369S, K371G, G372A, D374C, D374F, D374N, D374S, Y396D, Y396E, Y396F, Y396G, Y396H, Y396K, Y396L, Y396M, Y396N, Y396Q, Y396R, 397C, D397E, D397H, D397I, D397K, D397M, D397N, D397P, D397Q, D397R, D397S, D397T, D397V, D397Y, A398C, A398D, A398E, A398F, A398G, A398H, A398I, A398K, A398L, A398M, A398N, A398P, A398Q, A398R, A398S, A398T, A398V, A398W, A398Y, I399A, I399C, I399D, I399E, I399G, I399M, I399Q, I399S, I399T, I399W, I399Y, R402A, R402C, R402G, R402S, Q409D, V410A, V410C, V410I, V410L, V410N, V410R, V410S, V410T, V410W, T411D, T411E, T411G, T411H, T411N, T411Q, T411S, T411Y, S420C, A, R426A, R426E, R426F, R426I, R426K, R426N, R426P, R426Q, R426S, R426W, R426Y, G427C, G427E, G427F, G427H, G427K, G427N, G427Q, G427R, G427S, G427T, G427V, K428C, K428D, K428E, K428F, K428G, K428H, K428I, K428L, K428M, K428N, K428P, K428Q, K428R, K428S, K428T, K428V, K428W, K428Y, T445A, T445C, T445D, T445K, T445M, T445Q, T455S, V446C, G448A, G448C, G448D, G448E, G448F, G448N, G448S, G448T, G448Y, N449A, N449C, N454F, N454G, N454K, N454L, N454M, N454R, N454S, N454T, T454V, N455A, N455D, D455E, N455F, N455G, N455H, N455I, N455L, N455M, N455S, N455T, N455V, N455W, N455Y, Q467A, N473A, N473C, N473E, N473F, N473G, N474H, N473K, N473L, N473M, N473P, N473Q, N473R, N473S, N473T, N473V, N473W, S474A, S474C, S474D, S474F, S474G, S474I, S474K, S474M, S474N, S474Q, S474R, S474T, S474V, N475I, N475K, N475L, N475M, N475P, N475Q, N475R, N475S, N475T, N475V, N475W, N475Y, E489N, Q490P, Q490W, L492A, L492D, L492F, L492I, L492M, L492Q, L492Y, L492W, Q496G, Q496S, Q496W, V497A, V497I, V497T, K498A, K249F, K498H, K498I, K498N, K498Q, D521A, D521C, D521E, D521F, D521G, D521H, D521I, D521K, D521L, D521M, D521P, D521R, D521S, D521T, D521V, D521W, D521Y, V522A, 522C, V522F, V522G, V522H, V522I, V522K, V522L, V522M, V522N, V522P, V522Q, V522Q, V522S, V522T, V522W, V522Y, K534C, K534D, K534E, K534F, K534G, K534N, K534R, K534V, R542A, R542C, R542D, R542E, R542F, R542G, R542H, R542I, R542K, R542L, R542M, R542N, R542P, R542Q, R542S, R542T, R542V, R542W, R542Y, G547A, G547L, S548L, G554A, G554C, G554D, G554F, G554H, G554L, G554V, G554W, L555A, L555C, L555D, L555E, L555F, L555G, L555H, L555I, L555K, L555N, L555P, L555Q, L555V, L555W, L555Y, K560H, K560P, K560R, K560W, H561A, H561C, H561D, H561E, H561F, H561G, H561I, H561M, H561N, H561Q, H561S, H561V, H561W, D563A, D563C, D563F, D563I, D563L, D563Q, D563R, D563S, D563T, D563W, D563Y, D564A, D564C, D564F, D564K, D564L, D564R, D564T, D564V, R570A, R370D, R570G, R570H, R570I, R570S, R570V, Y571H, Y571M, K581W, N583C, N583D, N383E, N583F, N583G, N583H, N583I, N583K, N583L, N583M, N583P, N583R, N583S, N538T, N583W, N583Y, R586E, R586F, R586G, R586H, R586L, R586N, R586P, R586V, R586W, R586Y, S591D, V603A, V603D, V603G, V603H, V603N, V603Q, Y603R, V603Y, F611A, F611C, F611D, F611K, F611L, F611M, F611N, F611R, F611S, F611W, Q612C, Q612F, Q612G, Q612H, Q612I, Q612K, Q612L, Q612M, Q612R, Q612S, Q612W, A622H, A622K, Q626H, Q626M, V627P, T638A, T638D, T638E, T638F, T638G, T638I, T638K, T638L, T638M, T638P, T638Q, T638R, T638S, T638V, T638W, T638Y, S642A, S642C, S642E, S642F, S642G, S642H, S642I, S642K, S642L, S642M, S642N, S642P, S642Q, S642R, S642T, S642V, S642W, S642Y, A643C, A643F, A643G, A643H, A643K, A643L, A643M, A643Q, A643R, A643S, A643T, A643V, A643Y, R645A, R645D, R645F, R645G, R645G, R645I, R645K, R645L, R645M, R645P, R645Q, R645T, R645V, R645W, R645Y, K649A, K649C, K649F, K649L, K649N, K649Q, K649S, K649T, K649Y, Q650C, Q650D, Q650E, Q650F, Q650G, Q650H, Q650I, Q650K, Q650L, Q650M, Q650N, Q650R, Q650V, Q650Y, T660C, T660W, T660Y, P661C, P661F, P661H, P661I, P661K, P661L, P661M, P661Q, P661R, P661T, P661V, P661W, G662A, G662C, G662F, G662H, G662I, G662K, G662R, G662Y, Q663A, Q663C, Q663D, Q663E, Q663F, Q663I, Q663L, Q663M, Q663N, Q663R, Q663S, Q663V, Q663W, T666A, T666C, T666I, T666K, T666N, T666R, T666W, R672C, R672D, R672G, R672I, R672R, R672V, R672W, R673A, R673C, R673G, R673H, R673I, R673K, R673L, R673Q, R673T, R673V, R673W, R674L, R674M, R674T, R674Y, D675C, D680A, D680C, D680E, D680F, D680H, D680I, D680K, D680L, D680M, D680N, D680Q, D680R, D680S, D680V, D680W, D680Y, T681A, T681G, T681H, T681K, T681L, T681M, T681N, T681Q, T681R, T681W, S683A, S683C, S683D, S683F, S683G, S683I, S683L, S683P, S683R, S683V, S683W, Q684A, Q684D, K685A, K685F, K685G, K685I, K685L, K685M, K685N, K685Q, K685R, R685S, K685T, K685V, K685W, K685Y, S692E, S692H, S692K, S692L, S692Q, S692T, S692V, S692W, R702C, R702D, R702F, R702G, R702H, R702I, R702K, R702L, R702M, R702N, R702Q, R702S, R702T, R702V, R702W, R705C, R705F, R705H, R705L, R705L, R705M, R705P, R705S, R705T, and R705W, wherein the substitution consists of no more than a single replacement at each of the positions, and wherein the positions are numbered by correspondence with the amino acid sequence of a reference beta-glucosidase 1 (BGL1) set forth as SEQ ID NO:3. As described in the experiment section, exemplary beta-glucosidase variants have improved PCS hydrolysis activity (PI greater than 1).

The present disclosure further provides a beta-glucosidase variant comprising a substitution, wherein the substitution comprises one or more of the group consisting of: K022A, K022E, K022E, K022P, K022Q, N024C, N024P, N024Q, L025A, L025D, Q026C, Q026I, Q026K, Q026L, Q026P, Q026R, Q026S, Q026T, Q026W, S033C, Q033V, V035C, V035E, V035Q, V035R, V035S, V035T, V035Y, G036C, G036D, G036E, G036F, G036I, G036K, G036R, G036S, G036W, G036Y, S050C, S050P, K051A, K051C, K051D, K051G, K051H, K051M, K051Q, K051T, K051V, R091D, R092G, R091K, R091N, R091Q, E092A, E092C, E092D, E092F, E092H, E092I, E092L, E092N, E092R, E092V, E099Y, E100A, E100G, E100M, E100T, E100Y, E164G, E164S, Q165V, E166D, L167C, L167G, L167N, L167V, L167W, N168A, N168D, N168E, N168G, N168H, N168Q, N168R, N168T, N168Y, E176F, P176A, P176D, P176F, P176H, P176K, P176L, P176N, P176R, P176V, P176W, P176Y, D177C, D177F, D177H, D177L, D177M, D177R, D177W, D177Y, D178C, D178K, D178N, D178Y, R179K, R179M, R179S, R179W, R94A, Q194C, Q194E, Q194F, Q194G, Q194K, Q194L, N196E, N196L, N196Q, N196T, T209C, T209D, T209E, T209G, T209H, T209I, T209L, T209M, T209Q, T209S, T209V, T209Y, E214W, D215C, D215E, D215G, D215L, D215M, D215N, D215Q, D215S, Q216A, Q216C, Q216F, Q216G, Q216I, Q216K, Q216L, Q216M, G216S, Q216T, Q216W, Q216Y, K224R, K224V, D225F, D225G, D225H, D225I, D225L, D225M, D225T, D225V, D225W, D225Y, Q226A, Q226C, Q226F, Q226I, Q226L, Q226M, Q226N, Q226R, Q226V, Q226W, Q226Y, N238A, N238C, N238E, T242A, T242C, T242E, T242F, T242H, T242K, T242L, T242M, T242Q, T242V, T242W, T242Y, N248G, N248W, N248Y, N263C, N263E, N263F, N263G, N263Q, N263S, N263T, N263V, N263Y, N264C, R265E, R265K, N276C, S277A, S277C, S277F, S277I, S277M, S277P, S277R, S277W, S277Y, N278A, N278C, N278F, N278G, N278H, N278I, N278L, N278M, N278R, N278S, N278T, T278W, N278Y, Q279C, Q279V, Q279Y, T282C, D287C, D287S, Q301G, Q301K, D302A, D302C, D302F, D302G, Q303A, Q303C, Q303D, Q303P, Y306K, Y306N, Y306R, S312C, S312W, S312Y, Q316C, Q316P, Q316S, Q316T, Q316Y, K320C, K320N, K320S, K320T, K320Y, R324C, R324Y, R328M, R328S, D329A, D329G, D329N, D329S, L334A, L334C, L334F, L334M, L334T, L334V, K335D, K335R, K335V, K335W, K336R, D337T, D337V, A338C, A338D, A338G, A338I, A338V, A338W, N339E, K344D, K344F, K344I, K344L, K344P, K344Q, K344V, K345A, K345D, K345E, K345F, K345G, K345H, K345S, K345T, K345V, K345Y, A347D, A374Y, H361A, H361C, H361E, H361G, H361L, H361M, H361T, R363C, R363E, R363K, R363L, R363M, R363Q, R363W, R363Y, N369C, N369D, N369E, N369F, N369M, N369S, N369T, N369V, N369W, N369T, K371T, G372A, G372C, G372D, G372K, G372M, G372N, G372V, G372W, G372Y, D374C, D374F, D374G, D374L, G374M, D374Q, D374S, D374V, D375C, D375E, D375V, D375W, M380N, Y396C, Y396G, Y396K, D397A, D397C, D397E, D397F, D397H, D397I, D397K, D397L, D397M, D397N, D397P, D397Q, D397R, D397S, D397T, D397V, D397Y, A398C, A398D, A398E, A398F, A398I, A398K, A398N, A398P, A398Q, A398R, A398S, A398T, A398V, A398W, A398Y, I399A, I399C, I399D, I399E, I399F, I399Q, I399S, I399T, I399V, I399Y, R402A, R402F, R402G, R402L, R402S, R402W, T441D, T411E, T411F, T411G, T411H, T411K, T411L, T411N, T411Q, T411R, T411S, T411V, S420C, S420G, S420N, S420Q, S420T, S420V, S420Y, R426A, R426F, R426N, R426Q, R426T, R426W, G427C, G427F, G427Y, K428A, T445A, T445C, T445E, T445F, T445G, T445I, T445K, T445L, T445M, T445N, T445P, T445Q, T445R, T445S, T445V, T445Y, Y446K, Y446Q, Y446R, G448A, G448C, G448D, G448E, G448F, N449A, N449C, N449G, N449H, N449K, N449P, N454F, N455C, N455D, N455S, N455W, H460A, H460C, H460D, G469E, G460F, H460G, H460I, H460K, H460L, H460M, H460Q, H460R, H460S, H460W, H460Y, S474C, S474D, S474F, S474G, S474I, S474K, S474L, S474M, S474N, S474P, S474R, S474T, S474V, N475I, N475K, N475L, N475M, N475P, N475Q, N475R, G475S, N475T, N475V, N475W, G475Y, Q490C, Q490L, Q490V, Q490W, Q490Y, L492A, L492D, L492H, L492I, L492N, L492Q, L492T, L492Y, Q496S, Q496W, V497T, K498C, K498E, K498F, K498G, K498I, D521C, D521W, D521W, D521Y, V522A, V522C, V522F, V522G, V522K, V522I, V522M, V522N, V522P, V522Q, V522R, V522S, V522T, V522W, V522Y, K534C, K534D, K534E, K534F, K534G, K534V, R542A, R542D, R542I, R542L, R542N, R542T, R542W, G547A, S548C, S548E, S548F, S548L, S548N, S548Q, S548T, S548W, G554A, G554C, G554D, G554F, G554H, G554L, G554M, G554Q, G554W, L555C, L555E, L555G, L555H, L555K, L555M, L555P, L555Q, K560P, H561I, H561M, H561N, H561Q, H561S, H561V, H561W, D563A, D563I, D563L, D563Q, D563R, D563S, S563T, S563V, D563W, D563Y, D564A, D564C, D564F, D564G, D564K, D564L, D564M, D564N, D564R, D564T, D564V, D564Y, R570A, R570C, R570D, R570E, R570I, R570M, R570Q, R570T, R570V, Y571H, Y571M, Y571N, Y571R, K581A, K581C, K581D, K581E, K581F, K581G, K581M, K581W, N583A, N583C, N583D, N583G, N583V, R586D, R586F, R586N, R586P, R586V, R586W, R586Y, V603C, V603E, V603G, V603H, V603Y, F611A, F611C, F611D, F611K, F611M, F611R, F611W, Q612C, Q612D, Q612G, Q612S, A622E, A622H, Q626E, Q626F, Q626H, T638A, T638D, T638G, T638M, T638Q, T638R, T638S, T638V, T638W, T638Y, S642C, S642E, S642F, S642G, S642H, S642I, S642L, S642M, S642P, S642Q, S642T, S642V, S642W, S642Y, A643E, A643F, A643H, A643K, A643L, A643M, A643N, A643T, A643V, A643Y, R645G, R645K, R645M, R645W, R645Y, R649V, R649N, R649S, Q650C, Q650D, Q650T, Q650V, Q650Y, T660C, T660F, T660N, T660S, T660W, T660Y, P661C, P661D, P661E, P661F, P661H, P661I, P661K, P661L, P661M, P661Q, P661R, P661S, P661T, P661V, P661W, G662A, G662C, G662F, G662I, Q663D, Q663E, Q663G, Q663I, T666C, T666N, R672C, R672D, R672E, R672F, R672G, R672H, R672I, R672K, E672L, R672M, R672N, R672T, R672V, R672W, R673A, R673C, R673E, R673G, R673H, R673I, R673K, R673L, R673M, R673N, R673S, R673V, R674T, R674Y, D680A, D680C, D680E, D680F, D680H, D680I, D680M, D680Q, D680R, D680V, D680W, D680Y, T681G, T681H, T681K, T681L, T681M, T681P, T681Q, T681S, T681V, T681W, T681Y, S683C, S683D, S683E, S683F, S683G, S683I, S683M, S683P, S683Q, S683V, S683W, Q684C, Q684G, Q684N, K685A, K685E, K685G, K685I, K685L, K685M, K685N, K685Q, K685S, K685T, K685V, K685W, K685Y, S692C, S692H, S692I, S692L, S692M, S692W, R702C, R702D, R702F, R702G, R702H, R702I, R702K, R702L, R702N, R702Q, R702S, R702T, R702V, R702W, R795I, and R705V, wherein the substitution consists of no more than a single replacement at each of the positions, and wherein the positions are numbered by correspondence with the amino acid sequence of a reference beta-glucosidase 1 (BGL1) set forth as SEQ ID NO:3. As described in the experimental section, exemplary beta-glucosidase variants have improved cellobiose hydrolysis activity at pH 5 (PI greater than 1).

Also, the present disclosure provides a beta-glucosidase variant comprising a substitution, wherein the substitution comprises one or more of the group consisting of: K022E, K022F, K022H, K022P, K022Q, K022R, N024C, N024Q, L025A, L025D, L025N, Q026C, Q026H, Q026I, Q026K, Q026L, Q026P, Q026R, Q026S, Q026T, Q026W, D027C, K028S, K028V, S033C, S033G, V035C, V035E, V035G, V035H, V035K, V035L, V035N, V035Q, V035R, V035S, V035T, V035Y, G036C, G036D, G036E, G036F, G036I, G036K, G036N, G036R, G036S, G036W, G036Y, K051C, K051D, K051G, K051H, K051H, K051L, K051M, R051N, K051R, K051T, K051V, I052D, I052K, I052M, I052N, I052P, I052Q, I052T, I052V, R091C, R091Q, R091W, E092C, E092K, E092Y, E100A, E100G, E100I, E100M, E100N, E100Q, E100S, E100T, T100Y, Q165C, Q165G, Q165I, Q165K, Q165M, Q165N, Q165S, Q165V, E166D, L167C, L167V, L167V, L167Y, N168A, N168D, N168E, N168G, N168Y, E170F, E170Y, P176F, P176H, P176L, E176R, P176V, P176W, P176Y, D177E, D177F, D177H, D177L, D177M, D177Q, D177R, D177V, D177W, D177Y, D178Y, R179M, R179S, R179T, R179W, Q194L, N196L, N196Y, N208K, T209C, T209D, T209E, T209G, T209H, T209I, T209K, T209L, T209M, D209Q, T209S, T209V, T209Y, E214A, E214D, E214G, E214R, E214S, E214W, D215E, D215H, D215L, D215N, D215S, D215W, Q216A, Q216D, Q216F, Q216G, Q216H, Q216I, Q216K, Q216L, Q216M, Q216N, Q216S, Q216T, Q216W, Q216Y, K224H, K224R, K224V, D225E, D225F, D225G, D225H, D225I, D225L, D225M, D251T, D225V, D225W, D225Y, Q226A, Q226C, Q226D, Q226F, Q226I, Q226L, Q226W, Q226Y, N238A, N238C, N238E, T242C, T242E, T242H, T242Q, T242W, T242Y, N248G, N248W, N248Y, N263C, N263G, N263S, N263T, T264C, N276A, N276C, N276F, N276M, N276Q, S277C, S227W, S277Y, N278C, N278F, N278V, N278W, Q279C, Q279D, Q279K, Q279V, Q279Y, T282C, T282D, T282P, T282S, R284H, R284M, D287C, D287S, Q301K, D302A, D302C, D302E, D302F, D302G, D302L, D302M, D302N, Q303C, Y306K, Y306M, Y306Q, Y306R, S312C, S312K, S312W, S312Y, Q316C, Q316D, Q316G, Q316H, Q316I, Q316K, Q316P, Q316R, Q316S, Q316T, Q816Y, K320C, K320E, K320H, K320L, K320M, K320P, K320Q, K320R, K320S, K320T, T324V, T324Y, R328C, R328E, R328F, R328G, R328I, R328K, R328L, R328M, R328Q, R328S, R328V, R328Y, D329A, D329M, D329S, D329T, D329Y, L334A, L334T, K335N, K335V, D337A, D337C, D337T, D337V, A338C, A338D, A338F, A338G, A338I, A338P, A338V, A338W, K344D, K344F, K344I, K344V, K345A, K345E, K345F, K345G, K345Q, K345S, K345T, K345V, K345W, K345Y, A347Y, H361C, H361G, H361M, R363C, R363E, R363G, R363K, R363Q, R363S, R363T, R363W, R363Y, N369C, N369D, N369E, N369F, N369W, N369Y, K371T, G372A, G372K, G372M, G372W, G372Y, D374C, D374F, D374G, D374I, D374L, D374M, D374Q, D374S, D374T, D374V, D374Y, D375C, D375E, D375H, D375I, D375R, D375V, D375W, M380I, M380N, M380T, M380V, M380Y, W382F, Y396C, Y396D, Y396E, Y396F, Y396G, Y396H, Y396I, Y396K, Y396L, Y396M, Y396N, Y396Q, Y396R, Y396S, Y396V, Y396W, D397A, D397C, D397E, D397H, D397I, D397K, D397M, D397N, D397P, D397Q, D397R, D397S, D397T, D397V, D397Y, A398K, A398Q, A398R, A398W, I399A, I399C, I399D, I399E, D399G, I399Q, I399S, I399T, I399V, I399Y, R402A, R402E, R402G, R402L, R402Q, R402S, R402W, R402Y, V410C, V410F, V410H, V410I, V410R, V410S, V410W, V410Y, T411D, T411E, T411F, T411G, T411H, T411I, T411K, T411Q, T411R, T411S, T411V, T411Y, S420C, S420G, S420N, S420Q, S420T, S420V, S420Y, R426A, R426L, R420T, R426Y, G427C, G427F, G427P, G427V, K428A, T445A, T445G, T445F, T445G, T445M, T445N, T445P, T445V, T445Y, V446K, V446Q, V446R, E447K, E447L, E447S, E447V, E447Y, G448C, G448Y, N449C, N449H, N449K, N454F, N454V, N455C, N455D, N455S, N455V, N455W, H460A, H460C, H460E, H460F, H460G, H460I, H460K, H460L, H460M, H460N, H460Q, H460R, H460S, H460W, H460Y, N473W, S474A, S474C, S474E, S474F, S474K, S474L, S474N, S474P, S474T, N475I, N475M, N475S, N475T, N475W, N475Y, E489D, E489N, Q490C, Q490V, Q490W, Q490Y, L492A, L492D, L492F, L492H, L492I, L492N, L492R, L492T, L492Y, Q496W, K498A, K498E, K498F, K498M, K498V, D521C, V522A, V522C, V522G, V522K, V522L, V522M, V522Q, V522R, V522S, V522T, V522W, V522Y, K534C, K534D, K534E, K534R, K534V, K542A, R542C, R542D, R542E, R542F, R542G, R542H, R542I, R542L, R542M, R542N, R542Q, R542S, R542T, R542V, R542W, R542Y, G547A, G547C, S548T, E553I, E553Y, G554C, G554D, G554F, G554H, G554Q, G554W, L555D, L555E, L555F, L555G, L555H, L555K, L555M, L555P, L555Q, L555T, L555V, L555W, L555Y, H561A, H561C, H561D, H561G, H561M, H561S, H561W, D563A, D563E, D563L, D563M, D563Q, D563S, D563T, D563V, D563W, D563Y, D564A, D564C, D564F, D564K, D564L, D564N, D564Q, D564R, D564T, D564V, D564Y, R570A, R570C, R570D, R570E, R570M, R570Q, R570S, R570T, R570V, Y571N, K581A, K581C, K581D, K581F, K581G, K581I, K581S, K581V, K581W, K581Y, N583A, N583C, N583D, N583E, N583F, N583G, N583H, N583I, N583K, N583L, N583M, N583P, N583R, N583S, N583T, N583V, N583W, N583Y, R586D, R586F, R586G, R586L, R586N, R586P, R586V, R586W, R586Y, S591D, V603C, V603F, V603G, V603G, V603H, V603M, V603N, V603P, V603Q, V603R, V603S, V603T, V603W, V603Y, F611A, F611C, F611K, F611R, F611V, F611W, F611Y, Q612C, Q612D, Q612G, Q612H, Q612S, A622D, A622G, A622H, A622I, A622K, A622L, A622M, A622P, A622S, A622T, A622V, A622Y, Q626G, Q626H, Q626L, Q626T, Q626V, T638A, T638D, T638G, T638M, T638Q, T638R, T638S, T638V, T638W, T638Y, S642C, S642E, S642F, S642H, S642L, S642P, S642Q, S642T, S642W, S642Y, A643H, A643K, A643L, A643Q, A643T, A643V, A643W, A643Y, R645A, R645D, R645F, R645G, R645I, R645K, R645L, R645M, R645T, R645V, R645W, R645Y, R649T, Q650E, Q650G, Q650H, Q650I, Q650K, Q650L, Q650N, Q650R, Q650T, Q650Y, T660D, T660D, T660N, T660S, T660W, T660Y, P661A, P661C, P661D, P661E, P661F, P661G, P661H, P661I, P661K, P661L, P661M, P661Q, P661R, P661S, P661T, P661V, P661W, G662A, G662C, G662F, G662I, Q663C, Q663D, Q663E, Q663F, Q663G, Q663H, Q663I, T666C, T666N, T666R, R672C, R672D, R672E, R672F, R672G, R672H, R672I, R672K, R672L, R672M, R672N, R672T, R672V, R672W, R672Y, R673E, R673G, R673I, R673L, R673M, R673Q, R673S, R674T, R674Y, D675L, D680A, D680C, D680E, D680F, D680H, D680I, D680L, D680M, D680Q, D680V, D680W, D680Y, T681A, T681G, T681H, T681K, T681L, T681M, T681N, T681P, T681Q, T681S, T681V, T681W, S683E, S683F, S683I, S683L, S683M, S683P, S683V, S683W, Q684A, Q684C, Q684G, K685I, K685L, K685M, K685N, K685S, K685S, K685V, K685W, K685Y, S692C, S692H, S692I, S692M, S692T, S692V, S692W, R702C, R702D, R702G, R702L, R702Q, R702S, R702T, R702V, R702W, R705F, R705H, R705I, R705L, R705S, R705T, R705V, and R705W, wherein substitution consists of no more than a single replacement at each of the positions, and wherein the positions are numbered by correspondence with the amino acid sequence of a reference beta-glucosidase 1 (BGL1) set forth as SEQ ID NO:3. As described in the experimental section, exemplary beta-glucosidase variants have improved cellobiose hydrolysis activity at pH 6 (PI greater than 1).

The present disclosure further provides a beta-glucosidase variant comprising a substitution, wherein the substitution comprises one or more of the group consisting of: K022A, K022E, K022F, K022P, N024A, N024C, N024Q, D025D, L025A, L025S, Q026C, Q026D, Q026E, Q026K, Q026S, Q026T, Q026W, D027A, D027L, D027M, D027Q, D027S, S033C, V035C, V035E, V035G, G036D, G036E, G036S, G036Y, S030C, S050L, K051C, K051D, K051H, K051T, I052A, I052D, I052N, I052P, I052V, R091D, R091E, D091F, R091N, E092A, E092C, E100A, E100G, E100M, E100N, E100S, E100Y, L167C, L167W, N168Y, P176A, P176F, P176K, P176R, P176S, P176V, P176W, P176Y, D177E, D177F, D177M, D177N, D177V, D177W, D178A, Q194A, Q194C, N196E, N196L, T209C, T209D, T209E, T209G, T209L, T209S, T209V, T209W, T209Y, E214D, E214V, D215C, D215E, D215N, D215S, Q216A, Q216G, Q216H, Q216I, Q216L, Q216S, Q216W, Q216Y, D225E, D225G, G225H, D225I, D225L, D225T, D225W, D225Y, Q226C, Q226D, Q226F, Q226N, Q226R, Q226S, Q226W, Q226Y, N238A, T242C, T242E, T242H, T242L, T242S, T242W, T242Y, N248C, N248W, N263A, N263C, N263D, N263E, N263G, N263H, N263L, N263Q, N263R, N263S, N263T, N264C, N276A, N276C, N276F, N276K, S277C, S277W, N278F, N278W, Q279C, T282C, T282L, T282P, R284M, D287C, D287K, D302A, D302C, D302E, D302F, D302G, Q303C, Y306C, Y306G, Y306M, Y306Q, Y306V, Q312C, S312D, S312W, S312Y, Q316C, Q316P, Q316S, Q316T, Q316Y, K320C, K320N, R324C, R328S, D329A, D329S, K350D, N336A, N336C, N336H, D337A, D337C, D337K, D337M, D337T, A338C, A338D, A338E, A338F, A338G, A338K, A338L, A338M, A338P, A338V, A338W, A338Y, K344D, K344F, K344G, K344L, K344Q, K344R, K344V, K345A, K345E, K345F, K345S, K345Y, A347Y, H361G, H361G, R363C, R363E, R365C, R363G, E363K, E363M, R363Q, R363T, R363V, R363W, R363Y, N369C, N369D, N369E, N369T, N369W, K371L, K371T, G372A, D374C, D374L, D374M, D374S, D375C, M380T, M380V, G381H, W382F, D397C, D397N, D397R, D397T, D397V, D397Y, A398R, A398W, I399L, I399V, R402A, R402I, V410F, Y410R, V410S, T411E, T411H, T411N, S420C, S420D, S420G, S420N, S420T, S420V, R426A, G427C, G427E, G427F, G427H, G427L, G427Y, T445A, T455C, T445D, T445E, T445F, T445G, T445I, T445M, T445P, T445V, T445Y, V446A, V446C, G448C, G448F, G448H, N449A, N449C, N454F, N455C, N455D, N455W, H460D, H460F, H460G, H460K, H460Q, S474A, S474C, S474E, S474F, S474I, S474M, S474N, S474T, S474V, S474Y, N475S, Q490C, Q490E, Q490G. Q490H, Q490L, Q490V, Q490W, Q490Y, V497T, K498A, K498E, R498M, D521A, D521S, D052W, D521Y, V522C, V522S, V522W, V522Y, K534C, K534E, K534F, K534N, K534V, R542A, R542C, R542D, R542E, R542F, R542G, R542K, R542L, R542M, R542N, R542Q, R542T, R542V, R542W, G547A, S548C, S548E, S548F, S548W, E553N, G554C, G554F, G554Q, G554W, K560H, H561F, H561G, H561H, H561M, H561N, H561S, H561T, H561V, H561W, D563A, D563S, D564A, D564F, D564S, D564T, K581A, K581C, K581D, K581F, K581G, K581H, K581P, K581S, K581T, K581V, K581W, N583A, N583C, N538D, R586D, R586N, R586P, R586V, R586Y, V603A, V603C, V603D, V603E, V603F, V603G, V603H, V603Y, F611A, Q612C, A622D, A622E, A622F, A622G, A622H, A622M, A622N, A622R, A622S, A622T, A622V, Q626E, Q626F, Q626G, Q626H, A626M, T638A, T638G, T638W, S642F, S642L, S642W, A643V, R665G, K649A, K649C, K649S, Q650E, Q650G, Q650H, Q650V, Q650Y, T660W, P661A, P661C, P661D, P661F, P661I, P661K, P661L, P661M, P661Q, P661R, P661S, P661T, P661V, P661W, G662A, G662C, G662D, G662F, Q663A, Q663C, Q663D, Q663E, Q663F, Q663G, Q663H, Q663L, Q663N, Q663R, Q663S, Q663V, T666A, T666C, T666N, R672C, R672K, R672T, R673A, R673C, R673G, R673H, R673I, R673K, R673L, R673M, R673S, R673T, R673V, R673W, R574M, R674T, R674V, D680A, D680C, D680M, D680Q, D680V, D680W, D680Y, T681A, T681G, T681K, T681L, T681M, T681P, T681Q, T681S, T681V, T681W, A682M, S683E, S683M, S683V, S683W, Q684A, Q684C, Q684G, Q684N, K685A, K685E, K685I, K685L, K685M, K685S, K685T, K685W, K685Y, S692C, S692H, S692I, S692L, S692M, S692P, S692V, S692W, R702C, R702G, R702S, R705C, R705I, R705T, and R705V, wherein the substitution consists of no more than a single replacement at each of the positions, and wherein the positions are numbered by correspondence with the amino acid sequence of a reference beta-glucosidase 1 (BGL1) set forth as SEQ ID NO:3. As described in the experimental section, exemplary beta-glucosidase variants have improved cellobiose hydrolysis in presence of ammonia pretreated corncob (PI greater than 1).

The present disclosure further provides a beta-glucosidase variant comprising a substitution, wherein the substitution comprises one or more of the group consisting of: K022A, K022E, K022F, K022G, K022H, K022P, K022Q, K022R, K022S, K022V, K022W, K022Y, N024A, N024C, N024D, N024E, N024F, N024G, N024L, N024P, N024Q, N024R, N024S, N024V, N024Y, L025A, L025D, L025F, L025G, L025I, L025K, L025N, L025Q, L025R, L025S, L025T, L025V, L025W, L025Y, Q026C, Q026D, Q026E, Q026G, Q026H, Q026I, Q026K, Q026L, Q026P, Q026R, Q026S, Q026T, Q026V, Q026W, Q026Y, D027A, D027C, D027E, D027L, D027M, D027Q, D027S, D027T, D027V, K028S, K028V, S033C, S033G, S033T, V035E, V035E, V035R, V035H, V035K, V035L, V035N, V035P, V035Q, V035R, V035S, V035T, V035Y, G036C, G036E, G036F, G036I, G036K, G036N, G036R, G036S, G036W, G036Y, W037V, W037Y, S050A, S050C, S050F, S050G, S050I, S050L, S050M, S050N, S050P, S050R, S050T, S050V, K051A, K051C, K051D, K051E, K051G, K051H, K050I, K050L, K050M, K051N, K051Q, K051R, R051S, K051T, K051V, I052A, I052D, I052K, I052M, I052N, I052P, I052Q, I052T, I052V, R067A, R067C, R067D, R067F, K067G, R067N, R067P, R067Q, R067S, R067W, R091A, R092C, R091D, R091E, R091F, R091G, R091H, R091I, R091K, R091L, R091N, R091Q, R091T, R091V, R091W, R091Y, E092A, E092C, E092D, E092F, E092H, E092I, E092K, E092L, E092N, E092Q, E092R, E092T, E092V, E092Y, R093K, E099A, E099D, E099F, E099I, E099K, E099M, E099N, E099W, E099Y, E100A, E100G, E100I, E100M, E100N, E100Q, E100S, E100T, E100Y, K158H, K158T, E164G, E164S, Q165C, Q165F, Q165G, Q165H, Q165I, Q165K, Q165L, Q165M, Q165N, Q165R, Q165S, Q165T, Q165V, Q165W, Q165Y, E166D, E166K, E166L, E166P, E166Q, E166R, E166T, L167A, L167C, L167D, L167E, L167F, L167G, L167M, L167N, L167Q, L167R, L167S, L167V, L167W, L167Y, N168A, N168D, N168E, N168G, N168H, N168Q, N168R, N168T, N168Y, E170D, E170F, E170Y, P176A, P176D, P176E, P176F, P176G, P176H, P176K, P176L, P176M, P176Q, P176R, P176S, P176T, P176V, P176W, P176Y, D177D, D177F, D177H, D177K, D177L, D177M, D177N, D177Q, D177R, D177V, D177W, D177Y, D178A, D178C, D178K, D178N, D178Q, D178R, D178Y, R179A, R179C, R179G, R179I, R179K, R179M, R179Q, R179S, R179T, R179V, R179W, Q194A, Q194C, Q194E, Q194F, Q194G, Q194H, Q194K, Q194L, Q194M, Q194R, Q194T, Q194W, Q194Y, N196E, N195H, N196L, N196Q, N196R, N196T, S199A, S199G, S199N, S199T, S199V, Y204F, N208K, T209C, T209D, T209E, T209G, T209H, T209I, T209K, T209L, T209M, T209Q, T209R, T209S, T209V, T209W, T209Y, E214A, E214C, E214D, E214G, E214H, E214L, E214M, E214N, E214Q, E214R, E214S, E214T, E214V, E214W, E214Y, D215C, D215E, D215G, D215H, D215L, D215M, D215N, D215Q, D215S, D215W, Q216A, Q216C, Q216D, Q216E, Q216F, Q216G, Q216H, Q216I, Q216K, Q216L, Q216M, Q216N, Q216P, Q216R, Q216S, Q216T, Q216W, Q216Y, K224H, K224R, K224V, D225A, D225C, D225E, D225F, D225G, D225H, D225I, D225L, D225M, D255Q, D225S, D225T, D225V, D225W, D225Y, Q226A, Q226C, Q226D, Q226E, Q226F, Q226H, Q226I, Q226K, Q226L, Q226M, Q226N, Q226R, Q226S, Q226T, Q226V, Q226W, Q226Y, N238A, N238C, N238E, N238G, N238M, N238S, N238T, T242A, T242C, T242E, T242F, T242G, T242H, T242I, T242K, T242L, T242M, T242N, T242Q, T242R, T242S, T242V, T242W, T242Y, N248A, N248C, N248F, N248G, N248T, N248W, N248Y, S249A, S249G, S249M, S249V, N263A, N263C, N263D, N263E, N263F, N263G, N263H, N263L, N263Q, N263R, N263S, N263T, N263V, N263Y, N264C, R265A, R265E, R265I, R265K, R265L, R265M, R265N, R265Q, R265Y, N276A, N276C, N276F, N276K, N276M, N276Q, S277A, S277C, S277D, S277E, S277F, S277G, S277H, S277I, S277M, S277P, S277Q, S277R, S277W, S277Y, N278A, N278C, N278D, N278F, N278G, N278H, N278I, N278L, N278M, N278Q, N278R, N278S, N278T, N278V, N278W, N278Y, Q279C, Q279D, Q279E, Q279G, Q279H, Q279I, Q279K, Q179N, Q279S, Q279T, Q279V, Q279Y, T282C, T262D, T282K, T282L, T282P, T282S, R284H, R284M, D287C, D287E, D287G, D287H, D287I, D287K, D287M, D287N, D287S, Q301A, Q301E, Q301G, Q301K, Q306P, Q301N, Q301R, Q301S, Q301T, Q301V, D302A, D302C, D302E, D302P, D302G, D302K, D302L, D302M, D302N, D302P, D302S, D302T, D302W, D302Y, D303A, Q303C, Q303D, Q303E, Q303H, Q303I, Q303K, Q303L, Q303M, Q303N, Q303P, Q303R, Q303S, Q303T, Q303V, Q303W, Q303Y, Y306C, Y306G, Y306I, Y306K, Y306L, Y306M, Y306N, Y306P, Y306Q, Y306R, Y306S, Y306T, Y306V, S312C, S312D, S312G, S312K, S312N, S312Q, S312R, S312T, S312V, S312W, S312Y, R313A, R313C, R313D, R313G, R313K, R313N, Q316C, Q316D, Q316G, Q316H, Q316I, Q316K, Q316L, Q316M, Q316P, Q316R, Q316S, Q316T, Q316Y, K320C, K320E, K320G, K320H, K320L, K320M, K320N, K320P, K320Q, K320R, K320S, K320T, K320Y, R324C, R324D, R324E, R324F, R324H, R324I, R324K, R324L, R324M, R324Q, R324V, R324W, R324Y, R328C, R328E, R328F, R328G, R328I, R328K, R328L, R328M, R328Q, R328S, R328T, R328V, R328Y, D329A, D329E, D329G, D329H, D329M, D329N, D329Q, D329S, D329T, D329Y, L334A, L334C, L334F, L334M, L334T, L334V, L334W, K335A, K335D, K335F, K335H, K335I, K335L, K335M, K335N, K335R, K335S, K335T, K335V, K335W, N336A, N336C, N336G, N336H, N336L, N336M, N336Q, N336R, N336T, N336V, N336Y, D337A, D337C, D337E, D337G, D337H, D337K, D337L, D337M, D337N, D337R, D337S, D337T, D337V, D337W, D337Y, A338C, A338D, A338E, A338F, A338G, A338H, A338I, A338K, A338L, A338M, A338N, A338P, A338Q, A338R, A338V, A338W, A338Y, N339E, N339G, N339H, N339K, N339L, K344A, K344C, K344E, K344G, K344I, K344L, K344M, K344N, K344P, K344Q, K344R, K344S, K344T, K344V, K345A, K345D, K345E, K345F, K345G, K345H, K345N, K345P, K345Q, K345R, K345S, K345Y, K345V, K345W, K345Y, A347D, A347F, A347H, A347I, A347K, A347L, A347M, A347P, A347Q, A347R, A347S, A347Y, H361A, H361C, H361D, H361E, H361G, H361G, H361M, H361N, H361T, R363A, R363C, R363E, R363G, R363K, R363L, R363M, R363Q, R363S, R363T, R363V, R363W, R363Y, N369C, N369D, N369E, N369F, N369L, N369M, N369S, N369T, N369V, N369W, N369Y, D370E, D370F, D370G, D370S, D370W, D370Y, K371A, K371F, K371G, K371L, K371N, K371Q, K371R, K371S, K371T, K371V, G372A, G372C, G372D, G372E, G372K, G372L, G372M, G372N, G372T, G372V, G372W, G372Y, D374C, D374F, D374G, D374I, D374L, D374M, D374N, D374Q, D374S, D374T, D374V, D374Y, D375A, D375C, D375E, D375H, D375I, D375R, D375V, D375W, M380I, M380L, M380N, M380Q, M380S, M380T, M380V, M380Y, G381H, W382F, Y396A, Y396C, Y396D, Y396E, Y396F, Y396G, Y396H, Y396I, Y396L, Y396M, Y396N, Y396Q, Y396R, Y396S, Y396T, Y396V, Y396W, D397A, D397C, D397E, D397F, D397I, D397K, D397L, D397M, D397N, D397P, D397Q, D397R, D397S, D397T, D397V, D397Y, A398C, A398D, A398E, A398F, A398G, A398H, A398I, A398K, A398L, A398M, A398N, A398P, A398Q, A398R, A398S, A398T, A398V, A398W, A398Y, I399A, I399C, I399D, I399E, I399F, I399G, I399L, I399M, I399Q, I399S, I399T, I399V, I399W, I399Y, R402A, R402C, R402E, R402F, R402G, R402I, R402L, R402Q, R402S, R402W, R402Y, Q402D, Q409G, V410A, V410C, V410F, V410H, V410I, V410L, V410N, V410R, V410S, V410T, V410W, V410Y, T411D, T411E, T411F, T411G, T411H, T411I, T411K, T411L, T411N, T411Q, T411R, T411S, T411V, T411Y, S420C, S420D, S420G, S420G, S420K, S420N, S420Q, S420T, S420V, S420Y, R426A, R426E, R426F, R426I, R426K, R426L, R426N, R426P, R426Q, R426S, R426T, R426W, R426Y, G427C, G427D, G427E, G427F, G427H, G427K, G427L, G427M, G427N, G427P, G427Q, G427R, G427S, G437T, G427V, G427Y, K428A, K428C, K428D, K428E, K428F, K428G, K428H, K428I, K428L, K428M, K428N, K428P, K428Q, K428R, K428S, K428T, K428V, K428W, K428Y, T445A, T445D, T445E, T445T, T445G, T445I, T445K, T445L, T445M, T445N, T445P, T445Q, T445R, T445S, T445V, T445Y, V446A, V446C, V446K, V446Q, V446R, E447K, E447L, E447S, E447V, E447Y, G448A, G448C, G448D, G448E, G448F, G448H, G448N, G448S, G448T, G448Y, N449A, N449C, M449E, N449F, N449G, N449H, N449K, N449M, N449P, N449T, N449V, N454F, N454G, N454K, N454L, N454M, N454R, N454S, N454T, N454V, N455A, N455C, N455D, N455E, N455F, N455G, N455H, N455I, N455L, N455M, N455S, N455T, N455V, N455W, N455Y, H460A, H460C, H460D, H460E, H460F, H460G, H460I, H460K, H460L, H460M, H460N, H460Q, H460R, H460S, H460W, H460Y, Q467A, Q467P, Q467S, N473A, N473C, N473E, N473P, N473G, N473H, N473K, N473L, N473M, N473P, N473Q, N473R, N473S, N473T, N473V, N473W, S474A, S474C, S474D, S474E, S474F, S474G, S474I, S474K, S474L, S474M, S474N, S474P, S474Q, S474R, S474T, S474V, S474Y, N475I, N475K, N475L, N475M, N475P, N475Q, N475R, N475S, N475T, N475V, N475W, N475Y, E489D, E489N, Q490A, Q490C, Q490E, Q490F, Q490G, Q490H, Q490K, Q490L, Q490P, Q490R, Q490S, Q490T, Q490V, Q490W, Q490Y, L492A, L492D, L492F, L492H, L492I, L492M, L492N, L492Q, L492R, L492T, L492W, L492Y, Q496G, Q496S, Q496W, V497A, V497C, V497I, V497M, V497T, K498A, K498C, K498E, K498F, K498G, K498H, K498I, K498L, K498M, K498N, K498Q, K498T, K498V, K498Y, D521A, D521C, D521E, D521F, D521G, D521H, D521I, D521K, D521L, D521M, D521P, D521R, D521S, D521T, D521V, D521W, D521Y, V522A, V522C, V522F, V522G, V522H, V522I, V522K, V522L, V522M, V522N, V522P, V522Q, V522R, V522S, V522T, V522W, V522Y, K534C, K534D, K534E, K534F, K534G, K534N, K534R, K534V, R542A, R542C, R542D, R542E, R542F, R542G, R542H, R542I, R542K, R542L, R542M, R542N, R542P, R542Q, R542S, R542T, R542V, R542W, R542Y, G547A, G547C, G547L, G547P, S548C, S548E, S548F, S548H, S548I, S548L, S548M, S548N, S548Q, S548R, S548T, S548V, S548W, S548Y, E553I, E553N, E553Y, G554A, G554C, G554D, G554F, G554H, G554L, G554M, G554Q, G554V, G554W, L555A, L555C, L555D, L555E, L555F, G555G, G555I, L555K, L555M, L555N, N555P, L555Q, L555T, L555V, L555W, L555Y, K560A, K560E, K560G, K560H, K560P, K560R, K560W, H561A, H561C, H561D, H561E, H561F, H561G, H561I, H561M, H561N, H561Q, H561S, H561V, H561W, D563A, D563C, D563E, D563F, D563I, D563L, D563M, D563Q, D563R, D463S, D563T, D563V, D563W, D563Y, D564A, D564C, D564F, D564G, D564K, D564L, D564M, D564N, D564Q, D564R, D564S, D564T, D564V, D564Y, D564A, R570C, R570D, R570E, R570G, R570H, R570I, R570M, R570Q, R570S, R570T, R570V, Y571H, Y571M, Y571N, Y571R, Y571W, K581A, K581C, K581D, K581E, K581F, K581G, K581H, K581I, K581L, K581M, K581N, K581P, K581R, K581S, K581T, K581V, K581W, K581Y, N583A, N583C, N583D, N583E, N583F, N583G, N583H, N583I, N583K, N583L, N583M, N583P, N583R, R583S, N583T, N583V, N583W, N583Y, R586D, R586E, R586F, R586G, R586H, R586L, R586N, R586P, R586V, R586W, R586Y, S591D, V603A, V603C, V603D, V603E, V603F, V603G, V603H, V603M, V603N, V603P, V603Q, V603R, V603S, V603T, V603W, V603Y, F611A, F611C, F611D, F611K, F611L, F611M, F611N, F611R, F611S, F611V, F611W, F611Y, Q612C, Q612D, Q612F, Q612G, Q612H, Q612I, Q612K, Q612L, Q612M, Q612P, Q612S, Q612W, A622D, A622E, A622F, A622G, A622H, A622I, A922K, A622L, A622M, A622N, A622P, A622R, A622S, A622T, A622V, A622Y, Q626E, Q626F, Q626G, Q626H, Q626L, Q626M, Q626T, Q626V, V627P, T638A, T638D, T638E, T638F, T638G, T638I, T638K, T638L, T638M, T638P, T638Q, T638R, T638S, T638V, T638W, T638Y, S642A, S642C, S642E, S642F, S642G, S642H, S642I, S642K, S642L, S642M, S642N, S642P, S642Q, S642R, S642T, S642V, S642W, S642Y, A643C, A643E, A643F, A643G, A643H, A643K, A643L, A643M, A643N, A643Q, A643R, A643S, A643T, A643V, A643W, A643Y, R645A, R645D, R645F, R645G, R645H, R645I, R645K, R645F, R645M, R645P, R645Q, R645T, R645V, R645W, R645Y, K649A, K649C, K649F, K649I, K649L, K649M, K649N, K649Q, K649S, R649T, K649W, K649Y, Q650A, Q650C, Q650D, Q650E, Q650F, Q650G, Q650H, Q650L, Q650K, Q650L, Q656M, Q650N, Q650R, Q650T, Q650V, Q650Y, T660C, T660D, T660F, T660I, T660N, T660S, T660W, T660Y, P661A, P661C, P661D, P661E, P661F, P661G, P661H, P661I, P661K, P661L, P661M, P661Q, P661R, P661S, P661T, P661V, P661W, G662A, G662C, G662D, G662F, G662H, G662I, G662K, G662N, G662R, G662T, G662W, G662Y, Q663A, Q663C, Q663D, Q663E, Q663F, Q663G, Q663H, Q663I, Q663K, Q663L, Q663M, Q663N, Q663R, Q663S, Q663V, Q663W, T666A, T666C, T666D, T666H, T666K, T666N, T666R, T666W, R672C, R672D, R672E, R672F, R672G, R672H, R672I, R672K, R672L, R672M, R672N, R672T, R672V, R672W, R672Y, R673A, R673C, R673E, R673G, R673H, R673I, R673K, R673L, H673M, R673N, R673Q, R673S, R673T, R673V, R673W, R674L, R674M, R674T, R674V, R674Y, D675C, D675E, D675H, D675L, D675S, D675Y, D680A, D680C, D680E, D680F, D680H, D680I, D680K, D680L, D680M, D680N, D680Q, D680R, D680S, D680V, D680W, D680Y, T681A, T681G, T681H, T661K, T681L, T681M, T681N, T681P, T681Q, T681R, T681S, T681V, T681W, T681Y, A682M, S683A, S683C, S683D, S683E, S683F, S683G, S683I, S683L, S683M, S683P, S683Q, S683R, S683V, S683W, Q684A, Q684C, Q684D, Q684G, Q684N, Q684P, K685A, K685E, K685F, K685G, K685I, K685L, K683M, K685N, K685Q, K685R, K685S, K685T, K685Y, K685W, K685Y, S692C, S692E, S692H, S692I, S692K, S692L, S692M, S692N, S692P, S692Q, S692T, S692V, S692W, R702C, R702D, R702F, R702G, R702H, R702I, R702K, R702L, R702M, R702N, R702Q, R702S, R702T, R702V, R702W, R705C, R705F, R705H, K705I, R705L, R705M, R705P, R705S, R705T, R705V, and R705W, wherein the substitution consists of no more than a single replacement at each of the positions, and wherein the positions are numbered by correspondence with the amino acid sequence of a reference beta-glucosidase 1 (BGL1) set forth as SEQ ID NO:3. As described in the experimental section, exemplary beta-glucosidase variants have improved beta-glucosidase activity (PI great than 1 on each CNPG, PASC, PCS, G2 at pH 5, G2 at pH6, or G2+CC).

In still further embodiments, the present disclosure provides a beta-glucosidase variant of any of the preceding paragraphs of the summary, wherein the variant is isolated. The present disclosure provides a composition comprising the beta-glucosidase variant. In a preferred embodiment the composition is enriched in the beta-glucosidase variant.

In addition, the present disclosure provides an isolated nucleic acid encoding a beta-glucosidase variant of any of the preceding paragraphs of the summary. In a preferred embodiment, the disclosure provides an expression vector comprising the isolated nucleic acid operably linked to a regulatory sequence. In another embodiment, the disclosure provides a host cell comprising the expression vector. The present disclosure further provides a host cell comprising the expression vector. The present disclosure further cell in a culture medium under suitable conditions to produce the beta-glucosidase variant. As such in another embodiment, the disclosure provides a composition comprising the host cell and culture medium. Similarly the disclosure also provides a composition comprising the beta-glucosidase variant in supernatant of the culture medium.

Moreover, the present disclosure provides a method of converting biomass to sugars comprising contacting the biomass with a beta-glucosidase variant of any of the preceding paragraphs of the summary. The present disclosure further provides a method of producing a fuel comprising contacting a biomass composition with a composition comprising a beta-glucosidase variant of any of the preceding paragraphs of the summary, to yield a sugar solution; and culturing the sugar solution with a fermentative microorganism under conditions sufficient to produce a fuel.

BRIEF DESCRIPTION OF THE DRAWING

Figure 1:
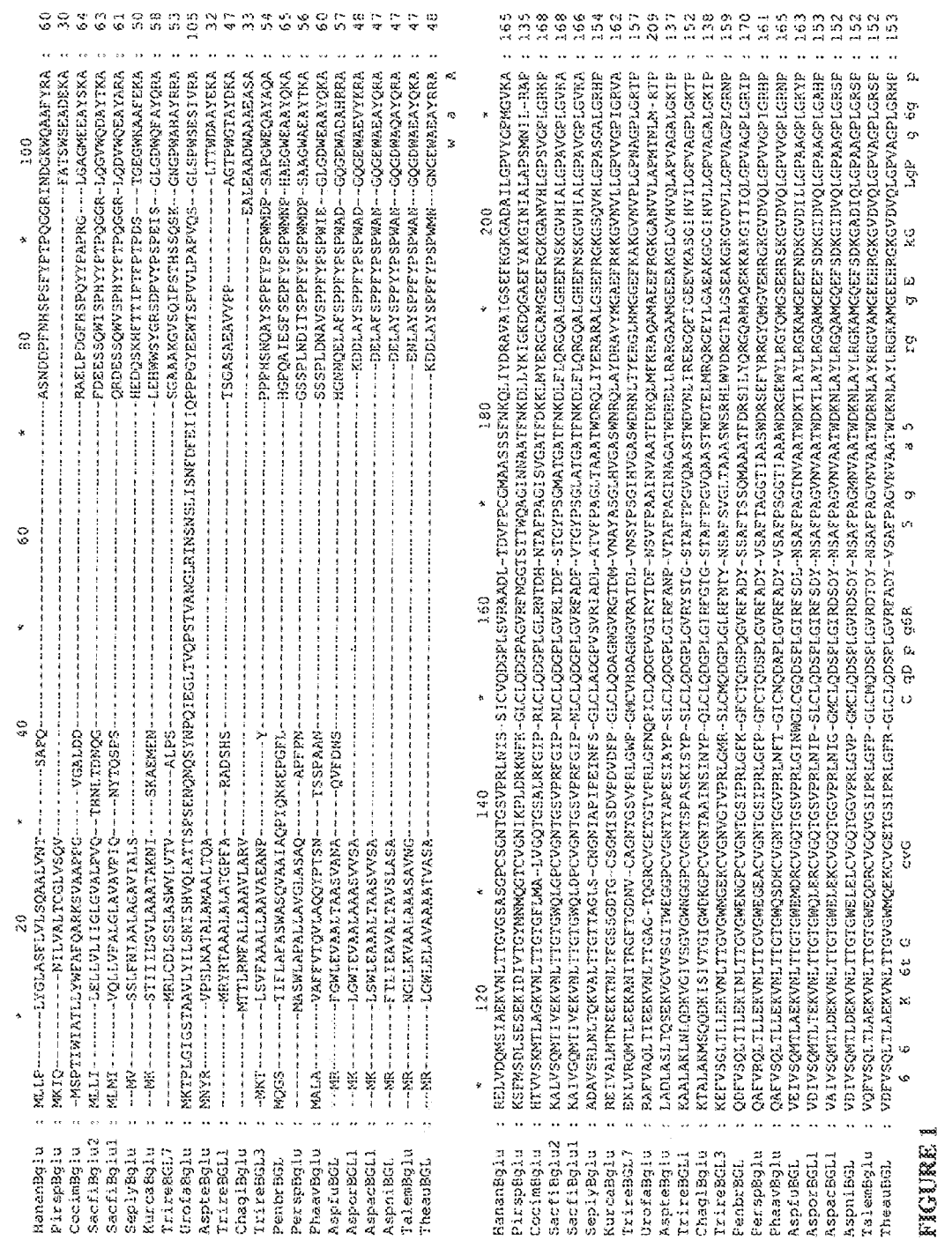
Figure 1:
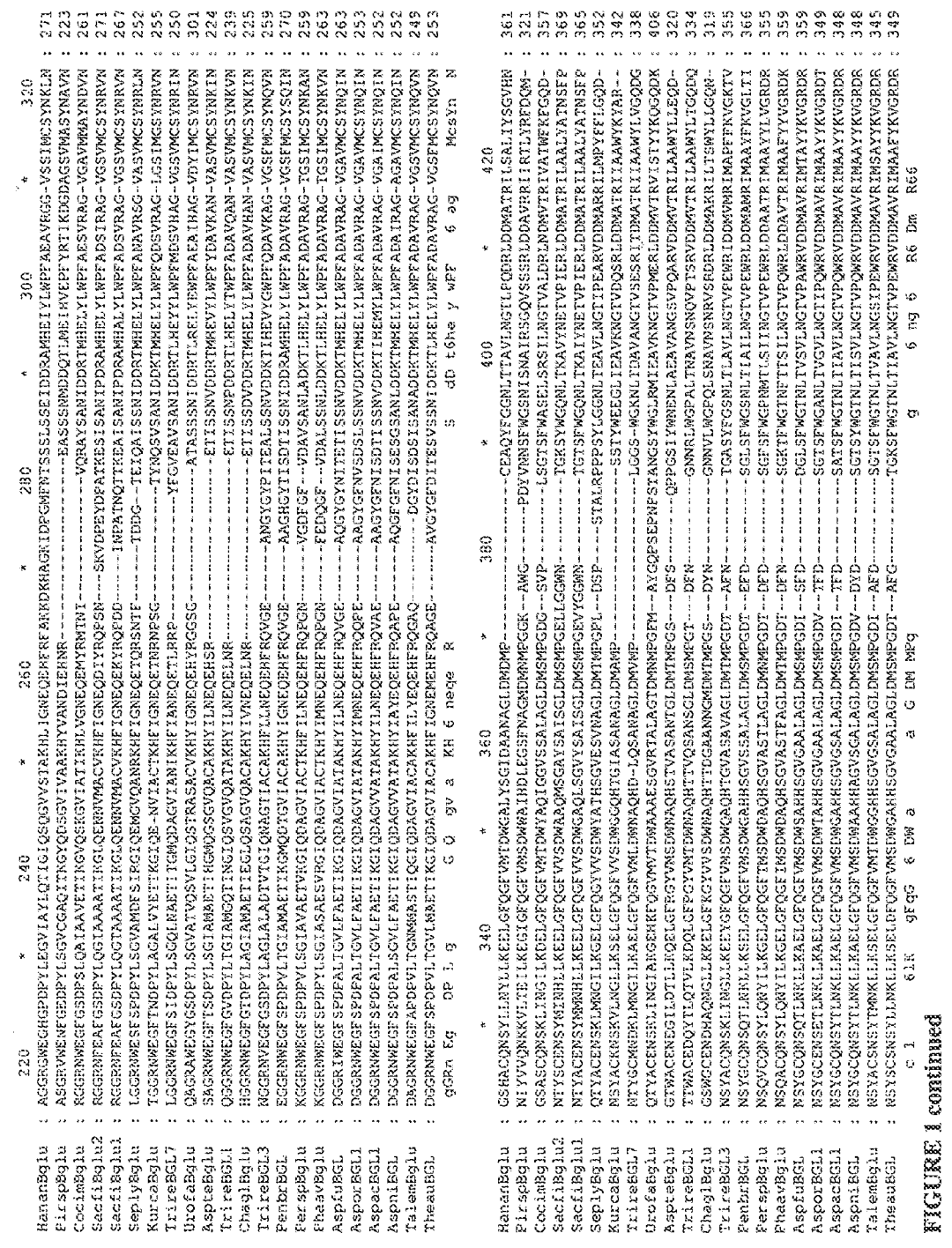
Figure 1:
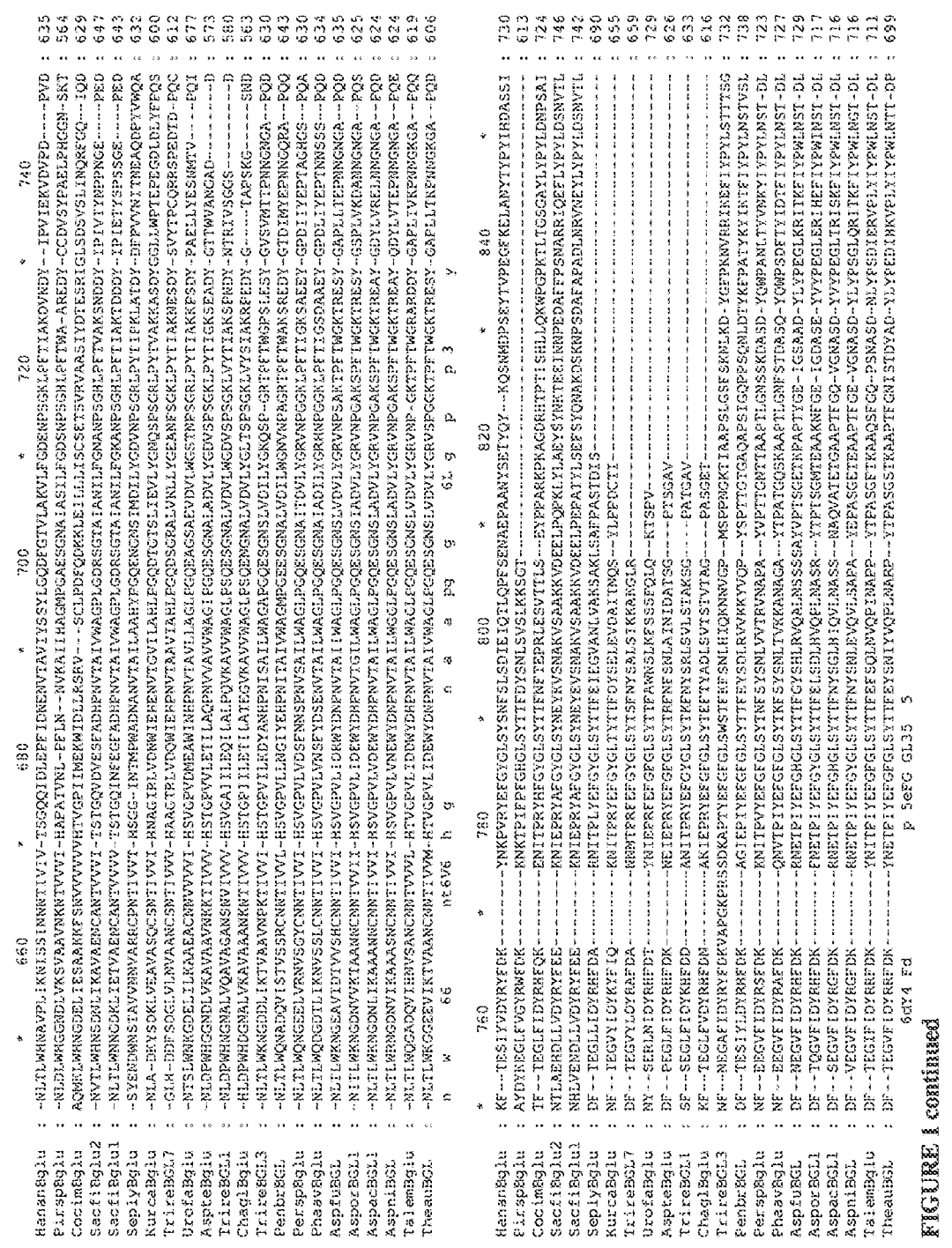
Figure 1:
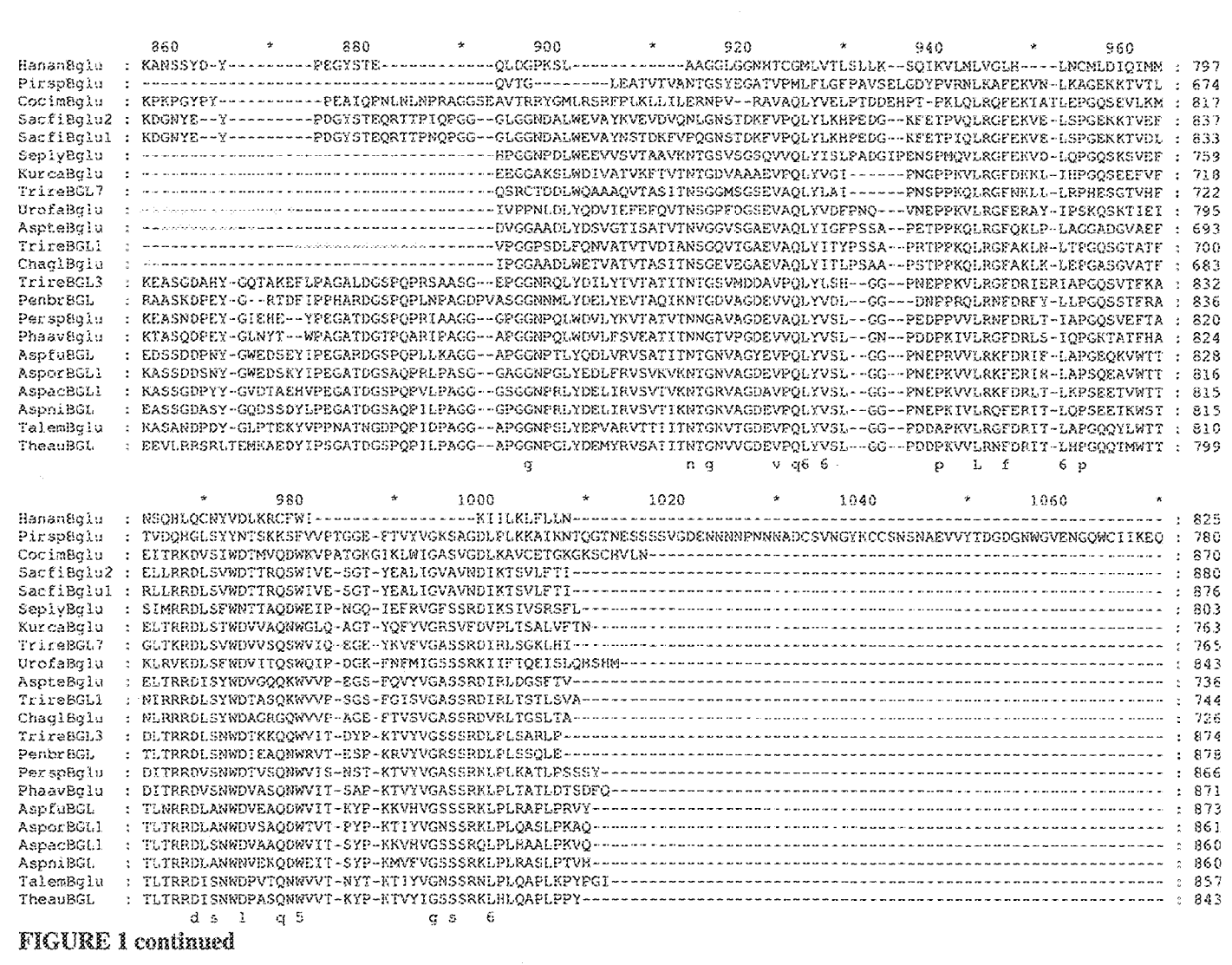
Figure 1:
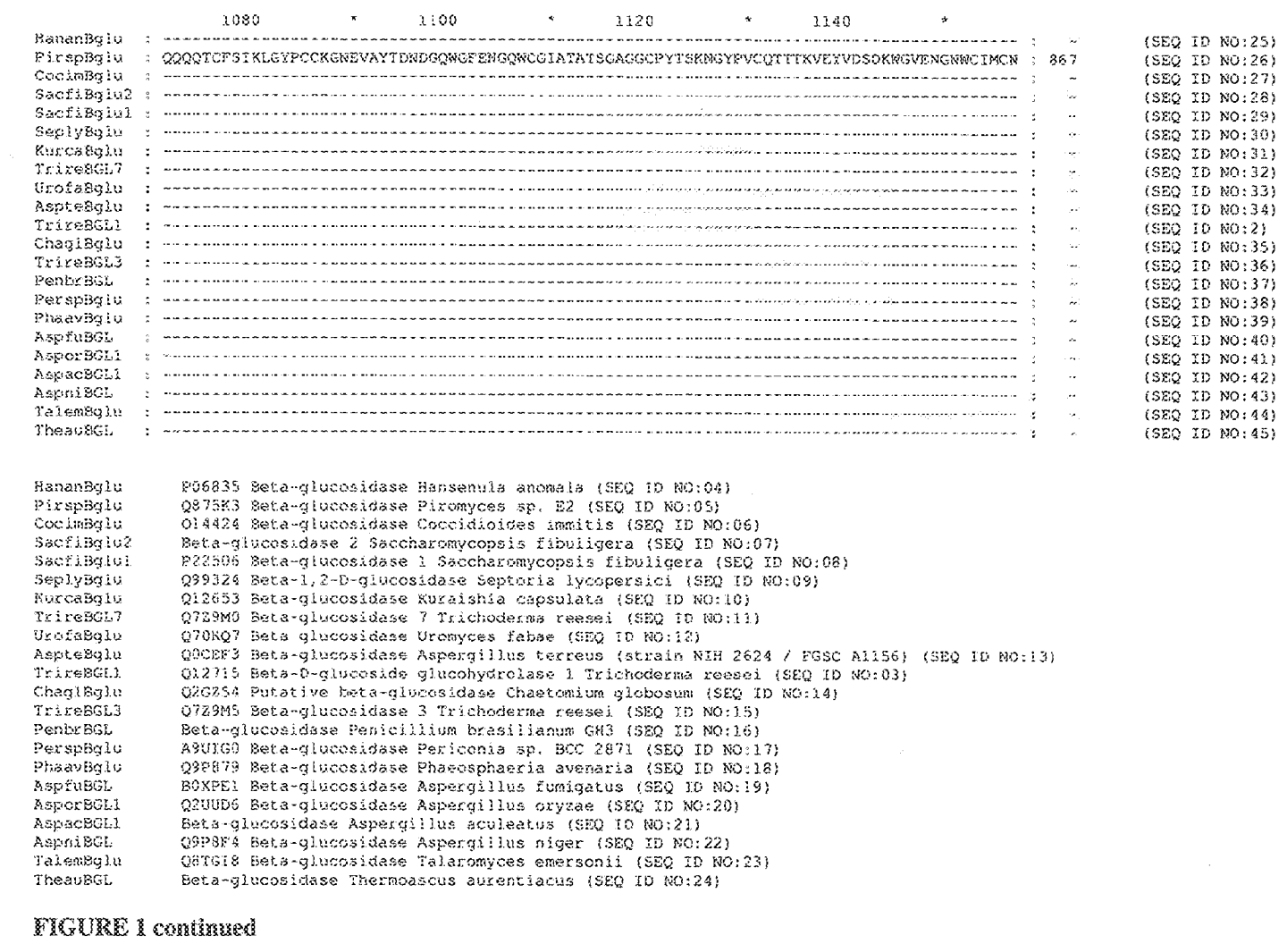

FIG. 1 provides an alignment of the amino acid sequences of the mature form of various cellulases: TrireBGL1, *Hypocrea jecorina* (also known as *Trichoderma reesei*) Q12715 beta-D-glucoside glucohydrolase 1 (SEQ ID NO:3); HananBglu, *Hansenula anomala* P06835 beta-glucosidase (SEQ ID NO:4); PirspBglu, *Piromyces* sp. E2 Q875K3 Beta-glucosidase (SEQ ID NO:5); CocimBglu, *Coccidioides immitis* O14424 Beta-glucosidase (SEQ ID NO:6); SacfiBglu2, *Saccharomycopsis fibuligera* beta-glucosidase 2 (SEQ ID NO:7); SacfiBglu1, *Saccharomycopsis fibuligera* P22506 beta-glucosidase 1 (SEQ ID NO:8); SeplyBglu, *Septoria lycopersici* Q99324 beta-1,2-D-glucosidase (SEQ ID NO:9); KurcaBglu, *Kuraishia capsulata* Q12653 beta-glucosidase (SEQ ID NO:10); TrireBGL7, *Trichoderma reesei* Q7Z9M0 beta-glucosidase 7 (SEQ ID NO:11); UrofaBglu, *Uromyces fabae* Q7OKQ7 beta glucosidase (SEQ ID NO:12); AspteBglu, *Aspergillus terreus* (strain NIH 2624/FGSC A1156) Q0CEF3 beta-glucosidase (SEQ ID NO:13); ChaglBglu, *Chaetomium globosum* Q2GZ54 Putative beta-glucosidase (SEQ ID NO:14); TrireBGL3, *Trichoderma reesei* Q7Z9M5 beta-glucosidase 3 (SEQ ID NO:15); PenbrBGL, *Penicillium brasilianum* GH3 beta-glucosidase (SEQ ID NO:16); PerspBglu, *Periconia* sp. BCC 2871 A9UIG0 beta-glucosidase (SEQ ID NO:17); PhaavBglu, *Phaeosphaeria avenaria* Q9P879 beta-glucosidase (SEQ ID NO:18); AspfuBGL, *Aspergillus fumigatus* B0XPE1 beta-glucosidase (SEQ ID NO:19); AsporBGL1, *Aspergillus oryzae* Q2UUD6 beta-glucosidase (SEQ ID NO:20); AspacBGL1, *Aspergillus aculeatus* beta-glucosidase (SEQ ID NO:21); AspniBGL, *Aspergillus niger* Q9P8F4 beta-glucosidase (SEQ ID NO:22); TalemBglu, *Talaromyces emersonii* Q8TGI8 beta-glucosidase (SEQ ID NO:23); and TheauBGL, *Thermoascus aurentiacus* beta-glucosidase (SEQ ID NO:24). The full length sequences shown of the various cellulases correspond to SEQ ID NOS: 25-34, 2, 35-45, respectively.

DETAILED DESCRIPTION

Figure 2:
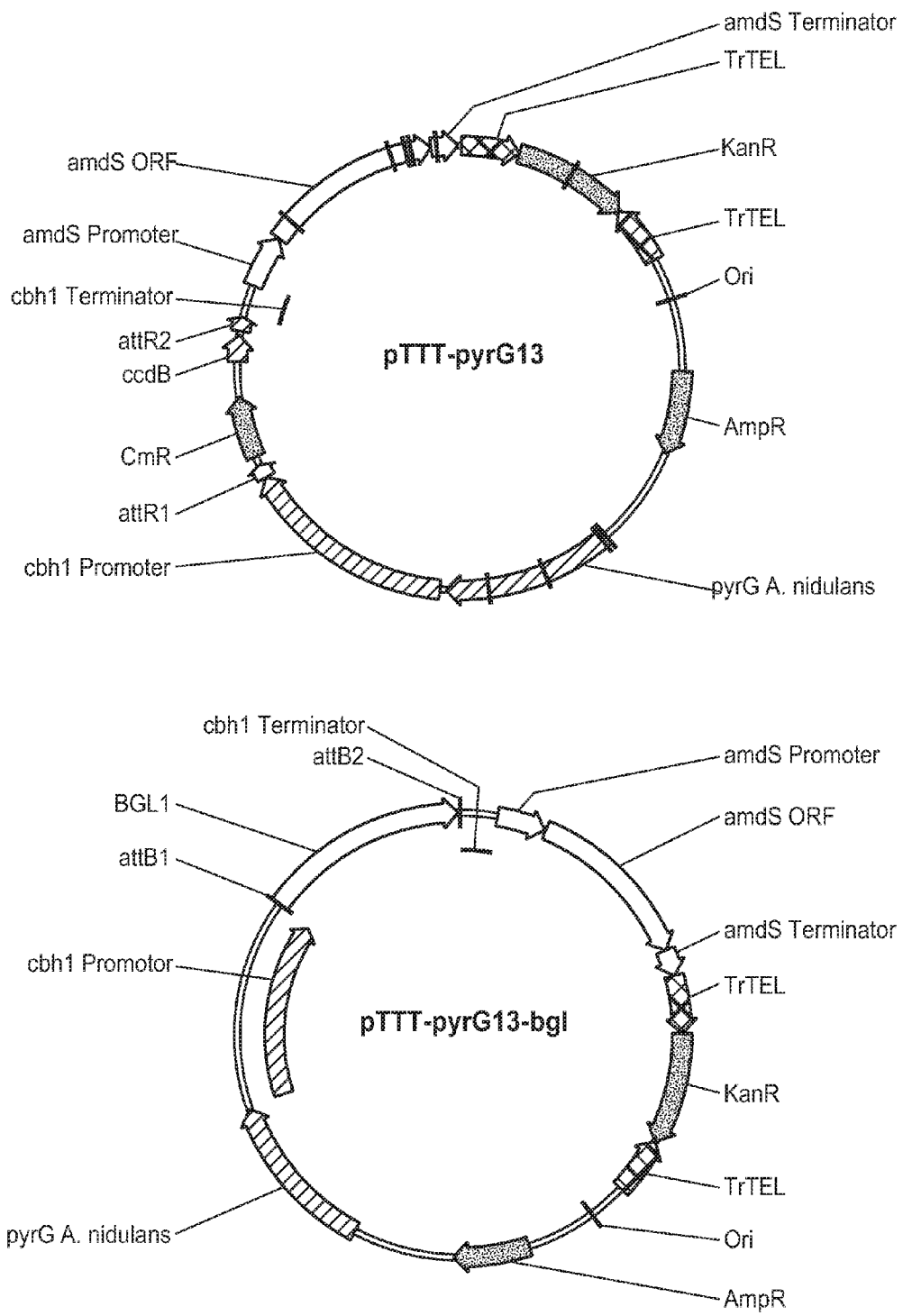
FIG. 2 depicts a destination vector pTTT-pyrG13 and an expression vector pTTT-pyrG-bgl1 as described herein.

The present disclosure is generally directed to enzymes and in particular beta-glucosidase variants. Also described are nucleic acids encoding beta-glucosidase variants, compositions comprising beta-glucosidase variants, methods of using beta-glucosidase variants, and methods of identifying additional useful beta-glucosidase variants It is to be understood that both the foregoing general description and the following detailed description are exemplary and explanatory only and are not restrictive of the compositions and methods described herein. Unless defined otherwise herein, all technical and scientific terms used herein have the same meaning as commonly understood by one of ordinary skill in the art to which this disclosure belongs. In this application, the use of the singular includes the plural unless specifically stated otherwise. The use of "or" means "and/of" unless stated otherwise. Likewise, the terms "comprise" "comprising," "comprises" "include," "including" and "includes" are not intended to be limiting. All patents and publications. Including all amino acid and nucleotide sequences disclosed within such patents and publications, referred to herein are expressly incorporated by reference. The headings provided herein are not limitations of the various aspects or embodiments of the disclosure, which can be had by reference to the specification as a whole. Accordingly, the terms herein are more fully defined by reference to the specification as a whole.

Unless defined otherwise herein, all technical and scientific terms used herein have the same meaning as commonly understood by one of ordinary skill in the art to which this disclosure belongs, Singleton, et al., DICTIONARY OF MICROBIOLOGY AND MOLECULAR BIOLOGY, 2nd Ed., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure. Although, any methods and materials similar or equivalent to those described herein can be used in the practice or testing of the present disclosure, the preferred methods and materials are described. Numeric ranges are inclusive of the numbers defining the range. Unless otherwise indicated, nucleic acids are written left to right in 5' to 3' orientation; amino acid sequences are written left to right in amino to carboxyl orientation, respectively. Practitioners are particularly directed to Sambrook et al., MOLECULAR CLONING: A LABORATORY MANUAL, (Second Edition), Cold Spring Harbor Press, Plainview, N.Y., 1989, and Ausubel F. M. et al., Current Protocols in Molecular Biology, John Wiley & Sons, Mew York, N.Y., 1993, for definitions and terms of the art. It is to be understood that this disclosure is not limited to the particular methodology, protocols, and reagents described, as these may vary.

I. Definitions

The terms below are more fully defined by reference to the specification as a whole.

The term "polypeptide" as used herein refers to a compound made up of a single chain of amino acid residues linked by peptide bonds. The term "protein" as used herein may be synonymous with the term "polypeptide".

"Variant" means a protein which is derived from a precursor protein (e.g., the native protein) by one or more of: addition(s) of one or more amino acids so one or more of the C-terminal end, the N-terminal end, and site(s) within the amino acid sequence; substitution of one or more amino acids at site(s) within the amino acid sequence; and deletion of one or more and acids at one or more of the C-terminal end, the N-terminal end, and sites within the amino acid sequence. The preparation of a beta-glucosidase variant may be performed by any means know in the art. In preferred embodiments, a beta-glucosidase variant is prepared by modifying a DNA sequence which encodes for the native protein, transformation of the modified DNA sequence into a suitable host, and expression of the modified DNA sequence to form the variant enzyme. The beta-glucosidase variant of the disclosure includes peptides comprising altered amino acid sequences in comparison with a precursor enzyme amino acid sequence wherein the variant beta-glucosidase retains the characteristic beta-glucosidase activity of the precursor enzyme but which may have altered properties in some specific aspect. For example, a variant beta-glucosidase may have an altered (increased or decreased) level of expression, activity and stability relative to a reference beta-glucosidase. It is contemplated that the variants according to the present disclosure may be derived from a DNA fragment encoding a cellulase variant wherein the functional activity of the expressed cellulase variant is retained. For example, a DNA fragment encoding a cellulase may further include a DNA sequence or portion thereof encoding a hinge or linker attached to the cellulase DNA sequence at either the 5' or 3' end wherein the functional activity of the encoded cellulase domain is retained. The terms variant, and derivative may used interchangeably herein. Moreover, "variant" as used herein can also refer to any polypeptide that has a different sequence from that of a wild type polypeptide. For example, a BGL1 variant polypeptide can be synthesized de novo, based on the variant sequence and one or more particular substitutions described herein. As such, the beta-glucosidase variants of the disclosure include polypeptides comprising altered amino acid sequences as compared so a wild-type BGL1.

For the purpose of the present disclosure, variants are often referred to by the substitutions at particular amino acid residues. For example, a variant can be referred to by the symbol "X(#)Y", which refers to a variant comprising a substitution at residue number "#," which is an X residue in the wild type polypeptide but is a Y residue at the same position in the variant. Accordingly a BGL1 variant X#Y refers to a BGL1 variant comprising a substitution at position or residue number #, where the X residue of the wild type BGL1 reference enzyme is replaced or substituted with a Y residue. Variants containing multiple substitutions are designated with "1" between different substitutions in the variant.

Equivalent residues which are functionally analogous to a specific residue of *H. jecorina* BGL1 are defined as those amino acids of a beta-glucosidase that may adopt a conformation such that they either alter, modify or contribute to protein structure, substrate binding or catalysis in a manner define and attributed to a specific residue of the *H. jecorina* BGL1. In some preferred embodiments, "equivalent residues" are residues that aligns with the amino acid sequence of *H. jecorina* BGL1.

The terms "nucleic acid molecule" includes RNA, DNA and cDNA molecules. It will be understood that, as a result of the degeneracy of the genetic code, a multitude of nucleotide sequences encoding a given protein such as BGL1 and/or variants thereof may be produced. The present disclosure contemplates every possible variant, nucleotide sequence, encoding variant cellulase such as BGL1, all of which are possible given the degeneracy of the genetic code.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

As used herein, the term the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded(ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a non-native gene (i.e., one that has been introduced into a host) that may be composed of parts of different genes. Including regulatory elements. A chimeric gene construct for transformation of a host cell, is typically composed of a transcriptional regulatory region (promoter) operably linked so a heterologous protein coding sequence, or, in a selectable marker chimeric gene, to a selectable marker gene encoding a protein conferring, for example, antibiotic resistance to transformed cells. A typical chimeric gene of the present disclosure, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors, linkers or primers for PCR are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

In general, nucleic acid molecules which encode the variant cellulase such as BGL1 will hybridize, under moderate to high stringency conditions to the wild type sequence such as provided herein as SEQ ID NO:1. However, in some cases a BGL1-encoding nucleotide sequence is employed that possesses a substantially different codon usage, while the protein encoded by the BG1-encoding nucleotide sequence has the same or substantially the same amino acid sequence as the native protein. For example, the coding sequence may be modified to facilitate faster expression of BGL1 in a particular prokaryotic or eukaryotic expression system, in accordance with the frequency with which a particular codon is utilized by the host (Te'o et al., FEMS Microbiology Letters, 190: 13-19, 2000, for example, describes the optimization of genes for expression in filamentous fungi).

A nucleic acid sequence is considered is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm−5° C. (5° C. below the Tm of the probe); "high stringency" at about 5-10° C. below the Tm; "moderate" or "intermediate stringency" at about 10-20° C. below the Tm of the probe; and "low stringency" at about 20-25° C. below the Tm of the probe. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel et al., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein or that the cell is derived from a cell so modified. Thus, for example, recombinant cells can express genes that are not found within the native (non-recombinant) form of the cell or express native genes that are otherwise over expressed, under expressed or not expressed at all.

As used herein, the term "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" In the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA) converted into an autonomous replicon, or transiently expressed (for example, transacted mRNA).

It follows that the term "BGL1 expression" refers to transcription and translation of the bgl1 gene or variants thereof, the products of which include precursor RNA, mRNA, polypeptide, post-translationally processed polypeptides, and derivatives thereof, including BGL1 from related species such as *Trichoderma koningii*, *Hypocrea jecorina* (also known as *Trichoderma longibrachiatum*, *Trichoderma reesei* or *Trichoderma viride*) and *Hypocrea schweinitzii*. By way of example, assays for BGL1 expression include Western blot and HPLC for BGL1 protein, Northern blot analysis and reverse transcriptase polymerase chain reaction (RT-PCR) assays for bgl1 mRNA.

The term "alternative splicing" refers to the process whereby multiple polypeptide isoforms are generated front a single gene, and involves the splicing together of nonconsecutive exons during the processing of some, but not all, transcripts of the gene. Thus a particular exon may be connected to any one of several alternative exons to form messenger RNAs. The alternatively-spliced mRNAs produce polypeptides ("splice variants") in which some parts are common while other parts are different.

The term "signal sequence" refers to a sequence of amino acids at the N-terminal portion of a protein that facilitates the secretion of the mature form of the protein outside the cell. The mature form of the extracellular protein lacks the signal sequence that is cleaved off during the secretion process.

Host cells for use in the present disclosure can be prokaryotic cells, such as *E. coli*, or eukaryotic cells such as yeast, plant, insect, amphibian, or mammalian cells.

The terms "filamentous fungi" means any and all filamentous fungi recognized by those of skill in the art. A preferred fungus is selected, from the group consisting of *Aspergillus, Trichoderma, Fusarium, Chrysoporium, Penicillium, Humicola, Neurospora*, or alternative sexual forms thereof such as *Emericella, Hypocrea*. It has now been demonstrated that the asexual industrial fungus *Trichoderma reesei* is a clonal derivative of the ascomycete *Hypocrea jecorina* (See, Kuhls et al., PNAS, 93:7755-7760, 1996).

The term "cellooligosaccharide" refers to oligosaccharide groups containing from 2-8 glucose units and having beta-1,4 linkages, e.g., cellobiose.

The "cellulase," "cellulolytic enzymes" or "cellulase enzymes" refer to a category of enzymes capable of hydrolyzing cellulose polymers to shorter cellooligosaccharide oligomers, cellobiase and/or glucose. Numerous examples of cellulase, such as exoglucanases, exo-cellobiohydrolases, endoglucanases, and glucosidases have been obtained from cellulolytic organisms, particularly including fungi, plants and bacteria. The enzymes made by these microbes are mixtures of proteins with three types of actions useful in the conversion of cellulose to glucose: endoglucanases (EG), cellobiohydrolases (CBH), and beta-glucosidase. These three different types of cellulase enzymes act synergistically to convert cellulose and its derivatives to glucose.

The term "beta-glucosidase activity" as used herein refers to a polypeptide capable of catalyzing the hydrolysis of β-D-glucoside substrates, such as cellobiose, laminaribiose, or para-nitrophenol-β-D-glucose, resulting in the release of beta-D-glucose. For instance, beta-glucosidase and active variants thereof are capable of releasing a glucose monomer from cellooligosaccharides (e.g., cellobiose, cellotriose, and cellotetraose). Beta-glucosidase activity can be detected by the hydrolysis of synthetic glycoside substrates including but not limited to para-nitrophenyl-beta-D-glucopyranoside to produce glucose and para-nitrophenol, or by the hydrolysis of cellobiose to produce two glucose molecules. For instance, beta-glucosidase activity can be determined by measuring either a cellobiase activity in the presence of ammonia pretreated corncob (CC), or by a CC hydrolysis activity.

Many microbes make enzymes that hydrolyze cellulose, including the wood rotting fungus *Trichoderma*, and the compost bacteria *Thermomonospora*, *Bacillus*, and *Cellulomonus; Streptomyces*; and the fungi *Humicola, Aspergillus, Chrysosporium*, and *Fusarium*.

The term "cellulose binding domain" as used herein refers to portion of the amino acid sequence of a cellulase or a region of the enzyme that is involved in the cellulose binding activity of a cellulase or derivative thereof. Cellulose binding domains generally function by non-covalently binding the cellulase to cellulose, a cellulose derivative or other polysaccharide equivalent thereof. Cellulose binding domains permit or facilitate hydrolysis of cellulose fibers by the structurally distinct catalytic core region, and typically function independent of the catalytic core. Thus, a cellulose binding domain will not possess the significant hydrolytic activity attributable to a catalytic core. In other words, a cellulose binding domain, is a structural element of the cellulase enzyme protein tertiary structure that is distinct from the structural element which possesses catalytic activity. Cellulose binding domain and cellulose binding module may be used interchangeably herein.

As used herein, the term "surfactant" refers to any compound generally recognized in the art as having surface active qualities. Thus, for example, surfactants comprise anionic, cationic and nonionic surfactants such as those commonly found in detergents. Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like.

As used herein, the term "cellulose containing fabric" refers to any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell).

As used herein, the term "cotton-containing fabric" refers to sewn or unsewn fabrics, yarns or fibers made of pure cotton or cotton blends including cotton woven fabrics, cotton knits, cotton denims, cotton yarns, raw cotton and the like.

As used herein, the term "stonewashing composition" refers to a formulation for use in stonewashing cellulose containing fabrics. Stonewashing compositions are used to modify cellulose containing fabrics prior to sale, i.e., during the manufacturing process. In contrast, detergent compositions are intended for the cleaning of soiled garments and are not used during the manufacturing process.

As used herein, the term "detergent composition" refers to a mixture which is intended for use in a wash medium for the laundering of soiled cellulose containing fabrics. In the context of the present disclosure, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers.

As used herein, the term "decrease or elimination in expression of the bgl1 gene" means that either that the bgl1 gene has been deleted from the genome and therefore cannot be expressed by the recombinant host microorganism; or that the bgl1 gene or transcript has been modified such that a functional BGL1 enzyme is not produced by the host microorganism or at levels that are significantly less than the unmodified bgl1 gene or transcript.

The term "variant bgl1 gene" means that the nucleic acid sequence of the bgl1 gene from *H. jecorina* been altered by removing from, adding to, and/or manipulating the coding sequence.

As used herein, the terms "active" and "biologically active" refer to a biological activity associated with a particular protein and are used interchangeably herein. For example, the enzymatic activity associated with a protease is proteolysis and, thus, an active protease has proteolytic activity. It follows that the biological activity of a given protein refers to any biological activity typically attributed to that protein by those of skill in the art.

As used herein, the term "enriched" means that the beta-glucosidase such as BGL1 is found in a concentration that is greater relative to the BGL1 concentration found in a wild-type, or naturally occurring, fungal cellulase composition. The terms enriched elevated and enhanced may be used interchangeably herein.

A wild type fungal cellulase composition is one produced by a naturally occurring fungal source and which comprises one or more BGL, CBH and EG components wherein each of these components is found at the ratio produced by the fungal source. Thus, as enriched BGL1 composition would have BGL1 at an altered ratio wherein the ratio of BGL1 to other cellulase components (i.e., EGs, CBHs and other endoglucanases) is elevated. This ratio may be increased by either increasing BGL1 or decreasing (or eliminating) at least one other component by any means known in the art.

The terms "isolated" or "purified" as used herein refers to a nucleic acid or amino acid that is removed from at least one component with which it is naturally associated. For the purpose of this application, "isolated" refers to nucleic acids or amino acids that are not parted of a library (e.g., screening library).

Thus, to illustrate, a naturally occurring cellulase system may be purified into substantially pure components by recognized separation techniques well published in the literature, including ion exchange chromatography at a suitable pH, affinity chromatography, size exclusion and the like. For example, in ion exchange chromatography (usually anion exchange chromatography), it is possible to separate the cellulase components by eluting with a pH gradient, or a salt gradient, or both a pH and a salt gradient. The purified BGL1 may then be added to the enzymatic solution resulting in an enriched BGL1 solution. It is also possible to elevate the amount of BGL1 produced by a microbe using molecular genetics methods to overexpress the gene encoding BGL1, possibly in conjunction with deletion of one or more genes encoding other cellulases.

Fungal cellulases may contain more than one beta-glucosidase component. The different components generally have different at isoelectric points that allow for their separation via ion exchange chromatography and the like. Either a single BGL1 component or a combination of BGL1 components may be employed in an enzymatic, solution.

When employed in enzymatic solutions, the variant BGL1 component is generally added its an amount sufficient to allow the highest rate of release of soluble sugars from the biomass. The amount of variant BGL1 component added depends upon the type of biomass to be saccharified, which can be readily determined by the skilled artisan. The weight percent of total protein of the variant BGL1 component present in the composition is from preferably between 0.1 and 1.00 with illustrative examples being about 0.1, preferably about 0.5, 1, preferably about 5, preferably about 10, preferably about 1.5, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 3 to about 50 weight percent, front about 10 about 20 weight percent, front about 10 to about 25 weight percent, from about 10 to about 30 weight percent, from about 100 about 35 weight percent, from about 10 to about 40 weight percent, from about 10 to about 45 weight percent, front about 10 to about 50 weight percent, from about 15 to about 60 weight percent, from about 15 to about 65 weight percent, from about 15 to about 70 weight percent, from about 15 to about 75 weight percent, from about 15 to about 80 weight percent, from about 15 so about 85 weight, percent, from about 15 to about 95 weight percent. However, when employed, the weight percent of the variant BGL1 component relative to any (EG or CBH type) enzyme components present in the cellulase composition is from preferably about 1, preferably about 5, preferably about 10, preferably about 15, or preferably about 20 weight, percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, bran about 5 to about 45 weight percent, from about 5 to about 50 weight percent, from about 10 to about 20 weight percent, from about 10 to about 25 weight percent, from about 10 to about 30 weight percent, from about 10 to about 35 weight percent, front about 10 to about 40 weight percent, from about 10 to about 45 weight percent, from about 10 to about 50 weight percent, from about 15 to about 20 weight percent, front about 15 to about 25 weight percent, from about 15 to about 30 weight percent, from about 15 to about 35 weight percent, from about 15 to about 40 weight percent, from about 15 to about 45 weight percent, from about 15 to about 50 weight percent.

As part of a composition, the weight percent (of total protein content) of the variant BGL1 component from preferably between 0.1 and 100, with illustrative examples being about 0.1 preferably about 0.5, 1 preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight, percent, from about 5 to about 25 weight, percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 60 weight percent, from about 15 to about 65 weight percent, from about 15 to about 70 weight percent, from about 15 to about 75 weight percent, from about 15 to about 80 weight percent, from about 15 to about 85 weight percent, from about 15 to about 95 weight percent. However, when employed, the weight percent of the variant BGL1 component relative to any (EG or CBH type) enzyme components present in the cellulase composition is from preferably about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 20 weight percent, from about 15 to about 25 weight percent, from about 15 to about 30 weight percent, from about 15 to about 35 weight percent, from about 15 to about 40 weight percent, from about 15 to about 45 weight percent, from about 15 to about 50 weight percent.

II. BGL1 Variants

The invention provides, inter alia, *H. jecorina* beta-glucosidase 1 (BGL1) variants that have various improved activities over wild type BGL1. Exemplary improved activities include, but are not limited to, (a) predicated corn stover (PCS) hydrolysis activity, (b) cellobiase activity, (c) protein expression, (d) beta-glucosidase activity as measured by either a cellobiase activity in the presence of ammonia preheated corncob (CC), or by a CC hydrolysis activity under the conditions described herein, (e) thermostability 66 degrees Celsius, (f) phosphoric acid swollen cellulose (PASC) hydrolysis activity, and (g) hydrolytic activity in the presence of glucose.

In some aspects, the BGL1 variant has a single substitution. In other aspects, the BGL1 variant has two or more substitutions. In other aspects, the BGL1 variant has 2, 3, 4, 5, 6, 7, 8, 9, or 10 or more substitutions. In any of these aspects, the BGL1 variant can have different activities and combinations of activities.

In some aspects, BGL1 variants with a single substitution have at least two improved activities (including two activities) over wild type BGL1, such as (a) pre-treated corn stover (PCS) hydrolysis activity, (b) cellobiase activity, (c) protein expression, (d) beta-glucosidase activity as measured by either a cellobiase activity in the presence of ammonia pretreated corncob (CC), or by a CC hydrolysis activity as described herein, (e) thermostability, (f) phosphoric acid swollen cellulose (PASC) hydrolysis activity, and (g) hydrolytic activity in the presence of glucose.

In some aspects, BGL1 variants with a single substitution have at least three improved activities over wild type BGL1 at least four improved activities over wild type BGL1, at least five improved activities over wild type BGL1, at least six improved activities over wild type BGL1 or at least seven improved activities over wild type BGL1.

In other aspects, BGL1 variants comprising two or more substitutions a have at least two improved activities (including two activities) over wild type BGL1, such as (a) pre-treated corn stover (PCS) hydrolysis activity, (b) cellobiase activity, (c) protein expression, (d) beta-glucosidase activity as measured by either a cellobiase activity in the presence of ammonia pretreated corncob (CC), or by a CC hydrolysis activity in accordance with the method described herein, (e) thermostability at 66 degrees Celsius, (f) phosphoric acid swollen cellulose (PASC) hydrolysis activity, and (g) hydrolytic activity is the presence of glucose.

In other aspects, BGL1 variants with a combination of substitutions have at least three improved activities over wild type BGL1, at least four improved activities over wild type BGL1 at least five improved activities over wild type BGL1, at least six improved activities over wild type BGL1, or at least seven improved activities over wild type BGL1.

Accordingly, in one aspect, the invention provides beta-glucosidase 1 (BGL1) variants having at least two improved activities over wild type BGL1 selected from the group consisting of: (a) pre-treated corn stover (PCS) hydrolysis activity, (b) cellobiase activity, (c) protein expression, (d) beta-glucosidase activity as measured by either a cellobiase activity in the presence of ammonia pretreated corncob (CC) or by a CC hydrolysis activity, (e) thermostability, (f) phosphoric acid swollen cellulose (PASC) hydrolysis activity, and (g) hydrolytic activity in the presence of glucose, wherein the BGL1 variant is any variant as shown in Tables 4-8, 3-2, 4-2 and 4-3.

Some BGL1 variants (e.g., variants comprising L266A, I567E, S283F, S283P, T258E, T258I, T258K, T258Q, P536T, P536W, I532Y, Y530T, P607D, Q406M, Q406S, V602T, G300M, A630S, A630T, T180H, T180M, A450M, I444E, I444F, I444N, I444W, I444Y, V500Q, A333I, S482P, A667V, A485L, A485W, Y678R, V603G, L266C, I567F, S624P, P607L, G606I, G606K, G606L, G606M, G606Q, G606V, G605R, I444E, A633V, A655W, Y678H, V522Y, G554F, L266N, F556L, S500I, S550T, S550V, T258L, P536I, P536V, F329R, S624G, S624N, S624Q, S242T, A601M, A630V, N463S, A450F, A450T, A450V, A450W, I486V, S482I, Y678I, G427F, D564T, Q684C, Q684G, Y530S, Q684N, A565G, A270C, T258D, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q223Y, N263G, N263S, N278F, A312Y, G316T, K345E, G427C, P661F, P661L, P661Q, T666C, S683W, F260D, F260G, F260Q, P607G, N400S, F260W, Y530F, Q406D, G605C, N263T, P607I, A450P, T242H, A630Y, P536C, A630Q, D215S, G372A, G547A, F611A, G662C, G662F, F260L, L293F, A633C, S312C, or N455D) can have the combination of improved (b) and (d) activities over wild type BGL1.

Some BGL1 variants (e.g., variants comprising P607H, T011E, T011Y, N146E, I567V, N566G, A630K, Y639K, Q245N, K320Y, A347Y, P536Q, N369E, N369W, N369Y, N146A, N146P, P607K, N369T, A655N, I167K, F260T, P607S, F260D, F260G, F260Q, P607G, N400S, P607F, P607I, A450P, T242H, T568E, A630Y, A655D, F602E, T568K, P536C, A630Q, G215S, G372A, G547A, F611A, G622C, G662F, F260L, or L293F) can have improved (b) and (e) and activities over wild typo BGL1.

Some BGL1 variants (e.g., variants comprising N261C, T258C, F392Q, S624E, P607C, P604M, A377Q, N461A, N461F, N461P, T436A, T436C, T436F, T436I, T436M, T436Q, T436Y, Q220G, A655L, T646H, Y678F, A468F, A177M, P661E, L266N, F556L, S550I, S550T, S550V, T258L, P536I, P536V, F392R, S624G, S624N, S624Q, S624T, A601M, A630V, N463S, A450F, A450T, A450V, A450W, I486V, S482I, Y679I, G427F, G564T, Q634C, Q684G, G566H, F556W, P604Y, L293V, A630G, N461C, G463T, D457C, Q220M, T221A, T221G, T221I, A655R, A468F, A468S, Q216I, D564V, P536Q, G369E, G369W, N369Y, T436E, A565G, A270C, T258S, P536D, P536E, S642F, S624F, S624I, S624V, A601C, A602Y, S308H, A630C, A639D, N463K, N463R, A450E, S482A, A667F, A667L, A667R, A667Y, A485T, V466S, Y678A, Y678C, Y678Q, A468C, Q226W, Q226Y, N263C, G263S, N278F, S312Y, Q316T, K345E, G427C, P661F, P661F, P661Q, T666C, S683W, F260W, Y530F, A461V, I671C, K206A, A450P, T242H, E170F, S507G, F260E, T568K, P536C, A630Q, D215S, G372A, G547A, F611A, G662C, G662F, L293F, A663C, S312C, or N455D) can have improved (b) and (f) activities over wild type BGL1.

Some BGL1 variants (e.g., variants comprising I567Q, A565F, A565K, A565Q, A565V, F556E, F260I, P607E, G605R, G300C, A377C, A377D, S308C, N146H, N146S, A655C, A655G, P176L, T209I, L266C, I567F, S624P, P607L, G606I, G606K, G606L, G606M, G606Q, G606V, G605E, I444V, A633V, A655W, Y678H, V522Y, G554F, N566H, P556V, P604Y, L293V, A630G, N461C, N463T, D457C, Q220M, T221A, T221G, T221I, A655R, A468F, A468S, Q216I, G564V, A565C, A655N, I671K, F260T, P607S, Y639V, A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263S, N233S, N278F, S312Y, Q316T, K345E, G427C, P661F, P661L, P661Q, T666C, S363W, F260D, F260G, F260Q, P607G, N400S, P607F, Q406D, G605C, N263T, N461I, I671C, K206A, T568E, E170F, F260E, T568K, P536C, A630Q, D215S, G372A, G547A, F611A, G662C, G662F, F260L, A633C, S312C, or N455D) can have improved (a) and (b) activities over wild type BGL1.

Some BGL1 variants (e.g., variants comprising I567K, I167R, A565E, A565S, A565Y, F392Y, Q406H, Q406T, P604C, N038F, T568A, N461G, Y639L, Y639M, T243A, T243C, Q245H, Q245M, Q245T, T646A, T646C, I671F, I671L, I567V, N566G, A630K, Y639K, Q245N, K320Y, A347Y, A565C, Y639G, Y530N, N461V, I671C, K206A, T568E, A630Y, A655D, S507G, F260E, T568, or F260L) can have improved (b) and (c) activities over wild type BGL1.

Some BGL1 variants (e.g., variant comprising I567S, G606E, G606H, G606N, G606S, L293A, S308R, I444C, M201D, R542N, L266C, I567F, S624P, P607L, G606I, G606K, G606L, G606M, G606Q, G606V, G605E, I444V, A633V, A655W, Y678H, V522Y, G554F, N566F, L293M, Q220P, S692L, A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263C, N263S, N278F, S312Y, Q316T, K345E, G427C, P661F, P661L, P661Q, T666C, S683W, F260D, F260G, P260Q, P607G, N400S, Q406D, G605C, N263T, S308E, A338D, P536C, A630Q, D215S, G372A, G547A, F611A, A662C, G662F, F260L, A633C, S312C, or N455D) can have improved (a) and (d) activities over wild type BGL1.

Some BGL1 variants (e.g., variants comprising L266F, I567Y, A270R, S384C, A630W, E128R, N146M, N146V, N146W, L181F, V043C, Y639P, S507F, Q245P, G662C, A630H, V466T, N146A, N146Q, P607K, N369T, S384F, L181M, V043A, V043G, V043N, Q060D, A655Y, T242S, S474D, P607F, A630Y, S308E, A655D, or L293F) can have improved (e) and (g) activities over wild type BGL1.

Some BGL1 variants (e.g., variants comprising N261E, N261K, N400A, V602K, L293I, N461S, D457A, V043Q, Q303N, K320S, G662D, F260A, S474R, I567V, N566G, A630K, Y639K, Q245N, K320Y, A347Y, A601D, S384E, L181M, V043A, Y043G, V043N, Q060D, A655Y, T242S, S474D, D564T, T568E, A655D, A338D, F260F, T568K, or F260L) can have improved (c) and (e) activities over wild type BGL1.

BGL1 variants (e.g., variants comprising N566P, N566P, N566W, A270K, A270N, F556H, F556K, P604N, N461D, N463E, K206G, A468Q, A468Y, N566F, N566H, F556V, P604Y, L293V, A630G, N461C, N463T, D457C, Q220M, T221A, T221G, T221I, A655R, A468F, A468S, Q216I, D564V, A468T, A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263C, N263S, N278F, S312Y, Q316T, K345E, G427C, P611F, P661L, P661Q, T666C, S683W, N461I, I671C, K206A, E170E, F260E, T568K, P536C, A630Q, D215S, G372A, G547A, P611A, F611A, G662C, G662F, A633C, S312C, or N455D) can have improved (a) and (f) activities over wild type BGL1.

Some BGL1 variants (e.g., variants comprising S283D, A270D, N146Y, F260A, S474R, A365C, K206S, D564T, N461V, I167C, K206A, T568E, A338D, F260E, T568K, or F260L) can have improved (a) and (c) activities over wild type BGL1. Other BGL1 variants (e.g., variants comprising F556G, P260S, P604E, P604V, N146D, Y639T, T221C, N473S, N583R, R645G, G662Y, F260A, S474R, A655N, I167K, F260T, P607S, S692L, D564T, F260D, F260G, F260Q, P607G, N400S, P607F, T568E, S308E, A338D, F260E, T568K, P536C, A630Q, D215S, Q372A, G547A, F611A, G662C, G662F, or F260L) can have improved (a) and (e) activities over wild type BGL1.

Some BGL1 variants (e.g., variants comprising D259S, T243V, Y530F, A338D, or F260L) can have improved (c) and (d) activities over wild type BGL1. Some BGL1 variants e.g., variants comprising S550Q, P660R, N400Q, V602F, A601G, A601L, L293K, Y575C, Y575R, A450Q, I486C, I486Y, A655S, Q245F, D329A, P536G, P607Q, A655Q, Y575A, Y575K, A630H, V466T, S692L, F260D, F260G, F260Q, P607G, N400S, P607I, A450P, T242H, S308E, A630Y, A338D, P536C, A630Q, D215S, G372A, G547A, F661A, G662C, G662F, F260L, or L293F) can have improved (d) and (e) activities over wild type BGL1.

Some BGL1 variants (e.g., variants comprising P536F, F392C, S624L, S624R, S624W, I486F, I486W, A667G, A667S, L266N, F556L, S550I, S550T, S550V, T258L, P536I, P536V, F392R, S624G, S624N, S624Q, S624T, A601M, A630V, N463S, A450F, A450T, A450V, A450W, I486V, S482I, Y678I, G427F, D564T, Q684C, Q684G, N566F, Y575A, Y575K, A565G, A270C, T258S, T258V, P536D, P536F, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263C, N263S, N278F, S312Y, Q316T, K345E, G427C, P661F, P661Q, T666C, S663W, F260W, P607I, A450P, T242H, P536C, A630Q, D215S, G372A, G547A, F611A, G662C, G662F, L293F, A633C, S312C, or N455D) can have improved (d) and (f) activities over wild type BGL1. Some BGL1 variants (e.g., variants comprising S384G, S384W, N038E, N038M, N038P, V043H, V043W, Y068E, Y068G, Y068M, L110C, L110G, L110Q, L110W, A655H, N264L, S384E, L181M, V043A, V043G, V043N, Q060D, A655Y, T242S, S474D, Y639G, K206S, A655D, or S507G) can have improved (c) and (g) activities over wild type BGL1.

Some BGL1 variants (e.g., variants comprising G606D, Y068V, L293M, Q220P, A630H, V466T, V530S, Q684N, F260W, Q406D, Q605C, N263T, S308E, A630Y, L293F, A633C, S312C, or N455D can have (d) and (g) activities. Some BGL1 variants e.g., variants comprising A377I, N461Y, N146A, N146Q, P607K, N369T, T436E, Y639G, Y530S, Q684N, Y637V, F260W, P607F, Q406D, G605C, N263T, A630Y, A655D, E170F, S507G, L293F, A633C, S312C, or N455D) can have improved (b) and (g) activities over wild type BGL1. Some BGL1 variants (e.g., variants comprising K206D, A601D, Y530F, N461V I671C, K206A, S507G, F260E, or T568K) can have improved (c) and (f) activities over wild type BGL1. Other BGL1 variants (e.g., variants comprising A468G, F536Q, N369E, N369W, N369Y, A601D, Y575A, Y575K, P607I, A450P, T242H, P260E, T568K, P536C, A630Q, D215S, G372A, G547A, F611A, G662C, G662F, or L293F) can have improved (e) and (f) activities over wild type BGL1.

Additionally, BGL1 variants can have at least three improved activities over wild type BGL1. For example, some BGL1 variants (e.g., variants comprising L266C, I567F, S624P, P607L, G606I, G606K, G606L, G606M, G606Q, G606V, G605E, I444V, A633V, A655W, Y678H, V522Y, G554F, A565S, A270C, T258S, T258V, P536D, P536E, S624F, S624I, S624V, A601C, A601Y, S308H, A630C, A630D, N463K, N463R, A450C, S482A, A667F, A667R, A667Y, A485T, V466S, Y678A, Y678C, Y678Q, A468C, Q226W, Q226Y, N263C, N263S, N278F, S312Y, Q316T, K345E, G427C, P661F, P661L, P661Q, T666C, S368W, F260D, F260G, F260Q, P607G, G400S, Q406D, G605C, N263T, P536C, A630Q, D215S, G372A, G347A, F611A, G662C, G662F, F260L, A633C, S312C, or N455D) can have improved activities selected from any two or all three of (a), (b), and (d) over wild type BGL1, while others (e.g., variants comprising L266N, F556L, S550I, S550T, S550V, T258L, N536I, P536V, F392R, S624G, S624N, S624Q, S624T, A610M, A630V, N463S, A450F, A450T, A450V, A450W, I486V, S482I, Y678I, G427F, D564T, Q684C, Q684G, A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263C, N263S, N278F, S312Y, Q316T, K345E, G427C, P661F, P661L, P611Q, T666C, S683W, F260W, Y530F, P607I, A450P, T242H, P536C, A630Q, D215S, G372A, G547A, F611A, G662C, G662F, A633C, S312C, N455D, or L293F) have improved activities selected from any two or all three of (b), (d), and (f) over wild type BGL1.

Some BGL1 variants (e.g., variants comprising F260A, S474R, D564T, T568E, A338D, F260E, T568K, or F260L) can have improved activities selected from any two or all three of (a), (c) and (e) over wild type BGL1, while other BGL1 variants (e.g., variants comprising I567V, N566G, A630K, Y639K, Q245N, K320Y, A347Y, T568E, A655D, F260E, T568K, or F260L) can have improved activities selected from any two or all three of (b), (c), and (e) over wild type BGL1. Some BGL1 variants (e.g., variants comprising N566F, A565G, A270C, T258S, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263C, N263S, N278F, S312Y, Q316T, K345E, G427C, P661F, P611L, P661Q, T666C, S683W, P536C, A630Q, D215S, G372A, G547A, F611A, G662C, G662F, A633C, S312C, or N455D) can have improved activities selected from any two or all three of (a), (d), and (f) over wild type BGL1. Other BGL1 variants (e.g., variants comprising N566H, F556V, P604Y, L293V, A630G, N461C, N463T, D457C, Q220M, T221A, T221G, T331I, A655R, A468F, A468S, Q216I, D564V, A565G, A270C, T258S, T258V, P536D, P536L, S624F, S624I, S624V, A601C, A601Y, S308H, A630C, A330D, N463K, N463R, A450E, S482A, A667F, A667L, A667R, A667Y, A485T, V466S, Y678A, Y678C, Y678Q, A468C, Q226W, Q226Y, N263C, N263S, N278F, S312Y, Q316T, K345E, G427C, P661F, P661L, P661Q, T666C, S683W, N461V, I671C, K206A, E170F, F260E, T568K, P536C, A630Q, D215S, G372A, G547A, F611A, G662C, G662F, A633C, S312C, or N455D) can have improved activities selected from any two or all three of (a), (b), and (f) over wild type BGL1.

Some BGL1 variants (e.g., variants comprising A565C, N461V, I167C, K206A, T568E, F260E, T568K, or F260L) can have improve activities selected from any two or all three of (a), (b), and (c) over wild type BGL1. Other BGL1 variants (e.g., variants comprising P536G, P607Q, A655Q, F260D, F260G, F260Q, P607G, N400S, P607I, A450P, T242H, A630Y, P536C, A630Q, D215S, D372A, G547A, F611A, G662C, G662F, F260L, or L293F) can have improved activities selected from any two or all three of (b), (d), and (e) over wild type BGL1. Yet other BGL1 variants (e.g., variants comprising P536Q, N369E, N369W, N369Y, P607I, A450P, T242H, F260E, T568K, P536C, A630Q, D215S, G372A, G547A, F611A, G662C, G662F, or L293F) can have improved activities selected, from any two or all three of (b), (e), and (f) over wild type BGL1.

Other BGL1 variants (e.g., variants comprising A601D, F260E or T568K) can have improved activities selected from any two or all three of (c), (e), and (f) over wild type BGL1. Some BGL1 variants (e.g., variants comprising L293M, Q220P, Q406D, G605C, N263T, S308E, A633C, S312C, or N455D) can have improved activities selected from any two or all three of (a), (d), and (g) over wild type BGL1. Other BGL1 variants (e.g., variants comprising Y575A, Y575K, P607I, A450P, T272H, P536C, A630Q, D215S, G372A, G547A, F611A, G662C, G622F, or L293F) can have improved activities selected from any two or all three of (d), (e), and (f) over wild type BGL1. Some BGL1 variants (e.g., variants comprising A630H, V466T, S308E, A630Y, or L293F) can have improved activities selected from any two or all three of (d), (e), and (g) over wild type BGL1.

Some BGL1 variants (e.g. variants comprising N146A, N146Q, P607K, N369T, P607F, A630Y, A655D, or L293F) can have improved activities selected from any two or all three of (b), (e), and (g) over wild type BGL1. Other BGL1 variants (e.g., variants comprising S384E, L181M, V043A, V043G, V043N, Q060D, A655Y, T242S, S474D, or A655D) can have improved activities selected from any two or all three of (c), (e), and (g) over wild type BGL1. Some BGL1 variants (e.g., variants comprising T436E, F260W, E170F, S507G, L293F, A633C, S312C, or N455D) can have improved activities selected from any two or all three of (b), (f), and (g) over wild type BGL1. Other BGL1 variants (e.g., variants comprising Y639G, P607F, A655D, or S507G) can have improved activities selected from any two or all three (b), (c), and (g) over wild type BGL1.

Some BGL1 variants (e.g., variants comprising A655N, I671K, F206T, P607S, F260D, F260G, F260Q, P607G, N400S, P607F, T568E, F260E, T568K, P536C, A630Q, D215S, G372A, G547A, F611A, G662C, G662F, or F260L) can have improved activities selected from any two or all three of (a), (b), and (e) over wild type BGL1. Other BGL1 variants (e.g., variants comprising K206S or P607F) can have improved activities selected from any two or all three of (a), (c) and (g) over wild type BGL1. Other BGL1 variants (e.g., variants comprising Y530S, Q684N, F260W, Q406D, G605C, N263T, A630Y, L293F, A633C, S312C, or N455D) can have improved activities selected from any two or all three of (b), (d), and (g) over wild type BGL1. Some BGL1 variants (e.g., variants comprising A468T, E170F, A633C, S312C, or N455D) can have improved activities selected from any two or all three of (a), (f), and (g) over wild type BGL1.

Some BGL1 variants e.g. variants comprising S692L, F620D, F260G, F260Q, P607G, N400S, S308E, A338D, P536C, A630Q, D215S, G372A, G547A, F611A, G662C, G662F, or F260L) can have improved activities selected from any two or all three of (a), (d), and (e) over wild type BGL1 while other BGL1 variants (e.g. Y639V) can have improved activities selected from any two or all three of (a), (b), and (g) over wild type BGL1.

Other BGL1 variants (e.g., variants comprising A565G, A270C, T258C, T258V, P536D, P536E, S624F, S624I, S624V, A601C, A601Y, S308H, A630C, A630D, N463K, N463R, A450E, S482A, A667F, A667L, A667R, A667Y, A485T, V466S, Y678A, Y678C, Y678Q, A468C, Q226W, Q226Y, N263C, N263S, N278F, S312Y, Q316T, K345E, G427C, P661F, P661L, P661Q, T666C, or S683W) can have improved activities selected from any two, any three, or all four of (a), (b), (d) and (f) over wild type BGL1.

Some BGL1 variants (e.g., variants comprising F260D, F260G, F260Q, P607G, or N400S) can have improved activities selected from any two, any three, or all four of (a), (b), (d) and (e) over wild type BGL1. Other BGL1 variants (e.g., variants comprising F260W, L293E, A633C, S312S, or N455D) can have improved activities selected from any two, any three, or all four of (b), (d), (f) and (g) over wild type BGL1. Other BGL1 variants (e.g., variants comprising Y530F) can have improved activities selected from any two, any three, or all four of (b), (c), (d) and (f) over wild over BGL1. Other BGL1 variants (e.g., variants comprising F607F) can have improved activities selected front any two, any three, or all four of (a), (b), (e) and (g) over wild type BGL1 Other BGL1 variants (e.g. variants comprising Q406D, G605C, N263T, A633C, S312C, or N455D) can have improved activities selected from any two, any three, or all four of (a), (b), (d) and (g) over wild type BGL1.

Other BGL1 variants (e.g., variants comprising N461V, I167C, K206A, F260E, or T568K) can have improved activities selected from any two, any three, or all four of (a), (b), (c) and (f) over wild type BGL1. Other BGL1 variants (e.g., variants comprising P607I, A450P, T242H, P536C, A630Q, D215S, G372A, G547A, F661A, G662C, G662F, or L293F) can have improved activities selected from any two, any three, or all four of (b), (d), (e) and (f) over wild type BGL1. Some BGL1 variants (e.g., variants comprising T568E, F260E, T368K, or F260L) can have improved activities selected from any two, any three, or all four of (a), (b), (c) and (e) over wild type BGL1. Other BGL1 variants (e.g., variants comprising S308E) can have improved activities selected from any two, any three, or all four of (a), (d), (e) and (g) activities over wild type BGL1. Other BGL1 variants (e.g., variants comprising A630Y or L293F) can have improved (b), (d), (e) and (g) over wild type BGL1.

Other BGL1 variants (e.g., variants comprising A655D) can have improved activities selected from any two, any three, or all four of (b), (c), (e) and (g) over wild type BGL1. Other BGL1 variants (e.g., variants comprising E170F, A633C, S312C, or N455D) can have improved activities selected from any two, any three, or all four of (a), (b), (f) and (g) over wild type BGL1. Other BGL1 variants (e.g., variants comprising A338D, or F260L) can have improved activities selected from any two, any three, or all four of (a), (c), (d) and (e) over wild type BGL1. Other BGL1 variants e.g., variants comprising S507G) can have improved activities selected from any two, any three, or all four of (b), (c), (f) and (g) over wild type BGL1.

Other BGL1 variants (e.g., variants comprising F260E or T586K) can have improved activities selected from any two, any three, any four, or all five of (a), (b), (c), (e) and (f) over wild type BGL1. Other BGL1 variants (e.g., variants comprising P536C, A630Q, D215S, G372A, G547A, F611A, G662C, or G662F) can have improved activities selected from any two, any three, any four, or all five of (a), (b), (d), (e) and (f) over wild type BGL1. Other BGL1 variants (e.g., variants comprising F260L) can have improved (a), (b), (c), (d) and (e) activities over wild type BGL1. Other BGL1 variants (e.g., variants comprising L293F) can have improved activities selected from any two, any three, four, or all five of (b), (d), (e), (f) and (g) over wild type BGL1. Other BGL1 variants (e.g., variants comprising A633C, S312C, or N455D) can have improved activities selected from any two, any three, any four, or all five of (a), (b), (d), (f) and (g) over wild type BGL1.

In one aspect, a suitable BGL1 variant can be any of the following: L266Y, I567S, A270D, S530D, T258S, P536D, P536V, F260D, F260G, Y530F, S624N, P607Q, G606M, Q406H, N400Q, G300M, N038L, N038M, A601Y, L293V, T568K, S308E, A630Y, N461D, N146D, A450E, V043L, Q220A, A655Q, S482A, A667L, A485T, K206A, or Y678Q.

The invention also provides for BGL1 variants that have at least two improved activities over wild type BGL1 selected from the group consisting of: (a) pre-treated corn stover (PCS) hydrolysis activity, (b) cellobiase activity, (c) protein expression, (d) beta-glycosidase activity as measured by an ammonia pretreated corncob (CC) hydrolysis activity, (e) thermostability, (f) phosphoric acid swollen cellulose (PASC) hydrolysis activity, and (g) hydrolytic activity in the presence of glucose, wherein the BGL1 variant comprises two or more substitutions from Table 5-1.

In other aspects, the invention provides BGL1 variants, as described above and throughout this specification, wherein the improved activities over wild type BGL1 are (a) and (c) and the substitutions are: L167W|D225Q|T242S|S312Y|D178K|A338K|S474D| G662L, K345E|N369T|G372A|K428N|P611|S683W, D177M|D225Q|D564V|Q384G, and D178N|N264K|A338D|S474R|G662K, D177M|D564T|Q626F|Q684A, K428N|S383W, K345E|K428N|S683W, Q226Y|G372A|V603G|T666C, L167W|G177M|Q626F, L167W|D177M|D225Q|D564V|Q684G, D177M|D225Q|D564T|Q684G, D177M|Q626F|Q684R, N238W|R265P|K656R, N264M|R265P (optionally also G662F), N264L|A338I|S474R|G662D, L167W|D225Q|D564V|Q626F|Q684N, D177M|G225Q|D564T|Q638A, D177M|D225Q|D564V|Q626F|Q684N, K345E|N369E|G372A|P661E, N369T|P611L|S683W, R265M|K560S, N369T|G372A|L661L|S683W, P176L|Q226W|K320Y|R363E, K345E|N369T|G372A|P661E|S683W, K320S|R363E, E170F|Q226Y|T242S|S312Y|G372A|V603G|P661F|T666C, T242S|T666C, Q226Y|T666C, Q216E|S312K|S692K, P176L|G662F, P176L|Q226W|Q316T|L320Y|R363E, P176L|Q226W|K320S|K363E|G662F, P176L|Q226W|Q316T|K320Y|V522Y, P176L|Q226W|K320Y|R363E|V522Y, Q226W|K320Y|R363E, Q316T|K320Y|R363E|G662F, Q226W|Q316T|R363E|V322Y|G662F, P176L|K320S|R363E|G662C, R363E|G547A|G662C, Q226W|K320S|G662C, P176L|Q226W|Q316T|K320Y|R363E|G662F, P176L|Q226W|Q316T|K320S|G662F, P176L|Q316T|K320S|R363E|V522Y|G662C, K320Y|R363E|G662C, K343E|N369E|P661L, E170F|V603G, K345E|N369E|G372A|S683W, N369E| S683W, G372A|P661E|S683W, P176L|Q316T|K320S|R363E|G662F, K345E|N369E|P661E|S683W, K345E|P661E|S683W, N263C|K345E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 (b) and (f) and the substitutions are: L167W|D177M|D225Q|Q626F|Q684G, L167W|D177M|D564V|Q684G, D215S|S312Y, E170F|S312Y|N369Y, L167W|D225Q|Q626F|Q684R, L167W|D564T|Q626F, P176L|Q226W|Q316T|K320S|V522Y|G662C, R363E|V522Y|G662F, Q316T|K320S|V522Y|Q662W, Q226W|K320Y|V522Y, Q316T|K320S|V522Y, and Q226W|K320S|R363E|V522Y|G662F, L167W|D177M|D225Q|D564V, D177M|D225Q|D564T|Q684A, D177M|D225Q|D564V|Q626F|Q684N, L167W|D177M|Q626F|Q684G, L167W|D177M|D563V|Q626F|Q684A, P176L|K570S|V522Y|G662C, K345E|N369T|G372A|P661E|S683W, K320S|R363E, E170F|Q226Y|T242S|S312Y|G372A|V603G|P661F|T666C, T242S|T666C, Q226Y|T666C, Q216E|S312K|S692K, P176L|G662F, P176L|Q225W|Q316T| K320Y|R363E, P176L|Q226W|K320S|R363E|G662F, P176L|Q226W|Q316T|K320Y|V522Y, P176L|Q226W|K320Y|R363E|V522Y, Q226W|K320Y|R363E, Q316T|K320Y|R363E|G662F, Q226W|Q316T|R363E|V522Y|G662F, P176L|K320S|R363E|G662C, R363E|G547A|G662C, Q226W|K320S|G662C, P176L|Q226W|Q316T|K320Y|R363E|G662F, P176L|Q226W|Q316T|K320S|G662F, P176L|Q316T|R320S|R363E|V522Y|G662C, K320Y|R363E|G662C, E170F|Q226Y|N369Y|G372A|P661F, and L167W|D177M|D564T|Q626F|Q684G, R345E|N369E|G372A|S683W, N369E|S683W, K345E|N369E|P661E|S683W, K345E|P661E|S683W, N263C|K345E|N369E, N263C|G369T|P661E, K345E|N369E|S683W, N263C|K345E|N369T|K428N, N263C|N369E|K428N|P661E, N263C|N369T|S683W, N263C|N369T, N369T|G372A|K428N|S683W, N263C|G373A, N263C|K345E|G373A|P661E, or P176L|Q226W|G547A|G662C.

In other aspects, the invention provides BGL1 variants, as described above and throughout this specification, wherein the improved activities over wild type BGL1 are (e) and (g) and the substitutions are: L167W|D225Q|Q626F|Q684D, L167W|D225Q|Q684N, L167W|D225Q|D564T|Q626F|Q684C, Q626F|Q684D, N264M|R265P|N369I|D370W, R179V|N238F|D370W, R179V|N238F|K656R, R179V|N264M|D370W, R179V|N238F|R265M, R179V|R265P|D370W|K656R, R179V|N238W|N264M|R265M|N369I, R179V|N369I|D370W|K656R, R179V|N264M|R265P|K656R, R379V|R265M|N369I, R179V|N264M|R265M|D370W|K656R, R179V|N264M|R265M|N369I, R179V|N238W|N264M, N238W|N264M|R265M|D370W, R179V|N238W|R265P|D379W, R179V|N238W|N264M|D370W|K656R, N264M|R265P, R265P|D370W (optionally also G662F), R179V|N264M|R265P|N369I|D370W, R265M|N369I, R179V|R265M|D370W, N238W|N264M|R265P, R179V|N238W|N264M|R265P, N264M|N369I, N238F|R265M|N369I, N263C|K345E|N369E|G372A|K428N|P661E|S683W, N263C|K345E|N369T|G372A|K428N|P661E|S683W, N263C|K345E|N369E|G372A, N263C|P661L|S683W, N263C|K345E|N369T|G372A|K428N, K345E|G372A|K428N|P661E, E170F|Q226Y|N369Y|G372A, Q226Y|T424S|G372A|P661F, Q216E|T282I|S312D|S692K, Q216I|T282K|S312K|A622K, P176L|Q316T|G662W|Q226W|Q316T|V522Y|G662F, P176L|Q316T, A347Y|R542N, N238F|N264M|R265M|N369I, L167W|D225Q|D524V|Q626F|Q684N, E170F|V603G, L167W|D177M|D564T|Q684N, K345E|N369E|G372A|S683W, N369E|S683W, G372A|P661E|S683W, P176L|Q316T|K320S|R363E|G662F, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are (d) and (f) and the substitutions are: L167W|D177M|D564V|Q684R, L170W|D225Q|D564V, D177M|D225Q|D546T|Q626F|Q684N, L167W|Q626F, D225Q|D564V|Q626F|Q684R, D177M|D225Q|D664V|Q684R, Q226W|K320Y, P176L|V522Y, R363E|G662C, L167W|D225Q|Q626F|Q684R, L167W|D564T|Q626F, P176L|Q226W|Q316T|K320S|V522Y|G662C, R363E|V522Y|G622F, Q316T|K320S|V522Y|G662F, Q226W|K320Y|V522Y, Q316T|K320S|V522Y, Q226W|K320S|R363E|V522Y|G662F, L167W|D177M|D564T|Q626F|Q684N, L167W|Q626F|Q684D, L167W|D177M|D564T|Q684R, L167W|D177M|D225Q|Q684D, R179V|R265P|N369I, Q316T|K320Y|R363E|V522Y|G662F, L167W|D177M|Q626F, L167W|P177M|D225Q|Q684V|Q684G, D177M|D225Q|D564T|Q684N, D177M|Q626F|Q684R, L176W|D177M|Q626F|Q684G, L167W|D177M|D564V|Q626F|Q684A, P176L|K320S|V522Y|G662C, K345E|N369T|G372A|P661E|S683W, K320S|R363E, E170F|Q226Y|T242S|S312Y|G372A|V603G|P661E|T666C, T242S|T666C, Q226Y|T666C, Q216E|S312K|S692K, P176L|G662F, P176L|Q226W|Q316T| K320Y|R363E, P176L|Q226W|K320S|R363E|G662F, P176L|Q226W|Q316T|K320Y|V522Y, P176L|Q226W|K320Y|R363E|V522Y, Q226W|K320Y|R363E, Q316T|K320Y|R363E|G662F, Q226W|Q316T|R363E|V522Y|G662F, P176L|K320S|R363E|G662C, R363E|G547A|G662C, Q226W|K320S|G662C, P176L|Q226W|Q316T|K320Y|R363E|G662F, P176L|Q226W|Q316T|K320S|G662F, P176L|Q316T|K320S|R363E|V522Y|G662C, K320Y|R363E|G662C, E170F|Q226Y|N369Y|G372A|P661F, L167W|D177M|D564T|Q626F|Q684G, K345E|N369E|P661E|S683W, K345E|P661E|S683W, N263C|K345E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are (b) and (e) and the substitutions are: K345E|N369E|R428N|P661L, Q316T|K320Y|V522Y, N369T|G372A|P661L|S683W, P176L|Q226W|K320Y|R363E, P176L|K320S|V522Y|G662C, K345E|N369E|P661L, L167W|D564T|Q684N, K343E|N369E|G372A|S683W, N369E|S683W, G372A|P661E|S683W, P176L|Q316T|K320S|R363E|G662F, K345E|N369E|P661E|S683W, K345E|P661E|S683W, N263C| K345E|N369E, N263C|N369T|P661E, R345E|N369E|S683W, N263C|K345E|N369T|K428N, N263C|N369E|K428N|P661E, N263C|N369T|S683W, N263E|N369T, N369T|G372A|K428N|S683W, N263C|G372A|N263E|K345E|N369E|G372A|P661E, or P176L|Q226W|G547A|G662C.

In other aspects, the invention provides BGL1 variants, as described above and throughout this specification, wherein the improved activities over wild type BGL1 are (d) and (e) and the substitutions are: N263C|K345E|N369E|P661L, N238F|N264M|R265M| N369I, P176L|K320S|V522Y|G662C, K345E|N369E|P661L, E170F|V603G, L167W| D177M|D564T|Q684N, G372A|P661E|S683W, P176L|Q316T|K320S|R363E|G662F, K345E|N369E|P661E|S683W, K345E|P661E|S683W, N263C|K345E|N369E, N263C|N369T|P661E, K345E|N369E|S683W, N263C|K345E|N369T|K428N, N263C|N363E|K428N|P661E, N263C|N369T|S683W, N263C|N369T, N369T|G372A|K422N|S683W, N263C|G372A, G263C|K345E|N369E|G372A|P661E, of P176L|Q226W|G547A|G662C.

In other aspects, the invention provides BGL1 variants, as described above and throughout this specification, wherein the improved activities over wild type BGL1 are (b) and (g) and the substitution are: E710F|T242S|N369Y|G372A|V603G|T666C, E170F|Q226Y|N369Y|V603G|T666C, E170F|Q226Y|S312Y, L167W|D177M|G225Q|D564V, L167W|D177M|Q626F|Q684G, L167W|D177M|D564V|Q626F|Q684A, E170F|Q226Y|N369Y|G372A|P661F, L167W|D177M|D564T|Q626F|Q684G, L167W|D177M|D564T|Q684N, K345E|N369E|G372A|S683W, N369E|S683W, G372A|P661E|S683W, P176L|Q316T|K320S|R363E|G662F, N263C|G369T, N369T| G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are (d) and (g) and the substitutions are: D178I|Q303E|A338I, Q316T|K320Y|G662F, L167W|D177M|D564T|Q626F|Q684N, L167W|Q626F|Q684D, L167W|D177M|D564T|Q634R, L167W|D177M|D225Q|Q684D, R179V|R265P|N369I, Q316T|K320Y|R563E|V522Y|G662F, N238F|N264M|R265M|N369I, N238W|R265P|K656R, N264M = R265P, (optionally also G662F), N264L = A338I = S474R|G662D, L167W|D177M|Q626F|Q684G, and L167W|D177M|D564V|Q626F|Q684A, E170F|V603G, E170F|Q226Y|N369Y|A372A|P661F, L167W|D177M|D564T|Q626F|Q684G, L167W|D177M|D564T|Q684N, G372A|P661E|S683W, P176L|Q316T|R320S|R363E|G662F, N263C|G369T, N369T|G372A|K428N|S683W, N263C|G372A, N263C|R345E|N369E|G372A|P661E, or P176L|Q226W|G547A|G662C.

In other aspects, the invention provides BGL1 variants, as described above and throughout this specification, wherein the improved activities over wild type BGL1 are selected from any two or all three of (b), (d), and (f) and the substitutions are: L167W|D225Q|Q626F|Q684R, L167W|D564T|Q626F, P176L|Q226W|Q316T|K320S|V522Y|G662C, R363E|Y522Y|G662F, Q316T|K320S|V522Y|G662F, Q226W|K320Y|Y522Y, Q316T|K320S|V522Y, Q226W|K320S|R363E|V522Y|G662F, L167W|D177M|Q626F|G684G, L167W|D177M|D564V|Q626F|Q684A, P176L|K320S|V522Y|G662C, K343E|N369T|G372A|P661E|S683W, K320S|R363E, E170F| Q226Y|T242S|S312Y|G372A|V603G|P661F|T666C, T242S|T666C, Q226Y|T666C, Q216E|S312K, P692K, P176F|G662F, P176L|Q226W|Q316T|K320Y|R363E, P176L|Q226W|K320S|R363E|G662F, P176L|Q226W|Q316T|K320Y|V522Y, P176L|Q226W|K320Y|R363E|V522Y, Q226W|K320Y|R363E, Q316T|K320Y|R363E|G662F, Q226W|Q316T|R363E|V522Y|G662F, P176L|K320S|R363E|G662C, R363E|G547A|G662C, Q226W|K320S|G662C, P176L|Q226W|Q316T|K320Y|R363E|G662F, P176L|Q226W|Q316T|K320S|G662F, P176L|Q316T|K320S|R363E|V522Y|G662C, K320Y|R363E|G662C, E170F|Q226Y|N363Y|G372A|P661F, L167W|D177M|D564T|Q626F|Q684G, K345E|N369E|P661E|S633W, K345E|P661E|S633W, N263C|K345E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|S683W, N2683C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two or all three of (d), (f), and (g) and the substitutions are: K167W|D177M|D564T|Q626F|Q684N, L167W|Q626F|Q684D, L167W|D177M|D564T|Q684R, L167W|D177M|D225Q|Q684D, R179V|R265P|N369I, Q316T|K320Y|K363E|V522Y|G662F, L167W|D177M|Q626F|Q684G, L167W|D177M|D564V|Q626F|Q684A, E170F|Q226Y|N369Y|G372A|P661F, L167W|D177M|D564T|Q626F|Q684G, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two or all three of (a), (c), and (e) and the substitutions are: K345E|N369T|G372A|K428N|P661L|S683W, L167W|D225Q|D564V|Q626F|Q684N, N369T|G372A|P661L|S683W, P176L|Q226W|K320Y|R363E|K345E|N369E|P661L, E170F|V603G, K345E|G369E|G372A|S683W, N369E|S683W, G372A|P661E| S683W, P176L|Q316T|K320S|R363E|G662F, K345E|N369E|P661E|S683W, K345E|P661E|S683W, N263C|K345E|N369E, N263C|N369T|P661E, G345E|N369E, |S683W, N263C|K345E|N369T|K428N, N263C|N369E|K428N|P661E, N263C|N369T|S683W, N263C|N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two or all three of (b), (f), and (g) and the substitutions are: L167 W|D177M|D225Q|D564V, L167W|D177M|Q626F|Q684G, L167W|D177M|D564V|Q626F|Q684A, E170F|Q226Y|N369Y|G372A|P661F, L167W|D177M|D564T|Q626F|Q684G, K345E|N369E|G372A|S683W, N369E|S683W, N283C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two or all three of (a), (c), and (d) and the substitutions are: D177M|D225Q|D564V|Q684G, D178N|N264K|A338D|S474R|G662K, L167W|D177M|Q626F, L167W|D177M|G225Q|D564V|Q684G, D177M|D225Q|D564T|Q684N, D177M|Q626F|Q684R, N238W|R265P|K656R, N264M|R265P (optionally also G662F), N264L|A338I|S474R|G662D, K345E|N369E|G372A|P661E, N369T|P661L| S683W, K345E|N369T|G372A|P661E|S683W, K320S|R363E, E170F|Q226Y|T242S|S312Y|G372A|V603G|P661F| T666C, T242S|T666C, Q226Y|T666C, Q236E|S312K|S692K, P176L|G662F, P176L|Q226W|Q316T|K320Y|R363E, P176L|Q226W|K320S|R363E|G662F, P176L|Q226W|Q316T|K320Y|V522Y, P176L|Q226W|K320Y|R363L|V522Y, Q226W|K320Y|R363E, Q316T|K320Y|R363E|G662F, Q226W|Q316T|R363E|V522Y|G662F, P176L|K320S|R363E|G662C, R363E| G547A|G662C, Q226W|K320S|G662C, P176L|Q226W|Q316T|K320Y|R363E|G662F, P176L|Q226W|Q316T|K320S|G662F, P176L|Q316T|K320S|R363E|V522Y|G662C, K320Y|R363E|G662C, K345E|N369E|P661L, E170F|V603G, G372A|P661E|S683W, P176L|Q316T|K320S|R363E|G662F, K345E|N369E|P661E|S683W, K345E|P661E|S683W, N263C|K345E|N369E, N263C|N369T|P661E, K345E| N369E|S683W, N263C|K345E|N369T|K428N, N263C|N369E|K428N|P661, N263C|N369T|S683W, N263C|N369T, N369T|G372A|K428N|S683W, N263C|G372A, N263C|K345E|N369E|G372A|P661E, or P176L|G226W|G547A|G662C.

In other aspects, the invention provides BGL1 variants, as described above and throughout this specification, wherein the improved activities over wild type BGL1 are selected from any two or all three of (a), (c), and (g) and the substitutions are: D177M|D564T|G626F|Q684A, N238W|R265P|K656R, N264M|R265P (optionally also G662F), N264L|A338I|S474R|G662D, D225Q|D564V|Q626F|Q684N, R265M|K560S, E170F|V603G, K345E|N369E|G372A|S663W, N369E|S683W, G372A|P661E|S683W, P176L|Q316T|K320S|R363E|G662F, N263C|N369T, N369T|G372A| K428N|S683W, N263C|G372A, N263C|K345E|N369E|G372A|P661E, or P176L|Q226W|G547A|G662F. In other aspects, the invention provides BGL1 variants, as described above and throughout this specification, wherein the improved activities over wild type BGL1 are selected from my two or all three of (d), (e), and (g) and the substitutions are: N238F|N264M|R265M|N369I, L170F|V603G, L167W|D177M|D564T|Q684N, G372A|P661E|S683W, P176L|Q316T|K320S|R363E|G662F, N263C|N369T, N369T| G372A|K428N|S683W, N263C|G372A, N263C|K345E|N369E|G372A|P661E, or P176L|Q226W|G547A|G662F. In other aspects, the invention provides BGL1 variants, as described above and throughout this specification, wherein the improved activities over wild type BGL1 are selected from any two or all three of (a), (b), and (c) and the substitutions are: K428N|S683W, K345E|K428N|S683W, Q226Y|G372A|V603G|T666C, D177M|D225Q|D564T|Q684A, D177M|D225Q|D564V|Q626F|Q684N, K345E|N369E|G372A|P661E, N369T|P661L|S683W, N369T|G372A|P661L|S683W, P176L|Q226W|K320Y|R363E, K345E|N369T|G372A|P661E|S683W, K320S|R363E, E170F|Q226Y|T242S|S312Y|G372A|V603G|P661F| T666C, T242S|T666C, Q226Y| T666C, Q216E|Q312K, S682K, P176L|G662F, P176L|Q226W, Q316T|K320Y|R363E, P176L|Q226W|R320S|R363E|G662F, P176L|Q226W|Q316T|K320Y|V522Y, P176L|Q226W|K320Y|R363E|V522Y, Q226W|K320Y|R363E, Q316T|K320Y|R363E|G662F, Q226W|Q316T|R363E|V522Y|G662F, P176L|K320S|R363E|G662C, R363E|G547A|G662C, Q226W|K320S|G662C, P176L|Q226W|Q316T|K320Y|R363E|G662F, P176L|Q226W|Q316T|K320S|G662F, P176L|Q316T|K320S|R363E|V522Y|G662C, K320Y|R363E|G662C, K345E|N369E|P661L, K345E|N369E|G372A|S683W, N369E|S683W, G372A|P661B|S683W, P176L| Q316T|K320S|R363E|G662F, K345E|N369E|P661E|S683W, R345E|P661E|S683W, N263C|K345E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, or all four of (a), (c), (d), and (f) and the substitutions are: L167W|D177M|Q626F, L167W|D177M|D225Q|D564V|Q684G, D177M|D225Q|D564T|Q684N, D177M|Q626F|Q684R, K345E|N369T|G372A|P661E|S683W, K320S|R363E, E170F|Q226Y|T242S|S312Y|G372A|V603G|P661F|T666C, T242S|T666C, Q226Y|T666C, Q216E|S312K|S692K, P176L|G662F, P761L|Q226W|Q316T| K320Y|R363E, P176L|Q226W|K320S|R363E|G662F, P176L|Q226W|Q316T|K320Y|V522Y, P176L|Q226W|K320Y|R363E|V522Y, Q226W|K320Y|R363E, Q316T|K320Y|R363E|G662F, Q226W|Q316T|R363E|V522Y|G662F, P176L|K320S|R363E|G662C, R363E|G547A|G662C, Q226W|K320S|G662C, P176L|Q226W|Q316T|R320Y|R363E|G662F, P176L|Q226W|Q316T|K320S|G662F, P176L|Q316T|R320S|R363E|V522Y|G662C, K320Y|R363E|G662C, K345E|N369E|P661E|S683W, K345E|P661E|S683W, N263C|R345E|N369E, G263C|N369T|P661E, K345E|G369E|S683W, N263C|K345E|N369T|K428N, N263C|N369E|R428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, or all four of (a), (c), (d), and (g) and the substitutions are: N238W|R265P|K656R, N264M|R265P (optionally also G662F), N264L|A381I|S474R|G662DE170F|V603G, G372A|P661E|S683W, P176L|Q316T|K320S|R363E|G662F, N263C|N369T, N362T|G372A|K428N|S683W, N263C|G372A, N263C|K345E|N369E|G372A|P661E, or P176L|Q226W|G547A|G662C. In other aspects, the invention provides BGL1 variants, as described above and throughout this specification, wherein the improved activities over wild type BGL1 are selected from any two, any three, or all four of (a), (c), (e), and (g) and the substitutions are: L167W|D225Q|D564V|Q626F|Q684N, E170F|V603G, K345E|N369E|G372A|S683W, N369E|S683W, G372A|P661E|S683W, P176L|Q316T|K320S|R363E|G662F, N263C|N369T, N369T|G372A| K428N|S683W, N263C|G372A, N263C|K345E|N369E|G372A|P661E, or P176L|Q226W|G547A|G662C. In other aspects, the invention provides BGL1 variants, as described above and throughout this specification, wherein the improved activities over wild type BGL1 are selected from any two, any three, or all four of (a), (b), (c), and (f) and the substitutions are: D177M|D225Q|D564T|Q684A, D177M|D225Q|D564V|Q626F|Q684N, K345E|N369T|G372A|P661E|S683W, K320S|R363E, E170F|Q226Y|T422S| S312Y|G372A|V603G|P661F|T666C, T242S|T666C, Q226Y|T666C, Q216E|S312K|S692K, P176L|G662F, P176L|Q226W|Q316T|K320Y|R363E, P176L|Q226W|K320S|R363E|P176L|Q226W|Q316T| K320Y|V522Y, P176L|Q226W|K320Y|R363E|V522Y, Q226W|K320Y|R363E, Q316T|K320Y|R363E|G662F, Q226W|Q316T|R363E|V522Y|G662F, P176L|K320S|R363E|G662C, R363E| G547A|G662C, Q226W|K320S|G662C, P176L|Q226W|Q316T|K320Y|R363E|G662F, P176L|Q226W|Q316T|K320S|G662F, P176L|Q316T|K320S|R363E|V522Y| G662C, K320Y|R363E|G662C, K345E|N369E|G372A|S683W, N369E|S683W, K345E|N369E|P661E|S683W, K345E|P661E|S683W, N263C|K345E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, or all four of (a), (b), (c), and (d)

and the substitutions are: K345E|N369E|G372A|P661E, N369T|P661L|S683W, K345E|N369E|G372A|P661E|S683W, K320S|R363E|70F|Q226Y|T242S|S312Y|G372A|V603G|P661F| T666C, T242S|T666C, Q226Y|T666C, Q216E|S312K|S692K, P176L|G662F, P176L|Q226W|Q316T|K320Y|R363E, P176L|Q226W|K320S|R363E|G662F, P176L|Q226W|Q316T|K320Y|V522Y, P176L|Q226W|K520Y|R363E|V522Y, Q226W|K320Y|R363E, Q316T|K320Y|R363E|G662F, Q226W|Q316T|R363E|V522Y|G662F, P176L|K320S|R363E|G662C, R368E|G547A|G662C, Q226W|K320S|G662C, P176L|Q226W|Q316T|K320Y|R363E|G662F, P176L|Q226W|Q316T|K320S|G662F, P176L|Q316T|K320S|R363E|V522Y|G662C, K320Y|R363E|G662C, K345E|N369E|P661L, G372A|P661E|S683W, P176L|Q316T|K320S|R363E|G662F, K345E|N369E|P661E|S633W, K345E|P661E|S683W, N263C|K345E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, or all four of (B), (D), (F), and (G) and the substitutions are: L167W|D177M|Q626F|Q684G, L167W|D177M|D564V|Q626F|Q684A, E170F|Q226Y|N369Y|G372A|P661F, L167W|D177M|D564T|Q626F|Q684G, K345E|N369E|G372A|S683W, N369E|S683W, N263C|N269T, N369T|G372A|K428N|S683W, N263C|G372A, N263C|K345E|N369E|G372A|P661E, or P176L|Q226W|G547A|G662C. In other aspects, the invention provides BGL1 variants, as described above and throughout this specification, wherein the improved activities over wild type BGL1 are selected from any two, any three, or all four of (a), (c), (f), and (g) and the substitutions are: R265M|K560S, K345E|N369E|G372A|S683W, N369E|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, or all four of (a), (b), (c), and (e) and the substitutions are: N369T|G372A|P661L|S683W, P176L|Q226W|K320Y|R363E, K345E|N369E|P661L, K345E|N369E|G372A|S683W, N369E|S683W, G372A|P661E|S683W, P176L|Q316T|K320S|R363E|G662F, K345E|N369E|P661E|S683W, K345E|P661E|S683W, N263C|K345E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C. In other aspects, the the invention provides BGL1 variants, as described above and throughout this specification, wherein the improved activities over wild type BGL1 are selected from any two, any three, or all four of (b), (d), (e), and (f) and the substitutions are: P176L|K320S|V522Y|G662C, K345E|N369E|P661E|S683W, K345E|P661E|S683W, N263C|K345E|N369E, N263C|N369T|P661E, K345E|N369E|S683W, N263C|K345E|N369T|K428N, N263C|N369T|K428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, any four, or all five of (a), (b), (c), (d), and (f) and the substitutions are: K345E|N369E|G372A|P661E|S683W|K320S|R363E, E170F|Q226Y|T242S|S312Y|G372A|V603G|P661F| T666C, T242S|T666C, Q226Y|T666C, Q216E|S312K|S692K, P176L|G662F, P176L|Q226W|Q316T|K320Y|R363E, P176L|Q226W|K320S|R363E|G662F, P176L|Q226W|Q316T|K320Y|V552Y, P176L|Q226W|K320Y|R363E|V522Y, Q226W|K320Y|R363E, Q316T|K320T|R363E|G662F, T226W|Q316T|R363E|V522Y|G662F, P176L|K320S|K363E|G662C, R363E|G547A|G662C, Q226W|K320S|G662C, P176L|Q226W|Q316T|L320T|R363E|G662F, P176L|Q226W|Q316T|K320S|G662F, P176L|Q316T|L320S|R363E|V522Y|G662C, K320Y|R363E|G662C, K345E|N369E|P611E|S683W, K345E|P661E|S683W, N263C|K345E|N369E, N263C|N369T|P661E, K345E|N369E|S683W, N263C|K345E|N369T|K428N, N263C|N369E|K428N|P661E, N263C|N369T|S683W, N263C|N369T, N369T|G372A|K428N|S683W, N263C|G372A, N263C|K345E|N369E|G377A|P661E, or P176L|Q226W|G547A|G662C.

In other aspects, the invention provides BGL1 variants, as described above and throughout this specification, wherein the improved activities over wild type BGL1 are selected from any two, any three, any four, or all five of (a), (b), (c), (d), and (e) and the substitutions are: K345E|N369E|P661L, G372A|P661E|S683W, P176L|Q316T|K320S| R363E|G662F, K345E|N369E|P661E|S683W, K345E|P661E|S683W, N263C|K345E|N369E, N263C|N369T|P661E, K345E|N369E|S683W, N263C|K345E|N369T|K428N, N263C|N369E|K428N|P661E, N263C|N369T|S683W, N263C|N369T, N369T|G373A|K428N|S683W, N263C|G372A, N263C|K345E|N369E|G372A|P661E, or P176L|Q226W|G547A|G662C. In other aspects, the invention provides BGL1 variants, as described above and throughout this specification, wherein the improved activities over wild type BGL1 are selected from any two, any three, any four, or all five of (a), (c), (d), (e), and (g) and the substitutions are: E170F|V603G, G372A|P661E|S683W, P176L|Q316T|K320S|R363E|G662F, N263C|N369T, N369T|G372A|K428N|S683W, N263C|G372A, N263C|K345E|N369E|G372A|P661E, and P176L|Q226W|G547A|G662C. In other aspects, the invention provides BGL1 variants, as described above and throughout this specification, wherein the improved activities over wild type BGL1 are selected from any two, any three, any four, or all five of (a), (b), (d), (f), and (g) and the substitutions are: E170F|Q226Y|N369Y|G372A|P661F, L167W|D177M|D564T|Q626F|Q684G, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, any four, or all five of (a), (b), (d), (e), and (g) and the substitutions are: L167W|D177M|D564T|Q684N, G372A|P661E|S683W, P176L|Q316T|K320S|R363E|G662F, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, any four, or all five, or all six of (a), (b), (c), (e), (f) and (g) and the substitutions are: K345E|N369E|G372A|S683W, N369E|S683W, N263C|N369T, N369T|G372A|K428N|S683W, N263C|G372A, N263C|K345E|N369E|G372A|P661E, or P176L|Q226W|G547A|G662C. In other aspects, the invention provides BGL1 variants, as described above and throughout this specification, wherein the improved activities over wild type BGL1 are selected from any two, any three, any four, any five, or all six of (a), (b), (c), (d), (e) and (g) and the substitutions are: G372A|P661E|S683W, P176L|Q316T|K320S|R363E|G662F, N263C|N369T, N369T|G372A|K428N|S683W, N263C|G372A, N263C|K345E|N369E|G372A|P661E, or P176L|Q226W|G547A|G662C. In other aspects, the invention provides BGL1 variants, as described above and throughout this specification, wherein the improved activities over wild type BGL1 are selected from any two, any three, any four, any five, or all six of (a), (b), (c), (d), (e), and (f) and the substitutions are: K345E|N369E|P661E|S683W, K345E|P661E|S683W, N263C|K345E|N369E, N263C|N369T|P661E, K345E|N369E|S683W, N263C|K345E|N369T|K428N, N263C|N369E|N428N|P661E, N263C|N369T|S683W, N263C|N369T, N369T|G372A|K428N|S683W, N263C|G372A, N263C|K345E|N369E|G372A|P661E, or P176L|Q226W|G547A|G662C.

In other aspects, the invention provides BGL1 variants, as described above and throughout this specification, wherein the improved activities over wild type BGL1 are selected from any two, any three, any four, any five, any six, or all seven of (a), (b), (c), (d), (e), (f), and (g) and the substitutions are: N263C|N369T, N369T|G372A|K428N|S683W, N263C|G372A, N263C|K345E|N369E|G372A|P661E, or P176L|Q226W|G547A|G662C.

III. Cellulases

Cellulases are known in the art as enzymes that hydrolyze cellulose (beta-1,4-glucan or beta D-glucosidic linkages) resulting in the formation of glucose, cellobiose, cellooligosaccharides, and the like. As set forth above, cellulases have been traditionally divided into three major classes: endoglucanases (EC 3.2.1.4) ("EG"), exoglucanases or cellobiohydrolases (EC 3.2.1.91) ("CBH") and beta-glucosidases (EC 3.2.1.21) ("BG").

Certain fungi produce complete cellulase systems which include exo-cellobiohydrolases or CBH-type cellulases, endoglucanases or EG-type cellulases and beta-glucosidases or BG-type cellulases. However, sometimes these systems lack CBH-type cellulases and bacterial cellulases also typically include little or no CBH-type cellulases. In addition, it has been shown that the EG components and CBH components synergistically interact to more efficiently degrade cellulose. The different components, i.e., the various endoglucanases and exo-cellobiohyrolases in a multi-component or complete cellulase system, generally have different properties, such as isoelectric point, molecular weight, degree of glycosylation, substrate specificity and enzymatic action patterns.

It is believed that endoglucanase-type cellulases hydrolyze internal beta-1,4-glucosidic bonds in regions of low crystallinity of the cellulose and exo-cellobiohydrolase-type cellulases hydrolyze cellobiose from the reducing or non-reducing end of cellulose. It follows that the action of endoglucanase components can greatly facilitate the action of exo-cellobiohydrolases by creating new chain ends which are recognized by exo-cellobiohydrolase components. Further, beta-glucosidase-type cellulases have been shown to catalyze the hydrolysis of alkyl and/or aryl beta-D-glucosides such as methyl beta-D-glucoside and p-nitrophenyl glucoside as well as glycosides containing only carbohydrate residues, such as cellobiose. This yields glucose as the sole product for the microorganism and reduces or eliminates cellobiose that inhibits cellobiohydrolases and endoglucanases.

Cellulases also find a number of uses in detergent compositions including to enhance cleaning ability, as a softening agent and to improve the feel of cotton fabrics (Hemmpel, ITB Dyeing/Printing/Finishing 3:5-14, 1991 Tyndall Textile Chemist and Colorist 24:23-26, 1992; and Kumar et al. Textile Chemist and Colorist, 29:37-42, 1997). While the mechanism is not part of the disclosure, softening and color restoration properties of cellulase have been attributed to the alkaline endoglucanase components in cellulase compositions, as exemplified by U.S. Pat. Nos. 5,648,263, 5,691, 178, and 5,776,757, which disclose that detergent compositions containing a cellulase composition enriched in a specified alkaline endoglucanase component impart color restoration and improved softening to treated garments as compared to cellulase compositions not enriched in such a component. In addition, the use of such alkaline endoglucanase components in detergent compositions has been shown to complement the pH requirements of the detergent composition (e.g., by exhibiting maximal activity at an alkaline pH of 7.5 to 10, as described in U.S. Pat. Nos. 5,648,263, 5,691,178, and 5,776,757).

Cellulase compositions have also been shown to degrade cotton-containing fabrics, resulting in reduced strength loss is the fabric (U.S. Pat. No. 4,822,516), contributing to reluctance to use cellulase compositions in commercial detergent applications. Cellulase compositions comprising endoglucanase components haw been suggested to exhibit reduced strength loss for cotton-containing fabrics as compared to compositions comprising a complete cellulase system.

Cellulases have also been shown to be useful in degradation of cellulase biomass to ethanol (wherein the cellulase degrades cellulose to glucose and yeast or other microbes further ferment the glucose into ethanol), in the treatment of mechanical pulp (Pere et al., In Proc. Tappi Pulping Conf., Nashville, Tenn. 27-31, pp. 693-696, 1996), for use as a feed additive (WO 91/04673) and in grain wet milling.

Most CBHs and EGs have a multidomain structure consisting of a core domain separated from a cellulose binding domain (CBD) by a linker peptide (Suurnakki et al., 2000). The core domain contains the active site whereas the CBD interacts with cellulose by binding the enzyme to it (van Tilbeurgh et al., FEBS Lett. 204:223-227, 1986; Tomme et al., Eur. J. Biochem. 170:575-581, 1988). The CBDs are particularly important in the hydrolysis of crystalline cellulose. It has been shown that the ability of cellobiohydrolases to degrade crystalline cellulose clearly decreases when the CBD is absent (Linder and Teeri, J. Biotechnol. 57:15-28, 1997). However, the exact role and action mechanism of CBDs is still a matter of speculation. It has been suggested that the CBD enhances the enzymatic activity merely by increasing the effective enzyme concentration at the surface of cellulose (Stahlberg et al., Bio/Technol. 9:286-290, 1991), and/or by loosening single cellulose chains from the cellulose surface (Tormo et al., EMBO J. vol. 15, no. 21, pp. 5739-5751, 1996. Most studies concerning the effects of cellulase domains on different substrates have been carried out with core proteins of cellobiohydrolases, as their core proteins can easily be produced by limited proteolysis with papain (Tomme et al., 1988). Numerous cellulases have been described in the scientific literature, examples of which include: from *Trichoderma reesei*; Shoemaker et. al., Bio/Technology, 1:691-696, 1983, which discloses CBH1; Teeri et al., Gene, 51:43-52, 1987, which discloses BGL1. Cellulases from species other than *Trichoderma* have also been described e.g., Ooi et al., Nucleic Acids Research, 18(19) 1990, which discloses the cDNA sequence coding for endoglucanase F1-CMC produced by *Aspergillus aculeatus*; Kawaguchi et al., Gene. 173:287-8, 1996, which discloses the cloning and sequencing of the cDNA encoding beta-glucosidase 1 from *Aspergillus aculeatus*; Sakamoto et al., Curr. Genet. 27:435-439, 1995, which discloses the cDNA sequence encoding the endoglucanase CMCase-1 from *Aspergillus kawachii* IFO 4308; Saarilahti et al., Gene, 90:9-14, 1990, which discloses an endoglucanase from *Erwinia carotovara*; Spilliaert et al., Eur J Biochem. 224: 923-30, 1994, which discloses the cloning and sequencing of bglA, coding for a thermostable beta-glucanase from *Rhodothermus marinus*; and Halldorsdottir et al., Appl Microbiol Biotechnol., 49:277-84, 1998, which discloses the cloning, sequencing and overexpression of a *Rhodothermus marinus* gene encoding a thermostable cellulase of glycosyl hydrolase family 12. However, there remains a need for identification and characterization of novel cellulases, with improved properties, such as improved performance under conditions of thermal stress or in the presence of surfactants, increased specific activity, altered substrate cleavage pattern, and/or high level expression in vitro.

The development of new and improved cellulase compositions that comprise varying amounts. CBH-type, EG-type and BG-type cellulases is of interest for use: (1) in detergent compositions that exhibit enhanced cleaning ability, function as a softening agent and/or improve the feel of cotton fabrics (e.g., "stone washing" or "biopolishing"); (2) in compositions for degrading wood pulp or other biomass into sugars (e.g., for bio-fuel production); and/or (3) in feed compositions.

Also provided are enzyme blends comprising one or more beta-glucosidase variants. In certain aspects, the enzyme blend comprises one or more beta-glucosidase variants and a whole cellulase. As used herein, a "whole cellulase" refers to both naturally occurring and non-naturally occurring cellulase containing compositions comprising at least two different enzyme types: (1) endoglucanase, which cleaves internal beta-1,4 linkages resulting in shorter glucooligosaccharides, (2) cellobiohydrolase, which acts in an "exo" manner releasing cellobiose units (beta-1,4 glucose-glucose disaccharide), and optionally (3) beta-glucosidase, releasing glucose monomer from short cellooligosaccharides (e.g., cellobiose).

A "naturally occurring" composition is one produced by a naturally occurring source and which comprises one or more cellobiohydrolase-type, one or more endoglucanase-type, and one or more beta-glucosidase components, wherein each of these component is found at the ratio produced by the source. A naturally occurring composition is one that is produced by an organism unmodified with respect to the cellulolytic enzymes such that the ratio of the component enzymes is unaltered from that produced by the native organism. A "non-naturally occurring" composition encompasses those compositions produced by: (1) combining component cellulolytic enzymes either in a naturally occurring ratio or non-naturally occurring, i.e., altered, ratio; or (2) modifying an organism to overexpress or underexpress one or more cellulolytic enzymes; or (3) modifying an organism such that at least one cellulolytic enzyme is deleted. Accordingly, in some embodiments, the whole cellulase preparation can have one or more of the various EGs and/or CBHs, and/or beta-glucosidase deleted or overexpressed.

In the present disclosure, the whole cellulase preparation can be from any microorganism that is useful for the hydrolysis of a cellulosic material. In some embodiments, the whole cellulase preparation is a filamentous fungal whole cellulase.

In some embodiments, the whole cellulase preparation is from an *Acremonium, Aspergillus, Chrysosporium, Emericella, Fusarium, Humicola, Mucor, Myceliophthora, Neurospora, Penicillium, Scytalidium, Thielavia, Tolypocladium,* or *Trichoderma* species.

In some embodiments, the whole cellulase preparation is an *Aspergillus aculeatus, Aspergillus awamori, Aspergillus foetidus, Aspergillus japonicus, Aspergillus nidulans, Aspergillus niger,* or *Aspergillus oryzae* whose cellulase. In another aspect, whose cellulase preparation is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarrochroum, Fusarium sporotrichioides, Fusarium sulphureum, Fusarium torulosum, Fusarium trichothecioides,* or *Fusarium venenatum* whose cellulase. In another aspect, the whole cellulase preparation is a *Humicola insolens, Humicola lanuginosa, Mucor miechei, Myceliophthora thermophila, Neurospora crassa, Penicillium purpurogenum, Penicillium funiculosum, Scytalidium thermophilum,* or *Thielavia terrestris* whole cellulase. In yet another aspect, the whole cellulase preparation is a *Trichoderma harzianum, Trichoderma koningii, Trichoderma longibrachiatum, Trichoderma reesei* (e.g. RL-P37 (Sheir-Neiss et al., Appl. Microbiol. Biotechnology, 20:46-53, 1984; and Montenecourt, Can., 1-20, 1987), QM9414 (ATCC No. 26921). NRRL 15209, ATCC 13631, 56764, 56466, 56767), or *Trichoderma viride,* e.g., ATCC 32098 and 32086, whole cellulase.

In some embodiments, the whole cellulase preparation is a *Trichoderma reesei* RutC30 whole cellulase, which is available from the American Type Culture Collection as *Trichoderma reesei* ATCC 56765. In some embodiments, the whole cellulase is *Penicillium funiculosum*, which is available from the American Type Culture Collection as *Penicillium funiculosum* ATCC Number: 10446.

The whole cellulase preparation may also be obtained from commercial sources. Examples of commercial cellulase preparations suitable for use in the present disclosure include, for example, CELLUCLAST™ and CELLIC™

(available from Novozymes A/S) and LAMINEX™ BG, INDIAGE™ 44L, PRIMAFAST™ 100, PRIMAFAST™ 200, SPEZYME™ CP, ACCELLERASE® 1000 and ACCELLERASE® 1500 (Danisco U.S. Inc., Genencor).

In the present disclosure, the whole cellulase preparation can be from any microorganism cultivation method known in the art resulting art the expression of enzymes capable of hydrolyzing a cellulosic material. Fermentation can include shake flask cultivation, small- or large-scale fermentation, such as continuous, batch, fed-batch, or solid state fermentation in laboratory or industrial fermenters performed in a suitable medium and under conditions allowing the cellulase to be expressed or isolated.

Generally, the microorganism is cultivated in a cell culture medium suitable for production of enzymes capable of hrydrolyzing a cellulosic material. The cultivation takes place in a suitable nutrient medium comprising carbon and nitrogen sources and inorganic salts, using procedures known in the art. Suitable culture media, temperature ranges and other conditions suitable for growth and cellulase production are known in the art. As a non-limiting example, the normal temperature range for the production of cellulases by *Trichoderma reesei* is 24° C. to 28° C.

Generally, the whole cellulase preparation is used as is produced by fermentation with no or minimal recovery and/or purification. For example, once cellulases are secreted by a cell, into the cell culture medium, the cell culture medium containing the cellulases can be used. In some embodiments the whole cellulase preparation comprises the unfractionated contents of fermentation material, including cell culture medium, extracellular enzymes and cells. Alternatively, the whole cellulase preparation can be processed by any convenient method, e.g., by precipitation, centrifugation, affinity, filtration or any other method known in the art. In some embodiments, the whole cellulase preparation can be concentrated, for example, and then used without further purification. In some embodiments the whole cellulase preparation comprises chemical agents that decrease cell viability or kills the cells. In some embodiments, the cells are lysed or permeabilized using methods known in the art.

The endoglucanase activity of the whole cellulase preparation may be determined using carboxymethyl cellulose (CMC) as a substrate. Determination of whole cellulase activity, measured in terms of CMC activity. This method measures the production of reducing ends created by the enzyme mixture acting on CMC wherein 1 unit is the amount of enzyme that liberates 1 μmol of product/minute (Ghose, Measurement of Cellulase Activities, Pure Appl. Chem., 59:257-268, 1987).

In certain aspects, the cellulase is a beta-glucosidase-enriched cellulase. Beta-glucosidase enhanced whole cellulases generally comprise beta-glucosidase and a whole cellulase preparation. However, it is to be understood that the beta-glucosidase enhanced whole cellulase compositions can be produced by recombinant means. For example, expressing beta-glucosidase in a microorganism capable of producing a whole cellulase. In some embodiments the beta-glucosidase enhanced whole cellulase composition comprises a whole cellulase preparation and beta-glucosidase. In specific embodiments, the beta-glucosidase enhanced whole cellulase composition comprises on a protein weight basis at least at least 5%, at least 7%, at least 10%, at least 15% or at least 20%, and up to 25%, 30%, 35%, up to 40%, or up to 50% beta-glucosidase.

IV. Methods of Producing Variant bgl1 Nucleic Acid Sequences

In one embodiment this disclosure provides for the expression of variant bgl1 genes under control of a promoter functional in a filamentous fungus. Therefore, this disclosure relies on routine techniques in the field of recombinant genetics (See, e.g., Sambrook et al., Molecular Cloning, A Laboratory Manual, 2nd ed., 1989; Kriegler, Gene Transfer and Expression: A Laboratory Manual, 1990; and Ausubel et al., eds., CURRENT PROTOCOLS IN MOLECULAR BIOLOGY, Greene Publishing and Wiley-Interscience, New York, 1994). Any method known in the art that can introduce mutations is contemplated by the present disclosure.

The present disclosure relates its the expression, purification and/or isolation and use of variant BGL1. These enzymes are preferably prepared by recombinant methods utilizing the bgl1 gene *H. jecorina*. The fermentation broth may be used with or without purification.

After the isolation and closing of the bgl1 gene from *H. jecorina*, other methods known in the art, such as site directed mutagenesis, are used to make the substitutions, additions or deletions that correspond to substituted amino acids in the expressed bgl1 variant. Again, site directed mutagenesis and other methods of incorporating amino acid changes in expressed proteins at the DNA level are known in the art (Sambrook et al., supra; and Ausubel et. al., supra).

DNA encoding an amino acid sequence variant of the *H. jecorina* BGL1 is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the *H. jecorina* BGL1.

Site-directed mutagenesis is a preferred method for preparing substitution variants. This technique is well known in the art (see, e.g., Carter et al. Nucleic Acids Res. 13:4431-4443, 1985; and Kunkel et al., Proc. Natl. Acad. Sci. USA 82:488; 1987). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting polypeptide, i.e., *H. jecorina* BGL1 (See, e.g., Higuchi, in PCR Protocols, pp. 177-183, Academic Press, 1990; Vallete et al., Nuc. Acids Res. 17:723-733, 1989; and Cadwell et al., PCR Methods and Applications, 2:28-33, 1992). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323, 198. The starting material is the plasmid (or other vector) comprising the starting polypeptide DNA to be mutated. The codon(s) in the starting DNA its be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a variant BGL1 can be determined, and a nucleic acid sequence encoding such amino acid sequence variant can be generated synthetically.

The variant BGL1 so prepared may be subjected to further modifications, often times depending on the intended use of the cellulase. Such modifications may involve further alteration of the amino acid sequence, fusion to heterologous polypeptide(s) and/or covalent modifications.

V. bgl1 Nucleic Acids and BGL1 Polypeptides

A. Variant bgl1 Nucleic Acids

The nucleic acid sequence for the wild type bgl1 is shown in SEQ ID NO:1. The disclosure encompasses a nucleic acid molecule encoding the variant beta-glucosidase described herein. The nucleic acid may be a DNA molecule. The disclosure further provides isolated, synthetic or recombinant nucleic acids comprising a nucleic acid sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid sequence encoding a variant beta-glucosidase described herein, over least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1350, 1900, 1950, 2000, or more residues.

The disclosure provides expression cassettes comprising a nucleic acid of the disclosure or a subsequence thereof. In one aspect, the expression cassette can comprise the nucleic acid operably linked its a promoter. The promoter can be a fungal, viral, bacterial, mammalian or plant promoter. The promoter can be a constitutive promoter an inducible promoter. In one aspect, the promoter is expressible in filamentous fungi, e.g., *Trichoderma reesei*. In specific embodiments, the promoter is from a filamentous fungus, e.g., the *Trichoderma reesei* cellobiohydrolase I ("CBHI") gene promoter.

The disclosure provides a recombinant cell (e.g., host cell) engineered to express a nucleic acid of the disclosure or an expression cassette of the disclosure. In certain aspects, the recombinant cell is a bacterial cell, a mammalian cell, a fungal cell, a yeast cell, an insect cell or a plant cell. In a specific aspect, the recombinant, cell is a filamentous fungal cell.

The disclosure provides transgenic plants comprising a nucleic acid of the disclosure or an expression cassette of the disclosure.

After DNA sequences that encode the BGL1 variants have been cloned into DNA constructs, the DNA is used to transform microorganisms. The microorganism to be transformed for the purpose of expressing a variant bgl1 according to the present disclosure may advantageously comprise a strain derived from *Trichoderma* sp. Thus, a preferred mode for preparing variant BGL1 cellulases according to the present disclosure comprises transforming a *Trichoderma* sp. host cell with a DNA construct comprising at least a fragment of DNA encoding a portion or all of the variant BGL1. The DNA construct will generally be functionally attached to a promoter. The transformed host cell is then grown under conditions so as to express the desired protein. Subsequently, the desired protein product may be purified to substantial homogeneity.

However, it may in fact be that the best expression vehicle for a given DNA encoding a variant BGL1 may differ from *H. jecorina*. Thus, it may be that it will be most advantageous to express a protein in a transformation host that bears phylogenetic similarity to the source organism for the variant BGL1. In an alternative embodiment, *Aspergillus niger* can be used as an expression vehicle. For a description of transformation techniques with *A. niger*, see WO 98/31821, the disclosure of which is incorporated by reference in its entirety.

Accordingly, the present description of an *Aspergillus* spp. expression system is provided for illustrative purposes only and as one option for expressing the variant BGL1 of the disclosure. One of skill in the art, however, may be inclined to express the DNA encoding variant BGL1 in a different host cell if appropriate and it should be understood that the source of the variant BGL1 should be considered in determining the optimal expression host. Additionally, the skilled worker in the field will be capable of selecting the best expression system for a particular gene through routine techniques utilizing the tools available in the art.

B. Variant BGL1 Polypeptides

The disclosure provides isolated, synthetic or recombinant, polypeptides comprising an amino acid sequence having at least about 80%, 81%, 82%, 83%, 84%, 85%, 86%, 87%, 86%, 89%, 90%, 91%, 92%, 93%, 94%, 95%, 96%, 97%, 98%, 99%, or more, or complete (100%) sequence identity to a polypeptide sequence of a variant beta-glucosidase over at least about 10, 15, 20, 25, 30, 35, 40, 45, 50, 55, 60, 65, 70, 75, 80, 85, 90, 95, 100, 125, 150, 175, 200, 225, 250, 275, 300, 325, 350 or more residues, or over the full length of the immature polypeptide or the full length mature polypeptide.

The variant beta-glucosidases of this disclosure have amino acid sequences that are derived from the amino acid sequence of a precursor BGL1. The amino acid sequence of the BGL1 variant differs from the precursor BGL1 amino acid sequence by the substitution, deletion or insertion of one or more amino acids of the precursor amino acid sequence. In a preferred embodiment, the precursor BGL1 is *Hypocrea jecorina* BGL1. The mature amino acid sequence of *H. jecorina* BGL1 is shown in Example 2 (SEQ ID NO:3). Thus, this disclosure is directed to BGL1 variants which contain amino acid residues at positions which are equivalent to the particular identified residue in *H. jecorina* BGL1. A residue (amino acid) of an BGL1 homolog is equivalent to a residue of *Hypocrea jecorina* BGL1 if it is either homologous (i.e., corresponding in position in either primary or tertiary structure) or is functionally analogous to a specific residue or portion of that residue in *Hypocrea jecorina* BGL1 (i.e., having the same or similar functional capacity to combine, react, or interact chemically or structurally). As used herein, numbering is intended to correspond to that of the mature BGL1 amino acid sequence (SEQ ID NO:3).

Alignment of amino acid sequences to determine homology is preferably determined by using a "sequence comparison algorithm." Optimal alignment of sequences for comparison can be conducted, e.g., by the local homology algorithm of Smith & Waterman. Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr. Madison, Wis.), or by visual inspection, Visual, inspection may utilize graphics packages such as, for example, MOE by Chemical Computing Group, Montreal Canada.

An example of an algorithm that is suitable for determining sequence similarity is the BLAST algorithm, which is described in Altschul, et al., J. Mol. Biol. 215:403-410 (1990). Software for performing BLAST analyses is publicly available through the National Center for Biotechnology Information (www.ncbi.nlm.nih.gov). This algorithm involves first identifying high scoring sequence pains (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when; the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915, 1989) alignments (B) of 50, expectation (E) of 10, M'5, N'-4, and a comparison of both strands.

The BLAST algorithm then performs a statistical analysis of the similarity between two sequences (see, e.g. Karlin and Altschul, Proc. Nat'l Acad. Sci. USA 90:5873-5787, 1993). One measure of similarity provided by the BLAST algorithm is the smallest sum probability (P(N)), which provides as indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

For purposes of the present disclosure, the degree of identity may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman and Wunsch, Journal of Molecular Biology, 48, 443-45, 1970), using GAP with the following settings for polynucleotide sequence comparison: GAP creation penalty of 5.0 and GAP extension penalty of 0.3.

A structural alignment between a *T. reesei* BGL1 and other cellulases may be used to identify equivalent/corresponding positions in other cellulases having a moderate to high degree of homology, e.g., about 50%, 55%, 60%, 65%, 70%, 75%, 80%, 81%, 83%, 84%, 85%, 86%, 87%, 88%, 89%, 90%, 92%, 93%, 94%, 95%, 96%, 97%, 98%, or 99% with *T. reesei* BGL1 (SEQ ID NO: 3). One method of obtaining the structural alignment is to use the Pile Up program from the GCG package using default values of gap penalties, i.e., a gap creation penalty of 3.0 and gap extension penalty of 0.1. Other structural alignment methods include the hydrophobic cluster analysis (Gaboriaud et al., FEBS Letters, 224:149-155, 1987) and reverse threading (Huber and Torda, Protein Science, 7:142-149, 1998).

An exemplary alignment of the mature form of various reference beta-glucosidases is provided as FIG. 1. The reference cellulases include; TrireBGL1, *Hypocrea jecorina* (also known as *Trichoderma reesei*) Q12715 Beta-D-glucoside glucohydrolase 1 (SEQ ID NO:3); HananBglu, *Hansenula anomala* P06835 Beta-glucosidase (SEQ ID NO:4); PirspBglu, *Piromyces* sp. E2 Q875K3 Beta-glucosidase (SEQ ID NO:5); CocimBglu, *Coccidioides immnitis* O14424 Beta-glucosidase (SEQ ID NO:6); SacfiBglu2, *Saccharomycopsis fibuligera* Beta-glucosidase 2 (SEQ ID NO:7); SacfiBglu1, *Saccharomycopsis fibuligera* P22506 Beta-glucosidase 1 (SEQ ID NO:8); SeplyBglu, *Septoria lycopersici* Q99324 Beta-1,2-D-glucosidase (SEQ ID NO:9); KurcaBglu, *Karaishia capsulata* Q12653 Beta-glucosidase (SEQ ID NO:10); TrireBGL7, *Trichoderma reesei* Q7Z9M0 Beta-glucosidase 7 (SEQ ID NO:11); UrofaBglu, *Uromyces fabae* Q70KQ7 Beta glucosidase (SEQ ID NO:12); AspteBglu, *Aspergillus terreus* (strain NIH 2624/FGSC A1156) Q0CEF3 Beta-glucosidase (SEQ ID NO:13); ChaglBglu, *Chaetomium globosum* Q2GZ54 Putative beta-glucosidase (SEQ ID NO:14); TrireBGL3, *Trichoderma reesei* Q7Z9M5 Beta-glucosidase 3 (SEQ ID NO:15); PenbrBGL, *Penicillium brasilianum* GH3 Beta-glucosidase (SEQ ID NO:16); PerspBglu, *Periconia* sp. BCC 2871 A9UIG0 Beta-glucosidase (SEQ ID NO:17) PhaavBglu, *Phaeosphaeria avenaria* Q9P879 Beta-glucosidase (SEQ ID NO:18); AspfuBGL, *Aspergillus fumigatus* B0XPE1 Beta-glucosidase (SE ID NO:19); AsporBGL1, *Aspergillus oryzae* Q2UUD6 Beta-glucosidase (SEQ ID NO:20); AspacBGL1, *Aspergillus aculeatus* Beta-glucosidase (SEQ ID NO:21); AspniBGL, *Aspergillus niger* Q9P8F4 Beta-glucosidase (SEQ ID NO:22); TalemBglu, *Talaromyces emersonii* Q8TG18 Beta-glucosidase (SEQ ID NO:23); TheauBGL, *Thermoascus aurentiacus* Beta-glucosidase (SEQ ID NO:24). Sequences were aligned using the ClustalW and MUSCLE multiple sequence alignment algorithms. A matrix showing the percent identity of beta-glucosidases of the sequence alignment of FIG. 1 is provided in Table 1. Numbers shown in bold indicate percentage identity with *T. reesei* BGL1.

TABLE 1

Beta-Glucosidase Percent Identity Matrix*

| SEQ ID NO | 04 | 05 | 06 | 07 | 08 | 09 | 10 | 11 | 12 | 13 | 04 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|
| 04 HumanBglu | + | 21 | 29 | 37 | 37 | 30 | 31 | 28 | 29 | 30 | 30 | 30 | 32 | 35 | 33 | 36 | 34 | 36 | 36 | 35 | 34 | 35 |

TABLE 1-continued

Beta-Glucosidase Percent Identity Matrix*

| SEQ ID NO | 04 | 05 | 06 | 07 | 08 | 09 | 10 | 11 | 12 | 13 | 04 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|
| 05 PirspBglu | | + | 22 | 25 | 25 | 25 | 24 | 26 | 26 | 32 | 31 | 31 | 26 | 26 | 27 | 26 | 26 | 26 | 27 | 27 | 26 | 27 |
| 06 CcimBglu | | | + | 35 | 36 | 30 | 30 | 29 | 33 | 33 | 33 | 32 | 34 | 36 | 37 | 36 | 38 | 39 | 38 | 38 | 37 | 38 |
| 07 SacfiBglu2 | | | | + | 32 | 32 | 34 | 33 | 33 | 35 | 34 | 33 | 38 | 39 | 39 | 39 | 39 | 39 | 41 | 40 | 38 | 38 |
| 08 SacfiBglu1 | | | | | + | 33 | 34 | 33 | 33 | 35 | 34 | 34 | 39 | 40 | 40 | 39 | 40 | 40 | 40 | 40 | 40 | 39 |
| 09 SeplyBglu | | | | | | + | 37 | 38 | 34 | 39 | 39 | 38 | 35 | 37 | 37 | 36 | 37 | 38 | 37 | 37 | 38 | 37 |
| 10 KurcaBglu | | | | | | | + | 47 | 32 | 37 | 35 | 36 | 35 | 36 | 38 | 38 | 36 | 37 | 37 | 37 | 38 | 38 |
| 11 TrireBGL7 | | | | | | | | + | 31 | 38 | 38 | 37 | 33 | 35 | 36 | 36 | 36 | 34 | 37 | 36 | 37 | 36 |
| 12 UrofaBglu | | | | | | | | | + | 38 | 35 | 34 | 34 | 35 | 35 | 36 | 36 | 36 | 36 | 36 | 37 | 36 |
| 13 AspteBglu | | | | | | | | | | + | 58 | 58 | 41 | 40 | 41 | 41 | 40 | 40 | 41 | 39 | 41 | 41 |
| 03 TrireBGL1 | | | | | | | | | | | + | 64 | 37 | 38 | 39 | 38 | 38 | 37 | 38 | 37 | 38 | 38 |
| 14 ChaglBglu | | | | | | | | | | | | + | 38 | 38 | 38 | 36 | 37 | 36 | 36 | 36 | 37 | 37 |
| 15 TrireBGL3 | | | | | | | | | | | | | + | 56 | 56 | 53 | 55 | 53 | 55 | 54 | 55 | 57 |
| 16 PenbrBGL | | | | | | | | | | | | | | + | 58 | 56 | 57 | 55 | 57 | 56 | 58 | 58 |
| 17 PerspBglu | | | | | | | | | | | | | | | + | 73 | 58 | 57 | 59 | 58 | 60 | 61 |
| 18 PhaavBglu | | | | | | | | | | | | | | | | + | 56 | 57 | 59 | 58 | 58 | 59 |
| 19 AspfuBGL | | | | | | | | | | | | | | | | | + | 76 | 76 | 75 | 68 | 70 |
| 20 AsporBGL1 | | | | | | | | | | | | | | | | | | + | 79 | 77 | 68 | 69 |
| 21 AspacBGL1 | | | | | | | | | | | | | | | | | | | + | 82 | 67 | 68 |
| 22 AspniBGL | | | | | | | | | | | | | | | | | | | | + | 66 | 68 |
| 23 TalemBglu | | | | | | | | | | | | | | | | | | | | | + | 73 |
| 24 TheauBGL | | | | | | | | | | | | | | | | | | | | | | + |

*Numbers in the top row and left column correspond to the SEQ ID NOS of the aligned sequences of FIG. 1.
(+)indicates 100% amino acid sequence identity.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated its all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.

VI. Expression of Recombinant bgl1 Variants

The disclosure further provides methods of producing recombinant beta-glucosidase variants comprising the steps of: (a) culturing a host cell engineered to express a beta-glucosidase variant of the disclosure; and (b) recovering the beta-glucosidase variant. Step (b) can entail recovering fermentation broth comprising the beta-glucosidase variant, and optionally can include further purification step(s).

The methods of the disclosure rely on the use cells to express variant bgl1, with no particular method of bgl1 expression required. The variant BGL1 is preferably secreted from the cells. The disclosure provides host cells which have been transduced, transformed or transfected with an expression vector comprising a variant BGL1-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell or yeast cell is transfected with an expression cassette having a promoter or biologically active promoter fragment or one or more (e.g., a series of) enhancers which functions in the host cell line, operably linked to a DNA segment encoding variant BGL1, such that variant bgl1 is expressed in the cell line.

A. Nucleic Acid Constructs/Expression Vectors

Natural or synthetic polynucleotide fragments encoding variant BGL1 ("BGL1-encoding nucleic acid sequences") may be incorporated into heterologous nucleic acid constructs or vectors, capable of introduction into, and replication in, a filamentous fungal or yeast cell. The vectors and methods disclosed herein are suitable for use in host cells for the expression of variant BGL1. Any vector may be used as long as it is replicable and viable in the cells into which it is introduced. Large numbers of suitable vectors and promoters are known to those of skill in the art, and are commercially available. Cloning and expression vectors are also described in Sambrook et al., 1989, Ausubel F M et al., 1989, and Strathern et al., The Molecular Biology of the Yeast *Saccharomyces*, 1981, each of which is expressly incorporated by reference herein. Appropriate expression vectors for fungi are described in van den Hondel et al, (1991) In: Bennett and Lasure (eds.) More Gene Manipulations in Fungi, Academic Press, pp. 396-428. The appropriate DNA sequence may be inserted into a plasmid or vector (collect very referred to herein as "vectors") by a variety of procedures. In general, the DNA sequence is inserted into an appropriate restriction endonuclease site(s) by standard procedures. Such procedures and related subcloning procedures are deemed to be within the scope of knowledge of those skilled in the art.

Recombinant filamentous fungi comprising the coding sequence for variant bgl1 may be produced by introducing a heterologous nucleic acid construct comprising the variant bgl1 coding sequence into the cells of a selected strain of the filamentous fungi.

Once the desired form of a variant bgl1 nucleic acid sequence is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

A selected variant bgl1 coding sequence may be inserted into a suitable vector according to well-known recombinant techniques and used to transform filamentous fungi capable of bgl1 expression. Due to the inherent degeneracy of the genetic code, other nucleic acid sequences which encode substantially the same or a functionally equivalent amino acid sequence may be used to clone and express variant bgl1. Therefore it is appreciated that such substitutions in the coding region fall within the sequence variants covered by the present disclosure. Any and all of these sequence variants can be utilized in the same way as described herein for a parent BGL1-encoding nucleic acid sequence.

The present disclosure also includes recombinant nucleic acid constructs comprising one or more of the variant BGL1-encoding nucleic acid sequences as described above. The constructs comprise a vector, such as a plasmid or viral vector, into which a sequence of the disclosure has been inserted, in a forward or reverse orientation.

Heterologous nucleic acid constructs may include the coding sequence for variant bgl1, (i) in isolation; (ii) in combination with additional coding sequences; such as fusion protein or signal peptide coding sequences, where the bgl1 coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the bgl1 coding sequence is a heterologous gene.

In one aspect of the present disclosure, a heterologous nucleic acid construct is employed to transfer a variant BGL1-encoding nucleic acid sequence into a cell in vitro, with established filamentous fungal and yeast lines preferred. For long-term, production of variant BGL1 stable expression is preferred. It follows that any method effective to generate stable transformants may be used is practicing the disclosure.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1.alpha. promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular filamentous fungus for expression purposes. It is operably linked to DNA sequence encoding a variant BGL1 polypeptide. Such linkage comprises positioning of the promoter with respect to the initiation codon of the DNA sequence encoding the variant BGL1 polypeptide in the disclosed expression vectors. The promoter sequence contains transcription and translation control sequence which mediate the expression of the variant BGL1 polypeptide. Examples include the promoters from the *Aspergillus niger*, *A. awamori* or *A. oryzae* glucoamylase, alpha-amylase, or alpha-glucosidase encoding genes; the *A. nidulans* gpdA or trpC Genes; the *Neurospora crassa* cbh1 or trp1 genes; the *A. niger* or *Rhizomucor miehei* aspartic proteinase encoding genes; the *H. jecorina* (*T. reesei*) bgl1, cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *T. reesei*, amdS from *A. nidulans*, pyr4 from *Neurospora crassa* or *T. reesei*, pyrG from *Aspergillus niger* or *A. nidulans*. Additional exemplary selectable marked include, but are not limited to trpc, trp1, oliC31, niaD or leu2, which are included in heterologous nucleic acid constructs used to transform a mutant strain such as trp⁻, pyr⁻, leu⁻ and the like.

Such selectable markers confer to transformants the ability to utilize a metabolite that is usually not metabolized by the filamentous fungi. For example, the amdS gene from *H. jecorina* which encodes the enzyme acetamidase that allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Exemplary plasmids include pUC18, pBR322, pRAX and pUC100. The pRAX plasmid contains AMA1 sequences from *A. nidulans*, which make it possible to replicate in *A. niger*.

The practice of the present disclosure will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, Animal Cell Culture, 1987; Ausubel, et al., 1993; and Coligan et al., Current Protocols in Immunology, 1991.

B. Host Cells and Culture Conditions for BGL1 Production (i) Filamentous Fungi

Thus, the present disclosure provides filamentous fungi comprising cells which have been modified, selected and cultured in a manner effective to result is variant BGL1 production or expression relative to the corresponding non-transformed parental fungi.

Examples of species of parental filamentous fungi that may be treated and/or modified for variant bgl1 expression include, but are not limited to *Trichoderma*, e.g., *Trichoderma reesei*, *Trichoderma longibrachiatum*, *Trichoderma viride*, *Trichoderma koningii*, *Penicillium* sp. *Humicola* sp., including *Humicola insolens*, *Aspergillus* sp. *Chrysoporium* sp., *Fusarium* sp. *Hypocrea* sp., and *Emericella* sp.

Cells expressing bgl1 are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert et al., Academic Press, pp. 71-86, 1988 and Ilmen et al., Appl. Environ. Microbiol. 63:1298-1306, 1997. Culture conditions are also standard, e.g., cultures are incubated at 28° C. in shaker cultures or fermenters until desired levels of bgl1 expression are achieved.

Preferred culture conditions for a given filamentous fungus may be found in the scientific literature and/or from the source of the fungi such as the American Type Culture Collection (ATCC; www.atcc.org/). After fungal growth has been established, the cells are exposed to conditions effective to cause or permit the expression of variant bgl1.

In cases where a BGL1 encoding sequence is under the control of an inducible promoter, the inducing agent, e.g., a sugar, metal salt or antibiotics, is added to the medium at a concentration elective to induce bgl1 expression.

In one embodiment the strain comprises *Aspergillus niger*, which is a useful strain for obtaining overexpressed protein. For example *A. niger* var *awamori* dgr246 is known to secrete elevated amounts of secreted cellulases (Goedegebuur et. al., Curr. Genet (2002) 41: 89-98). Other strains of a *Aspergillus niger* var *awamori* such as GCDAP3, GCDAP4 and GAP3-4 are known (Ward et al., 1993, Appl. Microbiol. Biotechnol. 39:738-743).

In another embodiment the strain comprises *Trichoderma reesei*, which is a useful strain for obtaining overexpressed protein. For example, RL-P37, described by Sheir-Neiss, et al., Appl. Microbiol. Biotechnol. 20:46-53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in overexpressing variant bgl1.

Where it is desired to obtain the variant BGL1 in the absence of potentially detrimental native cellulolytic activity, it is useful to obtain a *Trichoderma* host cell strain which has had one or more cellulase genes deleted prior to introduction of a DNA construct or plasmid containing the DNA fragment encoding the variant BGL1. Such strains may be prepared by the method disclosed in U.S. Pat. No. 5,246,853 and WO 92/06209, which disclosures are hereby incorporated by reference. By producing a variant BGL1 cellulase in a host microorganism that is missing one or more cellulase genes, the identification and subsequent purification procedures are simplified. Any gene from *Trichoderma* sp. which has been cloned can be deleted, for example, the bgl1, cbh1, cbh2, egl1, and egl2 genes as well as those encoding EG III and/or EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed microorganism. Any selectable marker gene that is expressed in the selected microorganism will be suitable. For example, with *Aspergillus* sp., the selectable marker is chosen so that the presence of the selectable marker in the transformants will not significantly affect the properties thereof. Such a selectable marker may be a gene that encodes as assayable product. For example, a functional copy of a *Aspergillus* sp. gene may be used which, if lacking in the host strain, results in the host strain displaying an auxotrophic phenotype. Similarly, selectable markers exist for *Trichoderma* sp.

In one embodiment, a pyrG⁻ derivative strain of *Aspergillus* sp. is transformed with a functional pyrG gene, which thus provides a selectable marker for transformation. A pyrG⁻ derivative strain may be obtained by selection of *Aspergillus* sp. strains that are resistant to fluoroorotic acid (FOA). The pyrG gene encodes orotidine-5'-monophosphate decarboxylase, an enzyme required for the biosynthesis of uridine. Strains with an intact pyrG gene grow in a medium lacking uridine but are sensitive to fluoroorotic acid. It is possible to select pyrG⁻ derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges and Barreau, Curr. Genet. 19:359-365, 1991; and van Hartingsveldt et al., Mol. Gen. Genet. 206:71-75, 1986). Selection of derivative strains is easily performed using the FOA resistance technique referred to above, and thus, the pyrG gene is preferably employed as a selectable marker.

In a second embodiment, a pyr4⁻ derivative strain of *Hypocrea* sp. (*Trichoderma* sp.) is transformed with a functional pyr4 gene, which thus provides a selectable marker for transformation. A pyr4⁻ derivative strain may be obtained by selection of *Hyprocrea* sp. (*Trichoderma* sp.) strains that are resistant to fluoroorotic acid (FOA). The pyr4 gene encodes orotidine-5'-monophosphate decarboxylase, an enzyme acquired for the biosynthesis of uridine. Strains with an intact pyr4gene grow in a medium lacking uridine but are sensitive to fluoroorotic acid. It is possible so select pyr4⁻ derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges and Barreau, 1991). Selection of derivative strains is easily performed using the FOA resistance technique referred to above, and thus, the pyr4 gene is preferably employed as a selectable marker.

To transform pyrG⁻ *Aspergillus* sp. or pyr4⁻ *Hyprocrea* sp. (*Trichoderma* sp.) so as to be lacking in the ability to express one or more cellulase genes, a single DNA fragment comprising a disrupted or deleted cellulase gene is then isolated from the deletion plasmid and used to transform an appropriate pyr⁻ *Aspergillus* or pyr⁻ *Trichoderma* host. Transformants are then identified and selected based on their ability to express the pyrG or pyr4, respectively, gene product and thus compliment the uridine auxotrophy of the host strain. Southern blot analysis is then carried out on the resultant transformants to identify and confirm a double crossover integration event that replaces part or all of the coding region of the genomic copy of the gene to be deleted with the appropriate pyr selectable markers.

Although the specific plasmid vectors described above relate to preparation of pyr⁻ transformants, the present, disclosure is not limited to these vectors. Various genes can be deleted and replaced in the *Aspergillus* sp. or *Hyprocrea* sp. (*Trichoderma* sp.) strain using the above techniques. In addition, any available selectable markers can be used, as discussed above. In fact, any host, e.g., *Aspergillus* sp. or *Hyprocrea* sp., gene that has been cloned, and thus identified, can be deleted front the genome using the above described strategy.

As stated above, the host strains used may be derivatives of *Hyprocrea* sp. (*Trichoderma* sp.) that lack or have a nonfunctional gene or genes corresponding to the selectable marker chosen. For example, if the selectable marker of pyrG is chosen for *Aspergillus* sp. then a specific pyrG⁻ derivative strain, is used as a recipient in the transformation procedure. Also, for example, if the selectable marker of pyr4 is chosen for a *Hyprocrea* sp., then a specific pyr4⁻ derivative strain is used as a recipient in the transformation procedure. Similarly, selectable markers comprising *Hyprocrea* sp. (*Trichoderma* sp.) genes equivalent to the *Aspergillus nidulans* genes amdS, argB, trpC, niaD may be used. The corresponding recipient strain must therefore be a derivative strain such as argB⁻, trpC⁻, niaD⁻, respectively.

DNA encoding the BGL1 variant is then prepared for insertion into an appropriate microorganism. According to the present disclosure, DNA encoding a BGL1 variant comprises the DNA necessary to encode for a protein that has functional cellulolytic activity. The DNA fragment encoding the BGL1 variant may be functionally attached to a fungal promoter sequence, for example, the promoter of the glaA gene in *Aspergillus* or the promoter of the cbh1 or egl1 genes in *Trichoderma*.

If is also contemplated that more than one copy of DNA encoding a BGL1 variant may be recombined into the strain to facilitate overexpression. The DNA encoding the BGL1 variant may be prepared by the construction of an expression vector carrying the DNA encoding the variant. The expression vector carrying the inserted DNA fragment encoding the BGL1 variant may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene-coding region, and terminator sequence all originate from the gene to be expressed. Gene truncation may be obtained where desired by deleting undesired DNA sequences (e.g., coding for unwanted domains) so leave the domain to be expressed under control of its own transcriptional and translational regulatory sequences. A selectable marker may also be contained on the vector allowing the selection for integration into the host of multiple copies of the novel gene sequences.

The second type of expression vector is preassembled and contains sequences required for high-level transcription and a selectable marker. It is contemplated that the coding region for a gene or part thereof can be inserted into this general-purpose expression vector such that it is under the transcriptional control of the expression cassette promoter and terminator sequences.

For example, in *Aspergillus*, pRAX is such a general-purpose expression vector. Genes or part thereof can be inserted downstream of the strong glaA promoter.

For example, in *Hypocrea*, pTREX is such a general-purpose expression vector. Genes or part thereof can be inserted downstream of the strong cbh1 promoter.

In the vector, the DNA sequence encoding the BGL1 variant of the present disclosure should be operably linked to transcriptional and translational sequences, i.e., a suitable promoter sequence and signal sequence in reading frame to the structural gene. The promoter may be any DNA sequence that shows transcriptional activity in the host cell and may be derived from genes encoding proteins either homologous or heterologous to the host cell. An optional signal peptide provides for extracellular production of the BGL1 variant. The DNA encoding the signal sequence is preferably that which is naturally associated with the gene to be expressed, however the signal sequence from any suitable source, for example an exo-cellobiohydrolase or endoglucanase from *Trichoderma*, is contemplated in the present disclosure. The procedures used to ligate the DNA sequences coding for the variant BGL1 of the present disclosure with the promoter, and insertion into suitable vectors are well known in the art.

The DNA vector or construct described above may be introduced in the host cell in accordance with known techniques such as transformation, transfection, microinjection, microporation, biolistic bombardment and the like.

In the preferred transformation technique, it must be taken into account that the permeability of the cell wall to DNA in *Hyprocrea* sp. (*Trichoderma* sp.) is very low. Accordingly, uptake of the desired DNA sequence, gene or gene fragment is at best minimal. There are a number of methods to increase the permeability of the *Hyprocrea* sp. (*Trichoderma* sp.) cell wall in the derivative strain (i.e., lacking a functional gene corresponding to the used selectable marker) prior to the transformation process.

It is understood that in certain circumstances higher or more efficient expression may be achieved by chromosomal integration, as compared to using expression using plasmids. Expression by chromosomal integration is also contemplated herein.

The preferred method in the present disclosure to prepare *Aspergillus* sp. or *Hyprocrea* sp. (*Trichoderma* sp.) for transformation involves the preparation of protoplasts from fungal mycelium (See Campbell et al., Curr. Genet. 16:53-56; 1989). The mycelium can be obtained from germinated vegetative spores. The mycelium is treated with art enzyme(s) that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of the DNA into the host strain, (*Aspergillus* sp. or *Hyprocrea* sp. (*Trichoderma* sp.)), is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 mM Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the host cell, by way of example either *Aspergillus* sp. or *Hyprocrea* sp. strain, and the plasmid DNA is transferred to the nucleus. This fusion frequently leaves multiple copies of the plasmid DNA integrated into the host chromosome.

Usually a suspension containing the *Aspergillus* sp. protoplasts or cells that have been subjected to a permeability treatment at a density of $10^5$ to $10^6$/mL, preferably 2-$10^5$/mL are used in transformation. Similarly, a suspension containing the *Hyprocrea* sp. (*Trichoderma* sp.) protoplasts or cells that have been subjected to a permeability treatment at a density of $10^8$ to $10^9$/mL, preferably 2 times $10^8$/mL are used in transformation. A volume of 100 μL of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, if is preferable to add about 0.25 volumes to the protoplast suspension. Additives such as dimethyl, sulfoxide, heparin, spermidine, potassium chloride and the like may also be added to the uptake solution and aid in transformation.

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated either at room temperature or on ice before the addition of a sorbitol and $CaCl_2$ solution. The protoplast suspension is then further added to molten aliquots of a growth medium. This growth medium permits the growth of transformants only. Any growth medium can be used in the present disclosure that is suitable to grow the desired transformants. However, if pyr+ transforming are being selected it is preferable to use a growth medium that contains no uridine. The subsequent colonies are transferred and purified on a growth medium depleted of uridine.

At this stage, stable transformants may be distinguished from unstable transformants by their faster growth rate and, in *Trichoderma*, for example, the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow or selective medium lacking uridine.

In a particular embodiment of the above method, the BGL1 variant(s) are recovered in active form from the host cell after growth in liquid media as a result of the appropriate post translational processing of the BGL1 variant.

(ii) Yeast

The present disclosure also contemplates the use of yeast as a host cell for BGL1 production. Several other genes encoding hydrolytic enzymes have been expressed in various strains of the yeast *S. cerevisiae*. These include sequences encoding for two endoglucanases (Penttila et al. Yeast, 3:175-185, 1987), two cellobiohydrolases (Penttila et al., Gene, 63: 103-112, 1988) and one beta-glucosidase from *Trichoderma reesei* (Cummings and Fowler, Curr. Genet. 29:227-233, 1996), a xylanase from *Aureobasidlium pullulans* (Li and Ljungdahl, Appl. Environ. Microbiol. 62:209-213, 1996), an alpha-amylase from wheat (Rothstein et al., Gene 55:353-356, 1987), etc. In addition, a cellulase gene cassette encoding the *Butyrivibrio fibrisolvens* endo-[beta]-1,4-glucanase (END1), *Phanerochaete chrysoporium* cellobiohydrolase (CBH1), the *Ruminococcus flavefaciens* cellodextrinase (CEL1) and the *Endomyces fibrilizer* cellobiase (BGL1) was successfully expressed in a laboratory strain of *S. cerevisiae* (Van Rensburg et al., Yeast, 14:67-76, 1998).

C. Introduction of a BGL1-Encoding Nucleic Acid Sequence into Host Cells.

The disclosure further provides cells and cell compositions which have been genetically modified to comprise an exogenously provided variant BGL1-encoding nucleic acid sequence. A parental cell or cell line may be genetically modified (i.e., transduced, transformed or transacted) with a cloning vector or an expression vector. The vector may be, for example, in the form of a plasmid a viral particle, a phage, etc, as further described above.

The methods of transformation of the present disclosure may result in the stable integration of all or part of the transformation vector into the genome of the filamentous fungus. However, transformation resulting in the maintenance of a self-replicating extrachromosomal transformation vector is also contemplated.

Many standard transfection methods can be used to produce *Trichoderma reesei* cell lines that express large quantities of the heterologous protein. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164, for *Aspergillus* Yelton, Hamer and Timberlake, 1984, Proc. Natl. Acad. Sci. USA 81: 1470-1474, for *Fusarium* Bajar, Podila and Kolattukudy, 1991, Proc. Natl. Acad. Sci. USA 88: 8202-8212, for *Streptomyces* Hopwood et al., 1985, The John Innes Foundation, Norwich, UK and for *Bacillus* Brigidi, DeRossi, Bertarini, Riccardi and Matteuzzi, 1990, FEMS Microbiol. Lett. 55: 135-138).

Other methods for introducing a heterologous nucleic acid construct (expression vector) into filamentous fungi (e.g., *H. jecorina*) include, but are not limited to the use of a particle or gene gun, permeabilization of filamentous fungi cells walls prior to the transformation process (e.g., by use of high concentrations of alkali, e.g., 0.05 M 0.4 M $CaCl_2$ or lithium acetate), protoplast fusion or *Agrobacterium* mediated transformation. An exemplary method for transformation of filamentous fungi by treatment of protoplasts or spheroplasts with polyethylene glycol and CaCl$_2$ is described (Campbell et al., Curr. Genet. 16:53-56, 1989; and Penttila et al., Gene, 63:11-22, 1988).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the heterologous gene.

In addition, heterologous nucleic acid constructs comprising a variant BGL1-encoding nucleic acid sequence can be transcribed in vitro, and the resulting RNA introduced into the host cell by well-known methods, e.g., by injection.

The disclosure further includes novel and useful transformants of filamentous fungi such as *H. jecorina* and *A. niger* for use in producing fungal cellulase compositions. The disclosure includes transformants of filamentous fungi especially fungi comprising the variant bgl1 coding sequence, or deletion of the endogenous bgl1 coding sequence.

Following introduction of a heterologous nucleic acid construct comprising the coding sequence for a variant bgl1 the genetically modified cells can be cultured in conventional nutrient media modified as appropriate for activating promoters, selecting transformants or amplifying expression of a variant BGL1-encoding nucleic acid sequence. The culture conditions, such as temperature, pH and site like, are those previously used for the host cell selected for expression, and will be apparent to those skilled in the art.

The progeny of cells into which such heterologous nucleic acid constructs have been introduced are generally considered to comprise the variant BGL1-encoding nucleic acid sequence found in the heterologous nucleic acid construct.

The disclosure further includes novel and useful transformants of filamentous fungi such as *H. jecorina* for use in producing fungal cellulase compositions. *Aspergillus niger* may also be used in producing the BGL1. The disclosure includes transformants of filamentous fungi especially fungi comprising the variant blg1 coding sequence, or deletion of the endogenous bgl1 coding sequence.

Stable transformants of filamentous fungi can generally be distinguished from unstable transformants by their faster growth rate and, in *Trichoderma*, for example, the formation of circular colonies with a smooth rather than ragged outline on solid culture medium. Additionally, in some cases, a further test of stability can be made by growing the transformants on solid non-selective medium, harvesting the spores from this culture medium and determining the percentage of these spores which will subsequently germinate and grow on selective medium.

VII. Isolation and Purification of Recombinant BGL1 Protein

In general, a variant BGL1 protein produced its cell culture is secreted into the medium and may be purified or isolated, e.g., by removing unwanted components from the cell culture medium. However, in some cases, a variant BGL1 protein may be produced in a cellular form necessitating recovery from a cell lysate. In such cases the variant BGL1 protein is purified from the cells in which it was produced using techniques routinely employed by those of skill in the art. Examples include, but are not limited to, affinity chromatography (Tilbeurgh et al., FEBS Lett. 16:215, 1984), ion-exchange chromatographic methods (Goyal et al., Bioresource Technol. 36:37-50, 1991; Fliess et al., Eur. J. Appl. Microbiol. Biotechnol. 17:314-318, 1983; Bhikbabbai et al., J. Appl. Biochem. 6:336-345, 1984; Ellouz et al., J. Chromatography 396:307-317, 1987), including ion-exchange using materials with high resolution power (Medve et. al., J. Chromatography A 808:153-165, 1998), hydrophobic interaction chromatography (Tomaz and Queiroz, J. Chromatography A 865:123-128, 1999), and two-phase partitioning (Brumbauer, et al., Bioseparation 7:287-295, 1999).

Typically, the variant BGL1 protein is fractionated to segregate proteins having selected properties, such as binding affinity to particular binding agents, e.g., antibodies or receptors; or which have a selected molecular weight range, or range of isoelectric points.

Once expression of a given variant BGL1 protein is achieved, the BGL1 protein thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. Various methods of protein purification may be employed and such methods are known in the art and described e.g. in Deutscher, Methods in Enzymology, 182:779, 1990); Scopes, Methods Enzymol. 90:479-91, 1982. The purification step(s) selected will depend, e.g., on the nature of the production process used and the particular protein produced.

VIII. Utility of bgl1 and BGL1

It can be appreciated that the variant bgl1 nucleic acids, the variant BGL1 protein and compositions comprising variant BGL1 protein activity find utility in a wide variety applications, some of which are described below.

The present disclosure also provides variant beta-glucosidase and enzyme blends that break down lignocellulose material. Such enzyme combinations or mixtures include a multi-enzyme composition that contains at least one variant beta-glucosidase of the present disclosure. Synergistic enzyme combinations and related methods are contemplated.

Due to the complex nature of most biomass sources, which can contain cellulose, hemicellulose, pectin, lignin, protein, and ash, among other components, in certain aspects enzyme blends of the disclosure can contain enzymes with a range of substrate specificities that work together to degrade biomass into fermentable sugars in the most efficient manner. One example of a multi-enzyme complex for lignocellulose saccharification is a mixture of cellobiohydrolase(s), xylanase(s), endoglucanase(s), beta-glucosidase(s), beta-xylosidase(s), and, optionally, accessory proteins.

Accordingly, the disclosure provides compositions (including products of manufacture, enzyme ensembles, or "blends") comprising a mixture (or "blend") of xylan-hydrolyzing, hemicellulose- and/or cellulose-hydrolyzing enzymes comprising at least one, several or all of a cellulase, a glucanase; a cellobiohydrolase; an L-alpha-arabinofuranosidase; a xylanase; optionally a beta-glucosidase; a beta-xylosidase, preferably including at least one a beta-glucosidase variant of the disclosure. The present disclosure provides enzyme blends that are non-naturally occurring. As used herein, the term "blend" refers to: (1) a composition made by combining component enzymes, whether in me form of fermentation broth or partially or completely isolated or purified; (2) a composition produced by an organism modified to express one or more component enzymes; optionally, the organism can be also modified to delete one or more genes, optionally encoding proteins affecting xylan hydrolysis, hemicellulose hydrolysis and/or cellulose hydrolysis; (3) a composition made by combining component enzymes simultaneously, separately or sequentially during a saccharification or fermentation reaction; (4) an enzyme mixture produced in situ, e.g., during a saccharification or fermentation reaction; and (5) a combination of any or all of the above (1)-(4).

The term "fermentation broth" as used herein refers to an enzyme preparation produced by fermentation that undergoes no or minimal recovery and/or purification. For example, microbial cultures are grown to saturation, incubated under carbon-limiting conditions to allow protein synthesis (e.g., expression of enzymes) and once the enzyme is secreted into the cell culture medium, the fermentation broth can be used. The fermentation broth can contain the unfractionated or fractioned contents of the fermentation materials derived at the end of the fermentation. Typically, the fermentation broth is unfractionated and comprises the spent culture medium and cell debris present after the microbial cells (e.g., filamentous fungal cells). In some embodiments, the fermentation broth contains the spent cell culture medium, extracellular enzymes, and live or killed, microbial cells. In some embodiments, the fermentation broth is fractionated to remove the microbial cells, and comprises the spent cell culture medium and extracellular enzymes.

It is also to be understood that any of the enzymes described specifically herein can be combined with any one or more of the enzymes described herein or with any other available and suitable enzymes, to produce a multi-enzyme composition. The disclosure is not restricted or limited to the specific exemplary combinations listed below.

The disclosure provides methods and processes for biomass saccharification, using enzymes of the disclosure, including the enzyme mixtures or "blends" of the disclosure. The biomass can include any composition comprising cellulose and/or hemicellulose (lignocellulosic biomass also comprises lignin), e.g., seeds, grains, tubers, plant, waste or byproducts of food processing or industrial processing (e.g., stalks), corn (including cobs, stover, and the like), grasses (e.g., Indian grass, such as *Sorghastrum nutans*; or, switchgrass, e.g., *Panicum* species, such as *Panicum virgatum*), wood (including wood chips, processing waste), paper, pulp, recycled paper (e.g., newspaper). Other biomass materials include, but are not limited to, potatoes, soybean (rapeseed), barley, rye, oats, wheat, beets or sugar cane bagasse.

The disclosure provides methods of saccharification comprising contacting a composition comprising a xylan, hemicellulose, cellulose or a fermentable sugar with a beta-glucosidase of the disclosure, or a polypeptide encoded by a nucleic acid of the disclosure, or any one of the mixtures or "blends" or products of manufacture of the disclosure.

The saccharified biomass (e.g., lignocellulosic material processed by enzymes of the disclosure) can be made into bio-based products by fermentation by a microorganism and/or by chemical synthesis. As used herein, a fermenting microorganism can be any microorganism suitable for use in a desired fermentation process for the production bio-based products. Suitable non-limiting examples of fermenting microorganisms include filamentous fungi, yeast, and bacteria. In some embodiments, the saccharified biomass can be made it into a fuel (e.g., a biofuel such as a bioethanol, biobutanol, biomethanol, a biopropanol, a biodiesel, jet fuel or the like) by fermentation and/or by chemical synthesis. In some embodiments, the saccharified biomass can be made into a commodity chemical (e.g., ascorbic acid, isoprene, 1,3-propanediol, lipids, amino acids, proteins and enzymes by fermentation and/or by chemical synthesis.

In addition to saccharification of biomass, the enzymes and enzyme blends of the disclosure can be used in industrial, agricultural, food and feed and food and feed supplement processing processes. Exemplary applications for the enzymes are described below.

The enzymes of the disclosure can be used in wood, wood product, wood waste or by-product, paper, paper product, paper or wood pulp, Kraft pulp, or wood or paper recycling treatment or industrial process, e.g., any wood, wood pulp, paper waste, paper or pulp treatment or wood or paper drinking process. In one aspect, enzymes of the disclosure can be used to treat/pretreat paper pulp, or recycled paper or paper pulp, and the like. In one aspect, enzyme(s) of the disclosure are used to increase the "brightness" of the paper via their use in treating/pretreating paper pulp, or recycled paper or paper pulp, and the like. The higher the grade of paper, the greater the brightness; paper brightness can impact the scan capability of optical scanning equipment; thus, the enzymes and processes of the disclosure can be used to make high grade, "bright" paper for, e.g., use in optical scanning equipment, including inkjet, laser and photo printing quality paper. The enzymes of the disclosure can be used to process or treat any cellulosic material, e.g., fibers from wood, cotton, hemp, flax or linen. In one aspect, the disclosure provides wood, wood pulp, paper, paper pulp, paper waste or wood or paper recycling treatment processes using an enzyme of the disclosure.

Enzymes of the disclosure can be used for drinking printed wastepaper, such as newspaper, or for drinking noncontact-printed wastepaper, e.g., xerographic and laser-printed paper, and mixtures of contact and noncontact-printed wastepaper (as described in U.S. Pat. Nos. 6,767,728 and 6,426,200; and Neo, J. Wood Chem. Tech. 6:147, 1986). Enzymes of the disclosure can be used in processes for the production of xylose from a paper-grade hardwood pulp by extracting xylan contained in pulp into a liquid phase, subjecting the xylan contained in the obtained liquid phase to conditions sufficient to hydrolyze xylan to xylose, and recovering the xylose, where the extracting step includes at least one treatment of an aqueous suspension of pulp or an alkali-soluble material an enzyme enzyme, as described in, e.g., U.S. Pat. No. 6,512,110. Enzymes of the disclosure can be used in processes for dissolving pulp from cellulosic fibers such as recycled paper products made front hardwood fiber, a mixture of hardwood fiber and softwood fiber, waste paper, e.g., from unprinted envelopes, de-inked envelopes, unprinted ledger paper, de-inked ledger paper, and the like, as described in, e.g., U.S. Pat. No. 6,254,722.

The disclosure provides methods of treating fibers and fabrics using one or more enzymes of the disclosure. The enzymes can be used in any fiber- or fabric-treating method, which are well known in the art, see, e.g., U.S. Pat. Nos. 6,261,828; 6,077,316; 6,024,766; 6,021,536; 6,017,751; 5,980,581; U.S. Patent Publication No. 20020142438 A1. For example, enzymes of the disclosing can be used in fiber and/or fabric desizing. In one aspect, the feel and appearance of a fabric is improved by a method comprising contacting the fabric with an enzyme of the disclosure in a solution. In one aspect, site fabric is treated with the solution under pressure. For example, enzymes of the disclosure can be used in the removal of stains.

The enzymes of the disclosure can be used to treat any cellulosic material, including fibers (e.g., fibers from cotton, hemp, flax or linen), sewn and unsewn fabrics, e.g., knits, wovens, denims, yarns, and toweling, made from cotton, cotton blends or natural or manmade cellulosics or blends thereof.

The textile treating processes of the disclosure (using enzymes of the disclosure) can be used in conjunction with other textile treatments, e.g., scouring and bleaching. Scouring is the removal of non-cellulosic material from the cotton fiber, e.g., the cuticle (mainly consisting of waxes) and primary cell wall (mainly consisting of pectin, protein and xyloglucan).

The enzymes of the disclosure have numerous applications in food processing industry. For example, in one aspect, the enzymes of the disclosure are used to improve the extraction of oil from oil-rich plant material, e.g., oil-rich seeds, for example, soybean oil from soybeans, olive oil from olives, rapeseed oil from rapeseed and/or sunflower oil from sunflower seeds.

The enzymes of the disclosure can be used for separation of components of plant cell materials. For example, enzymes of the disclosure can be used in the separation of plant cells into components. In one aspect, enzymes of the disclosure can be used to separate crops into valuable protein and oil and hull fractions. The separation process can be perforated by use of methods known in the art.

The enzymes of the disclosure can be used in the preparation of fruit or vegetable juices, syrups, extracts and the like to increase yield. The enzymes of the disclosure can be used in the enzymatic treatment of various plant cell wall-derived materials or waste materials, e.g., from cereals, grains, wine or juice production, or agricultural residues such as vegetable hulls, bean hulls, sugar beet pulp, olive pulp, potato pulp, and the like. The enzymes of the disclosure can be used to modify the consistency and appearance of processed fruit or vegetables. The enzymes of the disclosure can be used to treat plant material to facilitate processing of plant material, including foods, facilitate purification or extraction of plant components. The enzymes of the disclosure can be used to improve feed value, decrease the water binding capacity, improve the degradability in waste water plants and/or improve the conversion of plant material to ensilage, and the like.

In one aspect, enzymes of the disclosure are used in baking applications, e.g., cookies and crackers. In one aspect, enzymes of the disclosure are used to create non-sticky doughs that are not difficult to machine and to reduce biscuit size. Enzymes of the disclosure can be used to hydrolyze arabinoxylans to prevent rapid rehydration of the baked product resulting in loss of crispiness and reduced shelf-life. In one aspect, enzymes of the disclosure are used as additives in dough processing.

The disclosure provides methods for treating animal feeds and foods and food or feed additives (supplements) using enzymes of the disclosure, annuals including mammals (e.g., humans), birds, fish and the like. The disclosure provides animal feeds, foods, and additives (supplements) comprising enzymes of the disclosure. In one aspect, treating animal feeds, foods and additives using enzymes of the disclosure can help in the availability of nutrients, e.g., starch, protests, and the like, in the animal feed or additive (supplements). By breaking down difficult to digest proteins or indirectly or directly unmasking starch (or other nutrients), the enzymes make nutrients more accessible to other endogenous or exogenous enzymes. The enzymes can also simply cause the release of readily digestible and easily absorbed nutrients and sugars.

When added to animal feed, enzymes of the disclosure improve the in vivo break-down of plant cell wall material partly due to a reduction of the intestinal viscosity (see, e.g., Bedford et al., Proceedings of the 1st Symposium on Enzymes in Animal Nutrition, 1993, pp. 73-77), whereby a better utilization of the plant nutrients by the animal is achieved. Thus, by using enzymes of the disclosure in feeds the growth rate and/or feed, conversion ratio (i.e., the weight of ingested feed relative to weight gain) of the animal is improved.

The animal feed additive of the disclosure may be a granulated enzyme product which may readily be mixed with feed components. Alternatively, feed additives of the disclosure cart form a component of a pre-mix. The granulated enzyme product of the disclosure may be coated or uncoated. The particle size of the enzyme granulates can be compatible with that of feed and pre-mix components. This provides a safe and convenient mean of incorporating enzymes into feeds. Alternatively, the animal feed additive of the disclosure may be a stabilized liquid composition. This may be an aqueous or oil-based slurry. See, e.g., U.S. Pat. No. 6,245,546.

In another aspect, an enzyme of the disclosure can be supplied by expressing the enzymes directly in transgenic feed crops (as, e.g., transgenic plants, seeds and the like), such as grains, cereals, corn, soy bean, rapeseed, lupin and the like. As discussed above, the disclosure provides transgenic plants, plant parts and plant cells comprising a nucleic acid sequence encoding a polypeptide of the disclosure. In one aspect, the nucleic acid is expressed such that the enzyme of the disclosure is produced in recoverable quantities. The xylanase can be recovered from any plant or plant part. Alternatively, the plant or plant part containing the recombinant polypeptide can be used as such for improving the quality of a food or feed, e.g., improving nutritional value, palatability, and rheological properties, or to destroy an antinutritive factor.

In one aspect, the disclosure provides methods for removing oligosaccharides from feed prior to consumption by an animal subject using an enzyme of the disclosure. In this process a feed is formed having an increased metabolizable energy value. In addition to enzymes of the disclosure, galactosidases, cellulases, xylanases, and combinations thereof can be used.

In another aspect, the disclosure provides methods for utilizing an enzyme of the disclosure as a nutritional supplement in the diets of animals by preparing a nutritional supplement containing a recombinant enzyme of the disclosure, and administering the nutritional supplement to an animal to increase the utilization of hemicellulase contained in food ingested by the animal.

The enzymes of the disclosure can be used in a variety of other industrial applications, e.g., in waste treatment. For example, in one aspect the disclosure provides a solid waste digestion process using enzymes of the disclosure. The methods can comprise reducing the mass and volume of substantially untreated solid waste. Solid waste can be treated with an enzymatic digestive process in the presence of an enzymatic solution (including enzymes of the disclosure) at a controlled temperature. This results in a reaction without appreciable bacterial fermentation from added microorganisms. The solid waste is converted into a liquefied waste and any residual solid waste. The resulting liquefied waste can be separated from said any residual solidified waste. See e.g., U.S. Pat. No. 5,709,796.

The disclosure provides detergent, disinfectant or cleanser (cleaning or cleansing) compositions comprising one or more enzymes of the disclosure, and methods of making and using these compositions. The disclosure incorporates all methods of making and using detergent, disinfectant or cleanser compositions, see, e.g., U.S. Pat. Nos. 6,413,928; 6,399,561; 6,365,561; 6,380,147.

In specific embodiments, the detergent, disinfectant or cleanser compositions can be a one and two part aqueous composition, a non-aqueous liquid composition, a cast solid, a granular form, a particulate form, a compressed tablet, a gel and/or a paste and a slurry form. The enzymes of the disclosure can also be used as a detergent, disinfectant or cleanser additive product in a solid or a liquid form. Such additive products are intended to supplement or boost the performance of conventional detergent compositions and can be added at any stage of the cleaning process.

The present disclosure provides cleaning compositions including detergent compositions for cleaning hard surfaces, detergent compositions for cleaning fabrics, dishwashing compositions, oral cleaning compositions, denture cleaning compositions, and contact lens cleaning solutions.

When the enzymes of the disclosure are components of compositions suitable for use in a laundry machine washing method, the compositions can comprise in addition so an enzyme of the disclosure both a surfactant and a builder compound. They can additionally comprise one or more detergent components, e.g., organic polymeric compounds, bleaching agents, additional, enzymes, suds suppressors, dispersants, lime-soap dispersants, soil suspension and anti-redeposition agents and corrosion inhibitors.

Laundry compositions of the disclosure can also contain softening agents, as additional detergent components. Such compositions containing carbohydrase can provide fabric cleaning, stain removal, whiteness maintenance, softening, color appearance, dye transfer inhibition and sanitization when formulated a laundry detergent compositions.

New and improved cellulase compositions that comprise varying amounts BG-type, EG-type and variant CBH-type cellulases find utility in detergent compositions that exhibit enhanced cleaning ability, function as a softening agent and/or improve the feel of cotton fabrics (e.g., "stone washing" "biopolishing"), in compositions for degrading wood pulp into sugars (e.g., for bio-ethanol production), and/or in feed compositions. The isolation and characterization of cellulase of each type provides the ability to control the aspects of such compositions.

Since the rate of hydrolysis of cellulosic products may be increased by using a transformant having at least one additional copy of the bgl1 gene inserted into the genome, products that contain cellulose or heteroglycans can be degraded at a faster rate and to a greater extent. Products made from cellulose such as paper, cotton, cellulosic diapers and the like can be degraded more efficiently in a landfill. Thus, the fermentation product obtainable from the transformants or the transformants alone may be used in compositions to help degrade by liquefaction a variety of cellulose products that add to the overcrowded landfills.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol.

A large variety of feedstocks may be used with the inventive variant BGL1 and the one selected for use may depend on the region where the conversion is being done. For example, in the midwestern United States agricultural wastes such as wheat straw, corn stover and bagasse may predominate while in California rice straw may predominate. However, it should be understood that any available cellulosic biomass may be used in any region.

The methods of the present disclosure can be used in the production of monosaccharides, disaccharides, and polysaccharides as chemical or fermentation feedstocks for microorganism for the production of organic products, chemicals and fuels, plastics, end other products or intermediates. In particular, the value of processing residues (dried distillers grain, spent grains from brewing, sugarcane bagasse, etc.) can be increased by partial or complete solubilization or cellulose or hemicellulose. In addition to ethanol some chemicals that can be produced from cellulose include acetone, acetate, glycine, lysine, organic acids (e.g., lactic acid), 1,3-propanediol, butanediol, glycerol, ethylene glycol, furfural, polyhydroxyalkanoates, cis, cis-muconic acid, animal feed and xylose. Moreover, proteins and cells can be produced from cellulose.

In addition the variant bgl1 nucleic acid sequence finds utility in the identification and characterization of related nucleic acid sequences. A number of techniques useful for determining (predicting or continuing) the function of related genes or gene products include, but are not limited to, (A) DNA/RNA analysis, such as (1) overexpression, ectopic expression, and expression in other species; (2) gene knock-out (reverse genetics, targeted knock-out, viral induced gene silencing (VIGS, see Baulcombe, 100 Years of Virology, Calisher and Horzinek eds., Springer-Verlag, New York, N.Y. 15:189-201, 1999); (3) analysis of the methylation status of the gene, especially flanking regulatory regions; and (4) in situ hybridization; (B) gene product analysis such as (1) recombinant protein expression; (2) antisera production, (3) immunolocalization; (4) biochemical assays for catalytic or other activity; (5) phosphorylation status; and (6) interaction with other proteins via yeast two-hybrid analysis; (C) pathway analysis, such as placing a gene or gene product within a particular biochemical or signaling pathway based on its overexpression phenotype or by sequence homology with related genes; and (D) other analyses which may also be performed to determine or confirm the participation of the isolated gene and its product in a particular metabolic or signaling pathway, and help determine gene function.

EXAMPLES

Be present disclosure is described in further detail in the following examples, which are not in any way intended to limit the scope of the disclosure as claimed. The attached figures are meant to be considered as integral parts of the specification and description of the disclosure. The following examples are offered to illustrate, but not to limit the claimed disclosure In the experimental disclosure which follows, the following abbreviations apply; M (molar); mM (millimolar); μM (micromolar); nM (nanomolar); mol (moles); mmol (millimoles); μmol (micromoles); nmol (nanomoles); g and gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); HCl (hydrochloric acid); aa (amino acid); bp (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic add); $MgCl_2$ (magnesium chloride); NaCl (sodium chloride); w/v (weight to volume); v/v (volume to volume); g (gravity); OD (optical density); ABTS (2,2'-azino-bis(3-ethylbenzo-thiazoline-6-sulfonic acid) diammonium salt; APB (acid-pretreated bagasse); BGL (beta-glucosidase); CNP (2-chloro-4-nitrophenol); CNPG (chloro-nitro-phenyl-beta-D-glucoside); HPLC (high pressure liquid chromatography); PAGE (polyacrylamide gel electrophoresis); PASC (phosphoric acid swollen cellulose) PCR (polymerase chain reaction); PCS (acid-pretreated corn stover); Pi or PI (performance index); RT-PCR (reverse transcription PCR); and SEL (site evaluation library).

Example 1

Assays

The following assays were standard assays used in the examples described below. Occasionally specific protocols called for deviations from these standard assays. In those cases, deviations from these standard assay protocols below are identified in the examples. In these experiments, a spectrophotometer was used to measure the absorbance of the products formed after the completion of the reactions.

Measurement of Glucose

A. Hexokinase Assay for Measurement of Residual Glucose

Residual glucose from *H. jecorina* culture supernatants expressing BGL variants was measured using a hexokinase assay. Five (5) µL of supernatant was added to 195 µL of a glucose hexokinase assay mixture (Instrumentation Laboratory, Breda, Netherlands) in a 96-well microtiter plate (Costar Flat Bottom PS). The plates were incubated at room temperature for 15 min. Following incubation, absorbance of the supernatant was measured at 340 nm. Supernatants of cultures containing residual glucose were excluded from pooling for further studies.

B. ABTS Assay for Measurement of Glucose

Monomeric glucose generated in the beta-glucosidase activity assays was detected using the ABTS assay. The assay buffer contained 2.74 g/L 2,2'-azino-bis(3-ethylbenzothiazoline-6-sulfonic acid) diammonium salt (ABTS, Sigma, catalog no. A1888), 0.1 U/mL horseradish peroxidase Type VI-A (Sigma, catalog no. P8375), and 1 Unit/mL flood grade glucose oxidase (GENENCOR) in 50 mM sodium acetate buffer pH 5.0. Ten (10) µL (diluted) sample was added to 100 µL ABTS assay solution. The reaction was followed kinetically for 5 min at $OD_{420}$, at ambient temperature of 22° C. An appropriate calibration curve of glucose for each assay condition was always included.

HPLC Assay for Protein Content Determination

The concentration of BGL variant proteins from pooled culture supernatants was determined by an Agilent 1200 (Agilent Technologies) HPLC equipped with a Sbodex HIC PH-814 PHM gel 75×8 mm column (Phenomenex). Fifty (50) µL of sample was mixed with 50 µL of 1.6 M $(NH_4)_2SO_4$ and after 5 min filtered under vacuum over a 0.22 µm Millipore Multiscreen HTS 96 well filtration system. Forty (40) µL of the filtered sample was injected on the column. Two elation boilers were employed to build an elusion gradient: (1) Buffer A; 16 mM $NaH_2PO_4$ pH 6.75, 800 mM $(NH_4)_2SO_4$ (2) Buffer B; 16 mM $NaH_2PO_4$ pH 6.75. Elution was carried out at a flow rate of 1.8 mL/min, using the following program; 0% to 50% Buffer B from 0.25 min to 1.5 min followed by a gradient of 50% to 100% Buffer B from 1.5 min to 4 min. 100% Buffer B was pumped over the column from 4 to 4.5 min. Protein concentrations of BGL variants were calculated from a calibration curve generated using purified wild-type BGL1 (15.625, 31.25, 62.5, 125, 250, 500 µg/mL). To calculate performance index (PI), the concentration of a BGL variant was divided by that of the average wild-type BGL1 (e.g., a reference enzyme) in the same plate.

CNPGase Activity Assay

Be activity of the BGL variants towards chloro-nitrophenol-β-D-glucoside (CNPG) was determined. Culture supernatants expressing BGL variants were diluted 10-fold in a 50 mM sodium acetate buffer, pH 5.0. Twenty five (25) µL aliquots of diluted supernatant were added to 75 µL 1.33 mM CNPG in a 50 mM sodium acetate buffer, pH 5.0 (final concentration 1 mM CNPG) in quadruplicate, Kinetics of CNP release at $OD_{405}$ was recorded in a microtiter plate reader (Spectramax, Molecular Devices) for 3 min. Average specific activities for the wild-type BGL1 and BGL variants were calculated by dividing the averaged CNPG hydrolyzing activity by the BGL concentration. A performance index (PI) was calculated by dividing the specific activity of a BGL variant by the average specific activity of the wild-type BGL1 (e.g., a reference enzyme) on the same plate.

Thermostability Assay

Residual activity of BGL1 polypeptides (including wild type and variants) after heat incubation was determined using the CNPG assay. Culture supernatants expressing BGL1 polypeptides (including wild type and variants) were diluted 10-fold in 50 mM sodium acetate buffer pH 5.0. Fifty (50) µL aliquots wore incubated in quadruplicate in a skirted 96-well PCR plate in a thermocycler at 66° C. for 1 hr. After incubation the residual specific activity of BGL1 polypeptides was determined as described above. The residual activity of the variants and the wild-type enzyme was determined by the ratio of the averaged specific activity after incubation and the averaged specific activity before incubation. A performance index (PI) for the BGL variants was determined by dividing the residual activity of a BGL variant by the residual activity of the wild-type BGL1 (e.g. a reference enzyme).

Glucose Inhibition Assay

The effect of glucose on the hydrolytic activity of beta-glucosidase was determined by repeating the CNPGase activity assay as described above in the presence of 3.75 mM glucose. The residual activity of the variants and the wild-type protein was determined by the ratio of the averaged specific activity in the presence of glucose and the averaged specific activity in the absence of glucose. A performance index (PI) for the BGL variants was determined by dividing the residual activity of a BGL variant by the residual activity of the wild-type BGL1 (e.g., a reference enzyme).

Specific Activity in a Phosphoric Acid Swollen Cellulose (PASC) Hydrolysis Assay Phosphoric acid swollen cellulose (PASC) was prepared from Avicel according to published methods (See e.g., Walseth. *Tappi*, 35:228, 1971; and Wood, *Biochem J.*, 121: 353-362, 1971). This material was diluted with buffer and water to achieve a 1% w/v mixture wherein the final concentration of sodium acetate was 50 mM (pH 5.0). One hundred and fifty (150) µL of a 1% suspension of PASC in a 50 mM sodium acetate buffer (pH 5.0) was dispensed into a 96-well microtiter plate (Costar Flat Bottom PS). Ten (10) µL of a culture supernatant from a bgl1-deleted strain containing 0.75 mg/mL protein was added to the PASC suspension. Then 5, 10, 20, or 40 µL of a 40× diluted (in 50 mM sodium acetate buffer pH 5.0) pooled culture supernatant front H. jecorina cells expressing either wild-type BGL1 or a BGL variant were added to the PASC/deletion mutant supernatant mixture. Compensating volumes of acetate buffer were added to make up for differences in total volume. The microtiter plate was sealed and incubated in a thermostatted incubator at 50° C. with continuous shaking at 900 rpm. Alter 2 hr, the hydrolysis reaction was stopped by the addition of 100 µL 100 mM glycine buffer, pH 10 to each well. The plates were sealed and centrifuged at 3,500 rpm at room temperature for 5 min. The hydrolysis reaction products in the supernatant were analyzed by the ABTS assay. A dose response curve was generated for the wild-type BGL1. To calculate performance index (PI), the (average) total sugar produced by a variant BGL was divided by the (average) total sugar produced by the wild-type BGL1 (e.g., a reference enzyme) at the same dose.

Specific Activity in a Dilute Acid Pretreated Corn Stover (PCS) Hydrolysis Assay Corn stover was pretreated with 2% w/w $H_2SO_4$ (see, Schell et al., J. Appl. Biochem. Biotechnol. 105:69-86, 2003), followed by multiple washes with deionized water to obtain a paste having a pH of 4.5. A sodium acetate buffer (pH 5.0) was then added (to a final concentration of 50 mM sodium acetate) and, if necessary, this mixture was titrated to pH 5.0) using 1 N NaOH. The cellulose concentration in the reaction mixture was about 73%. Sixty five (65) µL of this cellulose suspension was added per well in a 96-well microtiter plate (Nunc Flat Bottom PS). Ten (10) µL of a culture supernatant from a bgl1-deleted strain containing 10 mg/mL protein was added to the PCS. Then 5, 10, 15, or 20 µL of a 5× diluted (in 50 mM sodium acetate buffer, pH 5.0) pooled culture supernatants from H. jecorina cells expressing either wild-type BGL1 or a BGL variant were added to the PCS/deletion mutant supernatant mixture. Compensating volumes of sodium acetate buffer were added to make up for the differences in total volume. After sealing, the plates were placed in a thermostatted incubator at 50° C. with continuous shaking at 900 rpm. After 16 hr the plates were put on ice for 5 min and the hydrolysis reaction was stopped by the addition of 100 µL. 100 mM glycine buffer, pH 10, to each well. The plates were sealed and centrifuged at 3000 rpm at room temperature for 5 min. The hydrolysis reaction products in the supernatant were analyzed by the ABTS assay. A dose response curve was generated for wild-type BGL1 protein. To calculate performance index (PI), the (average) total sugar produced by a variant BGL was divided by the (average) total sugar produced by the wild-type BGL1 (e.g., a reference enzyme) at the same dose.

Cellobiase Activity Assay (pH 5)

The cellobiose hydrolyzing ability at pH 5.0 of wild-type BGL1 and the BGL variants was tested. Varying amounts (e.g., 5, 10, 15, or 20 µL) of 20× diluted (in 50 mM sodium acetate buffer, pH 5.0) pooled culture supernatants from H. jecorina cells expressing either wild-type BGL1 or BGL variants were added so 80 µL of a 16.4 mM (5.63 mg/mL) cellobiose solution in a 50 mM sodium acetate buffer, pH 5.0. Compensating volumes of the sodium acetate buffer were added to make up for the differences in the total volume. The microtiter plate was sealed and incubated in a thermostatted incubator at 50° C. under continuous shaking at 900 rpm. After 30 min. the hydrolysis reaction was stopped by the addition of 100 µL 100 mM glycine buffer, pH 10 to each well. The hydrolysis reaction products were analyzed by the ABTS assay. A dose response curve was generated for the wild-type BGL1. To calculate performance index (PI), the (average) total sugar produced by a variant BGL was divided by the (average) total sugar produced by the wild-type BGL1 (e.g., a reference enzyme) at the same dose.

Cellobiase Activity Assay (pH 6)

The cellobiose hydrolyzing capability of wild-type BGL1 and the BGL1 variants at pH 6.0 was tested. Varying amounts (5, 10, 15, or 20 µL) of 20× diluted (in 50 mM sodium citrate buffer, pH 6.0) pooled culture supernatants from H. jecorina cells expressing either wild-type BGL1 or a BGL variant were added to 80 µL of a 16.4 mM (5.63 mg/mL) cellobiose solution in a 50 mM sodium citrate buffer, pH 6.0. Compensating volumes of citrate buffer were added to make up for the differences in total volume. The microtiter plate was sealed and incubated in a thermostatted incubator at 50° C. with continuous shaking at 900 rpm. After 30 min. the hydrolysis reaction was stopped by the addition of 100 µL of a 100 mM glycine buffer, pH 10, to each well. The hydrolysis reaction products were analyzed by the ABTS assay. A dose response curve was generated for wild-type BGL1 protein. To calculate performance index (PI), the (average) total sugar produced by a variant BGL was divided by the (average) total sugar produced by the wild-type BGL1 (e.g., a reference enzyme) at the same dose.

Determining Beta-Glucosidase Activity by Measuring Cellobiase Activity Assay in the Presence of Ammonia Pretreated Corncob (CC)

Corn cob was ground to pass a 0.9 mm screen and pretreated as described in PCT application publication WO 200611091. Pretreated CC was used as a 7% cellulose suspension in a 50 mM sodium acetate buffer, pH 5.0. Sixty five (65) µL of the suspension were added per well into a 96-well microtiter plate (Nunc Flat Bottom PS). Forty five (45) µL of a 35.1 mM (12.0 mg/mL) cellobiose solution was added to the pretreated corncob, and varying amounts (5, 10, 15, or 20 µL) of 20× diluted (in a 50 mM sodium acetate buffer, at pH 5.0) pooled culture supernatants from H. jecorina cells expressing either wild-type BGL1 or BGL variants were added. Compensating volumes of acetate buffer were added so make up for the differences in total volume. The microtiter plate was sealed and incubated in a thermostatted incubator at 50° C. with continuous shaking at 900 rpm. After 30 min. the hydrolysis reaction was stopped by the addition of 100 µL of a 100 mM glycine buffer, pH 10, to each well. After mixing, the plate was centrifuged for 5 min at 3,500 rpm. The hydrolysis reaction products were analyzed by the ABTS assay. A dose response curve was generated for wild-type BGL1 protein. To calculate performance index (PI), the (average) total sugar produced by a variant BGL was divided by the (average) total sugar produced by the wild-type BGL1 (e.g., a reference enzyme) at the same dose.

Example 2

Generation of *Hypocrea jecorina* BGL1 Site Evaluation Libraries ("SELs")

The pTTTpyrG-bgl1 plasmid containing the *Hypocrea jecorina* BGL1 protein encoding sequence (SEQ ID NO: 1) was sent to a number of vendors, for example, BASEClear (Leiden, The Netherlands), GeneArt AG (Regensburg, Germany), and Sloning BioTechnology GmbH (Puchheim, Germany) for the generation of Site Evaluation Libraries (SELs). The amino acid sequence of the full length BGL1 protein is shown in SEQ ID NO: 2. Vendors generated positional libraries at each of the sites in the BGL1 mature protein (SEQ ID NO: 3) shown in Table 2-1.

```
                                                              SEQ ID NO: 1
sets forth the reference H. jecorina bgl1 coding DNA sequence:
atgcgctaccgcaccgctgccgctttagccttagccaccggccccttcgccagagccgatagccacagcac ctccggcgctagtgctgaagctgttgtccctcctgctggcacccttggggcaccgcctacgacaaggcca aggccgccctcgccaagctcaacctccaggacaaggtcggcatcgtcagcggcgtcggctggaacggcggt ccctgcgtcggcaacaccagccccgccagcaagatcagctacccccagcctctgcctccaggacggcccct cggcgtccgctacagcaccggcagcaccgccttcacccctggcgtccaggccgccagcacctgggacgtca acctcatccgcgagcgcggccagttcatcggcgaagaggtcaaggccagcggcatccacgtcatcctcggt cccgttgctggtcccttaggcaagacccccagggcggtcgcaactgggagggcttcggcgtcgacccta cctcaccggcattgccatgggccagaccatcaacggcatccagagcgtcggcgtccaggccaccgccaagc actacatcctcaacgagcaagagttaaaccgcgagactatcagcagcaaccccgacgaccgcaccctccac gagttatacacctggccctttcgccgacgccgtccaggccaacgtcgccagcgtcatgtgcagctacaacaa ggtcaacaccacctgggcctgcgaggaccagtacaccctccagaccgtcctcaaggaccagctcggcttcc ccggctacgtcatgaccgactggaacgcccagcacaccaccgtccagagcgccaacagcggcctcgacatg agcatgcccggcaccgacttcaacggcaacaaccgcctctggggccctgccctcaccaacgccgtcaacag caaccaggtccccacctcccgcgtcgacgacatggtcacccgcatcctcgccgcctggtacttaaccggcc aagaccaggctggctatcccagcttcaacatcagccgcaacgtccagggcaaccacaagaccaacgtccgc gccattgcccgcgacggcatcgtcctcctcaagaacgacgccaacatcctccccctcaagaagcccgcctc tatcgccgtcgtcggcagcgccgccatcatcggcaaccacgcccgcaacagccccagctgcaacgacaagg gctgcgatgacggtgccctcggcatgggctggggctctggcgccgtcaactaccctacttcgtcgccccc tacgacgccatcaacacccgcgccagcagccagggcacccaggtcaccctcagcaacaccgacaatacttc ttctggcgcttctgctgctagaggcaaggacgtcgccatcgttttatcactgccgattctggcgaaggct acatcaccgtcgagggcaacgccggcgaccgcaacaacctcgacccctggcacaacggcaatgccctcgtc caggccgttgctggtgctaacagcaacgtcatcgtcgtcgtccacagcgtcggcgccatcatcctcgagca gatcctcgccctcccccaggtcaaggccgtcgtctgggccggcttacccagccaggaaagcggcaacgcct tagtcgacgtcctctggggtgacgtttcccctctggcaagctcgtctacaccattgccaagagccccaac gactacaacacccgcattgtcagcggcggcagcgacagcttcagcgagggcctcttcatcgactacaagca cttcgacgacgccaacattacccccgctacgagttcggctacggcctcagctacaccaagttcaactaca gccgcctcagcgtcctcagcaccgccaagagcggccctgccactggtgctgtcgtccctggtggcccttct gacctcttccagaacgtcgccacggtcaccgtcgacattgccaactccggccaggtcactggcgccgaggt cgcccagctctacatcacctaccccagcagcgcccctcgcactcctcccaagcagctcagaggcttcgcta agttaaacttaaccctggccagagcggcaccgccacctttaacatccgcagacgcgacctcagctactgg gacaccgccagccagaagtgggtcgtcccagcggcagcttcggcatctccgtcggcgccagctcccgcga catccgcctcaccagcaccctcagcgtcgcctgatga*
```

SEQ ID NO: 2
sets forth the sequeuce of the H. jecorina BGL1 full length protein:
WRYRTAAALALATGPFARADSHSTSGASAEAVVPPAGTPWGTAYDKAKAALAKLNLQDKV

GIVSGVGWNGGPCVGNTSPASHISYPSLCLQDGPLGVRYSTGSTAFTPGVQAASTWDVNL

IRERGQFIGEEVNASGIHVILGPVAGPLGNTPQGGPNNEGFGVDPYLIGIAMGQTINGIQ

SVGVQATAKHYILNEQELNRETISSNPDDRTLHELYTWPFADAVQANVASVMCSYNKVNT

IWACEDQYTLQTVLEDQLGPPGYVMTDWNAQHTTVQSANSGLDNSMPGIDFNGNNRLWGP

ALTNAVNSNQVPTSPVDDMVTRILAAWYLTGQDQAGYPSFHISRNVQGNHKTNVRAIAPD

GIVLLKNDANILPLKKPASIAVVGSAAIIGNKARNSPSCNDKGCDDGALGMGWGSGAVNY

FYFVAPYDAIMTRASSQGTQVTLSNTDNTSSGASAARGKDVAIVFITADSGKGYITVEGN

AGDRNNLDPWHNGNALVQAVAGANSNVIVVVHSVGAIILEGILALPQVKAVYWAGLPSQE

SGNALVDVLWGDVSPSGKLVYTIAKSPNDYNTRIVSGGSDSFSEGLFIDYKHFDDANITP

RYEFGYGLSYTKFNYSRLSVLSTAKSGPAIGAVVPGGPSDLFQNVAIVTVDIANSGQVTG

AEVAQLYITYPSSAPRIPPKQLRGFAKLNLTPGQSGTATFNIRRRDLSYWDTASQEWVVP

SGSFGISVGASSRDIRLTSTLSVA*

SEQ ID NO: 3
sets forth the seqence of the H. jecorina BGL1 mature protein:
VVPPAGTPWGTAYDKAKAALAKLNLQDKVGIVSGVGWNGGPCVGNTSPASKISYPSLCLQDGPLGV

RYSTGSTAFTPGVQAASTWDVNLIPERGQFIGEEVKASGIHVILGPVAGPLGKTPQGGPNWEGFGV

DPYLTGIAMGQTINGIQSVGVQATAKHYILNEQELNRETISSNPDDRTLHELYTWPFADAVQANVA

SVMCSYNKVNTTWACEDQYTLQTVLKDQLGFPGYVMTDWNAQHTTVQSANSGLDNSMPGTDFNGNN

RLWGPALINAVHSNQVPTSRVDDMVTRILAAWYLTGQDQAGYPSFMISRMVQGNHKTNVPAIAPDG

IVLLKNDANILPLKKPASIAVVGSAAIIGNHARNSPSCNDKGCDDGALGMGWGSGAVNYPYFVAPY

DAINTRASSQGTQVTLSNTDNTSSGASAARGKDVAIVFITADSGKGYITVEGNAGDPNNLDPWHNG

NALVQAVAGANSNVIVVVHSVGAIILEQILALPQVKAVVNAGLPSQESGNALVDVLWGDVSPGSEL

VYTIAKSPNDYNTPIVSGGSDSFSEGLFIDYKHFDDANITPRYEFGYGLSYTKFNYSRLSVLSTAK

SGPAIGAVVPGGPSDLFQNVAIVTVDIANSGQVTGAEVAGLYITYPSSAPRTPPKQLRGFAKLNLT

PGQSGTATFNIRRPDLSYWDTASQKWVVPSGSFGISVGASSRDIPLTSILSVA*

TABLE 2-1

Positions In The Mature BGL1 Protein Selected For The Generation Of SELs

| | | | | | | | |
|---|---|---|---|---|---|---|---|
| 22 | 163 | 226 | 313 | 380 | 454 | 561 | 661 |
| 24 | 164 | 236 | 316 | 381 | 455 | 563 | 662 |
| 25 | 165 | 237 | 320 | 382 | 460 | 564 | 663 |
| 26 | 166 | 238 | 324 | 396 | 467 | 570 | 666 |
| 27 | 167 | 242 | 328 | 397 | 473 | 571 | 672 |
| 28 | 168 | 248 | 329 | 398 | 474 | 581 | 673 |
| 33 | 169 | 249 | 334 | 399 | 475 | 583 | 674 |
| 35 | 170 | 263 | 335 | 402 | 489 | 586 | 675 |
| 36 | 176 | 264 | 336 | 409 | 490 | 591 | 680 |
| 37 | 177 | 265 | 337 | 410 | 492 | 603 | 681 |
| 50 | 178 | 276 | 338 | 411 | 496 | 611 | 682 |
| 51 | 179 | 277 | 339 | 420 | 497 | 612 | 683 |
| 52 | 194 | 278 | 344 | 426 | 498 | 622 | 684 |
| 61 | 196 | 279 | 345 | 427 | 521 | 626 | 685 |
| 67 | 199 | 282 | 347 | 428 | 522 | 627 | 692 |
| 91 | 204 | 284 | 361 | 441 | 534 | 638 | 702 |
| 92 | 208 | 287 | 363 | 445 | 542 | 642 | 705 |
| 93 | 209 | 291 | 369 | 446 | 547 | 643 | |
| 99 | 214 | 301 | 370 | 447 | 548 | 645 | |
| 100 | 215 | 302 | 371 | 448 | 553 | 649 | |
| 125 | 216 | 303 | 372 | 449 | 554 | 650 | |
| 158 | 224 | 306 | 374 | 452 | 555 | 656 | |
| 159 | 225 | 312 | 375 | 453 | 560 | 660 | |

For each of the 178 sites listed in Table 2-1 typically 14-16 substitution variants were obtained. The SEL variants were received as individually purified plasmids each encoding a BGL1 variant sequence substituted at the indicated position.

Production of BGL1 Variants

To enable the expression of BGL1 and variant BGL proteins in *Trichoderma reesei*, the bgl1 coding sequence was cloned into the Gateway compatible destination vector pTTT-pyrG13 (FIG. X) via the Gateway® LR recombination reaction. This vector contained the *T. reesei* cbh1-derived promoter and terminator regions allowing for a strong inducible expression of a gene of interest, the *Aspergillus nidulans* amdS and pyrG selective markers conferring growth of transformants on acetamide as a sole nitrogen source, and the *T. reesei* telomere regions allowing for non-chromosomal plasmid maintenance in a fungal cell. In addition, this vector allowed for selecting transformants of *T. reesei* strains with uridine auxotrophy. The cbh1 promoter and terminator regions are separated by the chloramphenicol resistance gene, $Cm^R$, and the lethal *E. coli* gene, ccdB, flanked by the bacteriophage lambda-based specific recombination sites attR1, attR2. Such configuration allowed for direct selection of recombinants containing the bgl1 gene under the control of the cbh1 regulatory elements in the right orientation via the Gateway® LR recombination reaction. The final expression vector pTTT-pyrG-bgl1 is shown in FIG. 2.

Purified pTTTpyrG-bgl1 plasmids ($p_{ebid}$, $Amp^R$, acetamidase expressing genes encoding BGL1 variant sequences were obtained from the vendors listed above. Protoplasts of *H. jecorina* strain (Δeg1, Δeg2, Δcbh1, Δcbh2, Δbgl1) were transformed with the individual pTTTpyrG constructs (a single BGL1 variant per transformation) and grown on selective agar containing acetamide at 28° C. for 7 d as previously described in, for example, PCT Patent Application Publication WO 2009/048488. Protoplasts of *H. jecorina* were generated, harvested, plated on acetamide agar, and incubated at 28° C. for 2 d. Spores were harvested in 15% glycerol and stored at −20° C. For BGL1 variant production, a volume of 10 μL spore suspension was added to 200 μL of a glycine minimal medium supplemented with 2% glucose/sophorose mixture in a PVDF filter plate. Each BGL1 variant was grown in quadruplicate. After sealing the plate with an oxygen permeable membrane, the plates were incubated at 28° C. for 6 d, with shaking at 220 rpm. Filtrates ware harvested by transferring the culture medium to a microtiter plate under vacuum. Residual glucose was measured using the hexokinase assay as described in Example 1A.

Example 3

Expression, Activity and Performance of BGL1 Variants

*H. jecorina* BGL1 SEL variant proteins were tested for various properties of interest. In particular, the beta-glucosidase variants were tested for protein expression using the HPLC assay (HPLC), CNPG hydrolyzing activity (CNPG), effect of glucose on activity (Gluc), thermostability (Heat), hydrolysis of PASC (PASC), hydrolysis of PCS (PCS), cellobiase activity at pH 5.0 (G2 pH 5), cellobiase activity at pH 6.0 (G2 pH 6), and beta-glucosidase activity measured by cellobiase activity in the presence of ammonia pretreated corncob (G2 CC) as described in Example 1. The performance indices for the BGL1 variants shown in Table 3-1 are rounded to the nearest hundredth. Performance index (PI) is the ratio of performance of the variant to wild-type BGL1. Performance indices less than or equal to 0.05 were generally fixed to 0.05. However, for HPLC protein values of 0.0, all values were fixed to 0.04. PI values for SEL enzymes with wild type residues were set at 1.00. PI values that were larger than 1 before rounding, are shown in bold, italic face in Table 3-1.

TABLE 3-1

Performance Index Data of BGL1 SEL Variants (3,153)

| variant | HPLC | CNPG | Gluc | Heat | PASC | PCS | G2 pH5 | G2 pH6 | G2 CC |
|---------|------|------|------|------|------|-----|--------|--------|-------|
| K022A | *1.17* | *1.07* | *1.10* | *1.39* | *1.06* | 0.95 | *1.07* | 0.99 | *1.05* |
| K022C | 0.04 | 0.04 | 0.04 | 0.04 | 0.04 | 0.04 | 0.04 | 0.04 | 0.04 |
| K022E | *1.22* | *1.08* | *1.15* | *1.77* | *1.04* | *1.00* | *1.14* | *1.02* | *1.06* |
| K022F | 0.66 | *1.19* | 0.93 | *1.16* | *1.14* | *1.19* | *1.20* | *1.23* | *1.10* |
| K022G | 0.87 | *1.06* | 0.93 | *1.01* | 0.96 | *1.02* | 0.99 | 0.94 | 0.90 |
| K022H | 0.47 | 0.84 | 0.79 | 0.57 | 0.97 | 0.97 | 0.85 | *1.02* | 0.71 |
| K022I | 0.78 | 0.99 | 0.93 | *1.03* | 0.96 | 0.97 | 0.95 | 0.93 | 0.86 |
| K022K | 1.00 | 1.00 | 1.00 | 1.00 | 1.00 | 1.00 | 1.00 | 1.00 | 1.00 |
| K022L | 0.04 | 0.04 | 0.04 | 0.04 | 0.04 | 0.04 | 0.04 | 0.04 | 0.04 |
| K022M | 0.04 | 0.04 | 0.04 | 0.04 | 0.04 | 0.04 | 0.04 | 0.04 | 0.04 |
| K022N | 0.58 | 0.91 | 0.83 | 0.79 | 0.91 | 0.85 | 0.78 | 0.98 | 0.66 |
| K022P | 0.89 | *1.17* | 1.00 | *1.24* | *1.04* | 0.90 | *1.09* | *1.07* | *1.05* |
| K022Q | 0.82 | *1.12* | 0.96 | *1.27* | *1.00* | 0.84 | *1.06* | *1.04* | 0.98 |
| K022R | 0.61 | 0.98 | 0.84 | 0.90 | 0.97 | 0.89 | 0.93 | *1.03* | 0.74 |
| K022S | *1.32* | *1.03* | *1.11* | *1.51* | 0.95 | 0.87 | 0.99 | 0.90 | 0.89 |
| K022T | 0.05 | 0.05 | 0.05 | 0.05 | 0.05 | 0.05 | 0.05 | 0.05 | 0.05 |
| K022V | 0.75 | *1.02* | 0.92 | *1.02* | 0.93 | 1.00 | 0.95 | 0.98 | 0.66 |
| K022W | *1.11* | *1.05* | 0.90 | *1.20* | 0.89 | *1.01* | 0.88 | 0.83 | 0.78 |

TABLE 3-1-continued

Performance Index Data of BGL1 SEL Variants (3,153)

| | | | | | | | | | |
|---|---|---|---|---|---|---|---|---|---|
| K022Y | 0.98 | *1.12* | 0.99 | *1.30* | 0.93 | 0.82 | 0.99 | 1.00 | 0.87 |
| N024A | *1.54* | *1.39* | 1.00 | *1.57* | 0.99 | *1.02* | 0.99 | 0.95 | *1.00* |
| N024C | 0.74 | *1.76* | 0.94 | *1.83* | *1.21* | *1.35* | *1.36* | *1.43* | *1.20* |
| N024D | *1.08* | 0.70 | *1.06* | 0.96 | 0.91 | *1.08* | 0.89 | 0.91 | 0.76 |
| N024E | *1.18* | 0.96 | *1.19* | *1.48* | 0.89 | *1.09* | 0.89 | 0.94 | 0.77 |
| N024F | 0.48 | 0.38 | *1.13* | 0.61 | *1.06* | *1.22* | 0.94 | 0.88 | 0.75 |
| N024G | 0.81 | 0.30 | *1.24* | 0.57 | 0.93 | *1.09* | 0.93 | 0.92 | 0.97 |
| N024K | 0.59 | 0.31 | *1.02* | 0.49 | 0.99 | 0.97 | 0.96 | 0.97 | 0.51 |
| N024L | *1.10* | 0.78 | *1.02* | 0.96 | 0.88 | *1.11* | 0.88 | 0.91 | 0.87 |
| N024M | 0.65 | 0.85 | *1.16* | *1.16* | 0.79 | 0.89 | 0.76 | 0.80 | 0.96 |
| N024N | 1.00 | 1.00 | 1.00 | 1.00 | 1.00 | 1.00 | 1.00 | 1.00 | 1.00 |
| N024P | *1.00* | 0.30 | *1.28* | 0.58 | 0.98 | *1.03* | *1.00* | 0.96 | 0.96 |
| N024Q | 0.34 | 0.28 | 0.05 | 0.68 | *1.68* | *1.60* | *1.81* | *1.79* | *1.30* |
| N024R | 0.67 | 0.05 | 0.05 | 0.22 | *1.02* | 0.92 | 0.90 | 0.73 | 0.77 |
| N024S | 0.96 | 0.30 | 0.05 | 0.79 | 0.88 | *1.09* | 0.85 | 0.88 | 0.88 |
| N024T | 0.96 | 0.35 | *1.24* | 0.67 | 0.92 | 0.82 | 0.84 | 0.86 | 0.82 |
| N024V | 0.62 | 0.30 | 0.98 | 0.54 | 0.93 | *1.06* | 0.86 | 0.78 | 0.60 |
| N024Y | 0.57 | 0.32 | 0.05 | 0.05 | *1.02* | *1.06* | 0.91 | 0.92 | 0.72 |
| L025A | 0.70 | *1.20* | 0.87 | 0.79 | 0.99 | 0.91 | *1.03* | *1.03* | *1.06* |
| L025D | 0.68 | *1.13* | 0.97 | 0.72 | *1.02* | 0.89 | *1.03* | *1.09* | *1.02* |
| L025F | 0.71 | *1.08* | 0.93 | 0.78 | 0.96 | 0.86 | 0.91 | 0.92 | 0.83 |
| L025G | 0.51 | *1.00* | 0.91 | 0.57 | 0.93 | 0.94 | 0.89 | 0.83 | 0.85 |
| L025H | 0.04 | 0.04 | 0.04 | 0.04 | 0.04 | 0.04 | 0.04 | 0.04 | 0.04 |
| L025I | 1.00 | *1.10* | 0.94 | *1.17* | 0.96 | 0.90 | 1.00 | 0.99 | 0.91 |
| L025K | 0.53 | *1.04* | 0.86 | 0.53 | 0.94 | *1.08* | 0.89 | 0.99 | 0.74 |
| L025L | 1.00 | 1.00 | 1.00 | 1.00 | 1.00 | 1.00 | 1.00 | 1.00 | 1.00 |
| L025N | 0.27 | 0.80 | 0.82 | 0.37 | 0.90 | *1.25* | 0.90 | *1.00* | 0.58 |
| L025P | 0.05 | 0.05 | 0.05 | 0.05 | 0.05 | 0.05 | 0.05 | 0.05 | 0.05 |
| L025Q | 0.64 | *1.10* | 0.93 | 0.92 | 0.92 | 0.94 | 0.98 | 0.92 | 0.84 |
| L025R | 0.60 | *1.04* | 0.89 | 0.63 | 0.93 | 0.99 | 0.91 | 0.85 | 0.84 |
| L025S | 0.85 | *1.01* | 0.96 | 0.89 | 0.91 | 0.82 | 0.89 | 0.88 | *1.00* |
| L025T | 0.96 | *1.04* | *1.01* | *1.11* | 0.92 | *1.08* | 0.95 | 0.91 | 0.82 |
| L025V | 0.68 | *1.09* | 0.95 | 0.83 | 0.92 | *1.18* | 0.92 | 0.89 | 0.92 |
| L025W | *1.07* | *1.06* | 0.99 | 0.98 | 0.98 | 0.77 | 0.95 | 0.92 | 0.97 |
| L025Y | 0.49 | *1.03* | 0.88 | 0.41 | 0.92 | *1.01* | 0.96 | 0.96 | 0.75 |
| Q026A | 0.94 | 0.90 | 0.80 | 0.74 | 0.89 | 0.89 | 0.85 | 0.89 | 0.88 |

TABLE 3-1-continued

Performance Index Data of BGL1 SEL Variants (3,153)

| | | | | | | | | | |
|---|---|---|---|---|---|---|---|---|---|
| Q026C | 0.40 | *1.43* | 0.99 | 0.61 | *1.33* | *1.30* | *1.32* | *1.40* | *1.41* |
| Q026D | 0.82 | 0.99 | *1.00* | 0.75 | 1.00 | *1.07* | 0.99 | 0.98 | *1.07* |
| Q026E | 0.71 | 0.97 | 0.92 | 0.66 | *1.07* | *1.14* | 0.94 | 0.92 | *1.05* |
| Q026F | 0.04 | 0.04 | 0.04 | 0.04 | 0.04 | 0.04 | 0.04 | 0.04 | 0.04 |
| Q026G | 0.48 | 0.99 | 0.93 | 0.39 | 0.93 | *1.05* | 0.92 | 0.93 | 0.96 |
| Q026H | 0.55 | *1.13* | 0.97 | *1.32* | *1.08* | 1.00 | 0.99 | *1.02* | 0.85 |
| Q026I | 0.47 | *1.09* | 0.98 | 0.72 | *1.22* | *1.02* | *1.04* | *1.07* | 0.91 |
| Q026K | 0.43 | *1.48* | 0.96 | *1.30* | *1.25* | *1.30* | *1.34* | *1.34* | *1.37* |
| Q026L | 0.67 | *1.15* | 0.86 | 0.77 | *1.13* | *1.26* | *1.06* | *1.04* | 0.81 |
| Q026M | 0.04 | 0.04 | 0.04 | 0.04 | 0.04 | 0.04 | 0.04 | 0.04 | 0.04 |
| Q026N | 0.04 | 0.04 | 0.04 | 0.04 | 0.04 | 0.04 | 0.04 | 0.04 | 0.04 |
| Q026P | 0.42 | *1.12* | *1.11* | 0.51 | *1.08* | *1.19* | *1.04* | *1.07* | 0.89 |
| Q026Q | 1.00 | 1.00 | 1.00 | 1.00 | 1.00 | 1.00 | 1.00 | 1.00 | 1.00 |
| Q026R | 0.47 | *1.18* | *1.02* | *1.14* | *1.13* | *1.12* | *1.10* | *1.10* | 0.88 |
| Q026S | 0.46 | *1.26* | 0.89 | *1.26* | *1.14* | *1.10* | *1.14* | *1.15* | *1.14* |
| Q026T | 0.17 | *1.60* | 0.89 | 0.67 | *1.65* | *1.88* | *1.63* | *1.58* | *1.32* |
| Q026V | 0.53 | *1.05* | 0.97 | 0.61 | *1.02* | *1.16* | 0.98 | 0.97 | 0.88 |
| Q026W | 0.39 | *1.38* | *1.10* | 0.56 | *1.38* | *1.20* | *1.32* | *1.37* | *1.19* |
| Q026Y | 0.70 | 0.86 | *1.15* | 0.60 | 0.84 | *1.02* | 0.80 | 0.82 | 0.73 |
| D027A | 0.81 | *1.09* | 1.00 | 0.74 | *1.09* | 0.70 | 0.93 | 1.00 | *1.03* |
| D027C | 0.28 | *1.07* | 0.99 | 0.34 | *33.47* | 0.22 | 0.92 | *1.03* | 0.92 |
| D027E | 0.71 | *1.15* | 0.99 | 0.88 | *1.08* | 0.86 | 0.92 | 0.99 | 0.82 |
| D027F | 0.05 | 0.05 | 0.05 | 0.05 | 0.05 | 0.05 | 0.05 | 0.05 | 0.55 |
| D027G | 0.20 | 0.90 | 0.93 | 0.21 | 0.22 | 0.08 | 0.76 | 0.79 | 1.00 |
| D027I | 0.17 | 0.87 | 0.92 | 0.17 | 0.47 | 0.06 | 0.71 | 0.73 | 0.83 |
| D027K | 0.05 | 0.05 | 0.05 | 0.05 | 0.05 | 0.05 | 0.05 | 0.05 | 0.05 |
| D027L | 0.34 | *1.17* | 0.93 | 0.44 | 0.60 | 0.24 | 0.84 | 0.92 | *1.28* |
| D027M | 0.29 | *1.11* | 0.89 | 0.39 | 0.22 | 0.21 | 0.83 | 0.88 | *1.14* |
| D027P | 0.06 | 0.05 | 0.05 | 0.05 | 0.05 | 0.05 | 0.05 | 0.05 | 0.48 |
| D027Q | 0.33 | *1.07* | 0.96 | 0.30 | 0.05 | 0.26 | 0.88 | 0.90 | *1.02* |
| D027R | 0.12 | 0.67 | 0.89 | 0.12 | 0.05 | 0.05 | 0.52 | 0.57 | 0.79 |
| D027S | 0.58 | *1.16* | 0.92 | 0.60 | 0.37 | 0.53 | 0.85 | 0.91 | *1.07* |
| D027T | 0.42 | *1.09* | 0.89 | 0.44 | 0.48 | 0.35 | 0.81 | 0.81 | 0.97 |
| D027V | 0.24 | *1.11* | 0.75 | 0.19 | 0.52 | 0.16 | 0.61 | 0.68 | 0.77 |
| D027W | 0.14 | 0.65 | 0.85 | 0.07 | 0.39 | 0.05 | 0.56 | 0.56 | 0.86 |
| D027Y | 0.23 | 0.78 | 0.94 | 0.17 | 0.37 | 0.12 | 0.58 | 0.71 | 0.91 |

TABLE 3-1-continued

Performance Index Data of BGL1 SEL Variants (3,153)

| | | | | | | | | | |
|---|---|---|---|---|---|---|---|---|---|
| K028C | 0.44 | 0.60 | 0.90 | 0.57 | 0.91 | 0.76 | 0.73 | 0.93 | 0.73 |
| K028E | 0.44 | 0.56 | 0.95 | 0.50 | 0.84 | 0.79 | 0.70 | 0.90 | 0.64 |
| K028F | 0.04 | 0.04 | 0.04 | 0.04 | 0.04 | 0.04 | 0.04 | 0.04 | 0.04 |
| K028G | 0.04 | 0.04 | 0.04 | 0.04 | 0.04 | 0.04 | 0.04 | 0.04 | 0.04 |
| K028I | 0.20 | 0.29 | 0.89 | 0.20 | 0.75 | 0.75 | 0.54 | 0.95 | 0.46 |
| K028K | 1.00 | 1.00 | 1.00 | 1.00 | 1.00 | 1.00 | 1.00 | 1.00 | 1.00 |
| K028L | 0.19 | 0.29 | *1.09* | 0.20 | 0.79 | 0.74 | 0.59 | 0.98 | 0.58 |
| K028M | 0.70 | 0.82 | *1.02* | 0.95 | 0.88 | 0.92 | 0.80 | 0.92 | 0.75 |
| K028N | 0.09 | 0.13 | *1.00* | 0.08 | 0.46 | 0.50 | 0.43 | 0.88 | 0.39 |
| K028P | 0.04 | 0.04 | 0.04 | 0.04 | 0.04 | 0.04 | 0.04 | 0.04 | 0.04 |
| K028Q | 0.42 | 0.62 | 0.96 | 0.49 | 0.90 | 0.94 | 0.80 | 0.98 | 0.67 |
| K028R | 0.53 | 0.76 | 0.90 | 0.69 | 0.91 | 0.97 | 0.84 | 0.96 | 0.73 |
| K028S | 0.19 | 0.28 | 0.98 | 0.18 | 0.71 | 0.60 | 0.56 | *1.00* | 0.48 |
| K028T | 0.04 | 0.04 | 0.04 | 0.04 | 0.04 | 0.04 | 0.04 | 0.04 | 0.04 |
| K028V | 0.15 | 0.26 | 0.91 | 0.18 | 0.72 | 0.63 | 0.55 | *1.03* | 0.41 |
| K028W | 0.27 | 0.05 | 0.05 | 0.05 | 0.18 | 0.05 | 0.05 | 0.14 | 0.18 |
| K028Y | 0.04 | 0.04 | 0.04 | 0.04 | 0.04 | 0.04 | 0.04 | 0.04 | 0.04 |
| S033A | 0.11 | 0.35 | 0.82 | 0.05 | 0.62 | 0.89 | 0.64 | 0.64 | 0.36 |
| S033C | 0.42 | *1.29* | 0.88 | 0.49 | *1.16* | *1.34* | *1.36* | *1.42* | *1.18* |
| S033D | 0.21 | 0.58 | 0.75 | 0.05 | 0.75 | 0.94 | 0.73 | 0.81 | 0.61 |
| S033E | 0.11 | 0.05 | 0.05 | 0.05 | 0.05 | 0.33 | 0.05 | 0.05 | 0.37 |
| S033F | 0.08 | 0.21 | 0.71 | 0.05 | 0.49 | 0.46 | 0.40 | 0.54 | 0.34 |
| S033G | 0.46 | *1.08* | 0.89 | 0.39 | 1.00 | 0.97 | *1.07* | *1.15* | 1.00 |
| S033H | 0.20 | 0.60 | 0.82 | 0.09 | 0.84 | 0.70 | 0.80 | 0.82 | 0.64 |
| S033I | 0.09 | 0.19 | 0.75 | 0.05 | 0.38 | 0.43 | 0.26 | 0.30 | 0.29 |
| S033K | 0.12 | 0.43 | 0.76 | 0.05 | 0.76 | 0.24 | 0.71 | 0.80 | 0.40 |
| S033L | 0.09 | 0.21 | 0.67 | 0.05 | 0.36 | 0.38 | 0.22 | 0.28 | 0.31 |
| S033M | 0.21 | 0.70 | 0.75 | 0.05 | 0.85 | 0.72 | 0.71 | 0.88 | 0.64 |
| S033N | 0.18 | 0.62 | 0.81 | 0.05 | 0.89 | 0.90 | 0.78 | 0.91 | 0.60 |
| S033P | 0.09 | 0.05 | 0.05 | 0.05 | 0.05 | 0.11 | 0.05 | 0.05 | 0.11 |
| S033Q | 0.09 | 0.30 | 0.91 | 0.05 | 0.72 | 0.60 | 0.55 | 0.66 | 0.30 |
| S033R | 0.15 | 0.52 | 0.77 | 0.05 | 0.80 | 0.54 | 0.74 | 0.96 | 0.50 |
| S033S | 1.00 | 1.00 | 1.00 | 1.00 | 1.00 | 1.00 | 1.00 | 1.00 | 1.00 |
| S033T | 0.71 | 0.94 | 0.97 | 0.84 | 0.92 | *1.05* | 0.89 | 0.91 | 0.84 |
| S033V | 0.33 | 0.99 | 0.77 | 0.30 | 0.93 | 0.94 | 0.88 | 0.97 | 0.70 |

TABLE 3-1-continued

Performance Index Data of BGL1 SEL Variants (3,153)

| | | | | | | | | | |
|---|---|---|---|---|---|---|---|---|---|
| S033W | 0.10 | 0.15 | 0.83 | 0.05 | 0.27 | 0.31 | 0.19 | 0.24 | 0.17 |
| S033Y | 0.10 | 0.15 | 0.05 | 0.05 | 0.24 | 0.21 | 0.17 | 0.26 | 0.26 |
| V035C | 0.77 | *1.42* | 0.90 | 0.85 | *1.02* | *1.07* | *1.16* | *1.22* | *1.05* |
| V035D | 0.04 | 0.04 | 0.04 | 0.04 | 0.04 | 0.04 | 0.04 | 0.04 | 0.04 |
| V035E | 0.77 | *1.31* | 0.92 | 0.77 | 0.95 | *1.02* | *1.02* | *1.11* | *1.09* |
| V035F | 0.26 | 0.05 | 0.05 | 0.07 | 0.20 | 0.09 | 0.12 | 0.10 | 0.10 |
| V035G | 0.99 | *1.17* | 0.90 | 0.36 | 0.86 | 0.66 | 0.98 | *1.03* | *1.09* |
| V035H | 0.81 | *1.19* | 0.86 | 0.31 | 0.96 | 0.72 | 0.98 | *1.07* | 0.83 |
| V035K | 0.59 | *1.40* | 0.87 | 0.74 | 0.99 | 0.89 | 0.97 | *1.08* | 0.91 |
| V035L | 0.78 | *1.22* | 0.95 | *1.03* | 0.98 | 0.87 | 0.98 | *1.03* | 0.79 |
| V035N | 0.69 | *1.21* | 0.88 | 0.64 | 0.90 | *1.05* | 0.97 | *1.07* | 0.85 |
| V035P | 0.44 | *1.34* | 0.88 | 0.05 | *1.08* | 0.33 | 0.92 | 0.92 | 0.79 |
| V035Q | 0.75 | *1.34* | 0.92 | 0.96 | 0.98 | 0.82 | *1.09* | *1.15* | 0.92 |
| V035R | 0.76 | *1.40* | 0.87 | 0.79 | 0.99 | 0.91 | *1.05* | *1.09* | 0.94 |
| V035S | *1.10* | *1.20* | 0.88 | *1.14* | 0.91 | 0.84 | *1.03* | *1.02* | 0.93 |
| V035T | 0.97 | *1.15* | 0.86 | *1.08* | *1.05* | 0.96 | *1.05* | *1.13* | 0.83 |
| V035V | 1.00 | 1.00 | 1.00 | 1.00 | 1.00 | 1.00 | 1.00 | 1.00 | 1.00 |
| V035W | *1.17* | 0.97 | 0.98 | 0.25 | 0.89 | 0.80 | 0.88 | 0.93 | 0.96 |
| V035Y | 0.83 | *1.20* | 0.99 | 0.09 | 0.96 | 0.71 | *1.03* | *1.00* | 0.90 |
| G036A | 0.33 | 0.53 | 0.74 | 0.05 | 0.74 | 0.70 | 0.73 | 0.65 | 0.70 |
| G036C | 0.18 | 0.60 | 0.77 | 0.05 | 1.00 | 0.70 | *1.12* | *1.07* | 0.83 |
| G036D | 0.52 | *1.02* | 0.86 | 0.05 | *1.21* | 0.67 | *1.28* | *1.15* | *1.12* |
| G036E | 0.46 | *1.08* | 0.88 | 0.05 | *1.14* | 0.63 | *1.23* | *1.15* | *1.01* |
| G036F | 0.09 | 0.41 | 0.71 | 0.05 | 0.70 | 0.17 | *1.16* | *1.13* | 0.65 |
| G036H | 0.04 | 0.04 | 0.04 | 0.04 | 0.04 | 0.04 | 0.04 | 0.04 | 0.04 |
| G036I | 0.10 | 0.43 | 0.75 | 0.05 | 0.70 | 0.28 | *1.14* | *1.01* | 0.68 |
| G036K | 0.27 | 0.89 | 0.73 | 0.05 | *1.07* | 0.85 | *1.16* | *1.14* | 0.82 |
| G036N | 0.10 | 0.43 | 0.70 | 0.05 | 0.86 | 0.55 | 0.78 | *1.04* | 0.64 |
| G036P | 0.04 | 0.04 | 0.04 | 0.04 | 0.04 | 0.04 | 0.04 | 0.04 | 0.04 |
| G036Q | 0.33 | 0.73 | 0.76 | 0.05 | 0.83 | 0.63 | 0.88 | 0.86 | 0.72 |
| G036R | 0.42 | *1.08* | 0.74 | 0.11 | *1.09* | 0.80 | *1.04* | *1.12* | 0.99 |
| G036S | 0.67 | *1.34* | 0.90 | 0.14 | *1.48* | *1.16* | *1.47* | *1.45* | *1.53* |
| G036V | 0.27 | 0.71 | 0.77 | 0.05 | 0.72 | 0.18 | 0.95 | 0.91 | 0.71 |
| G036W | 0.09 | 0.40 | 0.65 | 0.05 | 0.83 | 0.09 | *1.33* | *1.21* | 0.82 |
| G036Y | 0.07 | 0.83 | 0.71 | 0.05 | *2.08* | 0.15 | *3.08* | *2.99* | *1.25* |

TABLE 3-1-continued

Performance Index Data of BGL1 SEL Variants (3,153)

| | | | | | | | | |
|---|---|---|---|---|---|---|---|---|
| W037A | *1.50* | 0.85 | 0.88 | *1.40* | 0.66 | 0.79 | 0.73 | 0.63 | 0.78 |
| W037C | 0.46 | 0.70 | 0.64 | 0.35 | 0.62 | 0.85 | 0.84 | 0.75 | 0.82 |
| W037E | *1.33* | 0.91 | 0.98 | *1.11* | 0.60 | 0.82 | 0.67 | 0.66 | 0.68 |
| W037F | *1.21* | 1.00 | *1.09* | *1.39* | 0.59 | 0.68 | 0.68 | 0.63 | 0.65 |
| W037G | 0.93 | 0.72 | 0.70 | 0.45 | 0.53 | 0.67 | 0.66 | 0.55 | 0.62 |
| W037H | *1.40* | 0.85 | 0.83 | *1.41* | 0.61 | 0.75 | 0.69 | 0.71 | 0.71 |
| W037I | 0.07 | 0.31 | *1.05* | 0.05 | 0.05 | 0.27 | 0.14 | 0.05 | 0.31 |
| W037K | 0.80 | 0.68 | 0.65 | 0.63 | 0.45 | 0.68 | 0.56 | 0.42 | 0.49 |
| W037L | 0.11 | 0.32 | 0.84 | 0.08 | 0.44 | 0.90 | 0.56 | 0.39 | 0.57 |
| W037M | 0.99 | 0.91 | 0.97 | *1.14* | 0.56 | 0.69 | 0.72 | 0.61 | 0.69 |
| W037P | 0.88 | 0.90 | 0.72 | 0.84 | 0.59 | 0.71 | 0.73 | 0.62 | 0.71 |
| W037R | 0.69 | 0.87 | 0.88 | 0.73 | 0.53 | 0.78 | 0.63 | 0.53 | 0.59 |
| W037S | *1.08* | 0.93 | 0.87 | *1.05* | 0.63 | 0.87 | 0.75 | 0.67 | 0.82 |
| W037T | 0.64 | 0.91 | 0.80 | 0.63 | 0.54 | 0.69 | 0.66 | 0.55 | 0.75 |
| W037V | 0.65 | *1.07* | 0.98 | 0.90 | 0.56 | 0.76 | 0.65 | 0.64 | 0.70 |
| W037W | 1.00 | 1.00 | 1.00 | 1.00 | 1.00 | 1.00 | 1.00 | 1.00 | 1.00 |
| W037Y | *1.11* | *1.02* | 0.86 | *1.45* | 0.62 | 0.85 | 0.70 | 0.85 | 0.66 |
| S050A | 0.99 | *1.02* | 0.99 | *1.10* | 0.99 | 0.96 | 1.00 | 0.85 | 0.63 |
| S050C | 0.61 | 0.92 | *1.10* | 0.64 | *1.05* | *1.26* | *1.14* | 0.96 | *1.02* |
| S050F | 0.78 | 0.85 | *1.03* | 0.73 | 0.86 | *1.24* | 0.85 | 0.75 | 0.62 |
| S050G | 0.67 | 0.80 | *1.05* | 0.60 | 0.87 | *1.25* | 0.87 | 0.76 | 0.86 |
| S050I | 0.51 | 0.83 | 0.94 | 0.60 | 0.86 | *1.12* | 0.92 | 0.79 | 0.77 |
| S050K | 0.64 | 0.77 | *1.02* | 0.67 | 0.91 | 0.99 | 0.91 | 0.82 | 0.79 |
| S050L | 0.32 | 0.73 | 0.99 | 0.40 | *1.01* | *1.30* | 0.86 | 0.74 | *1.05* |
| S050M | 0.65 | 0.97 | 0.91 | 0.81 | 0.95 | *1.23* | 0.79 | 0.66 | 0.98 |
| S050N | 0.63 | 0.83 | 0.95 | 0.57 | 0.87 | *1.27* | 0.86 | 0.68 | 0.78 |
| S050P | 0.60 | 0.90 | *1.02* | 0.74 | 0.97 | *1.22* | *1.00* | 0.71 | 0.90 |
| S050Q | 0.65 | 0.86 | 0.98 | 0.73 | 0.89 | 0.98 | 0.93 | 0.71 | 0.64 |
| S050R | 0.77 | 0.91 | *1.00* | 0.81 | 0.92 | *1.07* | 0.95 | 0.80 | 0.82 |
| S050S | 1.00 | 1.00 | 1.00 | 1.00 | 1.00 | 1.00 | 1.00 | 1.00 | 1.00 |
| S050T | 0.55 | 0.75 | *1.09* | 0.63 | 0.91 | *1.14* | 0.89 | 0.80 | 0.83 |
| S050V | 0.73 | 0.99 | 0.96 | 0.79 | 0.88 | *1.08* | 0.95 | 0.86 | 0.86 |
| S050W | 0.74 | 0.91 | 0.98 | 0.75 | 0.93 | 0.97 | 0.91 | 0.90 | 0.92 |
| S050Y | 0.72 | 0.96 | *1.04* | 0.81 | 0.90 | 0.93 | 0.70 | 0.99 | 0.93 |
| K051A | *1.07* | 0.99 | *1.06* | *1.03* | 0.97 | *1.11* | *1.10* | 0.94 | 0.93 |
| K051C | 0.46 | *1.21* | 0.96 | 0.57 | *1.30* | *1.16* | *1.18* | *1.45* | *1.27* |

TABLE 3-1-continued

Performance Index Data of BGL1 SEL Variants (3,153)

| | | | | | | | | |
|---|---|---|---|---|---|---|---|---|
| K051D | 0.98 | *1.05* | *1.05* | 0.80 | 0.99 | *1.10* | *1.12* | *1.11* | *1.09* |
| K051E | 0.64 | *1.03* | 0.96 | 0.75 | *1.14* | 0.91 | 0.96 | 0.92 | 0.88 |
| K051F | 0.04 | 0.04 | 0.04 | 0.04 | 0.04 | 0.04 | 0.04 | 0.04 | 0.04 |
| K051G | 0.66 | *1.07* | *1.02* | 0.71 | *1.05* | 0.95 | *1.08* | *1.08* | 0.97 |
| K051H | 0.78 | *1.17* | *1.01* | *1.02* | *1.02* | *1.03* | *1.12* | *1.07* | *1.02* |
| K051I | 0.45 | 0.94 | 0.95 | 0.64 | *1.02* | *1.10* | 1.00 | *1.05* | 0.91 |
| K051K | 1.00 | 1.00 | 1.00 | 1.00 | 1.00 | 1.00 | 1.00 | 1.00 | 1.00 |
| K051L | 0.51 | 0.97 | 0.93 | 0.65 | 0.94 | *1.05* | 0.82 | *1.33* | 0.78 |
| K051M | 0.80 | *1.16* | *1.08* | *1.04* | *1.01* | 0.92 | *1.07* | *1.01* | 0.97 |
| K051N | 0.55 | 0.99 | 0.97 | 0.49 | 0.98 | 0.98 | 0.94 | *1.02* | 0.80 |
| K051P | 0.27 | 0.71 | 0.87 | 0.29 | 0.98 | 0.91 | 0.94 | 0.92 | 0.83 |
| K051Q | 0.55 | *1.14* | 0.94 | 0.77 | *1.07* | *1.09* | *1.15* | 0.99 | 0.81 |
| K051R | 0.64 | *1.07* | 0.96 | 0.78 | 0.99 | *1.06* | 0.98 | *1.09* | 0.81 |
| K051S | 0.34 | 0.84 | 0.91 | 0.49 | 0.94 | *1.06* | 0.91 | 0.90 | 0.74 |
| K051T | 0.75 | *1.20* | *1.03* | 0.93 | *1.03* | *1.02* | *1.08* | *1.17* | *1.21* |
| K051V | 0.50 | *1.07* | *1.03* | 0.70 | *1.06* | *1.10* | *1.06* | *1.04* | 0.90 |
| K051W | 0.44 | 0.77 | 0.95 | 0.23 | 0.89 | 0.85 | 0.86 | 0.95 | 0.82 |
| I052A | 0.27 | 0.21 | *1.19* | 0.05 | 0.62 | 0.44 | 0.44 | 0.83 | *1.19* |
| I052C | 0.32 | 0.12 | 0.05 | 0.11 | 0.24 | 0.07 | 0.09 | 0.52 | 0.33 |
| I052D | 0.10 | 0.19 | 0.84 | 0.10 | *1.01* | 0.69 | 0.62 | *1.86* | *1.53* |
| I052F | 0.26 | 0.17 | *1.01* | 0.05 | 0.45 | 0.25 | 0.28 | 0.82 | 0.54 |
| I052I | 1.00 | 1.00 | 1.00 | 1.00 | 1.00 | 1.00 | 1.00 | 1.00 | 1.00 |
| I052K | 0.10 | 0.22 | 0.57 | 0.06 | 0.74 | 0.37 | 0.31 | *1.69* | 0.64 |
| I052L | 0.27 | 0.28 | 0.87 | 0.12 | 0.61 | 0.43 | 0.50 | 0.92 | 0.80 |
| I052M | 0.17 | 0.18 | 0.87 | 0.05 | 0.61 | 0.34 | 0.34 | *1.17* | 0.86 |
| I052N | 0.09 | 0.17 | *1.03* | 0.05 | 0.77 | 0.29 | 0.40 | *1.92* | *1.17* |
| I052P | 0.10 | 0.13 | 0.05 | 0.05 | 0.88 | 0.26 | 0.41 | *1.74* | *1.00* |
| I052Q | 0.10 | 0.20 | 0.79 | 0.05 | 0.98 | 0.51 | 0.52 | *1.85* | 0.53 |
| I052R | 0.31 | 0.19 | 0.05 | 0.16 | 0.27 | 0.15 | 0.12 | 0.57 | 0.40 |
| I052S | 0.30 | 0.13 | *1.15* | 0.08 | 0.33 | 0.13 | 0.16 | 0.64 | 0.41 |
| I052T | 0.10 | 0.21 | 0.82 | 0.05 | *1.01* | 0.88 | 0.70 | *2.04* | 0.95 |
| I052V | 0.23 | 0.26 | 0.88 | 0.11 | 0.67 | 0.45 | 0.42 | *1.04* | *1.17* |
| I052W | 0.32 | 0.12 | 0.05 | 0.08 | 0.24 | 0.12 | 0.10 | 0.58 | 0.38 |
| I052Y | 0.32 | 0.18 | 0.65 | 0.05 | 0.32 | 0.16 | 0.15 | 0.61 | 0.56 |
| D061A | 0.92 | 0.06 | 0.12 | 0.05 | 0.05 | 0.05 | 0.05 | 0.05 | 0.07 |

TABLE 3-1-continued

Performance Index Data of BGL1 SEL Variants (3,153)

| | | | | | | | | | |
|---|---|---|---|---|---|---|---|---|---|
| D061C | 0.95 | 0.07 | 0.05 | 0.05 | 0.05 | 0.05 | 0.05 | 0.05 | 0.07 |
| D061D | 1.00 | 1.00 | 1.00 | 1.00 | 1.00 | 1.00 | 1.00 | 1.00 | 1.00 |
| D061E | *1.31* | 0.10 | 0.60 | 0.05 | 0.19 | 0.54 | 0.11 | 0.07 | 0.12 |
| D061F | 0.81 | 0.05 | 0.05 | 0.05 | 0.05 | 0.05 | 0.05 | 0.05 | 0.10 |
| D061G | *1.17* | 0.05 | 0.05 | 0.05 | 0.05 | 0.07 | 0.05 | 0.05 | 0.05 |
| D061H | 0.78 | 0.22 | 0.49 | 0.12 | 0.23 | 0.30 | 0.18 | 0.08 | 0.15 |
| D061I | 0.33 | 0.10 | 0.05 | 0.07 | 0.05 | 0.05 | 0.07 | 0.05 | 0.19 |
| D061K | 0.38 | 0.11 | 0.05 | 0.13 | 0.05 | 0.05 | 0.06 | 0.05 | 0.11 |
| D061L | 0.97 | 0.07 | 0.05 | 0.08 | 0.05 | 0.07 | 0.05 | 0.05 | 0.07 |
| D061M | 0.96 | 0.05 | 0.05 | 0.05 | 0.05 | 0.06 | 0.05 | 0.05 | 0.05 |
| D061N | *1.73* | 0.05 | 0.05 | 0.05 | 0.05 | 0.05 | 0.05 | 0.05 | 0.05 |
| D061P | *1.06* | 0.06 | 0.05 | 0.36 | 0.05 | 0.05 | 0.05 | 0.05 | 0.05 |
| D061R | 0.49 | 0.09 | 0.05 | 0.11 | 0.05 | 0.05 | 0.05 | 0.05 | 0.06 |
| D061T | 0.52 | 0.07 | 0.05 | 0.16 | 0.05 | 0.05 | 0.05 | 0.05 | 0.09 |
| D061V | 0.19 | 0.10 | 0.05 | 0.31 | 0.05 | 0.19 | 0.16 | 0.05 | 0.18 |
| D061W | 0.24 | 0.22 | 0.49 | 0.19 | 0.28 | 0.24 | 0.22 | 0.10 | 0.29 |
| D061Y | 0.69 | 0.07 | 0.05 | 0.05 | 0.05 | 0.05 | 0.05 | 0.05 | 0.12 |
| R067A | 0.44 | *1.48* | *1.25* | 0.05 | 0.05 | 0.05 | 0.06 | 0.15 | 0.49 |
| R067C | 0.28 | *1.45* | *1.15* | 0.05 | 0.05 | 0.25 | 0.08 | 0.18 | 0.43 |
| R067D | 0.16 | *3.11* | *1.31* | 0.05 | 0.06 | 0.22 | 0.11 | 0.26 | 0.45 |
| R067E | 0.45 | 0.75 | *1.46* | 0.05 | 0.05 | 0.07 | 0.08 | 0.12 | 0.35 |
| R067F | 0.43 | *1.15* | *1.28* | 0.05 | 0.05 | 0.06 | 0.11 | 0.19 | 0.42 |
| R067G | *1.20* | *1.04* | *1.22* | 0.05 | 0.05 | 0.05 | 0.05 | 0.09 | 0.26 |
| R067I | 0.94 | 0.66 | *1.08* | 0.05 | 0.05 | 0.05 | 0.07 | 0.08 | 0.21 |
| R067K | 0.71 | 0.05 | 0.05 | 0.06 | 0.05 | 0.05 | 0.05 | 0.06 | 0.12 |
| R067L | *1.50* | 0.75 | 0.99 | 0.05 | 0.05 | 0.05 | 0.05 | 0.05 | 0.18 |
| R067M | *1.11* | 0.63 | *1.21* | 0.05 | 0.05 | 0.05 | 0.05 | 0.07 | 0.23 |
| R067N | 0.29 | *5.24* | *1.03* | 0.05 | 0.05 | 0.05 | 0.07 | 0.13 | 0.43 |
| R067P | *1.07* | *1.03* | *1.11* | 0.05 | 0.05 | 0.05 | 0.05 | 0.07 | 0.34 |
| R067Q | 0.19 | *1.43* | 0.05 | 0.10 | 0.05 | 0.05 | 0.08 | 0.23 | 0.98 |
| R067R | 1.00 | 1.00 | 1.00 | 1.00 | 1.00 | 1.00 | 1.00 | 1.00 | 1.00 |
| R067S | 0.85 | *1.05* | *1.41* | 0.05 | 0.05 | 0.14 | 0.07 | 0.12 | 0.24 |
| R067T | *2.11* | 0.77 | *1.40* | 0.11 | 0.05 | 0.05 | 0.05 | 0.08 | 0.22 |
| R067V | *1.73* | 0.78 | *1.39* | 0.05 | 0.05 | 0.05 | 0.05 | 0.10 | 0.25 |
| R067W | 0.31 | *1.52* | *1.19* | 0.07 | 0.05 | 0.05 | 0.14 | 0.21 | 0.25 |

TABLE 3-1-continued

Performance Index Data of BGL1 SEL Variants (3,153)

| | | | | | | | | |
|---|---|---|---|---|---|---|---|---|
| R067Y | *1.34* | 0.79 | *1.14* | 0.08 | 0.05 | 0.09 | 0.05 | 0.12 | 0.23 |
| R091A | 0.20 | *2.01* | *1.22* | 0.23 | 0.82 | 0.96 | 0.93 | 0.94 | 0.77 |
| R091C | 0.08 | 0.05 | 0.05 | 0.17 | 0.59 | 0.53 | 0.80 | *1.10* | 0.73 |
| R091D | 0.40 | *1.22* | *1.09* | 0.36 | *1.09* | *1.37* | *1.13* | 0.96 | *1.01* |
| R091E | 0.88 | 0.96 | *1.04* | 0.81 | 0.98 | *1.01* | 0.98 | 0.86 | *1.13* |
| R091F | 0.57 | *1.08* | *1.04* | 0.51 | 0.93 | *1.16* | 0.96 | 0.90 | *1.12* |
| R091G | 0.96 | 0.86 | *1.17* | 0.83 | *1.10* | *1.25* | *1.01* | 0.87 | 0.90 |
| R091H | 0.61 | 0.93 | *1.11* | 0.52 | 0.88 | *1.12* | 0.91 | 0.85 | 0.83 |
| R091I | *1.02* | 0.91 | *1.01* | 0.85 | 0.96 | *1.17* | 0.94 | 0.86 | 0.90 |
| R091K | 0.93 | 0.97 | *1.04* | 0.87 | *1.04* | *1.29* | *1.06* | 0.96 | 0.97 |
| R091L | 0.29 | *1.39* | *1.07* | 0.34 | 0.84 | *1.03* | 0.97 | 0.97 | 0.90 |
| R091M | 0.04 | 0.04 | 0.04 | 0.04 | 0.04 | 0.04 | 0.04 | 0.04 | 0.04 |
| R091N | 0.98 | 0.94 | *1.08* | 0.94 | 0.99 | *1.21* | *1.00* | 0.92 | *1.05* |
| R091P | 0.07 | 0.05 | 0.05 | 0.16 | 0.07 | 0.96 | 0.26 | 0.71 | 0.44 |
| R091Q | 0.63 | *1.05* | *1.21* | 0.61 | *1.01* | *1.24* | *1.06* | *1.02* | 0.80 |
| R091R | 1.00 | 1.00 | 1.00 | 1.00 | 1.00 | 1.00 | 1.00 | 1.00 | 1.00 |
| R091S | 0.73 | 0.88 | *1.17* | 0.62 | 0.86 | 0.89 | 0.89 | 0.88 | 0.72 |
| R091T | *1.20* | 0.83 | *1.13* | 0.95 | 0.93 | *1.00* | 0.93 | 0.87 | 0.81 |
| R091V | 0.34 | *1.20* | *1.18* | 0.35 | 0.94 | *1.24* | 0.94 | 0.98 | 0.78 |
| R091W | 0.57 | *1.02* | *1.09* | 0.57 | 0.96 | *1.15* | 0.96 | *1.05* | 0.82 |
| R091Y | *1.41* | 0.86 | 0.98 | *1.08* | 0.94 | *1.05* | 0.92 | 0.94 | 0.81 |
| E092A | 0.59 | 0.95 | 0.82 | 0.62 | *1.04* | 0.98 | *1.17* | 0.90 | *1.02* |
| E092C | 0.66 | *1.14* | 0.87 | 0.46 | *1.20* | *1.28* | *1.50* | *1.07* | *1.24* |
| E092D | 0.97 | 0.92 | 0.85 | 0.32 | *1.01* | *1.09* | *1.11* | 0.88 | 0.93 |
| E092E | 1.00 | 1.00 | 1.00 | 1.00 | 1.00 | 1.00 | 1.00 | 1.00 | 1.00 |
| E092F | 0.61 | 0.95 | 0.84 | 0.50 | 0.94 | *1.12* | *1.05* | 0.88 | 0.73 |
| E092H | 0.49 | 0.91 | 0.85 | 0.71 | 0.92 | *1.23* | *1.05* | 0.84 | 0.68 |
| E092I | 0.69 | 1.00 | 0.82 | 0.78 | 0.94 | 0.97 | *1.06* | 0.93 | 0.83 |
| E092K | *1.48* | *1.04* | *1.01* | *1.43* | 0.99 | *1.16* | 0.95 | *1.07* | 0.94 |
| E092L | *1.09* | *1.04* | 0.93 | *1.26* | 0.95 | *1.19* | *1.04* | 0.97 | 0.82 |
| E092M | 0.91 | 0.93 | 0.98 | *1.05* | 0.88 | 0.93 | 0.82 | 0.88 | 0.75 |
| E092N | 0.72 | *1.04* | 0.88 | 0.44 | 0.98 | *1.10* | *1.16* | 0.96 | 0.99 |
| E092P | 0.04 | 0.04 | 0.04 | 0.04 | 0.04 | 0.04 | 0.04 | 0.04 | 0.04 |
| E092Q | 0.86 | 0.93 | 0.88 | 0.68 | 0.88 | *1.07* | 0.97 | 0.88 | 0.77 |
| E092R | 0.91 | 0.97 | 0.85 | 0.60 | 0.92 | *1.29* | *1.08* | 0.96 | 0.78 |
| E092S | 0.78 | 0.93 | 0.87 | 0.93 | 0.92 | 0.96 | 0.99 | 0.91 | 0.80 |

TABLE 3-1-continued

Performance Index Data of BGL1 SEL Variants (3,153)

| | | | | | | | | |
|---|---|---|---|---|---|---|---|---|
| E092T | *1.11* | 0.92 | *1.05* | 0.98 | 0.93 | *1.02* | 0.95 | 0.94 | 0.84 |
| E092V | 0.90 | 0.98 | 0.98 | 0.84 | 1.00 | *1.40* | *1.11* | 0.95 | 0.87 |
| E092W | 0.97 | 0.77 | 0.94 | 0.80 | 0.77 | 0.92 | 0.81 | 0.77 | 0.66 |
| E092Y | 0.77 | 0.91 | 0.95 | 0.05 | 0.90 | *1.01* | 0.96 | 0.92 | 0.76 |
| R093A | 0.40 | 0.43 | *1.47* | 0.05 | 0.48 | 0.12 | 0.32 | 0.47 | 0.28 |
| R093C | 0.38 | 0.37 | *1.40* | 0.05 | 0.45 | 0.18 | 0.29 | 0.50 | 0.33 |
| R093D | 0.14 | 0.10 | *1.21* | 0.08 | 0.31 | 0.66 | 0.20 | 0.32 | 0.21 |
| R093E | 0.37 | 0.40 | *1.38* | 0.05 | 0.44 | 0.12 | 0.31 | 0.43 | 0.20 |
| R093F | 0.20 | 0.34 | *1.25* | 0.05 | 0.30 | 0.12 | 0.31 | 0.49 | 0.15 |
| R093G | 0.08 | 0.15 | *1.51* | 0.05 | 0.29 | 0.43 | 0.22 | 0.50 | 0.24 |
| R093H | 0.23 | 0.49 | *1.12* | 0.05 | 0.78 | 0.70 | 0.62 | 0.76 | 0.47 |
| R093I | 0.11 | 0.05 | 0.05 | 0.15 | 0.05 | 0.05 | 0.05 | 0.18 | 0.11 |
| R093K | 0.18 | 0.31 | *1.01* | 0.05 | 0.56 | *1.20* | 0.44 | 0.62 | 0.26 |
| R093L | 0.51 | 0.51 | *1.37* | 0.08 | 0.37 | 0.10 | 0.20 | 0.41 | 0.22 |
| R093M | 0.63 | 0.54 | *1.39* | 0.05 | 0.43 | 0.17 | 0.21 | 0.54 | 0.19 |
| R093P | 0.05 | 0.05 | 0.05 | 0.05 | 0.05 | 0.05 | 0.05 | 0.05 | 0.05 |
| R093Q | 0.16 | 0.48 | *1.39* | 0.05 | 0.64 | 0.15 | 0.29 | 0.79 | 0.26 |
| R093R | 1.00 | 1.00 | 1.00 | 1.00 | 1.00 | 1.00 | 1.00 | 1.00 | 1.00 |
| R093S | 0.19 | 0.25 | *1.47* | 0.05 | 0.32 | 0.17 | 0.22 | 0.40 | 0.20 |
| R093T | 0.15 | 0.13 | *1.11* | 0.05 | 0.12 | 0.26 | 0.08 | 0.29 | 0.25 |
| R093V | 0.15 | 0.13 | *1.50* | 0.05 | 0.11 | 0.17 | 0.07 | 0.27 | 0.12 |
| R093W | 0.13 | 0.20 | *1.29* | 0.05 | 0.41 | 0.16 | 0.33 | 0.54 | 0.24 |
| R093Y | 0.11 | 0.05 | 0.05 | 0.05 | 0.05 | 0.05 | 0.05 | 0.16 | 0.09 |
| E099A | 0.74 | 0.75 | *1.02* | 0.71 | 0.91 | *1.17* | 0.83 | 0.80 | 0.80 |
| E099C | 0.05 | 0.05 | 0.05 | 0.05 | 0.05 | 0.05 | 0.05 | 0.05 | 0.05 |
| E099D | 0.16 | 0.26 | 0.98 | 0.17 | 0.81 | *1.65* | 0.66 | 0.76 | 0.46 |
| E099E | 1.00 | 1.00 | 1.00 | 1.00 | 1.00 | 1.00 | 1.00 | 1.00 | 1.00 |
| E099F | 0.48 | 0.72 | *1.08* | 0.56 | 0.96 | *1.15* | 0.97 | 0.86 | 0.90 |
| E099G | 0.11 | 0.05 | 0.05 | 0.05 | 0.11 | 0.22 | 0.11 | 0.27 | 0.10 |
| E099I | 0.53 | 0 67 | *1.10* | 0.62 | 0.90 | *1.24* | 0.79 | 0.83 | 0.77 |
| E099K | 0.59 | 0.75 | 0.97 | 0.72 | 0.89 | *1.42* | 0.79 | 0.84 | 0.69 |
| E099L | 0.05 | 0.05 | 0.05 | 0.05 | 0.05 | 0.05 | 0.05 | 0.05 | 0.05 |
| E099M | 0.70 | 0.78 | *1.02* | 0.78 | 0.85 | *1.23* | 0.75 | 0.80 | 0.70 |
| E099N | 0.70 | 0.90 | 0.94 | 0.86 | 0.87 | *1.12* | 0.84 | 0.83 | 0.88 |
| E099P | 0.10 | 0.05 | 0.05 | 0.05 | 0.10 | 0.16 | 0.06 | 0.29 | 0.24 |

TABLE 3-1-continued

Performance Index Data of BGL1 SEL Variants (3,153)

| | | | | | | | | | |
|---|---|---|---|---|---|---|---|---|---|
| E099Q | 0.11 | 0.05 | 0.05 | 0.05 | 0.05 | 0.18 | 0.05 | 0.17 | 0.05 |
| E099R | 0.10 | 0.05 | 0.05 | 0.05 | 0.05 | 0.05 | 0.05 | 0.17 | 0.15 |
| E099V | 0.57 | 0.69 | 1.00 | 0.70 | 0.86 | 0.98 | 0.77 | 0.82 | 0.79 |
| E099W | 0.51 | 0.66 | *1.15* | 0.49 | 0.91 | *1.36* | 0.89 | 0.88 | 0.78 |
| E099Y | 0.58 | 0.85 | *1.03* | 0.79 | *1.03* | *1.31* | *1.03* | *1.03* | 0.85 |
| E100A | 0.60 | *1.13* | 0.99 | 0.05 | *1.04* | 0.64 | *1.01* | *1.04* | *1.29* |
| E100C | 0.04 | 0.04 | 0.04 | 0.04 | 0.04 | 0.04 | 0.04 | 0.04 | 0.04 |
| E100D | 0.04 | 0.04 | 0.04 | 0.04 | 0.04 | 0.04 | 0.04 | 0.04 | 0.04 |
| E100E | 1.00 | 1.00 | 1.00 | 1.00 | 1.00 | 1.00 | 1.00 | 1.00 | 1.00 |
| E100G | 0.26 | *1.14* | 0.82 | 0.05 | *1.19* | 0.69 | *1.15* | *1.36* | *1.11* |
| E100H | 0.04 | 0.04 | 0.04 | 0.04 | 0.04 | 0.04 | 0.04 | 0.04 | 0.04 |
| E100I | 0.31 | *1.04* | *1.16* | 0.05 | 0.94 | 0.44 | 0.94 | *1.04* | 0.80 |
| E100K | 0.11 | 0.26 | *1.33* | 0.10 | 0.54 | 0.59 | 0.31 | 0.38 | 0.44 |
| E100L | 0.32 | 0.81 | *1.02* | 0.05 | 0.84 | 0.41 | 0.77 | 0.89 | 0.82 |
| E100M | 0.30 | *1.10* | 0.78 | 0.15 | 0.98 | 0.47 | *1.01* | *1.13* | *1.08* |
| E100N | 0.14 | 0.64 | 0.90 | 0.08 | *1.05* | 0.88 | 0.95 | *1.09* | *1.26* |
| E100P | 0.04 | 0.04 | 0.04 | 0.04 | 0.04 | 0.04 | 0.04 | 0.04 | 0.04 |
| E100Q | 0.41 | 0.99 | 0.78 | 0.11 | *1.01* | 0.81 | 0.95 | *1.06* | 0.93 |
| E100R | 0.04 | 0.04 | 0.04 | 0.04 | 0.04 | 0.04 | 0.04 | 0.04 | 0.04 |
| E100S | 0.52 | *1.09* | 0.81 | 0.06 | *1.03* | 0.78 | 0.97 | *1.04* | *1.01* |
| E100T | 0.47 | *1.17* | 0.86 | 0.10 | *1.04* | 0.76 | *1.05* | *1.15* | 0.96 |
| E100V | 0.30 | 0.82 | 0.77 | 0.08 | 0.89 | 0.40 | 0.86 | 0.96 | 0.75 |
| E100W | 0.04 | 0.04 | 0.04 | 0.04 | 0.04 | 0.04 | 0.04 | 0.04 | 0.04 |
| E100Y | 0.27 | 0.91 | *1.27* | 0.06 | *1.12* | 0.34 | *1.08* | *1.20* | *1.00* |
| R125A | *1.29* | 0.05 | 0.05 | 0.05 | 0.38 | 0.13 | 0.05 | 0.05 | 0.05 |
| R125C | 0.51 | 0.05 | 0.05 | 0.05 | 0.71 | 0.07 | 0.05 | 0.05 | 0.14 |
| R125D | *1.56* | 0.05 | 0.05 | 0.05 | 0.31 | 0.19 | 0.05 | 0.05 | 0.06 |
| R125E | 0.65 | 0.05 | 0.05 | 0.05 | 0.85 | 0.11 | 0.05 | 0.05 | 0.14 |
| R125F | 0.07 | 0.05 | 0.05 | 0.05 | 0.05 | 0.05 | 0.05 | 0.05 | 0.82 |
| R125G | 0.83 | 0.05 | 0.05 | 0.05 | 0.32 | 0.38 | 0.05 | 0.05 | 0.07 |
| R125I | 0.17 | 0.81 | 0.95 | 0.15 | 0.24 | 0.05 | 0.73 | 0.76 | 0.97 |
| R125L | 0.54 | 0.05 | 0.05 | 0.05 | 0.72 | 0.07 | 0.05 | 0.05 | 0.13 |
| R125M | 0.58 | 0.05 | 0.05 | 0.05 | 0.28 | 0.07 | 0.05 | 0.05 | 0.10 |
| R125P | 0.15 | 0.05 | 0.05 | 0.05 | 0.05 | 0.05 | 0.05 | 0.05 | 0.23 |
| R125R | 1.00 | 1.00 | 1.00 | 1.00 | 1.00 | 1.00 | 1.00 | 1.00 | 1.00 |

TABLE 3-1-continued

Performance Index Data of BGL1 SEL Variants (3,153)

| R125S | 0.84 | 0.05 | 0.05 | 0.05 | 0.66 | 0.08 | 0.05 | 0.05 | 0.05 |
|---|---|---|---|---|---|---|---|---|---|
| R125T | 0.93 | 0.05 | 0.05 | 0.05 | 0.71 | 0.18 | 0.05 | 0.05 | 0.08 |
| R125V | 0.68 | 0.05 | 0.05 | 0.05 | 0.05 | 0.06 | 0.05 | 0.05 | 0.08 |
| R125W | 0.21 | 0.05 | 0.05 | 0.05 | 0.05 | 0.05 | 0.05 | 0.05 | 0.21 |
| R125Y | 0.11 | 0.05 | 0.05 | 0.05 | 0.37 | 0.05 | 0.05 | 0.05 | 0.13 |
| K158A | *1.63* | 0.05 | 0.05 | 0.05 | 0.87 | 0.18 | 0.05 | 0.05 | 0.05 |
| K158C | *1.16* | 0.05 | 0.05 | 0.05 | 0.65 | 0.17 | 0.05 | 0.05 | 0.07 |
| K158E | 0.57 | 0.05 | 0.05 | 0.05 | 0.05 | 0.08 | 0.05 | 0.05 | 0.12 |
| K158F | 0.09 | 0.05 | 0.05 | 0.05 | 0.67 | 0.05 | 0.05 | 0.05 | 0.58 |
| K158G | *1.11* | 0.05 | 0.05 | 0.05 | 0.05 | 0.12 | 0.05 | 0.05 | 0.05 |
| K158H | 0.21 | 0.05 | 0.05 | 0.10 | *1.06* | 0.05 | 0.05 | 0.05 | 0.15 |
| K158I | 0.45 | 0.05 | 0.05 | 0.05 | 0.41 | 0.05 | 0.05 | 0.05 | 0.10 |
| K158K | 1.00 | 1.00 | 1.00 | 1.00 | 1.00 | 1.00 | 1.00 | 1.00 | 1.00 |
| K158L | 0.82 | 0.05 | 0.05 | 0.05 | 0.89 | 0.12 | 0.05 | 0.05 | 0.06 |
| K158M | 0.74 | 0.05 | 0.05 | 0.05 | 0.35 | 0.31 | 0.05 | 0.05 | 0.11 |
| K158P | 0.17 | 0.05 | 0.05 | 0.05 | 0.05 | 0.05 | 0.05 | 0.05 | 0.49 |
| K158Q | 0.64 | 0.05 | 0.05 | 0.05 | 0.05 | 0.10 | 0.05 | 0.05 | 0.09 |
| K158R | 0.75 | 0.05 | 0.05 | 0.05 | 0.05 | 0.13 | 0.05 | 0.05 | 0.09 |
| K158S | 0.67 | 0.05 | 0.05 | 0.05 | 0.51 | 0.09 | 0.05 | 0.05 | 0.08 |
| K158T | 0.69 | 0.05 | 0.05 | 0.05 | *1.33* | 0.10 | 0.05 | 0.05 | 0.06 |
| K158V | 0.57 | 0.05 | 0.05 | 0.05 | 0.53 | 0.10 | 0.05 | 0.05 | 0.10 |
| K158Y | 0.11 | 0.05 | 0.05 | 0.05 | 0.31 | 0.05 | 0.05 | 0.05 | 0.16 |
| H159A | *1.56* | 0.25 | 0.98 | 0.05 | 0.18 | 0.47 | 0.22 | 0.21 | 0.23 |
| H159C | *2.77* | 0.05 | 0.05 | 0.05 | 0.05 | 0.10 | 0.05 | 0.05 | 0.05 |
| H159D | 0.04 | 0.04 | 0.04 | 0.04 | 0.04 | 0.04 | 0.04 | 0.04 | 0.04 |
| H159E | *1.02* | 0.08 | *1.53* | 0.05 | 0.05 | 0.29 | 0.06 | 0.05 | 0.12 |
| H159F | 0.54 | 0.05 | 0.05 | 0.05 | 0.05 | 0.06 | 0.05 | 0.05 | 0.45 |
| H159G | *1.26* | 0.09 | *1.60* | 0.05 | 0.06 | 0.23 | 0.09 | 0.06 | 0.18 |
| H159H | 1.00 | 1.00 | 1.00 | 1.00 | 1.00 | 1.00 | 1.00 | 1.00 | 1.00 |
| H159I | 0.42 | 0.05 | 0.05 | 0.05 | 0.05 | 0.10 | 0.05 | 0.05 | 0.07 |
| H159K | 0.41 | 0.05 | 0.05 | 0.05 | 0.05 | 0.07 | 0.05 | 0.05 | 0.17 |
| H159L | 0.68 | 0.05 | 0.05 | 0.05 | 0.05 | 0.05 | 0.05 | 0.05 | 0.05 |
| H159M | 0.35 | 0.05 | 0.05 | 0.05 | 0.05 | 0.10 | 0.05 | 0.21 | 0.72 |
| H159N | *2.13* | 0.05 | 0.05 | 0.05 | 0.05 | 0.06 | 0.05 | 0.05 | 0.05 |
| H159Q | 0.40 | 0.05 | 0.05 | 0.05 | 0.05 | 0.15 | 0.05 | 0.05 | 0.14 |
| H159R | 0.67 | 0.05 | 0.05 | 0.05 | 0.05 | 0.09 | 0.05 | 0.05 | 0.08 |

TABLE 3-1-continued

Performance Index Data of BGL1 SEL Variants (3,153)

| | | | | | | | | | |
|---|---|---|---|---|---|---|---|---|---|
| H159S | *1.19* | 0.12 | 0.62 | 0.05 | 0.05 | 0.14 | 0.06 | 0.05 | 0.11 |
| H159T | 0.04 | 0.04 | 0.04 | 0.04 | 0.04 | 0.04 | 0.04 | 0.04 | 0.04 |
| H159V | 0.61 | 0.05 | 0.05 | 0.05 | 0.05 | 0.07 | 0.05 | 0.38 | 0.08 |
| H159W | *1.04* | 0.05 | 0.05 | 0.05 | 0.05 | 0.06 | 0.05 | 0.05 | 0.05 |
| H159Y | *1.70* | 0.05 | 0.05 | 0.05 | 0.05 | 0.06 | 0.05 | 0.05 | 0.05 |
| N163A | *1.11* | 0.61 | 0.33 | 0.05 | 0.43 | 0.58 | 0.33 | 0.31 | 0.33 |
| N163C | 0.88 | 0.79 | 0.37 | 0.05 | 0.53 | 0.76 | 0.58 | 0.45 | 0.56 |
| N163D | 0.84 | 0.99 | 0.64 | 0.05 | 0.72 | 0.85 | 0.73 | 0.62 | 0.65 |
| N163E | 0.22 | 0.05 | 0.05 | 0.05 | 0.05 | 0.11 | 0.05 | 0.05 | 0.05 |
| N163F | 0.32 | 0.13 | 0.90 | 0.05 | 0.05 | 0.06 | 0.05 | 0.05 | 0.06 |
| N163G | 0.69 | 0.86 | 0.36 | 0.05 | 0.48 | 0.71 | 0.45 | 0.51 | 0.45 |
| N163H | *1.02* | 0.35 | 0.23 | 0.05 | 0.28 | 0.34 | 0.22 | 0.33 | 0.14 |
| N163I | 0.26 | 0.36 | 0.10 | 0.05 | 0.15 | 0.36 | 0.22 | 0.20 | 0.17 |
| N163K | 0.04 | 0.04 | 0.04 | 0.04 | 0.04 | 0.04 | 0.04 | 0.04 | 0.04 |
| N163L | 0.94 | 0.41 | 0.35 | 0.05 | 0.19 | 0.30 | 0.14 | 0.26 | 0.21 |
| N163M | 0.74 | 0.17 | 0.43 | 0.05 | 0.15 | 0.25 | 0.08 | 0.12 | 0.09 |
| N163N | 1.00 | 1.00 | 1.00 | 1.00 | 1.00 | 1.00 | 1.00 | 1.00 | 1.00 |
| N163P | 0.90 | 0.45 | 0.31 | 0.05 | 0.28 | 0.37 | 0.19 | 0.23 | 0.21 |
| N163Q | 0.93 | 0.60 | 0.56 | 0.05 | 0.54 | 0.61 | 0.44 | 0.81 | 0.29 |
| N163R | 0.45 | 0.05 | 0.05 | 0.05 | 0.05 | 0.08 | 0 05 | 0.05 | 0.07 |
| N163S | *1.07* | 0.71 | 0.38 | 0.05 | 0.43 | 0.54 | 0.39 | 0.35 | 0.41 |
| N163T | 0.63 | 0.52 | 0.11 | 0.05 | 0.21 | 0.38 | 0.25 | 0.23 | 0.33 |
| N163V | 0.27 | 0.48 | 0.08 | 0.05 | 0.13 | 0.38 | 0.39 | 0.25 | 0.29 |
| N163W | 0.16 | 0.05 | 0.05 | 0.05 | 0.05 | 0.10 | 0.05 | 0.05 | 0.15 |
| N163Y | 0.86 | 0.56 | 0.38 | 0.58 | 0.40 | 0.69 | 0.46 | 0.32 | 0.45 |
| E164A | 0.04 | 0.04 | 0.04 | 0.04 | 0.04 | 0.04 | 0.04 | 0.04 | 0.04 |
| E164C | 0.65 | 0.95 | 0.91 | 0.05 | 0.75 | 0.84 | 0.93 | 0.80 | 0.96 |
| E164E | 1.00 | 1.00 | 1.00 | 1.00 | 1.00 | 1.00 | 1.00 | 1.00 | 1.00 |
| E164F | 0.12 | 0.34 | 0.70 | 0.05 | 0.19 | 0.30 | 0.57 | 0.09 | 0.22 |
| E164G | 0.20 | 0.67 | 0.83 | 0.05 | 0.74 | 0.74 | *1.13* | 0.53 | 0.61 |
| E164H | 0.06 | 0.05 | 0.05 | 0.05 | 0.05 | 0.17 | 0.13 | 0.05 | 0.15 |
| E164I | 0.08 | 0.05 | 0.05 | 0.05 | 0.05 | 0.05 | 0.05 | 0.05 | 0.07 |
| E164K | 0.10 | 0.05 | 0.05 | 0.05 | 0.05 | 0.05 | 0.05 | 0.05 | 0.17 |
| E164L | 0.09 | 0.05 | 0.05 | 0.05 | 0.05 | 0.05 | 0.05 | 0.05 | 0.17 |
| E164M | 0.10 | 0.26 | 0.68 | 0.06 | 0.14 | 0.21 | 0.44 | 0.05 | 0.17 |

TABLE 3-1-continued

Performance Index Data of BGL1 SEL Variants (3,153)

| | | | | | | | | | |
|---|---|---|---|---|---|---|---|---|---|
| E164N | 0.11 | 0.45 | 0.28 | 0.05 | 0.18 | 0.05 | 0.70 | 0.05 | 0.37 |
| E164P | 0.11 | 0.32 | 0.92 | 0.05 | 0.14 | 0.05 | 0.59 | 0.05 | 0.16 |
| E164Q | 0.15 | 0.50 | 0.83 | 0.05 | 0.55 | 0.23 | 0.96 | 0.42 | 0.58 |
| E164R | 0.10 | 0.05 | 0.05 | 0.05 | 0.05 | 0.05 | 0.05 | 0.05 | 0.12 |
| E164S | 0.69 | *1.22* | 0.93 | 0.05 | 0.80 | 0.65 | *1.01* | 0.99 | 0.87 |
| E164T | 0.43 | 0.98 | 0.86 | 0.67 | 0.78 | 0.72 | 0.90 | 0.80 | 0.96 |
| E164V | 0.10 | 0.45 | 0.65 | 0.05 | 0.18 | 0.05 | 0.68 | 0.10 | 0.39 |
| E164W | 0.07 | 0.05 | 0.05 | 0.05 | 0.05 | 0.05 | 0.05 | 0.05 | 0.12 |
| E164Y | 0.08 | 0.05 | 0.05 | 0.05 | 0.07 | 0.05 | 0.05 | 0.05 | 0.26 |
| Q165C | 0.53 | *1.57* | 0.98 | 0.05 | 0.94 | 0.75 | 0.90 | *1.10* | 0.88 |
| Q165D | 0.20 | 0.05 | *1.03* | 0.05 | 0.85 | 0.63 | 0.75 | 0.82 | 0.85 |
| Q165F | 0.66 | *1.18* | 0.96 | 0.09 | 0.82 | 0.69 | 0.75 | 0.95 | 0.63 |
| Q165G | 0.22 | 0.05 | 0.88 | 0.05 | 0.82 | 0.61 | 0.76 | *1.06* | 0.65 |
| Q165H | 0.28 | *4.57* | 0.92 | 0.05 | 0.81 | 0.59 | 0.68 | 0.94 | 0.63 |
| Q165I | 0.25 | *13.17* | *1.03* | 0.05 | *1.23* | 0.79 | 0.98 | *1.38* | 0.54 |
| Q165K | 0.16 | 0.05 | *1.03* | 0.05 | *1.08* | 0.82 | 0.75 | *1.01* | 0.45 |
| Q165L | 0.23 | *20.39* | *1.08* | 0.05 | 0.82 | 0.58 | 0.53 | 0.81 | 0.77 |
| Q165M | 0.37 | *3.23* | 0.91 | 0.05 | *1.24* | 0.87 | 0.96 | *1.30* | 0.69 |
| Q165N | 0.20 | 0.05 | 0.95 | 0.05 | *1.14* | 0.73 | 0.80 | *1.18* | 0.51 |
| Q165P | 0.31 | 0.78 | 0.05 | 0.05 | 0.16 | 0.26 | 0.08 | 0.07 | 0.27 |
| Q165Q | 1.00 | 1.00 | 1.00 | 1.00 | 1.00 | 1.00 | 1.00 | 1.00 | 1.00 |
| Q165R | 0.26 | *7.92* | *1.10* | 0.05 | 0.89 | 0.57 | 0.64 | 0.95 | 0.77 |
| Q165S | 0.49 | *1.75* | 0.91 | 0.05 | 0.91 | 0.64 | 0.81 | *1.05* | 0.98 |
| Q165T | 0.25 | *2.32* | 0.05 | 0.07 | 0.19 | 0.24 | 0.07 | 0.10 | 0.27 |
| Q165V | 0.25 | *12.11* | *1.06* | 0.05 | *1.44* | 0.84 | *1.02* | *1.54* | 0.93 |
| Q165W | 0.51 | *1.25* | *1.12* | 0.05 | 0.80 | 0.70 | 0.71 | 0.94 | 0.79 |
| Q165Y | 0.87 | *1.04* | *1.03* | 0.09 | 0.87 | 0.91 | 0.85 | 0.98 | 0.62 |
| E166A | 0.04 | 0.04 | 0.04 | 0.04 | 0.04 | 0.04 | 0.04 | 0.04 | 0.04 |
| E166C | 0.07 | 0.05 | 0.83 | 0.05 | 0.60 | 0.75 | 0.40 | 0.40 | 0.45 |
| E166D | 0.39 | *3.55* | 0.84 | 0.05 | *1.01* | 0.70 | *1.13* | *1.25* | 0.87 |
| E166E | 1.00 | 1.00 | 1.00 | 1.00 | 1.00 | 1.00 | 1.00 | 1.00 | 1.00 |
| E166F | 0.07 | 0.05 | *1.18* | 0.05 | 0.46 | 0.53 | 0.25 | 0.37 | 0.48 |
| E166G | 0.18 | 0.05 | 0.73 | 0.05 | 0.22 | 0.33 | 0.15 | 0.12 | 0.45 |
| E166H | 0.04 | 0.04 | 0.04 | 0.04 | 0.04 | 0.04 | 0.04 | 0.04 | 0.04 |
| E166I | 0.04 | 0.04 | 0.04 | 0.04 | 0.04 | 0.04 | 0.04 | 0.04 | 0.04 |

TABLE 3-1-continued

Performance Index Data of BGL1 SEL Variants (3,153)

| E166K | 0.23 | *17.91* | *1.60* | 0.05 | 0.16 | 0.23 | 0.07 | 0.10 | 0.26 |
|---|---|---|---|---|---|---|---|---|---|
| E166L | 0.23 | *11.43* | *1.34* | 0.05 | 0.20 | 0.25 | 0.07 | 0.09 | 0.35 |
| E166M | 0.04 | 0.04 | 0.04 | 0.04 | 0.04 | 0.04 | 0.04 | 0.04 | 0.04 |
| E166N | 0.17 | 0.05 | *1.29* | 0.05 | 0.22 | 0.29 | 0.17 | 0.17 | 0.28 |
| E166P | 0.24 | *5.51* | 0.85 | 0.05 | 0.18 | 0.12 | 0.08 | 0.09 | 0.22 |
| E166Q | 0.51 | *1.10* | 0.47 | 0.05 | 0.12 | 0.14 | 0.12 | 0.10 | 0.10 |
| E166R | 0.28 | *1.70* | *1.29* | 0.05 | 0.21 | 0.11 | 0.05 | 0.08 | 0.26 |
| E166S | 0.14 | 0.05 | *1.08* | 0.05 | 0.28 | 0.38 | 0.15 | 0.21 | 0.40 |
| E166T | 0.23 | *8.87* | *1.23* | 0.05 | 0.21 | 0.18 | 0.12 | 0.13 | 0.38 |
| E166V | 0.20 | 0.05 | 0.05 | 0.05 | 0.21 | 0.22 | 0.11 | 0.11 | 0.46 |
| E166W | 0.04 | 0.04 | 0.04 | 0.04 | 0.04 | 0.04 | 0.04 | 0.04 | 0.04 |
| E166Y | 0.32 | 0.74 | *1.13* | 0.05 | 0.17 | 0.12 | 0.06 | 0.06 | 0.34 |
| L167A | 0.97 | *1.06* | 0.77 | 0.94 | 0.93 | 0.83 | 0.91 | 0.84 | 0.89 |
| L167C | 0.74 | *1.12* | 0.72 | 0.82 | *1.03* | *1.12* | *1.06* | *1.03* | *1.02* |
| L167D | 0.76 | *1.06* | 0.68 | 0.05 | 0.99 | *1.12* | 0.99 | 0.97 | 0.91 |
| L167E | 0.72 | *1.05* | 0.72 | 0.65 | 0.97 | *1.04* | 0.99 | 0.94 | 0.85 |
| L167F | 0.59 | 0.91 | 0.73 | 0.55 | 0.98 | *1.02* | 0.95 | 0.94 | 0.77 |
| L167G | 0.68 | *1.06* | 0.68 | 0.33 | 0.98 | *1.04* | *1.00* | 0.99 | 0.85 |
| L167I | 0.72 | 0.94 | 0.69 | 0.88 | 0.90 | 0.93 | 0.87 | 0.82 | 0.75 |
| L167K | 0.62 | 0.97 | 0.63 | 0.87 | 0.88 | 0.91 | 0.94 | 0.87 | 0.90 |
| L167L | 1.00 | 1.00 | 1.00 | 1.00 | 1.00 | 1.00 | 1.00 | 1.00 | 1.00 |
| L167M | 0.55 | 0.94 | 0.69 | 0.70 | 0.83 | *1.15* | 0.95 | 0.79 | 0.81 |
| L167N | 0.48 | 0.88 | 0.69 | 0.41 | 0.94 | 1.00 | *1.05* | 0.88 | 0.87 |
| L167P | 0.12 | 0.07 | 0.05 | 0.05 | 0.13 | 0.05 | 0.05 | 0.17 | 0.10 |
| L167Q | 0.74 | *1.06* | 0.68 | 0.75 | 0.83 | 0.80 | 0.98 | 0.82 | 0.87 |
| L167R | 0.80 | *1.08* | 0.68 | *1.23* | 0.83 | 0.99 | 0.97 | 0.86 | 0.89 |
| L167S | 0.94 | *1.21* | 0.76 | 0.31 | 0.91 | 1.00 | 0.99 | 0.88 | 0.94 |
| L167T | 0.70 | 0.99 | 0.73 | 0.47 | 0.94 | 0.97 | 0.96 | 0.92 | 0.91 |
| L167V | 0.60 | *1.08* | 0.70 | 0.74 | 0.98 | *1.05* | *1.04* | *1.46* | 0.90 |
| L167W | *1.07* | *1.07* | 0.91 | *1.12* | *1.02* | *1.05* | *1.06* | *1.08* | *1.02* |
| L167Y | 0.94 | *1.11* | 0.75 | 0.66 | 0.96 | 0.90 | 0.97 | *1.02* | 0.88 |
| N168A | 0.72 | *1.04* | 0.69 | 0.67 | *1.01* | *1.06* | *1.05* | *1.02* | 0.97 |
| N168D | 0.66 | *1.04* | 0.67 | 0.70 | *1.05* | *1.21* | *1.07* | *1.10* | 0.98 |
| N168E | 0.54 | *1.02* | 0.65 | 0.66 | *1.07* | *1.07* | *1.10* | *1.11* | 1.00 |
| N168G | 0.66 | *1.09* | 0.70 | 0.76 | *1.09* | *1.14* | *1.11* | *1.08* | 0.91 |
| N168H | 0.54 | 0.90 | 0.62 | 0.58 | 0.94 | 0.95 | *1.02* | 0.93 | 0.99 |

TABLE 3-1-continued

Performance Index Data of BGL1 SEL Variants (3,153)

| | | | | | | | | | |
|---|---|---|---|---|---|---|---|---|---|
| N168I | 0.56 | 0.83 | 0.64 | 0.24 | 0.93 | 0.99 | 0.89 | 0.86 | 0.77 |
| N168K | 0.61 | 0.85 | 0.65 | 0.38 | 0.90 | 0.95 | 0.96 | 0.87 | 0.74 |
| N168L | 0.66 | 0.94 | 0.70 | 0.55 | 0.92 | 0.90 | 0.98 | 0.82 | 0.82 |
| N168M | 0.52 | 0.77 | 0.66 | 0.47 | 0.80 | 0.92 | 0.87 | 0.75 | 0.76 |
| N168N | 1.00 | 1.00 | 1.00 | 1.00 | 1.00 | 1.00 | 1.00 | 1.00 | 1.00 |
| N168P | 0.15 | 0.05 | 0.05 | 0.05 | 0.05 | 0.16 | 0.05 | 0.05 | 0.05 |
| N168Q | 0.54 | 0.90 | 0.63 | 0.45 | 0.84 | *1.01* | *1.01* | 0.87 | 0.85 |
| N168R | 0.51 | 0.87 | 0.58 | 0.35 | 0.84 | 0.89 | *1.01* | 0.92 | 0.77 |
| N168S | 0.58 | 0.93 | 0.66 | 0.49 | 0.87 | 0.94 | 0.99 | 0.86 | 0.83 |
| N168T | 0.58 | 0.92 | 0.66 | 0.55 | 0.88 | 0.96 | *1.08* | 0.99 | 0.97 |
| N168V | 0.05 | 0.05 | 0.05 | 0.05 | 0.05 | 0.05 | 0.05 | 0.05 | 0.05 |
| N168W | 0.04 | 0.04 | 0.04 | 0.04 | 0.04 | 0.04 | 0.04 | 0.04 | 0.04 |
| N168Y | 0.76 | *1.09* | 0.70 | 0.60 | *1.05* | *1.03* | *1.13* | *1.21* | *1.05* |
| R169A | *1.38* | 0.05 | *1.81* | 0.05 | 0.13 | 0.19 | 0.06 | 0.05 | 0.09 |
| R169C | *1.19* | 0.07 | *1.65* | 0.05 | 0.12 | 0.18 | 0.08 | 0.06 | 0.09 |
| R169D | *1.20* | 0.05 | 0.05 | 0.05 | 0.15 | 0.23 | 0.08 | 0.05 | 0.08 |
| R169E | *1.06* | 0.18 | *1.59* | 0.05 | 0.23 | 0.32 | 0.10 | 0.10 | 0.11 |
| R169F | 0.42 | 0.11 | *1.58* | 0.05 | 0.05 | 0.16 | 0.05 | 0.05 | 0.06 |
| R169G | 0.55 | 0.05 | 0.05 | 0.05 | 0.05 | 0.13 | 0.05 | 0.05 | 0.12 |
| R169H | 0.77 | 0.07 | *1.54* | 0.05 | 0.15 | 0.27 | 0.07 | 0.05 | 0.15 |
| R169I | 0.69 | 0.05 | 0.05 | 0.05 | 0.05 | 0.10 | 0.05 | 0.05 | 0.10 |
| R169K | *1.01* | 0.05 | 0.05 | 0.05 | 0.19 | 0.37 | 0.08 | 0.06 | 0.10 |
| R169L | 0.72 | 0.05 | 0.05 | 0.05 | 0.08 | 0.20 | 0.05 | 0.05 | 0.05 |
| R169M | 0.40 | 0.09 | 0.05 | 0.05 | 0.05 | 0.20 | 0.05 | 0.05 | 0.08 |
| R169P | 0.18 | 0.05 | 0.05 | 0.05 | 0.05 | 0.31 | 0.05 | 0.05 | 0.18 |
| R169Q | 0.56 | 0.13 | *1.91* | 0.05 | 0.39 | 0.37 | 0.21 | 0.20 | 0.23 |
| R169R | 1.00 | 1.00 | 1.00 | 1.00 | 1.00 | 1.00 | 1.00 | 1.00 | 1.00 |
| R169S | 0.96 | 0.05 | *1.83* | 0.05 | 0.10 | 0.18 | 0.07 | 0.05 | 0.08 |
| R169T | 0.67 | 0.10 | *1.68* | 0.05 | 0.07 | 0.12 | 0.05 | 0.05 | 0.14 |
| R169V | 0.56 | 0.08 | 0.05 | 0.05 | 0.05 | 0.15 | 0.05 | 0.05 | 0.06 |
| R169W | 0.34 | 0.05 | 0.05 | 0.05 | 0.05 | 0.12 | 0.05 | 0.05 | 0.13 |
| R169Y | 0.29 | 0.12 | 0.05 | 0.05 | 0.05 | 0.15 | 0.05 | 0.05 | 0.11 |
| E170A | *1.65* | 0.77 | 0.93 | 0.96 | 0.74 | 0.95 | 0.77 | 0.51 | 0.62 |
| E170D | 0.93 | 0.95 | 0.97 | 0.71 | *1.06* | *1.04* | 0.90 | 0.78 | 0.77 |
| E170E | 1.00 | 1.00 | 1.00 | 1.00 | 1.00 | 1.00 | 1.00 | 1.00 | 1.00 |

TABLE 3-1-continued

Performance Index Data of BGL1 SEL Variants (3,153)

| E170F | 0.51 | 0.98 | *1.12* | 0.84 | *1.19* | *1.13* | *1.20* | *1.20* | 0.84 |
|---|---|---|---|---|---|---|---|---|---|
| E170G | 0.05 | 0.05 | 0.05 | 0.05 | 0.05 | 0.05 | 0.05 | 0.05 | 0.05 |
| E170H | 0.04 | 0.04 | 0.04 | 0.04 | 0.04 | 0.04 | 0.04 | 0.04 | 0.04 |
| E170I | 0.70 | 0.63 | *1.03* | 0.58 | 0.87 | 0.85 | 0.82 | 0.72 | 0.70 |
| E170K | *1.09* | 0.41 | 0.31 | 0.59 | 0.52 | 0.67 | 0.58 | 0.56 | 0.58 |
| E170L | *1.38* | 0.82 | *1.15* | *1.30* | 0.78 | 0.84 | 0.68 | 0.60 | 0.55 |
| E170M | 0.75 | 0.52 | *1.05* | 0.64 | 0.72 | 0.79 | 0.66 | 0.50 | 0.61 |
| E170N | 0.05 | 0.05 | 0.05 | 0.05 | 0.05 | 0.05 | 0.05 | 0.05 | 0.05 |
| E170P | *1.48* | 0.79 | 0.90 | 0.61 | 0.75 | 0.82 | 0.78 | 0.56 | 0.62 |
| E170Q | 0.71 | 0.71 | 0.87 | 0.70 | 0.74 | 0.95 | 0.72 | 0.60 | 0.62 |
| E170R | 0.74 | 0.56 | 0.58 | 0.47 | 0.53 | 0.68 | 0.58 | 0.47 | 0.56 |
| E170S | 0.90 | 0.88 | 0.82 | 0.83 | 0.81 | 0.94 | 0.86 | 0.67 | 0.86 |
| E170T | 0.10 | 0.05 | 0.05 | 0.05 | 0.05 | 0.87 | 0.05 | 0.05 | 0.55 |
| E170V | 0.75 | 0.66 | *1.02* | 0.64 | 0.85 | 0.86 | 0.78 | 0.67 | 0.61 |
| E170W | *1.16* | 0.63 | *1.11* | 0.51 | 0.74 | 0.61 | 0.69 | 0.58 | 0.60 |
| E170Y | *1.11* | 0.53 | *1.17* | 0.69 | 0.82 | 0.93 | 0.86 | *1.03* | 0.67 |
| P176A | *1.40* | 1.00 | *1.00* | *1.30* | 0.84 | 0.89 | *1.04* | 0.97 | *1.05* |
| P176C | 0.04 | 0.04 | 0.04 | 0.04 | 0.04 | 0.04 | 0.04 | 0.04 | 0.04 |
| P176D | *1.93* | 0.95 | *1.01* | 0.48 | 0.82 | 0.92 | *1.03* | 0.93 | 0.94 |
| P176E | 0.86 | 0.98 | 0.90 | 0.30 | 0.81 | *1.12* | 0.99 | 0.96 | 0.78 |
| P176F | 0.73 | *1.00* | 0.85 | 0.06 | 0.87 | *1.20* | *1.04* | *1.08* | *1.27* |
| P176G | *1.25* | *1.06* | 0.94 | *1.26* | 0.86 | *1.08* | 1.00 | 0.93 | 0.78 |
| P176H | 0.61 | 0.91 | 0.89 | 0.20 | 0.96 | *1.12* | *1.12* | *1.03* | 0.92 |
| P176I | 0.26 | 0.05 | 0.05 | 0.12 | 0.18 | 0.47 | 0.14 | 0.08 | 0.78 |
| P176K | 0.27 | *1.08* | 0.82 | 0.05 | *1.33* | 0.90 | *1.51* | *1.38* | *1.24* |
| P176L | 0.64 | *1.13* | 0.91 | 0.73 | 0.99 | *1.24* | *1.18* | *1.07* | 0.92 |
| P176M | 0.79 | 0.99 | 0.99 | 0.27 | 0.84 | *1.02* | 0.93 | 0.97 | 0.63 |
| P176N | 0.04 | 0.04 | 0.04 | 0.04 | 0.04 | 0.04 | 0.04 | 0.04 | 0.04 |
| P176P | 1.00 | 1.00 | 1.00 | 1.00 | 1.00 | 1.00 | 1.00 | 1.00 | 1.00 |
| P176Q | 0.72 | 0.93 | 0.94 | 0.35 | 0.85 | *1.09* | 0.90 | 0.92 | 0.83 |
| P176R | 0.35 | *1.05* | *1.07* | 0.25 | *1.17* | *1.12* | *1.37* | *1.42* | *1.15* |
| P176S | 0.54 | 0.98 | 0.85 | 0.53 | 0.98 | *1.36* | 0.98 | 0.96 | *1.22* |
| P176T | 0.88 | *1.02* | 0.90 | 0.89 | 0.84 | *1.02* | 0.95 | 0.97 | 0.91 |
| P176V | 0.68 | *1.11* | 0.91 | 0.71 | 0.96 | *1.36* | *1.10* | *1.09* | *1.00* |
| P176W | 0.20 | *1.06* | 0.87 | 0.05 | *1.45* | *1.39* | *1.61* | *1.78* | *1.71* |

TABLE 3-1-continued

Performance Index Data of BGL1 SEL Variants (3,153)

| | | | | | | | | | |
|---|---|---|---|---|---|---|---|---|---|
| P176Y | 0.64 | 0.98 | 0.92 | 0.20 | *1.10* | *1.10* | *1.11* | *1.26* | *1.08* |
| D177A | 0.99 | 0.89 | *1.02* | 0.52 | 0.91 | 0.90 | 0.84 | 0.86 | 0.85 |
| D177C | *1.06* | 0.91 | 0.98 | 0.45 | 0.94 | 0.91 | 0.88 | 0.89 | 0.95 |
| D177D | 1.00 | 1.00 | 1.00 | 1.00 | 1.00 | 1.00 | 1.00 | 1.00 | 1.00 |
| D177E | 0.53 | 0.91 | 0.98 | 0.71 | *1.06* | 0.87 | *1.03* | *1.07* | *1.11* |
| D177F | 0.72 | 0.89 | 0.98 | 0.15 | *1.05* | *1.03* | *1.06* | *1.04* | *1.11* |
| D177G | *1.16* | 0.94 | *1.05* | 0.80 | 0.96 | 0.99 | 0.88 | 0.92 | 0.99 |
| D177H | 0.44 | 0.84 | 0.99 | 0.54 | *1.06* | 0.98 | *1.07* | *1.17* | 0.84 |
| D177I | 0.67 | 0.87 | 0.91 | 0.35 | 0.97 | 0.85 | 0.96 | 0.98 | 0.94 |
| D177K | *1.02* | 0.98 | 0.98 | 0.52 | 0.97 | *1.02* | 0.95 | 0.97 | 0.94 |
| D177L | 0.58 | 0.81 | *1.06* | 0.54 | *1.03* | *1.03* | *1.02* | *1.01* | 0.87 |
| D177M | 0.60 | 0.94 | *1.02* | 0.73 | *1.13* | *1.06* | *1.24* | *1.21* | *1.05* |
| D177N | *1.08* | 0.98 | *1.02* | 0.87 | 0.96 | *1.05* | 0.92 | 0.98 | *1.02* |
| D177Q | 0.72 | 0.89 | *1.13* | 0.61 | 0.97 | *1.05* | 0.98 | *1.02* | 0.80 |
| D177R | 0.73 | 0.91 | 0.96 | 0.40 | 0.98 | *1.06* | *1.02* | *1.07* | 0.92 |
| D177S | 0.13 | 0.05 | 0.05 | 0.05 | 0.05 | 0.05 | 0.05 | 0.14 | 0.23 |
| D177V | 0.95 | *1.01* | 0.99 | 0.59 | *1.01* | *1.17* | 0.97 | *1.05* | *1.21* |
| D177W | 0.34 | *1.10* | *1.01* | 0.09 | *1.44* | 0.05 | *1.60* | *1.63* | *1.20* |
| D177Y | 0.60 | 0.87 | 0.98 | 0.28 | *1.05* | 0.96 | *1.07* | *1.10* | 0.94 |
| D178A | *1.06* | *1.07* | 0.93 | *1.13* | 0.98 | *1.04* | 0.99 | 0.79 | *1.01* |
| D178C | 0.83 | *1.05* | 0.90 | 0.89 | *1.02* | *1.08* | *1.06* | 0.81 | 0.96 |
| D178D | 1.00 | 1.00 | 1.00 | 1.00 | 1.00 | 1.00 | 1.00 | 1.00 | 1.00 |
| D178E | *1.23* | 0.93 | 0.94 | 0.97 | 0.87 | 0.85 | 0.84 | 0.65 | 0.81 |
| D178G | 0.87 | 0.81 | 0.99 | 0.66 | 0.84 | 0.94 | 0.78 | 0.65 | 0.74 |
| D178I | 0.79 | 0.82 | 0.90 | 0.66 | 0.84 | 0.87 | 0.85 | 0.67 | 0.78 |
| D178K | 0.75 | 0.99 | 0.91 | 0.83 | 0.95 | 0.97 | *1.00* | 0.82 | 0.84 |
| D178L | 0.92 | 0.87 | 0.99 | 0.78 | 0.89 | 0.92 | 0.88 | 0.66 | 0.76 |
| D178M | 0.91 | 0.84 | 0.96 | 0.73 | 0.85 | 0.81 | 0.85 | 0.68 | 0.78 |
| D178N | 0.84 | 0.91 | 0.97 | 0.78 | 0.86 | *1.04* | 0.85 | 0.71 | 0.82 |
| D178P | *1.21* | 0.88 | 0.93 | 0.90 | 0.85 | 0.92 | 0.81 | 0.68 | 0.71 |
| D178Q | 0.92 | *1.04* | 0.98 | 0.94 | 0.95 | 0.90 | 0.97 | 0.84 | 0.86 |
| D178R | 0.73 | *1.06* | 0.88 | 0.84 | 0.97 | *1.05* | *1.03* | 0.92 | 0.87 |
| D178S | 0.89 | 0.81 | *1.04* | 0.71 | 0.88 | 0.92 | 0.82 | 0.71 | 0.76 |
| D178T | *1.11* | 1.00 | 0.94 | *1.06* | 0.88 | 0.83 | 0.88 | 0.77 | 0.77 |
| D178V | 0.65 | 0.82 | 0.94 | 0.57 | 0.84 | 0.81 | 0.80 | 0.73 | 0.76 |
| D178W | *1.09* | 0.90 | 0.90 | 0.75 | 0.86 | 0.99 | 0.85 | 0.70 | 0.72 |

TABLE 3-1-continued

Performance Index Data of BGL1 SEL Variants (3,153)

| | | | | | | | | | |
|---|---|---|---|---|---|---|---|---|---|
| D178Y | 0.22 | 0.80 | 0.97 | 0.05 | *1.18* | 0.25 | *1.60* | *1.32* | 0.91 |
| R179A | 0.24 | 0.56 | *1.04* | 0.19 | 0.99 | *1.52* | 0.94 | 0.84 | 0.55 |
| R179C | 0.12 | 0.34 | 0.96 | 0.10 | *1.01* | *1.35* | 0.86 | 0.77 | 0.38 |
| R179D | 0.04 | 0.04 | 0.04 | 0.04 | 0.04 | 0.04 | 0.04 | 0.04 | 0.04 |
| R179F | 0.09 | 0.05 | 0.05 | 0.05 | 0.10 | 0.18 | 0.05 | 0.05 | 0.19 |
| R179G | 0.23 | 0.56 | 0.90 | 0.19 | 0.95 | *1.28* | 0.85 | 0.80 | 0.53 |
| R179H | 0.09 | 0.12 | 0.05 | 0.07 | 0.05 | 0.23 | 0.05 | 0.05 | 0.15 |
| R179I | 0.12 | 0.42 | 0.86 | 0.14 | 0.84 | *1.30* | 0.84 | 0.78 | 0.28 |
| R179K | 0.45 | 0.79 | 0.99 | 0.43 | 0.94 | *1.28* | *1.03* | 0.88 | 0.72 |
| R179L | 0.05 | 0.05 | 0.05 | 0.05 | 0.05 | 0.05 | 0.05 | 0.05 | 0.05 |
| R179M | 0.07 | 0.40 | 0.88 | 0.13 | *1.28* | *1.30* | *1.17* | *1.18* | 0.34 |
| R179N | 0.04 | 0.04 | 0.04 | 0.04 | 0.04 | 0.04 | 0.04 | 0.04 | 0.04 |
| R179P | 0.11 | 0.05 | 0.05 | 0.06 | 0.05 | 0.66 | 0.05 | 0.05 | 0.08 |
| R179Q | 0.09 | 0.29 | 0.89 | 0.08 | 0.77 | *1.35* | 0.69 | 0.71 | 0.28 |
| R179R | 1.00 | 1.00 | 1.00 | 1.00 | 1.00 | 1.00 | 1.00 | 1.00 | 1.00 |
| R179S | 0.30 | 0.86 | 0.97 | 0.48 | *1.04* | *1.24* | *1.09* | *1.12* | 0.73 |
| R179T | 0.16 | 0.52 | 0.96 | 0.28 | 0.95 | *1.23* | 0.96 | *1.09* | 0.46 |
| R179V | 0.19 | 0.38 | *1.33* | 0.18 | 0.95 | *1.37* | 0.99 | 0.91 | 0.57 |
| R179W | 0.67 | *1.01* | 0.91 | 0.71 | 0.91 | 0.93 | *1.02* | *1.10* | 0.88 |
| R179Y | 0.04 | 0.04 | 0.04 | 0.04 | 0.04 | 0.04 | 0.04 | 0.04 | 0.04 |
| Q194A | *1.04* | *1.05* | *1.00* | *1.10* | 0.99 | *1.02* | *1.07* | 0.89 | *1.04* |
| Q194C | 0.67 | 0.95 | 0.98 | 0.89 | *1.04* | *1.07* | *1.16* | 0.94 | *1.07* |
| Q194E | 0.62 | 0.87 | 0.98 | 0.81 | 0.97 | *1.15* | *1.03* | 0.87 | 0.95 |
| Q194F | 0.72 | 0.95 | 0.98 | 0.92 | 0.96 | *1.18* | *1.08* | 0.91 | 0.89 |
| Q194G | 0.54 | 0.80 | 0.94 | 0.73 | 0.96 | *1.23* | *1.01* | 0.88 | 0.81 |
| Q194H | 0.73 | 0.84 | 0.95 | 0.86 | 0.89 | *1.28* | 0.94 | 0.79 | 0.90 |
| Q194I | 0.54 | 0.73 | 0.89 | 0.15 | 0.89 | 0.99 | 0.95 | 0.83 | 0.78 |
| Q194K | 0.90 | *1.05* | 0.92 | *1.08* | 0.90 | *1.24* | *1.01* | 0.91 | 0.87 |
| Q194L | 0.12 | 0.32 | 0.89 | 0.24 | 1.00 | *1.11* | *1.10* | *1.01* | 0.56 |
| Q194M | 0.66 | 0.91 | 0.89 | 0.91 | 0.92 | *1.13* | 0.92 | 0.87 | 0.98 |
| Q194N | 0.04 | 0.04 | 0.04 | 0.04 | 0.04 | 0.04 | 0.04 | 0.04 | 0.04 |
| Q194P | 0.13 | 0.07 | 0.05 | 0.12 | 0.05 | 0.20 | 0.05 | 0.05 | 0.10 |
| Q194Q | 1.00 | 1.00 | 1.00 | 1.00 | 1.00 | 1.00 | 1.00 | 1.00 | 1.00 |
| Q194R | 0.84 | 0.93 | 0.93 | *1.01* | 0.86 | *1.21* | 0.90 | 0.91 | 0.75 |
| Q194S | 0.77 | 0.91 | 0.95 | 0.86 | 0.87 | 0.94 | 0.88 | 0.85 | 0.80 |

TABLE 3-1-continued

Performance Index Data of BGL1 SEL Variants (3,153)

| | | | | | | | | |
|---|---|---|---|---|---|---|---|---|
| Q194T | 0.56 | 0.79 | 0.98 | 0.72 | 0.88 | *1.08* | 0.93 | 0.93 | 0.84 |
| Q194W | 0.83 | 0.89 | 0.98 | 0.70 | 0.89 | *1.21* | 0.88 | 0.89 | 0.83 |
| Q194Y | *1.13* | *1.07* | 0.92 | 0.99 | 0.92 | *1.00* | 0.96 | 0.98 | 0.94 |
| N196A | 0.25 | 0.43 | 0.93 | 0.22 | 0.81 | 0.95 | 0.85 | 0.69 | 0.61 |
| N196E | 0.59 | *1.01* | *1.03* | 0.69 | *1.03* | *1.12* | *1.17* | 0.88 | *1.10* |
| N196F | 0.04 | 0.04 | 0.04 | 0.04 | 0.04 | 0.04 | 0.04 | 0.04 | 0.04 |
| N196G | 0.70 | 0.89 | *1.02* | 0.66 | 0.91 | 0.89 | 0.89 | 0.81 | 0.80 |
| N196H | 0.65 | 0.95 | 0.98 | 0.69 | 0.97 | *1.05* | 0.99 | 0.88 | 0.88 |
| N196I | 0.15 | 0.05 | 0.05 | 0.05 | 0.05 | 0.07 | 0.07 | 0.05 | 0.13 |
| N196K | 0.14 | 0.05 | 0.05 | 0.05 | 0.05 | 0.05 | 0.06 | 0.05 | 0.14 |
| N196L | 0.33 | 0.95 | 0.97 | 0.55 | *1.17* | *1.25* | *1.35* | *1.12* | *1.17* |
| N196M | 0.48 | 0.76 | *1.01* | 0.45 | 0.89 | 0.99 | 0.92 | 0.76 | 0.77 |
| N196N | 1.00 | 1.00 | 1.00 | 1.00 | 1.00 | 1.00 | 1.00 | 1.00 | 1.00 |
| N196P | 0.17 | 0.19 | *1.04* | 0.07 | 0.41 | 0.69 | 0.50 | 0.39 | 0.29 |
| N196Q | 0.57 | 0.98 | 0.98 | 0.66 | *1.01* | 0.96 | *1.11* | 0.97 | 0.98 |
| N196R | 0.42 | 0.79 | 0.97 | 0.46 | *1.00* | *1.18* | 0.99 | 1.00 | 0.96 |
| N196T | 0.15 | 0.49 | 0.97 | 0.22 | *1.10* | *1.29* | *1.31* | *1.15* | 0.75 |
| N196V | 0.04 | 0.04 | 0.04 | 0.04 | 0.04 | 0.04 | 0.04 | 0.04 | 0.04 |
| N196Y | 0.40 | 0.50 | 0.99 | 0.25 | 0.73 | 0.89 | 0.71 | 0.74 | 0.58 |
| S199A | *1.73* | 0.88 | *1.07* | *1.98* | *1.01* | 0.92 | 0.88 | 0.91 | 0.94 |
| S199C | 0.92 | 0.96 | 0.95 | 0.80 | 0.90 | 0.90 | 0.85 | 0.95 | 0.99 |
| S199F | 0.06 | 0.05 | 0.05 | 0.05 | 0.05 | 0.38 | 0.05 | 0.13 | 0.26 |
| S199G | 0.56 | 1.00 | 0.89 | 0.52 | 0.98 | *1.04* | 0.94 | 0.96 | 0.99 |
| S199H | 0.10 | 0.05 | 0.05 | 0.05 | 0.08 | 0.19 | 0.05 | 0.05 | 0.14 |
| S199I | 0.15 | 0.42 | 0.63 | 0.05 | 0.47 | 0.55 | 0.52 | 0.75 | 0.57 |
| S199K | 0.12 | 0.05 | 0.05 | 0.05 | 0.05 | 0.17 | 0.05 | 0.05 | 0.13 |
| S199L | 0.07 | 0.10 | 0.57 | 0.05 | 0.14 | 0.19 | 0.17 | 0.18 | 0.19 |
| S199M | 0.07 | 0.05 | 0.05 | 0.05 | 0.06 | 0.38 | 0.11 | 0.11 | 0.36 |
| S199N | 0.17 | 0.40 | 0.97 | 0.07 | 0.61 | *1.26* | 0.58 | 0.88 | 0.68 |
| S199Q | 0.15 | 0.10 | 0.05 | 0.05 | 0.05 | 0.34 | 0.15 | 0.17 | 0.22 |
| S199R | 0.09 | 0.05 | 0.05 | 0.05 | 0.05 | 0.08 | 0.05 | 0.05 | 0.15 |
| S199T | 0.47 | 0.86 | 0.93 | 0.56 | 0.96 | *1.46* | 0.90 | 0.99 | 0.86 |
| S199V | 0.30 | 0.69 | 0.87 | 0.26 | 0.68 | *1.06* | 0.78 | 0.80 | 0.53 |
| S199W | 0.08 | 0.05 | 0.05 | 0.05 | 0.05 | 0.11 | 0.05 | 0.05 | 0.05 |
| S199Y | 0.16 | 0.05 | 0.05 | 0.05 | 0.05 | 0.48 | 0.05 | 0.05 | 0.09 |

TABLE 3-1-continued

Performance Index Data of BGL1 SEL Variants (3,153)

| | | | | | | | | | |
|---|---|---|---|---|---|---|---|---|---|
| Y204A | *1.39* | 0.05 | 0.05 | 0.05 | 0.05 | 0.12 | 0.10 | 0.05 | 0.06 |
| Y204C | 0.27 | 0.05 | 0.05 | 0.08 | 0.05 | 0.19 | 0.32 | 0.05 | 0.42 |
| Y204E | *1.06* | 0.05 | 0.05 | 0.21 | 0.06 | 0.21 | 0.15 | 0.05 | 0.23 |
| Y204F | 0.59 | *1.19* | 0.56 | 0.40 | 0.65 | 0.77 | 0.62 | 0.50 | 0.53 |
| Y204G | *1.72* | 0.05 | 0.05 | 0.05 | 0.05 | 0.13 | 0.09 | 0.05 | 0.20 |
| Y204H | *1.52* | 0.05 | 0.05 | 0.17 | 0.05 | 0.08 | 0.08 | 0.05 | 0.06 |
| Y204I | *1.00* | 0.08 | 0.05 | 0.11 | 0.05 | 0.13 | 0.13 | 0.05 | 0.09 |
| Y204K | *1.63* | 0.05 | 0.05 | 0.08 | 0.05 | 0.14 | 0.10 | 0.05 | 0.10 |
| Y204L | 0.74 | 0.60 | 0.55 | 0.46 | 0.31 | 0.53 | 0.44 | 0.27 | 0.32 |
| Y204M | 0.80 | 0.16 | *1.22* | 0.15 | 0.21 | 0.33 | 0.31 | 0.14 | 0.23 |
| Y204P | *1.43* | 0.05 | 0.05 | 0.06 | 0.05 | 0.09 | 0.08 | 0.05 | 0.05 |
| Y204Q | *1.09* | 0.05 | 0.05 | 0.05 | 0.05 | 0.14 | 0.13 | 0.05 | 0.22 |
| Y204R | *1.78* | 0.05 | 0.05 | 0.05 | 0.05 | 0.07 | 0.07 | 0.05 | 0.05 |
| Y204S | *1.15* | 0.06 | 0.05 | 0.17 | 0.05 | 0.06 | 0.10 | 0.05 | 0.17 |
| Y204T | *1.25* | 0.05 | 0.05 | 0.05 | 0.07 | 0.22 | 0.15 | 0.16 | 0.20 |
| Y204V | *1.44* | 0.07 | 0.05 | 0.05 | 0.13 | 0.25 | 0.16 | 0.20 | 0.17 |
| Y204W | *1.41* | 0.06 | 0.50 | 0.07 | 0.05 | 0.14 | 0.11 | 0.05 | 0.13 |
| Y204Y | 1.00 | 1.00 | 1.00 | 1.00 | 1.00 | 1.00 | 1.00 | 1.00 | 1.00 |
| N208A | 0.04 | 0.04 | 0.04 | 0.04 | 0.04 | 0.04 | 0.04 | 0.04 | 0.04 |
| N208C | 0.33 | 0.11 | 0.05 | 0.05 | 0.24 | 0.19 | 0.08 | 0.54 | 0.34 |
| N208D | 0.30 | 0.25 | 0.96 | 0.17 | 0.61 | 0.42 | 0.39 | 0.89 | 0.87 |
| N208E | 0.27 | 0.11 | 0.05 | 0.11 | 0.29 | 0.14 | 0.08 | 0.60 | 0.33 |
| N208F | 0.29 | 0.25 | 0.95 | 0.11 | 0.51 | 0.34 | 0.30 | 0.82 | 0.53 |
| N208G | 0.04 | 0.04 | 0.04 | 0.04 | 0.04 | 0.04 | 0.04 | 0.04 | 0.04 |
| N208H | 0.31 | 0.33 | 0.05 | 0.29 | 0.67 | 0.53 | 0.44 | 0.92 | 0.64 |
| N208K | 0.25 | 0.34 | 0.86 | 0.15 | 0.84 | 0.63 | 0.53 | *1.12* | 0.68 |
| N208N | 1.00 | 1.00 | 1.00 | 1.00 | 1.00 | 1.00 | 1.00 | 1.00 | 1.00 |
| N208R | 0.30 | 0.25 | *1.02* | 0.07 | 0.56 | 0.52 | 0.36 | 0.83 | 0.86 |
| N208T | 0.04 | 0.04 | 0.04 | 0.04 | 0.04 | 0.04 | 0.04 | 0.04 | 0.04 |
| N208V | 0.25 | 0.27 | 0.90 | 0.11 | 0.65 | 0.47 | 0.41 | 0.98 | 0.74 |
| N208W | 0.04 | 0.04 | 0.04 | 0.04 | 0.04 | 0.04 | 0.04 | 0.04 | 0.04 |
| T209A | 0.04 | 0.04 | 0.04 | 0.04 | 0.04 | 0.04 | 0.04 | 0.04 | 0.04 |
| T209C | 0.65 | *1.52* | 0.92 | 0.86 | *1.11* | *1.15* | *1.28* | *1.36* | *1.36* |
| T209D | 0.73 | *1.15* | 0.87 | 0.73 | 0.98 | *1.05* | *1.04* | *1.09* | *1.06* |
| T209E | 0.63 | *1.22* | 0.91 | 0.79 | 0.99 | *1.02* | *1.06* | *1.14* | *1.26* |
| T209G | 0.70 | *1.08* | 0.97 | 0.73 | *1.04* | *1.12* | *1.06* | *1.06* | *1.18* |

TABLE 3-1-continued

Performance Index Data of BGL1 SEL Variants (3,153)

| | | | | | | | | |
|---|---|---|---|---|---|---|---|---|
| T209H | 0.42 | *1.29* | 0.97 | 0.48 | *1.05* | *1.13* | *1.10* | *1.21* | 0.81 |
| T209I | 0.45 | *1.33* | 0.92 | 0.48 | *1.09* | *1.55* | *1.15* | *1.19* | 0.97 |
| T209K | 0.35 | *1.07* | *1.01* | 0.33 | 0.97 | *1.07* | 0.98 | *1.01* | 0.39 |
| T209L | 0.44 | *1.06* | *1.00* | 0.45 | *1.12* | *1.00* | *1.06* | *1.06* | *1.08* |
| T209M | 0.47 | *1.27* | *1.03* | 0.58 | *1.04* | *1.05* | *1.16* | *1.17* | 0.98 |
| T209P | 0.81 | 0.94 | 0.95 | 0.05 | 0.84 | 0.75 | 0.79 | 0.82 | 0.73 |
| T209Q | 0.63 | *1.24* | 0.95 | 0.63 | *1.05* | *1.12* | *1.10* | *1.06* | 0.86 |
| T209R | 0.69 | *1.07* | *1.06* | 0.61 | 0.99 | 1.00 | 1.00 | 0.98 | 0.92 |
| T209S | 0.72 | *1.14* | 0.97 | 0.82 | *1.08* | 0.97 | *1.09* | *1.07* | *1.08* |
| T209T | 1.00 | 1.00 | 1.00 | 1.00 | 1.00 | 1.00 | 1.00 | 1.00 | 1.00 |
| T209V | 0.73 | *1.22* | 0.96 | 0.77 | *1.09* | *1.04* | *1.21* | *1.19* | *1.21* |
| T209W | 0.60 | *1.08* | 0.95 | 0.41 | 0.95 | *1.05* | 0.95 | 0.99 | *1.04* |
| T209Y | 0.25 | *2.56* | 0.99 | 0.63 | *2.12* | *1.88* | *2.43* | *2.67* | *1.79* |
| E214A | 0.58 | *1.45* | *1.01* | 0.05 | 0.86 | 0.56 | 0.90 | *1.05* | 0.92 |
| E214C | 0.24 | *15.69* | 0.82 | 0.05 | 0.70 | 0.64 | 0.69 | 0.84 | 0.92 |
| E214D | 0.58 | *1.61* | 0.83 | 0.36 | 0.99 | *1.06* | 0.99 | *1.10* | *1.07* |
| E214E | 1.00 | 1.00 | 1.00 | 1.00 | 1.00 | 1.00 | 1.00 | 1.00 | 1.00 |
| E214F | 0.20 | 0.05 | 0.84 | 0.05 | 0.58 | 0.31 | 0.44 | 0.49 | 0.46 |
| E214G | 0.35 | *2.98* | 0.89 | 0.05 | 0.88 | 0.72 | 0.87 | *1.06* | 0.94 |
| E214H | 0.36 | *3.05* | 0.85 | 0.05 | 0.78 | 0.42 | 0.80 | 0.96 | 0.88 |
| E214I | 0.20 | 0.05 | 0.85 | 0.05 | 0.68 | 0.43 | 0.73 | 0.84 | 0.61 |
| E214K | 0.21 | 0.05 | *1.02* | 0.05 | 0.76 | 0.41 | 0.62 | 0.74 | 0.62 |
| E214L | 0.31 | *4.72* | 0.79 | 0.05 | 0.85 | 0.31 | 0.87 | 0.95 | 0.74 |
| E214M | 0.40 | *2.71* | 0.69 | 0.05 | 0.82 | 0.63 | 0.87 | 0.97 | 0.63 |
| E214N | 0.34 | *3.57* | 0.74 | 0.05 | 0.78 | 0.66 | 0.79 | 0.92 | 0.66 |
| E214P | 0.17 | 0.05 | *1.03* | 0.05 | 0.35 | 0.18 | 0.31 | 0.38 | 0.44 |
| E214Q | 0.52 | *1.62* | 0.89 | 0.30 | 0.91 | 0.88 | 0.83 | 0.97 | 0.57 |
| E214R | 0.26 | *6.73* | *1.07* | 0.05 | 0.74 | 0.32 | 0.76 | *1.01* | 0.61 |
| E214S | 0.40 | *2.39* | 0.87 | 0.05 | 0.87 | 0.62 | 0.86 | *1.01* | 0.82 |
| E214T | 0.31 | *4.47* | 0.63 | 0.05 | 0.80 | 0.65 | 0.78 | 0.93 | 0.64 |
| E214V | 0.21 | 0.05 | 0.81 | 0.05 | 0.75 | 0.31 | 0.73 | 0.86 | *1.02* |
| E214W | 0.08 | 0.05 | *1.02* | 0.05 | *1.24* | 0.69 | *1.20* | *1.42* | 0.59 |
| E214Y | 0.31 | *2.48* | *1.01* | 0.05 | 0.47 | 0.36 | 0.40 | 0.46 | 0.66 |
| D215A | 0.48 | 0.98 | *1.00* | 0.51 | 0.99 | 0.97 | 0.96 | 1.00 | 0.97 |
| D215C | 0.50 | 0.96 | *1.04* | 0.59 | *1.03* | *1.03* | *1.11* | 0.98 | *1.05* |

TABLE 3-1-continued

Performance Index Data of BGL1 SEL Variants (3,153)

| | | | | | | | | | |
|---|---|---|---|---|---|---|---|---|---|
| D215D | 1.00 | 1.00 | 1.00 | 1.00 | 1.00 | 1.00 | 1.00 | 1.00 | 1.00 |
| D215E | 0.39 | *1.17* | 0.97 | 0.65 | *1.06* | 0.86 | *1.16* | *1.12* | *1.01* |
| D215F | 0.16 | 0.49 | *1.02* | 0.19 | 0.63 | 0.67 | 0.46 | 0.63 | 0.45 |
| D215G | 0.44 | 0.96 | *1.07* | 0.60 | 0.99 | 0.93 | *1.00* | 0.95 | 0.93 |
| D215H | 0.34 | 0.94 | *1.12* | 0.50 | 0.98 | 0.90 | 0.97 | *1.03* | 0.65 |
| D215I | 0.10 | 0.18 | 0.05 | 0.17 | 0.12 | 0.26 | 0.05 | 0.27 | 0.05 |
| D215K | 0.25 | 0.79 | 0.90 | 0.34 | 0.82 | 0.81 | 0.67 | 0.85 | 0.46 |
| D215L | 0.14 | *1.10* | 0.87 | 0.40 | *1.20* | *1.30* | *1.19* | *1.19* | 0.60 |
| D215M | 0.25 | 0.98 | *1.14* | 0.47 | 0.90 | *1.06* | *1.04* | 0.98 | 0.66 |
| D215N | 0.46 | *1.40* | *1.00* | 0.97 | *1.09* | 0.99 | *1.30* | *1.13* | *1.22* |
| D215Q | 0.36 | *1.12* | *1.10* | 0.61 | *1.00* | 0.91 | *1.12* | 0.93 | 0.72 |
| D215R | 0.18 | 0.66 | 0.99 | 0.28 | 0.55 | 0.81 | 0.58 | 0.62 | 0.27 |
| D215S | 0.42 | *1.67* | *1.08* | *1.12* | *1.38* | *1.14* | *1.84* | *1.40* | *1.19* |
| D215V | 0.06 | 0.34 | *1.02* | 0.12 | 0.38 | 0.64 | 0.05 | 0.76 | 0.38 |
| D215W | 0.16 | 0.65 | *1.04* | 0.28 | 0.83 | *1.04* | 0.61 | *1.07* | 0.36 |
| Q216A | 0.93 | 0.97 | *1.10* | 0.73 | *1.06* | *1.14* | *1.03* | *1.10* | *1.08* |
| Q216C | 0.53 | 0.83 | *1.06* | 0.31 | 1.00 | *1.06* | *1.05* | 0.91 | 0.81 |
| Q216D | *1.60* | 0.79 | *1.12* | 0.76 | 0.99 | *1.25* | 0.94 | *1.01* | 0.92 |
| Q216E | *1.00* | 1.00 | *1.05* | *1.01* | *1.00* | *1.09* | 0.99 | 0.99 | 0.95 |
| Q216F | 0.72 | 0.97 | *1.08* | 0.66 | 0.98 | *1.15* | *1.06* | *1.03* | 0.98 |
| Q216G | 0.83 | *1.22* | 0.99 | 0.85 | *1.16* | *1.13* | *1.13* | *1.07* | *1.00* |
| Q216H | 0.81 | 0.97 | *1.01* | 0.62 | *1.04* | *1.16* | 0.99 | *1.03* | *1.05* |
| Q216I | 0.61 | *1.02* | *1.05* | 0.76 | *1.11* | *1.29* | *1.20* | *1.23* | *1.09* |
| Q216K | 0.95 | 0.92 | *1.07* | 0.89 | 0.97 | *1.10* | *1.00* | *1.03* | 0.96 |
| Q216L | 0.77 | *1.02* | *1.07* | *1.04* | *1.00* | 0.99 | *1.06* | *1.13* | *1.08* |
| Q216M | 0.51 | 0.94 | *1.02* | 0.92 | *1.03* | 0.98 | *1.16* | *1.11* | 0.93 |
| Q216N | *1.13* | *1.05* | 0.99 | *1.21* | *1.00* | *1.14* | 0.96 | *1.06* | 0.96 |
| Q216P | 0.53 | 0.82 | *1.03* | 0.52 | 0.94 | *1.04* | 1.00 | 0.96 | 0.85 |
| Q216Q | 1.00 | 1.00 | 1.00 | 1.00 | 1.00 | 1.00 | 1.00 | 1.00 | 1.00 |
| Q216R | *1.00* | 0.90 | *1.05* | 0.65 | 0.96 | *1.09* | 0.96 | 0.94 | 0.94 |
| Q216S | 0.46 | *1.03* | 0.96 | 0.87 | *1.06* | *1.23* | *1.21* | *1.13* | *1.04* |
| Q216T | 0.77 | 0.99 | *1.11* | 0.92 | 0.99 | *1.01* | *1.07* | *1.11* | 0.89 |
| Q216W | 0.58 | 0.97 | *1.10* | 0.79 | *1.12* | *1.37* | *1.30* | *1.19* | *1.15* |
| Q216Y | 0.73 | *1.13* | *1.07* | 0.86 | *1.16* | *1.16* | *1.27* | *1.29* | *1.22* |
| K224A | 0.08 | 0.05 | 0.05 | 0.05 | 0.14 | 0.06 | 0.05 | 0.05 | 0.37 |

TABLE 3-1-continued

Performance Index Data of BGL1 SEL Variants (3,153)

| | | | | | | | | | |
|---|---|---|---|---|---|---|---|---|---|
| K224C | 0.11 | 0.22 | 0.05 | 0.05 | 0.18 | 0.29 | 0.08 | 0.05 | 0.30 |
| K224D | 0.09 | 0.05 | 0.05 | 0.05 | 0.05 | 0.26 | 0.05 | 0.05 | 0.41 |
| K224E | 0.08 | 0.19 | 0.05 | 0.05 | 0.36 | 0.37 | 0.37 | 0.16 | 0.39 |
| K224F | 0.10 | 0.20 | 0.05 | 0.05 | 0.53 | 0.18 | 0.37 | 0.20 | 0.46 |
| K224G | 0.09 | 0.22 | 0.05 | 0.05 | 0.63 | 0.49 | 0.49 | 0.23 | 0.61 |
| K224H | 0.21 | 0.66 | 0.81 | 0.07 | *1.04* | 0.98 | 0.97 | *1.02* | 0.60 |
| K224I | 0.10 | 0.27 | 0.90 | 0.05 | 0.54 | 0.44 | 0.47 | 0.22 | 0.45 |
| K224K | 1.00 | 1.00 | 1.00 | 1.00 | 1.00 | 1.00 | 1.00 | 1.00 | 1.00 |
| K224L | 0.11 | 0.23 | 0.69 | 0.11 | 0.53 | 0.29 | 0.42 | 0.23 | 0.36 |
| K224M | 0.07 | 0.05 | 0.05 | 0.05 | 0.25 | 0.18 | 0.20 | 0.05 | 0.33 |
| K224N | 0.10 | 0.26 | 0.68 | 0.05 | 0.60 | 0.70 | 0.53 | 0.24 | 0.52 |
| K224P | 0.09 | 0.05 | 0.05 | 0.05 | 0.05 | 0.07 | 0.05 | 0.05 | 0.23 |
| K224R | 0.52 | *1.19* | 0.73 | 0.33 | *1.13* | *1.18* | *1.14* | *1.02* | 0.93 |
| K224S | 0.08 | 0.05 | 0.05 | 0.05 | 0.29 | 0.18 | 0.26 | 0.05 | 0.47 |
| K224T | 0.07 | 0.05 | 0.05 | 0.05 | 0.28 | 0.23 | 0.31 | 0.05 | 0.30 |
| K224V | 0.43 | *1.11* | 0.82 | 0.55 | *1.10* | 0.98 | *1.12* | *1.07* | 0.86 |
| K224W | 0.10 | 0.05 | 0.05 | 0.05 | 0.14 | 0.13 | 0.18 | 0.05 | 0.29 |
| K224Y | 0.12 | 0.34 | 0.72 | 0.05 | 0.64 | 0.70 | 0.54 | 0.35 | 0.53 |
| D225A | 0.94 | 0.76 | *1.11* | 0.94 | 0.89 | *1.07* | 0.93 | 0.90 | 0.96 |
| D225C | *1.35* | 0.85 | *1.09* | *1.31* | 0.91 | *1.10* | 0.96 | 0.99 | 0.90 |
| D225D | 1.00 | 1.00 | 1.00 | 1.00 | 1.00 | 1.00 | 1.00 | 1.00 | 1.00 |
| D225E | 0.25 | 0.49 | *1.01* | 0.46 | 0.91 | 0.81 | 0.91 | *1.03* | *1.02* |
| D225F | 0.53 | 0.81 | *1.04* | 0.86 | 0.95 | *1.12* | *1.08* | *1.27* | 0.94 |
| D225G | 0.63 | 0.95 | 1.00 | *1.14* | *1.06* | *1.11* | *1.13* | *1.13* | *1.04* |
| D225H | 0.40 | 0.73 | *1.03* | 0.76 | *1.06* | *1.15* | *1.08* | *1.15* | *1.04* |
| D225I | 0.47 | 0.77 | *1.06* | 0.62 | *1.01* | *1.14* | *1.12* | *1.10* | *1.16* |
| D225L | 0.67 | 0.88 | *1.09* | *1.25* | *1.04* | *1.15* | *1.06* | *1.28* | *1.12* |
| D225M | 0.47 | 0.81 | 0.96 | 0.84 | *1.02* | *1.07* | *1.06* | *1.09* | 0.99 |
| D225P | 0.05 | 0.05 | 0.05 | 0.05 | 0.10 | 0.50 | 0.05 | 0.05 | 0.18 |
| D225Q | 0.64 | 0.81 | *1.03* | *1.02* | 0.92 | *1.11* | 0.98 | 0.99 | 0.90 |
| D225R | 0.04 | 0.04 | 0.04 | 0.04 | 0.04 | 0.04 | 0.04 | 0.04 | 0.04 |
| D225S | 0.72 | 0.83 | 0.98 | *1.06* | 0.91 | *1.07* | 0.90 | 0.92 | 0.92 |
| D225T | 0.57 | 0.94 | *1.07* | *1.09* | *1.06* | *1.09* | *1.24* | *1.26* | *1.09* |
| D225V | 0.71 | *1.02* | *1.01* | *1.06* | *1.04* | *1.18* | *1.11* | *1.21* | 0.97 |
| D225W | 0.48 | 0.82 | *1.13* | 0.73 | *1.18* | *1.13* | *1.26* | *1.30* | *1.27* |
| D225Y | 0.52 | 0.88 | *1.01* | 0.92 | *1.09* | *1.22* | *1.16* | *1.22* | *1.11* |

TABLE 3-1-continued

Performance Index Data of BGL1 SEL Variants (3,153)

| | | | | | | | | | |
|---|---|---|---|---|---|---|---|---|---|
| Q226A | *1.10* | *1.04* | *1.03* | *1.01* | 0.94 | 0.95 | *1.04* | *1.07* | 0.98 |
| Q226C | 0.63 | 0.96 | *1.11* | 0.63 | 0.99 | *1.16* | *1.05* | *1.15* | *1.42* |
| Q226D | 0.52 | 0.89 | *1.04* | 0.45 | 1.00 | *1.11* | 0.98 | *1.06* | *1.06* |
| Q226E | 0.69 | 0.92 | *1.02* | 0.58 | 0.88 | *1.06* | 0.95 | 1.00 | 0.88 |
| Q226F | 0.53 | *1.03* | 0.92 | 0.51 | *1.15* | *1.20* | *1.18* | *1.14* | *1.17* |
| Q226H | 0.65 | 0.86 | 0.95 | 0.41 | 0.89 | *1.10* | 0.93 | 0.87 | 0.69 |
| Q226I | 0.41 | 0.89 | *1.06* | 0.45 | *1.10* | *1.54* | *1.10* | *1.04* | 0.79 |
| Q226K | 0.48 | 0.78 | *1.01* | 0.42 | 0.93 | *1.37* | 0.97 | 0.90 | 0.65 |
| Q226L | 0.52 | *1.00* | 0.91 | 0.48 | *1.05* | *1.25* | *1.08* | *1.00* | 0.88 |
| Q226M | 0.47 | 0.90 | 0.99 | 0.45 | *1.10* | *1.56* | *1.10* | 0.99 | 0.85 |
| Q226N | 0.33 | 0.85 | 0.97 | 0.29 | 0.98 | *1.31* | *1.01* | 0.91 | *1.03* |
| Q226Q | 1.00 | 1.00 | 1.00 | 1.00 | 1.00 | 1.00 | 1.00 | 1.00 | 1.00 |
| Q226R | 0.44 | 0.86 | 0.90 | 0.53 | *1.02* | *1.36* | *1.04* | 0.89 | *1.15* |
| Q226S | 0.22 | 0.05 | 0.05 | 0.09 | 0.26 | 0.50 | 0.15 | 0.13 | *1.06* |
| Q226T | 0.59 | 0.98 | 0.96 | 0.55 | 0.99 | *1.12* | 0.98 | 0.98 | 0.99 |
| Q226V | 0.31 | 0.85 | 0.96 | 0.37 | *1.14* | *1.63* | *1.03* | 0.94 | 0.98 |
| Q226W | 0.37 | *1.08* | *1.06* | 0.54 | *1.50* | *1.61* | *1.49* | *1.51* | *1.47* |
| Q226Y | 0.42 | *1.23* | 0.99 | 0.51 | *1.44* | *1.55* | *1.46* | *1.54* | *1.17* |
| D236A | *1.30* | 0.05 | 0.05 | 0.05 | 0.05 | 0.07 | 0.05 | 0.05 | 0.07 |
| D236C | 0.57 | 0.05 | 0.05 | 0.05 | 0.05 | 0.06 | 0.05 | 0.05 | 0.21 |
| D236D | 1.00 | 1.00 | 1.00 | 1.00 | 1.00 | 1.00 | 1.00 | 1.00 | 1.00 |
| D236E | 0.85 | 0.05 | 0.05 | 0.05 | 0.05 | 0.05 | 0.05 | 0.05 | 0.13 |
| D236F | 0.19 | 0.05 | 0.05 | 0.05 | 0.05 | 0.14 | 0.05 | 0.05 | 0.26 |
| D236G | *1.45* | 0.05 | 0.05 | 0.05 | 0.05 | 0.08 | 0.05 | 0.05 | 0.10 |
| D236H | 0.04 | 0.04 | 0.04 | 0.04 | 0.04 | 0.04 | 0.04 | 0.04 | 0.04 |
| D236I | 0.26 | 0.05 | 0.05 | 0.05 | 0.05 | 0.14 | 0.05 | 0.05 | 0.18 |
| D236K | 0.04 | 0.04 | 0.04 | 0.04 | 0.04 | 0.04 | 0.04 | 0.04 | 0.04 |
| D236L | 0.15 | 0.05 | 0.05 | 0.12 | 0.05 | 0.23 | 0.05 | 0.24 | 0.23 |
| D236M | 0.86 | 0.05 | 0.05 | 0.05 | 0.05 | 0.12 | 0.05 | 0.05 | 0.10 |
| D236P | *1.14* | 0.05 | 0.05 | 0.05 | 0.05 | 0.07 | 0.05 | 0.05 | 0.14 |
| D236Q | *1.83* | 0.05 | 0.05 | 0.05 | 0.05 | 0.07 | 0.05 | 0.05 | 0.05 |
| D236R | 0.06 | 0.05 | 0.05 | 0.05 | 0.05 | 0.64 | 0.05 | 0.07 | 0.33 |
| D236S | *1.29* | 0.05 | 0.05 | 0.05 | 0.05 | 0.05 | 0.05 | 0.05 | 0.08 |
| D236T | *1.40* | 0.05 | 0.05 | 0.05 | 0.05 | 0.05 | 0.05 | 0.05 | 0.06 |
| D236V | 0.21 | 0.05 | 0.05 | 0.05 | 0.05 | 0.20 | 0.05 | 0.06 | 0.45 |

TABLE 3-1-continued

Performance Index Data of BGL1 SEL Variants (3,153)

| | | | | | | | | | |
|---|---|---|---|---|---|---|---|---|---|
| D236W | 0.21 | 0.05 | 0.05 | 0.05 | 0.05 | 0.09 | 0.05 | 0.05 | 0.30 |
| D236Y | 0.16 | 0.05 | 0.05 | 0.05 | 0.05 | 0.19 | 0.05 | 0.06 | 0.23 |
| W237A | 1.00 | 0.06 | 0.05 | 0.05 | 0.06 | 0.13 | 0.05 | 0.05 | 0.14 |
| W237C | 0.43 | 0.05 | 0.05 | 0.05 | 0.05 | 0.06 | 0.05 | 0 05 | 0.12 |
| W237D | 0.58 | 0.05 | 0.05 | 0.05 | 0.05 | 0.05 | 0.05 | 0.05 | 0.16 |
| W237E | 0.78 | 0.05 | 0.05 | 0.05 | 0.05 | 0.05 | 0.05 | 0.05 | 0.07 |
| W237G | 0.46 | 0.05 | 0.05 | 0.05 | 0.05 | 0.05 | 0.05 | 0.05 | 0.30 |
| W237H | *1.28* | 0.05 | 0.05 | 0.05 | 0.05 | 0.05 | 0.05 | 0.05 | 0.10 |
| W237I | *1.89* | 0.05 | 0.05 | 0.05 | 0.05 | 0.05 | 0.05 | 0.05 | 0.05 |
| W237K | *1.68* | 0.05 | 0.05 | 0.05 | 0.05 | 0.05 | 0.05 | 0.05 | 0.21 |
| W237M | *1.31* | 0.05 | 0.05 | 0.05 | 0.05 | 0.06 | 0.05 | 0.05 | 0.05 |
| W237N | 0.93 | 0.05 | 0.05 | 0.05 | 0.05 | 0.05 | 0.05 | 0.05 | 0.09 |
| W237P | *1.87* | 0.05 | 0.05 | 0.05 | 0.05 | 0.05 | 0.05 | 0.05 | 0.05 |
| W237Q | 0.93 | 0.05 | 0.05 | 0.05 | 0.05 | 0.05 | 0.05 | 0.05 | 0.10 |
| W237R | *1.42* | 0.05 | 0.05 | 0.05 | 0.05 | 0.05 | 0.05 | 0.05 | 0.10 |
| W237S | *1.32* | 0.05 | 0.05 | 0.05 | 0.05 | 0.08 | 0.05 | 0.05 | 0.15 |
| W237T | *1.37* | 0.05 | 0.05 | 0.05 | 0.05 | 0.05 | 0.05 | 0.05 | 0.08 |
| W237V | 0.98 | 0.05 | 0.05 | 0.05 | 0.05 | 0.05 | 0.05 | 0.05 | 0.09 |
| W237W | 1.00 | 1.00 | 1.00 | 1.00 | 1.00 | 1.00 | 1.00 | 1.00 | 1.00 |
| W237Y | 0.74 | 0.39 | *1.51* | 0.05 | 0.22 | 0.17 | 0.21 | 0.28 | 0.30 |
| N238A | 0.78 | *1.36* | *1.02* | *1.20* | *1.22* | *1.23* | *1.23* | *1.06* | *1.09* |
| N238C | 0.38 | 0.92 | 1.00 | 0.48 | *1.31* | *1.03* | *1.43* | *1.27* | 0.96 |
| N238D | 0.89 | 0.88 | *1.05* | 0.69 | 0.95 | 0.95 | 0.92 | 0.93 | 0.79 |
| N238E | 0.44 | *1.16* | 0.91 | 0.45 | *1.12* | 0.92 | *1.19* | *1.05* | 0.83 |
| N238F | 0.49 | 0.20 | *1.33* | 0.27 | 0.49 | 0.50 | 0.33 | 0.36 | 0.31 |
| N238G | 0.43 | *1.09* | *1.02* | 0.71 | *1.04* | *1.31* | 0.93 | 0.89 | 0.61 |
| N238H | 0.49 | 0.80 | 0.78 | 0.20 | 0.66 | 0.70 | 0.80 | 0.69 | 0.59 |
| N238I | 0.39 | 0.86 | 0.67 | 0.06 | 0.46 | 0.51 | 0.68 | 0.61 | 0.45 |
| N238K | 0.33 | 0.79 | 0.73 | 0.05 | 0.34 | 0.40 | 0.68 | 0.51 | 0.32 |
| N238L | 0.60 | 0.82 | 0.90 | 0.42 | 0.45 | 0.78 | 0.76 | 0.74 | 0.54 |
| N238M | 0.32 | *1.01* | 0.77 | 0.54 | 0.58 | *1.03* | 0.92 | 0.87 | 0.60 |
| N238P | 0.11 | 0.42 | *1.18* | 0.05 | 0.20 | 0.25 | 0.16 | 0.32 | 0.24 |
| N238R | 0.39 | 0.52 | 0.57 | 0.10 | 0.27 | 0.27 | 0.57 | 0.42 | 0.24 |
| N238S | 0.56 | *1.09* | *1.05* | 0.73 | 0.85 | *1.00* | 0.88 | 0.89 | 0.76 |
| N238T | 0.55 | *1.28* | 0.87 | 0.47 | 0.65 | 0.96 | 0.94 | 0.84 | 0.72 |

TABLE 3-1-continued

Performance Index Data of BGL1 SEL Variants (3,153)

| | | | | | | | | | |
|---|---|---|---|---|---|---|---|---|---|
| N238V | 0.37 | 0.82 | 0.97 | 0.33 | 0.58 | 0.85 | 0.84 | 0.93 | 0.61 |
| N238W | 0.44 | 0.30 | *1.40* | 0.16 | 0.94 | 0.63 | 0.59 | 0.75 | 0.44 |
| N238Y | 0.53 | 0.83 | 0.87 | 0.48 | 0.75 | 0.77 | 0.77 | 0.89 | 0.59 |
| T242A | 0.75 | *1.21* | 0.82 | 0.09 | *1.07* | *1.00* | *1.02* | 0.95 | 0.92 |
| T242C | 0.62 | *1.39* | 0.94 | 0.47 | *1.29* | *1.19* | *1.36* | *1.28* | *1.17* |
| T242E | 0.96 | *1.28* | 0.89 | 0.46 | *1.10* | *1.10* | *1.09* | *1.02* | *1.03* |
| T242F | 0.50 | *1.14* | 0.84 | 0.17 | *1.10* | 0.70 | *1.03* | 0.92 | 0.84 |
| T242G | 0.75 | *1.18* | 0.86 | 0.27 | *1.08* | 0.89 | 1.00 | 0.89 | 0.87 |
| T242H | 0.94 | *1.31* | *1.06* | *1.23* | *1.19* | 0.93 | *1.27* | *1.24* | *1.17* |
| T242I | 0.38 | *1.10* | 0.66 | 0.05 | 0.96 | 0.05 | 0.94 | 0.81 | 0.73 |
| T242K | 0.48 | *1.19* | 0.81 | 0.36 | *1.04* | 0.72 | *1.04* | 0.99 | 0.82 |
| T242L | 0.80 | *1.39* | 0.87 | 0.05 | *1.12* | 0.46 | *1.10* | 0.99 | *1.05* |
| T242M | 0.52 | *1.22* | 0.85 | 0.07 | *1.17* | 0.58 | *1.14* | 0.98 | 0.94 |
| T242N | 0.82 | *1.16* | 0.90 | 0.93 | *1.04* | 0.86 | 0.95 | 0.91 | 0.90 |
| T242P | 0.09 | 0.05 | 0.05 | 0.05 | 0.09 | 0.05 | 0.05 | 0.05 | 0.39 |
| T242Q | 0.50 | *1.28* | 0.77 | 0.49 | *1.15* | 0.86 | *1.15* | *1.09* | 0.88 |
| T242R | 0.72 | *1.18* | 0.80 | 0.38 | *1.02* | 0.65 | 0.93 | 0.94 | 0.79 |
| T242S | *1.56* | 0.93 | *1.23* | *2.00* | *1.02* | *1.02* | 1.00 | 0.95 | *1.01* |
| T242T | 1.00 | 1.00 | 1.00 | 1.00 | 1.00 | 1.00 | 1.00 | 1.00 | 1.00 |
| T242V | 0.40 | *1.18* | 0.86 | 0.05 | *1.15* | 0.27 | *1.13* | 0.97 | 0.88 |
| T242W | 0.54 | *1.50* | 0.86 | 0.19 | *1.24* | 0.84 | *1.30* | *1.19* | *1.13* |
| T242Y | 0.52 | *1.36* | 0.82 | 0.21 | *1.23* | 0.95 | *1.22* | *1.18* | *1.03* |
| N248A | *1.07* | *1.02* | 0.98 | *1.10* | *1.01* | 0.80 | 0.95 | 0.95 | 0.99 |
| N248C | *1.22* | *1.02* | 0.99 | *1.35* | 0.95 | 0.89 | 0.95 | 0.93 | *1.03* |
| N248F | 0.58 | *1.01* | 0.88 | 0.79 | *1.02* | 0.72 | 0.94 | 0.99 | 0.96 |
| N248G | 0.25 | 0.90 | 0.84 | 0.45 | *1.21* | 0.92 | *1.18* | *1.27* | 0.99 |
| N248H | 0.70 | 0.88 | 0.89 | 0.76 | 0.94 | 0.68 | 0.86 | 0.82 | 0.77 |
| N248K | 0.51 | 0.84 | 0.87 | 0.59 | 0.96 | 0.71 | 0.87 | 0.83 | 0.78 |
| N248L | 0.93 | 0.98 | 0.93 | *1.10* | 0.96 | 0.75 | 0.86 | 0.84 | 0.82 |
| N248M | 0.61 | 0.89 | 0.83 | 0.70 | 0.85 | 0.69 | 0.77 | 0.79 | 0.75 |
| N248P | 0.13 | 0.34 | 0.92 | 0.08 | 0.72 | 0.30 | 0.70 | 0.74 | 0.58 |
| N248Q | 0.56 | 0.88 | 0.93 | 0.70 | 0.94 | 0.80 | 0.89 | 0.88 | 0.78 |
| N248R | 0.44 | 0.89 | 0.88 | 0.54 | 0.99 | 0.81 | 0.94 | 0.95 | 0.82 |
| N248S | 0.75 | 0.85 | 0.87 | 0.73 | 0.86 | 0.77 | 0.76 | 0.76 | 0.75 |
| N248T | 0.84 | *1.12* | 0.87 | *1.12* | *1.03* | *1.01* | 0.98 | 1.00 | 0.96 |
| N248V | 0.58 | 0.91 | 0.89 | 0.74 | 0.92 | 0.85 | 0.87 | 0.92 | 0.76 |

TABLE 3-1-continued

Performance Index Data of BGL1 SEL Variants (3,153)

| | | | | | | | | | |
|---|---|---|---|---|---|---|---|---|---|
| N248W | 0.64 | *1.20* | 0.91 | 1.00 | *1.09* | 0.96 | *1.19* | *1.15* | *1.14* |
| N248Y | 0.51 | 0.98 | 0.87 | 0.74 | 1.00 | 0.93 | *1.03* | *1.00* | 0.89 |
| S249A | *1.04* | 0.05 | 0.05 | 0.32 | 0.89 | *1.11* | 0.91 | 0.97 | 0.75 |
| S249C | 0.93 | 0.43 | 0.90 | 0.50 | 0.84 | 0.96 | 0.88 | 0.93 | 0.81 |
| S249D | 0.51 | 0.29 | 0.05 | 0.67 | 0.73 | 0.80 | 0.63 | 0.64 | 0.55 |
| S249E | 0.24 | 0.05 | 0.05 | 0.36 | 0.17 | 0.33 | 0.09 | 0.05 | 0.26 |
| S249G | 0.58 | 0.05 | 0.05 | 0.57 | 0.84 | *1.05* | 0.79 | 0.85 | 0.67 |
| S249H | 0.69 | 0.05 | 0.05 | 0.48 | 0.88 | 0.83 | 0.79 | 0.75 | 0.53 |
| S249I | 0.73 | 0.70 | 0.88 | *1.04* | 0.90 | 0.88 | 0.87 | 0.78 | 0.67 |
| S249K | 0.43 | 0.27 | 0.05 | 0.68 | 0.88 | 0.94 | 0.74 | 0.70 | 0.40 |
| S249L | 0.48 | 0.28 | 0.90 | 0.97 | 0.98 | 0.85 | 0.87 | 0.87 | 0.72 |
| S249M | 0.66 | 0.69 | *1.05* | 0.84 | *1.07* | 0.92 | 0.84 | 0.71 | 0.61 |
| S249N | 0.65 | 0.45 | 0.90 | 0.73 | 0.83 | 0.80 | 0.75 | 0.61 | 0.50 |
| S249P | 0.27 | 0.05 | 0.05 | 0.57 | 0.17 | 0.16 | 0.10 | 0.05 | 0.20 |
| S249Q | 0.81 | 0.05 | 0.05 | 0.44 | 0.92 | 0.97 | 0.90 | 0.72 | 0.62 |
| S249R | 0.74 | 0.40 | 0.87 | 0.63 | 0.79 | 0.81 | 0.77 | 0.57 | 0.56 |
| S249S | 1.00 | 1.00 | 1.00 | 1.00 | 1.00 | 1.00 | 1.00 | 1.00 | 1.00 |
| S249T | 0.81 | 0.28 | 0.05 | 0.66 | 0.87 | 0.99 | 0.83 | 0.73 | 0.82 |
| S249V | 0.55 | 0.53 | 0.76 | 0.36 | *1.03* | 0.76 | 0.97 | 0.71 | 0.74 |
| S249W | 0.52 | 0.05 | 0.05 | 0.05 | 0.86 | 0.85 | 0.79 | 0.81 | 0.62 |
| S249Y | 0.63 | 0.72 | 0.97 | 0.05 | 0.95 | 0.86 | 0.86 | 0.84 | 0.57 |
| N263A | 0.96 | *1.03* | *1.00* | 0.96 | 0.99 | *1.07* | 0.96 | 0.96 | *1.08* |
| N263C | 0.61 | *1.29* | *1.06* | 0.91 | *1.18* | *1.22* | *1.58* | *1.48* | *1.54* |
| N263D | 0.93 | 0.96 | *1.01* | 0.93 | *1.00* | *1.22* | 0.95 | 0.97 | *1.07* |
| N263E | 0.92 | 0.93 | *1.08* | 0.87 | 0.94 | 0.97 | *1.04* | 0.89 | *1.01* |
| N263F | 0.59 | 0.97 | *1.01* | 0.71 | 0.98 | 0.68 | *1.19* | 0.99 | 0.97 |
| N263G | 0.76 | *1.11* | 1.00 | 0.93 | *1.01* | 0.99 | *1.05* | *1.09* | *1.16* |
| N263H | 0.84 | *1.03* | *1.02* | 0.94 | 0.97 | 0.82 | 0.89 | 0.91 | *1.02* |
| N263I | 0.50 | 0.78 | *1.00* | 0.50 | 0.91 | 0.85 | 0.98 | 0.87 | 0.91 |
| N263K | 0.57 | 0.83 | *1.01* | 0.59 | 0.89 | 0.80 | 0.94 | 0.92 | 0.93 |
| N263L | 0.68 | 0.93 | *1.06* | 0.78 | 0.96 | 0.99 | 0.98 | 0.92 | *1.06* |
| N263M | 0.04 | 0.04 | 0.04 | 0.04 | 0.04 | 0.04 | 0.04 | 0.04 | 0.04 |
| N263N | 1.00 | 1.00 | 1.00 | 1.00 | 1.00 | 1.00 | 1.00 | 1.00 | 1.00 |
| N263P | 0.62 | 0.77 | *1.04* | 0.53 | 0.66 | 0.42 | 0.77 | 0.73 | 0.75 |
| N263Q | 0.61 | 0.95 | *1.05* | 0.67 | 0.96 | *1.01* | *1.05* | 0.97 | *1.02* |

TABLE 3-1-continued

Performance Index Data of BGL1 SEL Variants (3,153)

| | | | | | | | | |
|---|---|---|---|---|---|---|---|---|
| N263R | 0.68 | 0.93 | 0.97 | 0.68 | 0.92 | 0.82 | 0.92 | 0.87 | *1.02* |
| N263S | 0.47 | *1.30* | *1.10* | 0.86 | *1.28* | *1.45* | *1.47* | *1.50* | *1.56* |
| N263T | 0.51 | *1.01* | *1.11* | 0.71 | *1.09* | *1.16* | *1.38* | *1.18* | *1.25* |
| N263V | 0.47 | 0.83 | *1.11* | 0.52 | 0.94 | 0.85 | *1.07* | 0.94 | 0.88 |
| N263W | 0.04 | 0.04 | 0.04 | 0.04 | 0.04 | 0.04 | 0.04 | 0.04 | 0.04 |
| N263Y | 0.60 | 0.91 | 0.95 | 0.65 | 0.88 | 0.86 | *1.07* | 0.89 | 0.90 |
| N264A | 0.37 | 0.91 | *1.12* | 0.06 | 0.93 | 0.96 | 0.96 | 0.71 | 0.95 |
| N264C | 0.71 | *1.29* | *1.04* | 0.90 | *1.10* | *1.18* | *1.25* | *1.01* | *1.26* |
| N264D | *1.08* | 0.86 | *1.03* | 0.71 | 0.90 | 0.89 | 0.87 | 0.71 | 0.75 |
| N264E | *1.03* | 0.77 | *1.10* | 0.70 | 0.84 | 0.86 | 0.82 | 0.62 | 0.70 |
| N264G | 0.97 | 0.88 | *1.13* | 0.68 | 0.86 | 0.78 | 0.88 | 0.66 | 0.70 |
| N264H | *1.10* | 0.94 | *1.02* | 0.94 | 0.90 | 0.87 | 0.91 | 0.71 | 0.71 |
| N264K | 0.78 | 0.85 | *1.14* | 0.68 | 0.80 | 0.79 | 0.87 | 0.67 | 0.70 |
| N264L | *1.16* | 0.66 | *1.15* | 0.58 | 0.79 | 0.83 | 0.75 | 0.61 | 0.65 |
| N264M | 0.81 | 0.74 | *1.22* | 0.61 | 0.80 | 0.85 | 0.81 | 0.71 | 0.66 |
| N264N | 1.00 | 1.00 | 1.00 | 1.00 | 1.00 | 1.00 | 1.00 | 1.00 | 1.00 |
| N264P | 0.85 | 0.81 | 0.76 | 0.05 | 0.57 | 0.44 | 0.74 | 0.51 | 0.58 |
| N264Q | 0.78 | 0.91 | *1.09* | 0.66 | 0.91 | 1.00 | 0.96 | 0.80 | 0.91 |
| N264R | *1.01* | 0.85 | *1.04* | 0.91 | 0.77 | 0.78 | 0.83 | 0.72 | 0.76 |
| N264S | *1.17* | 0.87 | *1.12* | 0.89 | 0.90 | 0.87 | 0.88 | 0.75 | 0.82 |
| N264T | 0.86 | 0.81 | *1.10* | 0.61 | 0.81 | 0.95 | 0.81 | 0.71 | 0.70 |
| N264V | *1.03* | 0.84 | *1.09* | 0.70 | 0.83 | 0.76 | 0.84 | 0.69 | 0.73 |
| N264W | 0.04 | 0.04 | 0.04 | 0.04 | 0.04 | 0.04 | 0.04 | 0.04 | 0.04 |
| N264Y | *1.20* | 0.76 | *1.02* | 0.73 | 0.79 | 0.75 | 0.76 | 0.70 | 0.71 |
| R265A | *1.18* | 0.89 | *1.01* | 0.72 | 0.92 | *1.10* | 0.87 | 0.73 | 0.85 |
| R265E | 0.87 | *1.03* | *1.11* | 0.61 | 0.97 | *1.05* | *1.02* | 0.83 | 0.89 |
| R265F | 0.98 | 0.90 | *1.13* | 0.41 | 0.89 | 0.90 | 0.95 | 0.78 | 0.82 |
| R265G | *1.02* | 0.96 | *1.04* | 0.16 | 0.86 | 0.83 | 0.88 | 0.73 | 0.79 |
| R265I | 0.84 | 0.96 | *1.15* | 0.29 | 0.99 | *1.01* | 0.96 | 0.92 | 0.92 |
| R265K | 0.92 | *1.15* | 0.96 | 0.95 | 0.98 | 0.99 | *1.03* | 0.90 | 0.86 |
| R265L | 0.92 | *1.05* | 0.92 | 0.52 | 0.92 | *1.01* | 0.92 | 0.80 | 0.82 |
| R265M | 0.89 | 0.92 | *1.22* | 0.61 | 0.95 | *1.03* | 0.94 | 0.84 | 0.82 |
| R265N | 0.90 | *1.14* | 0.95 | 0.35 | 0.96 | 0.94 | 0.91 | 0.84 | 0.91 |
| R265P | 0.75 | 0.77 | *1.31* | 0.36 | 0.78 | 0.80 | 0.79 | 0.70 | 0.68 |
| R265Q | 0.98 | *1.04* | *1.01* | 0.87 | 0.93 | 0.99 | 0.93 | 0.86 | 0.95 |

TABLE 3-1-continued

Performance Index Data of BGL1 SEL Variants (3,153)

| | | | | | | | | | |
|---|---|---|---|---|---|---|---|---|---|
| R265R | 1.00 | 1.00 | 1.00 | 1.00 | 1.00 | 1.00 | 1.00 | 1.00 | 1.00 |
| R265S | 0.84 | 0.94 | *1.12* | 0.26 | 0.82 | 0.90 | 0.86 | 0.85 | 0.64 |
| R265T | 0.89 | 0.76 | *1.22* | 0.20 | 0.82 | 0.84 | 0.86 | 0.85 | 0.77 |
| R265V | 0.74 | 0.84 | *1.22* | 0.27 | 0.91 | 0.87 | 0.86 | 0.95 | 0.76 |
| R265W | 0.87 | 0.97 | 0.95 | 0.37 | 0.83 | 0.97 | 0.90 | 0.90 | 0.88 |
| R265Y | *1.22* | 0.91 | 0.96 | 0.50 | 0.85 | *1.00* | 0.90 | 0.91 | 0.72 |
| N276A | 0.28 | 0.51 | *1.02* | 0.27 | *1.12* | *1.07* | 0.95 | *1.33* | *1.44* |
| N276C | 0.09 | 0.34 | 0.98 | 0.17 | *1.78* | *1.69* | *1.30* | *2.73* | *1.75* |
| N276E | 0.27 | 0.26 | 0.90 | 0.14 | 0.62 | 0.44 | 0.39 | 0.87 | 0.45 |
| N276F | 0.19 | 0.39 | 0.98 | 0.21 | *1.18* | 0.87 | 0.95 | *1.68* | *1.15* |
| N276H | 0.30 | 0.28 | 0.85 | 0.11 | 0.49 | 0.40 | 0.27 | 0.77 | 0.72 |
| N276K | 0.25 | 0.35 | 0.82 | 0.05 | 0.68 | 0.52 | 0.48 | 0.98 | *1.01* |
| N276M | 0.24 | 0.29 | 0.86 | 0.15 | 0.70 | 0.49 | 0.48 | *1.01* | 0.50 |
| N276N | 1.00 | 1.00 | 1.00 | 1.00 | 1.00 | 1.00 | 1.00 | 1.00 | 1.00 |
| N276P | 0.20 | 0.19 | 0.73 | 0.12 | 0.41 | 0.21 | 0.13 | 0.74 | 0.28 |
| N276Q | 0.30 | 0.39 | 0.90 | 0.24 | 0.80 | 0.66 | 0.52 | *1.03* | 1.00 |
| N276R | 0.32 | 0.31 | 0.94 | 0.15 | 0.59 | 0.48 | 0.41 | 0.85 | 0.80 |
| N276T | 0.34 | 0.35 | 0.87 | 0.16 | 0.68 | 0.63 | 0.46 | 0.91 | 0.86 |
| N276V | 0.04 | 0.04 | 0.04 | 0.04 | 0.04 | 0.04 | 0.04 | 0.04 | 0.04 |
| N276W | 0.04 | 0.04 | 0.04 | 0.04 | 0.04 | 0.04 | 0.04 | 0.04 | 0.04 |
| S277A | *1.03* | 0.96 | *1.01* | 0.91 | 0.95 | *1.09* | *1.03* | 0.86 | 0.81 |
| S277C | 0.53 | 0.94 | *1.09* | 0.60 | *1.20* | *1.25* | *1.41* | *1.15* | *1.05* |
| S277D | *1.29* | 0.88 | *1.07* | 0.89 | 0.94 | *1.03* | 0.99 | 0.84 | 0.76 |
| S277E | 0.86 | 0.84 | *1.00* | 0.86 | 0.87 | *1.32* | 0.90 | 0.79 | 0.76 |
| S277F | 0.56 | 0.82 | *1.04* | 0.60 | *1.00* | *1.46* | *1.08* | 0.93 | 0.73 |
| S277G | 0.74 | 0.83 | *1.05* | 0.70 | 0.90 | *1.47* | 0.89 | 0.86 | 0.73 |
| S277H | 0.62 | 0.75 | 0.99 | 0.61 | 0.90 | *1.27* | 0.92 | 0.87 | 0.80 |
| S277I | 0.54 | 0.77 | 1.00 | 0.54 | 0.92 | *1.16* | *1.02* | 0.90 | 0.82 |
| S277K | 0.74 | 0.77 | 0.96 | 0.51 | 0.79 | 0.95 | 0.84 | 0.61 | 0.68 |
| S277L | 0.56 | 0.83 | 0.94 | 0.70 | 0.92 | 0.91 | 0.98 | 0.56 | 0.76 |
| S277M | 0.54 | 0.90 | *1.02* | 0.63 | 0.98 | *1.13* | *1.08* | 0.65 | 0.82 |
| S277N | 0.70 | 0.78 | *1.11* | 0.65 | 0.89 | 1.00 | 0.89 | 0.80 | 0.71 |
| S277P | 0.26 | 0.59 | 0.92 | 0.18 | 0.94 | *1.21* | *1.05* | 0.72 | 0.93 |
| S277Q | 0.69 | 0.87 | *1.02* | 0.73 | 0.95 | *1.04* | 0.99 | 0.88 | 0.87 |
| S277R | 0.73 | 0.89 | *1.03* | 0.68 | 0.92 | 0.97 | *1.06* | 0.71 | 0.74 |
| S277S | 1.00 | 1.00 | 1.00 | 1.00 | 1.00 | 1.00 | 1.00 | 1.00 | 1.00 |

TABLE 3-1-continued

Performance Index Data of BGL1 SEL Variants (3,153)

| S277T | 0.49 | 0.76 | 0.93 | 0.05 | 0.89 | 0.96 | 0.96 | 0.92 | 0.91 |
|---|---|---|---|---|---|---|---|---|---|
| S277V | 0.62 | 0.64 | 0.49 | 0.05 | 0.41 | 0.55 | 0.46 | 0.40 | 0.47 |
| S277W | 0.06 | *1.47* | *1.01* | 0.60 | *6.07* | *6.63* | *9.14* | *9.25* | *3.36* |
| S277Y | 0.56 | 0.97 | 0.94 | 0.79 | *1.08* | *1.18* | *1.24* | *1.22* | 0.93 |
| N278A | *1.01* | 0.97 | 1.00 | 0.79 | 1.00 | *1.41* | *1.08* | 0.93 | 0.90 |
| N278C | 0.90 | 1.00 | *1.04* | 0.72 | *1.05* | *1.25* | *1.19* | *1.02* | 0.98 |
| N278D | *1.59* | 0.88 | *1.03* | *1.17* | 0.97 | *1.13* | 0.94 | 0.88 | 0.80 |
| N278F | 0.50 | *1.09* | *1.00* | 0.69 | *1.25* | *2.26* | *1.57* | *1.32* | *1.33* |
| N278G | 0.80 | 0.92 | *1.01* | 0.79 | *1.04* | *1.14* | *1.08* | 0.92 | 0.88 |
| N278H | 0.15 | 0.41 | 0.73 | 0.05 | 0.61 | 0.12 | *1.21* | 0.64 | 0.59 |
| N278I | 0.59 | 0.84 | 0.98 | 0.57 | 0.94 | *1.50* | *1.12* | 0.95 | 0.88 |
| N278L | 0.67 | 0.89 | 0.97 | 0.74 | 0.91 | 0.99 | *1.06* | 0.78 | 0.87 |
| N278M | 0.72 | 0.93 | 0.92 | 0.65 | 0.91 | *1.21* | *1.05* | 0.90 | 0.76 |
| N278N | 1.00 | 1.00 | 1.00 | 1.00 | 1.00 | 1.00 | 1.00 | 1.00 | 1.00 |
| N278P | 0.22 | 0.34 | 0.90 | 0.05 | 0.70 | 0.44 | 0.85 | 0.69 | 0.52 |
| N278Q | 0.74 | 0.79 | *1.05* | 0.67 | 0.88 | *1.18* | 0.99 | 0.87 | 0.78 |
| N278R | 0.94 | 0.89 | *1.05* | 0.82 | 0.92 | *1.12* | *1.05* | 0.98 | 0.78 |
| N278S | 0.60 | 0.90 | 0.99 | 0.66 | 0.97 | *1.10* | *1.09* | 0.86 | 0.89 |
| N278T | 0.79 | 0.98 | 0.95 | 0.65 | 0.92 | *1.14* | *1.06* | 0.98 | 0.88 |
| N278V | 0.80 | 0.98 | *1.02* | 0.81 | *1.04* | *1.24* | *1.13* | *1.07* | 0.94 |
| N278W | 0.70 | 0.93 | 0.95 | 0.55 | 0.91 | *1.20* | 0.87 | *1.08* | *1.00* |
| N278Y | 0.60 | 0.82 | 0.99 | 0.74 | 0.98 | *1.29* | *1.10* | 0.92 | 0.95 |
| Q279A | 0.05 | 0.05 | 0.05 | 0.05 | 0.05 | 0.05 | 0.05 | 0.05 | 0.05 |
| Q279C | 0.63 | *1.36* | *1.02* | 0.81 | *1.31* | *1.35* | *1.38* | *1.47* | *1.50* |
| Q279D | 0.87 | 0.97 | *1.03* | 0.85 | 0.99 | *1.13* | 0.96 | *1.02* | 1.00 |
| Q279E | 0.68 | 0.78 | 0.95 | 0.60 | 0.81 | *1.04* | 0.78 | 0.81 | 0.82 |
| Q279G | 0.73 | 1.00 | 0.94 | 0.84 | 0.95 | *1.02* | 0.95 | 0.96 | 0.92 |
| Q279H | 0.52 | 0.89 | 0.93 | 0.58 | 0.91 | *1.11* | 0.85 | 0.95 | 0.75 |
| Q279I | 0.39 | 0.76 | 0.99 | 0.37 | 0.86 | *1.25* | 0.87 | 0.97 | 0.83 |
| Q279K | 0.28 | 0.79 | 0.89 | 0.37 | 0.88 | *1.32* | 0.99 | *1.09* | 0.70 |
| Q279L | 0.77 | 0.74 | 0.99 | 0.65 | 0.78 | 0.79 | 0.67 | 0.72 | 0.60 |
| Q279M | 0.73 | 0.74 | 0.97 | 0.59 | 0.73 | 0.94 | 0.63 | 0.69 | 0.70 |
| Q279N | 0.27 | 0.41 | 0.95 | 0.20 | 0.58 | *1.08* | 0.55 | 0.66 | 0.51 |
| Q279P | 0.12 | 0.18 | 0.96 | 0.05 | 0.35 | 0.47 | 0.51 | 0.46 | 0.32 |
| Q279S | 0.56 | 0.85 | 0.94 | 0.56 | 0.82 | *1.20* | 0.86 | 0.92 | 0.83 |

TABLE 3-1-continued

Performance Index Data of BGL1 SEL Variants (3,153)

| | | | | | | | | |
|---|---|---|---|---|---|---|---|---|
| Q279T | 0.61 | 0.87 | 0.93 | 0.64 | 0.85 | *1.06* | 0.82 | 0.86 | 0.80 |
| Q279V | 0.49 | 0.90 | *1.00* | 0.58 | 0.95 | *1.20* | *1.01* | *1.01* | 0.83 |
| Q279Y | 0.45 | 0.90 | 0.98 | 0.55 | 0.95 | *1.10* | *1.06* | *1.09* | 0.86 |
| T282C | 0.92 | *1.08* | 0.99 | *1.14* | *1.04* | 0.95 | *1.05* | *1.14* | *1.15* |
| T282D | *1.09* | 0.94 | *1.01* | *1.04* | 0.82 | 0.96 | 0.92 | *1.02* | 0.99 |
| T282E | 0.72 | 0.96 | 0.97 | 0.84 | 0.92 | 0.81 | 0.87 | 0.94 | 0.92 |
| T282F | 0.79 | 0.99 | 0.91 | 0.75 | 0.83 | 0.84 | 0.85 | 0.93 | 0.79 |
| T282G | 0.99 | 0.99 | 0.98 | *1.05* | 0.97 | 0.97 | 0.87 | 0.97 | 0.87 |
| T282H | 0.10 | 0.13 | *1.33* | 0.05 | 0.05 | 0.05 | 0.05 | 0.05 | 0.65 |
| T282I | 0.87 | 0.83 | 0.97 | 0.82 | 0.81 | 0.84 | 0.79 | 0.84 | 0.73 |
| T282K | 0.91 | 0.86 | *1.03* | 0.97 | 0.87 | *1.02* | 0.83 | 0.93 | 0.79 |
| T282L | 0.61 | 0.94 | 0.92 | 0.78 | 0.87 | 0.88 | 0.84 | 0.93 | *1.03* |
| T282M | 0.75 | 1.00 | 0.93 | 0.85 | 0.89 | 0.92 | 0.90 | 0.99 | 0.96 |
| T282N | *1.19* | 0.96 | 0.97 | *1.19* | 0.86 | 0.94 | 0.82 | 0.87 | 0.79 |
| T282P | 0.58 | 0.91 | 0.98 | 0.78 | 0.94 | 0.84 | 0.94 | *1.08* | *1.03* |
| T282Q | 0.88 | 0.87 | 0.98 | 0.84 | 0.82 | 0.79 | 0.80 | 0.85 | 0.78 |
| T282R | *1.24* | 0.96 | 0.97 | *1.10* | 0.89 | 0.96 | 0.91 | 0.96 | 0.84 |
| T282S | 0.47 | 0.98 | 0.91 | 0.71 | 0.98 | 0.94 | 0.97 | *1.19* | 0.99 |
| T282T | 1.00 | 1.00 | 1.00 | 1.00 | 1.00 | 1.00 | 1.00 | 1.00 | 1.00 |
| T282V | *1.10* | 0.99 | 0.97 | *1.10* | 0.90 | 0.95 | 0.90 | 0.97 | 0.87 |
| T282Y | 0.70 | 0.82 | 0.97 | 0.74 | 0.85 | 0.87 | 0.89 | 0.93 | 0.85 |
| R284A | 0.19 | 0.13 | 0.68 | 0.05 | 0.35 | 0.64 | 0.14 | 0.92 | 0.52 |
| R284C | 0.39 | 0.16 | 0.05 | 0.05 | 0.26 | 0.20 | 0.14 | 0.51 | 0.30 |
| R284E | 0.31 | 0.15 | 0.05 | 0.08 | 0.27 | 0.16 | 0.11 | 0.57 | 0.76 |
| R284F | 0.35 | 0.13 | 0.05 | 0.05 | 0.23 | 0.21 | 0.11 | 0.49 | 0.28 |
| R284G | 0.04 | 0.04 | 0.04 | 0.04 | 0.04 | 0.04 | 0.04 | 0.04 | 0.04 |
| R284H | 0.14 | 0.15 | 0.05 | 0.06 | 0.53 | 0.36 | 0.23 | *1.18* | 0.74 |
| R284I | 0.36 | 0.15 | 0.05 | 0.08 | 0.23 | 0.20 | 0.10 | 0.50 | 0.50 |
| R284K | 0.04 | 0.04 | 0.04 | 0.04 | 0.04 | 0.04 | 0.04 | 0.04 | 0.04 |
| R284M | 0.10 | 0.20 | 0.05 | 0.12 | 0.83 | 0.73 | 0.45 | *1.84* | *1.02* |
| R284N | 0.36 | 0.12 | *1.00* | 0.05 | 0.29 | 0.22 | 0.17 | 0.54 | 0.41 |
| R284P | 0.29 | 0.14 | 0.92 | 0.05 | 0.26 | 0.15 | 0.10 | 0.54 | 0.43 |
| R284R | 1.00 | 1.00 | 1.00 | 1.00 | 1.00 | 1.00 | 1.00 | 1.00 | 1.00 |
| R284S | 0.24 | 0.14 | 0.05 | 0.15 | 0.29 | 0.15 | 0.11 | 0.68 | 0.59 |
| R284T | 0.36 | 0.19 | 0.89 | 0.14 | 0.33 | 0.27 | 0.20 | 0.59 | 0.86 |

TABLE 3-1-continued

Performance Index Data of BGL1 SEL Variants (3,153)

| | | | | | | | | | |
|---|---|---|---|---|---|---|---|---|---|
| R284V | 0.31 | 0.64 | 0.25 | 0.05 | 0.47 | 0.43 | 0.27 | 0.73 | 0.43 |
| R284W | 0.04 | 0.04 | 0.04 | 0.04 | 0.04 | 0.04 | 0.04 | 0.04 | 0.04 |
| R284Y | 0.04 | 0.04 | 0.04 | 0.04 | 0.04 | 0.04 | 0.04 | 0.04 | 0.04 |
| D287C | 0.96 | *1.17* | *1.15* | 0.76 | *1.05* | *1.15* | *1.18* | *1.18* | *1.12* |
| D287D | 1.00 | 1.00 | 1.00 | 1.00 | 1.00 | 1.00 | 1.00 | 1.00 | 1.00 |
| D287E | 0.72 | *1.07* | 0.94 | 0.61 | 0.99 | 0.99 | 0.99 | 0.98 | 0.91 |
| D287F | 0.31 | 0.29 | *1.33* | 0.07 | 0.33 | 0.41 | 0.27 | 0.19 | 0.66 |
| D287G | 0.71 | 0.98 | 0.92 | 0.60 | 0.97 | *1.16* | 0.96 | 0.94 | 0.93 |
| D287H | 0.22 | 0.78 | *1.32* | 0.36 | 0.85 | *1.08* | 0.80 | 0.74 | 0.73 |
| D287I | 0.31 | 0.63 | *1.54* | 0.18 | 0.62 | *1.03* | 0.61 | 0.57 | 0.55 |
| D287K | 0.35 | 0.92 | *1.13* | 0.21 | 0.94 | *1.25* | 0.93 | 0.94 | *1.04* |
| D287L | 0.28 | 0.47 | *1.26* | 0.31 | 0.48 | 0.59 | 0.44 | 0.37 | 0.47 |
| D287M | 0.30 | 0.85 | *1.15* | 0.22 | 0.83 | *1.15* | 0.83 | 0.82 | 0.63 |
| D287N | 0.65 | *1.04* | 0.89 | 0.62 | 0.91 | *1.13* | 0.92 | 0.93 | 0.90 |
| D287P | 0.14 | 0.05 | 0.05 | 0.08 | 0.39 | 0.44 | 0.28 | 0.17 | 0.27 |
| D287R | 0.34 | 0.20 | 0.05 | 0.05 | 0.23 | 0.33 | 0.16 | 0.14 | 0.47 |
| D287S | 0.46 | *1.09* | 0.91 | 0.52 | *1.00* | *1.35* | *1.06* | *1.03* | 0.97 |
| D287V | 0.36 | 0.56 | *1.16* | 0.12 | 0.66 | 0.80 | 0.59 | 0.54 | 0.93 |
| D287W | 0.23 | 0.52 | *1.56* | 0.08 | 0.61 | 0.75 | 0.52 | 0.47 | 0.62 |
| D287Y | 0.29 | 0.32 | *2.51* | 0.05 | 0.37 | 0.44 | 0.29 | 0.22 | 0.08 |
| R291A | 0.08 | 0.30 | 0.91 | 0.05 | 0.29 | 0.83 | 0.35 | 0.41 | 0.30 |
| R291C | 0.08 | 0.05 | 0.05 | 0.05 | 0.05 | 0.48 | 0.05 | 0.11 | 0.23 |
| R291D | 0.07 | 0.05 | 0.05 | 0.05 | 0.05 | 0.34 | 0.05 | 0.05 | 0.26 |
| R291E | 0.07 | 0.05 | 0.05 | 0.05 | 0.05 | 0.50 | 0.05 | 0.05 | 0.21 |
| R291G | 0.06 | 0.05 | 0.05 | 0.05 | 0.05 | 0.87 | 0.05 | 0.18 | 0.25 |
| R291H | 0.05 | 0.05 | 0.05 | 0.05 | 0.05 | 0.05 | 0.05 | 0.05 | 0.05 |
| R291I | 0.05 | 0.05 | 0.05 | 0.05 | 0.05 | 0.25 | 0.05 | 0.05 | 0.31 |
| R291K | 0.08 | 0.27 | 0.05 | 0.05 | 0.20 | 0.98 | 0.31 | 0.47 | 0.37 |
| R291L | 0.05 | 0.05 | 0.05 | 0.05 | 0.05 | 0.05 | 0.05 | 0.05 | 0.05 |
| R291M | 0.05 | 0.05 | 0.05 | 0.05 | 0.05 | 0.05 | 0.05 | 0.05 | 0.05 |
| R291N | 0.06 | 0.05 | 0.05 | 0.05 | 0.05 | 0.33 | 0.05 | 0.09 | 0.31 |
| R291Q | 0.06 | 0.05 | 0.05 | 0.05 | 0.05 | 0.32 | 0.05 | 0.09 | 0.29 |
| R291S | 0.07 | 0.31 | 0.98 | 0.05 | 0.28 | 0.75 | 0.28 | 0.39 | 0.22 |
| R291T | 0.05 | 0.05 | 0.05 | 0.05 | 0.05 | 0.40 | 0.05 | 0.18 | 0.43 |
| R291V | 0.05 | 0.05 | 0.05 | 0.05 | 0.05 | 0.05 | 0.05 | 0.05 | 0.05 |
| R291W | 0.06 | 0.05 | 0.05 | 0.05 | 0.05 | 0.68 | 0.05 | 0.05 | 0.09 |

TABLE 3-1-continued

Performance Index Data of BGL1 SEL Variants (3,153)

| | | | | | | | | | |
|---|---|---|---|---|---|---|---|---|---|
| R291Y | 0.06 | 0.05 | 0.05 | 0.05 | 0.05 | 0.32 | 0.05 | 0.13 | 0.22 |
| Q301A | 0.67 | *1.20* | 0.88 | 0.06 | 0.93 | *1.03* | 1.00 | 0.84 | 0.93 |
| Q301E | 0.42 | 0.84 | *1.09* | 0.30 | 0.89 | *1.02* | 0.91 | 0.76 | 0.78 |
| Q301F | 0.22 | 0.75 | 0.95 | 0.05 | 0.61 | 0.68 | 0.64 | 0.53 | 0.34 |
| Q301G | 0.12 | 0.99 | 0.97 | 0.05 | *1.01* | *1.22* | *1.25* | 0.85 | 0.47 |
| Q301H | 0.20 | 0.96 | 0.96 | 0.05 | 0.82 | 0.90 | 0.86 | 0.75 | 0.47 |
| Q301K | 0.08 | *1.08* | 0.91 | 0.08 | *1.14* | *1.32* | *1.33* | *1.13* | 0.48 |
| Q301L | 0.33 | *1.09* | *1.05* | 0.05 | *1.01* | 0.98 | 0.95 | 0.95 | 0.79 |
| Q301N | 0.22 | *1.22* | 0.95 | 0.14 | 0.98 | 0.98 | 0.98 | 0.98 | 0.60 |
| Q301Q | 1.00 | 1.00 | 1.00 | 1.00 | 1.00 | 1.00 | 1.00 | 1.00 | 1.00 |
| Q301R | 0.22 | *1.19* | 0.85 | 0.05 | 0.88 | *1.09* | 0.88 | 0.97 | 0.57 |
| Q301S | 0.35 | *1.12* | 0.96 | 0.05 | 0.87 | 0.76 | 0.90 | 0.88 | 0.78 |
| Q301T | 0.21 | *1.03* | *1.05* | 0.05 | 0.89 | 0.83 | 0.95 | 0.90 | 0.58 |
| Q301V | 0.26 | *1.12* | *1.02* | 0.05 | 0.84 | 0.85 | 0.88 | 0.95 | 0.77 |
| Q301Y | 0.24 | 0.95 | 0.94 | 0.05 | 0.78 | 0.67 | 0.86 | 0.90 | 0.59 |
| D302A | 0.38 | *1.06* | 0.93 | 0.55 | *1.15* | *1.48* | *1.17* | *1.26* | *1.20* |
| D302C | 0.23 | *1.01* | 0.99 | 0.36 | *1.34* | *1.66* | *1.36* | *1.49* | *1.32* |
| D302D | 1.00 | 1.00 | 1.00 | 1.00 | 1.00 | 1.00 | 1.00 | 1.00 | 1.00 |
| D302E | 0.35 | 0.83 | 0.89 | 0.51 | *1.03* | *1.30* | 0.97 | *1.08* | *1.05* |
| D302F | 0.33 | 0.88 | 0.81 | 0.48 | *1.03* | *1.33* | *1.01* | *1.15* | *1.41* |
| D302G | 0.39 | 0.98 | 0.86 | 0.49 | *1.09* | *1.35* | *1.12* | *1.28* | *1.22* |
| D302I | 0.05 | 0.05 | 0.05 | 0.05 | 0.05 | 0.05 | 0.05 | 0.05 | 0.05 |
| D302K | 0.29 | 0.74 | 0.94 | 0.38 | *1.20* | *1.19* | 0.88 | 0.98 | 0.93 |
| D302L | 0.29 | 0.72 | 0.91 | 0.09 | 0.90 | 0.86 | 0.83 | *1.11* | 0.81 |
| D302M | 0.27 | 0.77 | 0.90 | 0.27 | *1.02* | *1.26* | 0.95 | *1.03* | 0.79 |
| D302N | 0.51 | 0.87 | 0.86 | 0.71 | 0.93 | *1.05* | 0.94 | *1.01* | 0.65 |
| D302P | 0.24 | 0.75 | 0.88 | 0.31 | 1.00 | *1.05* | 0.85 | 0.95 | 0.67 |
| D302S | 0.48 | 0.94 | 0.86 | 0.68 | 0.96 | *1.18* | 0.93 | 0.99 | 0.87 |
| D302T | 0.41 | 0.83 | 0.93 | 0.39 | *1.03* | *1.02* | 0.90 | 0.93 | 0.64 |
| D302V | 0.23 | 0.30 | 0.82 | 0.19 | 0.55 | 0.84 | 0.34 | 0.29 | 0.16 |
| D302W | 0.59 | *1.02* | 0.99 | 0.58 | 0.87 | *1.02* | 0.85 | 0.92 | 0.85 |
| D302Y | 0.50 | 0.93 | 0.85 | 0.48 | 0.97 | *1.37* | 0.83 | 0.94 | 0.83 |
| Q303A | *1.02* | *1.08* | 0.85 | *1.40* | *1.01* | 0.92 | *1.01* | 0.82 | 0.90 |
| Q303C | 0.56 | *1.28* | 0.91 | 0.95 | *1.31* | *1.09* | *1.51* | *1.10* | *1.28* |
| Q303D | 0.95 | 0.98 | 0.93 | *1.22* | 0.98 | *1.01* | *1.07* | 0.86 | 0.97 |

TABLE 3-1-continued

Performance Index Data of BGL1 SEL Variants (3,153)

| | | | | | | | | | |
|---|---|---|---|---|---|---|---|---|---|
| Q303E | *1.06* | *1.04* | 0.96 | *1.37* | 0.98 | 0.91 | 0.94 | 0.79 | 0.89 |
| Q303F | 0.88 | 0.91 | 0.91 | *1.19* | 0.92 | 0.95 | 0.86 | 0.71 | 0.85 |
| Q303G | 0.80 | 0.99 | 0.92 | *1.10* | 0.98 | 0.90 | 0.95 | 0.80 | 0.84 |
| Q303H | 0.74 | *1.06* | 0.94 | 0.93 | 0.98 | 0.92 | 0.99 | 0.85 | 0.86 |
| Q303I | 0.82 | *1.06* | 0.96 | *1.36* | 0.95 | 0.89 | 0.95 | 0.86 | 0.83 |
| Q303K | 0.74 | *1.09* | 0.88 | *1.31* | *1.04* | 0.93 | 0.99 | 0.88 | 0.94 |
| Q303L | 0.79 | *1.11* | 0.90 | *1.41* | 0.98 | 0.90 | 0.92 | 0.88 | 0.93 |
| Q303M | 0.87 | *1.03* | 0.91 | *1.34* | *1.01* | 0.95 | 0.87 | 0.80 | 0.87 |
| Q303N | *1.23* | *1.05* | 0.97 | *1.88* | 0.99 | 0.89 | 0.81 | 0.88 | 0.84 |
| Q303P | 0.37 | 0.97 | 0.85 | 0.66 | *1.05* | 0.85 | *1.00* | 0.87 | 0.91 |
| Q303Q | 1.00 | 1.00 | 1.00 | 1.00 | 1.00 | 1.00 | 1.00 | 1.00 | 1.00 |
| Q303R | 0.94 | *1.05* | 0.91 | *1.31* | 0.91 | *1.01* | 0.93 | 0.86 | 0.80 |
| Q303S | 0.92 | *1.07* | 0.91 | *1.43* | 0.93 | 0.92 | 0.90 | 0.90 | 0.80 |
| Q303T | 0.87 | *1.02* | 0.94 | *1.51* | 0.94 | 0.98 | 0.90 | 0.88 | 0.91 |
| Q303V | 0.85 | *1.11* | 0.91 | *1.17* | 0.86 | 0.84 | 0.95 | 0.94 | 0.86 |
| Q303W | 0.71 | 0.95 | 0.92 | 0.85 | 0.94 | *1.04* | 0.99 | 0.89 | 0.81 |
| Q303Y | 0.69 | *1.04* | 0.90 | *1.22* | 0.94 | 0.88 | 0.94 | 0.92 | 0.93 |
| Y306A | *1.28* | 0.84 | 0.88 | 0.44 | 0.81 | 0.83 | 0.77 | 0.77 | 0.86 |
| Y306C | 0.65 | *1.01* | *1.76* | 0.24 | 0.89 | 0.87 | 0.85 | 0.89 | 1.05 |
| Y306D | 0.11 | 0.05 | 0.05 | 0.05 | 0.36 | 0.44 | 0.30 | 0.22 | 0.81 |
| Y306E | *1.06* | 0.96 | 0.84 | 0.35 | 0.85 | 0.79 | 0.84 | 0.86 | 0.93 |
| Y306F | *1.03* | 0.95 | 0.90 | *1.05* | 0.92 | 0.79 | 0.86 | 0.88 | 0.91 |
| Y306G | 0.85 | *1.13* | 0.83 | 0.62 | *1.05* | 0.93 | 0.94 | 0.94 | *1.00* |
| Y306I | 1.00 | *1.08* | 0.87 | *1.02* | 0.88 | 0.97 | 0.84 | 0.86 | 0.90 |
| Y306K | 0.44 | *1.38* | 0.99 | 0.12 | *1.12* | 0.99 | *1.05* | *1.13* | 0.94 |
| Y306L | *1.19* | *1.12* | 0.89 | *1.21* | 0.92 | 0.83 | 0.94 | 0.94 | 0.78 |
| Y306M | 0.61 | *1.23* | 0.78 | 0.78 | *1.08* | *1.04* | 0.98 | *1.08* | 1.05 |
| Y306N | 0.57 | *1.20* | 0.86 | 0.48 | 0.98 | 0.94 | 0.93 | 0.92 | 1.00 |
| Y306P | 0.85 | *1.05* | 0.79 | 0.56 | 0.87 | 0.86 | 0.86 | 0.87 | 0.84 |
| Y306Q | 0.17 | *1.64* | 0.87 | 0.24 | *1.52* | 0.10 | *1.36* | *1.39* | *1.28* |
| Y306R | 0.44 | *1.44* | 0.05 | *1.03* | *1.19* | *1.39* | *1.20* | *1.20* | 0.98 |
| Y306S | 0.89 | *1.01* | 0.88 | 0.39 | 0.88 | 0.91 | 0.84 | 0.87 | 0.84 |
| Y306T | 0.79 | *1.03* | 0.81 | 0.52 | 0.86 | 0.91 | 0.83 | 0.85 | 0.94 |
| Y306V | 0.42 | *1.28* | 0.83 | 0.90 | *1.19* | *1.04* | 0.95 | 0.98 | *1.17* |
| Y306W | *1.33* | 0.95 | 0.92 | *1.40* | 0.88 | 0.89 | 0.84 | 0.87 | 0.88 |

TABLE 3-1-continued

Performance Index Data of BGL1 SEL Variants (3,153)

| | | | | | | | | | |
|---|---|---|---|---|---|---|---|---|---|
| Y306Y | 1.00 | 1.00 | 1.00 | 1.00 | 1.00 | 1.00 | 1.00 | 1.00 | 1.00 |
| S312A | *1.09* | 0.87 | *1.03* | 0.90 | 0.92 | 1.00 | 0.84 | 0.87 | 0.68 |
| S312C | 0.97 | *1.31* | *1.16* | *1.04* | *1.24* | *1.26* | *1.38* | *1.35* | *1.50* |
| S312D | *1.22* | 0.89 | *1.08* | 0.88 | *1.05* | *1.10* | 0.99 | 0.67 | *1.02* |
| S312F | 0.04 | 0.04 | 0.04 | 0.04 | 0.04 | 0.04 | 0.04 | 0.04 | 0.04 |
| S312G | *1.02* | 0.89 | *1.08* | 0.84 | 0.96 | *1.06* | 0.91 | 0.88 | 0.89 |
| S312I | *1.02* | 0.87 | *1.01* | 0.56 | 0.88 | 0.92 | 0.85 | 0.87 | 0.71 |
| S312K | 0.77 | 1.00 | *1.08* | 0.73 | 0.98 | 0.94 | 0.97 | *1.00* | 0.75 |
| S312L | 0.73 | 0.88 | *1.03* | 0.56 | 0.76 | 0.81 | 0.82 | 0.83 | 0.55 |
| S312M | 0.64 | 0.98 | *1.02* | 0.60 | 0.88 | 0.97 | 0.90 | 0.93 | 0.69 |
| S312N | *1.53* | 0.85 | *1.02* | *1.33* | 0.93 | *1.04* | 0.88 | 0.71 | 0.70 |
| S312P | 0.26 | 0.85 | 0.87 | 0.05 | 0.51 | 0.15 | 0.67 | 0.97 | 0.20 |
| S312Q | 0.94 | 0.96 | *1.11* | 0.90 | 0.92 | *1.03* | 0.96 | 0.99 | 0.67 |
| S312R | *1.04* | 0.81 | *1.04* | 0.68 | 0.85 | *1.08* | 0.83 | 0.91 | 0.70 |
| S312S | 1.00 | 1.00 | 1.00 | 1.00 | 1.00 | 1.00 | 1.00 | 1.00 | 1.00 |
| S312T | 0.86 | *1.08* | 0.98 | 0.94 | 0.92 | *1.02* | 0.96 | 0.97 | 0.72 |
| S312V | 0.85 | *1.07* | 0.99 | 0.68 | 0.98 | *1.19* | 0.97 | 0.99 | 0.86 |
| S312W | 0.13 | *6.54* | *1.02* | 0.88 | *3.60* | 0.06 | *5.39* | *5.54* | *2.47* |
| S312Y | 0.51 | *1.57* | *1.09* | 0.78 | *1.22* | *1.29* | *1.41* | *1.46* | *1.21* |
| R313A | 0.78 | 0.86 | 0.95 | 0.47 | 0.92 | *1.01* | 0.88 | 0.76 | 0.93 |
| R313C | 0.67 | 0.83 | 0.97 | 0.35 | 0.92 | *1.05* | 0.97 | 0.78 | 0.91 |
| R313D | *1.01* | 0.94 | 0.97 | 0.05 | 0.91 | *1.06* | 0.89 | 0.78 | 0.90 |
| R313E | *1.05* | 0.95 | *1.00* | 0.46 | 0.88 | 0.85 | 0.69 | 0.71 | 0.83 |
| R313F | 0.51 | 0.68 | 0.99 | 0.26 | 0.80 | 0.93 | 0.75 | 0.66 | 0.71 |
| R313G | 0.83 | 0.92 | *1.00* | 0.52 | 0.86 | *1.00* | 0.84 | 0.73 | 0.79 |
| R313H | 0.93 | 0.90 | 0.91 | 0.73 | 0.84 | 0.88 | 0.82 | 0.72 | 0.76 |
| R313I | 0.85 | 0.84 | 0.98 | 0.62 | 0.84 | 0.99 | 0.80 | 0.67 | 0.69 |
| R313K | 0.67 | 0.88 | 0.92 | 0.75 | 0.95 | *1.01* | 0.95 | 0.82 | 0.75 |
| R313L | 0.97 | 0.98 | *1.00* | 0.83 | 0.86 | 0.97 | 0.77 | 0.74 | 0.78 |
| R313M | 0.89 | 0.87 | 0.99 | 0.63 | 0.85 | 0.89 | 0.75 | 0.70 | 0.68 |
| R313N | 0.84 | 0.86 | 0.97 | 0.57 | 0.83 | *1.08* | 0.78 | 0.71 | 0.70 |
| R313P | 0.23 | 0.49 | 0.87 | 0.05 | 0.76 | 0.42 | 0.80 | 0.72 | 0.55 |
| R313R | 1.00 | 1.00 | 1.00 | 1.00 | 1.00 | 1.00 | 1.00 | 1.00 | 1.00 |
| R313S | 1.00 | 0.89 | *1.04* | 0.54 | 0.83 | 0.93 | 0.73 | 0.77 | 0.72 |
| R313V | 0.63 | 0.80 | *1.02* | 0.50 | 0.85 | 0.88 | 0.81 | 0.82 | 0.75 |
| R313W | 0.70 | 0.83 | *1.01* | 0.34 | 0.86 | 0.92 | 0.85 | 0.83 | 0.73 |

TABLE 3-1-continued

Performance Index Data of BGL1 SEL Variants (3,153)

| | | | | | | | | | |
|---|---|---|---|---|---|---|---|---|---|
| Q316A | *1.47* | 0.97 | *1.14* | 0.58 | 0.86 | 0.99 | 0.94 | 0.99 | 0.92 |
| Q316C | 0.89 | *1.01* | *1.06* | 0.33 | 0.95 | 0.97 | *1.03* | *1.15* | *1.04* |
| Q316D | *1.03* | 0.93 | *1.02* | 0.27 | 0.88 | 0.86 | 0.95 | *1.01* | 0.98 |
| Q316E | 0.87 | 0.93 | *1.05* | 0.75 | 0.89 | 0.92 | 0.88 | 0.89 | 0.79 |
| Q316F | *1.05* | 0.91 | *1.04* | 0.24 | 0.91 | 0.93 | 0.87 | 0.95 | 0.90 |
| Q316G | 0.66 | 0.78 | *1.06* | 0.24 | 0.92 | 0.99 | 0.71 | *1.04* | 0.82 |
| Q316H | 0.27 | 0.42 | *1.08* | 0.06 | 0.90 | 0.88 | 0.82 | *1.28* | 0.69 |
| Q316I | 0.74 | 0.91 | *1.01* | 0.05 | 0.95 | 0.91 | 0.92 | *1.05* | 0.92 |
| Q316K | 0.53 | 0.81 | *1.02* | 0.20 | *1.05* | *1.14* | 0.99 | *1.20* | 0.93 |
| Q316L | 0.84 | 0.92 | 0.97 | 0.15 | 0.87 | *1.03* | 0.77 | 0.83 | 0.79 |
| Q316M | 0.23 | 0.42 | 0.89 | 0.25 | 0.97 | *1.14* | 0.76 | 0.97 | 0.63 |
| Q316N | 0.49 | 0.66 | *1.07* | 0.06 | 0.92 | 0.94 | 0.80 | 0.95 | 0.73 |
| Q316P | 0.47 | *1.09* | *1.01* | 0.05 | *1.18* | 0.78 | *1.14* | *1.41* | *1.07* |
| Q316Q | 1.00 | 1.00 | 1.00 | 1.00 | 1.00 | 1.00 | 1.00 | 1.00 | 1.00 |
| Q316R | 0.37 | 0.61 | *1.04* | 0.16 | *1.03* | *1.02* | 0.90 | *1.05* | 0.79 |
| Q316S | 0.38 | 0.82 | *1.01* | 0.13 | *1.17* | 0.85 | *1.09* | *1.39* | *1.01* |
| Q316T | 0.50 | *1.26* | *1.01* | 0.52 | *1.40* | *1.58* | *1.54* | *1.54* | *1.31* |
| Q316V | 0.72 | 0.94 | *1.04* | 0.20 | 0.97 | 0.92 | 0.92 | 0.92 | 0.89 |
| Q316W | 0.46 | 0.54 | *1.06* | 0.14 | 0.84 | 0.91 | 0.68 | 0.85 | 0.62 |
| Q316Y | 0.78 | 1.00 | *1.09* | 0.14 | *1.01* | *1.12* | *1.11* | *1.11* | *1.05* |
| K320A | *1.68* | 0.73 | 0.97 | 0.77 | 0.77 | 0.89 | 0.82 | 0.70 | 0.69 |
| K320C | 0.86 | *1.27* | 1.00 | *1.35* | *1.23* | *1.21* | *1.41* | *1.66* | *1.23* |
| K320E | 0.94 | 0.93 | *1.02* | 0.30 | 0.81 | 0.91 | 0.96 | *1.21* | 0.95 |
| K320G | 0.98 | 0.82 | *1.05* | 0.80 | 0.84 | *1.05* | 0.87 | 0.78 | 0.93 |
| K320H | *1.55* | 0.80 | 0.98 | *1.48* | 0.78 | 0.93 | 0.87 | *1.29* | 0.66 |
| K320K | 1.00 | 1.00 | 1.00 | 1.00 | 1.00 | 1.00 | 1.00 | 1.00 | 1.00 |
| K320L | 0.52 | 0.74 | 0.99 | 0.40 | 0.57 | 0.86 | 0.66 | *1.88* | 0.77 |
| K320M | 0.87 | 0.84 | *1.02* | 0.80 | 0.75 | 0.98 | 0.79 | *1.31* | 0.91 |
| K320N | *1.62* | 0.95 | *1.05* | *1.78* | 0.84 | *1.06* | *1.01* | 0.89 | *1.02* |
| K320P | 0.82 | 0.93 | 0.94 | 0.65 | 0.84 | *1.02* | 0.90 | *1.90* | 0.87 |
| K320Q | 1.00 | 0.77 | 0.93 | 0.80 | 0.73 | 0.95 | 0.77 | *1.84* | 0.63 |
| K320R | 0.98 | 0.86 | 0.92 | 0.49 | 0.78 | 0.99 | 0.90 | *2.99* | 0.80 |
| K320S | *1.30* | 0.98 | 0.97 | *1.57* | 0.90 | *1.01* | *1.06* | *1.78* | 0.78 |
| K320T | 0.81 | 0.92 | *1.01* | 0.60 | 0.89 | 0.91 | *1.04* | *1.89* | 0.90 |
| K320V | 0.04 | 0.04 | 0.04 | 0.04 | 0.04 | 0.04 | 0.04 | 0.04 | 0.04 |

TABLE 3-1-continued

Performance Index Data of BGL1 SEL Variants (3,153)

| | | | | | | | | | |
|---|---|---|---|---|---|---|---|---|---|
| K320W | 0.85 | 0.88 | 0.95 | 0.71 | 0.59 | 0.79 | 0.92 | 0.64 | 0.90 |
| K320Y | *1.34* | 0.88 | 0.97 | *1.65* | 0.82 | *1.09* | *1.21* | 0.94 | 0.91 |
| R324C | 0.65 | 0.94 | *1.09* | 0.57 | 0.98 | *1.26* | *1.09* | *1.13* | *1.10* |
| R324D | 0.61 | 0.80 | *1.00* | 0.26 | 0.90 | *1.13* | 0.94 | 0.98 | 0.90 |
| R324E | 0.56 | 0.96 | 0.95 | 0.63 | 0.87 | *1.12* | 0.95 | 0.98 | 0.77 |
| R324F | 0.68 | 0.94 | 0.93 | 0.68 | 0.89 | *1.19* | 0.94 | 0.96 | 0.90 |
| R324H | 0.56 | 0.87 | 0.97 | 0.60 | 0.84 | *1.19* | 0.87 | 0.92 | 0.89 |
| R324I | 0.26 | 0.49 | 0.92 | 0.21 | 0.72 | *1.33* | 0.85 | 0.78 | 0.64 |
| R324K | 0.38 | 0.68 | 0.99 | 0.40 | 0.75 | *1.23* | 0.95 | 0.94 | 0.81 |
| R324L | 0.57 | 0.87 | 0.92 | 0.57 | 0.83 | *1.18* | 0.88 | 0.89 | 0.77 |
| R324M | 0.55 | 0.88 | 0.95 | 0.54 | 0.87 | *1.06* | 0.96 | 0.98 | 0.83 |
| R324N | 0.25 | 0.05 | 0.05 | 0.05 | 0.17 | 0.13 | 0.05 | 0.05 | 0.15 |
| R324P | 0.07 | 0.05 | 0.05 | 0.05 | 0.05 | 0.11 | 0.08 | 0.09 | 0.36 |
| R324Q | 0.46 | 0.77 | 0.91 | 0.41 | 0.79 | *1.06* | 0.91 | 0.90 | 0.75 |
| R324S | 0.14 | 0.05 | 0.05 | 0.05 | 0.05 | 0.16 | 0.05 | 0.06 | 0.11 |
| R324V | 0.28 | 0.53 | 0.92 | 0.22 | 0.73 | *1.25* | 0.89 | 0.89 | 0.63 |
| R324W | 0.36 | 0.67 | 0.97 | 0.35 | 0.76 | *1.37* | 0.91 | 0.92 | 0.79 |
| R324Y | 0.77 | 0.98 | 0.99 | 0.84 | 0.95 | *1.05* | *1.03* | *1.04* | 0.93 |
| R328C | 0.39 | *1.00* | *1.13* | 0.36 | 0.97 | *1.05* | 0.94 | *1.09* | 0.54 |
| R328D | 0.14 | 0.05 | 0.05 | 0.05 | 0.08 | 0.06 | 0.05 | 0.49 | 0.05 |
| R328E | 0.35 | *1.12* | *1.01* | 0.44 | 0.89 | 0.82 | 0.93 | *1.05* | 0.67 |
| R328F | 0.06 | 0.05 | 0.05 | 0.05 | 0.09 | 0.53 | 0.05 | *1.10* | 0.15 |
| R328G | 0.36 | *1.11* | 1.00 | 0.45 | 0.90 | 0.97 | 0.89 | *1.16* | 0.42 |
| R328I | 0.14 | 0.62 | *1.04* | 0.05 | 0.48 | 0.59 | 0.54 | *1.03* | 0.05 |
| R328K | 0.50 | *1.09* | 0.94 | 0.51 | 0.85 | *1.17* | 0.96 | *1.04* | 0.70 |
| R328L | 0.13 | *1.12* | *1.03* | 0.13 | 0.70 | 0.73 | 0.89 | *1.40* | 0.32 |
| R328M | 0.13 | *1.33* | 0.99 | 0.16 | 0.86 | 0.75 | *1.14* | *1.60* | 0.40 |
| R328N | 0.23 | 0.89 | 0.88 | 0.12 | 0.52 | 0.77 | 0.73 | 0.99 | 0.32 |
| R328P | 0.05 | 0.05 | 0.05 | 0.05 | 0.05 | 0.05 | 0.05 | 0.05 | 0.05 |
| R328Q | 0.39 | *1.06* | *1.04* | 0.43 | 0.82 | 0.99 | 0.97 | *1.07* | 0.57 |
| R328R | 1.00 | 1.00 | 1.00 | 1.00 | 1.00 | 1.00 | 1.00 | 1.00 | 1.00 |
| R328S | 0.12 | *4.02* | 0.97 | 0.05 | *2.59* | *1.67* | *3.38* | *3.43* | *1.34* |
| R328T | 0.83 | *1.06* | 0.94 | 0.91 | 0.93 | 0.88 | 0.98 | 0.97 | 0.79 |
| R328V | 0.41 | *1.13* | 0.91 | 0.30 | 0.99 | 0.97 | 0.99 | *1.09* | 0.61 |
| R328W | 0.12 | 0.05 | 0.05 | 0.05 | 0.06 | 0.21 | 0.05 | 0.51 | 0.39 |

TABLE 3-1-continued

Performance Index Data of BGL1 SEL Variants (3,153)

| | | | | | | | | | |
|---|---|---|---|---|---|---|---|---|---|
| R328Y | 0.06 | 0.05 | 0.05 | 0.05 | 0.20 | 0.44 | 0.09 | *2.09* | 0.16 |
| D329A | 0.93 | *1.24* | *1.00* | *1.34* | *1.05* | *1.08* | *1.10* | *1.00* | *1.16* |
| D329D | 1.00 | 1.00 | 1.00 | 1.00 | 1.00 | 1.00 | 1.00 | 1.00 | 1.00 |
| D329E | 0.69 | *1.17* | 0.97 | 0.91 | 0.94 | 0.85 | 0.92 | 0.91 | 0.72 |
| D329F | 0.12 | 0.60 | *1.18* | 0.18 | 0.40 | 0.44 | 0.37 | 0.85 | 0.53 |
| D329G | 0.67 | *1.20* | 0.99 | 0.80 | 0.94 | 0.98 | *1.00* | 0.94 | 0.73 |
| D329H | 0.24 | *1.18* | 0.95 | 0.26 | 0.77 | *1.05* | 0.93 | 0.97 | 0.41 |
| D329I | 0.07 | 0.05 | 0.05 | 0.05 | 0.05 | 0.05 | 0.05 | 0.73 | 0.05 |
| D329K | 0.09 | 0.48 | 0.05 | 0.05 | 0.22 | 0.28 | 0.27 | 0.90 | 0.34 |
| D329L | 0.05 | 0.05 | 0.05 | 0.05 | 0.05 | 0.05 | 0.05 | 0.05 | 0.05 |
| D329M | 0.21 | *1.32* | 1.00 | 0.29 | 0.69 | 0.87 | 0.92 | *1.13* | 0.38 |
| D329N | 0.60 | *1.34* | 0.95 | 0.85 | 0.77 | 0.89 | *1.04* | 0.99 | 0.72 |
| D329P | 0.05 | 0.05 | 0.05 | 0.05 | 0.05 | 0.05 | 0.05 | 0.05 | 0.05 |
| D329Q | 0.45 | *1.17* | *1.00* | 0.59 | 0.74 | 0.98 | 0.93 | 0.95 | 0.62 |
| D329R | 0.05 | 0.05 | 0.05 | 0.05 | 0.05 | 0.05 | 0.05 | 0.05 | 0.05 |
| D329S | 0.66 | *1.39* | 0.96 | 0.97 | 0.97 | *1.07* | *1.01* | *1.00* | *1.02* |
| D329T | 0.15 | *1.26* | *1.00* | 0.24 | 0.85 | 0.94 | 0.90 | *1.31* | 0.46 |
| D329V | 0.05 | 0.05 | 0.05 | 0.05 | 0.05 | 0.05 | 0.05 | 0.05 | 0.05 |
| D329W | 0.05 | 0.05 | 0.05 | 0.05 | 0.05 | 0.05 | 0.05 | 0.05 | 0.05 |
| D329Y | 0.22 | 0.95 | *1.03* | 0.20 | 0.76 | 1.00 | 0.72 | *1.06* | 0.39 |
| L334A | 0.12 | 0.33 | 0.90 | 0.19 | *1.22* | *1.84* | *1.32* | *1.14* | 0.70 |
| L334C | 0.49 | 0.67 | 0.97 | 0.47 | 0.99 | *1.40* | *1.04* | 0.89 | 0.89 |
| L334E | 0.09 | 0.07 | 0.05 | 0.05 | 0.05 | 0.10 | 0.05 | 0.05 | 0.14 |
| L334F | 0.13 | 0.31 | 0.87 | 0.15 | 0.93 | *1.37* | *1.06* | 0.95 | 0.97 |
| L334G | 0.04 | 0.04 | 0.04 | 0.04 | 0.04 | 0.04 | 0.04 | 0.04 | 0.04 |
| L334H | 0.05 | 0.05 | 0.05 | 0.05 | 0.05 | 0.05 | 0.05 | 0.05 | 0.05 |
| L334I | 0.20 | 0.38 | 0.98 | 0.23 | 0.91 | 0.99 | 0.98 | 0.89 | 0.44 |
| L334K | 0.09 | 0.06 | 0.05 | 0.08 | 0.07 | 0.43 | 0.05 | 0.05 | 0.16 |
| L334L | 1.00 | 1.00 | 1.00 | 1.00 | 1.00 | 1.00 | 1.00 | 1.00 | 1.00 |
| L334M | 0.44 | 0.72 | *1.00* | 0.53 | 0.93 | *1.20* | *1.04* | 0.95 | 0.66 |
| L334N | 0.12 | 0.08 | 0.05 | 0.09 | 0.05 | 0.18 | 0.06 | 0.06 | 0.10 |
| L334P | 0.10 | 0.13 | 0.05 | 0.11 | 0.17 | 0.37 | 0.24 | 0.31 | 0.22 |
| L334R | 0.04 | 0.04 | 0.04 | 0.04 | 0.04 | 0.04 | 0.04 | 0.04 | 0.04 |
| L334S | 0.11 | 0.07 | 0.05 | 0.10 | 0.12 | 0.31 | 0.14 | 0.15 | 0.07 |
| L334T | 0.16 | 0.35 | 0.93 | 0.24 | 0.96 | *1.28* | *1.09* | *1.08* | 0.70 |
| L334V | 0.53 | 0.70 | *1.04* | 0.67 | *1.01* | *1.11* | *1.08* | 0.98 | 0.88 |

TABLE 3-1-continued

Performance Index Data of BGL1 SEL Variants (3,153)

| | | | | | | | | |
|---|---|---|---|---|---|---|---|---|
| L334W | 0.90 | 0.92 | 0.93 | 0.84 | 0.86 | *1.04* | 0.94 | 0.96 | 0.86 |
| L334Y | 0.14 | 0.09 | 0.05 | 0.09 | 0.15 | 0.28 | 0.15 | 0.16 | 0.18 |
| K335A | 0.99 | *1.05* | *1.00* | *1.59* | *1.01* | *1.10* | 0.88 | 0.19 | 0.98 |
| K335D | 0.47 | *1.38* | 0.98 | 0.77 | *1.09* | *1.06* | *1.03* | 0.49 | *1.05* |
| K335F | 0.59 | *1.26* | 1.00 | 0.87 | 0.99 | 1.00 | 0.94 | 0.63 | 0.83 |
| K335G | 0.12 | 0.75 | *1.16* | 0.15 | 0.56 | 0.62 | 0.47 | 0.94 | 0.37 |
| K335H | 0.77 | *1.16* | 0.98 | 1.00 | *1.03* | *1.20* | 0.96 | 0.83 | 0.80 |
| K335I | 0.41 | *1.15* | 0.95 | 0.54 | 0.87 | 0.91 | 0.85 | 0.89 | 0.79 |
| K335K | 1.00 | 1.00 | 1.00 | 1.00 | 1.00 | 1.00 | 1.00 | 1.00 | 1.00 |
| K335L | *1.03* | *1.09* | 0.95 | *1.44* | 0.95 | *1.06* | 0.89 | 0.80 | 0.89 |
| K335M | 0.68 | *1.28* | 0.93 | 0.91 | 0.99 | 0.91 | 0.92 | 0.89 | 0.84 |
| K335N | 0.20 | *1.25* | 0.90 | 0.31 | 0.79 | 0.87 | 0.85 | *1.07* | 0.59 |
| K335P | 0.04 | 0.04 | 0.04 | 0.04 | 0.04 | 0.04 | 0.04 | 0.04 | 0.04 |
| K335R | 0.73 | *1.30* | 0.98 | *1.09* | 0.96 | *1.03* | *1.00* | 0.96 | 0.87 |
| K335S | *1.03* | *1.00* | *1.01* | *1.10* | 0.93 | *1.12* | 0.86 | 0.81 | 0.88 |
| K335T | *1.14* | *1.14* | *1.04* | *1.60* | 0.97 | 0.88 | 0.94 | 0.87 | 0.85 |
| K335V | 0.50 | *1.53* | *1.00* | 0.87 | *1.08* | *1.10* | *1.07* | *1.07* | 0.90 |
| K335W | 0.69 | *1.30* | *1.02* | *1.02* | *1.04* | *1.16* | *1.05* | 0.82 | 0.96 |
| N336A | 0.48 | 0.72 | 0.99 | 0.64 | *1.04* | *1.11* | 0.95 | 0.77 | *1.12* |
| N336C | 0.71 | 0.85 | 0.97 | 0.79 | 0.95 | *1.04* | 0.94 | 0.77 | *1.02* |
| N336F | 0.14 | 0.16 | 0.83 | 0.15 | 0.42 | 0.64 | 0.42 | 0.33 | 0.51 |
| N336G | 0.21 | 0.47 | 0.94 | 0.36 | *1.03* | *1.21* | 0.95 | 0.79 | 0.66 |
| N336H | 0.46 | 0.74 | 1.00 | 0.59 | 0.95 | *1.19* | 0.93 | 0.77 | *1.01* |
| N336I | 0.04 | 0.04 | 0.04 | 0.04 | 0.04 | 0.04 | 0.04 | 0.04 | 0.04 |
| N336K | 0.12 | 0.17 | 0.76 | 0.11 | 0.40 | 0.81 | 0.45 | 0.34 | 0.41 |
| N336L | 0.24 | 0.51 | 0.97 | 0.31 | 0.94 | *1.25* | 0.94 | 0.79 | 0.82 |
| N336M | 0.30 | 0.55 | 0.98 | 0.45 | 0.92 | *1.21* | 0.69 | 0.76 | 0.78 |
| N336N | 1.00 | 1.00 | 1.00 | 1.00 | 1.00 | 1.00 | 1.00 | 1.00 | 1.00 |
| N336P | 0.13 | 0.07 | 0.05 | 0.05 | 0.06 | 0.07 | 0.05 | 0.05 | 0.33 |
| N336Q | 0.21 | 0.43 | 0.96 | 0.30 | 0.89 | *1.14* | 0.93 | 0.82 | 0.77 |
| N336R | 0.10 | 0.30 | 0.86 | 0.19 | 0.97 | *1.45* | *1.03* | 0.92 | 0.40 |
| N336S | 0.56 | 0.72 | *1.04* | 0.59 | 0.93 | 0.90 | 0.86 | 0.78 | 0.88 |
| N336T | 0.27 | 0.51 | *1.00* | 0.37 | 0.90 | 1.17 | 0.90 | 0.82 | 0.74 |
| N336V | 0.12 | 0.32 | 0.97 | 0.17 | 0.96 | 1.22 | 0.92 | 0.92 | 0.63 |
| N336W | 0.04 | 0.04 | 0.04 | 0.04 | 0.04 | 0.04 | 0.04 | 0.04 | 0.04 |

TABLE 3-1-continued

Performance Index Data of BGL1 SEL Variants (3,153)

| | | | | | | | | | |
|---|---|---|---|---|---|---|---|---|---|
| N336Y | 0.32 | 0.55 | *1.00* | 0.42 | 0.91 | *1.09* | 0.87 | 0.81 | 0.84 |
| D337A | 0.83 | *1.08* | *1.03* | 0.90 | 0.53 | *1.07* | 0.91 | *1.01* | *1.13* |
| D337C | 0.71 | *1.17* | *1.03* | 0.87 | *2.28* | 0.83 | 0.97 | *1.11* | *1.18* |
| D337E | 0.57 | *1.07* | 0.97 | 0.66 | 0.21 | 0.52 | 0.93 | 0.93 | 0.90 |
| D337F | 0.48 | 0.99 | 0.98 | 0.51 | 0.05 | 0.46 | 0.83 | 0.89 | 0.94 |
| D337G | 0.92 | *1.16* | 0.95 | 0.93 | 0.91 | 0.97 | 0.93 | 0.98 | 0.81 |
| D337H | 0.36 | *1.09* | 0.96 | 0.45 | 0.57 | 0.37 | 0.92 | 0.93 | 0.98 |
| D337K | 0.53 | *1.09* | 0.95 | 0.54 | *1.08* | 0.56 | 0.81 | 0.88 | *1.07* |
| D337L | 0.35 | *1.07* | 0.89 | 0.40 | 0.30 | 0.33 | 0.87 | 0.94 | 0.93 |
| D337M | 0.37 | *1.10* | 0.99 | 0.47 | 0.61 | 0.38 | 0.96 | 0.92 | *1.03* |
| D337N | 0.68 | *1.14* | 0.95 | 0.75 | 0.84 | 0.66 | 0.94 | 0.98 | 0.97 |
| D337P | 0.24 | 0.67 | 0.96 | 0.20 | 0.53 | 0.15 | 0.53 | 0.65 | 0.66 |
| D337Q | 0.56 | 0.99 | 0.99 | 0.62 | 0.44 | 0.66 | 0.88 | 0.86 | 0.94 |
| D337R | 0.57 | *1.02* | 0.96 | 0.67 | 0.89 | 0.61 | 0.87 | 0.97 | 0.97 |
| D337S | 0.56 | *1.04* | 0.99 | 0.65 | 0.05 | 0.59 | 0.92 | 0.88 | 0.81 |
| D337T | 0.46 | *1.34* | 1.00 | 0.67 | 0.77 | 0.45 | *1.18* | *1.21* | *1.15* |
| D337V | 0.84 | *1.13* | 0.93 | 0.84 | 0.40 | 0.95 | *1.01* | *1.03* | 0.98 |
| D337W | 0.42 | 0.96 | *1.02* | 0.46 | *1.39* | 0.42 | 0.91 | 0.90 | 0.90 |
| D337Y | 0.54 | *1.03* | 0.96 | 0.56 | 0.57 | 0.46 | 0.88 | 0.88 | 0.97 |
| A338A | 1.00 | 1.00 | 1.00 | 1.00 | 1.00 | 1.00 | 1.00 | 1.00 | 1.00 |
| A338C | 0.92 | *1.21* | 0.97 | *1.09* | *1.03* | *1.07* | *1.19* | *1.24* | *1.55* |
| A338D | *1.71* | 0.93 | 1.00 | *1.69* | 0.95 | *1.24* | *1.03* | *1.03* | *1.18* |
| A338E | *1.05* | 0.97 | 0.98 | 0.95 | 0.83 | *1.18* | 0.94 | 0.96 | *1.27* |
| A338F | 0.81 | *1.00* | *1.04* | 0.85 | 0.87 | *1.14* | 0.95 | *1.02* | *1.05* |
| A338G | *1.04* | *1.07* | 1.00 | *1.25* | 0.95 | *1.12* | *1.03* | *1.05* | *1.24* |
| A338H | 0.69 | *1.02* | 0.99 | 0.65 | 0.84 | *1.23* | 0.90 | 0.97 | 0.92 |
| A338I | 0.89 | *1.17* | 0.99 | *1.03* | 0.92 | *1.22* | *1.06* | *1.10* | 0.98 |
| A338K | 0.84 | 0.96 | 0.99 | 0.86 | 0.81 | *1.27* | 0.90 | 0.94 | *1.06* |
| A338L | 0.85 | *1.11* | 0.96 | 0.91 | 0.87 | *1.07* | 1.00 | 1.00 | *1.12* |
| A338M | 0.88 | *1.11* | 0.91 | 0.74 | 0.84 | 0.94 | 0.97 | 1.00 | *1.11* |
| A338N | *1.04* | *1.06* | 0.93 | *1.06* | 0.81 | *1.14* | 0.91 | 0.93 | 0.97 |
| A338P | 0.56 | *1.16* | *1.01* | 0.57 | 0.91 | *1.29* | 0.98 | *1.01* | *1.03* |
| A338Q | 0.81 | 0.96 | *1.03* | 0.73 | 0.87 | *1.08* | 0.92 | 0.95 | 0.92 |
| A338R | *1.09* | *1.00* | 1.00 | 0.95 | 0.86 | *1.08* | 0.93 | 0.95 | 0.98 |
| A338S | 0.04 | 0.04 | 0.04 | 0.04 | 0.04 | 0.04 | 0.04 | 0.04 | 0.04 |

TABLE 3-1-continued

Performance Index Data of BGL1 SEL Variants (3,153)

| | | | | | | | | | |
|---|---|---|---|---|---|---|---|---|---|
| A338T | 0.04 | 0.04 | 0.04 | 0.04 | 0.04 | 0.04 | 0.04 | 0.04 | 0.04 |
| A338V | 0.86 | *1.12* | *1.03* | *1.16* | 0.98 | *1.27* | *1.07* | *1.12* | *1.07* |
| A338W | 0.66 | *1.90* | *1.00* | *1.01* | *1.20* | *1.29* | *1.62* | *1.63* | *1.61* |
| A338Y | 0.96 | 0.92 | *1.04* | 0.79 | 0.84 | *1.08* | 0.89 | 0.92 | *1.04* |
| N339A | 0.31 | 0.63 | 0.97 | 0.32 | 0.75 | 0.92 | 0.73 | 0.63 | 0.76 |
| N339C | 0.26 | 0.67 | 0.98 | 0.27 | 0.86 | 0.65 | 0.85 | 0.82 | 0.90 |
| N339D | 0.22 | 0.59 | *1.09* | 0.22 | 0.78 | 0.71 | 0.75 | 0.66 | 0.66 |
| N339E | 0.16 | 0.72 | 0.95 | 0.25 | *2.34* | 0.91 | *1.03* | 0.90 | 0.89 |
| N339F | 0.05 | 0.05 | 0.05 | 0.05 | 0.05 | 0.05 | 0.05 | 0.05 | 0.05 |
| N339G | 0.15 | 0.48 | 1.00 | 0.15 | *1.62* | 0.67 | 0.67 | 0.52 | 0.63 |
| N339H | 0.21 | 0.56 | 0.99 | 0.24 | *1.20* | 0.83 | 0.70 | 0.64 | 0.67 |
| N339I | 0.16 | 0.36 | *1.14* | 0.15 | 0.91 | 0.41 | 0.49 | 0.45 | 0.68 |
| N339K | 0.14 | 0.42 | 0.05 | 0.16 | *1.13* | 0.68 | 0.66 | 0.45 | 0.14 |
| N339L | 0.23 | 0.52 | *1.21* | 0.23 | *1.04* | 0.66 | 0.60 | 0.59 | 0.72 |
| N339N | 1.00 | 1.00 | 1.00 | 1.00 | 1.00 | 1.00 | 1.00 | 1.00 | 1.00 |
| N339P | 0.20 | 0.38 | *1.25* | 0.13 | 0.53 | 0.58 | 0.51 | 0.41 | 0.39 |
| N339Q | 0.14 | 0.39 | *1.13* | 0.14 | 0.64 | 0.56 | 0.56 | 0.50 | 0.42 |
| N339R | 0.18 | 0.46 | *1.88* | 0.16 | 0.65 | 0.81 | 0.64 | 0.46 | 0.75 |
| N339S | 0.26 | 0.65 | 0.89 | 0.25 | 0.80 | 0.73 | 0.71 | 0.68 | 0.63 |
| N339T | 0.20 | 0.48 | 0.95 | 0.19 | 0.71 | 0.67 | 0.64 | 0.56 | 0.49 |
| N339V | 0.19 | 0.41 | *1.40* | 0.14 | 0.57 | 0.53 | 0.58 | 0.43 | 0.61 |
| N339W | 0.29 | 0.46 | 0.97 | 0.18 | 0.58 | 0.62 | 0.48 | 0.44 | 0.73 |
| N339Y | 0.21 | 0.59 | *1.01* | 0.22 | 0.75 | 0.68 | 0.71 | 0.65 | 0.58 |
| K344D | 0.85 | *1.04* | *1.02* | 0.88 | *1.03* | *1.09* | *1.05* | *1.01* | *1.07* |
| K344E | 0.58 | *1.09* | 0.94 | 0.75 | 0.99 | 0.98 | 0.99 | 0.86 | 0.98 |
| K344F | 0.51 | *1.12* | 1.00 | 0 65 | *1.09* | *1.14* | *1.07* | *1.01* | *1.11* |
| K344G | 0.60 | *1.04* | 0.93 | 0.68 | 0.95 | 1.00 | 0.94 | 0.87 | *1.08* |
| K344I | 0.42 | *1.09* | 0.93 | 0.59 | *1.05* | 0.97 | *1.04* | *1.03* | 0.95 |
| K344K | 1.00 | 1.00 | 1.00 | 1.00 | 1.00 | 1.00 | 1.00 | 1.00 | 1.00 |
| K344L | 0.47 | *1.21* | 0.92 | 0.76 | *1.04* | *1.12* | *1.01* | 0.89 | *1.08* |
| K344M | 0.52 | *1.20* | 0.98 | 0.78 | *1.06* | *1.04* | 0.99 | 0.98 | 0.80 |
| K344N | 0.56 | *1.11* | 0.93 | 0.74 | 0.95 | *1.01* | 0.95 | 0.91 | 0.84 |
| K344P | 0.26 | 0.93 | 0.94 | 0.36 | *1.07* | *1.29* | *1.06* | 0.89 | 0.78 |
| K344Q | 0.37 | 0.97 | 0.93 | 0.51 | 0.98 | 0.95 | *1.00* | 0.92 | *1.01* |
| K344R | 0.69 | *1.06* | 0.94 | 0.79 | 0.97 | 0.99 | 0.92 | 0.94 | *1.02* |
| K344S | 0.80 | *1.27* | 0.95 | *1.21* | *1.05* | 1.00 | 0.99 | 0.98 | 0.98 |

TABLE 3-1-continued

Performance Index Data of BGL1 SEL Variants (3,153)

| | | | | | | | | |
|---|---|---|---|---|---|---|---|---|
| K344T | 0.45 | *1.09* | 0.98 | 0.67 | *1.03* | *1.17* | 0.98 | 0.95 | 0.81 |
| K344V | 0.48 | *1.32* | 0.96 | 0.72 | *1.08* | *1.06* | *1.13* | *1.01* | *1.06* |
| K344W | 0.05 | 0.05 | 0.05 | 0.05 | 0.05 | 0.05 | 0.05 | 0.05 | 0.05 |
| K345A | 0.94 | *1.03* | *1.06* | 0.96 | *1.02* | *1.01* | *1.07* | *1.07* | *1.15* |
| K345D | 0.51 | 0.86 | *1.09* | 0.49 | *1.01* | *1.20* | *1.09* | 0.94 | 0.95 |
| K345E | 0.43 | *1.38* | *1.01* | 0.80 | *1.30* | *1.21* | *1.44* | *1.34* | *1.26* |
| K345F | 0.12 | *2.99* | 0.99 | 0.89 | *3.98* | *3.64* | *5.33* | *5.28* | *2.82* |
| K345G | 0.23 | 0.91 | *1.03* | 0.33 | *1.18* | *1.41* | *1.26* | *1.12* | 0.76 |
| K345H | 0.68 | *1.06* | *1.02* | 0.76 | 0.99 | *1.13* | *1.06* | 0.94 | 0.94 |
| K345I | 0.05 | 0.05 | 0.05 | 0.05 | 0.05 | 0.05 | 0.05 | 0.05 | 0.05 |
| K345K | 1.00 | 1.00 | 1.00 | 1.00 | 1.00 | 1.00 | 1.00 | 1.00 | 1.00 |
| K345L | 0.05 | 0.05 | 0.05 | 0.05 | 0.05 | 0.05 | 0.05 | 0.05 | 0.05 |
| K345M | 0.05 | 0.05 | 0.05 | 0.05 | 0.05 | 0.05 | 0.05 | 0.05 | 0.05 |
| K345N | 0.25 | 0.78 | 0.99 | 0.34 | 0.94 | *1.28* | 0.92 | 0.80 | 0.41 |
| K345P | 0.48 | *1.00* | 0.98 | 0.62 | 0.98 | *1.16* | 1.00 | 0.91 | 0.93 |
| K345Q | 0.66 | *1.01* | *1.01* | 0.81 | 0.98 | 0.93 | 1.00 | *1.01* | 0.73 |
| K345R | 0.70 | *1.01* | 0.96 | 0.72 | 0.95 | *1.27* | 0.78 | 0.97 | 0.98 |
| K345S | 0.41 | *1.10* | 0.89 | 0.58 | *1.02* | *1.22* | *1.03* | *1.08* | *1.09* |
| K345T | 0.51 | *1.11* | 0.91 | 0.71 | 0.99 | 0.97 | *1.05* | *1.01* | 0.98 |
| K345V | 0.37 | *1.04* | 0.94 | 0.54 | *1.08* | *1.42* | *1.13* | *1.15* | 0.91 |
| K345W | 0.44 | 0.93 | 0.99 | 0.44 | 0.97 | *1.21* | 0.99 | *1.01* | 0.94 |
| K345Y | 0.11 | *1.98* | *1.02* | 0.58 | *3.27* | *3.12* | *3.91* | *4.23* | *1.59* |
| A347D | 1.00 | *1.03* | *1.05* | *1.11* | 0.96 | *1.04* | *1.01* | 0.96 | 0.98 |
| A347F | 0.99 | *1.10* | *1.03* | *1.12* | 0.96 | *1.05* | 0.97 | 0.92 | 0.96 |
| A347H | 0.81 | 0.94 | 0.99 | 0.85 | 0.91 | *1.14* | 0.92 | 0.84 | 0.95 |
| A347I | 0.66 | 0.93 | *1.04* | 0.74 | 0.92 | *1.09* | 0.95 | 0.90 | 0.79 |
| A347K | 0.68 | 0.88 | *1.07* | 0.77 | 0.91 | *1.09* | 0.97 | 0.88 | 0.81 |
| A347L | 0.61 | 0.91 | *1.10* | 0.76 | 0.99 | *1.14* | 0.93 | 0.93 | 0.94 |
| A347M | 0.77 | 0.98 | *1.10* | 0.94 | 0.98 | *1.03* | 0.95 | 0.87 | 0.84 |
| A347P | 0.72 | *1.02* | *1.02* | 0.96 | 0.99 | *1.10* | 0.99 | 0.86 | 0.96 |
| A347Q | 0.61 | 0.88 | *1.08* | 0.09 | 0.97 | *1.09* | 0.93 | 0.86 | 0.75 |
| A347R | 0.73 | 0.99 | *1.00* | 0.98 | 0.96 | *1.18* | 0.96 | 0.92 | 0.73 |
| A347S | 0.65 | 0.94 | *1.03* | 0.73 | *1.00* | *1.10* | 0.94 | 0.87 | 0.84 |
| A347T | 0.21 | 0.40 | 0.91 | 0.13 | 0.60 | 0.83 | 0.24 | 0.37 | 0.50 |
| A347V | 0.20 | 0.05 | 0.05 | 0.05 | 0.32 | 0.34 | 0.10 | 0.16 | 0.60 |

TABLE 3-1-continued

Performance Index Data of BGL1 SEL Variants (3,153)

| | | | | | | | | | |
|---|---|---|---|---|---|---|---|---|---|
| A347Y | *1.17* | *1.34* | *1.07* | *1.64* | *1.07* | *1.10* | *1.14* | *1.07* | *1.10* |
| H361A | 0.89 | 0.92 | *1.02* | 0.05 | *1.01* | *1.08* | *1.05* | 0.99 | 0.97 |
| H361C | 0.83 | 0.93 | *1.01* | 0.05 | *1.02* | 0.45 | *1.08* | *1.03* | 0.93 |
| H361D | 0.94 | 0.88 | 1.00 | 0.05 | 0.96 | 0.61 | 0.90 | 0.74 | *1.01* |
| H361E | 0.56 | 0.88 | *1.03* | 0.05 | 0.89 | 0.73 | *1.01* | 0.77 | 0.78 |
| H361F | 0.04 | 0.04 | 0.04 | 0.04 | 0.04 | 0.04 | 0.04 | 0.04 | 0.04 |
| H361G | 0.92 | *1.11* | *1.06* | 0.05 | *1.10* | *1.14* | *1.15* | *1.20* | *1.08* |
| H361H | 1.00 | 1.00 | 1.00 | 1.00 | 1.00 | 1.00 | 1.00 | 1.00 | 1.00 |
| H361I | 0.15 | 0.12 | 0.92 | 0.05 | 0.05 | 0.12 | 0.13 | 0.05 | 0.21 |
| H361K | 0.16 | 0.47 | *1.03* | 0.05 | 0.15 | 0.32 | 0.89 | 0.15 | 0.39 |
| H361L | 0.17 | 0 63 | *1.00* | 0.05 | 0.77 | 0.07 | *1.21* | 0.73 | 0.48 |
| H361M | 0.40 | 0.82 | *1.04* | 0.05 | 0.95 | 0.18 | *1.11* | *1.01* | 0.68 |
| H361N | 0.98 | 0.95 | 0.97 | 0.05 | 0.92 | 1.03 | 0.99 | 0.99 | 0.92 |
| H361P | 0.43 | 0.66 | *1.09* | 0.05 | 0.83 | 0.25 | 0.97 | 0.85 | 0.58 |
| H361R | 0.11 | 0.42 | 0.97 | 0.05 | 0.21 | 0.41 | 0.95 | 0.22 | 0.36 |
| H361S | 0.93 | 0.84 | *1.12* | 0.05 | 0.89 | 0.95 | 0.94 | 0.96 | 0.82 |
| H361T | 0.28 | 0.76 | 0.95 | 0.05 | 0.72 | 0.17 | *1.02* | 0.73 | 0.40 |
| H361V | 0.18 | 0.11 | 0.05 | 0.05 | 0.05 | 0.20 | 0.11 | 0.05 | 0.19 |
| H361Y | 0.19 | 0.13 | *1.06* | 0.05 | 0.05 | 0.15 | 0.19 | 0.05 | 0.07 |
| R363A | *1.22* | 0.92 | *1.10* | 0.62 | 0.99 | 0.96 | 0.99 | 0.99 | *1.11* |
| R363C | 0.45 | *1.06* | *1.01* | 0.16 | *1.19* | *1.31* | *1.22* | *1.25* | *1.29* |
| R363E | 0.38 | 0.90 | *1.06* | 0.86 | 0.92 | 0.05 | *1.03* | *1.04* | *1.08* |
| R363F | 0.04 | 0.04 | 0.04 | 0.04 | 0.04 | 0.04 | 0.04 | 0.04 | 0.04 |
| R363G | *1.19* | 0.97 | *1.05* | 0.05 | *1.03* | 0.93 | 0.97 | *1.01* | *1.19* |
| R363K | *1.05* | *1.06* | *1.01* | 0.80 | *1.05* | *1.02* | *1.11* | *1.09* | *1.14* |
| R363L | 0.81 | *1.00* | *1.03* | *1.06* | 0.99 | 0.91 | *1.03* | 0.98 | 0.80 |
| R363M | *1.10* | 0.98 | 0.98 | 0.98 | 0.96 | *1.03* | *1.03* | 0.98 | *1.16* |
| R363N | 0.22 | 0.51 | *1.06* | 0.10 | 0.60 | 0.93 | 0.41 | 0.72 | 0.45 |
| R363P | 0.05 | 0.05 | 0.05 | 0.05 | 0.05 | 0.05 | 0.05 | 0.05 | 0.05 |
| R363Q | 0.80 | *1.01* | *1.01* | 0.28 | *1.01* | *1.24* | *1.05* | *1.09* | *1.02* |
| R363R | 1.00 | 1.00 | 1.00 | 1.00 | 1.00 | 1.00 | 1.00 | 1.00 | 1.00 |
| R363S | 0.21 | 0.81 | *1.08* | 0.06 | *1.02* | *1.01* | 0.83 | *1.19* | 0.78 |
| R363T | 0.68 | *1.01* | *1.06* | 0.30 | 1.00 | *1.02* | 0.83 | *1.07* | *1.07* |
| R363V | *1.75* | 0.77 | *1.15* | 0.09 | 0.97 | *1.06* | 0.91 | 0.93 | *1.15* |
| R363W | 0.14 | *1.62* | *1.04* | 0.05 | *2.22* | *1.97* | *2.66* | *3.18* | *1.37* |

TABLE 3-1-continued

Performance Index Data of BGL1 SEL Variants (3,153)

| | | | | | | | | |
|---|---|---|---|---|---|---|---|---|
| R363Y | 0.13 | *2.65* | 0.93 | 0.05 | *3.32* | 0.10 | *4.39* | *4.92* | *1.47* |
| N369A | 0.11 | 0.38 | *1.10* | 0.24 | 0.62 | 0.80 | 0.30 | 0.72 | 0.27 |
| N369C | 0.30 | *1.88* | *1.05* | *1.09* | *1.77* | *1.28* | *2.22* | *2.09* | *1.45* |
| N369D | 0.96 | *1.06* | *1.08* | 0.32 | *1.08* | *1.20* | *1.11* | *1.08* | *1.00* |
| N369E | 0.74 | *1.31* | *1.05* | *1.83* | *1.11* | 0.86 | *1.20* | *1.07* | *1.06* |
| N369F | 0.50 | *1.33* | 0.98 | *1.33* | *1.09* | 0.74 | *1.16* | *1.10* | 0.95 |
| N369I | 0.46 | 0.90 | *1.33* | *1.03* | 0.85 | 0.69 | 0.83 | 0.76 | 0.54 |
| N369K | 0.05 | 0.05 | 0.05 | 0.05 | 0.05 | 0.05 | 0.05 | 0.05 | 0.05 |
| N369L | 0.63 | *1.15* | *1.08* | *1.54* | 0.91 | 0.84 | 0.97 | 0.94 | 0.77 |
| N369M | 0.70 | *1.28* | *1.01* | *1.87* | 0.97 | 0.85 | *1.14* | 0.96 | 0.84 |
| N369N | 1.00 | 1.00 | 1.00 | 1.00 | 1.00 | 1.00 | 1.00 | 1.00 | 1.00 |
| N369R | 0.94 | 0.88 | *1.06* | *1.56* | 0.76 | 0.80 | 0.82 | 0.69 | 0.72 |
| N369S | 0.47 | *1.20* | 0.96 | 0.93 | 0.97 | *1.07* | *1.15* | 0.93 | 0.94 |
| N369T | 0.76 | *1.14* | *1.12* | *1.44* | 0.94 | 0.96 | *1.12* | 0.93 | *1.08* |
| N369V | 0.91 | *1.12* | *1.05* | *1.95* | 0.89 | 0.68 | *1.01* | 0.91 | 0.83 |
| N369W | 0.26 | *2.12* | *1.01* | *1.38* | *1.82* | 0.98 | *2.22* | *2.13* | *1.08* |
| N369Y | 0.34 | *1.54* | *1.06* | *1.21* | *1.34* | 0.96 | *1.48* | *1.51* | 0.91 |
| D370D | 1.00 | 1.00 | 1.00 | 1.00 | 1.00 | 1.00 | 1.00 | 1.00 | 1.00 |
| D370E | *1.14* | *1.07* | *1.08* | 0.05 | 0.41 | 0.43 | 0.47 | 0.50 | 0.70 |
| D370F | 0.72 | *1.48* | *1.11* | 0.05 | 0.42 | 0.17 | 0.57 | 0.37 | 0.66 |
| D370G | 0.54 | *1.05* | 0.87 | 0.05 | 0.59 | 0.31 | 0.64 | 0.52 | 0.80 |
| D370I | 0.39 | 0.81 | 0.82 | 0.05 | 0.05 | 0.05 | 0.11 | 0.07 | 0.38 |
| D370K | 0.59 | 0.28 | 0.57 | 0.05 | 0.05 | 0.08 | 0.05 | 0.05 | 0.27 |
| D370L | 0.58 | 0.64 | 0.84 | 0.05 | 0.05 | 0.09 | 0.05 | 0.05 | 0.46 |
| D370M | 0.66 | 0.77 | 0.92 | 0.05 | 0.14 | 0.17 | 0.25 | 0.11 | 0.43 |
| D370N | 0.99 | 0.99 | 0.83 | 0.05 | 0.30 | 0.43 | 0.40 | 0.27 | 0.48 |
| D370P | 0.18 | 0.38 | 0.98 | 0.05 | 0.05 | 0.18 | 0.13 | 0.05 | 0.55 |
| D370Q | *1.08* | 0.78 | 0.78 | 0.05 | 0.23 | 0.37 | 0.32 | 0.21 | 0.48 |
| D370R | 0.36 | 0.19 | 0.64 | 0.05 | 0.05 | 0.09 | 0.05 | 0.05 | 0.21 |
| D370S | 0.75 | *1.08* | 0.82 | 0.05 | 0.49 | 0.55 | 0.56 | 0.45 | 0.70 |
| D370T | 0.36 | 0.94 | 0.83 | 0.05 | 0.13 | 0.06 | 0.29 | 0.13 | 0.66 |
| D370V | 0.62 | 0.99 | 0.85 | 0.05 | 0.12 | 0.05 | 0.20 | 0.12 | 0.42 |
| D370W | 0.75 | *1.14* | *1.45* | 0.05 | 0.25 | 0.07 | 0.32 | 0.21 | 0.52 |
| D370Y | 0.75 | *1.05* | *1.00* | 0.05 | 0.33 | 0.18 | 0.43 | 0.33 | 0.57 |
| K371A | *1.13* | *1.01* | *1.08* | 0.05 | *1.04* | 0.94 | 0.93 | 0.95 | *1.17* |
| K371C | 0.47 | 0.92 | 0.97 | 0.05 | 0.90 | 0.94 | 0.89 | 0.93 | 0.98 |

TABLE 3-1-continued

Performance Index Data of BGL1 SEL Variants (3,153)

| | | | | | | | | | |
|---|---|---|---|---|---|---|---|---|---|
| K371D | 0.94 | 0.95 | *1.08* | 0.05 | 0.85 | 0.73 | 0.89 | 0.85 | 0.86 |
| K371F | 0.38 | *1.07* | *1.04* | 0.05 | 0.75 | 0.05 | 0.82 | 0.80 | 0.87 |
| K371G | 0.65 | *1.04* | *1.08* | 0.05 | *1.01* | *1.05* | 0.67 | 0.86 | 0.92 |
| K371H | *1.06* | 0.97 | 0.95 | 0.30 | 0.85 | 0.86 | 0.85 | 0.77 | 1.00 |
| K371K | 1.00 | 1.00 | 1.00 | 1.00 | 1.00 | 1.00 | 1.00 | 1.00 | 1.00 |
| K371L | 0.88 | *1.13* | *1.08* | 0.05 | *1.04* | 0.90 | 0.95 | 0.88 | *1.14* |
| K371N | 0.41 | *1.06* | 0.91 | 0.05 | 0.81 | 0.56 | 0.84 | 0.73 | 0.98 |
| K371P | 0.37 | 0.84 | 0.72 | 0.05 | 0.14 | 0.07 | 0.21 | 0.10 | 0.36 |
| K371Q | 0.49 | *1.03* | 0.98 | 0.05 | 0.78 | 0.46 | 0.81 | 0.76 | 0.60 |
| K371R | 0.58 | *1.18* | 0.85 | 0.05 | 0.89 | 0.87 | 0.98 | 0.88 | 0.85 |
| K371S | 0.72 | *1.15* | *1.06* | 0.05 | 0.97 | 0.48 | 0.92 | 0.89 | 0.98 |
| K371T | 0.19 | *1.86* | *1.03* | 0.05 | *1.37* | 0.10 | *1.74* | *1.58* | *1.57* |
| K371V | 0.27 | *1.03* | 0.94 | 0.05 | 0.74 | 0.12 | 0.78 | 0.79 | 0.61 |
| K371W | 0.25 | 0.62 | *1.04* | 0.05 | 0.36 | 0.08 | 0.42 | 0.15 | 0.47 |
| K371Y | 0.32 | 0.58 | 0.98 | 0.05 | 0.27 | 0.06 | 0.31 | 0.16 | 0.32 |
| G372A | 0.65 | *1.44* | *1.10* | *1.19* | *1.21* | *1.19* | *1.47* | *1.24* | *1.21* |
| G372C | 0.51 | *1.03* | *1.05* | 0.11 | 0.98 | 0.98 | *1.08* | 0.89 | 0.77 |
| G372D | 0.66 | 0.97 | *1.08* | 0.05 | 0.93 | 0.94 | *1.07* | 0.92 | 0.86 |
| G372E | 0.59 | *1.10* | 0.91 | 0.05 | 0.70 | 0.48 | 0.86 | 0.79 | 0.73 |
| G372F | 0.14 | 0.69 | 0.61 | 0.05 | 0.42 | 0.05 | 0.74 | 0.48 | 0.38 |
| G372G | 1.00 | 1.00 | 1.00 | 1.00 | 1.00 | 1.00 | 1.00 | 1.00 | 1.00 |
| G372H | 0.20 | 0.88 | 0.68 | 0.05 | 0.55 | 0.12 | 0.94 | 0.73 | 0.48 |
| G372I | 0.10 | 0.14 | 0.05 | 0.06 | 0.05 | 0.28 | 0.05 | 0.05 | 0.26 |
| G372K | 0.09 | 0.67 | 0.96 | 0.07 | *1.03* | 0.65 | *1.66* | *1.47* | 0.73 |
| G372L | 0.14 | *1.00* | 0.75 | 0.05 | 0.39 | 0.08 | 0.63 | 0.52 | 0.43 |
| G372M | 0.28 | *1.14* | 0.85 | 0.05 | 0.63 | 0.41 | *1.13* | *1.06* | 0.73 |
| G372N | 0.35 | 0.96 | *1.04* | 0.12 | 0.61 | 0.53 | *1.02* | 0.98 | 0.71 |
| G372Q | 0.39 | 0.90 | 0.99 | 0.06 | 0.62 | 0.71 | 0.98 | 0.96 | 0.73 |
| G372R | 0.42 | 0.93 | 0.95 | 0.05 | 0.53 | 0.54 | 0.84 | 0.76 | 0.66 |
| G372S | 0.41 | 0.81 | *1.05* | 0.05 | 0.73 | 0.95 | 0.87 | 0.78 | 0.71 |
| G372T | 0.46 | *1.31* | 0.82 | 0.05 | 0.54 | 0.54 | 0.93 | 0.77 | 0.74 |
| G372V | 0.18 | *1.19* | 0.74 | 0.11 | 0.54 | 0.12 | *1.22* | 0.96 | 0.57 |
| G372W | 0.06 | 0.74 | 0.84 | 0.05 | *1.35* | 0.33 | *2.02* | *1.73* | 0.57 |
| G372Y | 0.17 | 0.97 | 0.74 | 0.05 | 0.84 | 0.20 | *1.23* | *1.10* | 0.54 |
| D374A | *1.14* | 0.76 | *1.08* | 0.05 | 0.89 | 0.82 | 0.82 | 0.74 | 0.79 |

TABLE 3-1-continued

Performance Index Data of BGL1 SEL Variants (3,153)

| | | | | | | | | | |
|---|---|---|---|---|---|---|---|---|---|
| D374C | 0.70 | *1.28* | 0.97 | 0.15 | *1.10* | *1.13* | *1.13* | *1.20* | *1.03* |
| D374F | 0.16 | *1.11* | 0.95 | 0.09 | 0.90 | *1.09* | *1.21* | *1.19* | 0.78 |
| D374G | 0.21 | *1.23* | 0.93 | 0.05 | 0.98 | 0.35 | *1.22* | *1.33* | 0.93 |
| D374I | 0.08 | 0.81 | *1.10* | 0.05 | 0.98 | 0.76 | 0.96 | *1.52* | 0.62 |
| D374K | 0.05 | 0.05 | 0.05 | 0.05 | 0.05 | 0.05 | 0.05 | 0.05 | 0.05 |
| D374L | 0.32 | *1.37* | 0.90 | 0.05 | *1.12* | 0.80 | *1.36* | *1.37* | *1.09* |
| D374M | 0.19 | *1.37* | 0.93 | 0.05 | *1.16* | 0.28 | *1.20* | *1.62* | *1.03* |
| D374N | 0.59 | *1.11* | 0.90 | 0.90 | 0.86 | *1.05* | 0.83 | 0.93 | 0.84 |
| D374P | 0.11 | 0.05 | 0.05 | 0.05 | 0.05 | 0.45 | 0.05 | 0.05 | 0.13 |
| D374Q | 0.20 | *1.16* | 0.92 | 0.05 | *1.03* | 0.44 | *1.41* | *1.48* | 0.68 |
| D374R | 0.06 | 0.36 | *1.02* | 0.05 | 0.09 | 0.78 | 0.21 | 0.37 | 0.43 |
| D374S | 0.50 | *1.24* | 0.93 | 0.05 | *1.03* | *1.11* | *1.04* | *1.20* | *1.02* |
| D374T | 0.21 | 0.88 | 0.92 | 0.05 | 0.76 | 0.24 | 0.82 | *1.00* | 0.65 |
| D374V | 0.21 | *1.03* | 0.93 | 0.05 | *1.21* | 0.56 | *1.11* | *1.30* | 0.78 |
| D374W | 0.07 | 0.39 | *1.05* | 0.05 | 0.31 | 0.59 | 0.36 | 0.67 | 0.44 |
| D374Y | 0.26 | 0.98 | 0.93 | 0.22 | 0.75 | 0.90 | 0.99 | *1.00* | 0.61 |
| D375A | 0.78 | *1.02* | 0.87 | 0.05 | 0.98 | 0.90 | 0.98 | 0.88 | 0.95 |
| D375C | 0.66 | *1.11* | 0.89 | 0.05 | *1.11* | 0.99 | *1.21* | *1.32* | *1.04* |
| D375D | 1.00 | 1.00 | 1.00 | 1.00 | 1.00 | 1.00 | 1.00 | 1.00 | 1.00 |
| D375E | 0.65 | *1.16* | 0.98 | 0.05 | *1.09* | 0.99 | *1.22* | *1.14* | 0.89 |
| D375F | 0.56 | 0.85 | 0.89 | 0.05 | 0.91 | 0.55 | 0.92 | 0.90 | 0.81 |
| D375G | 0.54 | 0.85 | 0.93 | 0.05 | 0.91 | 0.61 | 0.93 | 0.96 | 0.85 |
| D375H | 0.56 | 0.89 | 0.88 | 0.05 | 0.93 | 0.86 | 0.95 | *1.00* | 0.87 |
| D375I | 0.73 | *1.01* | 0.95 | 0.05 | 0.90 | 0.82 | 0.93 | *1.05* | 0.85 |
| D375K | 0.47 | 0.81 | 0.87 | 0.05 | 0.89 | 0.68 | 0.91 | 0.98 | 0.85 |
| D375L | 0.54 | 0.89 | 0.93 | 0.05 | 0.92 | 0.74 | 0.87 | 0.93 | 0.76 |
| D375M | 0.57 | 0.89 | 0.93 | 0.05 | 0.89 | 0.77 | 0.92 | 0.97 | 0.76 |
| D375N | 0.65 | 0.94 | 0.93 | 0.05 | 0.92 | 0.79 | 0.92 | 0.92 | 0.85 |
| D375P | 0.09 | 0.24 | 0.86 | 0.05 | 0.07 | 0.26 | 0.05 | 0.26 | 0.35 |
| D375Q | 0.31 | 0.62 | 0.90 | 0.05 | 0.88 | 0.96 | 0.86 | 0.91 | 0.56 |
| D375R | 0.45 | 0.80 | 0.85 | 0.05 | 0.88 | 0.76 | 0.85 | *1.13* | 0.76 |
| D375S | 0.58 | 0.90 | 0.91 | 0.05 | 0.88 | 0.92 | 0.86 | 0.90 | 0.69 |
| D375T | 0.55 | 0.91 | 0.96 | 0.05 | 0.96 | 0.80 | 0.95 | 0.97 | 0.80 |
| D375V | 0.60 | *1.07* | 0.92 | 0.05 | 0.97 | 0.68 | *1.03* | *1.06* | 0.83 |
| D375W | 0.41 | 0.93 | 0.91 | 0.05 | *1.08* | 0.66 | *1.09* | *1.20* | 0.96 |

TABLE 3-1-continued

Performance Index Data of BGL1 SEL Variants (3,153)

| D375Y | 0.62 | 0.90 | 0.88 | 0.05 | 0.89 | 0.56 | 0.87 | 0.93 | 0.73 |
|---|---|---|---|---|---|---|---|---|---|
| M380A | 0.18 | 0.05 | 0.05 | 0.05 | 0.05 | 0.07 | 0.05 | 0.05 | 0.09 |
| M380E | 0.79 | 0.98 | *1.17* | 0.05 | 0.89 | 0.84 | 0.95 | 0.85 | 0.84 |
| M380F | 0.52 | 0.97 | *1.07* | 0.05 | 0.97 | 0.77 | 0.95 | 0.99 | 0.94 |
| M380G | 0.14 | 0.47 | *1.05* | 0.05 | 0.79 | 0.22 | 0.84 | 0.95 | 0.62 |
| M380I | 0.50 | *1.16* | 0.94 | 0.05 | 1.00 | 0.69 | 0.97 | *1.12* | 0.98 |
| M380K | 0.06 | 0.05 | 0.05 | 0.05 | 0.15 | 0.36 | 0.13 | 0.40 | 0.35 |
| M380L | 0.56 | *1.18* | *1.05* | 0.05 | 1.00 | 0.77 | 0.91 | 0.98 | 0.83 |
| M380M | 1.00 | 1.00 | 1.00 | 1.00 | 1.00 | 1.00 | 1.00 | 1.00 | 1.00 |
| M380N | 0.12 | 0.75 | 0.95 | 0.05 | *1.17* | 0.13 | *1.15* | *1.25* | 0.53 |
| M380Q | 0.59 | *1.15* | *1.02* | 0.05 | 0.92 | 0.81 | 0.92 | 0.99 | 1.00 |
| M380R | 0.05 | 0.05 | 0.05 | 0.05 | 0.05 | 0.05 | 0.05 | 0.05 | 0.05 |
| M380S | 0.60 | *1.11* | 0.99 | 0.05 | 0.97 | 0.60 | 0.90 | 0.94 | 0.85 |
| M380T | 0.59 | *1.04* | *1.01* | 0.05 | 1.00 | 0.93 | 0.90 | *1.03* | *1.06* |
| M380V | 0.59 | *1.12* | *1.13* | 0.05 | *1.06* | 0.69 | 0.93 | *1.00* | *1.33* |
| M380W | 0.04 | 0.04 | 0.04 | 0.04 | 0.04 | 0.04 | 0.04 | 0.04 | 0.04 |
| M380Y | 0.12 | 0.55 | *1.03* | 0.05 | 0.79 | 0.40 | 0.96 | *1.34* | 0.42 |
| G381A | 0.21 | 0.05 | 0.05 | 0.05 | 0.05 | 0.08 | 0.05 | 0.05 | 0.16 |
| G381C | 0.18 | 0.05 | 0.05 | 0.05 | 0.05 | 0.07 | 0.05 | 0.05 | 0.07 |
| G381D | 0.11 | 0.05 | 0.05 | 0.05 | 0.05 | 0.07 | 0.05 | 0.06 | 0.16 |
| G381E | 0.18 | 0.05 | 0.05 | 0.05 | 0.05 | 0.11 | 0.05 | 0.05 | 0.07 |
| G381F | 0.17 | 0.05 | 0.05 | 0.05 | 0.05 | 0.05 | 0.05 | 0.08 | 0.08 |
| G381G | 1.00 | 1.00 | 1.00 | 1.00 | 1.00 | 1.00 | 1.00 | 1.00 | 1.00 |
| G381H | 0.06 | 0.05 | 0.05 | 0.05 | 0.05 | 0.19 | 0.05 | 0.05 | *1.18* |
| G381I | 0.05 | 0.05 | 0.05 | 0.05 | 0.05 | 0.24 | 0.05 | 0.06 | 0.13 |
| G381K | 0.07 | 0.05 | 0.05 | 0.05 | 0.05 | 0.17 | 0.05 | 0.05 | 0.22 |
| G381L | 0.05 | 0.05 | 0.05 | 0.05 | 0.05 | 0.05 | 0.05 | 0.05 | 0.05 |
| G381N | 0.13 | 0.05 | 0.05 | 0.06 | 0.05 | 0.10 | 0.05 | 0.05 | 0.05 |
| G381P | 0.05 | 0.05 | 0.05 | 0.05 | 0.05 | 0.05 | 0.05 | 0.05 | 0.05 |
| G381Q | 0.06 | 0.05 | 0.05 | 0.05 | 0.05 | 0.07 | 0.05 | 0.05 | 0.05 |
| G381R | 0.05 | 0.05 | 0.05 | 0.05 | 0.05 | 0.05 | 0.05 | 0.05 | 0.05 |
| G381S | 0.05 | 0.05 | 0.05 | 0.05 | 0.05 | 0.05 | 0.05 | 0.05 | 0.05 |
| G381T | 0.05 | 0.05 | 0.05 | 0.05 | 0.05 | 0.26 | 0.05 | 0.05 | 0.18 |
| G381V | 0.06 | 0.05 | 0.05 | 0.05 | 0.05 | 0.42 | 0.05 | 0.05 | 0.32 |
| G381W | 0.04 | 0.04 | 0.04 | 0.04 | 0.04 | 0.04 | 0.04 | 0.04 | 0.04 |
| G381Y | 0.04 | 0.04 | 0.04 | 0.04 | 0.04 | 0.04 | 0.04 | 0.04 | 0.04 |

TABLE 3-1-continued

Performance Index Data of BGL1 SEL Variants (3,153)

| | | | | | | | | | |
|---|---|---|---|---|---|---|---|---|---|
| W382A | 0.04 | 0.04 | 0.04 | 0.04 | 0.04 | 0.04 | 0.04 | 0.04 | 0.04 |
| W382C | 0.04 | 0.04 | 0.04 | 0.04 | 0.04 | 0.04 | 0.04 | 0.04 | 0.04 |
| W382D | 0.04 | 0.04 | 0.04 | 0.04 | 0.04 | 0.04 | 0.04 | 0.04 | 0.04 |
| W382E | 0.04 | 0.04 | 0.04 | 0.04 | 0.04 | 0.04 | 0.04 | 0.04 | 0.04 |
| W382F | 0.25 | 0.74 | 0.76 | 0.06 | *1.03* | 0.45 | 0.96 | *1.13* | *1.68* |
| W382G | 0.04 | 0.04 | 0.04 | 0.04 | 0.04 | 0.04 | 0.04 | 0.04 | 0.04 |
| W382H | 0.18 | 0.16 | 0.05 | 0.23 | 0.29 | 0.26 | 0.08 | 0.05 | 0.31 |
| W382I | 0.04 | 0.04 | 0.04 | 0.04 | 0.04 | 0.04 | 0.04 | 0.04 | 0.04 |
| W382K | 0.17 | 0.22 | 0.05 | 0.19 | 0.24 | 0.20 | 0.11 | 0.09 | 0.44 |
| W382L | 0.04 | 0.04 | 0.04 | 0.04 | 0.04 | 0.04 | 0.04 | 0.04 | 0.04 |
| W382M | 0.18 | 0.17 | 0.05 | 0.25 | 0.25 | 0.35 | 0.14 | 0.08 | 0.83 |
| W382N | 0.18 | 0.25 | *1.11* | 0.17 | 0.58 | 0.92 | 0.37 | 0.34 | 0.77 |
| W382P | 0.19 | 0.38 | 0.05 | 0.15 | 0.28 | 0.30 | 0.09 | 0.06 | 0.72 |
| W382R | 0.04 | 0.04 | 0.04 | 0.04 | 0.04 | 0.04 | 0.04 | 0.04 | 0.04 |
| W3S2S | 0.26 | 0.19 | 0.05 | 0.24 | 0.24 | 0.23 | 0.14 | 0.09 | 0.63 |
| W382T | 0.04 | 0.04 | 0.04 | 0.04 | 0.04 | 0.04 | 0.04 | 0.04 | 0.04 |
| W382V | 0.28 | 0.15 | 0.05 | 0.25 | 0.18 | 0.16 | 0.09 | 0.05 | 0.58 |
| W382Y | 0.49 | 0.91 | *1.02* | 0.14 | 1.00 | 0.26 | 0.95 | 0.99 | 0.87 |
| Y396A | *1.08* | *1.06* | 0.92 | 0.48 | *1.01* | 0.97 | 1.00 | 0.99 | 1.00 |
| Y396C | 0.86 | *1.07* | 0.98 | 0.41 | *1.01* | 0.97 | *1.02* | *1.06* | 0.92 |
| Y396D | 0.78 | *1.06* | 0.90 | 0.33 | 0.99 | *1.18* | 0.99 | *1.05* | 0.94 |
| Y396E | 0.79 | *1.01* | 0.91 | 0.39 | *1.00* | *1.01* | 0.99 | *1.04* | 0.86 |
| Y396F | 0.67 | *1.08* | 0.97 | 0.88 | *1.03* | *1.10* | 0.97 | *1.12* | 0.91 |
| Y396G | 0.74 | *1.06* | 0.94 | 0.12 | 1.00 | *1.00* | *1.06* | *1.13* | 0.92 |
| Y396H | 0.85 | 0.92 | 0.94 | 0.80 | 0.96 | *1.02* | 0.97 | *1.09* | 0.85 |
| Y396I | 0.76 | *1.02* | 0.94 | 0.75 | 0.92 | 0.95 | 0.95 | *1.03* | 0.84 |
| Y396K | 0.62 | *1.12* | 0.92 | 0.25 | *1.01* | *1.06* | *1.04* | *1.17* | 0.91 |
| Y396L | 0.67 | 0.98 | 0.93 | 0.66 | 0.93 | *1.06* | 0.96 | *1.07* | 0.75 |
| Y396M | 0.51 | 0.94 | 0.94 | 0.56 | 0.90 | *1.04* | 0.92 | *1.08* | 0.64 |
| Y396N | 0.56 | 0.94 | 0.95 | 0.48 | 0.99 | *1.12* | 0.98 | *1.12* | 0.82 |
| Y396P | 0.15 | 0.05 | 0.05 | 0.05 | 0.05 | 0.10 | 0.05 | 0.10 | 0.05 |
| Y396Q | 0.60 | 0.97 | 0.95 | 0.22 | 0.94 | *1.04* | 1.00 | *1.08* | 0.76 |
| Y396R | 0.61 | 1.00 | 0.96 | 0.06 | 0.97 | *1.06* | 0.97 | *1.09* | 0.67 |
| Y396S | 0.86 | 1.00 | 0.90 | 0.38 | 0.92 | 0.93 | 0.95 | *1.04* | 0.79 |
| Y396T | 0.77 | *1.02* | 1.00 | 0.10 | 0.94 | 0.93 | 0.92 | 0.99 | 0.72 |

TABLE 3-1-continued

Performance Index Data of BGL1 SEL Variants (3,153)

| | | | | | | | | |
|---|---|---|---|---|---|---|---|---|
| Y396V | 0.54 | 0.93 | 0.96 | 0.38 | *1.04* | 0.97 | 0.93 | *1.06* | 0.71 |
| Y396W | 0.82 | 0.93 | 0.92 | 0.81 | 0.96 | 0.99 | 0.91 | *1.04* | 0.80 |
| Y396Y | 1.00 | 1.00 | 1.00 | 1.00 | 1.00 | 1.00 | 1.00 | 1.00 | 1.00 |
| D397A | 0.67 | 0.97 | 0.94 | 0.11 | 0.97 | 0.99 | *1.05* | *1.03* | 0.99 |
| D397C | 0.61 | *1.29* | 1.00 | 0.24 | *1.22* | *1.32* | *1.50* | *1.48* | *1.30* |
| D397D | 1.00 | 1.00 | 1.00 | 1.00 | 1.00 | 1.00 | 1.00 | 1.00 | 1.00 |
| D397E | 0.70 | *1.21* | 0.89 | 0.44 | *1.12* | *1.09* | *1.15* | *1.11* | 0.93 |
| D397F | 0.18 | 0.05 | 0.05 | 0.05 | 0.05 | 0.05 | *1.13* | 0.05 | 0.25 |
| D397H | 0.50 | *1.23* | 0.77 | 0.09 | *1.12* | *1.11* | *1.11* | *1.10* | 0.93 |
| D397I | 0.60 | *1.23* | 0.74 | 0.05 | *1.07* | *1.23* | *1.07* | *1.01* | 0.90 |
| D397K | 0.87 | *1.13* | 0.88 | 0.05 | *1.05* | *1.11* | *1.09* | *1.05* | 1.00 |
| D397L | 0.56 | *1.08* | 0.79 | 0.05 | *1.05* | 0.98 | *1.05* | 0.94 | 0.92 |
| D397M | 0.57 | *1.12* | 0.84 | 0.07 | *1.07* | *1.07* | *1.05* | *1.06* | 0.91 |
| D397N | *1.13* | *1.15* | *1.06* | 0.77 | *1.05* | *1.01* | *1.12* | *1.31* | *1.10* |
| D397P | 0.73 | *1.27* | 0.72 | 0.33 | 0.93 | *1.06* | *1.05* | *1.01* | 0.87 |
| D397Q | 0.64 | *1.10* | 0.95 | 0.29 | *1.09* | *1.22* | *1.17* | *1.11* | 0.98 |
| D397R | 0.69 | *1.23* | 0.90 | 0.14 | *1.13* | *1.26* | *1.26* | *1.20* | *1.19* |
| D397S | 0.61 | *1.17* | 0.83 | 0.23 | *1.05* | *1.02* | *1.15* | *1.19* | 0.90 |
| D397T | 0.83 | *1.19* | 0.94 | 0.17 | *1.07* | *1.13* | *1.12* | *1.20* | *1.05* |
| D397V | 0.61 | *1.32* | 0.95 | 0.24 | *1.21* | *1.36* | *1.28* | *1.24* | *1.09* |
| D397Y | 0.58 | *1.13* | 0.91 | 0.05 | *1.11* | *1.15* | *1.16* | *1.14* | *1.02* |
| A398C | 0.87 | *1.07* | *1.10* | 0.72 | 0.98 | *1.09* | *1.11* | 0.74 | 0.72 |
| A398D | 0.59 | *1.27* | *1.01* | 0.46 | 0.99 | *1.45* | *1.01* | 0.99 | 0.77 |
| A398E | 0.65 | *1.34* | *1.03* | 0.77 | *1.01* | *1.27* | *1.12* | 0.97 | 0.74 |
| A398F | 0.46 | *1.60* | *1.04* | 0.36 | 0.89 | *1.48* | *1.05* | 0.84 | 0.82 |
| A398G | 0.49 | *1.33* | *1.02* | 0.28 | 0.84 | *1.53* | 0.91 | 0.80 | 0.76 |
| A398H | 0.63 | *1.30* | *1.03* | 0.58 | 1.00 | *1.35* | 0.99 | 0.93 | 0.93 |
| A398I | 0.55 | *1.33* | 0.97 | 0.63 | 0.86 | *1.63* | *1.01* | 0.80 | 0.82 |
| A398K | 0.39 | *2.16* | 0.97 | 0.45 | 0.99 | *1.70* | *1.15* | *1.07* | 0.90 |
| A398L | 0.58 | *1.36* | *1.01* | 0.61 | 0.97 | *1.46* | 0.97 | 0.90 | 0.91 |
| A398M | 0.39 | *1.68* | 0.98 | 0.41 | 0.72 | *1.70* | 0.96 | 0.75 | 0.62 |
| A398N | 0.33 | *2.68* | *1.00* | 0.42 | 0.97 | *2.75* | *1.17* | 0.93 | 0.84 |
| A398P | 0.69 | *1.26* | *1.04* | 0.66 | 0.98 | *1.64* | *1.01* | 0.92 | 0.94 |
| A398Q | 0.48 | *1.60* | 0.98 | 0.58 | 0.94 | *1.65* | *1.18* | *1.14* | 0.90 |
| A398R | 0.36 | *2.72* | 0.91 | 0.51 | *1.03* | *1.99* | *1.28* | *1.09* | *1.02* |

TABLE 3-1-continued

Performance Index Data of BGL1 SEL Variants (3,153)

| | | | | | | | | | |
|---|---|---|---|---|---|---|---|---|---|
| A398S | 0.42 | *1.68* | *1.09* | 0.47 | 0.90 | *1.37* | *1.01* | 0.82 | 0.77 |
| A398T | 0.64 | *1.35* | *1.00* | 0.86 | 0.97 | *1.60* | *1.15* | 0.91 | 0.93 |
| A398V | 0.54 | *1.62* | 0.99 | 0.76 | *1.00* | *1.71* | *1.15* | 0.93 | 0.92 |
| A398W | 0.30 | *4.14* | 0.97 | 0.43 | *1.20* | *2.97* | *1.55* | *1.33* | *1.16* |
| A398Y | 0.44 | *1.68* | *1.02* | 0.37 | 0.89 | *1.46* | *1.14* | 0.94 | 0.81 |
| I399A | 0.41 | 0.78 | 0.94 | 0.66 | 0.99 | *1.05* | *1.03* | *1.15* | 1.00 |
| I399C | 0.19 | 0.46 | 0.85 | 0.33 | *1.07* | *1.26* | *1.13* | *1.28* | 0.78 |
| I399D | 0.14 | 0.36 | 0.86 | 0.24 | 0.90 | *1.10* | *1.15* | *1.33* | 0.68 |
| I399E | 0.30 | 0.62 | 0.88 | 0.41 | 0.97 | *1.08* | *1.00* | *1.10* | 0.87 |
| I399F | 0.60 | 0.97 | 0.94 | 0.68 | 0.95 | 0.91 | *1.02* | 0.96 | 0.95 |
| I399G | 0.11 | 0.31 | 0.76 | 0.18 | 0.89 | *1.25* | 0.69 | *1.37* | 0.55 |
| I399H | 0.04 | 0.04 | 0.04 | 0.04 | 0.04 | 0.04 | 0.04 | 0.04 | 0.04 |
| I399I | 1.00 | 1.00 | 1.00 | 1.00 | 1.00 | 1.00 | 1.00 | 1.00 | 1.00 |
| I399K | 0.05 | 0.05 | 0.05 | 0.05 | 0.05 | 0.05 | 0.05 | 0.05 | 0.05 |
| I399L | *1.01* | *1.10* | *1.02* | *1.16* | 0.97 | 0.98 | 0.95 | 0.92 | *1.04* |
| I399M | 0.55 | 0.89 | 0.89 | 0.66 | 0.93 | *1.02* | 0.90 | 0.93 | 0.86 |
| I399N | 0.13 | 0.05 | 0.05 | 0.05 | 0.06 | 0.15 | 0.06 | 0.22 | 0.26 |
| I399P | 0.17 | 0.05 | 0.05 | 0.05 | 0.05 | 0.14 | 0.06 | 0.18 | 0.09 |
| I399Q | 0.14 | 0.39 | 0.80 | 0.18 | 0.94 | *1.12* | *1.22* | *1.41* | 0.49 |
| I399R | 0.14 | 0.05 | 0.05 | 0.05 | 0.05 | 0.10 | 0.08 | 0.07 | 0.17 |
| I399S | 0.22 | 0.52 | 0.86 | 0.33 | 0.90 | *1.12* | *1.08* | *1.09* | 0.74 |
| I399T | 0.24 | 0.63 | 0.83 | 0.39 | 1.00 | *1.02* | *1.18* | *1.29* | 0.74 |
| I399V | 0.58 | *1.01* | 0.90 | 0.78 | 0.99 | 0.94 | *1.07* | *1.04* | *1.01* |
| I399W | 0.43 | 0.73 | 0.89 | 0.34 | 0.93 | *1.06* | 0.96 | 0.85 | 0.74 |
| I399Y | 0.22 | 0.53 | 0.84 | 0.26 | *1.02* | *1.04* | *1.03* | *1.31* | 0.65 |
| R402A | 0.62 | *1.27* | 0.91 | *1.01* | *1.22* | *1.18* | *1.27* | *1.29* | *1.22* |
| R402C | 0.57 | 0.81 | *1.02* | 0.64 | 0.95 | *1.01* | 0.96 | 0.93 | 0.78 |
| R402D | 0.22 | 0.33 | 0.89 | 0.15 | 0.74 | 0.87 | 0.70 | 0.79 | 0.50 |
| R402E | 0.31 | 0.61 | *1.09* | 0.55 | *1.00* | 0.89 | 1.00 | *1.02* | 0.66 |
| R402F | 0.59 | 0.84 | 0.96 | 0.92 | 1.00 | 0.90 | *1.01* | 0.99 | 0.81 |
| R402G | 0.25 | 0.63 | *1.02* | 0.41 | *1.09* | *1.02* | *1.14* | *1.18* | 0.78 |
| R402I | 0.54 | 0.89 | *1.10* | 0.80 | 0.98 | 0.83 | 0.98 | 0.98 | *1.11* |
| R402K | 0.07 | 0.15 | 0.05 | 0.13 | 0.32 | 0.46 | 0.28 | 0.62 | 0.50 |
| R402L | 0.41 | 0.85 | *1.02* | 0.92 | *1.07* | 0.99 | *1.07* | *1.08* | 0.77 |
| R402N | 0.05 | 0.05 | 0.05 | 0.05 | 0.05 | 0.05 | 0.05 | 0.05 | 0.05 |
| R402P | 0.16 | 0.36 | *2.84* | 0.27 | 0.82 | 0.97 | 0.77 | 0.96 | 0.49 |

TABLE 3-1-continued

Performance Index Data of BGL1 SEL Variants (3,153)

| | | | | | | | | |
|---|---|---|---|---|---|---|---|---|
| R402Q | 0.32 | 0.65 | *1.05* | 0.49 | *1.02* | 0.90 | 0.96 | *1.03* | 0.46 |
| R402R | 1.00 | 1.00 | 1.00 | 1.00 | 1.00 | 1.00 | 1.00 | 1.00 |
| R402S | 0.18 | 0.76 | *1.10* | 0.34 | *1.39* | *1.04* | *1.45* | *1.50* | 0.87 |
| R402T | 0.12 | 0.05 | 0.05 | 0.11 | 0.05 | 0.05 | 0.05 | 0.07 | 0.26 |
| R402V | 0.52 | 0.80 | *1.21* | 0.77 | 0.95 | 0.83 | 0.95 | 0.95 | 0.89 |
| R402W | 0.47 | 0.94 | 0.98 | 0.85 | *1.04* | 0.98 | *1.02* | *1.16* | 0.94 |
| R402Y | 0.60 | 0.86 | *1.03* | 0.80 | 0.95 | *1.00* | 0.94 | *1.00* | 0.80 |
| Q409C | 0.18 | 0.48 | *1.34* | 0.14 | 0.76 | 0.79 | 0.68 | 0.63 | 0.52 |
| Q409D | 0.18 | 0.63 | *1.16* | 0.18 | 0.97 | 1.00 | 0.98 | 0.75 | 0.24 |
| Q409E | 0.13 | 0.43 | 0.86 | 0.31 | 0.92 | 0.84 | 0.63 | 0.59 | 0.35 |
| Q409G | 0.15 | 0.57 | *1.10* | 0.19 | *1.06* | 0.91 | 0.83 | 0.71 | 0.65 |
| Q409H | 0.15 | 0.51 | *1.73* | 0.16 | 0.74 | 0.72 | 0.75 | 0.66 | 0.53 |
| Q409I | 0.20 | 0.43 | *1.04* | 0.16 | 0.59 | 0.51 | 0.54 | 0.41 | 0.22 |
| Q409L | 0.20 | 0.35 | 0.96 | 0.15 | 0.52 | 0.55 | 0.33 | 0.33 | 0.48 |
| Q409M | 0.15 | 0.39 | 0.71 | 0.26 | 0.69 | 0.66 | 0.47 | 0.48 | 0.43 |
| Q409Q | 1.00 | 1.00 | 1.00 | 1.00 | 1.00 | 1.00 | 1.00 | 1.00 | 1.00 |
| Q409R | 0.04 | 0.04 | 0.04 | 0.04 | 0.04 | 0.04 | 0.04 | 0.04 | 0.04 |
| Q409S | 0.18 | 0.47 | 0.84 | 0.20 | 0.67 | 0.54 | 0.66 | 0.50 | 0.82 |
| Q409T | 0.23 | 0.58 | 0.89 | 0.26 | 0.81 | 0.74 | 0.77 | 0.70 | 0.52 |
| Q409V | 0.17 | 0.51 | *1.21* | 0.12 | 0.73 | 0.75 | 0.74 | 0.58 | 0.44 |
| Q409W | 0.04 | 0.04 | 0.04 | 0.04 | 0.04 | 0.04 | 0.04 | 0.04 | 0.04 |
| V410A | 0.96 | 0.97 | 0.99 | 0.65 | 0.97 | *1.13* | 0.98 | 1.00 | 0.96 |
| V410C | 0.95 | *1.01* | 0.97 | 0.93 | 0.93 | *1.07* | 0.95 | *1.00* | 0.96 |
| V410D | 0.14 | 0.14 | 0.97 | 0.05 | 0.42 | 0.61 | 0.29 | 0.66 | 0.38 |
| V410F | 0.67 | 0.86 | 1.00 | 0.53 | 0.98 | 0.92 | 0.88 | *1.09* | *1.00* |
| V410G | 0.22 | 0.25 | *1.02* | 0.16 | 0.60 | 0.73 | 0.49 | 0.82 | 0.49 |
| V410H | 0.22 | 0.39 | 0.96 | 0.18 | 0.91 | 0.95 | 0.72 | *1.20* | 0.64 |
| V410I | 0.63 | 0.82 | 0.99 | 0.79 | 0.92 | *1.07* | 0.95 | *1.04* | 0.87 |
| V410L | 0.95 | 0.97 | *1.05* | *1.07* | 0.92 | *1.04* | 0.86 | 0.91 | 0.89 |
| V410M | 0.68 | 0.87 | 0.98 | 0.89 | 0.96 | 0.98 | 0.90 | 0.86 | 0.84 |
| V410N | 0.22 | 0.46 | 0.91 | 0.32 | 0.99 | *1.36* | 0.87 | 0.96 | 0.75 |
| V410P | 0.27 | 0.41 | 0.98 | 0.24 | 0.85 | 0.97 | 0.68 | 0.89 | 0.61 |
| V410Q | 0.17 | 0.30 | 0.92 | 0.11 | 0.81 | 0.92 | 0.62 | 0.93 | 0.47 |
| V410R | 0.08 | 0.20 | 0.92 | 0.05 | 1.00 | *1.12* | 0.78 | *1.31* | *1.41* |
| V410S | 0.44 | 0.69 | 0.98 | 0.50 | 0.98 | *1.11* | 0.96 | *1.06* | *1.04* |

TABLE 3-1-continued

Performance Index Data of BGL1 SEL Variants (3,153)

| V410T | 0.83 | 0.95 | 0.97 | 0.88 | 0.90 | *1.12* | 0.87 | 0.89 | 0.81 |
|---|---|---|---|---|---|---|---|---|---|
| V410V | 1.00 | 1.00 | 1.00 | 1.00 | 1.00 | 1.00 | 1.00 | 1.00 | 1.00 |
| V410W | 0.35 | 0.53 | 0.99 | 0.28 | 0.91 | *1.05* | 0.82 | *1.12* | 0.64 |
| V410Y | 0.51 | 0.71 | 0.97 | 0.33 | 0.95 | 0.92 | 0.89 | *1.07* | 0.82 |
| T411D | 0.76 | *1.15* | 0.88 | 0.91 | *1.08* | *1.18* | *1.04* | *1.07* | 0.96 |
| T411E | 0.55 | *1.33* | 0.92 | 0.73 | *1.18* | 1.00 | *1.24* | *1.25* | *1.07* |
| T411F | 0.76 | *1.20* | 0.92 | *1.12* | *1.07* | 1.00 | *1.11* | *1.04* | 0.94 |
| T411G | 0.47 | *1.21* | 0.84 | 0.68 | *1.17* | *1.04* | *1.14* | *1.04* | 0.91 |
| T411H | 0.68 | *1.29* | 0.85 | *1.09* | *1.11* | 0.87 | *1.13* | *1.12* | *1.02* |
| T411I | 0.68 | *1.19* | 0.80 | 0.87 | *1.04* | 0.94 | 0.97 | *1.03* | 0.80 |
| T411K | 0.55 | *1.13* | 0.79 | 0.70 | *1.03* | 0.90 | *1.02* | 0.97 | 0.84 |
| T411L | 0.84 | *1.21* | 0.91 | *1.14* | *1.03* | 0.90 | *1.03* | 0.93 | 0.86 |
| T411M | 0.05 | 0.05 | 0.05 | 0.05 | 0.05 | 0.05 | 0.05 | 0.05 | 0.26 |
| T411N | 0.57 | *1.31* | 0.90 | 0.90 | *1.18* | *1.13* | *1.29* | *1.22* | *1.07* |
| T411P | 0.17 | 0.70 | 0.75 | 0.25 | 0.92 | 0.74 | 0.83 | 0.68 | 0.47 |
| T411Q | 0.74 | *1.25* | 0.92 | *1.06* | *1.11* | *1.17* | *1.13* | *1.16* | 0.95 |
| T411R | 0.77 | *1.18* | 0.85 | 0.86 | *1.03* | 0.98 | *1.04* | *1.03* | 0.89 |
| T411S | 0.60 | *1.07* | 0.92 | 0.86 | *1.01* | *1.09* | *1.05* | *1.02* | 0.92 |
| T411T | 1.00 | 1.00 | 1.00 | 1.00 | 1.00 | 1.00 | 1.00 | 1.00 | 1.00 |
| T411V | 0.82 | *1.20* | 0.90 | 0.98 | *1.04* | 0.99 | *1.05* | *1.02* | 0.97 |
| T411W | 0.04 | 0.04 | 0.04 | 0.04 | 0.04 | 0.04 | 0.04 | 0.04 | 0.04 |
| T411Y | 0.98 | *1.09* | 0.97 | *1.22* | 0.98 | *1.17* | 0.95 | *1.03* | 0.91 |
| S420A | *1.02* | 0.95 | 0.92 | *1.01* | 0.96 | 0.86 | 0.88 | 0.90 | 0.86 |
| S420C | 0.41 | *1.48* | 0.94 | 0.85 | *1.54* | *1.24* | *1.75* | *1.79* | *1.71* |
| S420D | *1.15* | *1.03* | 0.88 | *1.10* | 0.99 | 0.94 | 0.93 | 0.95 | *1.01* |
| S420F | 0.71 | 1.00 | 0.92 | 0.80 | 0.95 | 0.85 | 0.87 | 0.91 | 0.96 |
| S420G | 0.51 | *1.40* | 0.91 | 0.88 | *1.27* | 0.92 | *1.28* | *1.40* | *1.35* |
| S420H | 0.58 | 0.95 | 0.94 | 0.71 | *1.02* | 0.79 | 0.93 | 0.92 | 0.84 |
| S420I | 0.04 | 0.04 | 0.04 | 0.04 | 0.04 | 0.04 | 0.04 | 0.04 | 0.04 |
| S420K | 0.66 | *1.06* | 0.86 | 0.74 | *1.02* | 0.82 | 0.94 | 0.97 | 0.98 |
| S420L | 0.56 | 0.93 | 0.86 | 0.69 | 0.90 | 0.75 | 0.82 | 0.87 | 0.81 |
| S420M | 0.15 | 0.35 | 0.90 | 0.16 | 0.59 | 0.70 | 0.54 | 0.67 | 0.58 |
| S420N | 0.46 | *1.02* | 0.95 | 0.73 | *1.06* | 0.83 | *1.02* | *1.12* | *1.09* |
| S420Q | 0.41 | *1.09* | 0.84 | 0.68 | *1.11* | 0.96 | *1.11* | *1.21* | 0.97 |
| S420S | 1.00 | 1.00 | 1.00 | 1.00 | 1.00 | 1.00 | 1.00 | 1.00 | 1.00 |

TABLE 3-1-continued

Performance Index Data of BGL1 SEL Variants (3,153)

| | | | | | | | | | |
|---|---|---|---|---|---|---|---|---|---|
| S420T | 0.48 | *1.05* | 0.93 | 0.74 | *1.10* | 0.84 | *1.07* | *1.12* | *1.03* |
| S420V | 0.05 | 0.90 | 0.97 | 0.29 | *3.23* | 0.19 | *3.77* | *4.55* | *1.39* |
| S420W | 0.04 | 0.04 | 0.04 | 0.04 | 0.04 | 0.04 | 0.04 | 0.04 | 0.04 |
| S420Y | 0.70 | *1.11* | 0.86 | 0.92 | *1.00* | 0.96 | *1.05* | *1.04* | 0.96 |
| R426A | 0.06 | *2.43* | *1.03* | 0.84 | *9.13* | *5.60* | *11.42* | *12.31* | *3.54* |
| R426E | 0.90 | 0.95 | *1.03* | 0.89 | 0.95 | *1.02* | 0.99 | 0.98 | 0.89 |
| R426F | 0.87 | 0.96 | *1.09* | *1.03* | 0.98 | *1.10* | *1.08* | 0.99 | 0.93 |
| R426G | 0.05 | 0.05 | 0.05 | 0.05 | 0.05 | 0.05 | 0.05 | 0.05 | 0.05 |
| R426I | 0.89 | 0.80 | *1.12* | 0.76 | 0.88 | *1.23* | 0.96 | 0.90 | 0.91 |
| R426K | 0.90 | 0.85 | *1.11* | 0.97 | 0.92 | *1.07* | 0.95 | 0.92 | 0.80 |
| R426L | 0.77 | 0.99 | *1.01* | 0.97 | 0.93 | 0.93 | 1.00 | *1.08* | 0.85 |
| R426M | 0.68 | 0.80 | *1.03* | 0.61 | 0.88 | 0.98 | 0.92 | 0.95 | 0.78 |
| R426N | 0.97 | 0.94 | *1.10* | *1.02* | 0.95 | *1.17* | *1.05* | 0.97 | 0.86 |
| R426P | 0.24 | 0.52 | 0.92 | 0.19 | 0.98 | *1.12* | 0.99 | 0.93 | 0.48 |
| R426Q | 0.81 | 0.86 | *1.15* | 0.78 | 0.96 | *1.09* | *1.01* | 0.99 | 0.79 |
| R426R | 1.00 | 1.00 | 1.00 | 1.00 | 1.00 | 1.00 | 1.00 | 1.00 | 1.00 |
| R426S | 0.84 | 0.82 | *1.00* | 0.80 | 0.90 | *1.04* | 0.68 | 0.87 | 0.72 |
| R426T | 0.93 | *1.00* | *1.07* | 0.94 | 0.98 | 0.98 | *1.03* | *1.10* | 0.99 |
| R426V | 0.05 | 0.05 | 0.05 | 0.05 | 0.05 | 0.05 | 0.05 | 0.05 | 0.05 |
| R426W | 0.73 | 0.95 | 0.97 | 0.78 | 0.96 | *1.06* | *1.03* | 0.99 | 0.95 |
| R426Y | 0.92 | 0.90 | *1.10* | 0.92 | 0.96 | *1.02* | 1.00 | *1.06* | 0.74 |
| G427C | 0.38 | *1.39* | 0.99 | 0.68 | *1.49* | *1.24* | *1.57* | *1.54* | *1.25* |
| G427D | 0.95 | 0.97 | *1.06* | 0.88 | *1.01* | 0.90 | 0.97 | 0.98 | 0.95 |
| G427E | *1.27* | 1.00 | *1.08* | *1.24* | *1.02* | *1.00* | 0.95 | 0.94 | *1.12* |
| G427F | 0.53 | *1.35* | *1.04* | 0.94 | *1.33* | *1.07* | *1.28* | *1.19* | *1.48* |
| G427G | 1.00 | 1.00 | 1.00 | 1.00 | 1.00 | 1.00 | 1.00 | 1.00 | 1.00 |
| G427H | 0.93 | *1.07* | 0.95 | 0.98 | *1.01* | *1.06* | 0.93 | 0.84 | *1.06* |
| G427I | 0.42 | 0.90 | 0.93 | 0.48 | 1.00 | 1.00 | 0.87 | 0.82 | 0.78 |
| G427K | 0.61 | 0.93 | 0.96 | 0.69 | 0.88 | *1.06* | 0.89 | 0.86 | 0.82 |
| G427L | 0.89 | *1.05* | *1.06* | 0.98 | 0.99 | 0.93 | 0.94 | 0.91 | *1.03* |
| G427M | 0.59 | *1.04* | 0.98 | 0.74 | 0.97 | 0.88 | 0.90 | 0.93 | 0.92 |
| G427N | 0.57 | 0.94 | *1.03* | 0.65 | 0.89 | *1.03* | 0.77 | 0.91 | 0.81 |
| G427P | 0.19 | 0.65 | 0.97 | 0.13 | *1.14* | 0.97 | 0.94 | *1.21* | 0.73 |
| G427Q | 0.72 | 0.98 | *1.00* | 0.87 | 0.94 | *1.05* | 0.90 | 0.93 | 0.85 |
| G427R | 0.58 | 0.95 | 0.98 | 0.64 | 0.84 | *1.06* | 0.89 | 0.89 | 0.86 |
| G427S | *1.05* | *1.00* | *1.05* | *1.07* | 0.99 | *1.00* | 0.80 | 0.83 | 0.97 |

TABLE 3-1-continued

Performance Index Data of BGL1 SEL Variants (3,153)

| | | | | | | | | | |
|---|---|---|---|---|---|---|---|---|---|
| G427T | 0.60 | 0.96 | *1.00* | 0.70 | 0.96 | *1.07* | 0.85 | 0.91 | 0.76 |
| G427V | 0.32 | 0.94 | *1.00* | 0.45 | *1.03* | *1.02* | 0.96 | *1.04* | 0.76 |
| G427W | 0.94 | 0.89 | *1.03* | 0.89 | 0.93 | 0.88 | 0.80 | 0.68 | 0.82 |
| G427Y | 0.62 | *1.16* | 0.98 | 0.82 | *1.07* | 0.94 | *1.01* | 0.98 | *1.01* |
| K428A | *1.18* | *1.16* | *1.05* | *1.54* | *1.12* | 0.83 | *1.07* | *1.12* | 0.91 |
| K428C | 0.95 | 0.97 | 0.98 | 0.99 | 0.94 | *1.15* | 0.88 | 0.91 | 0.92 |
| K428D | 0.31 | 0.47 | 0.90 | 0.30 | 0.77 | *1.31* | 0.63 | 0.75 | 0.36 |
| K428E | 0.62 | 0.78 | 0.98 | 0.67 | 0.91 | *1.27* | 0.78 | 0.85 | 0.62 |
| K428F | 0.42 | 0.52 | 0.89 | 0.31 | 0.71 | *1.49* | 0.57 | 0.62 | 0.48 |
| K428G | 0.50 | 0.79 | 0.88 | 0.60 | 0.93 | *2.70* | 0.80 | 0.85 | 0.65 |
| K428H | 0.81 | 0.84 | 0.94 | 0.82 | 0.88 | *1.43* | 0.77 | 0.80 | 0.77 |
| K428I | 0.43 | 0.70 | 0.97 | 0.55 | 0.92 | *1.62* | 0.79 | 0.85 | 0.77 |
| K428K | 1.00 | 1.00 | 1.00 | 1.00 | 1.00 | 1.00 | 1.00 | 1.00 | 1.00 |
| K428L | 0.63 | 0.76 | 0.94 | 0.60 | 0.85 | *1.12* | 0.73 | 0.77 | 0.70 |
| K428M | 0.57 | 0.90 | 0.91 | 0.67 | 0.91 | *1.79* | 0.85 | 0.88 | 0.84 |
| K428N | 0.27 | 0.67 | 0.89 | 0.40 | *1.01* | *2.12* | 0.91 | 0.99 | 0.82 |
| K428P | 0.70 | 0.78 | *1.01* | 0.77 | 0.86 | *1.06* | 0.79 | 0.74 | 0.76 |
| K428Q | 0.47 | 0.74 | 0.93 | 0.56 | 0.87 | *1.96* | 0.76 | 0.83 | 0.83 |
| K428R | 0.52 | 0.86 | 0.92 | 0.62 | 0.92 | *1.32* | 0.91 | 0.91 | 0.85 |
| K428S | 0.96 | 0.90 | 0.92 | *1.06* | 0.90 | *1.08* | 0.77 | 0.78 | 0.80 |
| K428T | 0.66 | 0.82 | 0.93 | 0.73 | 0.87 | *1.23* | 0.76 | 0.80 | 0.77 |
| K428V | 0.52 | 0.81 | 0.96 | 0.62 | 0.91 | *1.50* | 0.84 | 0.85 | 0.78 |
| K428W | 0.43 | 0.50 | 0.97 | 0.31 | 0.70 | *1.71* | 0.58 | 0.68 | 0.53 |
| K428Y | 0.55 | 0.78 | 0.94 | 0.53 | 0.87 | *1.30* | 0.82 | 0.84 | 0.75 |
| E441A | *1.95* | 0.05 | 0.05 | 0.05 | 0.05 | 0.05 | 0.05 | 0.05 | 0.05 |
| E441C | *1.38* | 0.05 | 0.05 | 0.05 | 0.05 | 0.05 | 0.05 | 0.05 | 0.08 |
| E441D | *1.96* | 0.05 | 0.05 | 0.05 | 0.05 | 0.05 | 0.05 | 0.05 | 0.05 |
| E441E | 1.00 | 1.00 | 1.00 | 1.00 | 1.00 | 1.00 | 1.00 | 1.00 | 1.00 |
| E441F | 0.04 | 0.04 | 0.04 | 0.04 | 0.04 | 0.04 | 0.04 | 0.04 | 0.04 |
| E441G | *1.20* | 0.05 | 0.05 | 0.05 | 0.05 | 0.05 | 0.05 | 0.05 | 0.05 |
| E441H | 0.17 | 0.05 | 0.05 | 0.05 | 0.05 | 0.10 | 0.05 | 0.05 | 0.08 |
| E441I | 0.70 | 0.05 | 0.05 | 0.05 | 0.05 | 0.05 | 0.05 | 0.05 | 0.05 |
| E441K | 0.35 | 0.05 | 0.05 | 0.05 | 0.05 | 0.05 | 0.05 | 0.05 | 0.07 |
| E441L | 0.31 | 0.05 | 0.05 | 0.05 | 0.05 | 0.05 | 0.05 | 0.05 | 0.08 |
| E441M | 0.54 | 0.05 | 0.05 | 0.05 | 0.05 | 0.05 | 0.05 | 0.05 | 0.05 |

TABLE 3-1-continued

Performance Index Data of BGL1 SEL Variants (3,153)

| | | | | | | | | | |
|---|---|---|---|---|---|---|---|---|---|
| E441N | 0.87 | 0.05 | 0.05 | 0.05 | 0.05 | 0.05 | 0.05 | 0.05 | 0.12 |
| E441P | 0.28 | 0.05 | 0.05 | 0.05 | 0.05 | 0.09 | 0.05 | 0.05 | 0.05 |
| E441Q | 0.69 | 0.05 | 0.05 | 0.05 | 0.05 | 0.05 | 0.05 | 0.05 | 0.08 |
| E441R | 0.08 | 0.05 | 0.05 | 0.10 | 0.05 | 0.20 | 0.05 | 0.05 | 0.05 |
| E441S | 0.98 | 0.05 | 0.05 | 0.05 | 0.05 | 0.05 | 0.05 | 0.05 | 0.05 |
| E441T | 0.67 | 0.05 | 0.05 | 0.05 | 0.05 | 0.07 | 0.05 | 0.05 | 0.15 |
| E441V | 0.74 | 0.05 | 0.05 | 0.05 | 0.05 | 0.05 | 0.05 | 0.05 | 0.05 |
| E441Y | 0.27 | 0.08 | 0.05 | 0.05 | 0.05 | 0.05 | 0.05 | 0.05 | 0.05 |
| T445A | 0.88 | *1.01* | *1.08* | 0.91 | *1.03* | *1.11* | *1.11* | *1.01* | *1.06* |
| T445C | 0.32 | *1.15* | *1.03* | 0.60 | *1.31* | *1.64* | *1.79* | *1.65* | *1.54* |
| T445D | 0.74 | 0.96 | 0.98 | *1.49* | 0.97 | *1.15* | 0.95 | 0.97 | *1.02* |
| T445E | 0.61 | *1.01* | *1.04* | 0.74 | *1.06* | 0.91 | *1.08* | 0.94 | *1.06* |
| T445F | 0.55 | *1.07* | *1.04* | 0.78 | *1.04* | 0.99 | *1.19* | *1.24* | *1.12* |
| T445G | 0.61 | *1.01* | *1.23* | *1.14* | *1.05* | 0.89 | *1.18* | *1.19* | *1.16* |
| T445H | 0.04 | 0.04 | 0.04 | 0.04 | 0.04 | 0.04 | 0.04 | 0.04 | 0.04 |
| T445I | 0.57 | 1.00 | 1.00 | 0.68 | 0.95 | 0.95 | *1.10* | 0.98 | *1.09* |
| T445K | 0.48 | 0.85 | 0.96 | 0.53 | 0.86 | *1.03* | *1.12* | 0.97 | 0.99 |
| T445L | 0.57 | 0.98 | 0.97 | 0.65 | 0.94 | 0.85 | *1.11* | 0.89 | 0.88 |
| T445M | 0.46 | *1.07* | *1.06* | 0.72 | *1.11* | *1.01* | *1.22* | *1.16* | *1.13* |
| T445N | 0.27 | 0.75 | 0.93 | 0.36 | 0.97 | 1.00 | *1.11* | *1.11* | 0.96 |
| T445P | 0.43 | 0.99 | *1.11* | 0.42 | *1.02* | 0.60 | *1.21* | *1.08* | *1.04* |
| T445Q | 0.42 | 0.81 | *1.03* | 0.47 | 0.88 | *1.09* | *1.07* | 0.92 | 0.94 |
| T445R | 0.65 | 0.92 | 0.92 | 0.67 | 0.88 | 0.91 | *1.04* | 0.95 | 0.86 |
| T445S | 0.43 | 0.83 | *1.06* | 0.52 | 0.96 | *1.09* | *1.11* | 0.99 | 0.97 |
| T445T | 1.00 | 1.00 | 1.00 | 1.00 | 1.00 | 1.00 | 1.00 | 1.00 | 1.00 |
| T445V | 0.49 | *1.05* | *1.02* | 0.70 | *1.03* | 0.89 | *1.17* | *1.14* | *1.11* |
| T445W | 0.05 | 0.05 | 0.05 | 0.05 | 0.05 | 0.05 | 0.05 | 0.05 | 0.05 |
| T445Y | 0.61 | *1.03* | *1.07* | 0.75 | *1.02* | 0.78 | *1.18* | *1.01* | *1.01* |
| V446A | *1.16* | 0.99 | 0.94 | 0.05 | 0.92 | 0.90 | 0.96 | 0.96 | *1.13* |
| V446C | 0.82 | 0.87 | 0.89 | 0.05 | 0.95 | *1.08* | 0.96 | 0.90 | *1.06* |
| V446E | 0.26 | 0.54 | 0.81 | 0.05 | 0.85 | 0.18 | 0.88 | 0.94 | 0.60 |
| V446F | 0.17 | 0.29 | 0.87 | 0.05 | 0.67 | 0.33 | 0.72 | 0.79 | 0.70 |
| V446G | 0.23 | 0.39 | 0.91 | 0.05 | 0.84 | 0.18 | 0.84 | 0.78 | 0.79 |
| V446I | 0.70 | 0.83 | 0.85 | 0.05 | 0.86 | 0.86 | 0.89 | 0.84 | 0.86 |
| V446K | 0.11 | 0.34 | 0.72 | 0.05 | 0.92 | 0.36 | *1.04* | *1.02* | 0.48 |

TABLE 3-1-continued

Performance Index Data of BGL1 SEL Variants (3,153)

| | | | | | | | | | |
|---|---|---|---|---|---|---|---|---|---|
| V446L | 0.23 | 0.52 | 0.89 | 0.05 | 0.92 | 0.54 | 0.79 | 0.84 | 0.70 |
| V446M | 0.05 | 0.05 | 0.05 | 0.05 | 0.05 | 0.05 | 0.05 | 0.05 | 0.05 |
| V446N | 0.29 | 0.55 | 0.90 | 0.09 | 0.81 | 0.32 | 0.82 | 0.81 | 0.71 |
| V446P | 0.12 | 0.17 | 0.71 | 0.05 | 0.39 | 0.13 | 0.39 | 0.50 | 0.34 |
| V446Q | 0.26 | 0.73 | 0.86 | 0.11 | *1.12* | 0.92 | *1.25* | *1.16* | 0.82 |
| V446R | 0.12 | 0.43 | 0.78 | 0.05 | *1.09* | 0.54 | *1.30* | *1.30* | 0.50 |
| V446S | 0.35 | 0.71 | 0.91 | 0.05 | 0.96 | 0.76 | 1.00 | 0.94 | 0.86 |
| V446V | 1.00 | 1.00 | 1.00 | 1.00 | 1.00 | 1.00 | 1.00 | 1.00 | 1.00 |
| V446W | 0.12 | 0.29 | 0.88 | 0.05 | 0.75 | 0.23 | 0.79 | 0.94 | 0.36 |
| E447A | *1.00* | 0.96 | 1.02 | 0.05 | 0.87 | 0.82 | 0.83 | 0.87 | 0.81 |
| E447C | 0.08 | 0.08 | 0.05 | 0.05 | 0.09 | 0.05 | 0.05 | 0.05 | 0.14 |
| E447E | 1.00 | 1.00 | 1.00 | 1.00 | 1.00 | 1.00 | 1.00 | 1.00 | 1.00 |
| E447F | 0.40 | 0.60 | 0.92 | 0.05 | 0.92 | 0.25 | 0.86 | 0.96 | 0.52 |
| E447G | 0.07 | 0.05 | 0.05 | 0.05 | 0.05 | 0.39 | 0.05 | 0.05 | 0.28 |
| E447I | 0.48 | 0.56 | 0.96 | 0.05 | 0.81 | 0.20 | 0.78 | 0.91 | 0.69 |
| E447K | 0.42 | 0.62 | 0.96 | 0.05 | 0.87 | 0.34 | 0.85 | *1.02* | 0.66 |
| E447L | 0.42 | 0.66 | *1.01* | 0.05 | 0.92 | 0.56 | 0.89 | *1.03* | 0.80 |
| E447M | 0.05 | 0.05 | 0.05 | 0.05 | 0.05 | 0.11 | 0.05 | 0.05 | 0.05 |
| E447N | *1.01* | 0.86 | 0.95 | 0.05 | 0.82 | 0.70 | 0.75 | 0.88 | 0.74 |
| E447P | 0.07 | 0.11 | 0.98 | 0.05 | 0.13 | 0.15 | 0.06 | 0.05 | 0.25 |
| E447R | 0.56 | 0.56 | 0.95 | 0.06 | 0.69 | 0.28 | 0.59 | 0.68 | 0.59 |
| E447S | 0.53 | 0.76 | 0.93 | 0.05 | 0.92 | 0.60 | 0.89 | *1.15* | 0.92 |
| E447T | 0.05 | 0.05 | 0.05 | 0.05 | 0.05 | 0.05 | 0.05 | 0.05 | 0.17 |
| E447V | 0.35 | 0.63 | 0.93 | 0.05 | *1.03* | 0.23 | 0.99 | *1.13* | 0.85 |
| E447W | 0.45 | 0.48 | *1.08* | 0.10 | 0.75 | 0.20 | 0.61 | 0.72 | 0.59 |
| E447Y | 0.25 | 0.44 | 0.87 | 0.05 | 0.96 | 0.30 | 0.90 | *1.07* | 0.56 |
| G448A | *1.01* | *1.07* | 0.97 | 0.05 | 0.98 | *1.05* | *1.02* | 0.90 | 0.95 |
| G448C | 0.82 | *1.33* | 0.92 | 0.07 | *1.09* | *1.12* | *1.22* | *1.02* | *1.04* |
| G448D | *1.14* | *1.02* | *1.04* | 0.06 | *1.01* | *1.26* | *1.01* | 0.90 | 0.92 |
| G448E | 0.85 | *1.05* | *1.13* | 0.05 | *1.02* | *1.20* | *1.04* | 0.90 | 0.98 |
| G448F | *1.32* | 0.99 | *1.12* | 0.05 | *1.04* | *1.02* | *1.10* | 0.90 | *1.05* |
| G448G | 1.00 | 1.00 | 1.00 | 1.00 | 1.00 | 1.00 | 1.00 | 1.00 | 1.00 |
| G448H | 0.87 | *1.01* | *1.09* | 0.05 | 0.97 | 1.00 | 0.96 | 0.99 | *1.02* |
| G448K | 0.85 | 0.94 | *1.01* | 0.05 | 0.93 | 0.93 | 0.92 | 0.90 | 0.88 |
| G448L | 0.69 | 0.99 | *1.04* | 0.05 | 0.97 | 0.89 | 0.92 | 0.88 | 0.74 |
| G448M | *1.02* | 1.00 | *1.02* | 0.05 | 0.95 | 0.98 | 0.94 | 0.88 | 0.85 |

TABLE 3-1-continued

Performance Index Data of BGL1 SEL Variants (3,153)

| | | | | | | | | | |
|---|---|---|---|---|---|---|---|---|---|
| G448N | *1.36* | 0.97 | *1.12* | 0.21 | *1.02* | *1.10* | 0.96 | 0.95 | 0.98 |
| G448P | 0.18 | 0.87 | 0.99 | 0.05 | 0.61 | 0.11 | 0.97 | 0.76 | 0.44 |
| G448Q | 0.82 | 0.94 | *1.11* | 0.05 | 0.97 | 0.98 | 1.00 | 0.98 | 0.82 |
| G448R | *1.30* | 0.94 | 0.97 | 0.05 | 0.95 | 0.90 | 0.92 | 0.99 | 0.88 |
| G448S | *1.00* | 0.99 | *1.08* | 0.05 | 0.93 | *1.00* | 0.93 | 0.99 | 0.91 |
| G448T | *1.05* | *1.04* | *1.00* | 0.05 | 0.98 | *1.02* | 0.99 | 0.98 | 0.89 |
| G448V | 0.96 | 0.85 | *1.10* | 0.05 | 0.93 | 0.63 | 0.83 | 0.85 | 0.81 |
| G448W | 0.98 | 0.92 | 0.99 | 0.05 | 0.88 | 0.81 | 0.86 | 0.91 | 0.73 |
| G448Y | *1.08* | 0.89 | *1.06* | 0.05 | 0.94 | *1.03* | 0.94 | *1.04* | 0.93 |
| N449A | 0.83 | *1.04* | 0.99 | 0.05 | *1.00* | *1.04* | *1.04* | 1.00 | *1.13* |
| N449C | 0.66 | *1.07* | *1.09* | 0.23 | *1.02* | *1.10* | *1.06* | *1.04* | *1.10* |
| N449E | 0.73 | *1.06* | *1.12* | 0.05 | *1.00* | 0.88 | 0.95 | 0.94 | 0.93 |
| N449F | 0.47 | *1.03* | 0.97 | 0.05 | 0.92 | 0.47 | 0.97 | 0.93 | 0.93 |
| N449G | 0.22 | 0.64 | *1.02* | 0.05 | *1.01* | 0.11 | *1.15* | 0.87 | 0.69 |
| N449H | 0.41 | 0.88 | 0.95 | 0.05 | 0.98 | 0.94 | *1.02* | *1.07* | 0.73 |
| N449K | 0.16 | 0.46 | *1.22* | 0.05 | *1.01* | 0.14 | *1.08* | *1.01* | 0.79 |
| N449L | 0.34 | 0.85 | *1.17* | 0.05 | 0.87 | 0.27 | 0.81 | 0.89 | 0.66 |
| N449M | 0.73 | *1.12* | 0.94 | 0.05 | 0.94 | 0.78 | 0.82 | 0.85 | 0.91 |
| N449N | 1.00 | 1.00 | 1.00 | 1.00 | 1.00 | 1.00 | 1.00 | 1.00 | 1.00 |
| N449P | 0.12 | *1.06* | 0.60 | 0.05 | 0.69 | 0.10 | *1.24* | 0.54 | 0.36 |
| N449Q | 0.68 | 0.98 | 0.98 | 0.05 | 0.86 | 0.93 | 0.81 | 0.80 | 0.79 |
| N449R | 0.74 | 0.87 | *1.12* | 0.05 | 0.91 | 0.76 | 0.84 | 0.81 | 0.85 |
| N449S | 0.66 | 1.00 | 0.92 | 0.05 | 0.93 | 0.92 | 0.84 | 0.87 | 0.77 |
| N449T | 0.76 | *1.13* | 0.99 | 0.05 | 0.94 | 0.90 | 0.87 | 0.86 | 0.66 |
| N449V | 0.79 | *1.09* | *1.11* | 0.05 | 0.92 | 0.81 | 0.85 | 0.86 | 0.75 |
| N449W | 0.43 | 0.92 | *1.09* | 0.05 | 0.87 | 0.26 | 0.82 | 0.85 | 0.72 |
| N449Y | 0.04 | 0.04 | 0.04 | 0.04 | 0.04 | 0.04 | 0.04 | 0.04 | 0.04 |
| D452A | 0.05 | 0.05 | 0.05 | 0.05 | 0.05 | 0.05 | 0.05 | 0.05 | 0.05 |
| D452C | 0.04 | 0.04 | 0.04 | 0.04 | 0.04 | 0.04 | 0.04 | 0.04 | 0.04 |
| D452D | 1.00 | 1.00 | 1.00 | 1.00 | 1.00 | 1.00 | 1.00 | 1.00 | 1.00 |
| D452E | 0.14 | 0.05 | 0.05 | 0.05 | 0.05 | 0.17 | 0.05 | 0.05 | 0.29 |
| D452F | 0.18 | 0.05 | 0.05 | 0.05 | 0.05 | 0.05 | 0.07 | 0.05 | 0.39 |
| D452G | 0.05 | 0.05 | 0.05 | 0.05 | 0.05 | 0.05 | 0.05 | 0.05 | 0.05 |
| D452H | 0.04 | 0.04 | 0.04 | 0.04 | 0.04 | 0.04 | 0.04 | 0.04 | 0.04 |
| D452I | 0.13 | 0.05 | 0.05 | 0.05 | 0.07 | 0.17 | 0.13 | 0.05 | 0.30 |

TABLE 3-1-continued

Performance Index Data of BGL1 SEL Variants (3,153)

| | | | | | | | | |
|---|---|---|---|---|---|---|---|---|
| D452K | 0.14 | 0.05 | 0.05 | 0.05 | 0.05 | 0.05 | 0.05 | 0.12 |
| D452L | 0.14 | 0.05 | 0.05 | 0.05 | 0.05 | 0.05 | 0.07 | 0.05 | 0.20 |
| D452M | 0.14 | 0.05 | 0.05 | 0.05 | 0.05 | 0.05 | 0.11 | 0.05 | 0.26 |
| D452N | 0.26 | 0.20 | *1.07* | 0.05 | 0.20 | 0.13 | 0.24 | 0.23 | 0.29 |
| D452P | 0.13 | 0.05 | 0.05 | 0.05 | 0.05 | 0.06 | 0.05 | 0.05 | 0.25 |
| D452Q | 0.04 | 0.04 | 0.04 | 0.04 | 0.04 | 0.04 | 0.04 | 0.04 | 0.04 |
| D452R | 0.14 | 0.05 | 0.05 | 0.05 | 0.11 | 0.10 | 0.05 | 0.05 | 0.16 |
| D452S | 0.04 | 0.04 | 0.04 | 0.04 | 0.04 | 0.04 | 0.04 | 0.04 | 0.04 |
| D452T | 0.14 | 0.08 | 0.05 | 0.05 | 0.05 | 0.05 | 0.14 | 0.05 | 0.24 |
| D452V | 0.15 | 0.05 | 0.05 | 0.05 | 0.05 | 0.05 | 0.05 | 0.05 | 0.28 |
| D452W | 0.13 | 0.05 | 0.05 | 0.05 | 0.05 | 0.07 | 0.17 | 0.05 | 0.24 |
| D452Y | 0.14 | 0.05 | 0.05 | 0.05 | 0.05 | 0.05 | 0.17 | 0.05 | 0.28 |
| R453A | 0.19 | 0.08 | *1.36* | 0.05 | 0.05 | 0.10 | 0.18 | 0.05 | 0.24 |
| R453C | 0.20 | 0.05 | 0.05 | 0.05 | 0.05 | 0.11 | 0.08 | 0.05 | 0.54 |
| R453D | 0.20 | 0.05 | 0.05 | 0.05 | 0.05 | 0.05 | 0.10 | 0.05 | 0.14 |
| R453E | 0.08 | 0.12 | *1.60* | 0.05 | 0.18 | 0.25 | 0.74 | 0.16 | 0.38 |
| R453F | 0.08 | 0.05 | 0.05 | 0.08 | 0.05 | 0.15 | 0.09 | 0.05 | 0.14 |
| R453I | 0.04 | 0.04 | 0.04 | 0.04 | 0.04 | 0.04 | 0.04 | 0.04 | 0.04 |
| R453K | 0.09 | 0.17 | 1.00 | 0.07 | 0.25 | 0.14 | 0.70 | 0.41 | 0.34 |
| R453L | 0.11 | 0.12 | *1.60* | 0.05 | 0.22 | 0.25 | 0.52 | 0.37 | 0.49 |
| R453M | 0.17 | 0.30 | *1.33* | 0.05 | 0.59 | 0.25 | 0.70 | 0.68 | 0.52 |
| R453N | 0.09 | 0.09 | 0.05 | 0.05 | 0.09 | 0.09 | 0.42 | 0.20 | 0.23 |
| R453P | 0.11 | 0.05 | 0.05 | 0.05 | 0.05 | 0.05 | 0.08 | 0.05 | 0.31 |
| R453Q | 0.10 | 0.12 | *1.61* | 0.05 | 0.25 | 0.06 | 0.62 | 0.40 | 0.63 |
| R453S | 0.05 | 0.10 | *1.52* | 0.05 | 0.06 | 0.28 | 0.73 | 0.26 | 0.18 |
| R453T | 0.17 | 0.05 | 0.05 | 0.05 | 0.05 | 0.05 | 0.11 | 0.05 | 0.09 |
| R453V | 0.15 | 0.05 | 0.05 | 0.05 | 0.05 | 0.05 | 0.12 | 0.05 | 0.16 |
| R453W | 0.19 | 0.05 | 0.05 | 0.05 | 0.05 | 0.08 | 0.05 | 0.05 | 0.25 |
| R453Y | 0.18 | 0.05 | 0.05 | 0.05 | 0.05 | 0.06 | 0.05 | 0.05 | 0.12 |
| N454A | *1.32* | 0.98 | 0.92 | 0.48 | 0.94 | 0.91 | 0.91 | 0.85 | 0.94 |
| N454C | 0.80 | 1.00 | 0.90 | 0.47 | 0.98 | 0.70 | 0.94 | 0.95 | 0.97 |
| N454D | 0.77 | 0.88 | 0.96 | 0.05 | 0.93 | 0.90 | 0.87 | 0.88 | 0.83 |
| N454F | 0.27 | 0.95 | 0.92 | 0.30 | *1.45* | *1.94* | *1.34* | *1.50* | *1.08* |
| N454G | 0.58 | 0.81 | 0.87 | 0.09 | 0.86 | *1.61* | 0.74 | 0.83 | 0.80 |
| N454K | 0.61 | 0.92 | 0.84 | 0.52 | 0.92 | *1.17* | 0.82 | 0.91 | 0.86 |

TABLE 3-1-continued

Performance Index Data of BGL1 SEL Variants (3,153)

| | | | | | | | | | |
|---|---|---|---|---|---|---|---|---|---|
| N454L | 0.52 | 0.81 | 0.86 | 0.32 | 0.88 | *1.65* | 0.79 | 0.85 | 0.69 |
| N454M | 0.49 | 0.83 | 0.78 | 0.33 | 0.88 | *1.12* | 0.80 | 0.85 | 0.72 |
| N454N | 1.00 | 1.00 | 1.00 | 1.00 | 1.00 | 1.00 | 1.00 | 1.00 | 1.00 |
| N454R | 0.62 | 0.77 | 0.88 | 0.35 | 0.79 | *1.08* | 0.79 | 0.84 | 0.65 |
| N454S | 0.62 | 0.88 | 0.86 | 0.39 | 0.88 | *1.66* | 0.81 | 0.85 | 0.82 |
| N454T | 0.62 | 0.82 | 0.86 | 0.30 | 0.85 | *1.19* | 0.78 | 0.83 | 0.72 |
| N454V | 0.49 | 0.96 | 0.86 | 0.43 | 0.99 | *1.14* | 0.93 | *1.03* | 0.84 |
| N455A | 1.00 | 0.94 | *1.00* | 0.54 | 0.93 | *1.01* | 0.90 | 0.93 | 0.96 |
| N455C | 0.81 | *1.14* | *1.06* | 0.27 | *1.13* | 0.93 | *1.15* | *1.22* | *1.21* |
| N455D | 0.43 | *1.48* | *1.11* | 0.94 | *1.75* | *2.43* | *1.79* | *2.08* | *1.82* |
| N455E | 0.65 | 0.81 | 0.98 | 0.21 | 0.89 | *1.58* | 0.78 | 0.81 | 0.91 |
| N455F | 0.70 | 0.84 | 0.96 | 0.40 | 0.89 | *1.25* | 0.83 | 0.83 | 0.83 |
| N455G | 0.73 | 0.81 | 0.91 | 0.26 | 0.82 | *2.69* | 0.77 | 0.82 | 0.75 |
| N455H | 0.59 | 0.93 | 0.95 | 0.56 | 0.98 | *1.35* | 0.95 | 0.99 | 0.89 |
| N455I | 0.49 | 0.64 | *1.01* | 0.05 | 0.84 | *1.76* | 0.77 | 0.86 | 0.66 |
| N455L | 0.60 | 0.78 | 0.87 | 0.16 | 0.78 | *1.32* | 0.76 | 0.82 | 0.59 |
| N455M | 0.48 | 0.78 | 0.93 | 0.25 | 0.86 | *1.48* | 0.79 | 0.91 | 0.78 |
| N455N | 1.00 | 1.00 | 1.00 | 1.00 | 1.00 | 1.00 | 1.00 | 1.00 | 1.00 |
| N455R | 0.79 | 0.79 | 0.96 | 0.21 | 0.77 | 0.73 | 0.75 | 0.78 | 0.57 |
| N455S | 0.54 | 0.95 | 0.94 | 0.39 | *1.03* | *1.09* | *1.00* | *1.09* | 0.82 |
| N455T | 0.41 | 0.70 | 0.92 | 0.22 | 0.88 | *1.18* | 0.82 | 0.89 | 0.71 |
| N455V | 0.37 | 0.76 | 0.91 | 0.11 | *1.00* | *1.32* | 0.94 | *1.05* | 0.58 |
| N455W | 0.38 | *1.25* | 0.91 | 0.45 | *1.44* | *1.44* | *1.49* | *1.65* | *1.45* |
| N455Y | 0.52 | 0.82 | 0.94 | 0.38 | 0.90 | *1.05* | 0.90 | 0.98 | 0.83 |
| H460A | 0.21 | 0.45 | 0.84 | 0.05 | 0.93 | 0.36 | *1.08* | *1.20* | 0.76 |
| H460C | 0.24 | 0.56 | 0.82 | 0.05 | 0.98 | 0.49 | *1.16* | *1.21* | 0.82 |
| H460D | 0.60 | 0.89 | 0.90 | 0.05 | 0.97 | 0.56 | *1.04* | 0.96 | *1.01* |
| H460E | 0.33 | 0.72 | 0.94 | 0.05 | *1.02* | 0.67 | *1.16* | *1.12* | 0.93 |
| H460F | 0.51 | 0.94 | 0.81 | 0.05 | 0.99 | 0.87 | *1.15* | *1.03* | *1.03* |
| H460G | 0.39 | 0.84 | 0.92 | 0.05 | *1.00* | 0.26 | *1.22* | *1.20* | *1.10* |
| H460H | 1.00 | 1.00 | 1.00 | 1.00 | 1.00 | 1.00 | 1.00 | 1.00 | 1.00 |
| H460I | 0.43 | 0.83 | 0.78 | 0.05 | 0.94 | 0.68 | *1.02* | *1.03* | 0.92 |
| H460K | 0.52 | 0.91 | 0.88 | 0.05 | 0.96 | 0.90 | *1.06* | *1.08* | *1.03* |
| H460L | 0.24 | 0.64 | 0.82 | 0.05 | 0.98 | 0.42 | *1.20* | *1.26* | 0.71 |
| H460M | 0.34 | 0.85 | 0.77 | 0.05 | *1.01* | 0.53 | *1.12* | *1.20* | 0.96 |
| H460N | 0.61 | 1.00 | 0.94 | 0.05 | 0.96 | 0.79 | 0.97 | *1.05* | 0.95 |

TABLE 3-1-continued

Performance Index Data of BGL1 SEL Variants (3,153)

| | | | | | | | | | |
|---|---|---|---|---|---|---|---|---|---|
| H460Q | 0.41 | 0.91 | 0.87 | 0.05 | *1.07* | 0.81 | *1.16* | *1.26* | *1.00* |
| H460R | 0.27 | 0.65 | 0.80 | 0.05 | 1.00 | 0.44 | *1.17* | *1.30* | 0.97 |
| H460S | 0.25 | 0.65 | 0.93 | 0.05 | *1.01* | 0.48 | *1.19* | *1.34* | 0.81 |
| H460V | 0.11 | 0.05 | 0.05 | 0.05 | 0.05 | 0.17 | 0.05 | 0.12 | 0.05 |
| H460W | 0.45 | 0.83 | 0.86 | 0.05 | 0.97 | 0.61 | *1.08* | *1.14* | 0.96 |
| H460Y | 0.53 | 0.92 | 0.89 | 0.05 | 0.98 | 0.95 | *1.04* | *1.09* | 0.93 |
| Q467A | 0.12 | 0.47 | *2.35* | 0.10 | 0.83 | *1.10* | 0.81 | 0.73 | 0.54 |
| Q467C | 0.18 | 0.54 | *1.02* | 0.14 | 0.82 | 0.91 | 0.77 | 0.62 | 0.58 |
| Q467D | 0.18 | 0.50 | *2.63* | 0.11 | 0.76 | 0.77 | 0.77 | 0.56 | 0.30 |
| Q467E | 0.13 | 0.42 | *1.04* | 0.10 | 0.71 | 0.66 | 0.72 | 0.57 | 0.67 |
| Q467H | 0.14 | 0.45 | *2.01* | 0.09 | 0.90 | 0.59 | 0.69 | 0.56 | 0.33 |
| Q467I | 0.10 | 0.39 | 0.83 | 0.06 | 0.85 | 0.78 | 0.76 | 0.49 | 0.42 |
| Q467K | 0.07 | 0.30 | *1.10* | 0.05 | 0.62 | 0.80 | 0.64 | 0.38 | 0.10 |
| Q467L | 0.18 | 0.41 | 0.85 | 0.11 | 0.61 | 0.58 | 0.54 | 0.44 | 0.40 |
| Q467N | 0.13 | 0.49 | *1.02* | 0.23 | 0.77 | 0.95 | 0.78 | 0.61 | 0.43 |
| Q467P | 0.08 | 0.29 | 0.05 | 0.11 | *1.07* | 0.86 | 0.59 | 0.34 | 0.63 |
| Q467Q | 1.00 | 1.00 | 1.00 | 1.00 | 1.00 | 1.00 | 1.00 | 1.00 | 1.00 |
| Q467S | 0.15 | 0.57 | *1.04* | 0.17 | *1.04* | 0.90 | 0.94 | 0.80 | 0.65 |
| Q467T | 0.09 | 0.34 | 0.05 | 0.05 | 0.68 | 0.52 | 0.53 | 0.28 | 0.81 |
| Q467V | 0.13 | 0.40 | *1.26* | 0.09 | 0.81 | 0.90 | 0.78 | 0.51 | 0.46 |
| Q467W | 0.16 | 0.44 | *1.37* | 0.07 | 0.72 | 0.63 | 0.73 | 0.50 | 0.60 |
| Q467Y | 0.15 | 0.32 | *2.10* | 0.05 | 0.53 | 0.55 | 0.55 | 0.40 | 0.38 |
| N473A | 0.74 | 0.90 | 0.99 | 0.81 | *1.00* | *1.34* | 0.88 | 0.81 | 0.92 |
| N473C | 0.94 | 0.92 | 0.91 | 0.80 | 0.92 | *1.04* | 0.83 | 0.78 | 0.83 |
| N473E | 0.67 | 0.98 | 0.99 | 0.87 | *1.02* | *1.39* | 0.91 | 0.84 | 0.92 |
| N473F | 0.14 | 0.22 | *1.05* | 0.06 | 0.60 | *1.25* | 0.56 | 0.60 | 0.25 |
| N473G | 0.61 | 0.96 | 0.97 | 0.94 | 0.97 | *1.10* | 0.94 | 0.83 | 0.89 |
| N473H | 0.83 | 0.90 | 0.95 | 0.83 | 0.89 | *1.14* | 0.87 | 0.77 | 0.75 |
| N473K | 0.33 | 0.59 | 0.94 | 0.52 | 0.88 | *1.19* | 0.80 | 0.77 | 0.75 |
| N473L | 0.56 | 0.93 | 0.98 | 0.84 | *1.00* | *1.35* | 0.94 | 0.83 | 0.84 |
| N473M | 0.58 | 0.86 | 0.96 | 0.84 | 0.93 | *1.12* | 0.84 | 0.80 | 0.69 |
| N473N | 1.00 | 1.00 | 1.00 | 1.00 | 1.00 | 1.00 | 1.00 | 1.00 | 1.00 |
| N473P | 0.29 | 0.42 | *1.08* | 0.30 | 0.76 | *1.17* | 0.63 | 0.61 | 0.44 |
| N473Q | 0.67 | 0.77 | *1.01* | 0.79 | 0.81 | *1.12* | 0.78 | 0.71 | 0.63 |
| N473R | 0.30 | 0.68 | *1.01* | 0.54 | *1.12* | *1.49* | 0.90 | 0.98 | 0.76 |

TABLE 3-1-continued

Performance Index Data of BGL1 SEL Variants (3,153)

| | | | | | | | | |
|---|---|---|---|---|---|---|---|---|
| N473S | *1.02* | *1.04* | *1.01* | *1.20* | 0.94 | *1.28* | 0.91 | 0.84 | 0.99 |
| N473T | 0.64 | 0.96 | *1.02* | 0.92 | 0.98 | *1.04* | 0.98 | 0.90 | 0.79 |
| N473V | 0.42 | 0.77 | *1.00* | 0.60 | 0.94 | *1.26* | 0.83 | 0.84 | 0.67 |
| N473W | 0.05 | 0.19 | 0.97 | 0.08 | *1.06* | *2.36* | 0.98 | *1.00* | 0.20 |
| S474A | 0.89 | 0.99 | 1.00 | 0.89 | *1.01* | *1.03* | 0.96 | *1.08* | *1.00* |
| S474C | 0.76 | *1.10* | 0.94 | 0.82 | *1.11* | *1.01* | *1.17* | *1.09* | *1.14* |
| S474D | *1.96* | 0.76 | *1.25* | *1.53* | *1.00* | *1.08* | *1.03* | 0.93 | 0.91 |
| S474E | 0.86 | 0.96 | 0.98 | 0.76 | 0.95 | 0.86 | 0.98 | *1.04* | *1.01* |
| S474F | 0.91 | *1.04* | 0.96 | 0.94 | 0.98 | *1.03* | *1.10* | *1.02* | *1.04* |
| S474G | *1.39* | 0.98 | *1.05* | *1.22* | *1.01* | *1.04* | *1.05* | 0.94 | 0.96 |
| S474I | 0.98 | *1.09* | 0.97 | *1.13* | 0.96 | *1.08* | *1.06* | 0.99 | 1.05 |
| S474K | *1.38* | 0.94 | *1.04* | *1.19* | *1.02* | *1.07* | *1.10* | *1.05* | 0.99 |
| S474L | 0.56 | *1.02* | *1.03* | 0.74 | *1.05* | 0.98 | *1.05* | *1.05* | 0.97 |
| S474M | 0.91 | *1.05* | *1.02* | *1.01* | 0.95 | *1.01* | *1.07* | 0.99 | *1.13* |
| S474N | *1.40* | *1.02* | *1.05* | *1.40* | *1.00* | *1.09* | *1.05* | *1.02* | *1.10* |
| S474P | 0.87 | *1.07* | 0.97 | 1.00 | 0.96 | 0.98 | *1.07* | *1.13* | 0.96 |
| S474Q | 0.95 | 0.96 | *1.00* | 0.94 | 0.92 | *1.02* | 1.00 | 0.90 | 0.90 |
| S474R | *1.23* | *1.02* | *1.00* | *1.35* | 0.97 | *1.15* | *1.09* | 0.91 | 0.99 |
| S474S | 1.00 | 1.00 | 1.00 | 1.00 | 1.00 | 1.00 | 1.00 | 1.00 | 1.00 |
| S474T | *1.03* | *1.05* | 0.97 | *1.19* | 0.97 | *1.09* | *1.08* | *1.03* | *1.04* |
| S474V | *1.37* | 0.98 | *1.08* | *1.30* | 0.99 | *1.08* | *1.06* | 0.99 | *1.05* |
| S474W | 0.04 | 0.04 | 0.04 | 0.04 | 0.04 | 0.04 | 0.04 | 0.04 | 0.04 |
| S474Y | *1.06* | *1.00* | 0.93 | *1.00* | 0.93 | 0.91 | 0.99 | 0.99 | *1.00* |
| N475I | 0.27 | *4.50* | *1.01* | 0.37 | *1.01* | *3.43* | *1.29* | *1.11* | 0.87 |
| N475K | 0.08 | 0.05 | *1.06* | 0.05 | 0.30 | *2.11* | *1.02* | 0.43 | 0.19 |
| N475L | 0.33 | *2.36* | *1.03* | 0.45 | 0.89 | *1.99* | *1.15* | 0.90 | 0.79 |
| N475M | 0.42 | *2.03* | 0.98 | 0.61 | *1.00* | *2.86* | *1.12* | *1.03* | 0.98 |
| N475N | 1.00 | 1.00 | 1.00 | 1.00 | 1.00 | 1.00 | 1.00 | 1.00 | 1.00 |
| N475P | 0.31 | *2.60* | *1.04* | 0.44 | 0.97 | *3.03* | *1.30* | 0.96 | 0.79 |
| N475Q | 0.59 | *1.46* | 0.95 | 0.72 | 1.00 | *1.52* | *1.06* | 0.91 | 0.91 |
| N475R | 0.62 | *1.31* | 0.94 | 0.70 | 0.98 | *1.54* | *1.10* | 0.94 | 0.84 |
| N475S | 0.23 | *16.69* | 0.99 | 0.53 | *1.38* | *3.29* | *1.96* | *1.70* | *1.24* |
| N475T | 0.21 | *256.40* | *1.04* | 0.32 | *1.03* | *2.63* | *1.47* | *1.17* | 0.80 |
| N475V | 0.34 | *2.39* | *1.04* | 0.46 | 0.98 | *1.83* | *1.11* | 0.93 | 0.78 |
| N475W | 0.40 | *2.03* | *1.01* | 0.54 | 0.99 | *1.80* | *1.19* | *1.04* | 0.88 |

TABLE 3-1-continued

Performance Index Data of BGL1 SEL Variants (3,153)

| | | | | | | | | | |
|---|---|---|---|---|---|---|---|---|---|
| N475Y | 0.41 | *2.02* | *1.02* | 0.50 | *1.07* | *1.56* | *1.26* | *1.05* | 0.76 |
| E489A | 0.04 | 0.04 | 0.04 | 0.04 | 0.04 | 0.04 | 0.04 | 0.04 | 0.04 |
| E489D | *1.16* | 0.94 | 0.97 | 0.99 | 0.99 | 0.94 | 0.94 | *1.01* | 0.96 |
| E489E | 1.00 | 1.00 | 1.00 | 1.00 | 1.00 | 1.00 | 1.00 | 1.00 | 1.00 |
| E489F | 0.04 | 0.04 | 0.04 | 0.04 | 0.04 | 0.04 | 0.04 | 0.04 | 0.04 |
| E489G | 0.04 | 0.04 | 0.04 | 0.04 | 0.04 | 0.04 | 0.04 | 0.04 | 0.04 |
| E489H | 0.04 | 0.04 | 0.04 | 0.04 | 0.04 | 0.04 | 0.04 | 0.04 | 0.04 |
| E489I | 0.13 | 0.05 | 0.05 | 0.05 | 0.05 | 0.05 | 0.05 | 0.11 | 0.33 |
| E489K | 0.04 | 0.04 | 0.04 | 0.04 | 0.04 | 0.04 | 0.04 | 0.04 | 0.04 |
| E489L | 0.04 | 0.04 | 0.04 | 0.04 | 0.04 | 0.04 | 0.04 | 0.04 | 0.04 |
| E489M | 0.04 | 0.04 | 0.04 | 0.04 | 0.04 | 0.04 | 0.04 | 0.04 | 0.04 |
| E489N | 0.14 | 0.23 | *1.02* | 0.13 | 0.82 | *1.05* | 0.62 | *1.07* | 0.56 |
| E489P | 0.04 | 0.04 | 0.04 | 0.04 | 0.04 | 0.04 | 0.04 | 0.04 | 0.04 |
| E489Q | 0.04 | 0.04 | 0.04 | 0.04 | 0.04 | 0.04 | 0.04 | 0.04 | 0.04 |
| E489R | 0.04 | 0.04 | 0.04 | 0.04 | 0.04 | 0.04 | 0.04 | 0.04 | 0.04 |
| E489S | 0.05 | 0.05 | 0.05 | 0.05 | 0.05 | 0.05 | 0.05 | 0.05 | 0.05 |
| E489T | 0.04 | 0.04 | 0.04 | 0.04 | 0.04 | 0.04 | 0.04 | 0.04 | 0.04 |
| E489V | 0.19 | 0.05 | 0.05 | 0.05 | 0.05 | 0.10 | 0.05 | 0.14 | 0.26 |
| E489W | 0.04 | 0.04 | 0.04 | 0.04 | 0.04 | 0.04 | 0.04 | 0.04 | 0.04 |
| E489Y | 0.04 | 0.04 | 0.04 | 0.04 | 0.04 | 0.04 | 0.04 | 0.04 | 0.04 |
| Q490A | 0.81 | *1.13* | 0.99 | 0.90 | 0.96 | 0.92 | 0.89 | 0.95 | 0.91 |
| Q490C | 0.61 | *6.60* | *1.01* | 0.79 | *1.12* | 0.95 | *1.02* | *1.12* | *1.11* |
| Q490E | 0.65 | *2.93* | 0.97 | 0.68 | 0.91 | 0.98 | 0.91 | 0.93 | *1.13* |
| Q490F | 0.51 | *10.91* | 0.92 | 0.61 | 0.99 | 0.91 | 0.90 | 0.86 | 1.00 |
| Q490G | 0.54 | *3.16* | *1.00* | 0.58 | 0.97 | 0.91 | 0.95 | 0.98 | *1.19* |
| Q490H | 0.47 | *9.13* | 0.90 | 0.62 | *1.04* | 0.86 | 0.96 | 0.98 | *1.08* |
| Q490K | 0.64 | *3.19* | 0.94 | 0.79 | 0.95 | 0.79 | 0.83 | 0.91 | 0.83 |
| Q490L | 0.54 | *2.26* | 0.96 | 0.84 | *1.07* | 0.89 | *1.03* | 1.00 | *1.17* |
| Q490P | 0.50 | 0.43 | 0.92 | 0.67 | 0.99 | *1.06* | 0.92 | 0.89 | 0.95 |
| Q490Q | 1.00 | 1.00 | 1.00 | 1.00 | 1.00 | 1.00 | 1.00 | 1.00 | 1.00 |
| Q490R | 0.57 | *1.92* | 0.99 | 0.75 | *1.01* | 0.86 | 0.91 | 0.95 | 0.96 |
| Q490S | 0.59 | *1.70* | 0.95 | 0.74 | 0.99 | 0.89 | 0.90 | 0.92 | 0.95 |
| Q490T | 0.74 | *1.36* | 0.96 | 0.96 | 1.00 | 0.85 | 0.93 | 1.00 | 0.88 |
| Q490V | 0.44 | *5.38* | 0.99 | 0.67 | *1.10* | 0.85 | *1.01* | *1.18* | *1.05* |
| Q490W | 0.40 | 0.48 | 0.99 | 0.74 | *1.36* | *1.05* | *1.30* | *1.40* | *1.32* |
| Q490Y | 0.57 | *1.45* | 0.97 | 0.76 | *1.04* | 0.97 | *1.02* | *1.14* | *1.01* |

TABLE 3-1-continued

Performance Index Data of BGL1 SEL Variants (3,153)

| L492A | 0.56 | *1.10* | 0.91 | 0.57 | *1.17* | *1.23* | *1.18* | *1.14* | 0.95 |
|---|---|---|---|---|---|---|---|---|---|
| L492D | 0.46 | *1.05* | 0.97 | 0.61 | *1.29* | *1.19* | *1.25* | *1.17* | 0.89 |
| L492F | 0.27 | 0.74 | 0.91 | 0.30 | *1.03* | *1.04* | 0.80 | *1.08* | 0.69 |
| L492G | 0.21 | 0.43 | 0.96 | 0.18 | 0.76 | 0.68 | 0.63 | 0.78 | 0.38 |
| L492H | 0.46 | *1.01* | 0.90 | 0.45 | 0.94 | 0.93 | *1.04* | *1.03* | 0.87 |
| L492I | 0.59 | 0.97 | 0.98 | 0.58 | 0.97 | *1.03* | *1.03* | *1.06* | 0.84 |
| L492K | 0.13 | 0.34 | 0.88 | 0.09 | 0.55 | 0.78 | 0.55 | 0.75 | 0.27 |
| L492L | 1.00 | 1.00 | 1.00 | 1.00 | 1.00 | 1.00 | 1.00 | 1.00 | 1.00 |
| L492M | 0.45 | 0.91 | 0.98 | 0.52 | 0.69 | *1.05* | 0.97 | 0.91 | 0.52 |
| L492N | 0.37 | *1.04* | 0.90 | 0.56 | 0.91 | 0.97 | *1.14* | *1.05* | 0.55 |
| L492P | 0.17 | 0.43 | 0.96 | 0.05 | 0.42 | 0.69 | 0.63 | 0.80 | 0.56 |
| L492Q | 0.48 | 0.97 | 0.93 | 0.46 | 0.76 | *1.00* | *1.03* | 1.00 | 0.79 |
| L492R | 0.17 | 0.50 | 0.95 | 0.17 | 0.62 | 0.82 | 0.80 | *1.01* | 0.30 |
| L492S | 0.12 | 0.05 | 0.05 | 0.05 | 0.08 | 0.05 | 0.05 | 0.12 | 0.17 |
| L492T | 0.39 | 0.99 | 0.95 | 0.48 | 0.86 | *1.04* | *1.07* | *1.00* | 0.54 |
| L492V | 0.13 | 0.05 | 0.05 | 0.05 | 0.05 | 0.16 | 0.05 | 0.13 | 0.05 |
| L492W | 0.37 | 0.85 | 0.86 | 0.35 | *1.01* | *1.05* | 0.97 | 0.97 | 0.54 |
| L492Y | 0.53 | 0.92 | *1.05* | 0.55 | *1.05* | 0.96 | *1.01* | *1.05* | 0.74 |
| Q496A | 0.17 | 0.61 | *1.02* | 0.15 | 0.90 | 0.90 | 0.92 | 0.76 | 0.67 |
| Q496C | 0.16 | 0.40 | 0.81 | 0.09 | 0.61 | 0.80 | 0.60 | 0.49 | 0.53 |
| Q496D | 0.16 | 0.43 | 0.96 | 0.05 | 0.67 | 0.71 | 0.67 | 0.43 | 0.51 |
| Q496F | 0.09 | 0.05 | 0.05 | 0.05 | 0.42 | 0.50 | 0.27 | 0.10 | 0.36 |
| Q496G | 0.17 | 0.53 | *1.07* | 0.16 | *1.00* | *1.04* | 0.80 | 0.60 | 0.53 |
| Q496K | 0.18 | 0.29 | *1.52* | 0.05 | 0.38 | 0.52 | 0.40 | 0.30 | 0.64 |
| Q496L | 0.13 | 0.05 | 0.05 | 0.05 | 0.35 | 0.27 | 0.29 | 0.10 | 0.56 |
| Q496N | 0.17 | 0.49 | *1.03* | 0.14 | 0.65 | 0.74 | 0.66 | 0.55 | 0.59 |
| Q496P | 0.13 | 0.36 | *1.37* | 0.16 | 0.56 | 0.60 | 0.83 | 0.44 | 0.16 |
| Q496Q | 1.00 | 1.00 | 1.00 | 1.00 | 1.00 | 1.00 | 1.00 | 1.00 | 1.00 |
| Q496S | 0.25 | 0.78 | 0.99 | 0.28 | 1.00 | *1.03* | *1.10* | 0.93 | 0.74 |
| Q496T | 0.15 | 0.44 | *2.52* | 0.10 | 0.74 | 0.52 | 0.69 | 0.45 | 0.64 |
| Q496V | 0.21 | 0.34 | *1.75* | 0.09 | 0.48 | 0.50 | 0.45 | 0.33 | 0.48 |
| Q496W | 0.07 | 0.56 | *1.48* | 0.09 | *1.34* | *1.37* | *1.46* | *1.02* | 0.47 |
| V497A | 0.78 | *1.07* | 0.98 | *1.05* | 0.96 | *1.01* | 0.90 | 0.84 | 0.90 |
| V497C | 0.74 | 0.96 | *1.09* | 0.77 | *1.02* | 0.98 | 0.97 | 0.95 | 0.95 |
| V497D | 0.05 | 0.05 | 0.05 | 0.05 | 0.07 | 0.46 | 0.05 | 0.05 | 0.17 |

TABLE 3-1-continued

Performance Index Data of BGL1 SEL Variants (3,153)

| | | | | | | | | | |
|---|---|---|---|---|---|---|---|---|---|
| V497E | 0.05 | 0.05 | 0.05 | 0.05 | 0.05 | 0.05 | 0.05 | 0.05 | 0.05 |
| V497F | 0.05 | 0.05 | 0.05 | 0.05 | 0.05 | 0.10 | 0.05 | 0.05 | 0.07 |
| V497G | 0.07 | 0.05 | 0.05 | 0.10 | 0.17 | 0.28 | 0.19 | 0.05 | 0.46 |
| V497H | 0.04 | 0.04 | 0.04 | 0.04 | 0.04 | 0.04 | 0.04 | 0.04 | 0.04 |
| V497I | 0.59 | 0.89 | 0.94 | *1.07* | 0.97 | *1.03* | 0.89 | 0.80 | 0.88 |
| V497K | 0.08 | 0.05 | 0.05 | 0.05 | 0.05 | 0.11 | 0.05 | 0.05 | 0.13 |
| V497M | 0.51 | 0.99 | 0.96 | *1.16* | *1.01* | 0.90 | 0.97 | 0.83 | 0.96 |
| V497N | 0.17 | 0.46 | *1.03* | 0.35 | 0.78 | 0.81 | 0.78 | 0.42 | 0.48 |
| V497Q | 0.05 | 0.05 | 0.05 | 0.05 | 0.05 | 0.33 | 0.05 | 0.05 | 0.13 |
| V497R | 0.06 | 0.05 | 0.05 | 0.05 | 0.09 | 0.47 | 0.19 | 0.05 | 0.17 |
| V497S | 0.05 | 0.05 | 0.05 | 0.05 | 0.05 | 0.05 | 0.05 | 0.05 | 0.05 |
| V497T | 0.45 | *1.05* | 0.94 | *1.21* | *1.08* | *1.05* | *1.08* | 0.90 | *1.04* |
| V497V | 1.00 | 1.00 | 1.00 | 1.00 | 1.00 | 1.00 | 1.00 | 1.00 | 1.00 |
| V497W | 0.04 | 0.04 | 0.04 | 0.04 | 0.04 | 0.04 | 0.04 | 0.04 | 0.04 |
| V497Y | 0.04 | 0.04 | 0.04 | 0.04 | 0.04 | 0.04 | 0.04 | 0.04 | 0.04 |
| K498A | 0.87 | 0.99 | *1.13* | 0.76 | *1.05* | *1.08* | 0.98 | *1.03* | *1.07* |
| K498C | 0.63 | 0.91 | *1.15* | 0.56 | *1.06* | 0.98 | *1.09* | 0.97 | 0.96 |
| K498E | 0.45 | *1.00* | *1.07* | 0.60 | *1.15* | 0.94 | *1.06* | *1.07* | *1.15* |
| K498F | 0.29 | 0.81 | *1.04* | 0.38 | *1.16* | *1.03* | *1.10* | *1.04* | 0.83 |
| K498G | 0.37 | 0.81 | *1.01* | 0.40 | *1.00* | 0.87 | *1.01* | 0.88 | 0.81 |
| K498H | 0.66 | 0.92 | *1.12* | 0.68 | 0.99 | *1.08* | 0.99 | 0.97 | 0.94 |
| K498I | 0.43 | 0.91 | *1.07* | 0.53 | *1.09* | *1.01* | *1.01* | 0.95 | 0.72 |
| K498K | 1.00 | 1.00 | 1.00 | 1.00 | 1.00 | 1.00 | 1.00 | 1.00 | 1.00 |
| K498L | 0.69 | *1.01* | 0.98 | 0.79 | 0.89 | 0.89 | 0.89 | 0.88 | 0.59 |
| K498M | 0.44 | *1.01* | 0.95 | 0.62 | *1.12* | 0.94 | 0.97 | *1.03* | *1.18* |
| K498N | 0.59 | 0.93 | 0.98 | 0.68 | 0.96 | *1.04* | 0.95 | 0.95 | 0.78 |
| K498P | 0.05 | 0.05 | 0.05 | 0.05 | 0.05 | 0.05 | 0.05 | 0.05 | 0.05 |
| K498Q | 0.67 | 0.93 | *1.09* | 0.81 | 0.97 | *1.07* | 0.94 | 0.94 | 0.87 |
| K498R | 0.60 | 0.85 | *1.06* | 0.66 | 0.99 | 0.89 | 0.99 | 0.96 | 0.82 |
| K498S | 0.54 | 0.88 | *1.03* | 0.63 | 0.97 | 0.88 | 0.76 | 0.81 | 0.85 |
| K498T | 0.48 | 0.90 | *1.02* | 0.60 | *1.04* | 0.97 | 0.92 | 0.93 | 0.98 |
| K498V | 0.55 | *1.01* | 0.99 | 0.63 | 0.98 | 0.92 | 0.95 | *1.02* | 0.97 |
| K498W | 0.06 | 0.23 | 0.05 | 0.05 | 0.21 | 0.09 | 0.10 | 0.05 | 0.20 |
| K498Y | 0.44 | 0.90 | *1.00* | 0.52 | *1.02* | 0.90 | 0.98 | 0.92 | 0.77 |
| D521A | *1.04* | *1.02* | 0.97 | *1.05* | *1.03* | *1.31* | 0.89 | 0.78 | *1.03* |

TABLE 3-1-continued

Performance Index Data of BGL1 SEL Variants (3,153)

| | | | | | | | | |
|---|---|---|---|---|---|---|---|---|
| D521C | 0.15 | 0.55 | 0.93 | 0.25 | *1.48* | *2.37* | *1.63* | *1.16* | 0.76 |
| D521D | 1.00 | 1.00 | 1.00 | 1.00 | 1.00 | 1.00 | 1.00 | 1.00 | 1.00 |
| D521E | 0.85 | 0.88 | *1.04* | 0.88 | 0.92 | *1.00* | 0.88 | 0.70 | 0.94 |
| D521F | 0.82 | 0.87 | *1.07* | 0.90 | 0.87 | *1.18* | 0.81 | 0.69 | 0.91 |
| D521G | 0.44 | 0.70 | 0.99 | 0.56 | 0.93 | *1.09* | 0.92 | 0.67 | 0.85 |
| D521H | 0.89 | 0.94 | 0.97 | 0.90 | 0.93 | *1.05* | 0.85 | 0.75 | 0.91 |
| D521I | 0.47 | 0.71 | 0.97 | 0.49 | 0.86 | *1.43* | 0.86 | 0.69 | 0.79 |
| D521K | 0.47 | 0.78 | 0.98 | 0.57 | 0.92 | *1.28* | 0.94 | 0.75 | 0.72 |
| D521L | 0.72 | 0.89 | 1.00 | 0.82 | 0.92 | *1.26* | 0.89 | 0.72 | 0.95 |
| D521M | 0.62 | 0.87 | 0.90 | 0.75 | 0.94 | *1.43* | 0.90 | 0.75 | 0.99 |
| D521P | 0.24 | 0.40 | *1.06* | 0.26 | 0.83 | *1.22* | 0.77 | 0.61 | 0.80 |
| D521R | 0.43 | 0.73 | 0.98 | 0.50 | 0.95 | *1.34* | 0.91 | 0.73 | 0.81 |
| D521S | 0.92 | 0.98 | 0.94 | *1.05* | 0.97 | *1.22* | 0.87 | 0.79 | *1.05* |
| D521T | 0.66 | 0.88 | *1.02* | 0.79 | 0.91 | *1.07* | 0.89 | 0.83 | 1.00 |
| D521V | 0.56 | 0.89 | *1.02* | 0.76 | 0.95 | *1.03* | 0.92 | 0.66 | 0.90 |
| D521W | 0.63 | 0.95 | 1.00 | 0.76 | *1.06* | *1.66* | *1.03* | 0.76 | *1.16* |
| D521Y | 0.22 | 0.58 | 0.87 | 0.05 | 0.87 | *1.60* | *1.21* | 0.88 | *1.13* |
| V522A | 0.86 | *1.08* | 1.00 | 0.73 | *1.05* | *1.26* | *1.02* | *1.09* | 0.94 |
| V522C | 0.90 | *1.21* | 1.00 | 0.89 | *1.08* | *1.43* | *1.09* | *1.17* | *1.09* |
| V522F | 0.51 | *1.42* | 0.99 | 0.51 | 0.92 | *2.44* | *1.03* | 0.97 | 0.77 |
| V522G | 0.11 | 0.05 | *1.00* | 0.13 | 0.91 | *5.72* | *1.53* | *1.32* | 0.54 |
| V522H | 0.73 | *1.27* | 0.90 | 0.81 | 0.99 | *1.29* | 1.00 | 0.93 | 0.84 |
| V522I | 0.56 | *1.32* | 0.92 | 0.57 | 0.97 | *1.80* | 0.98 | 0.92 | 0.70 |
| V522K | 0.36 | *2.44* | *1.01* | 0.43 | *1.03* | *2.09* | *1.13* | *1.12* | 0.81 |
| V522L | 0.46 | *1.83* | 0.99 | 0.57 | *1.03* | *1.74* | *1.26* | *1.13* | 0.92 |
| V522M | 0.60 | *1.45* | 0.95 | 0.70 | *1.01* | *1.57* | *1.04* | *1.06* | 0.83 |
| V522N | 0.19 | 0.05 | *1.02* | 0.21 | 0.68 | *3.16* | *1.08* | 0.86 | 0.48 |
| V522P | 0.18 | 0.05 | 0.84 | 0.14 | 0.71 | *2.34* | *1.18* | 0.87 | 0.59 |
| V522Q | 0.37 | *2.26* | 0.94 | 0.42 | *1.04* | *2.41* | *1.31* | *1.20* | 0.76 |
| V522R | 0.30 | *3.23* | 0.94 | 0.39 | *1.02* | *3.23* | *1.28* | *1.15* | 0.92 |
| V522S | 0.46 | *1.69* | 0.96 | 0.55 | *1.05* | *2.11* | *1.19* | *1.05* | *1.04* |
| V522T | 0.51 | *1.50* | 0.98 | 0.59 | 0.97 | *1.51* | *1.06* | *1.01* | 0.98 |
| V522V | 1.00 | 1.00 | 1.00 | 1.00 | 1.00 | 1.00 | 1.00 | 1.00 | 1.00 |
| V522W | 0.24 | *11.89* | 0.98 | 0.49 | *1.48* | *2.65* | *2.09* | *2.05* | *1.30* |
| V522Y | 0.56 | *1.37* | 0.96 | 0.56 | 1.00 | *2.10* | *1.21* | *1.03* | *1.15* |
| K534A | 0.69 | 0.89 | 0.90 | 0.49 | 0.95 | 0.95 | 0.92 | 0.85 | 0.90 |

TABLE 3-1-continued

Performance Index Data of BGL1 SEL Variants (3,153)

| | | | | | | | | | |
|---|---|---|---|---|---|---|---|---|---|
| K534C | 0.63 | 0.99 | 0.92 | 0.62 | *1.07* | *1.23* | *1.10* | *1.06* | *1.11* |
| K534D | 0.19 | 0.50 | *1.01* | 0.18 | *1.13* | *1.43* | *1.18* | *1.09* | 0.87 |
| K534E | 0.48 | 0.97 | *1.04* | 0.64 | *1.12* | *1.10* | *1.20* | *1.09* | *1.16* |
| K534F | 0.68 | *1.02* | 0.99 | 0.65 | *1.05* | *1.13* | *1.04* | 0.97 | *1.07* |
| K534G | 0.22 | 0.46 | *1.04* | 0.05 | 0.86 | *1.00* | *1.00* | 0.87 | 0.77 |
| K534H | 0.55 | 0.76 | *1.01* | 0.43 | 0.90 | 0.99 | 0.85 | 0.90 | 0.81 |
| K534I | 0.66 | 0.84 | *1.04* | 0.57 | 0.93 | 0.96 | 0.87 | 0.89 | 0.83 |
| K534K | 1.00 | 1.00 | 1.00 | 1.00 | 1.00 | 1.00 | 1.00 | 1.00 | 1.00 |
| K534M | 0.53 | 0.79 | 0.94 | 0.41 | 0.90 | 0.88 | 0.86 | 0.88 | 0.76 |
| K534N | 0.65 | 0.91 | *1.08* | 0.56 | *1.01* | *1.09* | 0.97 | 0.95 | *1.06* |
| K534P | 0.04 | 0.04 | 0.04 | 0.04 | 0.04 | 0.04 | 0.04 | 0.04 | 0.04 |
| K534Q | *1.17* | 0.97 | *1.05* | 0.83 | 0.94 | 0.91 | 0.89 | 0.98 | 0.97 |
| K534R | 0.84 | 0.98 | 0.98 | 0.81 | *1.02* | *1.05* | 0.98 | *1.10* | 0.98 |
| K534S | 0.53 | 0.78 | *1.03* | 0.48 | 0.88 | 0.93 | 0.85 | 0.88 | 0.84 |
| K534T | 0.62 | 0.78 | *1.02* | 0.52 | 0.88 | 0.95 | 0.82 | 0.89 | 0.80 |
| K534V | 0.75 | *1.03* | *1.06* | 0.70 | *1.02* | *1.18* | *1.08* | *1.07* | *1.07* |
| K534W | 0.16 | 0.05 | 0.05 | 0.05 | 0.05 | 0.17 | 0.11 | 0.05 | 0.26 |
| R542A | *1.34* | 0.98 | *1.02* | 0.91 | 0.95 | *1.05* | *1.09* | *1.09* | *1.36* |
| R542C | 0.76 | *1.17* | *1.04* | 0.47 | 0.93 | *1.14* | 0.98 | *1.09* | *1.11* |
| R542D | *1.08* | 0.95 | *1.08* | 0.44 | 0.89 | *1.15* | *1.01* | *1.03* | *1.20* |
| R542E | 0.51 | *1.79* | 0.90 | 0.37 | 0.90 | *1.10* | 0.92 | *1.16* | *1.19* |
| R542F | 0.55 | *1.57* | *1.05* | 0.38 | 0.92 | *1.30* | 0.95 | *1.15* | *1.08* |
| R542G | 0.83 | *1.09* | 0.99 | 0.47 | 0.93 | *1.07* | 0.97 | *1.05* | *1.21* |
| R542H | 0.60 | *1.62* | 0.92 | 0.49 | 0.89 | *1.01* | 0.94 | *1.09* | 0.86 |
| R542I | 0.54 | *1.78* | *1.04* | 0.05 | 0.91 | *1.35* | *1.02* | *1.15* | 0.98 |
| R542K | 0.81 | *1.07* | *1.05* | 0.60 | 0.81 | *1.11* | 0.96 | 0.99 | *1.09* |
| R542L | 0.54 | *1.76* | 0.86 | 0.41 | 0.93 | *1.19* | *1.03* | *1.18* | *1.35* |
| R542M | 0.55 | *1.69* | 0.89 | 0.42 | 0.96 | *1.18* | 0.97 | *1.17* | *1.24* |
| R542N | 0.90 | *1.28* | 0.88 | 0.70 | 0.90 | *1.35* | *1.10* | *1.10* | *1.57* |
| R542P | 0.54 | *1.17* | *1.13* | 0.18 | 0.89 | *1.32* | 0.69 | 0.91 | 0.64 |
| R542Q | 0.62 | *1.37* | *1.01* | 0.39 | 0.87 | *1.48* | 0.87 | *1.02* | *1.02* |
| R542R | 1.00 | 1.00 | 1.00 | 1.00 | 1.00 | 1.00 | 1.00 | 1.00 | 1.00 |
| R542S | 0.68 | *1.33* | *1.06* | 0.55 | *1.02* | *1.09* | 0.98 | *1.15* | 0.85 |
| R542T | 0.75 | *1.16* | 0.99 | 0.53 | 0.97 | *1.17* | *1.03* | *1.12* | *1.30* |
| R542V | 0.74 | *1.32* | 0.82 | 0.57 | 0.90 | *1.19* | 0.97 | *1.05* | *1.05* |

TABLE 3-1-continued

Performance Index Data of BGL1 SEL Variants (3,153)

| | | | | | | | | |
|---|---|---|---|---|---|---|---|---|
| R542W | 0.60 | *1.64* | *1.03* | 0.45 | 0.99 | *1.17* | *1.09* | *1.20* | *1.08* |
| R542Y | 0.62 | *1.33* | *1.04* | 0.44 | 0.94 | *1.04* | 0.96 | *1.05* | 0.90 |
| G547A | 0.38 | *1.47* | *1.08* | *1.55* | *1.73* | *1.27* | *1.91* | *2.15* | *1.67* |
| G547C | 0.56 | 0.95 | *1.02* | 0.88 | *1.06* | 0.96 | 0.93 | *1.12* | 0.88 |
| G547E | *1.25* | 0.96 | *1.04* | *1.31* | 0.85 | 0.97 | 0.71 | 0.57 | 0.74 |
| G547F | 0.54 | 0.76 | *1.10* | 0.83 | 0.95 | 0.74 | 0.80 | 0.79 | 0.75 |
| G547G | 1.00 | 1.00 | 1.00 | 1.00 | 1.00 | 1.00 | 1.00 | 1.00 | 1.00 |
| G547I | 0.63 | 0.80 | 0.99 | 0.86 | 0.90 | 0.76 | 0.78 | 0.82 | 0.79 |
| G547K | 0.81 | 0.87 | *1.05* | *1.02* | 0.90 | 0.87 | 0.80 | 0.87 | 0.77 |
| G547L | *1.26* | *1.11* | *1.08* | *1.52* | 0.93 | *1.01* | 0.79 | 0.86 | 0.91 |
| G547N | 0.37 | 0.59 | *1.04* | 0.61 | 0.95 | 0.76 | 0.73 | 0.82 | 0.80 |
| G547P | *1.02* | *1.09* | *1.08* | *1.44* | 0.97 | 0.89 | 0.91 | 0.90 | 0.92 |
| G547Q | 0.45 | 0.67 | *1.11* | 0.74 | 0.95 | 0.80 | 0.76 | 0.80 | 0.73 |
| G547R | 0.77 | 0.96 | *1.02* | *1.06* | 0.96 | 0.91 | 0.86 | 0.94 | 0.84 |
| G547T | 0.63 | 0.82 | *1.10* | 0.96 | 0.96 | 0.81 | 0.83 | 0.86 | 0.83 |
| G547V | 0.75 | 0.93 | *1.09* | *1.19* | 0.97 | 0.91 | 0.82 | 0.83 | 0.91 |
| G547W | 0.04 | 0.04 | 0.04 | 0.04 | 0.04 | 0.04 | 0.04 | 0.04 | 0.04 |
| G547Y | 0.61 | 0.80 | *1.04* | 0.87 | 0.96 | 0.78 | 0.82 | 0.86 | 0.92 |
| S548A | 0.05 | 0.05 | 0.05 | 0.05 | 0.05 | 0.05 | 0.05 | 0.05 | 0.05 |
| S548C | 0.87 | *1.14* | 0.94 | *1.07* | *1.05* | 0.92 | *1.03* | 0.96 | *1.04* |
| S548E | *1.05* | *1.12* | *1.02* | *1.20* | *1.05* | 0.89 | *1.02* | 0.91 | *1.01* |
| S548F | *1.02* | *1.19* | *1.03* | *1.41* | *1.05* | 0.93 | *1.10* | 0.92 | *1.03* |
| S548H | *1.14* | *1.01* | 0.99 | *1.20* | 0.97 | 0.86 | 0.90 | 0.84 | 0.79 |
| S548I | 0.91 | *1.12* | *1.06* | *1.17* | 0.98 | 0.82 | 1.00 | 0.88 | 0.97 |
| S548K | 0.50 | 0.98 | 0.97 | 0.60 | 0.88 | 0.78 | 0.84 | 0.84 | 0.69 |
| S548L | *1.10* | *1.14* | *1.05* | *1.47* | *1.03* | *1.02* | *1.05* | 0.91 | 0.95 |
| S548M | 0.74 | *1.17* | 0.97 | *1.01* | *1.00* | 0.94 | 0.96 | 0.88 | 0.88 |
| S548N | 0.50 | *1.26* | 0.98 | 0.83 | 0.96 | 0.92 | *1.12* | 0.96 | 0.79 |
| S548Q | 0.46 | *1.12* | *1.10* | 0.73 | *1.01* | 0.96 | *1.05* | 0.97 | 0.73 |
| S548R | 0.53 | *1.04* | 0.93 | 0.73 | 0.84 | 0.89 | 0.86 | 0.86 | 0.61 |
| S548S | 1.00 | 1.00 | 1.00 | 1.00 | 1.00 | 1.00 | 1.00 | 1.00 | 1.00 |
| S548T | 0.56 | *1.34* | *1.02* | 0.97 | *1.15* | 0.94 | *1.23* | *1.11* | 0.89 |
| S548V | 0.65 | *1.17* | *1.01* | *1.01* | 0.91 | 0.92 | 0.98 | 0.90 | 0.74 |
| S548W | 0.77 | *1.36* | *1.02* | *1.13* | *1.16* | 0.94 | *1.25* | 0.96 | *1.04* |
| S548Y | 0.55 | *1.09* | 0.95 | 0.81 | 0.98 | 0.89 | 0.94 | 0.96 | 0.72 |

TABLE 3-1-continued

Performance Index Data of BGL1 SEL Variants (3,153)

| | | | | | | | | | |
|---|---|---|---|---|---|---|---|---|---|
| E553A | 0.42 | 0.50 | 0.87 | 0.13 | 0.70 | 0.71 | 0.75 | 0.85 | 0.67 |
| E553C | 0.33 | 0.35 | 0.95 | 0.12 | 0.54 | 0.59 | 0.56 | 0.68 | 0.27 |
| E553D | 0.38 | 0.30 | *1.15* | 0.14 | 0.59 | 0.56 | 0.56 | 0.51 | 0.47 |
| E553E | 1.00 | 1.00 | 1.00 | 1.00 | 1.00 | 1.00 | 1.00 | 1.00 | 1.00 |
| E553H | 0.41 | 0.33 | 0.95 | 0.05 | 0.53 | 0.49 | 0.42 | 0.47 | 0.44 |
| E553I | 0.11 | 0.22 | *1.08* | 0.08 | 0.75 | 0.83 | 0.99 | *1.18* | 0.94 |
| E553K | 0.25 | 0.22 | *1.04* | 0.13 | 0.40 | 0.42 | 0.46 | 0.61 | 0.39 |
| E553M | 0.24 | 0.26 | 0.94 | 0.10 | 0.47 | 0.48 | 0.52 | 0.61 | 0.55 |
| E553N | 0.28 | 0.26 | 0.88 | 0.25 | 0.46 | 0.66 | 0.48 | 0.63 | *1.09* |
| E553Q | 0.19 | 0.14 | *1.22* | 0.09 | 0.35 | 0.47 | 0.28 | 0.44 | 0.90 |
| E553R | 0.25 | 0.20 | 0.87 | 0.07 | 0.33 | 0.36 | 0.40 | 0.51 | 0.22 |
| E553V | 0.19 | 0.16 | 0.93 | 0.08 | 0.36 | 0.38 | 0.29 | 0.45 | 0.79 |
| E553W | 0.36 | 0.28 | *1.04* | 0.12 | 0.47 | 0.49 | 0.44 | 0.41 | 0.56 |
| E553Y | 0.10 | 0.23 | *1.25* | 0.05 | 0.88 | 0.51 | 0.75 | *1.04* | 0.65 |
| G554A | 0.87 | 1.00 | *1.02* | 0.69 | 0.98 | *1.15* | *1.04* | 1.00 | 0.98 |
| G554C | 0.62 | 0.95 | *1.08* | 0.59 | *1.03* | *1.45* | *1.09* | *1.17* | *1.10* |
| G554D | 0.99 | *1.03* | *1.07* | 0.75 | *1.03* | *1.10* | *1.09* | *1.01* | 0.96 |
| G554F | 0.43 | 0.95 | *1.04* | 0.44 | *1.07* | *1.40* | *1.17* | *1.20* | *1.14* |
| G554G | 1.00 | 1.00 | 1.00 | 1.00 | 1.00 | 1.00 | 1.00 | 1.00 | 1.00 |
| G554H | 0.59 | 0.94 | *1.03* | 0.60 | *1.01* | *1.05* | *1.08* | *1.02* | 0.94 |
| G554K | 0.80 | 0.84 | *1.04* | 0.74 | 0.82 | 0.95 | 0.86 | 0.83 | 0.75 |
| G554L | 0.74 | *1.04* | *1.04* | 0.56 | 0.97 | *1.05* | *1.11* | 0.97 | 0.89 |
| G554M | 0.62 | *1.03* | *1.02* | 0.74 | *1.01* | 0.97 | *1.03* | 0.96 | 0.77 |
| G554P | 0.04 | 0.04 | 0.04 | 0.04 | 0.04 | 0.04 | 0.04 | 0.04 | 0.04 |
| G554Q | 0.86 | *1.05* | *1.12* | *1.12* | *1.04* | 0.87 | *1.10* | *1.06* | *1.00* |
| G554R | 0.84 | 0.85 | *1.04* | 0.86 | 0.83 | 0.97 | 0.82 | 0.77 | 0.89 |
| G554S | 0.31 | 0.71 | *1.01* | 0.40 | 0.92 | 0.96 | 0.94 | 0.76 | 0.61 |
| G554T | 0.62 | 0.95 | *1.00* | 0.71 | 0.93 | 1.00 | 0.98 | 0.90 | 0.78 |
| G554V | 0.55 | 0.88 | 0.95 | 0.47 | 0.94 | *1.01* | 0.94 | 1.00 | 0.66 |
| G554W | 0.47 | *1.07* | *1.02* | 0.54 | *1.17* | *1.43* | *1.27* | *1.24* | *1.00* |
| L555A | 0.69 | 0.97 | 0.63 | 0.51 | 0.97 | *1.01* | 0.95 | 0.92 | 0.82 |
| L555C | 0.88 | *1.03* | 0.77 | 0.80 | *1.00* | *1.05* | *1.01* | 0.98 | 0.90 |
| L555D | 0.69 | 0.86 | 0.77 | 0.59 | *1.03* | *1.11* | 0.98 | *1.02* | 0.77 |
| L555E | 0.36 | 0.71 | 0.60 | 0.44 | *1.04* | *1.04* | *1.06* | *1.06* | 0.75 |
| L555F | 0.49 | 0.84 | 0.60 | 0.54 | 0.98 | *1.07* | 0.96 | *1.22* | 0.78 |
| L555G | 0.50 | 0.95 | 0.64 | 0.53 | *1.12* | *1.16* | *1.11* | *1.16* | 0.87 |

TABLE 3-1-continued

Performance Index Data of BGL1 SEL Variants (3,153)

| | | | | | | | | |
|---|---|---|---|---|---|---|---|---|
| L555H | 0.45 | 0.86 | 0.64 | 0.42 | *1.03* | *1.15* | *1.08* | *1.08* | 0.97 |
| L555I | 0.69 | *1.00* | 0.66 | 0.73 | 0.95 | *1.05* | 0.93 | 0.96 | 0.82 |
| L555K | 0.47 | 0.89 | 0.68 | 0.45 | *1.10* | *1.24* | *1.20* | *1.18* | 0.89 |
| L555L | 1.00 | 1.00 | 1.00 | 1.00 | 1.00 | 1.00 | 1.00 | 1.00 | 1.00 |
| L555M | 0.60 | 0.97 | 0.66 | 0.66 | 1.00 | 0.93 | *1.00* | *1.05* | 0.87 |
| L555N | 0.63 | 0.94 | 0.68 | 0.63 | *1.01* | *1.08* | 0.89 | 0.96 | 0.76 |
| L555P | 0.43 | 0.92 | 0.59 | 0.53 | *1.02* | *1.15* | *1.12* | *1.07* | 0.84 |
| L555Q | 0.61 | 0.90 | 0.64 | 0.53 | 0.97 | *1.12* | *1.01* | *1.02* | 0.77 |
| L555R | 0.16 | 0.05 | 0.05 | 0.05 | 0.05 | 0.21 | 0.05 | 0.05 | 0.05 |
| L555S | 0.58 | 0.91 | 0.66 | 0.51 | 0.93 | 0.85 | 0.99 | 0.93 | 0.75 |
| L555T | 0.62 | 0.97 | 0.67 | 0.65 | 0.99 | 0.99 | 0.97 | *1.04* | 0.77 |
| L555V | 0.90 | *1.09* | 0.76 | 0.82 | 0.99 | *1.06* | 1.00 | *1.05* | 0.91 |
| L555W | 0.39 | 0.73 | 0.59 | 0.25 | 0.89 | *1.13* | 0.94 | *1.02* | 0.87 |
| L555Y | 0.58 | 0.91 | 0.63 | 0.43 | 0.97 | *1.14* | 0.98 | *1.05* | 0.78 |
| K560A | 0.63 | 0.80 | *1.18* | 0.44 | *1.06* | 0.96 | 0.84 | 0.81 | 1.00 |
| K560C | 0.59 | 0.73 | *1.16* | 0.32 | 0.93 | 0.93 | 0.78 | 0.83 | 0.93 |
| K560D | 0.05 | 0.05 | 0.05 | 0.05 | 0.05 | 0.05 | 0.05 | 0.05 | 0.05 |
| K560E | 0.43 | 0.69 | *1.16* | 0.05 | *1.01* | 0.82 | 0.80 | 0.74 | 0.97 |
| K560G | 0.40 | 0.74 | *1.08* | 0.29 | *1.05* | 0.94 | 0.81 | 0.74 | 0.95 |
| K560H | *1.01* | 0.90 | *1.10* | 0.42 | 0.98 | *1.01* | 0.87 | 0.83 | *1.00* |
| K560I | 0.19 | 0.33 | *1.19* | 0.11 | 0.76 | 0.60 | 0.55 | 0.42 | 0.49 |
| K560K | 1.00 | 1.00 | 1.00 | 1.00 | 1.00 | 1.00 | 1.00 | 1.00 | 1.00 |
| K560L | 0.63 | 0.83 | *1.10* | 0.49 | 1.00 | 0.88 | 0.82 | 0.82 | 0.96 |
| K560M | 0.67 | 0.84 | *1.11* | 0.52 | 0.97 | 0.87 | 0.83 | 0.86 | 0.94 |
| K560N | 0.25 | 0.51 | *1.04* | 0.15 | 0.90 | 0.72 | 0.66 | 0.59 | 0.50 |
| K560P | 0.12 | 0.55 | *1.09* | 0.10 | *1.49* | *1.12* | *1.31* | 0.94 | 0.89 |
| K560Q | 0.65 | 0.80 | *1.20* | 0.09 | 0.97 | 0.79 | 0.82 | 0.82 | 0.79 |
| K560R | 0.72 | 0.98 | *1.03* | 0.90 | *1.01* | *1.05* | 0.92 | 0.94 | 0.78 |
| K560S | 0.37 | 0.57 | *1.24* | 0.27 | 0.98 | 0.92 | 0.76 | 0.69 | 0.96 |
| K560T | 0.39 | 0.66 | *1.12* | 0.26 | 0.94 | 0.74 | 0.73 | 0.68 | 0.74 |
| K560V | 0.19 | 0.39 | *1.11* | 0.10 | 0.83 | 0.68 | 0.59 | 0.36 | 0.58 |
| K560W | 0.64 | 0.90 | 0.99 | 0.07 | *1.00* | *1.02* | 0.91 | 0.76 | 0.94 |
| K560Y | 0.50 | 0.78 | *1.05* | 0.45 | 0.98 | 0.87 | 0.85 | 0.90 | 0.66 |
| H561A | 0.68 | 0.05 | 0.05 | 0.37 | 0.94 | *1.04* | 0.91 | *1.01* | 1.00 |
| H561C | 0.63 | 0.80 | *1.04* | 0.75 | 0.97 | *1.18* | 0.96 | *1.06* | 0.91 |

TABLE 3-1-continued

Performance Index Data of BGL1 SEL Variants (3,153)

| | | | | | | | | | |
|---|---|---|---|---|---|---|---|---|---|
| H561D | 0.54 | 0.50 | *1.20* | 0.53 | 0.93 | *1.32* | 0.90 | *1.01* | 0.85 |
| H561E | 0.36 | 0.05 | 0.05 | 0.47 | 1.00 | *1.21* | 0.88 | 0.92 | 0.88 |
| H561F | 0.43 | 0.05 | 0.05 | 0.54 | 0.89 | *1.15* | 0.84 | 0.85 | *1.00* |
| H561G | 0.57 | 0.94 | *1.10* | 0.87 | *1.00* | *1.11* | 0.99 | *1.03* | 1.08 |
| H561H | 1.00 | 1.00 | 1.00 | 1.00 | 1.00 | 1.00 | 1.00 | 1.00 | 1.00 |
| H561I | 0.51 | 0.56 | 1.00 | 0.53 | *1.05* | *1.10* | *1.07* | 0.97 | *1.09* |
| H561M | 0.61 | *1.31* | *1.10* | 0.82 | *1.10* | *1.19* | *1.15* | *1.00* | *1.66* |
| H561N | 0.36 | *1.11* | *1.01* | *1.39* | *1.17* | *1.16* | *1.18* | 0.94 | *1.02* |
| H561P | 0.30 | 0.05 | 0.05 | 0.48 | 0.22 | 0.20 | 0.12 | 0.05 | 0.25 |
| H561Q | 0.55 | 0.49 | 0.93 | 0.61 | *1.14* | *1.11* | *1.20* | 0.92 | 0.87 |
| H561R | 0.89 | 0.42 | 0.05 | 0.27 | 0.84 | 0.75 | 0.88 | 0.74 | 0.91 |
| H561S | 0.40 | 0.41 | 0.97 | 0.49 | *1.19* | *1.18* | *1.15* | *1.01* | *1.20* |
| H561T | 0.65 | 0.34 | *1.03* | 0.56 | 0.90 | 0.95 | 0.90 | 0.79 | *1.13* |
| H561V | 0.52 | 0.27 | 0.99 | 0.35 | *1.00* | *1.02* | *1.02* | 0.87 | *1.42* |
| H561W | 0.64 | 0.48 | *1.02* | 0.61 | *1.18* | *1.28* | *1.14* | *1.20* | *1.16* |
| D563A | 0.89 | *1.01* | *1.04* | *1.20* | *1.06* | *1.17* | *1.07* | *1.05* | *1.10* |
| D563C | 0.28 | 0.66 | 0.94 | 0.16 | 0.87 | *1.21* | 0.89 | 0.67 | 0.68 |
| D563D | 1.00 | 1.00 | 1.00 | 1.00 | 1.00 | 1.00 | 1.00 | 1.00 | 1.00 |
| D563E | 0.82 | 0.98 | 0.97 | *1.03* | 0.98 | 0.91 | 0.98 | *1.08* | 0.89 |
| D563F | 0.39 | 0.81 | 0.95 | 0.47 | 0.92 | *1.12* | 0.96 | 0.93 | 0.89 |
| D563I | 0.39 | 0.79 | *1.02* | 0.42 | 0.99 | *1.32* | *1.02* | 0.89 | 0.84 |
| D563L | 0.56 | 0.98 | 0.98 | 0.65 | 0.98 | *1.05* | *1.03* | *1.07* | 0.90 |
| D563M | 0.79 | *1.02* | 0.93 | 0.99 | 0.94 | 0.94 | 0.93 | *1.06* | 0.96 |
| D563Q | 0.53 | *1.01* | 0.99 | 0.96 | *1.08* | *1.06* | *1.10* | *1.09* | 0.90 |
| D563R | 0.24 | 0.63 | *1.00* | 0.38 | 0.99 | *1.41* | *1.02* | 0.83 | 0.74 |
| D563S | 0.45 | 0.97 | *1.06* | 0.78 | *1.03* | *1.05* | *1.21* | *1.13* | *1.01* |
| D563T | 0.45 | 0.94 | 0.96 | 0.73 | *1.04* | *1.26* | *1.07* | *1.09* | 0.85 |
| D563V | 0.43 | 0.79 | *1.03* | 0.54 | 0.95 | 1.00 | *1.04* | *1.01* | 0.88 |
| D563W | 0.42 | 0.82 | 0.94 | 0.30 | 0.95 | *1.12* | *1.02* | *1.09* | 0.80 |
| D563Y | 0.47 | 0.87 | *1.06* | 0.51 | *1.03* | *1.03* | *1.13* | *1.12* | 0.96 |
| D564A | 0.62 | *1.07* | *1.08* | 0.70 | *1.14* | *1.07* | *1.22* | *1.16* | *1.11* |
| D564C | 0.77 | *1.01* | *1.02* | 0.67 | *1.07* | *1.07* | *1.12* | *1.16* | 0.78 |
| D564D | 1.00 | 1.00 | 1.00 | 1.00 | 1.00 | 1.00 | 1.00 | 1.00 | 1.00 |
| D564E | 0.49 | 0.74 | *1.04* | 0.50 | 0.95 | 0.95 | 0.92 | 0.85 | 0.76 |
| D564F | 0.65 | *1.01* | *1.04* | 0.74 | *1.10* | *1.02* | *1.18* | *1.10* | *1.02* |

TABLE 3-1-continued

Performance Index Data of BGL1 SEL Variants (3,153)

| | | | | | | | | | |
|---|---|---|---|---|---|---|---|---|---|
| D564G | 0.52 | 0.89 | *1.05* | 0.56 | *1.06* | 0.99 | *1.07* | 0.99 | 0.79 |
| D564I | 0.05 | 0.05 | 0.05 | 0.05 | 0.05 | 0.05 | 0.05 | 0.05 | 0.05 |
| D564K | 0.49 | 0.85 | 0.97 | 0.48 | *1.01* | *1.01* | *1.11* | *1.06* | 0.73 |
| D564L | 0.56 | *1.10* | 0.94 | 0.69 | *1.08* | *1.14* | *1.11* | *1.07* | 0.89 |
| D564M | 0.60 | *1.05* | 0.90 | 0.66 | *1.04* | 0.96 | *1.09* | 0.97 | 0.83 |
| D564N | 0.64 | 0.98 | *1.03* | 0.74 | *1.02* | 0.91 | *1.07* | *1.00* | 0.86 |
| D564P | 0.16 | 0.47 | 0.91 | 0.13 | 0.98 | 0.78 | 0.71 | 0.79 | 0.36 |
| D564Q | 0.56 | 0.90 | 0.93 | 0.55 | *1.00* | 0.97 | 0.98 | *1.11* | 0.77 |
| D564R | 0.63 | 0.94 | 0.97 | 0.65 | 0.97 | *1.15* | *1.07* | *1.13* | 0.90 |
| D564S | 0.67 | 0.99 | 0.98 | 0.76 | 0.99 | 0.97 | 0.76 | 0.98 | *1.75* |
| D564T | 0.59 | *1.16* | 0.98 | 0.78 | *1.11* | *1.02* | *1.22* | *1.31* | *1.33* |
| D564V | 0.40 | *1.17* | 0.96 | 0.72 | *1.37* | *1.11* | *1.50* | *1.66* | 0.88 |
| D564Y | 0.58 | 0.99 | *1.02* | 0.63 | *1.06* | 0.91 | *1.09* | *1.11* | 0.92 |
| R570A | 0.58 | *1.04* | 0.92 | 0.71 | *1.17* | *1.11* | *1.13* | *1.08* | 0.96 |
| R570C | 0.31 | 0.78 | 0.93 | 0.29 | *1.19* | 0.96 | *1.18* | *1.16* | 0.87 |
| R570D | 0.20 | 0.61 | 1.00 | 0.17 | *1.29* | *1.30* | *1.10* | *1.33* | 0.62 |
| R570E | 0.48 | 0.86 | *1.05* | 0.57 | *1.04* | 0.98 | *1.03* | *1.06* | 0.77 |
| R570F | 0.12 | 0.22 | 0.95 | 0.09 | 0.65 | 0.56 | 0.46 | 0.56 | 0.45 |
| R570G | 0.18 | 0.45 | *1.06* | 0.17 | *1.07* | *1.01* | 0.81 | 0.94 | 0.65 |
| R570H | 0.19 | 0.47 | 0.95 | 0.17 | 0.82 | *1.09* | 0.73 | 0.92 | 0.58 |
| R570I | 0.22 | 0.69 | 0.96 | 0.28 | *1.15* | *1.13* | *1.17* | 0.97 | 0.68 |
| R570M | 0.27 | 0.67 | *1.00* | 0.34 | 0.99 | 0.99 | *1.05* | *1.09* | 0.51 |
| R570N | 0.11 | 0.29 | *1.05* | 0.07 | 0.91 | 0.76 | 0.65 | 0.93 | 0.31 |
| R570P | 0.15 | 0.05 | 0.05 | 0.05 | 0.10 | 0.20 | 0.05 | 0.14 | 0.05 |
| R570Q | 0.52 | 0.91 | *1.01* | 0.67 | *1.05* | 0.97 | *1.03* | *1.10* | 0.57 |
| R570R | 1.00 | 1.00 | 1.00 | 1.00 | 1.00 | 1.00 | 1.00 | 1.00 | 1.00 |
| R570S | 0.22 | 0.63 | 0.96 | 0.23 | *1.05* | *1.05* | 0.93 | *1.08* | 0.42 |
| R570T | 0.36 | 0.85 | *1.01* | 0.44 | *1.07* | 0.90 | *1.09* | *1.18* | 0.68 |
| R570V | 0.23 | 0.62 | *1.02* | 0.27 | *1.21* | *1.04* | *1.07* | *1.20* | 0.59 |
| R570W | 0.04 | 0.04 | 0.04 | 0.04 | 0.04 | 0.04 | 0.04 | 0.04 | 0.04 |
| R570Y | 0.18 | 0.40 | 0.88 | 0.14 | 0.82 | 0.90 | 0.68 | 0.80 | 0.42 |
| Y571A | 0.05 | 0.05 | 0.05 | 0.05 | 0.05 | 0.05 | 0.05 | 0.05 | 0.05 |
| Y571D | 0.05 | 0.05 | 0.05 | 0.05 | 0.05 | 0.05 | 0.05 | 0.05 | 0.05 |
| Y571E | 0.05 | 0.05 | 0.05 | 0.05 | 0.05 | 0.05 | 0.05 | 0.05 | 0.05 |
| Y571H | 0.14 | 0.05 | *1.09* | 0.28 | *1.02* | *1.07* | *1.43* | 0.88 | 0.98 |
| Y571K | 0.05 | 0.05 | 0.05 | 0.05 | 0.05 | 0.05 | 0.05 | 0.05 | 0.05 |

TABLE 3-1-continued

Performance Index Data of BGL1 SEL Variants (3,153)

| Y571L | 0.05 | 0.05 | 0.05 | 0.05 | 0.05 | 0.05 | 0.05 | 0.05 | 0.05 |
|---|---|---|---|---|---|---|---|---|---|
| Y571M | 0.15 | 0.05 | *1.06* | 0.29 | *1.12* | *1.01* | *1.57* | 0.78 | 0.91 |
| Y571N | 0.05 | 0.05 | 0.05 | 0.17 | 0.21 | 0.66 | *1.42* | *1.25* | 0.75 |
| Y571P | 0.05 | 0.05 | 0.05 | 0.05 | 0.05 | 0.05 | 0.05 | 0.05 | 0.05 |
| Y571Q | 0.04 | 0.04 | 0.04 | 0.04 | 0.04 | 0.04 | 0.04 | 0.04 | 0.04 |
| Y571R | 0.05 | 0.05 | 0.05 | 0.12 | 0.05 | 0.76 | *1.32* | 0.05 | 0.87 |
| Y571S | 0.05 | 0.05 | 0.05 | 0.05 | 0.05 | 0.05 | 0.05 | 0.05 | 0.05 |
| Y571T | 0.04 | 0.04 | 0.04 | 0.04 | 0.04 | 0.04 | 0.04 | 0.04 | 0.04 |
| Y571V | 0.05 | 0.05 | 0.05 | 0.05 | 0.05 | 0.05 | 0.05 | 0.05 | 0.05 |
| Y571W | 0.65 | *1.74* | *1.02* | 0.59 | 0.94 | 0.98 | 0.97 | 0.97 | 0.98 |
| Y571Y | 1.00 | 1.00 | 1.00 | 1.00 | 1.00 | 1.00 | 1.00 | 1.00 | 1.00 |
| K581A | 0.69 | *1.62* | 0.96 | 0.80 | *1.06* | 0.85 | *1.04* | *1.01* | *1.02* |
| K581C | 0.39 | 0.05 | *1.03* | 0.51 | *1.05* | 0.97 | *1.03* | *1.10* | *1.17* |
| K581D | 0.53 | *2.94* | *1.00* | 0.64 | *1.07* | 0.94 | *1.03* | *1.07* | *1.13* |
| K581E | 0.49 | *4.42* | 0.79 | 0.61 | *1.08* | 0.71 | *1.06* | 0.99 | 0.88 |
| K581F | 0.47 | *5.15* | 0.94 | 0.64 | *1.07* | 0.78 | *1.00* | *1.10* | *1.20* |
| K581G | 0.51 | *3.70* | *1.02* | 0.70 | *1.01* | 0.88 | *1.09* | *1.17* | *1.14* |
| K581H | 0.54 | *2.97* | 0.97 | 0.77 | *1.06* | 0.91 | 0.88 | 0.93 | *1.01* |
| K581I | 0.55 | *2.77* | 0.98 | 0.68 | *1.05* | 0.97 | 0.91 | *1.01* | 0.90 |
| K581K | 1.00 | 1.00 | 1.00 | 1.00 | 1.00 | 1.00 | 1.00 | 1.00 | 1.00 |
| K581L | 0.66 | *1.87* | *1.03* | 0.85 | *1.08* | 0.93 | 0.96 | 0.98 | 0.99 |
| K581M | 0.63 | *2.03* | 0.99 | 0.73 | *1.03* | 0.92 | *1.02* | 0.90 | 1.00 |
| K581N | 0.55 | *2.78* | *1.02* | 0.69 | *1.04* | 0.89 | 0.93 | 0.89 | 0.81 |
| K581P | 0.40 | 0.05 | 0.91 | 0.44 | 0.97 | 0.86 | 0.91 | 0.79 | *1.03* |
| K581R | 0.57 | *2.56* | 0.92 | 0.73 | *1.04* | 0.96 | 1.00 | 0.99 | 0.90 |
| K581S | 0.67 | *1.77* | 1.00 | 0.80 | *1.02* | 0.89 | 0.92 | *1.03* | *1.07* |
| K581T | 0.60 | *2.02* | *1.05* | 0.64 | 1.00 | 0.79 | 0.91 | 0.99 | *1.07* |
| K581V | 0.69 | *1.52* | 0.98 | 0.80 | 0.98 | 0.88 | 0.92 | *1.17* | *1.08* |
| K581W | 0.62 | *2.57* | 0.80 | 0.90 | *1.12* | *1.07* | *1.00* | *1.22* | *1.13* |
| K581Y | 0.81 | *1.32* | 0.96 | 0.90 | *1.06* | 0.95 | 0.96 | *1.11* | 0.97 |
| N583A | 0.82 | *1.05* | 0.92 | 0.95 | *1.01* | *1.02* | *1.06* | *1.07* | *1.01* |
| N583C | 0.57 | *1.18* | 0.88 | 0.97 | *1.19* | *1.37* | *1.38* | *1.43* | *1.29* |
| N583D | *1.08* | *1.04* | *1.03* | *1.19* | *1.04* | *1.03* | *1.09* | *1.02* | *1.05* |
| N583E | 0.60 | 0.86 | 0.91 | 0.66 | 0.99 | *1.08* | 0.94 | *1.03* | 0.92 |
| N583F | 0.62 | 0.85 | 0.92 | 0.65 | 0.95 | *1.16* | 0.91 | *1.01* | 0.90 |

TABLE 3-1-continued

Performance Index Data of BGL1 SEL Variants (3,153)

| | | | | | | | | |
|---|---|---|---|---|---|---|---|---|
| N583G | 0.66 | *1.02* | 0.92 | 0.91 | *1.04* | *1.27* | *1.14* | *1.17* | 0.96 |
| N583H | 0.56 | 0.92 | 0.83 | 0.75 | *1.05* | *1.33* | 0.96 | *1.13* | 0.89 |
| N583I | 0.48 | 0.83 | 0.89 | 0.67 | 0.99 | *1.21* | 0.93 | *1.18* | 0.87 |
| N583K | 0.60 | 0.88 | 0.89 | 0.67 | 0.93 | *1.11* | 0.93 | *1.07* | 0.84 |
| N583L | 0.53 | 0.81 | 0.92 | 0.75 | 0.97 | *1.09* | 0.94 | *1.08* | 0.63 |
| N583M | 0.51 | 0.82 | 0.84 | 0.71 | 0.91 | *1.12* | 0.91 | *1.08* | 0.68 |
| N583N | 1.00 | 1.00 | 1.00 | 1.00 | 1.00 | 1.00 | 1.00 | 1.00 | 1.00 |
| N583P | 0.21 | 0.43 | 0.77 | 0.29 | 0.79 | *1.49* | 0.74 | *1.20* | 0.32 |
| N583R | 0.85 | *1.03* | 0.97 | *1.17* | 0.96 | *1.43* | 0.92 | *1.13* | 0.90 |
| N583S | 0.53 | 0.80 | 0.90 | 0.71 | 0.94 | *1.11* | 0.93 | *1.09* | 0.67 |
| N583T | 0.53 | 0.81 | 0.85 | 0.71 | 0.94 | *1.16* | 0.90 | *1.08* | 0.67 |
| N583V | 0.75 | *1.05* | 0.88 | 0.98 | 0.99 | 0.80 | *1.03* | *1.12* | 0.84 |
| N583W | 0.70 | 0.92 | 0.89 | 0.82 | 0.89 | *1.11* | 0.91 | *1.00* | 0.78 |
| N583Y | 0.66 | 0.88 | 0.83 | 0.57 | 0.92 | *1.24* | 0.91 | *1.11* | 0.81 |
| R586C | 0.13 | 0.05 | 0.05 | 0.05 | 0.05 | 0.18 | 0.05 | 0.05 | 0.26 |
| R586D | *1.25* | 0.98 | *1.05* | *1.18* | 1.00 | 0.94 | *1.10* | *1.08* | *1.06* |
| R586E | 0.73 | *1.00* | 0.90 | 0.72 | 0.94 | *1.14* | 0.97 | 0.94 | 0.94 |
| R586F | 0.64 | *1.04* | 0.98 | 0.67 | 0.99 | *1.19* | *1.00* | *1.09* | 0.96 |
| R586G | 0.38 | 0.84 | 0.93 | 0.48 | 0.92 | *1.10* | 0.90 | *1.03* | 0.87 |
| R586H | 0.08 | 0.14 | 0.05 | 0.05 | 0.36 | *1.05* | 0.16 | 0.38 | 0.34 |
| R586I | 0.04 | 0.04 | 0.04 | 0.04 | 0.04 | 0.04 | 0.04 | 0.04 | 0.04 |
| R586K | 0.61 | 0.94 | 0.97 | 0.60 | 0.93 | 0.99 | 0.90 | 0.98 | 0.87 |
| R586L | 0.45 | *1.02* | 0.96 | 0.56 | 0.98 | *1.21* | 0.96 | *1.05* | 0.90 |
| R586N | 0.66 | *1.10* | 0.98 | 0.82 | *1.00* | *1.03* | *1.06* | *1.07* | *1.01* |
| R586P | 0.18 | *1.03* | 0.90 | 0.37 | *1.40* | *1.88* | *1.54* | *1.87* | *1.09* |
| R586Q | 0.10 | 0.05 | 0.05 | 0.05 | 0.05 | 0.29 | 0.05 | 0.05 | 0.09 |
| R586R | 1.00 | 1.00 | 1.00 | 1.00 | 1.00 | 1.00 | 1.00 | 1.00 | 1.00 |
| R586S | 0.10 | 0.05 | 0.05 | 0.05 | 0.05 | 0.16 | 0.05 | 0.05 | 0.06 |
| R586V | 0.53 | *1.47* | 0.96 | 0.99 | *1.22* | *1.41* | *1.41* | *1.46* | *1.44* |
| R586W | 0.49 | *1.06* | 0.89 | 0.55 | *1.02* | *1.15* | *1.11* | *1.09* | 0.96 |
| R586Y | 0.51 | 0.98 | 0.94 | 0.52 | 0.99 | *1.09* | *1.04* | *1.07* | *1.01* |
| S591C | 0.29 | 0.26 | *1.12* | 0.16 | 0.44 | 0.66 | 0.45 | 0.61 | 0.32 |
| S591D | 0.25 | 0.42 | *1.03* | 0.22 | 0.82 | *1.01* | 0.87 | *1.03* | 0.48 |
| S591F | 0.23 | 0.18 | *1.05* | 0.09 | 0.33 | 0.53 | 0.38 | 0.47 | 0.25 |
| S591G | 0.20 | 0.19 | *1.08* | 0.14 | 0.44 | 0.80 | 0.49 | 0.63 | 0.44 |

TABLE 3-1-continued

Performance Index Data of BGL1 SEL Variants (3,153)

| | | | | | | | | |
|---|---|---|---|---|---|---|---|---|
| S591H | 0.23 | 0.27 | *1.40* | 0.36 | 0.61 | 0.79 | 0.56 | 0.72 | 0.27 |
| S591I | 0.27 | 0.20 | *1.32* | 0.20 | 0.39 | 0.55 | 0.37 | 0.47 | 0.14 |
| S591K | 0.17 | 0.14 | *1.27* | 0.17 | 0.36 | 0.55 | 0.33 | 0.41 | 0.26 |
| S591M | 0.23 | 0.15 | *1.12* | 0.18 | 0.32 | 0.33 | 0.32 | 0.45 | 0.30 |
| S591N | 0.26 | 0.28 | 0.97 | 0.35 | 0.53 | 0.81 | 0.51 | 0.52 | 0.31 |
| S591P | 0.13 | 0.32 | *1.02* | 0.36 | 0.90 | 0.11 | 0.64 | 0.67 | 0.38 |
| S591Q | 0.22 | 0.22 | *1.16* | 0.29 | 0.44 | 0.77 | 0.52 | 0.56 | 0.43 |
| S591R | 0.04 | 0.04 | 0.04 | 0.04 | 0.04 | 0.04 | 0.04 | 0.04 | 0.04 |
| S591S | 1.00 | 1.00 | 1.00 | 1.00 | 1.00 | 1.00 | 1.00 | 1.00 | 1.00 |
| S591V | 0.29 | 0.29 | *1.11* | 0.39 | 0.50 | 0.73 | 0.53 | 0.65 | 0.36 |
| V603A | 0.93 | *1.01* | 0.99 | *1.47* | 0.89 | *1.01* | 0.97 | 0.98 | *1.83* |
| V603C | 0.95 | *1.02* | 0.94 | 0.75 | 0.97 | 1.00 | *1.06* | *1.40* | *1.18* |
| V603D | 0.54 | *1.03* | 0.96 | 0.82 | 0.76 | *1.10* | 0.82 | *1.35* | *2.32* |
| V603E | 0.94 | *1.11* | 0.96 | *1.23* | 0.94 | 0.96 | *1.00* | 0.75 | *1.01* |
| V603F | 0.71 | *1.01* | 0.91 | 0.81 | 0.77 | 1.00 | 0.84 | *1.19* | *1.72* |
| V603G | 0.40 | *1.05* | 0.94 | 0.72 | *1.00* | *1.06* | *1.28* | *2.79* | *2.16* |
| V603H | 0.59 | *1.31* | 0.91 | *1.15* | *1.17* | *1.25* | *1.20* | *3.34* | *1.32* |
| V603L | *2.39* | 0.59 | 0.97 | 0.93 | 0.64 | 0.83 | 0.60 | 0.42 | 0.59 |
| V603M | *1.96* | 0.72 | 0.92 | *1.74* | 0.71 | 0.87 | 0.69 | *1.39* | 0.59 |
| V603N | 0.82 | 0.95 | 0.94 | *1.25* | 0.88 | *1.04* | 0.87 | *1.36* | 0.87 |
| V603P | 0.21 | 0.82 | 0.90 | 0.28 | 0.54 | 0.83 | 0.65 | *8.07* | 0.56 |
| V603Q | *1.07* | 0.90 | 0.88 | *1.50* | 0.84 | *1.06* | 0.83 | *2.37* | 0.73 |
| V603R | 0.62 | 0.85 | 0.86 | 0.86 | 0.77 | *1.05* | 0.70 | *2.42* | 0.59 |
| V603S | *1.03* | *1.03* | 0.91 | *1.41* | 0.87 | 0.86 | 0.86 | *1.42* | 0.67 |
| V603T | 0.48 | *1.02* | 0.95 | 0.57 | 0.70 | 0.91 | 0.69 | *1.58* | 0.97 |
| V603V | 1.00 | 1.00 | 1.00 | 1.00 | 1.00 | 1.00 | 1.00 | 1.00 | 1.00 |
| V603W | 0.16 | *2.11* | 0.05 | 0.13 | 0.16 | 0.26 | 0.25 | *1.57* | 0.72 |
| V603Y | 0.33 | *6.94* | 0.96 | 0.87 | *2.22* | *1.86* | *2.53* | *8.79* | *1.55* |
| F611A | 0.67 | *1.32* | 0.93 | *1.26* | *1.21* | *1.18* | *1.55* | *1.36* | *1.52* |
| F611C | 0.38 | 0.65 | 0.94 | 0.41 | *1.02* | *1.11* | *1.17* | *1.06* | 0.86 |
| F611D | 0.21 | 0.33 | 0.92 | 0.19 | 0.79 | *1.15* | *1.05* | 0.93 | 0.65 |
| F611G | 0.67 | 0.74 | *1.00* | 0.58 | 0.84 | 0.96 | 0.92 | 0.83 | 0.77 |
| F611I | 0.16 | 0.29 | *1.04* | 0.17 | 0.77 | 0.98 | 0.95 | 0.99 | 0.52 |
| F611K | 0.32 | 0.57 | 0.95 | 0.42 | 0.91 | *1.17* | *1.09* | *1.11* | 0.77 |
| F611L | 0.70 | 0.92 | *1.02* | 0.77 | 0.89 | *1.01* | 0.97 | 0.90 | 0.82 |
| F611M | 0.58 | 0.82 | 0.99 | 0.70 | 0.90 | *1.04* | *1.00* | 0.97 | 0.83 |

TABLE 3-1-continued

Performance Index Data of BGL1 SEL Variants (3,153)

| | | | | | | | | | |
|---|---|---|---|---|---|---|---|---|---|
| F611N | 0.65 | 0.80 | *1.00* | 0.66 | 0.86 | *1.03* | 0.93 | 0.86 | 0.81 |
| F611P | 0.54 | 0.70 | 0.98 | 0.53 | 0.86 | 0.86 | 0.91 | 0.95 | 0.66 |
| F611Q | 0.45 | 0.61 | 0.93 | 0.46 | 0.82 | 0.79 | 0.92 | 0.95 | 0.74 |
| F611R | 0.23 | 0.41 | *1.06* | 0.30 | 0.91 | *1.39* | *1.06* | *1.22* | 0.75 |
| F611S | 0.60 | 0.76 | *1.01* | 0.63 | 0.86 | *1.01* | 0.92 | 0.97 | 0.89 |
| F611T | 0.52 | 0.66 | *1.03* | 0.50 | 0.80 | 0.87 | 0.92 | 0.99 | 0.69 |
| F611V | 0.53 | 0.69 | *1.13* | 0.51 | 0.81 | 0.92 | 0.96 | *1.03* | 0.87 |
| F611W | 0.61 | 0.78 | 0.96 | 0.58 | 0.94 | *1.04* | *1.01* | *1.11* | 0.86 |
| F611Y | 0.70 | 0.80 | *1.00* | 0.70 | 0.96 | 0.93 | 0.96 | *1.09* | 0.94 |
| Q612C | 0.79 | *1.17* | *1.12* | 0.84 | *1.18* | *1.26* | *1.26* | *1.35* | *1.28* |
| Q612D | *1.41* | 0.94 | *1.16* | *1.27* | 1.00 | 0.77 | *1.03* | *1.08* | 0.97 |
| Q612F | 0.66 | 0.92 | 0.95 | 0.70 | 0.93 | *1.64* | 0.91 | 1.00 | 0.72 |
| Q612G | *1.31* | *1.06* | *1.04* | *1.16* | *1.01* | *1.11* | *1.01* | *1.01* | 0.84 |
| Q612H | 0.42 | 0.77 | *1.04* | 0.50 | 0.97 | *2.04* | 0.94 | *1.14* | 0.84 |
| Q612I | 0.75 | 0.76 | *1.02* | 0.67 | 0.81 | *1.43* | 0.80 | 0.83 | 0.68 |
| Q612K | *1.05* | 0.96 | 0.95 | 0.73 | 0.87 | *1.18* | 0.87 | 0.92 | 0.80 |
| Q612L | 0.53 | 0.78 | 0.95 | 0.56 | 0.82 | *3.33* | 0.80 | 0.84 | 0.76 |
| Q612M | 0.56 | 0.81 | 0.94 | 0.57 | 0.87 | *1.14* | 0.81 | 0.90 | 0.65 |
| Q612P | 0.42 | 0.64 | 0.97 | 0.45 | 0.83 | 0.94 | 0.83 | 0.92 | 0.66 |
| Q612Q | 1.00 | 1.00 | 1.00 | 1.00 | 1.00 | 1.00 | 1.00 | 1.00 | 1.00 |
| Q612R | 0.98 | 0.91 | 0.99 | 0.84 | 0.85 | *1.10* | 0.88 | 0.90 | 0.80 |
| Q612S | 0.47 | *1.03* | 0.92 | 0.39 | *1.11* | *1.47* | *1.10* | *1.24* | 0.89 |
| Q612T | 0.66 | 0.74 | 0.95 | 0.28 | 0.79 | 0.80 | 0.73 | 0.79 | 0.60 |
| Q612V | *1.09* | 0.96 | 0.99 | 0.97 | 0.92 | 0.94 | 0.90 | 0.94 | 0.91 |
| Q612W | 0.72 | 0.78 | *1.01* | 0.66 | 0.81 | *1.10* | 0.83 | 0.89 | 0.76 |
| Q612Y | 0.88 | 0.75 | 0.99 | 0.66 | 0.81 | 0.93 | 0.75 | 0.76 | 0.72 |
| A622A | 1.00 | 1.00 | 1.00 | 1.00 | 1.00 | 1.00 | 1.00 | 1.00 | 1.00 |
| A622D | 0.88 | 0.99 | *1.02* | *1.06* | 0.90 | 0.85 | 0.98 | *1.08* | *1.06* |
| A622E | 0.87 | *1.36* | *1.01* | 0.91 | *1.03* | 0.95 | *1.13* | 0.66 | *1.20* |
| A622F | 0.68 | *1.00* | 0.95 | 0.93 | 0.80 | 0.79 | 0.84 | 0.54 | *1.73* |
| A622G | 0.56 | *1.22* | 0.92 | *1.03* | 0.95 | 0.95 | 0.99 | *2.10* | *1.06* |
| A622H | 0.71 | *1.28* | 0.91 | *1.09* | 0.98 | *1.04* | *1.01* | *1.68* | *1.66* |
| A622I | 0.83 | 0.95 | 0.91 | *1.15* | 0.78 | 0.88 | 0.82 | *1.91* | 0.91 |
| A622K | 0.69 | *1.11* | 0.95 | 0.93 | 0.78 | *1.02* | 0.82 | *1.12* | 0.98 |
| A622L | *1.33* | *1.06* | *1.00* | *1.86* | 0.91 | 0.97 | 0.90 | *1.25* | 0.91 |

TABLE 3-1-continued

Performance Index Data of BGL1 SEL Variants (3,153)

| | | | | | | | | | |
|---|---|---|---|---|---|---|---|---|---|
| A622M | 0.48 | *1.03* | 0.90 | 0.68 | 0.60 | 0.83 | 0.67 | *1.58* | *1.37* |
| A622N | 0.90 | 0.98 | 0.95 | *1.47* | 0.84 | 0.84 | 0.79 | 0.63 | *1.08* |
| A622P | 0.11 | 0.05 | 0.05 | 0.05 | 0.05 | 0.19 | 0.10 | *16.24* | 0.74 |
| A622R | 0.99 | *1.16* | 0.95 | *1.41* | 0.92 | 0.95 | 0.93 | 0.62 | *1.15* |
| A622S | 0.85 | *1.14* | 0.99 | *1.28* | 0.90 | 0.98 | 0.98 | *1.51* | *1.03* |
| A622T | 0.52 | *1.16* | 0.97 | 0.57 | 0.73 | 0.84 | 0.82 | *1.56* | *1.05* |
| A622V | 0.47 | *1.19* | 1.00 | 0.59 | 0.78 | 0.90 | 0.82 | *1.69* | *1.28* |
| A622W | *1.51* | 0.93 | 0.96 | *1.11* | 0.84 | 0.86 | 0.83 | 0.38 | 0.87 |
| A622Y | *1.15* | 0.94 | 0.90 | *1.40* | 0.78 | 0.89 | 0.89 | *1.24* | 0.83 |
| Q626D | 0.04 | 0.04 | 0.04 | 0.04 | 0.04 | 0.04 | 0.04 | 0.04 | 0.04 |
| Q626E | 0.82 | *1.39* | 0.99 | *1.02* | *1.07* | 0.89 | *1.14* | 0.73 | *1.39* |
| Q626F | 0.53 | *1.19* | 0.96 | 0.87 | 0.94 | 0.93 | *1.08* | 0.69 | *1.58* |
| Q626G | 0.47 | *1.01* | 0.88 | 0.51 | 0.70 | 0.80 | 0.77 | *1.57* | *1.53* |
| Q626H | 0.09 | 0.91 | 0.93 | 0.24 | *2.26* | *2.17* | *2.55* | *2.77* | *1.31* |
| Q626I | *4.62* | 0.05 | 0.05 | 0.05 | 0.05 | 0.12 | 0.05 | 0.05 | 0.07 |
| Q626K | 0.05 | 0.05 | 0.05 | 0.05 | 0.05 | 0.05 | 0.05 | 0.05 | 0.05 |
| Q626L | *1.18* | 0.95 | 0.96 | *1.58* | 0.81 | 0.88 | 0.75 | *1.14* | 0.85 |
| Q626M | 0.31 | *1.03* | 0.87 | 0.36 | 0.66 | *1.03* | 0.58 | 0.81 | *1.97* |
| Q626P | 0.04 | 0.04 | 0.04 | 0.04 | 0.04 | 0.04 | 0.04 | 0.04 | 0.04 |
| Q626Q | 1.00 | 1.00 | 1.00 | 1.00 | 1.00 | 1.00 | 1.00 | 1.00 | 1.00 |
| Q626R | 0.04 | 0.04 | 0.04 | 0.04 | 0.04 | 0.04 | 0.04 | 0.04 | 0.04 |
| Q626S | 0.04 | 0.04 | 0.04 | 0.04 | 0.04 | 0.04 | 0.04 | 0.04 | 0.04 |
| Q626T | *1.05* | *1.04* | 0.96 | *1.64* | 0.89 | 0.92 | 0.88 | *1.42* | 0.88 |
| Q626V | *1.06* | 0.95 | 0.92 | 0.96 | 0.80 | 0.89 | 0.79 | *1.40* | 0.80 |
| Q626W | 0.40 | 0.66 | 0.88 | 0.54 | 0.37 | 0.60 | 0.43 | 0.93 | 0.47 |
| Q626Y | 0.12 | 0.05 | 0.05 | 0.05 | 0.09 | 0.79 | 0.08 | 0.41 | 0.64 |
| V627D | 0.29 | 0.17 | *1.54* | 0.06 | 0.36 | 0.47 | 0.32 | 0.44 | 0.35 |
| V627K | 0.26 | 0.15 | *3.95* | 0.30 | 0.28 | 0.65 | 0.31 | 0.37 | 0.12 |
| V627P | 0.11 | 0.20 | *1.23* | 0.13 | 0.76 | *1.25* | 0.88 | 0.86 | 0.57 |
| V627Q | 0.28 | 0.21 | *1.12* | 0.21 | 0.37 | 0.67 | 0.40 | 0.30 | 0.78 |
| V627R | 0.26 | 0.21 | *1.25* | 0.24 | 0.39 | 0.59 | 0.43 | 0.36 | 0.52 |
| V627S | 0.31 | 0.25 | *1.11* | 0.31 | 0.38 | 0.53 | 0.42 | 0.52 | 0.72 |
| V627V | 1.00 | 1.00 | 1.00 | 1.00 | 1.00 | 1.00 | 1.00 | 1.00 | 1.00 |
| V627Y | 0.27 | 0.21 | *2.02* | 0.07 | 0.42 | 0.55 | 0.42 | 0.54 | 0.18 |
| T638A | 0.91 | *1.05* | *1.02* | 0.94 | *1.01* | *1.07* | *1.00* | *1.07* | *1.09* |

TABLE 3-1-continued

Performance Index Data of BGL1 SEL Variants (3,153)

| | | | | | | | | |
|---|---|---|---|---|---|---|---|---|
| T638D | *1.12* | *1.02* | *1.08* | *1.03* | *1.05* | *1.06* | *1.06* | *1.07* | 0.85 |
| T638E | 0.73 | *1.02* | 1.00 | 0.74 | 0.90 | *1.03* | 0.90 | 0.93 | 0.93 |
| T638F | 0.43 | 0.99 | 0.90 | 0.40 | 0.82 | *1.18* | 0.89 | 0.92 | 0.80 |
| T638G | 0.84 | *1.15* | 1.00 | 0.85 | *1.01* | *1.14* | *1.05* | *1.09* | *1.05* |
| T638I | 0.87 | *1.01* | 0.96 | 0.78 | 0.90 | *1.24* | 0.98 | 0.92 | 0.98 |
| T638K | 0.69 | *1.03* | 0.98 | 0.60 | 0.95 | *1.20* | 0.95 | 0.97 | 0.98 |
| T638L | 0.77 | *1.02* | 0.91 | 0.77 | 0.88 | *1.19* | 0.85 | 0.96 | 0.86 |
| T638M | 0.66 | *1.18* | 0.96 | 0.77 | 0.93 | *1.12* | *1.07* | *1.02* | 0.92 |
| T638P | 0.16 | 0.62 | 0.97 | 0.13 | 0.59 | *1.06* | 0.68 | 0.84 | 0.52 |
| T638Q | 0.71 | *1.03* | *1.00* | 0.74 | 0.93 | *1.24* | *1.07* | *1.01* | 0.95 |
| T638R | 0.89 | *1.06* | *1.03* | 0.79 | 0.99 | *1.16* | *1.10* | *1.02* | 0.93 |
| T638S | 0.87 | *1.08* | 0.98 | 0.94 | 0.98 | *1.20* | *1.04* | *1.09* | 0.95 |
| T638T | 1.00 | 1.00 | 1.00 | 1.00 | 1.00 | 1.00 | 1.00 | 1.00 | 1.00 |
| T638V | 0.76 | *1.03* | 0.96 | 0.73 | 0.95 | *1.14* | *1.05* | *1.02* | 0.91 |
| T638W | 0.06 | *3.96* | 0.98 | 0.38 | *4.86* | *5.15* | *7.44* | *8.32* | *2.49* |
| T638Y | 0.55 | *1.15* | 0.97 | 0.55 | 0.94 | *1.03* | *1.12* | *1.11* | 0.97 |
| S642A | 0.91 | 0.92 | 0.98 | 0.71 | 0.93 | *1.04* | 0.87 | 0.92 | 0.77 |
| S642C | 0.85 | *1.05* | 0.98 | 0.69 | 0.97 | *1.37* | *1.13* | *1.04* | 0.71 |
| S642D | *1.38* | 0.73 | *1.09* | 0.80 | 0.98 | 0.79 | 0.96 | 0.93 | 0.92 |
| S642E | 0.59 | *1.54* | 1.00 | 0.77 | *1.09* | *1.57* | *1.04* | *1.13* | 0.90 |
| S642F | 0.30 | *4.47* | *1.04* | 0.47 | *1.33* | *2.28* | *1.70* | *1.59* | *1.02* |
| S642G | 1.00 | 0.96 | *1.05* | 0.86 | *1.02* | *1.21* | *1.00* | 0.94 | 0.71 |
| S642H | 0.49 | *1.70* | 0.95 | 0.63 | *1.07* | *1.66* | *1.13* | *1.10* | 0.88 |
| S642I | 0.54 | *1.45* | *1.07* | 0.52 | *1.01* | *1.93* | *1.11* | 0.99 | 0.95 |
| S642K | 0.99 | 0.86 | 0.99 | 0.71 | 0.94 | *1.22* | 0.89 | 0.82 | 0.79 |
| S642L | 0.43 | *1.99* | *1.05* | 0.57 | *1.04* | *2.93* | *1.19* | *1.22* | *1.02* |
| S642M | 0.48 | *1.62* | *1.02* | 0.53 | 0.91 | *1.76* | *1.22* | 1.00 | 0.70 |
| S642N | 0.89 | *1.05* | *1.02* | 0.82 | 1.00 | *1.21* | 0.95 | 0.93 | 0.73 |
| S642P | 0.55 | *1.43* | 0.94 | 0.67 | 1.00 | *1.53* | *1.08* | *1.01* | 0.75 |
| S642Q | 0.74 | *1.27* | 0.99 | 0.86 | *1.03* | *1.54* | *1.28* | *1.09* | 0.91 |
| S642R | 0.97 | *1.02* | 0.99 | 0.85 | *1.01* | *1.17* | 0.98 | 0.98 | 0.75 |
| S642S | 1.00 | 1.00 | 1.00 | 1.00 | 1.00 | 1.00 | 1.00 | 1.00 | 1.00 |
| S642T | 0.67 | *1.27* | 0.98 | 0.67 | *1.01* | *1.21* | *1.04* | *1.03* | 0.70 |
| S642V | 0.76 | *1.15* | 0.98 | 0.67 | 1.00 | *1.71* | *1.13* | 0.98 | 0.82 |
| S642W | 0.35 | *2.99* | 0.92 | 0.46 | *1.23* | *2.99* | *1.51* | *1.46* | *1.41* |
| S642Y | 0.27 | *6.12* | 0.97 | 0.45 | *1.39* | *4.90* | *2.03* | *1.74* | 0.98 |

TABLE 3-1-continued

Performance Index Data of BGL1 SEL Variants (3,153)

| A643A | 1.00 | 1.00 | 1.00 | 1.00 | 1.00 | 1.00 | 1.00 | 1.00 | 1.00 |
|---|---|---|---|---|---|---|---|---|---|
| A643C | 0.77 | 0.82 | 0.97 | 0.60 | 0.99 | *1.09* | 1.00 | 0.91 | 0.90 |
| A643D | 0.04 | 0.04 | 0.04 | 0.04 | 0.04 | 0.04 | 0.04 | 0.04 | 0.04 |
| A643E | 0.96 | 0.98 | *1.06* | 0.96 | 0.96 | 0.99 | *1.02* | 0.91 | 0.94 |
| A643F | 0.36 | 0.51 | *1.02* | 0.17 | 0.82 | *1.17* | *1.03* | 0.94 | 0.73 |
| A643G | 0.52 | 0.60 | *1.11* | 0.43 | 0.90 | *1.04* | 0.95 | 0.87 | 0.85 |
| A643H | 0.55 | 0.75 | *1.01* | 0.68 | 0.96 | *1.12* | *1.02* | *1.02* | 0.78 |
| A643K | 0.25 | 0.48 | *1.03* | 0.28 | *1.09* | *1.41* | *1.26* | *1.29* | 0.89 |
| A643L | 0.83 | *1.03* | 0.99 | 0.98 | 0.98 | *1.07* | *1.11* | *1.07* | 0.99 |
| A643M | *1.11* | *1.12* | *1.04* | *1.12* | 0.96 | *1.17* | *1.05* | 1.00 | 0.93 |
| A643N | 0.66 | 0.76 | *1.10* | 0.62 | 0.92 | 0.99 | *1.02* | 0.97 | 0.90 |
| A643Q | 0.48 | 0.58 | *1.11* | 0.44 | 0.92 | *1.11* | 0.99 | *1.07* | 0.80 |
| A643R | 0.64 | 0.77 | 0.91 | 0.62 | 0.93 | *1.11* | 0.93 | 0.96 | 0.77 |
| A643S | 0.87 | 0.88 | *1.08* | 0.88 | 0.92 | *1.07* | 0.99 | 0.97 | 0.87 |
| A643T | 0.92 | 0.96 | *1.04* | 0.95 | 0.93 | *1.04* | *1.01* | *1.03* | 0.90 |
| A643V | 0.89 | 0.92 | *1.11* | 0.87 | *1.02* | *1.07* | *1.09* | *1.02* | *1.01* |
| A643W | 0.43 | 0.54 | *1.05* | 0.44 | 0.88 | 0.96 | 0.89 | *1.05* | 0.89 |
| A643Y | 0.54 | 0.70 | *1.04* | 0.45 | 0.97 | *1.06* | *1.08* | *1.21* | 0.89 |
| R645A | 0.57 | 0.87 | *1.03* | 0.79 | *1.04* | *1.27* | 0.98 | *1.12* | 0.81 |
| R645C | 0.18 | 0.32 | 0.96 | 0.27 | 0.88 | 0.86 | 0.73 | 0.80 | 0.33 |
| R645D | 0.80 | 0.89 | *1.12* | *1.03* | 0.95 | *1.09* | 0.93 | *1.03* | 0.82 |
| R645E | 0.37 | 0.49 | *1.15* | 0.60 | 0.93 | 0.82 | 0.76 | 0.85 | 0.57 |
| R645F | 0.52 | 0.76 | *1.05* | 0.65 | 0.98 | *1.02* | 0.94 | *1.10* | 0.77 |
| R645G | 0.89 | *1.17* | 0.98 | *1.23* | *1.04* | *1.22* | *1.08* | *1.19* | *1.02* |
| R645H | 0.52 | 0.68 | *1.01* | 0.72 | 0.95 | *1.01* | 0.82 | 0.97 | 0.85 |
| R645I | 0.44 | 0.65 | *1.00* | 0.60 | *1.02* | *1.03* | 0.89 | *1.03* | 0.73 |
| R645K | 0.85 | *1.07* | 1.00 | *1.06* | *1.06* | *1.06* | *1.11* | *1.16* | 0.98 |
| R645L | 0.45 | 0.71 | *1.04* | 0.70 | *1.05* | *1.00* | 0.97 | *1.28* | 0.74 |
| R645M | 0.46 | 0.82 | *1.07* | 0.89 | *1.17* | *1.09* | *1.07* | *1.32* | 0.97 |
| R645P | 0.95 | 0.78 | *1.00* | 0.93 | 0.88 | *1.08* | 0.77 | 0.82 | 0.77 |
| R645Q | 0.65 | 0.63 | *1.03* | 0.62 | 0.81 | *1.02* | 0.68 | 0.76 | 0.59 |
| R645R | 1.00 | 1.00 | 1.00 | 1.00 | 1.00 | 1.00 | 1.00 | 1.00 | 1.00 |
| R645S | 0.69 | 0.73 | *1.06* | 0.89 | 0.91 | 0.98 | 0.86 | 0.91 | 0.80 |
| R645T | 0.56 | 0.79 | *1.04* | 0.71 | 0.98 | *1.01* | 0.90 | *1.06* | 0.79 |
| R645V | 0.42 | 0.63 | *1.05* | 0.53 | 1.00 | *1.05* | 0.93 | *1.17* | 0.71 |

TABLE 3-1-continued

Performance Index Data of BGL1 SEL Variants (3,153)

| | | | | | | | | | |
|---|---|---|---|---|---|---|---|---|---|
| R645W | 0.30 | 0.66 | *1.09* | 0.56 | *1.34* | *1.06* | *1.28* | *1.53* | 0.95 |
| R645Y | 0.57 | 0.89 | *1.04* | 0.80 | *1.14* | *1.16* | *1.13* | *1.19* | 0.98 |
| K649A | *1.24* | *1.04* | *1.01* | 0.71 | 0.79 | *1.03* | 0.88 | 0.89 | *1.07* |
| K649C | 0.69 | *1.08* | 0.96 | 0.80 | *1.02* | *1.04* | *1.07* | 0.97 | *1.02* |
| K649E | 0.40 | 0.78 | 0.90 | 0.42 | 0.89 | 1.00 | 0.86 | 0.80 | 0.96 |
| K649F | 0.77 | *1.06* | 0.97 | 0.77 | 0.97 | *1.05* | 0.95 | 0.90 | 1.00 |
| K649I | 0.67 | *1.01* | 0.96 | 0.88 | 0.97 | 0.97 | 0.92 | 0.90 | 0.82 |
| K649K | 1.00 | 1.00 | 1.00 | 1.00 | 1.00 | 1.00 | 1.00 | 1.00 | 1.00 |
| K649L | 0.86 | *1.04* | 0.98 | *1.30* | 0.99 | *1.07* | 0.98 | 0.90 | 0.92 |
| K649M | 0.94 | *1.12* | 0.93 | *1.33* | 0.92 | 0.95 | 0.91 | 0.94 | 0.88 |
| K649N | 0.09 | 0.37 | 0.86 | 0.14 | *1.33* | *1.57* | *1.54* | 0.82 | 0.58 |
| K649P | 0.41 | 0.20 | 0.77 | 0.07 | 0.23 | 0.32 | 0.18 | 0.14 | 0.30 |
| K649Q | 0.82 | *1.02* | *1.01* | *1.15* | 0.93 | *1.02* | 0.91 | 0.91 | 0.83 |
| K649S | 0.89 | *1.08* | 0.98 | 0.85 | 0.97 | *1.06* | *1.02* | 0.96 | *1.09* |
| K649T | 0.48 | 0.97 | 0.98 | 0.73 | *1.04* | *1.09* | 0.99 | *1.00* | 0.99 |
| K649W | *1.03* | *1.00* | *1.01* | *1.09* | 0.94 | 1.00 | 0.95 | 0.84 | 0.92 |
| K649Y | 0.80 | *1.10* | 0.96 | 1.00 | 0.99 | *1.03* | 0.99 | 0.99 | 0.84 |
| Q650A | 0.82 | 0.99 | 0.90 | 0.81 | *1.00* | 0.98 | 0.97 | 0.92 | 1.00 |
| Q650C | 0.97 | 0.97 | 0.99 | 0.73 | *1.05* | *1.18* | *1.01* | 0.98 | 0.99 |
| Q650D | *1.16* | 0.94 | *1.01* | 0.68 | *1.05* | *1.16* | *1.01* | 0.95 | 0.93 |
| Q650E | 0.52 | 0.80 | 0.92 | 0.59 | 0.95 | *1.07* | 0.92 | *1.13* | *1.07* |
| Q650F | 0.26 | 0.50 | 0.90 | 0.28 | *1.05* | *1.19* | 0.80 | 0.99 | 0.73 |
| Q650G | 0.80 | 0.96 | 0.94 | 0.71 | *1.08* | *1.20* | 0.97 | *1.03* | *1.03* |
| Q650H | 0.61 | 0.91 | 0.91 | 0.77 | 0.94 | *1.17* | 0.93 | *1.00* | *1.00* |
| Q650I | 0.50 | 0.84 | 0.92 | 0.51 | 0.97 | *1.12* | 0.93 | *1.06* | 0.83 |
| Q650K | 0.39 | 0.62 | 0.93 | 0.34 | *1.09* | *1.22* | 0.90 | *1.15* | 0.76 |
| Q650L | 0.57 | 0.89 | 0.94 | 0.67 | 0.98 | *1.12* | 0.96 | *1.02* | 0.96 |
| Q650M | 0.50 | 0.79 | 0.91 | 0.55 | 0.97 | *1.07* | 0.91 | 1.00 | 0.97 |
| Q650N | 0.54 | 0.88 | 0.94 | 0.53 | *1.09* | *1.27* | 1.00 | *1.26* | 1.00 |
| Q650Q | 1.00 | 1.00 | 1.00 | 1.00 | 1.00 | 1.00 | 1.00 | 1.00 | 1.00 |
| Q650R | 0.41 | 0.68 | 0.83 | 0.43 | *1.00* | *1.26* | 0.88 | *1.18* | 0.74 |
| Q650T | 0.76 | 0.94 | 0.97 | 0.65 | *1.01* | 0.98 | *1.02* | *1.04* | 0.98 |
| Q650V | 0.89 | 0.98 | 0.96 | 0.92 | *1.03* | *1.23* | *1.04* | 1.00 | *1.03* |
| Q650W | 0.26 | 0.53 | 0.82 | 0.26 | 0.86 | 0.90 | 0.79 | 0.96 | 0.75 |
| Q650Y | 0.55 | 0.91 | 0.87 | 0.61 | *1.04* | *1.17* | *1.03* | *1.11* | *1.04* |

TABLE 3-1-continued

Performance Index Data of BGL1 SEL Variants (3,153)

| | | | | | | | | | |
|---|---|---|---|---|---|---|---|---|---|
| K656A | 0.07 | 0.05 | 0.05 | 0.05 | 0.05 | 0.36 | 0.05 | 0.05 | 0.35 |
| K656C | 0.07 | 0.05 | 0.05 | 0.05 | 0.06 | 0.25 | 0.05 | 0.05 | 0.44 |
| K656D | 0.07 | 0.05 | 0.05 | 0.05 | 0.08 | 0.14 | 0.05 | 0.05 | 0.37 |
| K656E | 0.06 | 0.05 | 0.05 | 0.09 | 0.07 | 0.12 | 0.05 | 0.05 | 0.33 |
| K656F | 0.05 | 0.05 | 0.05 | 0.05 | 0.05 | 0.05 | 0.05 | 0.05 | 0.05 |
| K656G | 0.05 | 0.05 | 0.05 | 0.05 | 0.05 | 0.35 | 0.05 | 0.05 | 0.28 |
| K656I | 0.08 | 0.05 | 0.05 | 0.05 | 0.08 | 0.31 | 0.05 | 0.05 | 0.37 |
| K656K | 1.00 | 1.00 | 1.00 | 1.00 | 1.00 | 1.00 | 1.00 | 1.00 | 1.00 |
| K656L | 0.06 | 0.05 | 0.05 | 0.05 | 0.07 | 0.13 | 0.05 | 0.05 | 0.44 |
| K656M | 0.05 | 0.05 | 0.05 | 0.05 | 0.05 | 0.05 | 0.05 | 0.05 | 0.05 |
| K656P | 0.07 | 0.05 | 0.05 | 0.05 | 0.05 | 0.16 | 0.05 | 0.05 | 0.43 |
| K656Q | 0.05 | 0.05 | 0.05 | 0.05 | 0.05 | 0.05 | 0.05 | 0.05 | 0.05 |
| K656R | 0.40 | 0.58 | *1.19* | 0.46 | 0.93 | 0.97 | 0.92 | 0.95 | 0.82 |
| K656S | 0.05 | 0.05 | 0.05 | 0.05 | 0.05 | 0.05 | 0.05 | 0.05 | 0.05 |
| K656T | 0.05 | 0.05 | 0.05 | 0.05 | 0.05 | 0.05 | 0.05 | 0.05 | 0.05 |
| K656V | 0.05 | 0.05 | 0.05 | 0.05 | 0.05 | 0.05 | 0.05 | 0.05 | 0.05 |
| K656W | 0.05 | 0.05 | 0.05 | 0.05 | 0.05 | 0.05 | 0.05 | 0.05 | 0.05 |
| K656Y | 0.05 | 0.05 | 0.05 | 0.05 | 0.05 | 0.05 | 0.05 | 0.05 | 0.05 |
| T660C | 0.59 | *1.06* | *1.04* | *1.08* | *1.17* | *1.16* | *1.25* | *1.20* | 0.90 |
| T660D | 0.85 | *1.08* | 0.99 | *1.24* | *1.05* | 0.98 | 1.00 | *1.01* | 0.95 |
| T660E | 0.86 | 0.92 | *1.08* | *1.24* | 0.95 | 0.84 | 0.91 | 0.82 | 0.98 |
| T660F | 0.61 | 0.86 | *1.06* | *1.08* | 0.97 | 0.96 | *1.01* | 0.96 | 0.86 |
| T660G | 0.83 | 0.92 | *1.08* | 0.30 | 1.00 | 0.80 | 0.93 | 0.93 | 0.86 |
| T660H | 0.62 | 0.92 | 0.95 | *1.20* | 0.97 | 0.93 | 0.95 | 0.91 | 0.80 |
| T660I | 0.90 | *1.01* | *1.11* | *1.60* | 0.99 | 0.99 | 0.99 | 0.95 | 0.80 |
| T660K | 0.68 | 0.90 | *1.02* | *1.06* | 0.95 | 0.78 | 0.86 | 0.92 | 0.76 |
| T660L | 0.42 | 0.80 | 0.97 | 0.92 | 0.98 | 0.91 | 0.98 | 0.92 | 0.58 |
| T660M | 0.61 | 0.84 | *1.10* | *1.13* | 0.95 | 0.83 | 0.90 | 0.89 | 0.69 |
| T660N | 0.47 | 0.88 | *1.06* | 0.95 | 1.07 | 0.94 | *1.04* | *1.03* | 0.88 |
| T660P | 0.16 | 0.33 | *1.25* | 0.30 | 0.66 | 0.55 | 0.57 | 0.70 | 0.32 |
| T660Q | 0.61 | 0.87 | *1.02* | *1.06* | 1.00 | 0.97 | 0.91 | 0.89 | 0.67 |
| T660R | 0.18 | 0.42 | *1.16* | 0.32 | 0.87 | 0.80 | 0.75 | 0.87 | 0.38 |
| T660S | 0.52 | 0.94 | *1.03* | 0.97 | *1.05* | 0.80 | *1.01* | *1.05* | 0.76 |
| T660T | 1.00 | 1.00 | 1.00 | 1.00 | 1.00 | 1.00 | 1.00 | 1.00 | 1.00 |
| T660V | 0.66 | 0.93 | *1.04* | *1.09* | 0.94 | 0.87 | 0.90 | 0.90 | 0.90 |
| T660W | 0.29 | *1.33* | *1.08* | *1.14* | *1.83* | *1.52* | *1.99* | *2.12* | *1.44* |

TABLE 3-1-continued

Performance Index Data of BGL1 SEL Variants (3,153)

| | | | | | | | | |
|---|---|---|---|---|---|---|---|---|
| T660Y | 0.62 | 0.97 | *1.09* | *1.19* | *1.01* | *1.11* | *1.04* | *1.01* | 0.83 |
| P661A | 0.82 | 0.94 | *1.02* | 0.99 | *1.03* | 0.97 | 1.00 | *1.17* | *1.00* |
| P661C | 0.62 | *1.22* | *1.03* | *1.05* | *1.28* | *1.09* | *1.37* | *1.51* | *1.52* |
| P661D | 0.75 | *1.04* | *1.03* | *1.03* | *1.04* | 0.86 | *1.07* | *1.11* | *1.16* |
| P661E | 0.45 | 0.98 | 1.00 | 0.93 | *1.18* | 0.88 | *1.14* | *1.06* | 0.86 |
| P661F | 0.23 | *1.07* | *1.01* | 0.75 | *1.71* | *1.48* | *1.88* | *1.74* | *1.43* |
| P661G | 0.66 | 0.87 | *1.07* | 0.93 | 0.91 | 0.98 | 0.95 | *1.09* | 0.94 |
| P661H | 0.36 | 0.86 | 0.98 | 0.66 | *1.18* | *1.06* | *1.17* | *1.24* | 0.90 |
| P661I | 0.28 | *1.07* | *1.05* | 0.87 | *1.52* | *1.14* | *1.64* | *1.74* | *1.56* |
| P661K | 0.47 | 0.83 | 0.98 | 0.74 | *1.04* | *1.03* | *1.02* | *1.14* | *1.05* |
| P661L | 0.19 | *1.18* | 0.94 | 0.84 | *1.94* | *1.29* | *2.28* | *2.24* | *1.63* |
| P661M | 0.15 | 0.79 | 0.88 | 0.51 | *1.61* | *1.17* | *1.72* | *1.90* | *1.02* |
| P661P | 1.00 | 1.00 | 1.00 | 1.00 | 1.00 | 1.00 | 1.00 | 1.00 | 1.00 |
| P661Q | 0.37 | 0.99 | 0.98 | 0.81 | *1.29* | *1.16* | *1.41* | *1.48* | *1.10* |
| P661R | 0.47 | 0.91 | 0.95 | 0.83 | *1.09* | *1.09* | *1.08* | *1.26* | *1.17* |
| P661S | 0.37 | *1.16* | 0.93 | *1.04* | *1.33* | 0.98 | *1.61* | *1.43* | *1.28* |
| P661T | 0.24 | 0.95 | 0.98 | 0.75 | *1.49* | *1.09* | *1.55* | *1.64* | *1.21* |
| P661V | 0.48 | *1.13* | 0.99 | *1.07* | *1.14* | *1.00* | *1.24* | *1.28* | *1.12* |
| P661W | 0.14 | *1.06* | 0.93 | 0.59 | *2.40* | *1.51* | *2.61* | *2.81* | *1.70* |
| G662A | 0.30 | *1.33* | 0.96 | 0.96 | *1.81* | *1.34* | *1.93* | *1.81* | *1.46* |
| G662C | 0.16 | *1.77* | 0.99 | *1.27* | *3.34* | *2.49* | *4.24* | *4.02* | *2.74* |
| G662D | *1.27* | 0.97 | 0.99 | *1.44* | 0.98 | 0.91 | 0.93 | 0.88 | *1.05* |
| G662E | *1.33* | 0.86 | *1.02* | *1.49* | 0.91 | 0.98 | 0.78 | 0.76 | 0.81 |
| G662F | 0.59 | *1.36* | *1.01* | *1.71* | *1.35* | *1.14* | *1.48* | *1.33* | *1.42* |
| G662G | 1.00 | 1.00 | 1.00 | 1.00 | 1.00 | 1.00 | 1.00 | 1.00 | 1.00 |
| G662H | 0.89 | *1.01* | 0.97 | *1.39* | *1.01* | *1.07* | 0.94 | 0.90 | 0.85 |
| G662I | 0.21 | 0.67 | *1.12* | 0.11 | *1.32* | *1.03* | *1.36* | *1.38* | 0.69 |
| G662K | 0.77 | 0.97 | *1.05* | *1.36* | 0.97 | *1.05* | 0.88 | 0.87 | 0.74 |
| G662L | *1.02* | 0.94 | *1.01* | *1.51* | 0.95 | 0.98 | 0.89 | 0.80 | 0.85 |
| G662M | 0.90 | 0.97 | *1.04* | *1.36* | 0.98 | 0.98 | 0.88 | 0.85 | 0.83 |
| G662N | 0.67 | 0.98 | *1.07* | *1.32* | *1.03* | 0.86 | 0.99 | 0.92 | 0.79 |
| G662P | 0.25 | 0.56 | 0.96 | 0.50 | 0.87 | 0.92 | 0.78 | 0.78 | 0.44 |
| G662Q | 0.95 | 0.91 | *1.12* | *1.41* | 0.92 | 0.87 | 0.84 | 0.80 | 0.63 |
| G662R | 0.76 | 0.91 | 0.99 | *1.18* | 0.92 | *1.00* | 0.88 | 0.84 | 0.71 |
| G662S | *1.13* | 0.84 | *1.13* | *1.26* | 0.90 | 0.95 | 0.74 | 0.74 | 0.80 |

TABLE 3-1-continued

Performance Index Data of BGL1 SEL Variants (3,153)

| | | | | | | | | |
|---|---|---|---|---|---|---|---|---|
| G662T | *1.00* | *1.03* | 0.99 | *1.58* | 0.95 | 0.80 | 0.92 | 0.89 | 0.80 |
| G662V | 0.54 | 0.87 | 1.00 | 1.00 | 0.95 | 0.81 | 0.94 | 0.87 | 0.67 |
| G662W | 0.99 | *1.02* | *1.02* | *1.20* | 0.97 | 0.93 | 0.92 | 0.75 | 0.88 |
| G662Y | 0.73 | *1.02* | 1.00 | *1.24* | 0.99 | *1.20* | 0.93 | 0.97 | 0.80 |
| Q663A | 0.84 | *1.07* | 0.82 | 0.70 | 0.92 | *1.07* | 0.96 | 0.99 | *1.33* |
| Q663C | 0.77 | *1.01* | 0.97 | 0.64 | 0.96 | *1.06* | 0.99 | *1.03* | *1.44* |
| Q663D | *1.10* | *1.09* | 0.96 | 0.78 | 0.98 | *1.21* | *1.05* | *1.03* | *1.49* |
| Q663E | 0.30 | *1.24* | 0.92 | 0.54 | *1.46* | *1.61* | *1.56* | *1.73* | *1.80* |
| Q663F | 0.66 | 0.96 | 0.93 | 0.49 | 0.90 | *1.25* | 0.95 | *1.01* | *1.33* |
| Q663G | *1.13* | *1.04* | 0.85 | 0.98 | 0.95 | 0.96 | *1.05* | *1.00* | *1.31* |
| Q663H | 0.50 | 0.94 | 0.98 | 0.61 | 0.90 | 0.99 | 0.92 | *1.03* | *1.03* |
| Q663I | 0.60 | *1.09* | 0.85 | 0.62 | 0.93 | *1.30* | *1.06* | *1.09* | 0.97 |
| Q663K | 0.89 | *1.04* | 0.84 | 0.67 | 0.84 | 0.91 | 0.92 | 0.94 | 0.99 |
| Q663L | 0.68 | 0.94 | 0.79 | 0.68 | 0.87 | *1.11* | 0.94 | 0.97 | *1.09* |
| Q663M | 0.70 | 0.97 | 0.77 | 0.71 | 0.88 | *1.18* | 0.97 | 0.96 | 0.99 |
| Q663N | 0.78 | 0.97 | 0.78 | 0.74 | 0.88 | *1.10* | 0.92 | 0.92 | *1.23* |
| Q663Q | 1.00 | 1.00 | 1.00 | 1.00 | 1.00 | 1.00 | 1.00 | 1.00 | 1.00 |
| Q663R | 0.81 | 1.00 | 0.83 | 0.53 | 0.84 | *1.13* | 0.94 | 0.88 | *1.19* |
| Q663S | 0.85 | *1.00* | 0.98 | 0.84 | 0.91 | *1.07* | 0.95 | 0.96 | *1.17* |
| Q663T | 0.04 | 0.04 | 0.04 | 0.04 | 0.04 | 0.04 | 0.04 | 0.04 | 0.04 |
| Q663V | 0.89 | 0.89 | *1.00* | 0.72 | 0.86 | *1.09* | 0.92 | 0.87 | *1.12* |
| Q663W | 0.96 | *1.09* | *1.00* | 0.82 | 0.91 | *1.16* | 0.99 | 1.00 | 0.93 |
| Q663Y | 0.04 | 0.04 | 0.04 | 0.04 | 0.04 | 0.04 | 0.04 | 0.04 | 0.04 |
| T666A | *1.01* | *1.02* | *1.08* | *1.18* | 0.99 | *1.01* | 0.94 | 0.95 | *1.04* |
| T666C | 0.43 | *1.28* | *1.03* | 0.90 | *1.45* | *1.38* | *1.56* | *1.50* | *1.27* |
| T666D | 0.65 | 0.90 | *1.03* | 0.75 | *1.03* | 1.00 | 0.94 | 0.95 | 0.82 |
| T666E | 0.70 | 0.89 | *1.03* | 0.83 | 0.94 | 0.92 | 0.85 | 0.85 | 0.79 |
| T666F | 0.82 | 0.77 | *1.05* | 0.77 | 0.84 | 0.95 | 0.77 | 0.76 | 0.65 |
| T666G | 0.51 | 0.79 | *1.04* | 0.63 | 0.93 | 0.87 | 0.87 | 0.84 | 0.77 |
| T666H | 0.56 | 0.82 | *1.01* | 0.72 | 0.91 | *1.02* | 0.84 | 0.88 | 0.72 |
| T666I | 0.64 | 0.79 | 1.00 | 0.80 | 0.84 | 0.96 | 0.81 | 0.90 | 0.77 |
| T666K | 0.67 | 0.89 | 0.97 | 0.74 | 0.90 | *1.10* | 0.87 | 0.97 | 0.85 |
| T666L | 0.65 | 0.93 | *1.04* | 0.86 | 0.81 | 0.96 | 0.86 | 0.83 | 0.83 |
| T666M | 0.62 | 0.97 | 1.00 | 0.89 | 0.88 | 0.99 | 0.95 | 0.86 | 0.84 |
| T666N | 0.49 | *1.17* | 0.99 | 0.91 | *1.09* | *1.15* | *1.21* | *1.19* | *1.01* |

TABLE 3-1-continued

Performance Index Data of BGL1 SEL Variants (3,153)

| | | | | | | | | | |
|---|---|---|---|---|---|---|---|---|---|
| T666P | 0.47 | 0.85 | 0.98 | 0.77 | 0.91 | 0.98 | 0.83 | 0.88 | 0.64 |
| T666R | 0.61 | 0.88 | 0.99 | 0.75 | 0.83 | *1.05* | 0.90 | *1.01* | 0.74 |
| T666S | 0.68 | 0.89 | *1.02* | 0.94 | 0.95 | 0.98 | 0.86 | 0.92 | 0.81 |
| T666T | 1.00 | 1.00 | 1.00 | 1.00 | 1.00 | 1.00 | 1.00 | 1.00 | 1.00 |
| T666V | 0.69 | 0.92 | *1.04* | 0.89 | 0.88 | 0.80 | 0.86 | 0.91 | 0.86 |
| T666W | 0.63 | 0.80 | 0.99 | 0.71 | 0.90 | *1.00* | 0.83 | 0.81 | 0.74 |
| T666Y | 0.77 | 0.90 | *1.01* | 0.77 | 0.90 | 0.92 | 0.82 | 0.81 | 0.81 |
| R672A | 0.56 | 0.80 | 0.84 | 0.53 | 0.97 | 0.97 | 0.91 | 0.98 | 0.92 |
| R672C | 0.36 | 0.75 | 0.83 | 0.42 | *1.07* | *1.08* | *1.20* | *1.24* | *1.06* |
| R672D | 0.07 | 0.24 | 0.65 | 0.06 | *1.22* | *1.62* | *1.75* | *1.83* | 0.78 |
| R672E | 0.12 | 0.31 | 0.74 | 0.05 | 0.91 | 0.95 | *1.15* | *1.29* | 0.73 |
| R672F | 0.37 | 0.70 | 0.80 | 0.39 | 0.89 | 0.91 | *1.02* | *1.04* | 0.83 |
| R672G | 0.27 | 0.61 | 0.81 | 0.29 | *1.01* | *1.12* | *1.12* | *1.20* | 0.94 |
| R672H | 0.51 | 0.92 | 0.84 | 0.61 | 0.99 | 0.86 | *1.15* | *1.09* | 0.98 |
| R672I | 0.23 | 0.52 | 0.81 | 0.27 | 0.95 | *1.05* | *1.16* | *1.25* | 0.86 |
| R672K | 0.76 | *1.08* | 0.84 | 0.77 | 0.96 | *1.04* | *1.02* | *1.02* | *1.05* |
| R672L | 0.49 | 0.88 | 0.89 | 0.55 | *1.01* | 0.92 | *1.10* | *1.09* | 0.93 |
| R672M | 0.18 | 0.67 | *1.24* | 0.05 | *1.01* | 0.94 | *1.39* | *1.68* | 0.79 |
| R672N | 0.48 | 0.93 | 0.85 | 0.48 | *1.00* | 0.92 | *1.03* | *1.08* | 0.98 |
| R672P | 0.14 | 0.11 | 0.63 | 0.06 | 0.24 | 0.49 | 0.32 | 0.55 | 0.28 |
| R672Q | 0.15 | 0.19 | 0.76 | 0.05 | 0.47 | 0.77 | 0.67 | 0.86 | 0.34 |
| R672R | 1.00 | 1.00 | 1.00 | 1.00 | 1.00 | 1.00 | 1.00 | 1.00 | 1.00 |
| R672S | 0.11 | 0.13 | 0.75 | 0.05 | 0.38 | 0.68 | 0.48 | 0.83 | 0.36 |
| R672T | 0.32 | 0.87 | 0.85 | 0.44 | *1.17* | 0.97 | *1.38* | *1.48* | *1.12* |
| R672V | 0.56 | 0.92 | 0.92 | 0.57 | *1.00* | *1.01* | *1.05* | *1.07* | 0.96 |
| R672W | 0.16 | 0.43 | 0.85 | 0.17 | 0.99 | *1.25* | *1.28* | *1.53* | 0.75 |
| R672Y | 0.16 | 0.29 | 0.79 | 0.07 | 0.68 | 0.98 | 0.82 | *1.06* | 0.60 |
| R673A | 0.77 | 0.95 | 0.85 | 0.74 | 0.94 | *1.00* | *1.01* | 0.94 | *1.03* |
| R673C | 0.90 | 0.99 | 0.89 | 0.82 | 0.98 | *1.16* | *1.09* | 0.97 | *1.10* |
| R673E | 0.48 | 0.80 | 0.86 | 0.59 | 0.99 | 0.93 | *1.07* | *1.05* | 0.95 |
| R673F | 0.43 | 0.43 | *1.45* | 0.05 | 0.37 | 0.11 | 0.32 | 0.47 | 0.41 |
| R673G | 0.57 | 0.88 | 0.91 | 0.52 | *1.07* | *1.07* | *1.03* | *1.02* | *1.06* |
| R673H | 0.70 | 0.99 | 0.91 | 0.86 | 0.98 | *1.16* | *1.09* | 0.98 | *1.10* |
| R673I | 0.72 | 0.99 | 0.91 | 0.65 | 1.00 | *1.07* | *1.01* | *1.00* | *1.03* |
| R673K | 0.98 | *1.05* | 0.98 | 0.78 | *1.00* | *1.12* | *1.07* | 0.96 | *1.02* |
| R673L | 0.37 | 0.94 | 0.90 | 0.55 | *1.19* | *1.35* | *1.32* | *1.45* | *1.15* |

TABLE 3-1-continued

Performance Index Data of BGL1 SEL Variants (3,153)

| | | | | | | | | |
|---|---|---|---|---|---|---|---|---|
| R673M | 0.62 | 0.93 | 0.91 | 0.62 | 0.99 | 1.00 | *1.03* | *1.01* | *1.02* |
| R673N | *1.11* | *1.08* | *1.04* | 0.96 | *1.03* | 0.97 | *1.04* | 0.94 | 0.98 |
| R673P | 0.20 | 0.31 | 0.77 | 0.16 | 0.67 | 0.92 | 0.89 | 0.99 | 0.64 |
| R673Q | 0.76 | 0.97 | 0.88 | 0.72 | 0.99 | *1.03* | 1.00 | *1.01* | 0.95 |
| R673R | 1.00 | 1.00 | 1.00 | 1.00 | 1.00 | 1.00 | 1.00 | 1.00 | 1.00 |
| R673S | 0.79 | *1.02* | 0.96 | 0.83 | *1.02* | 0.94 | *1.10* | *1.04* | *1.07* |
| R673T | 0.89 | *1.08* | 0.94 | 0.85 | *1.03* | *1.00* | 0.96 | 1.00 | *1.10* |
| R673V | 0.99 | 1.00 | 0.96 | 0.76 | 0.99 | *1.10* | *1.01* | 0.93 | *1.09* |
| R673W | *1.21* | 0.98 | *1.01* | *1.11* | 0.93 | *1.07* | 0.97 | 0.96 | *1.07* |
| R674A | 0.39 | 0.05 | 0.05 | 0.19 | 0.39 | 0.51 | 0.30 | 0.27 | 0.34 |
| R674C | 0.42 | 0.05 | 0.05 | 0.50 | 0.37 | 0.40 | 0.29 | 0.27 | 0.75 |
| R674D | 0.04 | 0.04 | 0.04 | 0.04 | 0.04 | 0.04 | 0.04 | 0.04 | 0.04 |
| R674E | 0.24 | 0.05 | 0.05 | 0.32 | 0.20 | 0.27 | 0.11 | 0.05 | 0.38 |
| R674G | 0.22 | 0.05 | 0.05 | 0.32 | 0.55 | 0.75 | 0.39 | 0.27 | 0.49 |
| R674H | 0.26 | 0.05 | 0.05 | 0.53 | 0.19 | 0.24 | 0.13 | 0.05 | 0.15 |
| R674I | 0.25 | 0.05 | 0.05 | 0.40 | 0.16 | 0.31 | 0.08 | 0.05 | 0.20 |
| R674K | 0.83 | 0.42 | *1.25* | 0.31 | 0.77 | 0.93 | 0.83 | 0.83 | 0.66 |
| R674L | 0.38 | 0.44 | *1.08* | 0.60 | 0.83 | *1.07* | 0.88 | 0.73 | 0.79 |
| R674M | 0.32 | 0.28 | 0.05 | 0.70 | 0.92 | *1.12* | 0.89 | 0.93 | *1.07* |
| R674P | 0.26 | 0.05 | 0.05 | 0.23 | 0.21 | 0.32 | 0.10 | 0.05 | 0.16 |
| R674Q | 0.28 | 0.43 | *1.15* | 0.94 | 0.71 | 0.82 | 0.62 | 0.63 | 0.38 |
| R674R | 1.00 | 1.00 | 1.00 | 1.00 | 1.00 | 1.00 | 1.00 | 1.00 | 1.00 |
| R674S | 0.26 | 0.05 | 0.05 | 0.29 | 0.28 | 0.40 | 0.19 | 0.09 | 0.60 |
| R674T | 0.06 | 0.05 | 0.05 | 0.12 | *1.59* | *2.22* | *1.50* | *1.02* | *1.18* |
| R674V | 0.39 | 0.05 | 0.05 | 0.19 | 0.78 | 0.72 | 0.58 | 0.55 | *1.04* |
| R674W | 0.29 | 0.05 | 0.05 | 0.36 | 0.63 | 0.76 | 0.59 | 0.54 | 0.96 |
| R674Y | 0.07 | 0.05 | 0.05 | 0.33 | *2.36* | *2.46* | *2.09* | *2.15* | 0.42 |
| D675A | 0.09 | 0.05 | 0.05 | 0.11 | 0.17 | 0.27 | 0.44 | 0.52 | 0.58 |
| D675C | 0.09 | 0.05 | 0.05 | 0.13 | 0.24 | *1.06* | 0.45 | 0.64 | 0.75 |
| D675D | 1.00 | 1.00 | 1.00 | 1.00 | 1.00 | 1.00 | 1.00 | 1.00 | 1.00 |
| D675E | 0.21 | *2.24* | *1.11* | 0.20 | 0.62 | 0.95 | 0.99 | 0.83 | 0.55 |
| D675F | 0.11 | 0.05 | 0.05 | 0.21 | 0.44 | 0.78 | 0.79 | 0.85 | 0.94 |
| D675G | 0.07 | 0.05 | 0.05 | 0.11 | 0.05 | 0.52 | 0.34 | 0.70 | 0.72 |
| D675H | 0.28 | *1.78* | *1.04* | 0.30 | 0.80 | 0.94 | 0.96 | 0.85 | 0.80 |
| D675I | 0.04 | 0.04 | 0.04 | 0.04 | 0.04 | 0.04 | 0.04 | 0.04 | 0.04 |

TABLE 3-1-continued

Performance Index Data of BGL1 SEL Variants (3,153)

| D675K | 0.07 | 0.05 | 0.05 | 0.08 | 0.08 | 0.05 | 0.47 | 0.61 | 0.46 |
|---|---|---|---|---|---|---|---|---|---|
| D675L | 0.10 | 0.05 | 0.05 | 0.21 | 0.38 | 0.41 | 0.67 | *1.38* | 0.67 |
| D675M | 0.09 | 0.05 | 0.05 | 0.17 | 0.35 | 0.05 | 0.64 | 0.74 | 0.74 |
| D675N | 0.10 | 0.05 | 0.05 | 0.22 | 0.40 | 0.48 | 0.66 | 0.82 | 0.87 |
| D675P | 0.08 | 0.05 | 0.05 | 0.08 | 0.05 | 0.05 | 0.35 | 0.50 | 0.41 |
| D675R | 0.04 | 0.04 | 0.04 | 0.04 | 0.04 | 0.04 | 0.04 | 0.04 | 0.04 |
| D675S | 0.23 | *1.89* | *1.09* | 0.24 | 0.71 | 0.80 | 0.83 | 0.84 | 0.70 |
| D675T | 0.07 | 0.05 | 0.05 | 0.07 | 0.12 | 0.68 | 0.69 | 0.58 | 0.70 |
| D675V | 0.07 | 0.05 | 0.05 | 0.08 | 0.05 | 0.05 | 0.29 | 0.67 | 0.62 |
| D675W | 0.07 | 0.05 | 0.05 | 0.10 | 0.05 | 0.05 | 0.25 | 0.65 | 0.48 |
| D675Y | 0.22 | *1.92* | *1.15* | 0.23 | 0.66 | 0.98 | 0.92 | 0.95 | 0.66 |
| D680A | 0.60 | *1.04* | 0.91 | 0.63 | 0.97 | *1.05* | *1.07* | *1.10* | *1.00* |
| D680C | 0.88 | *1.10* | 0.91 | 0.92 | *1.05* | *1.09* | *1.18* | *1.13* | *1.18* |
| D680D | 1.00 | 1.00 | 1.00 | 1.00 | 1.00 | 1.00 | 1.00 | 1.00 | 1.00 |
| D680E | 0.77 | *1.06* | 0.98 | 0.75 | 0.99 | *1.02* | *1.08* | *1.02* | 0.99 |
| D680F | 0.30 | 0.90 | 0.88 | 0.44 | *1.03* | *1.42* | *1.11* | *1.18* | 0.97 |
| D680G | 0.61 | 0.92 | 0.93 | 0.63 | 0.93 | 0.98 | 0.99 | 0.96 | 0.87 |
| D680H | 0.41 | 0.95 | 0.91 | 0.51 | 0.99 | *1.31* | *1.11* | *1.19* | 0.90 |
| D680I | 0.28 | 0.95 | 0.87 | 0.37 | *1.07* | *1.39* | *1.22* | *1.26* | 0.85 |
| D680K | 0.84 | 0.97 | 0.86 | 0.75 | 1.00 | *1.07* | 0.98 | 0.92 | 0.84 |
| D680L | 0.25 | 0.71 | 0.92 | 0.27 | 0.88 | *1.53* | 0.95 | *1.02* | 0.78 |
| D680M | 0.50 | *1.08* | 0.86 | 0.61 | *1.01* | *1.23* | *1.07* | *1.05* | *1.06* |
| D680N | 0.43 | 0.90 | 0.91 | 0.46 | 0.95 | *1.20* | 0.99 | 0.99 | 0.94 |
| D680P | 0.09 | 0.15 | 0.05 | 0.05 | 0.25 | 0.91 | 0.31 | 0.16 | 0.33 |
| D680Q | 0.65 | *1.06* | 0.90 | 0.70 | *1.01* | *1.10* | *1.03* | *1.10* | *1.01* |
| D680R | 0.87 | *1.00* | 0.92 | 0.86 | 1.00 | *1.11* | *1.08* | 0.95 | 0.93 |
| D680S | 0.20 | 0.48 | 0.87 | 0.19 | 0.69 | *1.03* | 0.70 | 0.69 | 0.58 |
| D680V | 0.66 | *1.08* | 0.90 | 0.72 | *1.08* | *1.15* | *1.09* | *1.10* | *1.16* |
| D680W | 0.29 | 0.85 | 0.90 | 0.36 | 0.99 | *1.27* | *1.12* | *1.11* | *1.03* |
| D680Y | 0.48 | *1.10* | 0.91 | 0.63 | *1.06* | *1.25* | *1.21* | *1.21* | *1.02* |
| T681A | 0.87 | *1.06* | 0.99 | 0.91 | *1.04* | *1.45* | 0.99 | *1.08* | *1.10* |
| T681F | 0.04 | 0.04 | 0.04 | 0.04 | 0.04 | 0.04 | 0.04 | 0.04 | 0.04 |
| T681G | 0.48 | *1.05* | *1.02* | 0.70 | *1.06* | *1.04* | *1.23* | *1.22* | *1.30* |
| T681H | 0.49 | 0.89 | 0.93 | 0.56 | 0.93 | *1.11* | *1.01* | *1.05* | 0.91 |
| T681K | 0.52 | 0.99 | 0.92 | 0.61 | 0.99 | *1.04* | *1.10* | *1.11* | *1.06* |

TABLE 3-1-continued

Performance Index Data of BGL1 SEL Variants (3,153)

| | | | | | | | | | |
|---|---|---|---|---|---|---|---|---|---|
| T681L | 0.67 | 0.93 | *1.02* | 0.77 | 0.95 | *1.02* | *1.15* | *1.01* | *1.01* |
| T681M | 0.53 | *1.00* | 0.97 | 0.61 | 1.00 | *1.03* | *1.10* | *1.19* | *1.19* |
| T681N | 0.59 | 0.93 | 0.99 | 0.65 | 0.94 | *1.06* | 0.97 | *1.01* | 0.95 |
| T681P | 0.44 | 0.92 | 0.95 | 0.56 | *1.01* | 0.96 | *1.19* | *1.09* | *1.06* |
| T681Q | 0.57 | 0.98 | 0.96 | 0.65 | *1.02* | *1.05* | *1.19* | *1.18* | *1.04* |
| T681R | 0.69 | 0.86 | 0.95 | 0.66 | 0.93 | *1.06* | 0.96 | 0.92 | 0.97 |
| T681S | 0.60 | *1.04* | 0.99 | 0.76 | *1.04* | 0.95 | *1.16* | *1.08* | *1.15* |
| T681T | 1.00 | 1.00 | 1.00 | 1.00 | 1.00 | 1.00 | 1.00 | 1.00 | 1.00 |
| T681V | 0.66 | 1.00 | 0.99 | 0.78 | *1.04* | 0.95 | *1.07* | *1.09* | *1.15* |
| T681W | 0.73 | *1.08* | 0.98 | 0.86 | *1.02* | *1.10* | *1.07* | *1.13* | *1.11* |
| T681Y | 0.61 | 0.80 | 0.96 | 0.57 | 0.73 | 0.93 | *1.15* | 0.96 | 0.90 |
| A682A | 1.00 | 1.00 | 1.00 | 1.00 | 1.00 | 1.00 | 1.00 | 1.00 | 1.00 |
| A682C | 0.45 | 0.33 | *1.02* | 0.16 | 0.51 | 0.73 | 0.49 | 0.55 | 0.39 |
| A682D | 0.45 | 0.42 | 0.87 | 0.22 | 0.62 | 0.86 | 0.61 | 0.73 | 0.56 |
| A682E | 0.26 | 0.21 | *1.11* | 0.13 | 0.41 | 0.64 | 0.41 | 0.53 | 0.29 |
| A682F | 0.28 | 0.27 | 0.86 | 0.17 | 0.47 | 0.62 | 0.54 | 0.65 | 0.59 |
| A682I | 0.11 | 0.14 | *2.29* | 0.14 | 0.49 | 0.90 | 0.60 | 0.87 | 0.42 |
| A682L | 0.26 | 0.26 | *1.68* | 0.18 | 0.54 | 0.66 | 0.61 | 0.73 | 0.45 |
| A682M | 0.30 | 0.21 | *1.40* | 0.10 | 0.39 | 0.67 | 0.42 | 0.48 | *1.09* |
| A682N | 0.33 | 0.34 | *1.06* | 0.47 | 0.53 | 0.62 | 0.59 | 0.70 | 0.67 |
| A682P | 0.28 | 0.22 | *1.31* | 0.22 | 0.42 | 0.61 | 0.40 | 0.57 | 0.26 |
| A682R | 0.04 | 0.04 | 0.04 | 0.04 | 0.04 | 0.04 | 0.04 | 0.04 | 0.04 |
| A682S | 0.29 | 0.24 | *1.96* | 0.12 | 0.45 | 0.61 | 0.45 | 0.54 | 0.51 |
| A682T | 0.33 | 0.30 | 0.94 | 0.16 | 0.48 | 0.65 | 0.47 | 0.57 | 0.28 |
| A682V | 0.34 | 0.41 | 0.80 | 0.22 | 0.64 | 0.93 | 0.60 | 0.72 | 0.52 |
| A682W | 0.37 | 0.28 | *1.34* | 0.15 | 0.49 | 0.61 | 0.45 | 0.57 | 0.35 |
| A682Y | 0.38 | 0.31 | *1.54* | 0.16 | 0.49 | 0.63 | 0.48 | 0.58 | 0.38 |
| S683A | 0.91 | 0.96 | *1.03* | 0.88 | 0.98 | *1.10* | 0.92 | 0.97 | 0.95 |
| S683C | 0.87 | 0.91 | *1.03* | 0.83 | 0.95 | *1.21* | *1.12* | 0.94 | 0.75 |
| S683D | 0.45 | 0.65 | *1.06* | 0.39 | 0.87 | *1.04* | *1.01* | 0.90 | 0.86 |
| S683E | 0.58 | 0.91 | *1.00* | 0.67 | 0.93 | 0.93 | *1.03* | *1.01* | *1.04* |
| S683F | 0.14 | 0.50 | 0.96 | 0.22 | *1.03* | *1.35* | *1.41* | *1.34* | 0.84 |
| S683G | 0.86 | *1.01* | 0.98 | 0.88 | 0.98 | *1.21* | *1.04* | 0.96 | 0.98 |
| S683I | 0.31 | 0.77 | 0.95 | 0.38 | 0.96 | *1.19* | *1.15* | *1.08* | 0.98 |
| S683K | *1.01* | 0.87 | *1.06* | 0.84 | 0.92 | 0.89 | 0.89 | 0.88 | 0.96 |
| S683L | 0.62 | 0.95 | *1.02* | 0.72 | 0.97 | *1.11* | 0.98 | *1.11* | 0.90 |

TABLE 3-1-continued

Performance Index Data of BGL1 SEL Variants (3,153)

| | | | | | | | | | |
|---|---|---|---|---|---|---|---|---|---|
| S683M | 0.53 | 0.92 | 1.00 | 0.60 | 0.97 | 0.99 | *1.28* | *1.07* | *1.01* |
| S683P | 0.57 | 0.90 | 1.00 | 0.62 | 0.89 | *1.08* | *1.02* | *1.05* | 0.96 |
| S683Q | 0.66 | 0.87 | 0.99 | 0.69 | 0.94 | 0.98 | *1.10* | 0.96 | 0.96 |
| S683R | 0.96 | 0.90 | *1.05* | 0.86 | 0.95 | *1.56* | 0.95 | 0.97 | 0.92 |
| S683S | 1.00 | 1.00 | 1.00 | 1.00 | 1.00 | 1.00 | 1.00 | 1.00 | 1.00 |
| S683V | 1.00 | *1.00* | *1.02* | *1.06* | *1.01* | *1.33* | *1.10* | *1.07* | *1.03* |
| S683W | 0.51 | *1.26* | 0.88 | 0.82 | *1.14* | *1.27* | *1.37* | *1.47* | *1.35* |
| Q684A | 0.53 | *1.14* | 0.95 | 0.54 | 0.88 | *1.10* | 0.93 | *1.04* | *1.05* |
| Q684C | 0.37 | *3.31* | *1.02* | 0.89 | *1.93* | 0.05 | *2.27* | *1.80* | *1.67* |
| Q684D | *1.03* | 0.87 | *1.04* | 0.86 | 0.91 | *1.06* | 0.90 | 0.71 | 0.85 |
| Q684E | 0.86 | 0.94 | *1.05* | 0.75 | 0.88 | 0.99 | 0.92 | 0.70 | 0.90 |
| Q684F | *1.52* | 0.84 | *1.11* | *1.32* | 0.90 | 0.91 | 0.89 | 0.68 | 0.87 |
| Q684G | 0.23 | *7.48* | *1.05* | 0.83 | *2.67* | 0.11 | *3.16* | *2.43* | *2.20* |
| Q684H | *1.25* | 0.97 | *1.00* | *1.17* | 0.96 | 0.98 | 0.92 | 0.75 | 0.99 |
| Q684I | 0.66 | 0.98 | *1.11* | 0.61 | 0.85 | 0.85 | 0.89 | 0.71 | 0.83 |
| Q684K | *1.15* | 0.83 | *1.05* | *1.05* | 0.81 | 0.93 | 0.85 | 0.69 | 0.86 |
| Q684L | *1.40* | 0.88 | *1.02* | *1.23* | 0.91 | 0.97 | 0.79 | 0.69 | 0.89 |
| Q684M | *1.53* | 0.80 | *1.10* | *1.31* | 0.88 | 0.86 | 0.82 | 0.70 | 0.85 |
| Q684N | 0.69 | *1.37* | *1.14* | 0.92 | *1.09* | 0.12 | *1.19* | 1.00 | *1.17* |
| Q684P | 0.35 | *1.28* | *1.15* | 0.34 | 0.82 | 0.93 | 0.86 | 0.77 | 0.90 |
| Q684Q | 1.00 | 1.00 | 1.00 | 1.00 | 1.00 | 1.00 | 1.00 | 1.00 | 1.00 |
| Q684R | *1.12* | 0.86 | *1.03* | 0.98 | 0.85 | 0.90 | 0.81 | 0.73 | 0.75 |
| Q684S | *1.86* | 0.79 | 1.00 | *1.39* | 0.87 | 0.97 | 0.81 | 0.69 | 0.79 |
| Q684T | *1.18* | 0.86 | *1.13* | *1.02* | 0.89 | 0.90 | 0.88 | 0.74 | 0.79 |
| Q684W | 0.04 | 0.04 | 0.04 | 0.04 | 0.04 | 0.04 | 0.04 | 0.04 | 0.04 |
| K685A | 0.67 | *1.23* | 0.98 | *1.02* | *1.16* | *1.02* | *1.18* | 0.99 | *1.16* |
| K685E | 0.69 | *1.12* | 0.95 | 0.92 | *1.03* | 0.86 | *1.01* | 0.81 | *1.09* |
| K685F | 0.60 | *1.13* | 0.98 | 0.89 | *1.02* | *1.15* | 0.99 | 0.85 | 0.62 |
| K685G | 0.41 | *1.15* | 0.94 | 0.75 | *1.22* | *1.24* | *1.14* | 0.95 | 0.96 |
| K685I | 0.35 | *1.13* | 0.95 | 0.72 | *1.25* | *1.27* | *1.15* | *1.12* | *1.07* |
| K685K | 1.00 | 1.00 | 1.00 | 1.00 | 1.00 | 1.00 | 1.00 | 1.00 | 1.00 |
| K685L | 0.65 | *1.30* | 0.98 | *1.16* | *1.15* | *1.07* | *1.19* | *1.01* | *1.13* |
| K685M | 0.53 | *1.32* | 0.99 | 0.97 | *1.13* | *1.23* | *1.21* | *1.05* | *1.18* |
| K685N | 0.37 | *1.21* | 0.94 | 0.76 | 0.93 | *1.10* | *1.25* | *1.09* | 0.95 |
| K685P | 0.04 | 0.04 | 0.04 | 0.04 | 0.04 | 0.04 | 0.04 | 0.04 | 0.04 |

TABLE 3-1-continued

Performance Index Data of BGL1 SEL Variants (3,153)

| | | | | | | | | |
|---|---|---|---|---|---|---|---|---|
| K685Q | 0.46 | *1.14* | 0.98 | 0.79 | *1.04* | *1.13* | *1.16* | 1.00 | 0.90 |
| K685R | 0.57 | *1.11* | 0.97 | 0.91 | 0.78 | *1.11* | 0.99 | 0.89 | 0.84 |
| K685S | 0.76 | *1.30* | 0.99 | *1.16* | *1.11* | *1.06* | *1.07* | *1.03* | *1.18* |
| K685T | 0.39 | *1.20* | 0.98 | 0.77 | *1.17* | *1.21* | *1.22* | *1.11* | *1.17* |
| K685V | 0.42 | *1.22* | 0.96 | 0.85 | 0.96 | *1.01* | *1.20* | *1.03* | 0.97 |
| K685W | 0.51 | *1.33* | 0.99 | 0.89 | *1.28* | *1.17* | *1.33* | *1.01* | *1.14* |
| K685Y | 0.53 | *1.18* | 0.98 | 0.81 | *1.11* | *1.07* | *1.01* | *1.07* | *1.01* |
| S692C | 0.77 | *1.31* | 0.94 | 0.95 | *1.11* | 0.90 | *1.15* | *1.18* | *1.29* |
| S692D | 0.82 | 1.00 | 0.93 | 0.71 | 0.96 | 0.84 | 0.97 | 0.94 | 0.94 |
| S692E | 0.77 | *1.03* | 0.98 | 0.77 | 0.94 | *1.01* | 0.92 | 0.88 | 0.96 |
| S692F | 0.04 | 0.04 | 0.04 | 0.04 | 0.04 | 0.04 | 0.04 | 0.04 | 0.04 |
| S692G | 0.60 | 0.98 | 0.98 | 0.67 | 0.94 | 0.94 | 0.86 | 0.98 | 0.99 |
| S692H | 0.86 | *1.20* | *1.03* | *1.03* | *1.03* | *1.03* | *1.04* | *1.15* | *1.19* |
| S692I | 0.56 | *1.17* | 0.92 | 0.77 | *1.03* | 1.00 | *1.03* | *1.08* | *1.07* |
| S692K | 0.89 | *1.15* | 1.00 | *1.03* | 0.98 | *1.03* | 0.94 | 0.96 | 0.99 |
| S692L | 0.90 | *1.21* | *1.00* | *1.21* | *1.02* | *1.21* | *1.04* | 0.96 | *1.12* |
| S692M | 0.70 | *1.22* | 0.98 | *1.06* | *1.03* | 0.95 | *1.04* | *1.06* | *1.09* |
| S692N | 0.91 | *1.02* | *1.00* | 0.97 | 0.91 | 0.98 | 0.84 | 0.83 | 0.90 |
| S692P | 0.60 | *1.05* | 0.89 | 0.63 | 0.92 | 0.92 | 0.85 | 0.91 | *1.01* |
| S692Q | 0.79 | *1.06* | 0.99 | 0.84 | 0.97 | *1.14* | 0.88 | 0.98 | 0.90 |
| S692R | 0.95 | 0.89 | 0.98 | 0.73 | 0.83 | 0.92 | 0.80 | 0.80 | 0.92 |
| S692S | 1.00 | 1.00 | 1.00 | 1.00 | 1.00 | 1.00 | 1.00 | 1.00 | 1.00 |
| S692T | 0.89 | *1.14* | *1.03* | *1.01* | 0.99 | *1.05* | 0.97 | *1.00* | 0.89 |
| S692V | 0.86 | *1.12* | *1.10* | 0.80 | *1.05* | *1.21* | 1.00 | *1.06* | *1.12* |
| S692W | 0.66 | *1.18* | 0.99 | 0.62 | *1.02* | *1.11* | *1.07* | *1.25* | *1.02* |
| S692Y | 0.04 | 0.04 | 0.04 | 0.04 | 0.04 | 0.04 | 0.04 | 0.04 | 0.04 |
| R702C | 0.56 | 0.90 | *1.08* | 0.52 | *1.05* | *1.10* | *1.11* | *1.02* | *1.03* |
| R702D | 0.24 | 0.79 | *1.01* | 0.20 | *1.24* | *1.61* | *1.24* | *1.11* | 0.89 |
| R702F | 0.28 | 0.80 | *1.06* | 0.16 | *1.12* | *1.24* | *1.11* | 0.96 | 0.55 |
| R702G | 0.46 | *1.10* | *1.05* | 0.57 | *1.22* | *1.34* | *1.32* | *1.20* | *1.11* |
| R702H | 0.38 | 0.94 | 0.94 | 0.47 | *1.01* | *1.31* | *1.09* | 0.95 | 0.81 |
| R702I | 0.57 | 0.91 | *1.05* | 0.61 | 0.95 | *1.04* | *1.04* | 0.94 | 0.75 |
| R702K | 0.99 | 0.90 | *1.07* | 0.83 | 0.94 | *1.06* | *1.04* | 0.99 | 0.98 |
| R702L | 0.51 | 1.00 | *1.02* | 0.69 | 0.99 | *1.28* | *1.10* | *1.01* | 0.96 |
| R702M | 0.53 | 0.86 | *1.09* | 0.59 | 0.91 | *1.01* | 0.97 | 0.87 | 0.73 |

TABLE 3-1-continued

Performance Index Data of BGL1 SEL Variants (3,153)

| | | | | | | | | | |
|---|---|---|---|---|---|---|---|---|---|
| R702N | 0.53 | 0.96 | 1.00 | 0.49 | 0.94 | *1.29* | *1.07* | 0.94 | 0.77 |
| R702P | 0.05 | 0.05 | 0.05 | 0.05 | 0.05 | 0.80 | 0.05 | 0.05 | 0.28 |
| R702Q | 0.57 | 0.91 | *1.06* | 0.56 | 0.95 | *1.13* | *1.01* | *1.04* | 0.84 |
| R702R | 1.00 | 1.00 | 1.00 | 1.00 | 1.00 | 1.00 | 1.00 | 1.00 | 1.00 |
| R702S | 0.43 | 0.93 | *1.01* | 0.44 | *1.01* | *1.04* | *1.05* | *1.11* | *1.01* |
| R702T | 0.39 | 0.94 | 0.97 | 0.43 | *1.01* | *1.30* | *1.06* | *1.01* | 0.83 |
| R702V | 0.65 | 0.97 | *1.05* | 0.64 | *1.05* | *1.11* | *1.13* | *1.18* | 0.82 |
| R702W | 0.56 | 0.95 | *1.12* | 0.58 | 0.98 | *1.18* | *1.11* | *1.20* | 0.94 |
| R705C | 0.64 | 0.97 | 0.83 | 0.67 | 1.00 | *1.05* | 0.97 | 0.96 | *1.01* |
| R705D | 0.25 | 0.37 | 0.99 | 0.13 | 0.72 | 0.94 | 0.56 | 0.74 | 0.52 |
| R705E | 0.24 | 0.44 | 0.85 | 0.23 | 0.71 | 0.87 | 0.61 | 0.83 | 0.76 |
| R705F | 0.47 | 0.93 | 0.96 | 0.53 | *1.04* | *1.18* | 0.99 | *1.11* | 0.95 |
| R705G | 0.33 | 0.76 | 0.90 | 0.34 | 0.96 | 1.00 | 0.89 | 0.98 | 0.79 |
| R705H | 0.37 | 0.84 | 0.96 | 0.71 | 0.99 | *1.09* | 0.95 | *1.08* | 0.85 |
| R705I | 0.59 | *1.02* | 0.92 | 0.84 | *1.15* | *1.22* | *1.13* | *1.23* | *1.07* |
| R705L | 0.49 | 0.96 | 0.88 | *1.07* | *1.07* | *1.08* | 0.96 | *1.10* | 0.81 |
| R705M | 0.42 | 0.90 | 0.77 | 0.70 | *1.06* | *1.19* | 0.92 | 0.99 | 0.87 |
| R705N | 0.28 | 0.59 | 1.00 | 0.40 | 0.85 | 0.90 | 0.72 | 0.87 | 0.82 |
| R705P | 0.27 | 0.67 | *1.04* | 0.41 | 0.85 | *1.07* | 0.77 | 0.94 | 0.67 |
| R705R | 1.00 | 1.00 | 1.00 | 1.00 | 1.00 | 1.00 | 1.00 | 1.00 | 1.00 |
| R705S | 0.35 | 0.87 | 0.91 | 0.61 | *1.06* | *1.07* | 0.93 | *1.05* | 0.86 |
| R705T | 0.41 | 0.94 | 0.85 | 0.70 | *1.03* | *1.08* | 0.98 | *1.10* | *1.24* |
| R705V | 0.56 | *1.03* | 0.95 | 0.80 | *1.07* | 0.98 | *1.00* | *1.05* | *1.15* |
| R705W | 0.43 | 0.93 | 0.83 | 0.51 | *1.05* | *1.15* | 0.97 | *1.08* | 0.87 |
| R705Y | 0.35 | 0.80 | 0.92 | 0.34 | 0.94 | 0.93 | 0.85 | 0.84 | 0.89 |

Various terms, for example, Heat, CNPG, PASC, PCS, GLUC, G2 pH 5, G2 pH 6, G2 CC, are used to describe the mutations with respect to activity and/or stability in the table above. Up mutations have a PI of 1 greater; neutral mutations have a PI greater than or equal to 0.5; non-deleterious mutations have a PI greater than 0.05; and deleterious mutations have a PI of 0.05. Positions at which mutations occur are classified as follows: non-fully restrictive positions have at least one neutral mutation for at least one property, while fully restrictive positions have no neutral mutations for activity and stability.

As determined during development of the present disclosure, positions 441 and 452 of *H. jecorina* BGL1 are fully restrictive positions. The data presented in Table 3-1 may be used to engineer any beta-glucosidase, even if the BGL1 to be engineered has an amino acid different from that of *H. jecorina* BGL1 at a particular position. For instance, the data in Table 3-1 may be used to find a substitution that will alter the desired property of a BGL, by identifying the best choice substitution, including a substitution to the *H. jecorina* BGL1 wild type amino acid.

All BGL1 variants (3,153) were categorized as described above. Combinable mutations are mutations that can be combined to deliver proteins with appropriate performance indices for one or more desired properties. Briefly, 2,609 moderately combinable variants having a PI greater than or equal to 0.5 for at least one property were identified. In addition, 365 highly combinable variants having a PI of at least 0.5 for protein expression (HPLC) and a PI greater than 0.8 for all other properties were identified, while 213 of these highly combinable variants were found to have a PI greater than 0.8 for all properties. Non-combinable variants are those for which all PI values are ≤0.05. Any BGL1 variant that has one of the above substitutions relative to *Hypocrea jecorina* BGL1 can be improved by mutating that amino acid to one of the computable substitutions at that position. Of the 3153 BGL1 variants listed in Table 3-1, 2,268 up variants having a PI of 1.0 or greater for at least one property were identified, while 1,836 up variants having a PI greater than 1.1 for at least one property were identified.

In some embodiments, the variants are improved variants having a PI greater than or equal to 1.0 in at least one property of interest. However, in other embodiments, BGL1 variants of interest have a PI between 0.1 and 1.0 for expression. In particular, in instances when moderate to high levels of expression of a BGL1 variant are deleterious for protein production in a fermentator, variants with a PI between 0.1 and 1.0 for expression are desirable. Likewise, in circumstances in which an optimal ratio of enzyme concentrations is desired in the culture medium of a recombinant host cell, it may be desirable to utilize a variant, having a reduced but measureable level of expression (0.1<PI<1.0).

In further embodiments, the BGL1 variants of interest have a PI between 0.1 and 1.0 for thermostability. For instance when a variant has reduced thermostability as compared to the wild type or reference BGL but improved activity under conditions of interest, then variants with a PI between 0.1 and 1.0 for thermostability are desirable. Likewise, in circumstances in which an optimal ratio of enzyme activities is desired in the culture medium of a recombinant host cell, it is desirable to utilize a variant having a reduced but appreciable level of thermostability (0.1<PI<1.0).

Likewise in some embodiments, the BGL1 variants of interest have a PI between 0.1 and 1.0 for activity. For instance when a variant has reduced activity as compared to the wild type or reference BGL but improved thermostability under conditions of interest, then variants with a PI between 0.1 and 1.0 for activity are desirable. Likewise, in circumstances in which an optimal ratio of enzyme activities is desired its the culture medium of a recombinant host cell, it is desirable to utilize a variant having a reduced but appreciable level of activity (0.1<PI<0.1).

Table 3-2 provides a summary of variants of particular interest identified from the above-described study that have a number of improved activities over wild type BGL1.

TABLE 3-2

| Variant | Glu | Heat | HPLC | PASC | PCS | G2 pH5 | G2 pH6 | CNPG | G2 spiked CC |
|---|---|---|---|---|---|---|---|---|---|
| L167W | wt | + | wt | wt | wt | wt | wt | wt | wt |
| E170F | + | − | −− | + | + | ++ | ++ | wt | − |
| P176L | wt | −− | −− | wt | ++ | + | wt | + | wt |
| D177M | wt | −− | −− | + | wt | ++ | ++ | wt | wt |
| D178I | wt | −− | −− | − | − | − | −− | − | −− |
| D178K | wt | − | −− | wt | wt | wt | − | wt | − |
| D178N | wt | −− | − | − | wt | − | −− | wt | − |
| R179K | wt | −− | −− | wt | ++ | wt | − | −− | −− |
| R179S | wt | −− | −− | wt | ++ | wt | + | − | −− |
| R179V | ++ | −− | −− | wt | ++ | wt | wt | −− | −− |
| S199T | wt | −− | −− | wt | ++ | wt | wt | − | − |
| T209I | wt | −− | −− | wt | +++ | + | + | ++ | wt |
| D215S | wt | + | −− | ++ | + | +++ | ++ | +++ | + |
| Q216E | wt | wt | wt | wt | wt | wt | wt | wt | wt |
| Q216I | wt | −− | −− | + | ++ | ++ | ++ | wt | wt |
| Q216K | wt | − | wt | wt | + | wt | wt | wt | wt |
| D225Q | wt | wt | −− | wt | + | wt | wt | − | − |
| Q226W | wt | −− | −− | ++ | +++ | ++ | +++ | wt | ++ |
| Q226Y | wt | −− | −− | ++ | +++ | ++ | +++ | ++ | + |
| N238F | ++ | −− | −− | −− | −− | −− | −− | −− | −− |
| N238W | ++ | −− | −− | wt | −− | −− | −− | −− | −− |
| T242H | wt | ++ | wt | + | wt | ++ | ++ | ++ | + |
| T242S | ++ | ++++ | +++ | wt | wt | wt | wt | wt | wt |
| N263C | wt | wt | −− | + | ++ | +++ | ++ | ++ | +++ |
| N263S | wt | − | −− | ++ | ++ | ++ | ++ | ++ | +++ |
| N263T | + | −− | −− | wt | + | ++ | + | wt | ++ |
| N264D | wt | −− | wt | − | − | − | −− | − | − |
| N264K | + | −− | −− | −− | −− | − | −− | − | −− |
| N264L | + | −− | + | −− | − | −− | −− | −− | −− |
| N264M | ++ | −− | − | − | − | − | −− | −− | −− |
| R265M | ++ | −− | − | wt | wt | wt | − | wt | − |
| R265P | ++ | −− | −− | −− | − | −− | −− | −− | −− |
| N278F | wt | −− | −− | ++ | ++++ | +++ | ++ | wt | ++ |
| T282D | wt | wt | wt | − | wt | wt | wt | wt | wt |
| T282I | wt | − | − | − | − | −− | − | − | − |
| T282K | wt | wt | wt | − | wt | − | wt | − | −− |
| Q303E | wt | ++ | wt | wt | wt | wt | −− | wt | − |
| Q303I | wt | ++ | − | wt | − | wt | − | wt | − |
| Q303N | wt | +++ | ++ | wt | − | − | − | wt | − |
| Q303R | wt | ++ | wt | wt | wt | wt | − | wt | − |
| S312C | + | wt | wt | ++ | ++ | ++ | ++ | ++ | +++ |
| S312D | wt | − | ++ | wt | wt | wt | −− | − | wt |
| S312I | wt | −− | wt | − | wt | − | − | − | −− |
| S312K | wt | −− | −− | wt | wt | wt | wt | wt | −− |
| S312Y | wt | −− | −− | ++ | ++ | ++ | ++ | +++ | ++ |
| Q316T | wt | −− | −− | ++ | +++ | +++ | +++ | ++ | ++ |
| K320S | wt | +++ | ++ | − | wt | wt | +++ | wt | −− |
| K320Y | wt | +++ | ++ | − | wt | ++ | wt | − | wt |
| D329A | wt | ++ | wt | wt | wt | wt | wt | ++ | + |
| A338D | wt | +++ | +++ | wt | ++ | wt | wt | wt | + |
| A338I | wt | wt | − | wt | ++ | wt | wt | + | wt |
| A338K | wt | − | − | − | ++ | wt | wt | wt | wt |
| K345E | wt | − | −− | ++ | ++ | ++ | ++ | ++ | ++ |
| A347D | wt | + | wt | wt | wt | wt | wt | wt | wt |
| A347Y | wt | +++ | + | wt | wt | + | wt | ++ | wt |
| N369E | wt | +++ | −− | + | − | ++ | wt | ++ | wt |
| N369I | ++ | wt | −− | − | −− | − | −− | − | −− |
| N369T | + | ++ | −− | wt | wt | + | wt | + | wt |
| N369W | wt | ++ | −− | +++ | wt | ++++ | ++++ | ++++ | wt |
| N369Y | wt | +++ | −− | ++ | wt | ++ | +++ | +++ | wt |
| D370W | ++ | −− | −− | −− | −− | −− | −− | + | −− |
| G372A | wt | + | −− | ++ | + | ++ | ++ | ++ | ++ |
| G427C | wt | −− | −− | ++ | ++ | +++ | +++ | ++ | ++ |
| G427F | wt | wt | −− | ++ | wt | ++ | + | ++ | ++ |
| K428N | − | −− | −− | wt | ++++ | wt | wt | −− | − |

TABLE 3-2-continued

| Variant | Glu | Heat | HPLC | PASC | PCS | G2 pH5 | G2 pH6 | CNPG | G2 spiked CC |
|---|---|---|---|---|---|---|---|---|---|
| N455D | + | wt | -- | +++ | ++++ | +++ | ++++ | ++ | +++ |
| N473S | wt | ++ | wt | wt | ++ | wt | - | wt | wt |
| S474D | ++ | +++ | +++ | wt | wt | wt | wt | -- | wt |
| S474I | wt | + | wt | wt | wt | wt | wt | wt | wt |
| S474R | wt | ++ | ++ | wt | + | wt | wt | wt | wt |
| K498A | + | -- | - | wt | wt | wt | wt | wt | wt |
| K498F | wt | -- | -- | + | wt | wt | wt | - | - |
| K498H | + | -- | -- | wt | wt | wt | wt | wt | wt |
| D521A | wt | wt | wt | wt | ++ | - | -- | wt | wt |
| D521R | wt | -- | -- | wt | ++ | wt | -- | -- | - |
| V522Y | wt | -- | -- | wt | ++++ | ++ | wt | ++ | + |
| R542N | - | -- | - | - | ++ | wt | wt | ++ | +++ |
| G547A | wt | +++ | -- | +++ | ++ | +++ | ++++ | ++ | +++ |
| G554C | wt | -- | -- | wt | ++ | wt | + | wt | wt |
| G554F | wt | -- | -- | wt | ++ | + | + | wt | + |
| K560S | ++ | -- | -- | wt | wt | -- | -- | -- | wt |
| D564T | wt | -- | -- | + | wt | ++ | ++ | + | ++ |
| D564V | wt | -- | -- | ++ | + | ++ | +++ | + | - |
| N583R | wt | + | - | wt | ++ | wt | + | wt | wt |
| V603G | wt | -- | -- | wt | wt | ++ | ++++ | wt | ++++ |
| F611A | wt | ++ | -- | ++ | + | +++ | ++ | ++ | +++ |
| F611R | wt | -- | -- | wt | ++ | wt | ++ | -- | -- |
| R645G | wt | ++ | - | wt | ++ | wt | + | + | wt |
| R645K | wt | wt | - | wt | wt | + | + | wt | wt |
| K656R | + | -- | -- | wt | wt | wt | wt | -- | - |
| P661E | wt | wt | -- | + | - | + | wt | wt | - |
| P661F | wt | -- | -- | +++ | ++ | +++ | +++ | wt | ++ |
| P661L | wt | -- | -- | +++ | ++ | ++++ | ++++ | + | +++ |
| P661Q | wt | - | -- | ++ | + | ++ | ++ | wt | + |
| G662C | wt | ++ | -- | ++++ | ++++ | ++++ | ++++ | +++ | ++++ |
| G662D | wt | ++ | ++ | wt | wt | wt | - | wt | wt |
| G662F | wt | +++ | -- | ++ | + | ++ | ++ | ++ | ++ |
| G662K | wt | ++ | -- | wt | wt | - | - | wt | -- |
| G662L | wt | +++ | wt | wt | wt | - | -- | wt | - |
| G662Y | wt | ++ | -- | wt | ++ | wt | wt | wt | -- |
| T666C | wt | wt | -- | ++ | ++ | +++ | ++ | ++ | ++ |
| S683W | - | - | -- | + | ++ | ++ | ++ | ++ | ++ |
| Q684A | wt | -- | -- | - | + | wt | wt | + | wt |
| Q684C | wt | - | -- | +++ | -- | ++++ | +++ | ++++ | +++ |
| Q684D | wt | - | wt | wt | wt | - | -- | - | - |
| Q684G | wt | - | -- | ++++ | -- | ++++ | ++++ | ++++ | ++++ |
| Q684N | + | wt | -- | wt | -- | + | wt | ++ | + |
| Q684R | wt | wt | + | - | - | - | -- | - | -- |
| S692E | wt | -- | -- | wt | wt | wt | - | wt | wt |
| S692K | wt | wt | - | wt | wt | wt | wt | + | wt |
| S692L | wt | ++ | - | wt | ++ | wt | wt | ++ | + |

++++ PI > 2
+++ 2 > PI > 1.5
++ 1.5 > PI > 1.2
+ 1.2 > PI > 1.1
wt 1.1 > PI > 0.9
- 0.9 > PI > 0.8
-- 0.8 > PI

Example 4

Expression, Activity and Performance of Additional BGL Variants

4-1. Assays

A modified HPLC assay was used to determine the protein content when studying the BGL variants in this library as compared to those described in Example 1. The specific procedure is described below. The glucose inhibition assay was also modified, thus the procedure used was described below.

HPLC Assay for Protein Content Determination

The concentration of BGL variants from pooled culture supernatants was determined by an Agilent 1200 (Agilent Technologies) HPLC equipped with a Proswift RP-2H 50×4.6 mm column (Dionex) calibrated at 50° C. Fifty (50) μL of sample was mixed with 50 μL of 10% acetonitrile, and after 5 min. filtered under vacuum using a 0.22 μm Millipore Multiscreen HTS 96 well filtration system. Ten (10) μL of the altered sample was loaded onto the column. Two buffers were used to construct an elution gradient having a flow rate of 1 mL/min: (1) Buffer A: 0.3% PEG1000, 0.1% TFA in deionized water; and (2) Buffer B: 64.63% acetonitrile, 35% 2-propanol, 0.3% PEG1000, 0.07% TFA in deionized water. Elution was carried out using the following program: from 0 min to 0.25 min with 5% Buffer B, followed by a gradient of 0.25 min to 1 min of from 5% Buffer B to 35% Boiler B, followed by a gradient of 1 min to 5 min of from 35% Buffer B to 55% Buffer B. A calibration curve was generated using purified wild type BGL1. Concentrations of BGL variants were determined using that standard calibration curve. To calculate performance index (PI), the concentration of a BGL variant was divided by the average concentration of wild-type BGL1 (e.g., a reference enzyme) in the same plate.

Glucose Inhibition Assay

The effect of glucose on the hydrolytic activity of beta-glucosidase was determined by conducting the CNPGase activity assay as described above in the presence of 2.5 mM glucose. The relative residual activity of the variants and the wild-type protein was determined by the ratio of the averaged specific activity in the presence of glucose and the averaged specific activity in the absence of glucose. A performance index (PI) for the BGL variants was determined by dividing the relative residual activity of a BGL variant by the relative residual activity of the wild-type BGL1 (e.g., a reference enzyme).

4-2. Generation of Additional *H. jecorina* BGL1 Site Evaluation Libraries

The pTTTpyrG-bgl1 plasmid containing the wild type *H. jecorina* BGL1 encoding sequence (SEQ ID NO: 1) was sent to BASEClear (Leiden, The Netherlands), who then generated positional libraries at each of the sites in Table 4-1 below. The sites were numbered in reference to the residue numbers of BGL1 mature protein SEQ ID NO:3.

TABLE 4-1

Additional Positions In The Mature BGL1 Protein Selected For The Generation Of SELs

| 11 |
| 38 |
| 43 |
| 60 |
| 68 |
| 110 |
| 128 |
| 146 |
| 180 |
| 181 |
| 184 |
| 201 |
| 206 |
| 217 |
| 220 |
| 221 |
| 243 |
| 245 |
| 255 |
| 258 |
| 259 |
| 260 |
| 261 |
| 266 |
| 270 |
| 283 |
| 293 |
| 300 |
| 308 |
| 377 |
| 384 |
| 392 |
| 400 |
| 406 |
| 436 |
| 442 |
| 443 |
| 444 |
| 450 |
| 457 |
| 461 |
| 463 |
| 466 |
| 468 |
| 482 |
| 485 |
| 486 |

TABLE 4-1-continued

Additional Positions In The Mature BGL1 Protein Selected For The Generation Of SELs

| 491 |
| 500 |
| 507 |
| 530 |
| 532 |
| 536 |
| 550 |
| 556 |
| 565 |
| 566 |
| 567 |
| 568 |
| 575 |
| 601 |
| 602 |
| 604 |
| 605 |
| 606 |
| 607 |
| 624 |
| 630 |
| 633 |
| 639 |
| 646 |
| 655 |
| 667 |
| 671 |
| 678 |

For each of the 75 sites in Table 4-1, about 14 to 16 substitution variants were made. These variants were then produced as described in Example 2.

4-3 Expression, Stability, Activity and Performance of BGL1 Variants

The expression levels of the variants were measured using the HPLC assay, as described herein. PI values were calculated and listed in Table 4-2 under the column marked "HPLC." The CNPG hydrolyzing activities were also measured. Corresponding PI values were calculated and the results are listed in Table 4-2 under the column marked "CNPG." Effects of glucose on activity, or glucose inhibition, were also determined and the results are listed under the column marked "Glue."

Thermostability measurements were listed under the column marked "Heat," specific activities in hydrolysis of PASC were listed under the column marked "PASC," and specific activities in hydrolysis of PCS were listed under the column marked "PCS." Cellobiase activities of these variants were also measured at pH 5.0, the results of which were listed under the column marked "G2 pH 5." The specific activity of hydrolysis of ammonia retreated corncob (CC) was likewise measured, and the results were listed under the column marked "CC." The PIs listed in Table 4-2 are classified based on ranges, as marked below the table in the margins. Specifically, PI is the ratio of performance of the variant to the parent or reference beta-glucosidase.

Table 4-2 lists 1501 additional substitutions tested in the second SEL library.

TABLE 4-2

Table 4-2 Performance of BGL1 variants

| Variant | Gluc | Heat | HPLC | PASC | PCS | G2 | CNPG | CC |
|---------|------|------|------|------|-----|-----|------|-----|
| T011A | wt | wt | − | wt | wt | + | + | wt |
| T011C | wt | −− | − | wt | wt | + | ++ | wt |
| T011D | wt | − | wt | wt | wt | wt | wt | wt |

TABLE 4-2-continued

Table 4-2 Performance of BGL1 variants

| Variant | Gluc | Heat | HPLC | PASC | PCS | G2 | CNPG | CC |
|---|---|---|---|---|---|---|---|---|
| T011E | wt | ++ | wt | wt | wt | + | + | wt |
| T011F | wt | -- | -- | -- | -- | -- | -- | ++ |
| T011G | wt | wt | -- | wt | - | wt | wt | wt |
| T011H | wt | -- | -- | wt | wt | + | ++ | wt |
| T011I | wt | -- | -- | wt | wt | wt | + | wt |
| T011K | wt | + | - | - | -- | - | wt | - |
| T011L | wt | - | -- | wt | - | wt | + | wt |
| T011M | wt | - | - | - | - | - | wt | wt |
| T011N | wt | wt | -- | - | -- | -- | -- | wt |
| T011P | -- | -- | -- | -- | -- | -- | -- | -- |
| T011Q | -- | -- | -- | -- | -- | -- | -- | -- |
| T011R | wt | -- | -- | wt | - | wt | wt | wt |
| T011S | wt | -- | -- | wt | wt | + | + | wt |
| T011T | -- | -- | -- | -- | -- | -- | -- | -- |
| T011V | - | wt | -- | wt | wt | wt | + | + |
| T011W | wt | ++ | wt | wt | - | wt | -- | wt |
| T011Y | wt | + | -- | wt | wt | + | wt | - |
| N038A | - | - | -- | - | wt | -- | - | + |
| N038C | wt | wt | wt | wt | wt | wt | - | wt |
| N038D | wt | - | -- | wt | wt | + | wt | wt |
| N038E | + | - | ++ | -- | -- | -- | -- | wt |
| N038F | wt | - | ++ | wt | - | + | ++ | wt |
| N038G | -- | -- | -- | -- | -- | -- | -- | -- |
| N038H | -- | -- | -- | -- | -- | -- | -- | wt |
| N038I | wt | -- | - | - | - | - | -- | wt |
| N038K | + | -- | -- | -- | -- | - | - | wt |
| N038L | ++ | wt | wt | -- | -- | -- | -- | wt |
| N038M | ++ | wt | ++ | -- | -- | -- | -- | wt |
| N038N | -- | -- | -- | -- | -- | -- | -- | -- |
| N038P | + | wt | ++ | -- | -- | -- | -- | wt |
| N038Q | wt | wt | + | -- | -- | -- | -- | wt |
| N038R | wt | + | wt | -- | -- | -- | -- | wt |
| N038S | wt | -- | -- | - | - | -- | wt | wt |
| N038T | wt | -- | -- | wt | - | wt | wt | wt |
| N038V | wt | -- | ++ | wt | -- | wt | wt | wt |
| N038W | -- | -- | -- | -- | -- | -- | -- | -- |
| N038Y | wt | -- | ++++ | wt | -- | wt | -- | wt |
| V043A | +++ | ++ | ++ | -- | -- | -- | -- | - |
| V043C | ++ | + | - | -- | -- | -- | -- | -- |
| V043D | wt | -- | + | -- | -- | -- | -- | -- |
| V043E | -- | -- | -- | -- | -- | -- | -- | -- |
| V043F | +++ | -- | wt | -- | -- | -- | -- | - |
| V043G | ++ | ++ | ++ | -- | -- | -- | -- | -- |
| V043H | + | -- | +++ | -- | -- | -- | -- | -- |
| V043I | wt | ++ | -- | -- | -- | -- | -- | - |
| V043K | -- | -- | -- | -- | -- | -- | -- | -- |
| V043L | +++ | - | -- | wt | wt | wt | -- | wt |
| V043M | -- | -- | -- | -- | -- | -- | -- | -- |
| V043N | ++ | +++ | ++ | -- | -- | -- | -- | - |
| V043P | -- | -- | -- | -- | -- | -- | wt | -- |
| V043Q | wt | ++ | ++ | -- | - | -- | -- | -- |
| V043R | -- | wt | + | -- | -- | -- | -- | -- |
| V043S | -- | -- | -- | -- | -- | -- | -- | -- |
| V043T | wt | -- | -- | -- | wt | -- | ++ | - |
| V043V | -- | -- | -- | -- | -- | -- | -- | -- |
| V043W | ++++ | -- | +++ | -- | -- | -- | -- | -- |
| V043Y | -- | -- | +++ | -- | -- | -- | -- | -- |
| Q060A | -- | -- | +++ | -- | -- | -- | + | - |
| Q060C | -- | ++++ | -- | -- | -- | -- | -- | -- |
| Q060D | + | ++ | ++ | wt | wt | -- | -- | - |
| Q060E | wt | -- | ++ | wt | wt | - | wt | wt |
| Q060F | wt | -- | ++++ | - | -- | wt | wt | - |
| Q060G | - | -- | +++ | -- | -- | -- | -- | -- |
| Q060H | -- | wt | ++++ | wt | -- | wt | wt | - |
| Q060I | wt | -- | - | -- | -- | - | - | - |
| Q060K | -- | +++ | -- | -- | -- | -- | -- | -- |
| Q060L | -- | -- | -- | -- | -- | -- | -- | wt |
| Q060M | - | -- | ++ | - | - | - | + | wt |
| Q060N | - | -- | +++ | - | -- | -- | - | wt |
| Q060P | -- | -- | -- | -- | -- | -- | -- | -- |
| Q060Q | -- | -- | -- | -- | -- | -- | -- | -- |
| Q060R | -- | wt | -- | -- | -- | -- | -- | -- |
| Q060S | -- | -- | -- | -- | -- | -- | -- | -- |
| Q060T | -- | -- | + | -- | -- | -- | wt | wt |
| Q060V | + | -- | - | -- | -- | -- | wt | -- |
| Q060W | -- | -- | wt | -- | -- | -- | - | -- |
| Q060Y | wt | -- | +++ | -- | -- | -- | - | wt |
| Y068A | ++ | -- | wt | wt | - | wt | ++ | wt |
| Y068C | -- | -- | -- | -- | -- | -- | -- | -- |
| Y068D | ++ | -- | -- | wt | - | wt | + | wt |
| Y068E | ++ | -- | ++ | - | - | -- | wt | wt |
| Y068F | -- | -- | -- | -- | -- | -- | -- | -- |
| Y068G | ++ | -- | ++ | - | - | - | + | wt |
| Y068H | ++ | -- | - | -- | -- | -- | - | wt |
| Y068I | ++ | -- | -- | - | -- | - | - | wt |
| Y068K | ++ | -- | -- | -- | -- | -- | wt | wt |
| Y068L | ++ | -- | wt | -- | - | -- | ++ | wt |
| Y068M | ++ | -- | ++ | - | -- | - | wt | wt |
| Y068N | ++ | -- | wt | wt | wt | wt | -- | wt |
| Y068P | ++ | -- | - | -- | -- | -- | ++ | -- |
| Y068Q | -- | -- | -- | -- | -- | -- | -- | -- |
| Y068R | ++ | -- | -- | -- | -- | -- | - | wt |
| Y068S | ++ | -- | wt | - | - | wt | ++ | wt |
| Y068T | ++ | -- | wt | - | -- | - | + | wt |
| Y068V | ++ | -- | -- | wt | -- | wt | ++ | + |
| Y068W | -- | -- | -- | -- | -- | -- | -- | -- |
| Y068Y | -- | -- | -- | -- | -- | -- | -- | -- |
| L110A | ++ | -- | - | -- | -- | -- | -- | wt |
| L110C | ++ | -- | + | -- | -- | -- | -- | wt |
| L110D | wt | -- | -- | -- | -- | -- | -- | wt |
| L110E | ++ | -- | -- | -- | -- | -- | -- | wt |
| L110F | ++ | -- | wt | -- | -- | -- | -- | wt |
| L110G | +++ | -- | ++++ | -- | -- | -- | -- | -- |
| L110H | ++ | -- | -- | -- | -- | -- | -- | wt |
| L110I | wt | -- | -- | -- | -- | -- | -- | wt |
| L110K | + | -- | -- | -- | -- | -- | -- | - |
| L110L | | | | | | | | |
| L110M | ++ | - | -- | wt | wt | - | -- | wt |
| L110N | wt | -- | -- | -- | -- | -- | -- | - |
| L110P | ++ | -- | -- | -- | -- | -- | -- | -- |
| L110Q | ++ | -- | ++ | -- | -- | -- | -- | wt |
| L110R | + | -- | -- | -- | -- | -- | -- | -- |
| L110S | + | -- | - | -- | -- | -- | -- | - |
| L110T | | | | | | | | |
| L110V | ++ | -- | -- | | | | | |
| L110W | ++ | -- | ++ | -- | -- | -- | -- | -- |
| L110Y | +++ | -- | -- | -- | -- | -- | -- | -- |
| E128A | wt | -- | -- | -- | -- | -- | - | -- |
| E128C | wt | -- | -- | -- | -- | -- | -- | wt |
| E128D | wt | -- | - | -- | -- | -- | - | - |
| E128E | | | | | | | | |
| E128F | + | wt | -- | -- | -- | -- | -- | -- |
| E128G | wt | -- | -- | -- | -- | -- | - | -- |
| E128H | wt | -- | -- | -- | -- | -- | -- | -- |
| E128I | wt | -- | -- | -- | -- | -- | -- | -- |
| E128K | - | -- | -- | -- | -- | -- | -- | -- |
| E128L | | | | | | | | |
| E128M | | | | | | | | |
| E128N | wt | -- | + | -- | -- | -- | -- | -- |
| E128P | | | | | | | | |
| E128Q | ++ | - | -- | -- | -- | -- | -- | -- |
| E128R | + | +++ | -- | -- | -- | -- | -- | -- |
| E128S | -- | -- | - | -- | -- | -- | -- | -- |
| E128T | | | | | | | | |
| E128V | + | -- | -- | -- | -- | -- | -- | -- |
| E128W | wt | -- | -- | -- | -- | -- | -- | -- |
| E128Y | wt | ++ | -- | -- | -- | -- | -- | -- |
| N146A | + | ++ | wt | wt | wt | wt | + | - |
| N146C | wt | -- | wt | - | wt | wt | -- | wt |
| N146D | wt | +++ | -- | wt | + | wt | - | wt |
| N146E | wt | ++ | -- | wt | wt | ++ | wt | wt |
| N146F | wt | -- | -- | wt | wt | ++ | +++ | wt |
| N146G | wt | wt | ++ | - | - | wt | wt | wt |
| N146H | wt | wt | wt | wt | + | + | wt | wt |
| N146I | wt | -- | wt | wt | wt | wt | ++ | - |
| N146K | wt | ++ | -- | - | wt | wt | wt | - |
| N146L | | | | | | | | |
| N146M | + | +++ | -- | - | wt | wt | - | wt |
| N146N | | | | | | | | |
| N146P | -- | -- | -- | -- | -- | -- | -- | - |
| N146Q | + | ++ | -- | wt | wt | ++ | wt | wt |
| N146R | -- | -- | -- | -- | -- | -- | -- | -- |

TABLE 4-2-continued

Table 4-2 Performance of BGL1 variants

| Variant | Gluc | Heat | HPLC | PASC | PCS | G2 | CNPG | CC |
|---|---|---|---|---|---|---|---|---|
| N146S | wt | wt | wt | wt | + | ++ | ++ | wt |
| N146T | wt | wt | -- | wt | wt | + | wt | wt |
| N146V | + | ++ | wt | - | - | wt | - | wt |
| N146W | ++ | ++ | -- | -- | -- | -- | -- | wt |
| N146Y | wt | wt | ++ | - | + | wt | + | - |
| T180A | wt | wt | -- | wt | wt | wt | wt | wt |
| T180C | wt | - | - | wt | wt | + | ++ | wt |
| T180D | wt | -- | -- | wt | wt | wt | - | wt |
| T180E | wt | -- | -- | wt | wt | wt | -- | ++ |
| T180F | wt | -- | -- | wt | wt | wt | -- | ++ |
| T180G | - | - | -- | wt | wt | wt | -- | ++ |
| T180H | wt | -- | -- | wt | wt | + | - | ++ |
| T180I | wt | - | -- | wt | - | - | -- | wt |
| T180K | wt | -- | -- | wt | - | wt | -- | ++ |
| T180L | wt | -- | -- | -- | - | -- | -- | wt |
| T180M | wt | -- | -- | wt | wt | ++ | - | +++ |
| T180N | wt | wt | -- | wt | wt | wt | - | + |
| T180P | wt | - | -- | wt | - | - | - | wt |
| T180Q | wt | - | -- | - | - | - | -- | wt |
| T180R | wt | -- | -- | - | -- | -- | -- | + |
| T180S | wt | - | -- | wt | wt | wt | -- | ++ |
| T180T | | | | | | | | |
| T180V | wt | wt | -- | wt | wt | wt | wt | wt |
| T180W | - | -- | -- | wt | wt | wt | - | ++ |
| T180Y | wt | -- | -- | wt | wt | wt | wt | wt |
| L181A | wt | wt | -- | wt | wt | wt | wt | wt |
| L181C | wt | + | -- | wt | wt | wt | wt | wt |
| L181D | wt | - | -- | wt | wt | + | - | - |
| L181E | wt | + | -- | - | wt | wt | - | - |
| L181F | + | + | - | - | wt | wt | - | wt |
| L181G | wt | wt | -- | - | - | wt | wt | - |
| L181H | ++ | wt | -- | - | wt | wt | - | - |
| L181I | wt | wt | -- | -- | wt | wt | - | - |
| L181K | - | -- | -- | - | - | wt | - | -- |
| L181L | | | | | | | | |
| L181M | + | + | + | wt | - | - | - | wt |
| L181N | -- | -- | -- | -- | -- | -- | -- | -- |
| L181P | -- | -- | -- | -- | -- | -- | -- | -- |
| L181Q | wt | wt | wt | wt | wt | wt | wt | wt |
| L181R | - | -- | -- | - | -- | wt | -- | - |
| L181S | wt | + | wt | wt | wt | wt | wt | wt |
| L181T | + | wt | -- | - | - | - | - | - |
| L181V | ++ | wt | -- | - | wt | - | -- | wt |
| L181W | wt | wt | wt | - | - | -- | -- | - |
| L181Y | wt | wt | -- | - | - | wt | wt | wt |
| L184A | wt | - | -- | - | wt | - | -- | - |
| L184C | wt | - | wt | wt | wt | wt | wt | - |
| L184D | wt | wt | -- | wt | wt | wt | - | wt |
| L184E | - | - | -- | - | -- | -- | -- | wt |
| L184F | wt | - | -- | wt | -- | wt | - | ++ |
| L184G | | | | | | | | |
| L184H | -- | -- | -- | -- | -- | -- | -- | -- |
| L184I | - | -- | -- | wt | -- | wt | - | wt |
| L184K | | | | | | | | |
| L184L | | | | | | | | |
| L184M | -- | wt | ++ | wt | - | wt | wt | wt |
| L184N | -- | wt | -- | -- | -- | -- | -- | -- |
| L184P | -- | -- | -- | -- | -- | -- | -- | -- |
| L184Q | - | -- | -- | -- | -- | -- | wt | wt |
| L184R | -- | -- | -- | -- | -- | -- | -- | wt |
| L184S | wt | -- | -- | wt | - | wt | -- | ++ |
| L184T | wt | wt | -- | - | - | -- | -- | wt |
| L184V | wt | - | -- | - | - | -- | - | - |
| L184W | wt | -- | -- | -- | -- | -- | -- | +++ |
| L184Y | -- | -- | -- | -- | -- | -- | -- | -- |
| M201A | -- | -- | -- | -- | -- | -- | -- | -- |
| M201C | wt | -- | -- | -- | -- | -- | - | - |
| M201D | -- | -- | -- | -- | ++++ | -- | -- | + |
| M201E | -- | -- | -- | -- | -- | -- | -- | -- |
| M201F | -- | -- | -- | -- | -- | -- | -- | + |
| M201G | -- | -- | wt | -- | -- | -- | -- | -- |
| M201H | -- | -- | -- | -- | -- | -- | -- | -- |
| M201I | | | | | | | | |
| M201K | -- | -- | -- | -- | -- | -- | -- | wt |
| M201L | -- | -- | -- | - | -- | wt | wt | + |
| M201M | | | | | | | | |
| M201N | -- | -- | -- | -- | -- | -- | -- | + |
| M201P | | | | | | | | |
| M201Q | +++ | -- | -- | -- | -- | -- | -- | - |
| M201R | -- | -- | -- | -- | -- | -- | -- | wt |
| M201S | -- | -- | wt | -- | -- | -- | -- | -- |
| M201T | -- | -- | -- | -- | -- | -- | -- | -- |
| M201V | -- | -- | -- | -- | -- | -- | -- | -- |
| M201W | -- | -- | -- | -- | -- | -- | -- | wt |
| M201Y | -- | -- | -- | -- | -- | -- | -- | wt |
| K206A | wt | -- | ++ | + | ++ | + | ++ | wt |
| K206C | | | | | | | | |
| K206D | wt | -- | + | + | wt | wt | wt | wt |
| K206E | | | | | | | | |
| K206F | +++ | -- | -- | wt | wt | - | - | wt |
| K206G | wt | -- | -- | + | ++ | wt | wt | wt |
| K206H | wt | -- | -- | - | -- | - | - | wt |
| K206I | | | | | | | | |
| K206K | | | | | | | | |
| K206L | wt | wt | wt | wt | + | wt | wt | wt |
| K206M | wt | -- | - | wt | wt | wt | wt | - |
| K206N | wt | -- | wt | wt | wt | wt | - | wt |
| K206P | + | -- | wt | - | wt | -- | - | wt |
| K206Q | - | wt | wt | wt | wt | wt | wt | wt |
| K206R | wt | wt | -- | wt | wt | wt | - | wt |
| K206S | + | -- | + | wt | + | wt | wt | - |
| K206T | + | -- | -- | wt | wt | wt | wt | wt |
| K206V | wt | -- | ++ | wt | wt | wt | wt | wt |
| K206W | ++ | -- | - | wt | wt | - | - | - |
| K206Y | wt | -- | wt | wt | wt | -- | -- | wt |
| Y217A | wt | wt | ++ | wt | wt | wt | wt | wt |
| Y217C | - | -- | -- | wt | wt | wt | + | wt |
| Y217D | wt | wt | -- | wt | + | wt | + | wt |
| Y217E | - | -- | -- | wt | wt | wt | wt | wt |
| Y217F | -- | -- | -- | -- | + | wt | + | wt |
| Y217G | wt | wt | +++ | wt | wt | wt | - | - |
| Y217H | + | wt | - | wt | wt | - | - | - |
| Y217I | wt | - | -- | wt | wt | wt | wt | wt |
| Y217K | wt | - | wt | wt | wt | wt | wt | wt |
| Y217L | wt | wt | -- | wt | wt | wt | wt | - |
| Y217M | - | - | -- | wt | + | wt | wt | wt |
| Y217N | - | wt | - | wt | wt | - | - | - |
| Y217P | ++ | -- | -- | wt | wt | wt | wt | wt |
| Y217Q | wt | -- | wt | wt | wt | wt | wt | wt |
| Y217R | -- | wt | - | wt | wt | wt | wt | wt |
| Y217S | -- | - | -- | wt | + | wt | wt | wt |
| Y217T | wt | -- | -- | wt | wt | wt | + | wt |
| Y217V | - | wt | -- | wt | wt | wt | - | wt |
| Y217W | -- | -- | -- | -- | -- | -- | -- | -- |
| Y217Y | | | | | | | | |
| Q220A | | | | | | | | |
| Q220C | wt | -- | -- | + | wt | + | ++ | wt |
| Q220D | wt | wt | + | wt | wt | wt | wt | wt |
| Q220E | wt | wt | -- | wt | wt | wt | wt | wt |
| Q220F | wt | + | -- | wt | wt | wt | - | wt |
| Q220G | - | - | wt | wt | wt | wt | wt | wt |
| Q220H | - | wt | ++ | wt | wt | wt | wt | wt |
| Q220I | wt | -- | -- | wt | wt | wt | + | wt |
| Q220K | -- | - | -- | wt | ++ | wt | + | wt |
| Q220L | wt | - | wt | wt | wt | wt | wt | wt |
| Q220M | - | -- | -- | + | + | + | + | wt |
| Q220N | | | | | | | | |
| Q220P | ++ | wt | -- | wt | + | wt | -- | + |
| Q220Q | | | | | | | | |
| Q220R | wt | -- | -- | wt | + | wt | wt | wt |
| Q220S | wt | wt | -- | wt | wt | wt | wt | wt |
| Q220T | -- | -- | -- | -- | -- | -- | -- | -- |
| Q220V | - | - | -- | + | wt | wt | + | wt |
| Q220W | | | | | | | | |
| Q220Y | wt | -- | -- | wt | + | wt | wt | wt |
| T221A | wt | -- | -- | ++ | ++ | + | +++ | wt |
| T221C | wt | + | -- | wt | + | wt | ++ | wt |
| T221D | -- | -- | -- | -- | -- | -- | -- | -- |
| T221E | wt | wt | ++ | - | wt | - | -- | wt |
| T221F | wt | -- | - | wt | wt | - | wt | wt |
| T221G | wt | wt | -- | + | + | + | ++ | wt |
| T221H | wt | wt | wt | - | - | -- | -- | -- |

TABLE 4-2-continued

Table 4-2 Performance of BGL1 variants

| Variant | Gluc | Heat | HPLC | PASC | PCS | G2 | CNPG | CC |
|---|---|---|---|---|---|---|---|---|
| T221I | wt | − | −− | ++ | ++ | + | +++ | wt |
| T221K | wt | wt | −− | wt | − | −− | − | − |
| T221L | | | | | | | | |
| T221M | wt | +++ | −− | wt | wt | −− | wt | wt |
| T221N | wt | + | − | − | − | − | −− | wt |
| T221P | −− | − | −− | −− | −− | −− | −− | − |
| T221Q | −− | −− | −− | −− | −− | −− | −− | −− |
| T221R | −− | −− | −− | −− | −− | −− | −− | −− |
| T221S | wt | wt | −− | wt | ++ | wt | ++ | wt |
| T221T | | | | | | | | |
| T221V | −− | −− | −− | −− | −− | −− | −− | −− |
| T221W | wt | −− | + | − | − | − | − | −− |
| T221Y | −− | −− | −− | −− | −− | −− | −− | −− |
| T243A | wt | −− | +++ | wt | wt | + | wt | wt |
| T243C | wt | wt | +++ | wt | wt | + | wt | wt |
| T243D | wt | −− | ++ | wt | wt | wt | − | wt |
| T243E | wt | −− | −− | wt | − | −− | −− | wt |
| T243F | −− | −− | −− | −− | −− | −− | −− | wt |
| T243G | wt | − | wt | wt | − | − | −− | wt |
| T243H | | | | | | | | |
| T243I | wt | −− | − | wt | wt | wt | wt | wt |
| T243K | −− | +++ | −− | −− | −− | −− | −− | −− |
| T243L | wt | −− | wt | wt | − | − | −− | wt |
| T243M | − | − | −− | wt | − | − | wt | + |
| T243N | −− | − | −− | − | − | − | −− | wt |
| T243P | wt | −− | −− | wt | − | − | − | wt |
| T243Q | − | − | −− | wt | − | − | − | wt |
| T243R | wt | −− | wt | − | − | wt | − | wt |
| T243S | − | −− | +++ | wt | wt | wt | wt | wt |
| T243T | | | | | | | | |
| T243V | wt | −− | ++ | wt | wt | wt | wt | + |
| T243W | −− | −− | −− | −− | −− | −− | −− | − |
| T243Y | −− | −− | −− | −− | −− | −− | −− | wt |
| Q245A | −− | −− | −− | −− | −− | −− | −− | −− |
| Q245C | −− | −− | −− | −− | −− | −− | −− | −− |
| Q245D | −− | −− | −− | −− | −− | −− | −− | −− |
| Q245E | | | | | | | | |
| Q245F | wt | +++ | − | − | − | wt | − | + |
| Q245G | −− | + | −− | − | −− | − | wt | wt |
| Q245H | −− | wt | +++ | wt | wt | + | wt | − |
| Q245I | wt | wt | ++ | wt | wt | wt | + | − |
| Q245K | wt | ++ | −− | −− | − | −− | −− | wt |
| Q245L | − | wt | wt | wt | wt | wt | wt | wt |
| Q245M | wt | − | ++ | wt | wt | ++ | ++ | wt |
| Q245N | wt | ++ | ++ | wt | wt | + | wt | wt |
| Q245P | + | ++ | −− | − | − | −− | −− | wt |
| Q245Q | | | | | | | | |
| Q245R | | | | | | | | |
| Q245S | | | | | | | | |
| Q245T | wt | wt | ++++ | wt | wt | ++ | wt | − |
| Q245V | − | wt | ++ | wt | wt | wt | wt | wt |
| Q245W | wt | wt | wt | wt | wt | wt | wt | wt |
| Q245Y | wt | wt | wt | wt | wt | wt | − | wt |
| M255A | wt | −− | wt | wt | −− | wt | + | wt |
| M255C | − | −− | −− | −− | wt | wt | wt | wt |
| M255D | −− | −− | −− | −− | −− | −− | −− | wt |
| M255E | wt | −− | −− | −− | −− | −− | + | wt |
| M255F | wt | −− | −− | −− | −− | −− | −− | − |
| M255G | −− | −− | −− | −− | −− | −− | −− | wt |
| M255H | ++ | −− | −− | −− | −− | −− | −− | wt |
| M255I | wt | −− | ++++ | −− | −− | −− | −− | − |
| M255K | −− | −− | −− | −− | −− | −− | −− | − |
| M255L | wt | −− | −− | − | wt | wt | ++ | + |
| M255M | | | | | | | | |
| M255N | | | | | | | | |
| M255P | wt | −− | −− | − | wt | − | ++ | + |
| M255Q | wt | −− | ++++ | −− | − | −− | wt | wt |
| M255R | −− | −− | −− | −− | −− | −− | −− | − |
| M255S | −− | −− | −− | −− | −− | −− | −− | wt |
| M255T | − | −− | −− | − | wt | wt | + | + |
| M255V | − | −− | +++ | − | wt | wt | ++ | wt |
| M255W | −− | −− | −− | −− | −− | −− | − | − |
| M255Y | −− | −− | wt | −− | −− | −− | −− | −− |
| T258A | | | | | | | | |
| T258C | −− | −− | −− | + | wt | ++ | wt | wt |
| T258D | −− | −− | −− | −− | wt | − | − | wt |
| T258E | −− | −− | −− | wt | wt | ++ | −− | + |
| T258F | −− | −− | −− | − | − | wt | − | wt |
| T258G | −− | −− | − | wt | wt | + | ++ | wt |
| T258H | −− | −− | −− | wt | −− | wt | −− | + |
| T258I | −− | −− | −− | wt | − | +++ | −− | ++ |
| T258K | −− | −− | −− | wt | − | ++ | −− | ++ |
| T258L | −− | −− | −− | + | −− | +++ | −− | ++ |
| T258M | −− | −− | −− | wt | −− | wt | −− | wt |
| T258N | −− | −− | −− | wt | − | wt | − | wt |
| T258P | −− | −− | −− | −− | −− | −− | −− | wt |
| T258Q | −− | −− | −− | wt | − | ++ | −− | ++ |
| T258R | −− | −− | −− | −− | −− | −− | −− | −− |
| T258S | wt | wt | −− | ++ | ++ | ++ | ++ | + |
| T258T | | | | | | | | |
| T258V | −− | −− | −− | + | + | +++ | −− | ++ |
| T258W | −− | −− | −− | −− | −− | −− | −− | wt |
| T258Y | −− | −− | −− | −− | −− | −− | −− | + |
| D259A | −− | −− | −− | wt | − | wt | + | wt |
| D259C | − | −− | −− | wt | −− | + | −− | wt |
| D259D | | | | | | | | |
| D259E | − | −− | +++ | wt | − | wt | wt | wt |
| D259F | − | −− | − | − | −− | − | wt | wt |
| D259G | wt | −− | + | − | −− | wt | wt | wt |
| D259H | − | −− | +++ | wt | −− | wt | wt | wt |
| D259I | −− | −− | −− | −− | −− | −− | − | − |
| D259K | −− | −− | −− | −− | −− | − | −− | wt |
| D259L | −− | −− | − | −− | −− | − | wt | wt |
| D259M | −− | −− | ++ | −− | −− | −− | − | wt |
| D259N | wt | ++ | − | wt | − | wt | − | wt |
| D259P | wt | −− | ++ | − | −− | − | wt | wt |
| D259Q | −− | −− | −− | − | − | − | − | − |
| D259R | −− | −− | + | −− | −− | −− | −− | wt |
| D259S | wt | wt | ++++ | wt | wt | wt | wt | + |
| D259T | | | | | | | | |
| D259V | | | | | | | | |
| D259W | wt | −− | −− | − | −− | wt | wt | wt |
| D259Y | wt | −− | −− | − | −− | wt | −− | wt |
| F260A | −− | +++ | ++ | wt | + | wt | wt | wt |
| F260C | −− | − | −− | wt | + | wt | wt | wt |
| F260D | −− | + | − | wt | ++ | ++ | ++ | + |
| F260E | −− | +++ | ++ | + | ++ | ++ | + | wt |
| F260F | | | | | | | | |
| F260G | −− | ++ | −− | wt | ++ | ++ | ++ | + |
| F260H | −− | wt | −− | wt | wt | wt | + | + |
| F260I | −− | wt | −− | wt | ++ | + | +++ | wt |
| F260K | −− | +++ | −− | wt | wt | wt | −− | wt |
| F260L | wt | ++ | ++ | wt | + | + | +++ | + |
| F260M | −− | −− | −− | −− | −− | −− | −− | wt |
| F260N | | | | | | | | |
| F260P | −− | −− | −− | −− | −− | −− | −− | wt |
| F260Q | −− | ++ | −− | wt | + | wt | + | + |
| F260R | | | | | | | | |
| F260S | −− | ++ | −− | wt | + | wt | wt | wt |
| F260T | −− | ++ | −− | wt | + | ++ | +++ | wt |
| F260V | −− | ++ | wt | wt | wt | wt | wt | wt |
| F260W | ++ | wt | −− | + | wt | + | −− | + |
| F260Y | −− | ++ | wt | wt | wt | wt | − | wt |
| N261A | | | | | | | | |
| N261C | wt | − | −− | + | wt | ++ | − | wt |
| N261D | wt | − | wt | wt | wt | wt | + | wt |
| N261E | wt | ++ | ++ | wt | wt | wt | wt | − |
| N261F | wt | + | wt | wt | −− | wt | wt | wt |
| N261G | wt | wt | −− | wt | wt | wt | − | wt |
| N261H | wt | wt | −− | wt | wt | wt | + | wt |
| N261I | wt | wt | − | wt | wt | −− | wt | wt |
| N261K | wt | ++ | +++ | wt | − | wt | wt | wt |
| N261L | wt | + | − | wt | wt | wt | wt | wt |
| N261M | − | wt | ++ | wt | − | wt | ++ | wt |
| N261N | | | | | | | | |
| N261P | | | | | | | | |
| N261Q | wt | −− | −− | wt | wt | wt | wt | wt |
| N261R | −− | −− | −− | −− | −− | −− | −− | −− |
| N261S | wt | wt | wt | wt | − | wt | − | wt |
| N261T | wt | wt | wt | wt | − | wt | wt | wt |
| N261V | wt | wt | −− | wt | −− | wt | −− | wt |
| N261W | wt | −− | −− | wt | −− | wt | −− | wt |

TABLE 4-2-continued

Table 4-2 Performance of BGL1 variants

| Variant | Gluc | Heat | HPLC | PASC | PCS | G2 | CNPG | CC |
|---|---|---|---|---|---|---|---|---|
| N261Y | wt | -- | -- | -- | -- | -- | -- | wt |
| L266A | - | -- | -- | wt | wt | + | ++ | + |
| L266C | - | wt | - | wt | + | + | ++ | + |
| L266D | - | -- | - | wt | wt | + | ++ | wt |
| L266E | - | -- | -- | wt | wt | wt | wt | + |
| L266F | + | ++ | - | wt | wt | wt | wt | wt |
| L266G | -- | -- | -- | - | -- | - | wt | + |
| L266H | - | wt | -- | wt | - | - | - | + |
| L266I | wt | -- | wt | wt | - | - | wt | wt |
| L266K | - | + | - | - | -- | - | - | wt |
| L266L | | | | | | | | |
| L266M | - | wt | -- | wt | wt | wt | + | wt |
| L266N | - | -- | -- | + | - | + | ++ | + |
| L266P | wt | -- | -- | - | - | - | - | wt |
| L266Q | | | | | | | | |
| L266R | | | | | | | | |
| L266S | -- | -- | -- | - | -- | -- | -- | wt |
| L266T | wt | -- | -- | - | - | -- | -- | wt |
| L266V | -- | - | -- | wt | - | - | - | + |
| L266W | | | | | | | | |
| L266Y | wt | wt | wt | wt | + | wt | wt | wt |
| A270A | | | | | | | | |
| A270C | wt | wt | -- | ++ | ++ | ++ | wt | + |
| A270D | wt | wt | ++ | wt | ++ | wt | wt | wt |
| A270E | wt | wt | wt | wt | wt | wt | - | wt |
| A270F | wt | wt | -- | wt | wt | wt | wt | wt |
| A270G | | | | | | | | |
| A270H | wt | wt | + | wt | - | wt | wt | wt |
| A270I | wt | wt | ++ | wt | wt | wt | wt | wt |
| A270K | wt | wt | -- | + | + | wt | wt | wt |
| A270L | wt | wt | -- | wt | wt | wt | + | wt |
| A270M | | | | | | | | |
| A270N | wt | wt | -- | + | ++ | wt | wt | wt |
| A270P | - | -- | -- | wt | wt | wt | ++ | wt |
| A270Q | -- | -- | -- | -- | -- | -- | -- | -- |
| A270R | + | ++ | - | wt | wt | wt | wt | wt |
| A270S | wt | ++ | -- | wt | wt | wt | wt | wt |
| A270T | wt | + | - | wt | wt | wt | wt | wt |
| A270V | - | - | -- | wt | wt | wt | ++ | wt |
| A270W | wt | wt | ++ | - | - | wt | wt | wt |
| A270Y | - | -- | wt | wt | wt | wt | wt | wt |
| S283A | | | | | | | | |
| S283C | -- | -- | -- | -- | -- | -- | -- | - |
| S283D | wt | wt | ++ | wt | ++ | wt | - | - |
| S283E | wt | wt | ++ | - | - | wt | wt | wt |
| S283F | wt | - | wt | wt | wt | + | ++ | + |
| S283G | wt | wt | ++ | - | wt | wt | - | wt |
| S283H | - | wt | wt | - | - | - | - | - |
| S283I | wt | - | -- | - | - | - | - | - |
| S283K | wt | wt | -- | -- | -- | -- | -- | -- |
| S283L | wt | wt | -- | wt | wt | wt | + | - |
| S283M | wt | wt | wt | - | wt | - | wt | wt |
| S283N | wt | wt | wt | - | wt | - | - | wt |
| S283P | wt | -- | -- | wt | wt | + | - | + |
| S283Q | wt | wt | -- | wt | - | - | wt | wt |
| S283R | wt | wt | -- | wt | - | wt | wt | wt |
| S283S | | | | | | | | |
| S283T | wt | wt | -- | wt | wt | wt | -- | + |
| S283V | wt | wt | -- | wt | - | - | -- | wt |
| S283W | | | | | | | | |
| S283Y | - | -- | wt | wt | - | wt | wt | wt |
| L293A | wt | -- | -- | wt | ++ | wt | - | ++ |
| L293C | wt | - | -- | wt | wt | wt | - | + |
| L293D | wt | ++++ | -- | -- | -- | -- | -- | -- |
| L293E | wt | -- | -- | -- | -- | -- | -- | -- |
| L293F | ++ | ++ | -- | ++++ | -- | ++++ | +++ | ++++ |
| L293G | wt | -- | -- | -- | -- | -- | -- | +++ |
| L293H | -- | -- | -- | -- | -- | -- | -- | -- |
| L293I | wt | ++ | + | - | wt | - | - | wt |
| L293K | wt | +++ | -- | -- | -- | -- | -- | +++ |
| L293L | | | | | | | | |
| L293M | + | -- | -- | wt | + | wt | wt | + |
| L293N | - | -- | -- | -- | -- | -- | -- | +++ |
| L293P | -- | -- | -- | -- | -- | -- | -- | -- |
| L293Q | - | ++ | -- | -- | -- | -- | -- | -- |
| L293R | wt | -- | -- | -- | -- | -- | -- | -- |
| L293S | wt | -- | -- | -- | wt | -- | -- | ++ |
| L293T | wt | wt | -- | wt | ++ | wt | - | wt |
| L293V | wt | - | -- | + | ++ | ++ | ++ | wt |
| L293W | ++ | -- | -- | -- | -- | -- | -- | -- |
| L293Y | wt | - | -- | -- | -- | -- | -- | -- |
| G300A | wt | -- | - | wt | wt | wt | + | wt |
| G300C | wt | - | -- | wt | ++ | ++ | ++ | wt |
| G300D | -- | -- | -- | wt | wt | wt | wt | wt |
| G300E | wt | wt | - | wt | - | wt | wt | wt |
| G300F | wt | -- | -- | wt | wt | ++ | ++ | wt |
| G300G | | | | | | | | |
| G300H | wt | -- | -- | wt | wt | wt | + | wt |
| G300I | wt | -- | -- | wt | wt | ++ | wt | wt |
| G300K | wt | wt | -- | wt | wt | - | wt | wt |
| G300L | -- | -- | -- | -- | -- | -- | -- | -- |
| G300M | wt | -- | -- | wt | wt | ++ | wt | + |
| G300N | wt | wt | -- | wt | wt | wt | wt | wt |
| G300P | + | -- | -- | -- | -- | -- | -- | -- |
| G300Q | wt | wt | -- | wt | wt | wt | wt | wt |
| G300R | | | | | | | | |
| G300S | + | wt | -- | wt | wt | wt | - | - |
| G300T | wt | -- | -- | wt | wt | wt | wt | wt |
| G300V | wt | -- | -- | wt | wt | wt | -- | wt |
| G300W | wt | wt | -- | wt | wt | ++ | + | wt |
| G300Y | wt | - | -- | wt | wt | + | wt | wt |
| S308A | | | | | | | | |
| S308C | wt | - | -- | wt | + | ++ | ++ | wt |
| S308D | wt | -- | ++ | wt | wt | wt | wt | wt |
| S308E | ++ | + | -- | wt | ++ | wt | wt | ++ |
| S308F | wt | wt | ++ | wt | wt | wt | wt | wt |
| S308G | wt | - | wt | wt | wt | wt | wt | wt |
| S308H | - | -- | -- | ++ | +++ | ++ | + | ++ |
| S308I | - | -- | -- | wt | wt | wt | wt | wt |
| S308K | - | -- | -- | + | + | wt | ++ | wt |
| S308L | wt | -- | -- | wt | wt | wt | + | + |
| S308M | | | | | | | | |
| S308N | wt | wt | -- | wt | wt | wt | wt | + |
| S308P | | | | | | | | |
| S308Q | -- | -- | -- | -- | -- | -- | -- | -- |
| S308R | - | -- | -- | wt | ++ | wt | wt | + |
| S308S | | | | | | | | |
| S308T | -- | -- | -- | -- | -- | -- | -- | -- |
| S308V | wt | wt | +++ | wt | wt | wt | wt | wt |
| S308W | wt | wt | + | wt | - | wt | - | wt |
| S308Y | wt | - | -- | wt | wt | -- | -- | wt |
| A377A | | | | | | | | |
| A377C | wt | -- | -- | wt | + | +++ | ++ | wt |
| A377D | wt | -- | -- | wt | + | ++ | ++ | wt |
| A377E | wt | -- | -- | wt | -- | wt | + | wt |
| A377F | wt | -- | -- | wt | - | ++ | ++ | wt |
| A377G | wt | -- | -- | wt | - | + | ++ | wt |
| A377H | -- | -- | -- | -- | -- | -- | -- | -- |
| A377I | + | -- | -- | -- | -- | + | -- | wt |
| A377K | - | -- | -- | -- | -- | -- | -- | -- |
| A377L | wt | -- | -- | -- | -- | -- | +++ | wt |
| A377M | | | | | | | | |
| A377N | - | -- | wt | -- | -- | -- | -- | -- |
| A377P | | | | | | | | |
| A377Q | -- | -- | -- | ++ | wt | +++ | -- | wt |
| A377R | -- | -- | -- | -- | -- | -- | -- | -- |
| A377S | wt | -- | -- | wt | wt | wt | wt | wt |
| A377T | wt | -- | -- | wt | wt | wt | ++ | wt |
| A377V | wt | -- | -- | wt | -- | wt | wt | wt |
| A377W | ++ | -- | -- | wt | -- | -- | -- | wt |
| A377Y | wt | -- | -- | -- | -- | - | -- | - |
| S384A | | | | | | | | |
| S384C | + | ++++ | -- | -- | -- | -- | -- | -- |
| S384D | + | - | -- | -- | -- | -- | -- | - |
| S384E | ++ | +++ | ++++ | -- | -- | -- | -- | -- |
| S384F | + | -- | -- | -- | -- | -- | -- | -- |
| S384G | ++ | -- | ++ | -- | -- | -- | -- | -- |
| S384H | - | -- | -- | -- | -- | -- | -- | -- |
| S384I | - | -- | ++ | -- | -- | -- | -- | -- |
| S384K | wt | -- | wt | -- | -- | -- | -- | -- |
| S384L | -- | -- | wt | -- | -- | -- | -- | -- |
| S384M | ++ | -- | - | -- | -- | -- | -- | -- |

TABLE 4-2-continued

Table 4-2 Performance of BGL1 variants

| Variant | Gluc | Heat | HPLC | PASC | PCS | G2 | CNPG | CC |
|---|---|---|---|---|---|---|---|---|
| S384N | | | | | | | | |
| S384P | wt | -- | -- | -- | -- | -- | -- | - |
| S384Q | - | -- | + | -- | -- | -- | -- | -- |
| S384R | wt | - | wt | -- | -- | -- | -- | -- |
| S384S | | | | | | | | |
| S384T | - | -- | - | -- | -- | -- | -- | -- |
| S384V | wt | -- | +++ | -- | -- | -- | -- | -- |
| S384W | + | -- | ++ | -- | -- | -- | -- | -- |
| S384Y | + | -- | -- | -- | -- | -- | -- | -- |
| F392A | -- | -- | -- | -- | -- | -- | -- | -- |
| F392C | wt | -- | -- | + | -- | wt | - | + |
| F392D | wt | -- | -- | - | -- | wt | wt | -- |
| F392E | wt | -- | wt | -- | -- | wt | wt | -- |
| F392F | | | | | | | | |
| F392G | wt | - | -- | -- | -- | -- | -- | -- |
| F392H | wt | -- | -- | -- | -- | -- | -- | -- |
| F392I | wt | -- | wt | -- | wt | -- | - | -- |
| F392K | wt | -- | -- | -- | -- | -- | -- | -- |
| F392L | wt | -- | wt | - | + | + | wt | |
| F392M | wt | -- | -- | wt | wt | wt | wt | + |
| F392N | wt | -- | -- | wt | wt | wt | -- | ++ |
| F392P | -- | -- | -- | -- | -- | -- | -- | -- |
| F392Q | - | -- | -- | + | -- | ++ | ++ | wt |
| F392R | - | -- | -- | ++ | -- | ++ | -- | +++ |
| F392S | wt | -- | -- | -- | - | - | - | - |
| F392T | - | -- | wt | -- | -- | - | wt | -- |
| F392V | | | | | | | | |
| F392W | wt | -- | -- | -- | - | -- | -- | |
| F392Y | wt | -- | +++ | wt | wt | + | + | wt |
| N400A | wt | + | + | wt | wt | wt | wt | wt |
| N400C | wt | wt | -- | wt | wt | wt | wt | wt |
| N400D | -- | -- | -- | -- | -- | -- | -- | -- |
| N400E | wt | wt | -- | wt | wt | wt | wt | wt |
| N400F | wt | -- | -- | wt | wt | + | wt | wt |
| N400G | wt | ++ | -- | wt | wt | wt | -- | wt |
| N400H | wt | ++ | wt | wt | - | - | - | wt |
| N400I | -- | -- | -- | -- | -- | -- | -- | -- |
| N400K | | | | | | | | |
| N400L | | | | | | | | |
| N400M | -- | -- | -- | -- | -- | -- | -- | -- |
| N400N | | | | | | | | |
| N400P | wt | -- | -- | wt | wt | wt | -- | ++ |
| N400Q | wt | ++ | -- | wt | wt | wt | - | + |
| N400R | -- | -- | -- | -- | -- | -- | -- | -- |
| N400S | - | + | -- | wt | + | + | -- | + |
| N400T | | | | | | | | |
| N400V | - | -- | -- | wt | wt | + | - | wt |
| N400W | -- | -- | -- | -- | -- | -- | -- | -- |
| N400Y | | | | | | | | |
| Q406A | -- | -- | -- | -- | -- | -- | -- | -- |
| Q406C | -- | -- | -- | -- | -- | -- | -- | -- |
| Q406D | + | -- | -- | wt | ++ | ++++ | wt | ++ |
| Q406E | wt | -- | wt | -- | -- | wt | ++ | wt |
| Q406F | wt | wt | ++++ | - | wt | wt | ++ | wt |
| Q406G | wt | -- | - | -- | -- | -- | wt | wt |
| Q406H | wt | wt | +++ | - | -- | ++ | +++ | wt |
| Q406I | | | | | | | | |
| Q406K | -- | -- | -- | -- | -- | -- | -- | -- |
| Q406L | -- | -- | -- | -- | -- | -- | -- | wt |
| Q406M | - | -- | -- | - | -- | +++ | +++ | + |
| Q406N | -- | -- | -- | -- | -- | -- | -- | wt |
| Q406P | | | | | | | | |
| Q406Q | | | | | | | | |
| Q406R | - | -- | -- | -- | wt | wt | wt | |
| Q406S | - | -- | -- | - | -- | ++ | ++ | + |
| Q406T | wt | -- | ++++ | wt | -- | + | +++ | wt |
| Q406V | -- | -- | -- | -- | wt | -- | -- | + |
| Q406W | -- | -- | -- | -- | -- | -- | -- | wt |
| Q406Y | -- | -- | -- | -- | -- | -- | -- | -- |
| T436A | wt | -- | -- | + | wt | + | ++ | wt |
| T436C | wt | -- | -- | + | -- | ++ | +++ | wt |
| T436D | wt | -- | + | wt | wt | wt | + | wt |
| T436E | + | -- | -- | + | -- | + | ++ | wt |
| T436F | wt | -- | -- | ++ | -- | +++ | +++ | -- |
| T436G | wt | -- | -- | + | - | wt | wt | wt |
| T436H | wt | -- | -- | wt | -- | + | wt | - |
| T436I | wt | -- | -- | + | -- | ++ | ++ | wt |
| T436K | | | | | | | | |
| T436L | wt | -- | -- | - | -- | -- | -- | - |
| T436M | - | -- | -- | + | -- | + | +++ | wt |
| T436N | wt | -- | -- | -- | -- | + | + | - |
| T436P | wt | -- | -- | wt | -- | wt | + | - |
| T436Q | -- | -- | -- | + | -- | + | ++ | wt |
| T436R | wt | -- | wt | wt | wt | wt | wt | wt |
| T436S | | | | | | | | |
| T436T | | | | | | | | |
| T436V | + | -- | -- | wt | -- | wt | wt | wt |
| T436W | wt | -- | -- | wt | -- | +++ | wt | -- |
| T436Y | wt | -- | -- | ++ | -- | ++++ | +++ | -- |
| G442A | -- | -- | -- | -- | -- | -- | -- | -- |
| G442C | - | -- | -- | - | - | - | wt | wt |
| G442D | - | -- | - | wt | wt | wt | ++ | - |
| G442E | -- | -- | wt | wt | wt | wt | + | wt |
| G442F | -- | -- | -- | - | - | - | wt | - |
| G442G | | | | | | | | |
| G442H | -- | -- | -- | -- | -- | -- | -- | wt |
| G442I | -- | -- | -- | -- | -- | -- | ++ | - |
| G442K | wt | -- | -- | -- | -- | -- | -- | wt |
| G442L | -- | -- | -- | -- | -- | - | - | -- |
| G442M | -- | -- | -- | -- | -- | -- | -- | -- |
| G442N | -- | -- | -- | -- | -- | -- | -- | -- |
| G442P | - | -- | -- | - | -- | -- | -- | -- |
| G442Q | -- | -- | -- | - | -- | wt | ++ | - |
| G442R | -- | -- | -- | -- | -- | - | wt | - |
| G442S | -- | -- | -- | -- | - | -- | wt | - |
| G442T | -- | -- | -- | -- | -- | -- | wt | -- |
| G442V | -- | -- | -- | ++ | -- | -- | wt | - |
| G442W | -- | -- | -- | -- | -- | -- | wt | - |
| G442Y | -- | -- | -- | -- | -- | - | wt | wt |
| Y443A | -- | -- | -- | -- | -- | -- | -- | -- |
| Y443C | - | -- | wt | -- | -- | -- | - | -- |
| Y443D | - | -- | ++++ | -- | -- | -- | -- | -- |
| Y443E | - | -- | -- | -- | -- | -- | ++ | -- |
| Y443F | - | -- | -- | - | -- | wt | +++ | wt |
| Y443G | -- | -- | -- | -- | -- | -- | -- | + |
| Y443H | wt | -- | -- | -- | -- | -- | + | - |
| Y443I | -- | -- | ++ | -- | -- | -- | + | -- |
| Y443K | -- | -- | -- | -- | -- | -- | -- | -- |
| Y443L | -- | -- | wt | -- | -- | -- | - | -- |
| Y443M | -- | -- | -- | -- | -- | -- | +++ | wt |
| Y443N | -- | -- | -- | -- | -- | -- | ++ | -- |
| Y443P | -- | -- | + | -- | -- | -- | wt | -- |
| Y443Q | wt | -- | -- | -- | -- | -- | ++ | -- |
| Y443R | -- | -- | wt | -- | -- | -- | -- | -- |
| Y443S | -- | -- | ++ | -- | -- | -- | -- | -- |
| Y443T | wt | -- | ++++ | -- | -- | -- | wt | -- |
| Y443V | -- | -- | -- | -- | -- | -- | ++ | -- |
| Y443W | -- | -- | -- | -- | -- | -- | -- | -- |
| Y443Y | | | | | | | | |
| I444A | -- | -- | -- | -- | -- | - | -- | wt |
| I444C | -- | -- | -- | - | ++ | wt | -- | ++ |
| I444D | -- | -- | -- | -- | -- | -- | - | wt |
| I444E | -- | -- | -- | wt | wt | +++ | -- | +++ |
| I444F | -- | -- | -- | -- | wt | +++ | - | ++ |
| I444G | -- | -- | -- | -- | -- | - | -- | ++ |
| I444H | -- | -- | -- | -- | -- | -- | -- | wt |
| I444I | | | | | | | | |
| I444K | -- | -- | -- | - | -- | wt | -- | ++ |
| I444L | - | -- | -- | wt | wt | + | + | wt |
| I444M | wt | -- | -- | wt | wt | + | wt | wt |
| I444N | -- | -- | -- | - | -- | + | -- | ++ |
| I444P | -- | -- | -- | -- | -- | -- | -- | + |
| I444Q | wt | -- | -- | - | -- | - | wt | wt |
| I444R | -- | -- | -- | -- | -- | -- | -- | ++ |
| I444S | -- | -- | -- | -- | -- | - | -- | ++ |
| I444T | -- | -- | -- | -- | wt | -- | wt | ++ |
| I444V | -- | -- | -- | wt | + | ++ | -- | ++ |
| I444W | -- | -- | -- | -- | wt | +++ | -- | +++ |
| I444Y | - | -- | -- | -- | wt | +++ | -- | +++ |
| A450A | | | | | | | | |
| A450C | + | - | -- | -- | -- | -- | -- | wt |
| A450D | -- | -- | -- | -- | -- | -- | -- | -- |

TABLE 4-2-continued

Table 4-2 Performance of BGL1 variants

| Variant | Gluc | Heat | HPLC | PASC | PCS | G2 | CNPG | CC |
|---|---|---|---|---|---|---|---|---|
| A450E | wt | -- | -- | + | + | ++ | ++ | ++ |
| A450F | wt | -- | -- | ++ | wt | ++ | +++ | + |
| A450G | wt | -- | -- | wt | wt | - | -- | + |
| A450H | wt | ++ | - | - | -- | -- | -- | wt |
| A450I | wt | -- | -- | wt | - | wt | - | ++ |
| A450K | -- | ++ | -- | - | - | - | - | wt |
| A450L | wt | -- | -- | + | wt | wt | + | wt |
| A450M | - | wt | wt | wt | wt | + | ++ | + |
| A450N | | | | | | | | |
| A450P | -- | + | -- | + | wt | + | ++ | + |
| A450Q | wt | ++ | -- | wt | - | wt | + | + |
| A450R | wt | ++ | - | wt | -- | wt | wt | wt |
| A450S | - | -- | -- | wt | - | - | - | wt |
| A450T | wt | -- | -- | + | wt | + | ++ | + |
| A450V | -- | -- | -- | + | wt | + | ++ | + |
| A450W | wt | -- | -- | + | wt | + | ++ | + |
| A450Y | + | -- | -- | wt | - | - | -- | wt |
| D457A | wt | + | ++ | wt | wt | wt | + | wt |
| D457C | wt | -- | -- | ++ | ++ | ++ | +++ | wt |
| D457D | | | | | | | | |
| D457E | wt | - | wt | wt | wt | wt | + | wt |
| D457F | wt | -- | -- | wt | wt | wt | + | wt |
| D457G | - | -- | ++ | wt | wt | wt | ++ | wt |
| D457H | wt | -- | -- | - | - | -- | wt | - |
| D457I | wt | -- | - | - | - | - | wt | wt |
| D457K | wt | -- | -- | - | - | - | - | -- |
| D457L | wt | -- | wt | - | - | - | wt | wt |
| D457M | - | -- | wt | - | -- | -- | wt | wt |
| D457N | wt | -- | -- | - | - | -- | -- | wt |
| D457P | -- | -- | -- | -- | -- | -- | -- | wt |
| D457Q | wt | -- | -- | wt | - | wt | wt | wt |
| D457R | -- | -- | -- | -- | -- | -- | -- | + |
| D457S | wt | -- | -- | wt | wt | wt | + | wt |
| D457T | wt | -- | -- | wt | + | wt | ++ | wt |
| D457V | -- | -- | + | wt | - | wt | + | wt |
| D457W | -- | -- | -- | -- | -- | -- | -- | - |
| D457Y | wt | -- | - | - | - | -- | -- | wt |
| N461A | wt | -- | -- | + | - | ++ | ++ | wt |
| N461C | wt | - | -- | ++ | ++ | +++ | +++ | wt |
| N461D | wt | wt | - | + | + | wt | wt | wt |
| N461E | | | | | | | | |
| N461F | wt | wt | -- | + | wt | + | wt | wt |
| N461G | wt | wt | ++ | wt | wt | + | + | wt |
| N461H | - | - | wt | wt | - | wt | wt | wt |
| N461I | wt | -- | -- | wt | wt | wt | wt | wt |
| N461K | -- | -- | -- | -- | -- | -- | -- | -- |
| N461L | wt | wt | - | wt | wt | wt | wt | wt |
| N461M | | | | | | | | |
| N461N | | | | | | | | |
| N461P | wt | -- | -- | + | -- | ++ | wt | wt |
| N461Q | | | | | | | | |
| N461R | wt | - | -- | wt | wt | wt | wt | wt |
| N461S | wt | ++ | ++ | wt | wt | wt | wt | - |
| N461T | wt | -- | + | wt | wt | wt | + | wt |
| N461V | wt | -- | + | wt | + | + | ++ | wt |
| N461W | wt | -- | -- | wt | wt | + | + | wt |
| N461Y | + | wt | wt | wt | wt | + | wt | wt |
| N463A | -- | -- | -- | -- | -- | -- | -- | -- |
| N463C | -- | -- | -- | -- | ++++ | -- | -- | wt |
| N463D | -- | -- | wt | wt | - | - | wt | - |
| N463E | wt | -- | -- | + | ++ | wt | + | wt |
| N463F | -- | -- | -- | -- | -- | -- | -- | -- |
| N463G | wt | -- | -- | + | wt | wt | + | wt |
| N463H | -- | -- | -- | -- | -- | -- | -- | -- |
| N463I | wt | -- | -- | wt | wt | wt | + | wt |
| N463K | wt | -- | -- | +++ | +++ | ++++ | +++ | ++ |
| N463L | | | | | | | | |
| N463M | - | -- | - | wt | wt | wt | ++ | wt |
| N463N | | | | | | | | |
| N463P | - | -- | -- | wt | ++ | wt | ++ | wt |
| N463Q | | | | | | | | |
| N463R | wt | -- | -- | ++ | +++ | +++ | + | ++ |
| N463S | wt | -- | -- | + | wt | + | +++ | + |
| N463T | - | -- | -- | + | + | + | ++ | wt |
| N463V | wt | -- | - | + | wt | wt | ++ | wt |
| N463W | | | | | | | | |
| N463Y | - | -- | -- | wt | wt | - | wt | wt |
| V466A | -- | -- | -- | -- | -- | -- | -- | -- |
| V466C | wt | wt | wt | wt | wt | wt | - | wt |
| V466D | -- | -- | -- | -- | -- | -- | -- | wt |
| V466E | -- | -- | -- | -- | -- | -- | -- | wt |
| V466F | wt | -- | -- | wt | - | - | wt | wt |
| V466G | wt | -- | -- | wt | wt | wt | - | wt |
| V466H | -- | -- | -- | -- | -- | -- | -- | wt |
| V466I | wt | -- | ++ | wt | wt | wt | + | wt |
| V466K | -- | -- | -- | -- | -- | -- | -- | -- |
| V466L | wt | -- | wt | + | wt | wt | ++ | wt |
| V466M | -- | -- | -- | -- | -- | -- | -- | wt |
| V466N | -- | -- | -- | -- | -- | -- | -- | wt |
| V466P | wt | -- | -- | wt | wt | wt | + | wt |
| V466Q | wt | wt | -- | - | -- | -- | -- | wt |
| V466R | -- | -- | -- | -- | -- | -- | -- | wt |
| V466S | wt | -- | -- | +++ | ++ | ++++ | ++++ | ++ |
| V466T | + | + | -- | wt | wt | wt | wt | + |
| V466V | | | | | | | | |
| V466W | -- | -- | -- | -- | -- | -- | -- | wt |
| V466Y | -- | -- | -- | -- | -- | -- | -- | wt |
| A468A | | | | | | | | |
| A468C | wt | wt | -- | ++ | ++ | +++ | +++ | + |
| A468D | wt | - | -- | wt | + | wt | wt | - |
| A468E | wt | -- | wt | wt | wt | wt | + | wt |
| A468F | wt | - | -- | ++ | +++ | ++ | ++ | wt |
| A468G | wt | ++ | -- | + | wt | wt | wt | wt |
| A468H | wt | wt | -- | wt | wt | wt | wt | wt |
| A468I | wt | -- | -- | + | - | ++ | ++ | wt |
| A468K | wt | -- | -- | wt | - | wt | wt | wt |
| A468L | | | | | | | | |
| A468M | -- | ++ | -- | -- | -- | -- | -- | -- |
| A468N | - | -- | -- | wt | -- | wt | wt | wt |
| A468P | -- | -- | -- | -- | -- | -- | -- | -- |
| A468Q | wt | -- | -- | + | ++ | wt | + | wt |
| A468R | wt | -- | wt | wt | -- | wt | wt | wt |
| A468S | wt | -- | -- | + | ++++ | + | ++ | wt |
| A468T | + | - | -- | + | ++++ | wt | wt | wt |
| A468V | wt | -- | -- | wt | -- | wt | wt | wt |
| A468W | wt | wt | -- | wt | ++ | wt | wt | wt |
| A468Y | wt | -- | -- | + | +++ | wt | wt | wt |
| S482A | wt | -- | -- | ++ | + | +++ | wt | ++ |
| S482C | wt | -- | wt | wt | wt | + | + | - |
| S482D | - | -- | -- | -- | -- | -- | -- | ++ |
| S482E | +++ | -- | -- | -- | -- | -- | -- | -- |
| S482F | -- | -- | -- | -- | -- | -- | -- | -- |
| S482G | -- | -- | -- | -- | -- | -- | -- | -- |
| S482H | wt | -- | -- | -- | -- | -- | -- | -- |
| S482I | - | - | -- | ++ | - | ++++ | -- | ++++ |
| S482K | -- | -- | -- | -- | -- | -- | -- | -- |
| S482L | -- | -- | -- | -- | -- | -- | -- | -- |
| S482M | -- | -- | -- | -- | -- | -- | -- | -- |
| S482N | -- | -- | -- | -- | -- | -- | -- | -- |
| S482P | -- | -- | -- | wt | - | +++ | -- | ++++ |
| S482Q | -- | -- | -- | -- | -- | -- | -- | -- |
| S482R | -- | -- | -- | -- | -- | -- | -- | -- |
| S482S | | | | | | | | |
| S482T | | | | | | | | |
| S482V | wt | -- | -- | wt | -- | - | -- | + |
| S482W | -- | -- | -- | -- | -- | -- | -- | -- |
| S482Y | -- | -- | -- | -- | -- | -- | -- | -- |
| A485A | | | | | | | | |
| A485C | | | | | | | | |
| A485D | wt | -- | -- | wt | wt | wt | wt | wt |
| A485E | -- | -- | -- | wt | - | wt | wt | wt |
| A485F | wt | -- | -- | - | -- | -- | -- | ++ |
| A485G | | | | | | | | +++ |
| A485H | -- | -- | -- | -- | -- | -- | -- | -- |
| A485I | wt | -- | -- | wt | wt | wt | - | + |
| A485K | -- | -- | -- | - | - | - | - | ++ |
| A485L | wt | -- | -- | wt | wt | wt | ++ | ++ |
| A485M | wt | -- | -- | wt | wt | wt | -- | + |
| A485N | -- | -- | -- | -- | -- | -- | -- | +++ |
| A485P | wt | - | ++ | wt | - | wt | + | wt |
| A485Q | wt | wt | -- | -- | -- | -- | -- | wt |
| A485R | | | | | | | | |

TABLE 4-2-continued

Table 4-2 Performance of BGL1 variants

| Variant | Gluc | Heat | HPLC | PASC | PCS | G2 | CNPG | CC |
|---|---|---|---|---|---|---|---|---|
| A485S | -- | -- | -- | -- | -- | -- | -- | +++ |
| A485T | - | -- | -- | ++ | + | ++ | - | ++ |
| A485V | -- | -- | -- | -- | -- | -- | -- | -- |
| A485W | -- | -- | -- | wt | -- | ++ | -- | +++ |
| A485Y | wt | -- | -- | -- | -- | -- | -- | -- |
| I486A | | | | | | | | |
| I486C | wt | + | - | wt | wt | wt | wt | + |
| I486D | -- | -- | -- | -- | -- | -- | -- | +++ |
| I486E | -- | -- | -- | -- | -- | -- | -- | wt |
| I486F | -- | wt | -- | ++ | wt | wt | ++ | ++ |
| I486G | -- | -- | -- | -- | -- | -- | -- | + |
| I486H | -- | -- | -- | -- | -- | -- | -- | ++ |
| I486I | | | | | | | | |
| I486K | -- | -- | -- | -- | -- | -- | -- | +++ |
| I486L | - | -- | -- | - | -- | -- | -- | wt |
| I486M | - | -- | -- | wt | - | - | + | wt |
| I486N | -- | -- | -- | -- | -- | -- | -- | ++ |
| I486P | | | | | | | | |
| I486Q | -- | -- | -- | -- | -- | -- | -- | ++ |
| I486R | -- | -- | -- | -- | -- | -- | -- | +++ |
| I486S | -- | -- | -- | -- | -- | -- | -- | ++ |
| I486T | | | | | | | | |
| I486V | wt | wt | -- | + | wt | + | +++ | ++ |
| I486W | - | -- | -- | ++ | -- | wt | -- | +++ |
| I486Y | -- | ++ | -- | -- | -- | -- | ++ | ++ |
| I491A | wt | -- | -- | -- | -- | -- | -- | -- |
| I491C | wt | -- | -- | wt | wt | + | + | wt |
| I491D | wt | wt | -- | -- | -- | -- | -- | -- |
| I491E | wt | - | -- | -- | -- | -- | -- | -- |
| I491F | - | -- | -- | wt | wt | + | ++ | wt |
| I491G | wt | -- | -- | -- | -- | -- | -- | -- |
| I491H | wt | -- | -- | wt | - | wt | wt | - |
| I491I | | | | | | | | |
| I491K | -- | -- | -- | -- | -- | -- | -- | -- |
| I491L | wt | - | -- | wt | wt | wt | wt | + |
| I491M | - | wt | ++ | wt | wt | wt | wt | wt |
| I491N | wt | -- | -- | -- | -- | -- | -- | -- |
| I491P | wt | -- | -- | -- | -- | -- | -- | -- |
| I491Q | wt | wt | -- | -- | -- | -- | -- | -- |
| I491R | wt | -- | -- | -- | -- | -- | -- | -- |
| I491S | wt | -- | -- | -- | -- | -- | -- | -- |
| I491T | -- | -- | -- | -- | -- | -- | -- | -- |
| I491V | wt | -- | -- | wt | wt | + | wt | wt |
| I491W | | | | | | | | |
| I491Y | + | -- | -- | wt | - | wt | - | wt |
| V500A | | | | | | | | |
| V500C | wt | -- | wt | - | wt | - | - | - |
| V500D | -- | -- | -- | -- | -- | -- | -- | wt |
| V500E | -- | -- | -- | -- | -- | -- | -- | - |
| V500F | wt | -- | - | - | - | - | - | + |
| V500G | -- | -- | -- | -- | -- | -- | -- | -- |
| V500H | | | | | | | | |
| V500I | wt | - | ++ | wt | wt | wt | wt | - |
| V500K | -- | -- | -- | -- | -- | -- | -- | wt |
| V500L | wt | wt | wt | wt | - | - | - | + |
| V500M | wt | -- | - | - | - | - | - | wt |
| V500N | -- | -- | -- | -- | -- | -- | -- | ++ |
| V500P | -- | -- | -- | -- | -- | -- | -- | + |
| V500Q | -- | -- | -- | wt | -- | ++++ | -- | ++ |
| V500R | -- | -- | -- | -- | -- | -- | -- | wt |
| V500S | wt | -- | -- | - | -- | -- | -- | ++ |
| V500T | - | -- | -- | - | -- | -- | -- | + |
| V500V | | | | | | | | |
| V500W | -- | -- | -- | -- | -- | -- | -- | - |
| V500Y | -- | -- | -- | -- | -- | -- | -- | wt |
| S507A | | | | | | | | |
| S507C | wt | -- | -- | -- | -- | -- | -- | wt |
| S507D | -- | -- | -- | -- | -- | -- | -- | - |
| S507E | -- | -- | -- | -- | -- | -- | -- | wt |
| S507F | + | ++ | -- | -- | -- | -- | -- | wt |
| S507G | + | -- | ++ | + | wt | + | - | wt |
| S507H | -- | -- | -- | -- | -- | -- | -- | - |
| S507I | -- | -- | -- | -- | -- | -- | -- | - |
| S507K | -- | -- | -- | -- | -- | -- | -- | wt |
| S507L | -- | -- | -- | -- | -- | -- | -- | - |
| S507M | -- | -- | -- | -- | -- | -- | -- | -- |
| S507N | -- | -- | -- | - | -- | wt | -- | wt |
| S507P | | | | | | | | |
| S507Q | ++ | -- | -- | -- | -- | wt | wt | - |
| S507R | -- | -- | -- | -- | -- | -- | -- | - |
| S507S | | | | | | | | |
| S507T | - | -- | -- | wt | wt | wt | wt | wt |
| S507V | -- | -- | -- | -- | -- | -- | -- | wt |
| S507W | -- | -- | -- | -- | -- | -- | -- | - |
| S507Y | wt | - | ++++ | wt | wt | wt | ++ | - |
| Y530A | wt | - | - | wt | wt | + | wt | wt |
| Y530C | -- | -- | ++++ | wt | wt | wt | + | wt |
| Y530D | -- | -- | -- | -- | -- | -- | -- | - |
| Y530E | - | -- | +++ | wt | wt | wt | wt | wt |
| Y530F | wt | wt | ++ | + | wt | ++ | ++ | + |
| Y530G | - | -- | -- | wt | wt | ++ | wt | wt |
| Y530H | wt | -- | ++ | wt | wt | wt | wt | - |
| Y530I | -- | -- | wt | wt | wt | + | ++ | wt |
| Y530K | ++ | - | -- | -- | -- | -- | -- | - |
| Y530L | wt | -- | -- | wt | wt | wt | - | + |
| Y530M | -- | -- | +++ | wt | wt | wt | + | wt |
| Y530N | - | -- | -- | wt | wt | wt | -- | wt |
| Y530P | | | | | | | | |
| Y530Q | | | | | | | | |
| Y530R | wt | -- | -- | - | wt | wt | -- | wt |
| Y530S | + | wt | -- | wt | wt | + | - | + |
| Y530T | -- | -- | -- | wt | wt | + | wt | + |
| Y530V | wt | -- | -- | wt | wt | + | wt | wt |
| Y530W | - | -- | ++ | - | - | -- | -- | - |
| Y530Y | | | | | | | | |
| I532A | | | | | | | | |
| I532C | wt | -- | -- | -- | wt | -- | -- | ++ |
| I532D | -- | -- | -- | -- | -- | -- | -- | + |
| I532E | -- | -- | -- | -- | -- | -- | -- | ++++ |
| I532F | wt | wt | -- | wt | wt | wt | -- | ++ |
| I532G | -- | -- | -- | -- | -- | -- | -- | +++ |
| I532H | -- | -- | -- | -- | -- | -- | -- | + |
| I532I | | | | | | | | |
| I532K | -- | -- | -- | -- | -- | -- | -- | + |
| I532L | - | -- | -- | wt | wt | wt | ++ | wt |
| I532M | - | -- | -- | wt | wt | wt | wt | wt |
| I532N | | | | | | | | |
| I532P | -- | -- | -- | -- | -- | -- | -- | +++ |
| I532Q | -- | -- | -- | -- | -- | -- | -- | ++ |
| I532R | -- | -- | -- | -- | -- | -- | -- | +++ |
| I532S | -- | -- | -- | -- | -- | -- | -- | +++ |
| I532T | -- | -- | -- | - | -- | -- | -- | +++ |
| I532V | wt | - | - | wt | wt | wt | wt | + |
| I532W | wt | -- | -- | -- | -- | -- | -- | +++ |
| I532Y | wt | -- | -- | wt | -- | ++ | -- | +++ |
| P536A | | | | | | | | |
| P536C | wt | + | -- | +++ | ++ | +++ | ++++ | + |
| P536D | wt | wt | -- | + | + | + | wt | ++ |
| P536E | wt | - | -- | ++ | + | ++ | wt | + |
| P536F | -- | -- | -- | + | - | wt | -- | ++ |
| P536G | wt | + | - | wt | wt | + | wt | + |
| P536H | - | -- | -- | wt | -- | - | -- | + |
| P536I | - | -- | -- | + | wt | ++ | ++ | + |
| P536K | -- | -- | -- | -- | -- | -- | -- | -- |
| P536L | - | -- | -- | -- | -- | -- | -- | -- |
| P536M | -- | -- | -- | -- | -- | -- | -- | -- |
| P536N | -- | -- | -- | -- | -- | -- | -- | -- |
| P536P | | | | | | | | |
| P536Q | - | + | -- | + | wt | + | ++ | wt |
| P536R | -- | -- | -- | -- | -- | -- | -- | -- |
| P536S | wt | -- | -- | wt | - | -- | -- | ++ |
| P536T | -- | wt | -- | wt | wt | + | -- | ++ |
| P536V | wt | wt | wt | + | wt | ++ | ++ | + |
| P536W | wt | -- | -- | wt | wt | + | -- | + |
| P536Y | - | wt | -- | wt | wt | - | wt | wt |
| S550A | - | wt | -- | wt | wt | - | wt | wt |
| S550C | wt | wt | -- | - | wt | + | + | + |
| S550D | wt | wt | -- | wt | wt | wt | wt | + |
| S550E | wt | ++ | -- | wt | wt | wt | wt | wt |
| S550F | wt | + | -- | wt | wt | wt | + | wt |
| S550G | wt | wt | -- | wt | wt | wt | wt | wt |
| S550H | wt | wt | -- | wt | wt | wt | wt | + |

TABLE 4-2-continued

Table 4-2 Performance of BGL1 variants

| Variant | Gluc | Heat | HPLC | PASC | PCS | G2 | CNPG | CC |
|---|---|---|---|---|---|---|---|---|
| S550I | − | wt | −− | + | wt | + | ++ | ++ |
| S550K | wt | wt | −− | wt | wt | wt | − | + |
| S550L | | | | | | | | |
| S550M | wt | wt | −− | wt | − | wt | + | wt |
| S550N | wt | + | −− | wt | wt | wt | wt | wt |
| S550P | wt | wt | wt | − | − | − | wt | wt |
| S550Q | wt | + | −− | wt | − | wt | − | ++ |
| S550R | − | wt | −− | wt | −− | − | wt | + |
| S550S | | | | | | | | |
| S550T | wt | wt | −− | + | wt | + | ++ | + |
| S550V | wt | wt | −− | ++++ | wt | ++++ | ++++ | +++ |
| S550W | − | −− | −− | wt | − | − | wt | wt |
| S550Y | | | | | | | | |
| F556A | | | | | | | | |
| F556C | wt | − | −− | + | −− | wt | wt | wt |
| F556D | wt | wt | −− | wt | wt | wt | wt | − |
| F556E | wt | wt | −− | wt | ++ | + | wt | wt |
| F556F | | | | | | | | |
| F556G | wt | ++ | −− | wt | ++ | wt | wt | wt |
| F556H | wt | −− | −− | + | +++ | wt | wt | wt |
| F556I | wt | −− | −− | ++ | −− | wt | wt | wt |
| F556K | wt | −− | −− | + | ++ | wt | wt | − |
| F556L | wt | −− | −− | ++ | − | + | wt | + |
| F556M | −− | −− | −− | wt | ++ | wt | ++ | wt |
| F556N | wt | − | −− | wt | wt | wt | wt | wt |
| F556P | −− | −− | −− | −− | −− | −− | −− | −− |
| F556Q | −− | −− | −− | −− | −− | −− | −− | −− |
| F556R | wt | wt | −− | + | wt | wt | wt | wt |
| F556S | wt | − | −− | wt | ++ | wt | − | wt |
| F556T | | | | | | | | |
| F556V | wt | wt | −− | + | ++ | + | − | wt |
| F556W | − | − | − | wt | − | − | − | − |
| F556Y | wt | wt | − | wt | wt | wt | wt | wt |
| A565A | | | | | | | | |
| A565C | −− | −− | + | wt | + | ++ | ++ | − |
| A565D | wt | wt | +++ | wt | wt | wt | − | wt |
| A565E | wt | − | +++ | wt | wt | + | + | wt |
| A565F | wt | −− | −− | wt | + | ++ | ++ | wt |
| A565G | −− | −− | −− | + | ++ | ++ | ++ | + |
| A565H | −− | −− | −− | wt | wt | wt | wt | wt |
| A565I | −− | −− | wt | wt | wt | + | ++ | wt |
| A565K | − | wt | −− | wt | ++ | +++ | + | wt |
| A565L | −− | −− | ++ | wt | wt | wt | wt | wt |
| A565M | wt | wt | −− | −− | − | − | −− | wt |
| A565N | − | −− | ++ | wt | wt | wt | wt | wt |
| A565P | −− | −− | −− | −− | −− | −− | −− | wt |
| A565Q | − | wt | wt | wt | + | ++ | + | wt |
| A565R | −− | −− | −− | −− | −− | −− | −− | wt |
| A565S | wt | wt | +++ | wt | + | + | + | wt |
| A565T | − | − | +++ | wt | wt | wt | + | wt |
| A565V | − | − | − | wt | + | + | + | wt |
| A565W | − | wt | ++ | wt | wt | wt | wt | wt |
| A565Y | wt | −− | ++ | wt | + | ++ | ++ | wt |
| N566A | wt | − | −− | wt | + | wt | + | wt |
| N566C | | | | | | | | |
| N566D | wt | + | −− | wt | wt | wt | wt | − |
| N566E | wt | wt | −− | wt | − | wt | + | wt |
| N566F | − | −− | −− | + | ++ | wt | + | + |
| N566G | wt | ++ | ++ | wt | − | wt | wt | wt |
| N566H | − | −− | −− | + | ++++ | + | ++ | − |
| N566I | wt | −− | −− | wt | +++ | wt | + | wt |
| N566K | wt | −− | −− | wt | wt | wt | ++ | − |
| N566L | −− | −− | −− | + | +++ | wt | wt | wt |
| N566M | −− | −− | −− | −− | −− | −− | −− | −− |
| N566N | | | | | | | | |
| N566P | wt | wt | −− | + | +++ | wt | −− | wt |
| N566Q | − | −− | −− | wt | wt | wt | ++ | wt |
| N566R | wt | − | wt | wt | wt | wt | wt | − |
| N566S | wt | − | wt | wt | − | wt | wt | wt |
| N566T | | | | | | | | |
| N566V | | | | | | | | |
| N566W | wt | wt | −− | + | ++++ | wt | wt | wt |
| N566Y | −− | −− | −− | −− | −− | −− | −− | |
| I567A | −− | −− | −− | −− | −− | −− | −− | −− |
| I567C | wt | wt | wt | wt | wt | ++ | wt | − |
| I567D | wt | wt | −− | wt | wt | wt | −− | wt |
| I567E | wt | wt | −− | wt | wt | + | wt | + |
| I567F | wt | wt | −− | wt | + | ++ | wt | + |
| I567G | −− | −− | −− | −− | −− | −− | −− | − |
| I567H | −− | −− | −− | −− | −− | −− | −− | −− |
| I567I | | | | | | | | |
| I567K | wt | − | +++ | wt | wt | ++ | + | wt |
| I567L | −− | −− | −− | −− | −− | −− | −− | wt |
| I567M | −− | − | wt | wt | wt | ++ | ++ | wt |
| I567N | −− | −− | −− | wt | − | wt | − | wt |
| I567P | −− | −− | −− | −− | −− | −− | −− | wt |
| I567Q | −− | −− | −− | wt | + | ++ | ++ | wt |
| I567R | − | −− | ++ | wt | wt | + | wt | −− |
| I567S | −− | −− | −− | wt | + | wt | wt | wt |
| I567T | wt | wt | wt | wt | wt | + | wt | wt |
| I567V | wt | + | ++++ | wt | wt | + | wt | wt |
| I567W | −− | −− | −− | −− | −− | −− | −− | −− |
| I567Y | + | wt | ++ | wt | wt | wt | −− | wt |
| T568A | wt | −− | ++ | wt | wt | + | wt | wt |
| T568C | wt | −− | −− | − | −− | −− | −− | wt |
| T568D | −− | −− | −− | −− | −− | −− | −− | −− |
| T568E | wt | ++ | +++ | wt | + | + | wt | wt |
| T568F | −− | −− | −− | −− | −− | −− | −− | − |
| T568G | − | − | wt | wt | wt | wt | wt | wt |
| T568H | − | wt | wt | wt | wt | wt | wt | wt |
| T568I | | | | | | | | |
| T568K | − | ++ | + | + | ++ | + | ++ | wt |
| T568L | wt | wt | + | wt | wt | wt | − | wt |
| T568M | wt | + | wt | wt | wt | wt | wt | wt |
| T568N | | | | | | | | |
| T568P | wt | − | −− | − | wt | −− | −− | wt |
| T568Q | − | − | wt | wt | wt | − | wt | wt |
| T568R | wt | wt | ++ | wt | wt | wt | wt | − |
| T568S | wt | wt | ++ | − | − | − | wt | wt |
| T568T | | | | | | | | |
| T568V | −− | −− | −− | −− | −− | −− | −− | −− |
| T568W | wt | wt | −− | − | wt | − | −− | − |
| T568Y | −− | −− | −− | −− | −− | −− | −− | wt |
| Y575A | | ++ | | + | − | | − | ++ |
| Y575C | wt | +++ | −− | − | −− | −− | −− | ++ |
| Y575D | −− | −− | −− | −− | −− | −− | −− | ++ |
| Y575E | −− | −− | −− | −− | −− | −− | −− | −− |
| Y575F | | | | | | | | |
| Y575G | | | | | | | | |
| Y575H | −− | −− | −− | −− | −− | −− | −− | wt |
| Y575I | | | | | | | | |
| Y575K | −− | + | −− | ++ | −− | − | + | +++ |
| Y575L | wt | wt | −− | − | − | − | −− | ++ |
| Y575M | −− | −− | −− | −− | −− | −− | −− | −− |
| Y575N | −− | −− | −− | −− | −− | −− | −− | +++ |
| Y575P | −− | −− | −− | −− | −− | −− | −− | +++ |
| Y575Q | −− | −− | −− | −− | −− | −− | −− | ++ |
| Y575R | −− | + | −− | wt | −− | −− | −− | ++ |
| Y575S | −− | −− | −− | −− | −− | −− | −− | ++ |
| Y575T | −− | −− | −− | −− | −− | −− | −− | ++ |
| Y575V | −− | −− | −− | − | −− | −− | −− | ++ |
| Y575W | wt | − | −− | wt | − | wt | ++ | + |
| Y575Y | | | | | | | | |
| A601A | | | | | | | | |
| A601C | wt | wt | −− | ++ | + | ++ | ++ | + |
| A601D | wt | ++ | ++ | + | wt | wt | wt | wt |
| A601E | wt | wt | − | wt | − | wt | wt | wt |
| A601F | | | | | | | | |
| A601G | wt | ++ | −− | wt | wt | wt | −− | ++ |
| A601H | wt | + | −− | wt | wt | wt | − | wt |
| A601I | wt | wt | wt | − | − | − | − | wt |
| A601K | wt | wt | wt | wt | wt | − | wt | wt |
| A601L | wt | + | −− | wt | wt | wt | wt | + |
| A601M | wt | wt | −− | + | wt | + | wt | ++ |
| A601N | wt | − | −− | wt | wt | wt | + | wt |
| A601P | wt | wt | −− | wt | wt | wt | wt | + |
| A601Q | −− | −− | −− | −− | −− | −− | −− | ++ |
| A601R | wt | wt | −− | wt | wt | wt | wt | wt |
| A601S | | | | | | | | |
| A601T | −− | −− | −− | −− | −− | −− | −− | ++ |
| A601V | −− | −− | −− | −− | −− | −− | −− | ++ |
| A601W | wt | wt | −− | wt | wt | wt | + | + |

TABLE 4-2-continued

Table 4-2 Performance of BGL1 variants

| Variant | Gluc | Heat | HPLC | PASC | PCS | G2 | CNPG | CC |
|---|---|---|---|---|---|---|---|---|
| A601Y | wt | wt | -- | + | + | + | + | ++ |
| V602A | wt | - | wt | wt | wt | wt | - | wt |
| V602C | wt | wt | ++ | wt | wt | wt | - | - |
| V602D | wt | wt | -- | - | - | -- | - | - |
| V602E | wt | wt | -- | - | - | wt | -- | ++ |
| V602F | wt | + | -- | wt | wt | wt | wt | + |
| V602G | wt | -- | -- | wt | wt | + | + | wt |
| V602H | wt | - | wt | - | wt | - | -- | - |
| V602I | - | -- | wt | wt | wt | - | - | - |
| V602K | wt | + | ++ | - | - | -- | -- | -- |
| V602L | - | -- | -- | wt | wt | + | ++ | wt |
| V602M | - | -- | wt | - | wt | - | wt | wt |
| V602N | - | -- | -- | wt | wt | wt | ++ | + |
| V602P | wt | - | -- | wt | - | - | - | wt |
| V602Q | wt | wt | -- | - | - | - | -- | - |
| V602R | wt | -- | wt | - | wt | -- | -- | -- |
| V602S | wt | wt | wt | wt | wt | wt | wt | + |
| V602T | - | - | -- | wt | wt | + | + | + |
| V602V | | | | | | | | |
| V602W | wt | wt | -- | wt | - | - | -- | wt |
| V602Y | wt | - | wt | - | - | -- | - | - |
| P604A | | | | | | | | |
| P604C | wt | wt | ++ | wt | wt | ++ | ++ | - |
| P604D | | | | | | | | |
| P604E | wt | ++ | -- | wt | ++++ | wt | - | wt |
| P604F | wt | ++ | -- | -- | -- | -- | -- | -- |
| P604G | wt | wt | -- | ++ | wt | wt | wt | - |
| P604H | wt | - | -- | wt | + | wt | - | - |
| P604I | wt | wt | -- | wt | wt | wt | wt | - |
| P604K | - | -- | -- | ++ | - | wt | -- | - |
| P604L | wt | wt | -- | wt | wt | wt | wt | wt |
| P604M | wt | wt | -- | + | wt | + | + | wt |
| P604N | wt | - | -- | + | ++++ | wt | wt | wt |
| P604P | | | | | | | | |
| P604Q | - | -- | -- | wt | wt | wt | + | - |
| P604R | | | | | | | | |
| P604S | wt | - | -- | wt | + | wt | wt | wt |
| P604T | wt | - | ++ | wt | -- | wt | + | wt |
| P604V | wt | ++ | -- | wt | ++ | wt | wt | wt |
| P604W | wt | -- | -- | wt | -- | wt | -- | wt |
| P604Y | wt | wt | -- | + | ++++ | + | wt | - |
| G605A | - | -- | -- | -- | -- | -- | -- | wt |
| G605C | + | - | -- | wt | +++ | ++++ | - | + |
| G605D | -- | -- | -- | -- | -- | -- | -- | -- |
| G605E | -- | -- | -- | -- | + | +++ | -- | + |
| G605F | -- | -- | -- | ++ | -- | -- | -- | wt |
| G605G | | | | | | | | |
| G605H | ++ | -- | -- | -- | -- | -- | -- | - |
| G605I | -- | -- | -- | -- | -- | -- | -- | - |
| G605K | wt | -- | -- | -- | -- | -- | -- | wt |
| G605L | - | -- | -- | wt | - | -- | -- | + |
| G605M | -- | -- | -- | -- | - | wt | -- | wt |
| G605N | -- | -- | -- | -- | -- | -- | -- | - |
| G605P | | | | | | | | |
| G605Q | - | -- | -- | -- | -- | -- | -- | wt |
| G605R | wt | -- | -- | wt | ++ | ++++ | -- | wt |
| G605S | wt | -- | -- | -- | wt | wt | + | + |
| G605T | wt | wt | -- | + | -- | -- | -- | wt |
| G605V | -- | -- | -- | -- | -- | -- | -- | wt |
| G605W | -- | -- | -- | -- | -- | -- | -- | wt |
| G605Y | wt | -- | -- | -- | -- | -- | -- | wt |
| G606A | wt | -- | -- | -- | - | -- | -- | ++ |
| G606C | wt | -- | -- | - | wt | -- | ++ | + |
| G606D | ++ | -- | -- | -- | - | -- | + | + |
| G606E | wt | -- | -- | -- | + | - | ++ | + |
| G606F | -- | -- | -- | -- | -- | -- | -- | wt |
| G606G | | | | | | | | |
| G606H | wt | - | -- | -- | + | - | wt | ++ |
| G606I | wt | -- | -- | - | ++ | ++ | + | ++ |
| G606K | wt | -- | -- | - | ++ | +++ | wt | + |
| G606L | wt | -- | -- | - | + | + | ++ | ++ |
| G606M | wt | -- | -- | -- | ++ | + | ++ | ++ |
| G606N | wt | wt | -- | -- | + | wt | - | + |
| G606P | + | -- | -- | -- | -- | -- | -- | wt |
| G606Q | wt | -- | -- | -- | ++ | ++++ | - | ++ |
| G606R | -- | -- | -- | -- | -- | -- | -- | + |
| G606S | wt | - | -- | -- | + | wt | wt | + |
| G606T | -- | -- | -- | -- | -- | -- | -- | -- |
| G606V | - | -- | -- | -- | ++ | ++ | ++ | ++ |
| G606W | wt | -- | -- | -- | wt | wt | -- | + |
| G606Y | wt | - | -- | -- | wt | wt | -- | ++ |
| P607A | -- | -- | -- | -- | -- | -- | -- | -- |
| P607C | wt | wt | -- | + | wt | ++ | ++ | wt |
| P607D | wt | wt | -- | wt | wt | ++ | + | ++ |
| P607E | wt | - | -- | wt | ++ | + | + | wt |
| P607F | + | +++ | -- | wt | ++ | ++ | wt | wt |
| P607G | wt | ++ | -- | wt | + | ++ | + | ++ |
| P607H | wt | + | -- | wt | wt | + | wt | wt |
| P607I | - | + | -- | ++ | wt | +++ | ++ | ++ |
| P607K | ++ | ++ | -- | wt | wt | + | wt | wt |
| P607L | wt | wt | -- | wt | + | + | wt | + |
| P607M | wt | - | -- | wt | wt | wt | wt | wt |
| P607N | wt | wt | wt | wt | wt | + | wt | wt |
| P607P | | | | | | | | |
| P607Q | wt | ++ | -- | wt | wt | ++ | + | + |
| P607R | - | + | -- | wt | wt | wt | wt | ++ |
| P607S | wt | + | -- | wt | + | + | wt | wt |
| P607T | wt | -- | - | wt | wt | wt | wt | wt |
| P607V | | | | | | | | |
| P607W | wt | wt | -- | -- | -- | -- | -- | wt |
| P607Y | wt | - | -- | wt | wt | wt | wt | + |
| S624A | - | -- | ++ | wt | wt | - | wt | wt |
| S624C | - | -- | -- | wt | wt | wt | + | wt |
| S624D | wt | -- | - | wt | + | wt | + | wt |
| S624E | - | -- | -- | + | wt | wt | ++ | wt |
| S624F | wt | -- | -- | ++ | + | ++ | ++ | + |
| S624G | -- | -- | -- | + | wt | + | ++ | + |
| S624H | - | - | -- | wt | wt | wt | wt | + |
| S624I | -- | -- | -- | ++ | ++ | ++ | +++ | + |
| S624K | - | wt | - | wt | wt | wt | + | wt |
| S624L | - | -- | -- | + | wt | wt | wt | + |
| S624M | | | | | | | | |
| S624N | -- | -- | -- | + | wt | + | wt | + |
| S624P | wt | -- | -- | wt | + | ++ | -- | + |
| S624Q | wt | wt | -- | + | - | + | - | + |
| S624R | wt | wt | -- | + | wt | wt | wt | + |
| S624S | | | | | | | | |
| S624T | - | - | -- | + | wt | ++ | wt | + |
| S624V | -- | -- | -- | ++ | + | +++ | wt | + |
| S624W | -- | -- | -- | + | wt | wt | wt | + |
| S624Y | - | -- | - | wt | wt | - | wt | wt |
| A630A | | | | | | | | |
| A630C | - | wt | -- | + | + | +++ | ++ | + |
| A630D | wt | -- | -- | ++ | + | ++ | ++ | + |
| A630E | | | | | | | | |
| A630F | -- | -- | -- | -- | -- | -- | -- | -- |
| A630G | wt | -- | -- | + | + | ++ | + | wt |
| A630H | + | ++ | -- | wt | wt | wt | wt | + |
| A630I | -- | -- | -- | -- | -- | -- | -- | -- |
| A630K | - | + | ++ | wt | wt | + | wt | - |
| A630L | -- | -- | -- | -- | -- | -- | -- | -- |
| A630M | - | - | -- | wt | wt | ++ | ++ | wt |
| A630N | wt | wt | -- | wt | wt | + | wt | wt |
| A630P | | | | | | | | |
| A630Q | wt | + | -- | + | ++ | +++ | ++ | + |
| A630R | wt | ++ | - | wt | wt | wt | wt | wt |
| A630S | wt | wt | -- | wt | wt | ++ | + | + |
| A630T | wt | wt | -- | wt | wt | ++ | ++ | + |
| A630V | -- | -- | -- | ++ | -- | ++++ | -- | + |
| A630W | ++ | + | -- | -- | -- | -- | -- | - |
| A630Y | + | ++ | -- | wt | wt | ++ | + | ++ |
| A633A | | | | | | | | |
| A633C | + | wt | -- | ++ | ++ | ++ | + | + |
| A633D | -- | -- | -- | -- | -- | -- | -- | wt |
| A633E | -- | -- | -- | -- | -- | -- | -- | wt |
| A633F | -- | -- | -- | -- | -- | -- | -- | -- |
| A633G | -- | -- | -- | -- | -- | -- | -- | -- |
| A633H | -- | -- | -- | -- | -- | -- | -- | wt |
| A633I | wt | - | -- | wt | wt | + | wt | + |
| A633K | -- | -- | -- | -- | -- | -- | -- | wt |
| A633L | wt | - | - | wt | wt | ++ | ++ | wt |
| A633M | -- | -- | -- | -- | -- | -- | -- | wt |

TABLE 4-2-continued

Table 4-2 Performance of BGL1 variants

| Variant | Gluc | Heat | HPLC | PASC | PCS | G2 | CNPG | CC |
|---|---|---|---|---|---|---|---|---|
| A633N | -- | -- | -- | -- | -- | -- | ++ | wt |
| A633P | wt | wt | -- | - | wt | -- | wt | + |
| A633Q | -- | -- | -- | -- | -- | -- | -- | wt |
| A633R | -- | -- | -- | -- | -- | -- | -- | wt |
| A633S | wt | -- | -- | - | wt | - | ++ | wt |
| A633T | wt | - | -- | wt | wt | + | + | wt |
| A633V | wt | wt | wt | wt | + | ++ | ++ | + |
| A633W | | | | | | | | |
| A633Y | -- | -- | -- | -- | -- | -- | -- | wt |
| Y639A | -- | -- | -- | -- | -- | -- | -- | -- |
| Y639C | -- | -- | -- | -- | -- | -- | -- | -- |
| Y639D | | | | | | | | |
| Y639E | | | | | | | | |
| Y639F | + | wt | - | wt | wt | wt | - | wt |
| Y639G | + | - | ++ | wt | wt | + | wt | wt |
| Y639H | | | | | | | | |
| Y639I | wt | wt | -- | wt | wt | wt | wt | - |
| Y639K | wt | ++ | ++ | wt | wt | + | wt | wt |
| Y639L | wt | -- | + | wt | wt | + | + | wt |
| Y639M | wt | - | +++ | wt | wt | + | wt | - |
| Y639N | wt | - | -- | wt | - | wt | -- | wt |
| Y639P | + | ++ | -- | wt | wt | wt | - | - |
| Y639Q | wt | wt | - | wt | wt | wt | wt | - |
| Y639R | wt | + | -- | wt | wt | wt | - | wt |
| Y639S | wt | - | wt | wt | wt | wt | + | wt |
| Y639T | wt | ++ | -- | wt | + | wt | - | wt |
| Y639V | + | wt | - | wt | + | + | wt | wt |
| Y639W | wt | wt | wt | wt | wt | wt | - | - |
| Y639Y | | | | | | | | |
| T646A | wt | wt | ++ | wt | wt | + | wt | wt |
| T646C | wt | wt | ++ | wt | wt | + | wt | wt |
| T646D | -- | -- | -- | -- | -- | -- | -- | -- |
| T646E | wt | wt | -- | wt | - | wt | + | wt |
| T646F | wt | wt | -- | wt | wt | wt | wt | wt |
| T646G | wt | ++ | -- | wt | wt | wt | wt | wt |
| T646H | - | -- | -- | ++ | -- | ++++ | -- | wt |
| T646I | | | | | | | | |
| T646K | wt | -- | -- | -- | -- | -- | -- | -- |
| T646L | - | -- | -- | wt | wt | wt | ++ | wt |
| T646M | -- | -- | -- | -- | -- | -- | -- | -- |
| T646N | wt | - | -- | wt | wt | wt | + | wt |
| T646P | wt | wt | -- | wt | wt | wt | -- | - |
| T646Q | wt | wt | -- | wt | wt | + | - | wt |
| T646R | wt | wt | -- | wt | wt | + | wt | - |
| T646S | wt | + | -- | wt | wt | wt | wt | wt |
| T646T | | | | | | | | |
| T646V | wt | wt | -- | wt | wt | wt | + | wt |
| T646W | | | | | | | | |
| T646Y | wt | wt | -- | wt | wt | wt | + | wt |
| A655A | | | | | | | | |
| A655C | wt | wt | -- | wt | + | + | wt | wt |
| A655D | + | + | ++ | wt | wt | + | - | wt |
| A655E | wt | wt | wt | wt | wt | + | wt | wt |
| A655F | | | | | | | | |
| A655G | wt | wt | -- | wt | ++ | + | + | wt |
| A655H | + | wt | ++ | wt | wt | wt | - | wt |
| A655I | | | | | | | | |
| A655K | wt | - | - | wt | wt | wt | wt | wt |
| A655L | wt | wt | -- | + | wt | ++ | + | wt |
| A655M | wt | wt | wt | wt | wt | + | wt | wt |
| A655N | wt | +++ | -- | wt | + | + | + | wt |
| A655P | -- | -- | -- | -- | -- | -- | -- | wt |
| A655Q | wt | ++ | -- | wt | wt | ++ | ++ | wt |
| A655R | wt | wt | - | + | + | + | + | wt |
| A655S | wt | ++ | - | wt | wt | wt | wt | + |
| A655T | wt | -- | -- | wt | wt | wt | wt | + |
| A655V | wt | wt | wt | wt | wt | wt | wt | wt |
| A655W | wt | -- | -- | wt | + | + | + | + |
| A655Y | + | + | ++ | wt | wt | wt | - | wt |
| A667A | | | | | | | | |
| A667C | | | | | | | | |
| A667D | -- | -- | -- | -- | -- | -- | -- | -- |
| A667E | -- | -- | -- | wt | - | wt | -- | + |
| A667F | wt | -- | -- | ++ | + | ++ | wt | + |
| A667G | wt | -- | -- | -- | + | wt | + | + |
| A667H | - | wt | - | wt | - | - | -- | wt |
| A667I | - | wt | wt | wt | - | - | - | wt |
| A667K | -- | -- | -- | wt | wt | wt | - | ++ |
| A667L | wt | - | -- | ++ | + | ++ | - | ++ |
| A667M | - | wt | -- | wt | - | - | - | wt |
| A667N | -- | -- | -- | wt | - | -- | -- | wt |
| A667P | -- | -- | -- | wt | wt | wt | -- | ++ |
| A667Q | | | | | | | | |
| A667R | - | wt | -- | + | + | ++ | -- | ++ |
| A667S | -- | -- | -- | + | wt | wt | wt | + |
| A667T | - | - | -- | wt | wt | wt | wt | wt |
| A667V | - | wt | -- | wt | wt | + | -- | + |
| A667W | -- | -- | -- | - | - | -- | - | + |
| A667Y | - | -- | -- | ++ | ++ | ++ | -- | ++ |
| I671A | wt | + | -- | wt | wt | wt | wt | wt |
| I671C | wt | wt | +++ | + | + | ++ | wt | wt |
| I671D | -- | -- | -- | -- | -- | -- | -- | - |
| I671E | -- | -- | -- | -- | -- | -- | -- | wt |
| I671F | wt | - | +++ | wt | wt | ++ | wt | wt |
| I671G | -- | -- | -- | -- | -- | -- | -- | wt |
| I671H | wt | wt | - | wt | wt | wt | wt | wt |
| I671I | | | | | | | | |
| I671K | wt | + | - | wt | + | + | - | wt |
| I671L | wt | wt | ++++ | wt | wt | + | + | wt |
| I671M | -- | -- | -- | -- | -- | -- | -- | -- |
| I671N | -- | -- | -- | -- | -- | -- | -- | wt |
| I671P | -- | -- | -- | -- | -- | -- | -- | wt |
| I671Q | -- | -- | -- | -- | -- | -- | -- | -- |
| I671R | -- | -- | -- | -- | -- | -- | -- | -- |
| I671S | -- | -- | -- | -- | -- | -- | -- | wt |
| I671T | + | wt | -- | -- | -- | -- | -- | wt |
| I671V | -- | -- | -- | -- | -- | -- | -- | wt |
| I671W | -- | -- | -- | -- | -- | -- | -- | - |
| I671Y | -- | -- | -- | -- | -- | -- | -- | wt |
| Y678A | - | -- | -- | ++ | + | ++ | + | + |
| Y678C | - | wt | -- | ++ | + | ++ | ++ | + |
| Y678D | -- | -- | -- | wt | - | - | -- | ++ |
| Y678E | -- | - | -- | wt | - | -- | -- | wt |
| Y678F | wt | wt | -- | ++ | wt | ++ | ++ | wt |
| Y678G | - | wt | -- | wt | wt | wt | -- | wt |
| Y678H | - | -- | -- | wt | + | ++ | -- | ++ |
| Y678I | - | wt | -- | + | wt | ++ | ++ | + |
| Y678K | - | -- | - | wt | wt | - | -- | ++ |
| Y678L | -- | -- | wt | wt | wt | - | wt | wt |
| Y678M | - | -- | - | wt | - | - | wt | wt |
| Y678N | - | -- | - | wt | - | - | wt | wt |
| Y678P | -- | -- | -- | -- | -- | -- | -- | -- |
| Y678Q | - | wt | -- | ++ | + | ++ | wt | ++ |
| Y678R | - | - | -- | wt | wt | +++ | -- | ++ |
| Y678S | - | wt | -- | wt | wt | - | -- | wt |
| Y678T | - | - | -- | wt | - | wt | wt | wt |
| Y678V | wt | wt | + | wt | wt | wt | - | wt |
| Y678W | - | wt | -- | wt | wt | -- | -- | + |
| Y678Y | | | | | | | | |

++++ PI > 2
+++ 2 > PI > 1.5
++ 1.5 > PI > 1.2
+ 1.2 > PI > 1.4
wt 1.1 > PI > 0.9
- 0.9 > PI > 0.8
-- 0.8 > PI

Some variants of interest were manually selected. Table 4-3 includes 35 additional such variants from the second SEL library.

TABLE 4-3

| Variant | Inh | Heat | HPLC | PASC | PCS | G2 | CNPG | CC |
|---|---|---|---|---|---|---|---|---|
| L266Y | wt | wt | -- | wt | + | wt | wt | wt |
| I567S | wt | -- | -- | wt | + | wt | wt | ++ |
| A270D | wt | wt | -- | wt | ++ | wt | wt | wt |
| S550D | wt | wt | -- | wt | wt | wt | wt | + |
| T258S | wt | wt | -- | ++ | ++ | ++ | ++ | + |

TABLE 4-3-continued

| Variant | Inh | Heat | HPLC | PASC | PCS | G2 | CNPG | CC |
|---|---|---|---|---|---|---|---|---|
| P536D | wt | wt | -- | + | + | + | wt | ++ |
| P536V | wt | wt | -- | + | wt | ++ | ++ | + |
| F260D | -- | + | -- | wt | ++ | ++ | ++ | + |
| F260G | -- | ++ | -- | wt | ++ | ++ | ++ | + |
| Y530F | wt | wt | -- | + | wt | ++ | ++ | + |
| S624N | -- | -- | -- | + | wt | + | wt | + |
| P607Q | wt | ++ | -- | wt | wt | ++ | + | + |
| G606M | wt | -- | -- | - | ++ | + | ++ | ++ |
| Q406H | wt | wt | -- | - | wt | ++ | +++ | wt |
| N400Q | wt | ++ | -- | wt | wt | wt | - | + |
| G300M | wt | -- | -- | wt | wt | ++ | wt | + |
| N038L | ++ | wt | -- | -- | -- | -- | -- | wt |
| N038M | ++ | wt | -- | -- | -- | -- | -- | wt |
| A601Y | wt | wt | -- | + | + | + | + | ++ |
| L293V | wt | - | -- | + | ++ | ++ | ++ | wt |
| T568K | -- | ++ | -- | + | ++ | + | ++ | wt |
| S308E | ++ | + | -- | wt | ++ | wt | wt | ++ |
| A630Y | + | ++ | -- | wt | wt | ++ | + | ++ |
| N461D | wt | wt | -- | + | + | wt | wt | wt |
| N146D | wt | +++ | -- | wt | + | wt | - | wt |
| A450E | wt | - | -- | + | + | ++ | ++ | ++ |
| V043L | +++ | - | -- | wt | wt | wt | -- | wt |
| Q220A | wt | -- | -- | -- | -- | -- | -- | -- |
| A655Q | wt | ++ | -- | wt | wt | ++ | ++ | + |
| S482A | wt | -- | -- | ++ | + | +++ | wt | ++ |
| A667L | wt | - | -- | ++ | + | ++ | - | ++ |
| A485T | - | -- | -- | ++ | + | ++ | - | ++ |
| K206A | wt | -- | -- | + | ++ | + | ++ | wt |
| Y678Q | - | wt | -- | ++ | + | ++ | wt | ++ |

++++ PI > 2
+++ 2 > PI > 1.5
++ 1.5 > PI > 1.2
+ 1.2 > PI > 1.1
wt 1.1 > PI > 0.9
- 0.9 > PI > 0.8
-- 0.8 > PI

The results of the substitutions from the first (Example 3) and second (Example 4) SEL screens were analyzed for various activities as described above and grouped accordingly to those variants that had two, three, four, five, or six (or more) activities. Variants possessing these multiple activities are shown below in Table 4-4 to Table 4-7:

TABLE 4-4

Variants with Two Improved Activities

| PCS + G2 | HPLC + G2 | PCS + CC | Gluc + Heat | G2 + CC | Heat + HPLC | PASC + G2 | PASC + PCS | Heat + PCS | Heat + CC | PASC + CC | Gluc + HPLC | Gluc + CC | Gluc + PSC |
|---|---|---|---|---|---|---|---|---|---|---|---|---|---|
| I567Q | I567K | I567S | L266F | L266A | N261E | N261C | N566L | F556G | S550Q | P536F | S384G | G606D | R179V |
| A565F | I567R | G606E | I567Y | I567E | N261K | T258C | N566P | F260S | P607R | F392C | S384W | Y068V | |
| A565K | A565E | G606H | A270R | S283F | N400A | F392Q | N566W | P604E | N400Q | S624L | N038E | | |
| A565Q | A565S | G606N | S384C | S283P | V602K | S624E | A270K | P604V | V602F | S624R | N038M | Gluc + G2 | |
| A565V | A565Y | G606S | A630W | T258E | L293I | P607C | A270N | N146D | A601G | S624W | N038P | A377I | |
| F556E | F392Y | L293A | E128R | T258I | N461S | P604M | F556H | Y639T | A601L | I486F | V043H | N461Y | |
| F260I | Q406H | S308R | N146M | T258K | D457A | A377Q | F556K | T221C | L293K | I486W | V043W | | |
| P607E | Q406T | I444C | N146V | T258Q | V043Q | N461A | P604N | N473S | Y575C | A667G | Y068E | HPLC + PASC | |
| G605R | P604C | M201D | N146W | P536T | Q303N | N461F | N461D | N583R | Y575R | A667S | Y068G | K206D | |
| G300C | N038F | R542N | L181F | P536W | K320S | N461P | N463E | R645G | A450Q | | Y068M | | |
| A377C | T568A | | V043C | I532Y | G662D | T436A | K206G | G662Y | I486C | | L110C | Heat + PASC | |
| A377D | N461G | | Y639P | Y530T | | T436C | A468Q | | I486Y | | L110G | A468G | |
| S308C | Y639L | | S507F | P607D | Heat + G2 | T436F | A468Y | | A655S | | L110Q | | |
| N146H | Y639M | | Q245P | Q406M | P607H | T436I | | | Q245F | | L110W | | |
| N146S | T243A | | | Q406S | T011E | T436M | | | D329A | | A655H | | |
| A655C | T243C | HPLC + CC | | V602T | T011Y | T436Q | | | | | N264L | | |
| A655G | Q245H | D259S | | G300M | N146E | T436Y | | | | | | | |
| P176L | Q245M | T243V | | A630S | | Q220C | | | | | | | |
| T209I | Q245T | | | A630T | | A655L | | | | | | | |
| | T646A | | | T180H | | T646H | | | | | | | |
| HPLC + PCS | T646C | | | T180M | | Y678F | | | | | | | |
| S283D | I671F | | | A450M | | A468I | | | | | | | |
| A270D | I671L | | | I444E | | D177M | | | | | | | |
| N146Y | | | | I444F | | P661E | | | | | | | |
| | | | | I444N | | | | | | | | | |
| | | | | I444W | | | | | | | | | |
| | | | | I444Y | | | | | | | | | |
| | | | | V500Q | | | | | | | | | |
| | | | | A633I | | | | | | | | | |
| | | | | S482P | | | | | | | | | |
| | | | | A667V | | | | | | | | | |
| | | | | A485L | | | | | | | | | |
| | | | | A485W | | | | | | | | | |
| | | | | Y678R | | | | | | | | | |
| | | | | V603G | | | | | | | | | |

TABLE 4-5

Variants with Three Improved Activities

| Heat + HPLC + PCS | Heat + HPLC + G2 | PASC + PCS + G2 | Heat + PASC + CC | Gluc + Heat + HPLC | Heat + PCS + G2 |
|---|---|---|---|---|---|
| F260A | I567V | N566H | Y575A | S384E | F260T |
| S474R | N566G | F556V | Y575K | L181M | P607S |
| D564T | A630K | P604Y | Gluc + Heat + CC | V043A | A655N |
| PASC + PCS + CC | Y639K | L293V | A630H | V043G | I671K |
| N566F | Q245N | A630G | V466T | V043N | Gluc + PASC + PCS |
| HPLC + PCS + G2 | K320Y | N461C | Gluc + Heat + G2 | Q060D | A468T |
| A565C | A347Y | N463T | P607K | A655Y | Heat + PCS + CC |
| Heat + G2 + CC | Heat + PASC + G2 | D457C | N146A | T242S | S692L |
| P536G | P536Q | Q220M | N146Q | S474D | Gluc + PCS + G2 |
| P607Q | N369E | T221A | N369T | Gluc + HPLC + PCS | Y639V |
| A655Q | N369W | T221G | Gluc + PASC + G2 | K206S | |
| Heat + HPLC + PASC | N369Y | T221I | T436E | Gluc + G2 + CC | |
| A601D | Gluc + PCS + CC | A655R | Gluc + HPLC + G2 | Y530S | |
| | L293M | A468F | Y639G | Q684N | |
| | Q220P | A468S | | | |
| | | Q216I | | | |
| | | D564V | | | |

TABLE 4-6

Variants with Four Improved Activities

| | |
|---|---|
| Heat + PASC + G2 + CC | Gluc + PASC + PCS + G2 |
| P607I | E170F |
| A450P | Heat + HPLC + PCS + CC |
| T242H | A338D |
| Heat + HPLC + PCS + G2 | Gluc + Heat + PCS + CC |
| T568E | S308E |
| Gluc + Heat + G2 + CC | Gluc + HPLC + PASC + G2 |
| A630Y | S507G |
| Gluc + Heat + HPLC + G2 | |
| A655D | |

TABLE 4-7

Variants with Five Improved Activities

| | |
|---|---|
| Heat + HPLC + PCS + PASC + G2 | Heat + PASC + PCS + G2 + CC |
| F260E | P536C |
| T568K | A630Q |
| Heat + HPLC + PCS + G2 + CC | D215S |
| F260L | G372A |
| Gluc + PASC + PCS + G2 + CC | G547A |
| A633C | F611A |
| S312C | G662C |
| N455D | G662F |
| | Gluc + Heat + PASC + G2 + CC |
| | L293F |

In summary, Table 4-8 lists all variants having two or more improved activities selected from (1) Heat (thermostability), (2) HPLC (protein expression), (3) PCS, (4) (PASC), (5) G2 (cellobiohydrolase activity), (6) beta-glucosidase activity measured by G2+CC or CC hydrolysis.

TABLE 4-8

| | | | | | | | | |
|---|---|---|---|---|---|---|---|---|
| I567Q | I567K | I567S | L266A | N261C | N566L | S550Q | S384G | F260T |
| A565F | I567R | G606E | I567E | T258C | N566P | P607R | S384W | P607S |
| A565K | A565E | G606H | S283F | F392Q | N566W | N400Q | N038E | A655N |
| A565Q | A565S | G606N | S283P | S624E | A270K | V602F | N038M | I671K |
| A565V | A565Y | G606S | T258E | P607C | A270N | A601G | N038P | P607I |
| F556E | F392Y | L293A | T258I | P604M | F556H | A601L | V043H | A450P |
| F260I | Q406H | S308R | T258N | A377Q | F556K | L293K | V043W | T242H |
| P607E | Q406T | I444C | T258Q | N461A | P604N | Y575C | Y068E | T568E |
| G605R | P604C | M201D | P536T | N461D | Y575R | Y068G | A630Y |
| G300C | N038F | R542N | P536W | N461F | N461D | Y068M | A655D |
| A377C | T568A | D259S | I532Y | T436A | K206G | I486C | L110C | E170F |
| A377D | N461G | T243V | Y530T | T436C | A468Q | I486Y | L110G | A338D |
| S308C | Y639L | L266F | P607D | T436F | A468Y | A655S | L110Q | S308E |
| N146H | Y639M | I567Y | Q406M | T436I | F556G | Q245F | L110W | S507G |
| N146S | T243A | A270R | Q406S | T436M | F260S | D329A | A655H | F260E |
| A655C | T243C | S384C | V602T | T436Q | P604E | P536F | N264L | T568K |
| A655G | Q245H | A630W | G300M | T436Y | P604V | F392C | N566H | F260L |
| P176L | Q245M | E128R | A630S | Q220C | N146D | S624L | F556W | A633C |
| T209I | Q245T | N146M | A630T | A655L | Y639T | S624R | P604Y | S312C |
| S283D | T646A | N146V | T180H | T646H | T221C | S624W | L293V | N455D |
| A270D | T646C | N146W | T180M | Y678F | N473S | I486F | A630G | P536C |
| N146Y | I671F | L181F | A450M | A468I | N583R | I486W | N461C | A630Q |
| N261E | I671L | V043C | I444E | D177M | R645G | A667G | N463T | D215S |
| N261K | P607H | Y639P | I444F | P661E | G662Y | A667S | D457C | G372A |
| N400A | T011E | S507F | I444N | P536G | P536Q | S384E | Q220M | G547A |
| V602K | T011Y | Q245P | I444W | P607Q | N369E | L181M | T221A | F611A |
| L293I | N146E | R179V | I444Y | A655Q | N369W | V043A | T221G | G662C |
| N461S | G606D | F260A | V500Q | I567V | N369Y | V043G | T221I | G662F |
| D457A | Y068V | S474R | A633I | N566G | P607K | V043N | A655R | L293F |
| V043Q | A377I | D564T | S482P | A630K | N146A | Q060D | A468F | |
| Q303N | N461Y | N566F | A667V | Y639K | N146Q | A655Y | A468S | |

TABLE 4-8-continued

| K320S | K206D | A565C | A485L | Q245N | N369T | T242S | Q216I |
| G662D | A468G | A601D | A485W | K320Y | Y639G | S474D | D564V |
| L293M | Y575A | A630H | Y678R | A347Y | K206S | Y530S | S692L |
| Q220P | Y575K | V466T | V603G | T436E | A468T | Q684N | Y639V |

Example 5

BGL1 Combinatorial Library Variants and Activities Thereof 5.1 Assays:

HPLC Assay for Protein Content Determination

The concentration of each BGL polypeptide (wild type or variant) in pooled culture supernatant was determined using an Agilent 1200 (Agilent Technologies) HPLC equipped with a Shodex HIC PH-814 PHM gel 75×8 mm column (Phenomenex) equilibrated at 35° C. Forty five (45) µL of a supernatant was incubated with 15 µL of 80 ppm recombinantly expressed S. plicatus glycosidase EndoH (e.g. NEB P0702L) in 200 mM of sodium acetate buffer, at pH 5.0, and incubated at 37° C. overnight with shaking at 900 rpm. Sixty (60) µL 1.6 M $(NH_4)_2SO_4$ was added to the supernatant and after 5 min. the mixture was filtered under vacuum using a 0.22 µm Millipore Multiscreen HTS 96 well filtration system. Forty (40) µL of the filtered sample was loaded onto the column. Two elation buffers were employed to build an elation gradient: (1) Buffer A: 16 mM $NaH_2PO_4$, pH 6.75, 800 mM $(NH_4)_2SO_4$ and (2) Buffer B: 16 mM $NaH_2PO_4$ pH 6.75. Elution was carried out at a flow rate of 1.8 mL/min, using the following program: 0% buffer B from 0 min to 0.5 min, followed by a gradient of 0% buffer B to 50% (from 0.5 min to 1 min. followed by 50% buffer B to 100% from 1 min to 6 min, followed by 100% buffer B from 6 to 8 min. Protein concentrations of BGL variants were determined using a calibration curve generated with purified wild-type BGL1. To calculate performance index (PI), the concentration of a BGL variant was divided by the average concentration of wild-type BGL1 (e.g., a reference enzyme) in the same plate.

Using CNPGase Activity Assay to Determine Required Sample Dilution for Assays

The activity of the BGL variants towards chloro-nitrophenol-β-D-glucoside (CNPG) was measured to determine the BGL1 production levels. Five (5) µL of supernatant were added to 95 µL of 1 mM CNPG in a 50 mM sodium acetate buffer, pH 5, and $OD_{405}$ readings were recorded in a microplate reader for 3 min. Based on the CNPG activities, and relative to the activity of a wild type BGL1 control, the supernatants were diluted to a level of between 25 and 300 ppm BGL1.

CNPGase Activity Assay

The activity of the BGL variants towards chloro-nitrophenol-β-D-glucoside (CNPG) was determined. Culture supernatants expressing BGL variants were diluted 5, 6.67, 10 and 20-fold in a 50 mM sodium acetate buffer, pH 5.0, containing 0.1 mg/mL bovine serum albumin (BSA). Fifty (50) µL aliquots of diluted supernatants were added to 50 µL of 2 mM CNPG in a 50 mM sodium acetate buffer, pH 5.0, achieving a final concentration of 1 mM CNPG. Kinetics of CNP release was determined by monitoring $OD_{405}$, which was recorded in a microtiter plate reader (Spectramax, Molecular Devices) for 3 min. Average specific activities for the wild-type BGL1 and BGL variants were calculated by dividing the averaged CNPG hydrolyzing activity by the BGL polypeptide concentration. A performance index (PI) was calculated by dividing the specific activity of a BGL variant by the average specific activity of wild-type BGL1 (e.g., a reference enzyme) on the same plate.

Thermostability Assay

Residual activity of BGL1 variants after heat incubation was determined using the CNPG assay. Culture supernatants expressing BGL variants were diluted 5, 6.67, 10 and 20-fold in a 50 mM sodium acetate buffer, pH 5.0, containing 0.1 mg/mL BSA. Eighty (80) µL aliquots were incubated in quadruplicate in a skirted 96-well PCR plate in a thermocycler at 66° C. for 1 hr. After 5 min of cooling on ice, the residual specific activity of each of the wild type and BGL1 variants was determined as described above. The residual activity of the variants and the wild type BGL1 was determined by the ratio of the averaged specific activity after incubation and the averaged specific activity before incubation. A performance index (PI) for the BGL variants was determined by dividing the residual activity of a BGL1 variant by the relative residual activity of the wild-type BGL1 (e.g., a reference enzyme).

Glucose Inhibition Assay

The effect of glucose on the hydrolytic activity of beta-glucosidase was determined by repeating the CNPGase activity assay as described above in the presence of 18.75 mM glucose. The relative residual activity of the variants and the wild-type protein was determined by the ratio of the averaged specific activity in the presence of glucose and the averaged specific activity in the absence of glucose. A performance index (PI) for the BGL variants was determined by dividing the relative residual activity of a BGL variant by the relative residual activity of the wild-type BGL1 (e.g., a reference enzyme).

Specific Activity in a Phosphoric Acid Swollen Cellulose (PASC) Hydrolysis Assay Phosphoric acid swollen cellulose (PASC) was prepared from Avicel according to published methods (see, e.g. Walseth. Tappi 35:228, 1971; and Wood, Biochem. J. 121: 353-362, 1971). This material was diluted with a sodium acetate buffer and water to achieve a 1% w/v mixture, wherein the final concentration of sodium acetate was 50 mM, and pH was 5.0. One hundred and fifty (150) µL of a 1% suspension of PASC in a 50 mM sodium acetate buffer, pH 5.0, was dispensed into a 96-well microtiter plate (Costar Flat Bottom PS). Ten (10) µL of a culture supernatant from a bgl1-deleted strain containing 0.75 mg/mL protein was added to the PASC. Then 5, 10, 20, or 40 µL of 8-fold diluted (in 50 mM sodium acetate buffer pH 5.0) pooled culture supernatants from H. jecorina cells expressing either wild-type BGL1 or a BGL variant were added to the PASC/deletion mutant supernatant mixture. Compensating volumes of sodium acetate buffer were added to make up for differences in total volume. The microtiter plate was sealed and incubated in a thermostatted incubator at 50° C. with continuous shaking at 900 rpm. After two hours, the hydrolysis reaction was stopped by the addition of 100 µL of a 100 mM glycine buffer, pH 10, to each well. The plates were sealed and centrifuged at 3000 rpm at room temperature for 5 min. The hydrolysis reaction products in the supernatant were analyzed by the ABTS assay. A dose response curve was generated for wild-type BGL1 protein. To calculate performance index (PI), the (average) total sugar produced by a variant BGL was divided by the (average) total sugar produced by the wild-type BGL1 (e.g., a reference enzyme) at the same dose.

Specific Activity in a Dilute Acid Pretreated Corn Stover (PCS) Hydrolysis Assay Corn stover was pretreated with 2% w/w $H_2SO_4$ (see, Schell et al., *J. Appl. Biochem. Biotechnol.*, 105:69-86, 2003), followed by multiple washes with deionized water to obtain a paste of pH 4.5. A sodium acetate buffer (pH 5.0) was then added (to a final concentration of 50 mM sodium acetate) and, if necessary, this mixture was further titrated to pH 5.0 using 1 N NaOH. The cellulose concentration in the reaction mixture was approximately 7%. Sixty five (65) µL of this cellulose suspension was added per well into a 96-well microtiter plate (Nunc Flat Bottom PS). Ten (10) µL of a culture supernatant from a bgl1-deleted strain containing 10 mg/mL protein was added to the PCS. Then 5, 10, 20, or 40 µL of 2-fold diluted (in a 50 mM sodium acetate buffer, pH 5.0) pooled culture supernatants from *H. jecorina* cells expressing either wild-type BGL1 or a BGL variant were added to the PCS/deletion mutant supernatant mixture. Compensating volumes of sodium acetate buffer were added to make up for the differences in total volume. After sealing, the plates were placed in a thermostatted incubator at 50° C. with continuous shaking at 900 rpm. After 16 hours the plates were placed on ice for 5 min and the hydrolysis reaction was stopped by the addition of 100 µL of a 100 mM glycine buffer, pH 10, to each well. The plates were sealed and centrifuge at 3,000 rpm for 5 min at room temperature. The hydrolysis reaction products that were present in the supernatants were analyzed by the ABTS assay (above). A dose response curve was generated from a purified wild-type BGL1. To calculate performance index (PI), the (average) total sugar produced by a variant BGL was divided by the (average) total sugar produced by the wild-type BGL1 (e.g., a reference enzyme) at the same dose.

Cellobiase Activity Assay

The cellobiose hydrolyzing capability of wild-type BGL1 and the BGL variants at pH 5.0) was tested. Varying amounts (5, 10, 15, or 20 µL) of 4-fold diluted (in a 50 mM sodium acetate buffer, pH 5.0) pooled culture supernatants from *H. jecorina* cells expressing either wild-type BGL1 or BGL variants were added to 80 µL of a 16.4 mM (5.63 mg/mL) cellobiose solution in a 50 mM sodium acetate buffer, pH 5.0. Compensating volumes of sodium acetate buffer were added to make up for the differences in the total volume. The microtiter plate was sealed and incubated in a thermostatted incubator at 50° C. with continuous shaking at 900 rpm. After 30 min, the plates were cooled on ice and 100 µL of a 100 mM glycine buffer, pH 10, was added to each well. The hydrolysis reaction products were analyzed by the ABTS assay (above). A dose response curve was generated using purified wild-type BGL1. To calculate performance index (PI), the (average) total sugar produced by a variant BGL was divided by the (average) total sugar produced by the wild-type BGL1 (e.g., a reference enzyme) at the same dose.

Specific Beta-Glucosidase Activity in an Ammonia Pretreated Corncob Hydrolysis Assay Corn cob was ground to pass a 0.9 mm screen and pretreated as described in PCT Patent Application Publication WO 200611091. Pretreated corn cob was used as a 7% cellulose suspension in a 50 mM sodium acetate buffer, pH 5.0. Sixty five (65) µL of the suspension was added per well into a 96-well microtiter plate (Nunc Flat Bottom PS). Ten (10) µL of a *T. reesei* strain overexpressing *T. reesei* endoxylanase gene xyn3, *Fusarium verticillioides* β-xylosidase gene Fv3A, *F. verticillioides* β-xylosidase gene Fv43D, and *F. verticillioides* α-arabinofuranosidase gene Fv51A containing 0.76 mg/mL protein in 50 mM sodium acetate buffer, pH 5.0, was added to the pretreated corn cob. Varying amounts (5, 10, 20, or 40 µL) of pooled culture supernatants from *H. jecorina* cells expressing the wild-type BGL1 or BGL variants were added. Compensating volumes of sodium acetate buffer were added to make up for the differences in total volume. The microtiter plate was sealed and incubated in a thermostatted incubator at 50° C. with continuous shaking at 900 rpm. After 24 hrs, the hydrolysis reaction was stopped by the addition of 100 µL of a 100 mM glycine buffer, pH 10, to each well. After mixing, the plate was centrifuged for 5 min at 3,000 rpm. The hydrolysis reaction products were analyzed by the ABTS assay (above). A dose response curve was generated using purified wild-type BGL1. To calculate performance index (PI), the (average) total sugar produced by a variant BGL was divided by the (average) total sugar produced by the wild-type BGL1 (e.g., a reference enzyme) at the same dose.

5-2. Generation of *Hypocrea jecorina* BGL Combinatorial Variants

Combinatorial BGL variants were constructed or purchased from commercial vendors, e.g., Sloning Biotechnology GmbH (Puchheim, Germany), BASEClear (Leiden, The Netherlands). Table 5-1 lists substitutions that were selected for inclusion in BGL combinatorial libraries. The amino acid residue numbers were assigned in reference to the reference wild type BGL1 mature amino acid sequence, SEQ ID NO:3.

TABLE 5-1

BGL1 substitutions selected for construction of combinatorial variants.

| K51A | Q226Y | Q303R | N369Y | S550N | G662F |
|---|---|---|---|---|---|
| E92V | N238F | Q303N | N369W | G554C | G662K |
| L167W | N238W | S312D | D370W | G554F | G662L |
| E170F | T242H | S312I | G372A | K560S | G662Y |
| P176L | T242S | S312K | G427C | D564T | T666C |
| D177M | N263C | S312Y | G427F | D564V | S683W |
| D178I | N263T | S312C | K428N | N583R | Q684A |
| D178K | N263S | Q316T | N455D | V603G | Q684C |
| D178N | N264D | K320S | N473S | F611A | Q684D |
| R179K | N264K | K320Y | S474D | F611R | Q684G |
| R179S | N264L | D329A | S474I | R636E | Q684N |
| R179V | N264M | A338D | S474R | R645G | Q684R |
| S199T | R265M | A338I | K498F | R645K | S692E |
| T209I | R265P | A338K | K498H | K656R | S692K |
| D215S | N278F | K345E | K498A | P661E | S692L |
| Q216E | T282D | A347D | D521A | P661F | |
| Q216I | T282I | A347Y | D521R | P661L | |
| Q216K | T282K | N369E | V522Y | P661Q | |
| D225Q | Q303E | N369I | R542N | G662C | |
| Q226W | Q303I | N369T | G547A | G662D | |

Combinatorial variants derived from pTTTpyrG-bgl1 were generated in *E. coli* and plated onto 2×TY agar plates (16 g/L Bacto Tryptone (Difco, USA), 10 g/L Bacto Yeast Extract (Difco, USA), 5 g/L NaCl, 16 g/L Bacto Agar (Difco, USA)) with 100 µg/mL ampicillin. After overnight incubation at 37° C., *E. coli* colonies harboring the bgl1 variants were picked from the 2×TY agar plates containing 100 µg/mL ampicillin and grown for 24 hr at 37° C. in a microtiter plate containing 1 mL of a 2×TY medium with 100 µg/mL ampicillin and 50 µg/mL kanamycin. Bacterial cultures were used for purification of plasmid DNA.

Purified pTTTpyrG-bgl1 derived plasmids encoding bgl1 combinatorial variants were used in *H. jecorina* transformations at concentrations of 150-300 ng/μL. These replicative plasmids expressing bgl1 variants under the cbh1 promoter conferred transformed *H. jecorina* cells for growth on acetamide. Five (5) μL of plasmids was used for fungal transformation as described in, for example, U.S. Patent Application Publication US2006/0094080 A1. Protoplasts of *H. jecorina* strain (Δeg1, Δeg2, Δcbh2, Δbgl1) were transformed with individual pTTTpyrG-bgl1 constructs (i.e., including a single BGL1 variant per transformation; and grown in 24-well microtiter plates on selective medium containing acetamide at 28° C. for 7 d.

Spores from the initial population of *H. jecorina* transformants of individual variants were harvested and reselected on acetamide agar plates. Spores were harvested using saline physiological solution, re-arrayed in 96 microtiter plates, and used for inoculation of a number of production media to generate BGL variant samples. For this purpose, 96-well filter plates (Corning, Art. No. 3505) containing in each well 250 μL of a glycine production medium, containing 4.7 g/L $(NH_4)_2SO_4$; 33 g/L 1,4-piperazinebis(propanesulfonic acid) pH 5.5; 6.0 g/L glycine; 5.0 g/L $KH_2PO_4$; 1.0 g/L $CaCl_2 \times 2H_2O$; 1.0 g/L $MgSO_4 \times 7H_2O$; 2.5 mL/L of 400× *T. reesei* trace elements, containing 5 g/L $FeSO_4 \times 7H_2O$, 1.4 g/L $ZnSO_4 \times 7H_2O$, 1.6 g/L $MnSO_4 \times H_2O$, 3.7 g/L $CoCl_2 \times 6H_2O$; 20 g/L Glucose; and 6.5 g/L Sophorose, were inoculated in quadruplicate with spore suspensions of *H. jecorina* transformants. Plates were incubated at 28° C. and 80% humidity for 6 to 8 d. Culture supernatants were harvested by vacuum filtration. Residual glucose in these supernatants filtrates were measured using the hexokinase assay as described in Example 1A.

Combinations of substitutions were tested for the various activities as described above. Results of this testing is shown below in Table 5-2.

TABLE 5-2

Performance of Combinatorial BGL variants

| Variant | Gluc | Heat | HPLC | PASC | PCS | G2 | CNPG | CC |
|---|---|---|---|---|---|---|---|---|
| L167W \| D225Q | wt | − | −− | wt | ++ | wt | + | wt |
| D177M \| D225Q \| D564T \| Q626F \| Q684A | −− | −− | −− | | | | | |
| D177M \| D225Q \| Q684R | −− | −− | −− | wt | − | wt | + | wt |
| L167W \| D225Q \| Q626F \| Q684R | −− | −− | −− | ++ | wt | + | ++ | + |
| L167W \| D177M \| D225Q \| Q626F \| Q684G | wt | −− | −− | + | wt | + | ++ | −− |
| L167W \| D177M \| Q626F | wt | −− | −− | ++ | ++ | wt | wt | ++ |
| D177M \| D564T \| Q684C | −− | −− | −− | − | −− | wt | ++ | wt |
| L167W \| D225Q \| Q626F \| Q684D | ++ | ++ | −− | wt | wt | wt | wt | wt |
| L167W \| D225Q \| D564V \| Q684N | wt | −− | −− | + | −− | − | wt | wt |
| L167W \| D177M \| D225Q \| D564T \| Q684A | −− | −− | −− | | | | | |
| L167W \| D177M \| D564V \| Q684R | − | −− | −− | +++ | −− | wt | + | ++ |
| L167W \| D177M \| D225Q \| D564V \| Q684G | wt | −− | −− | ++ | + | wt | wt | + |
| L167W \| D225Q \| D564V | −− | −− | −− | +++ | wt | wt | wt | ++ |
| D177M \| D225Q \| D564T \| Q626F \| Q684N | −− | −− | −− | ++ | −− | wt | ++ | ++ |
| D177M \| D225Q \| D564T \| Q684N | wt | −− | −− | ++ | +++ | wt | ++ | + |
| L167W \| D225Q \| Q684N | ++++ | +++ | −− | wt | wt | wt | −− | wt |
| L167W \| D177M \| Q626F \| Q684N | ++ | −− | −− | wt | −− | − | −− | wt |
| Q684D | − | −− | −− | | | | | |
| L167W \| D177M \| Q626F \| Q684G | + | −− | −− | +++ | −− | + | wt | ++ |
| L167W \| D225Q \| D564T \| Q626F \| Q684A | − | −− | −− | ++ | −− | wt | + | wt |
| D177M \| Q626F \| Q684R | − | −− | −− | ++ | ++++ | wt | wt | ++ |
| D225Q \| Q626F \| Q684R | wt | − | −− | wt | wt | wt | + | wt |
| L167W \| Q626F | wt | −− | −− | + | − | − | ++ | + |
| D177M \| D225Q \| D564T \| Q626F \| Q684R | −− | −− | −− | | | | | |
| L167W \| D177M \| D564T \| Q626F \| Q684N | ++ | −− | −− | ++ | −− | −− | −− | + |
| D225Q \| D564V \| Q684A | +++ | wt | −− | | | | | |
| D225Q \| D564T \| Q626F | ++++ | wt | −− | | | | | |
| Q684R | wt | wt | −− | wt | −− | − | − | wt |
| Q684A | −− | ++++ | −− | | | | | |
| L167W \| Q626F \| Q684D | + | −− | −− | + | −− | wt | − | + |
| D564T | wt | ++ | −− | wt | ++ | wt | − | wt |
| D225Q \| D564V \| Q626F \| Q684R | − | wt | −− | +++ | −− | wt | wt | ++ |
| L167W \| D177M \| D225Q \| D564T \| Q626F \| Q684A | −− | −− | −− | | | | | |
| D225Q \| D564T \| Q684A | wt | − | −− | wt | − | − | wt | + |
| L167W \| D225Q \| D564T \| Q626F \| Q684C | ++++ | ++++ | −− | | | | | |
| L167W \| D177M \| D564T \| Q684R | ++ | −− | −− | ++ | −− | wt | − | ++ |
| D177M \| D225Q \| D564V \| Q684R | wt | −− | −− | +++ | −− | wt | − | ++ |
| L167W \| D564T \| Q626F | wt | wt | −− | ++ | wt | ++ | ++ | ++ |
| L167W \| D177M \| D225Q \| D564V \| Q626F \| Q684N | − | −− | −− | wt | − | − | wt | + |
| L167W \| D177M \| D225Q \| D564T \| Q684D | ++ | −− | −− | wt | wt | wt | − | wt |

TABLE 5-2-continued

Performance of Combinatorial BGL variants

| Variant | Gluc | Heat | HPLC | PASC | PCS | G2 | CNPG | CC |
|---|---|---|---|---|---|---|---|---|
| L167W | D225Q | D564V | Q626F | Q684N | ++++ | ++++ | -- | wt | + | wt | - | wt |
| L167W | D177M | D564T | wt | ++ | -- | | | | | |
| L167W | D177M | D564V | Q626F | Q684A | +++ | -- | -- | ++ | -- | + | wt | ++ |
| L167W | D177M | D225Q | D564T | Q626F | Q684G | -- | ++ | -- | | | | | |
| L167W | D177M | D564T | Q684N | ++++ | ++++ | -- | +++ | -- | ++ | wt | ++ |
| L167W | D225Q | D564T | Q626F | Q684D | - | -- | -- | | | | | |
| D177M | D564V | Q684D | + | -- | -- | | | | | |
| D177M | D225Q | D564V | Q684G | wt | -- | -- | wt | ++++ | - | wt | + |
| L167W | D177M | D225Q | Q626F | Q684C | -- | -- | -- | | | | | |
| D177M | D564T | Q626F | Q684A | + | -- | -- | wt | ++ | - | + | wt |
| D177M | D564T | Q626F | Q684R | -- | -- | -- | | | | | |
| L167W | D177M | D225Q | Q684D | ++ | -- | -- | ++ | wt | wt | -- | ++ |
| L167W | D177M | D564V | Q626F | Q684N | -- | -- | -- | | | | | |
| D177M | D225Q | D564T | Q626F | Q684D | -- | -- | -- | | | | | |
| Q626F | Q684D | ++++ | ++++ | -- | | | | | |
| L167W | D177M | D564T | Q626F | Q684G | + | -- | -- | ++ | + | ++ | -- | - |
| L167W | D177M | D564V | Q684G | wt | -- | -- | + | wt | ++ | wt | - |
| D177M | D225Q | D564T | Q684A | -- | -- | -- | + | + | ++ | -- | -- |
| L167W | D177M | D225Q | D564V | + | -- | -- | + | wt | ++ | wt | - |
| Q626F | Q684N | ++ | wt | +++ | wt | wt | wt | ++ | -- |
| L167W | D177M | D225Q | D564V | Q626F | Q684R | ++ | -- | -- | ++ | ++ | ++ | -- | + |
| D177M | D225Q | D564V | Q626F | Q684N | wt | -- | -- | ++ | + | ++ | wt | wt |
| N369I | D370W | -- | -- | -- | | | | | |
| N264M | R265P | N369I | D370W | +++ | ++++ | -- | | | | | |
| R179V | N238F | D370W | ++++ | ++++ | -- | | | | | |
| R179V | R265P | N369I | K656R | -- | ++++ | -- | | | | | |
| R179V | N238F | K656R | ++ | ++++ | -- | | | | | |
| R179V | R265P | wt | ++++ | -- | | | | | |
| R179V | N238W | N264M | R265P | N369I | D370W | ++++ | wt | -- | | | | | |
| R179V | N238W | R265P | ++++ | -- | -- | | | | | |
| N264M | + | -- | -- | | | | | |
| R179V | N264M | D370W | ++ | ++++ | -- | | | | | |
| N238F | N264M | R265M | N369I | ++++ | +++ | -- | wt | - | - | -- | + |
| R179V | R265M | K656R | -- | ++++ | -- | | | | | |
| R179V | N238F | R265M | ++ | ++++ | -- | | | | | |
| R179V | N238W | N264M | N369I | D370W | K656R | -- | -- | -- | | | | | |
| R179V | R265P | D370W | K656R | ++++ | ++++ | -- | | | | | |
| R179V | N369I | D370W | + | wt | -- | | | | | |
| R179V | N238W | N264M | R265M | N369I | ++++ | ++++ | -- | | | | | |
| R179V | N369I | D370W | K656R | ++ | ++++ | -- | | | | | |
| R179V | N238F | R265P | -- | +++ | -- | | | | | |
| R179V | N264M | R265M (+P229S) | -- | ++++ | -- | | | | | |
| R179V | N238W | N264M | D370W | -- | ++++ | -- | | | | | |
| N238F | R265M | D370W | K656R | -- | +++ | -- | | | | | |
| R179V | N264M | R265P | K656R | ++++ | ++++ | -- | | | | | |
| R179V | N238W | R265M | + | wt | -- | | | | | |
| R179V | R265M | N369I | K656R | wt | ++++ | -- | | | | | |
| R179V | R265M | N369I | ++ | ++++ | -- | | | | | |
| R179V | N238F | -- | wt | -- | | | | | |
| R179V | N264M | R265M | D370W | K656R | + | ++++ | -- | | | | | |
| R179V | N238W | N264M | R265M | K656R | -- | ++ | -- | | | | | |
| R179V | N238F | R265P | D370W | K656R | -- | ++++ | -- | | | | | |
| R179V | N264M | R265M | N369I | + | ++++ | -- | | | | | |
| R179V | N238W | N264M | ++++ | ++++ | -- | | | | | |
| R179V | N238F | N264M | R265P | N369I | - | ++ | -- | | | | | |
| N238W | N264M | R265M | D370W | ++++ | +++ | -- | | | | | |
| R179V | N238W | N264M | N369I | -- | ++++ | -- | | | | | |

TABLE 5-2-continued

Performance of Combinatorial BGL variants

| Variant | Gluc | Heat | HPLC | PASC | PCS | G2 | CNPG | CC |
|---|---|---|---|---|---|---|---|---|
| N264M \| R265P \| N369I | -- | +++ | -- | | | | | |
| R179V \| N238F \| N264M \| R265P \| N369I \| D370W | -- | ++++ | -- | | | | | |
| N238W \| R265P \| D370W \| K656R | wt | ++++ | -- | | | | | |
| R179V \| N238W \| R265P \| D370W | ++ | +++ | -- | | | | | |
| R179V \| N238W \| N264M \| D370W \| K656R | ++++ | ++++ | -- | | | | | |
| R179V \| N238F \| N264M \| R265M \| N369I \| D370W \| K656R | -- | -- | -- | | | | | |
| R179V \| N264M \| R265M \| K656R (+A157T) | -- | ++++ | -- | | | | | |
| R179V \| N264M \| R265M \| N369I \| D370W | -- | + | -- | | | | | |
| R179V \| N238F \| N264M \| R265P \| K656R | - | -- | -- | | | | | |
| N264M \| R265P | ++++ | ++++ | -- | | | | | |
| N264M \| N369I \| D370W | ++++ | -- | -- | | | | | |
| R265P \| D370W (+G662F) | +++ | ++ | -- | | | | | |
| N238F \| R265M \| N369I \| D370W | - | ++++ | -- | | | | | |
| R179V \| N264M \| R265P \| N369I \| D370W | ++++ | ++++ | -- | | | | | |
| R265M \| N369I | +++ | ++++ | -- | | | | | |
| R179V \| R265M \| D370W | +++ | ++++ | -- | | | | | |
| N238W \| N264M \| R265P | ++++ | ++++ | -- | | | | | |
| R179V \| N264M \| N369I \| D370W \| K656R | -- | +++ | -- | | | | | |
| R179V \| N238W \| N264M \| R265P | ++++ | +++ | -- | | | | | |
| N264M \| N369I | ++++ | ++ | -- | wt | - | - | -- | wt |
| R265M \| K560S | ++++ | -- | -- | ++ | ++ | - | -- | wt |
| N238W \| R265P \| K656R | ++++ | - | -- | - | ++ | -- | -- | ++ |
| N264M \| R265P (+G662F) | ++ | -- | -- | wt | + | wt | -- | ++ |
| N238F \| R265M \| N369I | ++++ | +++ | -- | -- | -- | -- | -- | wt |
| R179V \| R265P \| N369I | ++ | - | -- | ++ | wt | -- | -- | ++ |
| K345E \| N369T \| P661E | - | + | wt | wt | wt | wt | wt | wt |
| N263C \| K345E \| N369E \| P661L \| S683W | - | + | -- | | | | | |
| K345E \| N369E \| P661E \| S683W | wt | +++ | -- | + | ++ | ++ | ++ | ++ |
| K345E \| P661E \| S683W | - | +++ | -- | + | + | ++ | ++ | +++ |
| K345E \| N369E \| G372A \| S683W | ++ | +++ | -- | ++ | ++++ | +++ | +++ | wt |
| N263C \| N369T | ++ | ++ | -- | ++ | +++ | +++ | +++ | ++ |
| K428N \| S683W | -- | -- | -- | wt | ++++ | +++ | +++ | wt |
| K345E \| K428N \| S683W | - | -- | -- | wt | ++++ | ++ | +++ | wt |
| K345E \| N369T \| G372A \| P661E \| S683W | -- | wt | -- | + | +++ | +++ | ++ | ++++ |
| N263C \| N369E \| P661E | - | +++ | -- | | | | | |
| N263C \| K345E \| N369E | - | ++ | -- | ++ | +++ | ++++ | +++ | +++ |
| N263C \| N369T \| P661E | wt | ++ | -- | ++ | ++++ | ++++ | +++ | ++++ |
| N369T \| K428N \| P661L \| S683W | -- | +++ | -- | | | | | |
| N263C \| K345E \| K428N \| S683W | -- | +++ | -- | | | | | |
| N263C \| K345E \| N369E \| G372A \| K428N \| P661E \| S683W | + | + | -- | | | | | |
| N263C \| N369T \| G372A \| P661E \| S683W | + | wt | -- | | | | | |
| K345E \| N369T \| P661E \| S683W | -- | wt | -- | | | | | |
| K345E \| P661L | -- | ++++ | -- | | | | | |
| N263C \| K345E \| N369T \| G372A \| K428N \| P661E \| S683W | ++ | +++ | -- | | | | | |
| N369E \| S683W | + | ++++ | -- | ++ | ++ | +++ | +++ | wt |
| N369T \| G372A \| P661E | -- | ++++ | -- | | | | | |
| N263C \| K345E \| K428N \| P661E | -- | + | -- | | | | | |
| N263C \| K345E \| N369E \| G372A | ++ | ++ | -- | | | | | |
| G372A \| P661E \| S683W | ++ | ++ | -- | wt | + | +++ | +++ | ++ |
| N263C \| P661L \| S683W | +++ | ++++ | -- | | | | | |
| K345E \| N369E \| S683W | wt | +++ | -- | ++ | ++ | ++++ | +++ | + |
| N369T \| G372A \| P661L \| S683W | wt | +++ | -- | wt | ++++ | +++ | wt | -- |
| N263C \| K345E \| N369T \| K428N | wt | +++ | -- | ++ | ++ | ++++ | +++ | ++ |
| N263C \| K345E \| N369T \| P661L | wt | wt | -- | | | | | |
| N263C \| N369T \| G372A \| K428N \| P661L \| S683W | wt | ++ | -- | | | | | |
| K345E \| N369E \| G372A \| P661E \| K428N \| P661L \| S683W | wt | wt | -- | wt | ++ | ++ | ++ | +++ |
| K345E \| N369E \| P661L | - | + | -- | wt | ++ | ++ | ++ | +++ |
| K345E \| K428N \| P661L \| S683W | -- | +++ | -- | | | | | |
| K345E \| N369T \| G372A \| K428N \| P661L \| S683W | - | ++ | -- | - | ++++ | wt | - | -- |
| N369T \| G372A \| K428N \| S683W | ++ | +++ | -- | + | + | +++ | ++ | ++ |

TABLE 5-2-continued

Performance of Combinatorial BGL variants

| Variant | Gluc | Heat | HPLC | PASC | PCS | G2 | CNPG | CC |
|---|---|---|---|---|---|---|---|---|
| N263C | K345E | N369T | G372A | K428N | ++ | ++++ | -- | | | | | |
| N369T | P661L | S683W | wt | wt | -- | wt | ++++ | +++ | +++ | ++++ |
| N263C | G372A | K428N | -- | +++ | -- | | | | | |
| N263C | K428N | P661L | S683W | - | wt | -- | | | | | |
| N263C | N369E | K428N | P661E | wt | +++ | -- | +++ | ++++ | ++++ | ++++ | ++++ |
| N263C | N369E | G372A | K428N | P661L | S683W | wt | +++ | -- | | | | | |
| N263C | K345E | N369T | G372A | P661E | | | | | | | | |
| K345E | N369E | K428N | P661L | - | +++ | -- | wt | -- | ++ | - | wt |
| N263C | K345E | N369E | K428N | S683W | -- | -- | -- | | | | | |
| K345E | G372A | K428N | P661E | + | + | -- | | | | | |
| N263C | K345E | N369E | P661L | wt | ++ | -- | wt | - | wt | - | + |
| K345E | P661L | S683W | -- | wt | -- | | | | | |
| N263C | N369T | S683W | wt | ++ | -- | ++ | ++++ | ++++ | ++++ | ++ |
| N263C | G372A | ++ | + | -- | + | ++ | ++ | +++ | + |
| N263C | K345E | N369E | G372A | P661E | ++ | +++ | -- | +++ | +++ | ++++ | ++++ | ++ |
| K320S | R363E | wt | wt | -- | +++ | +++ | ++++ | +++ | ++ |
| E170F | S312Y | N369Y | G372A | V603G | wt | | | | | | | |
| Q226Y | G372A | V603G | F611A | -- | | | | | | | |
| E170F | Q226Y | S312Y | G372A | P661F | -- | | | | | | | |
| T242S | S312Y | N369Y | G372A | P661F | -- | | | | | | | |
| Q226Y | T242S | S312Y | N369Y | V603G | F611A | wt | | | | | | | |
| E170F | Q226Y | G372A | T666C | + | | | | | | | |
| E170F | Q226Y | S312Y | N369Y | V603G | F611A | P661F | T666C | -- | | | | | | |
| Q226Y | T242S | S312Y | G372A | F611A | wt | | | | | | | |
| S312Y | G372A | V603G | -- | | | | | | | |
| E170F | T242S | S312Y | G372A | V603G | -- | | | | | | | |
| E170F | Q226Y | N369Y | F611A | T666C | -- | | | | | | | |
| E170F | Q226Y | T242S | S312Y | F611A | P661F | ++++ | | | | | | | |
| Q226Y | S312Y | G372A | V603G | P661F | T666C | -- | | | | | | | |
| E170F | Q226Y | T242S | N369Y | V603G | -- | | | | | | | |
| Q226Y | T242S | N369Y | G372A | -- | | | | | | | |
| E170F | Q226Y | S312Y | V603G | F611A | T666C | -- | | | | | | | |
| E170F | Q226Y | T242S | N369Y | G372A | F611A | -- | | | | | | | |
| E170F | S312Y | F611A | P661F | T666C | -- | | | | | | | |
| Q226Y | T242S | S312Y | N369Y | V603G | F611A | T666C | -- | | | | | | | |
| E170F | Q226Y | S312Y | N369Y | F611A | P661F | T666C | -- | -- | | | | | | |
| T242S | N369Y | V603G | - | -- | wt | - | wt | | | |
| Q226Y | N369Y | V603G | F611A | T666C | -- | | | | | | | |
| T242S | V603G | F611A | T666C | -- | | | | | | | |
| E170F | T242S | S312Y | T666C | -- | | | | | | | |
| Q226Y | S312Y | V603G | F611A | P661F | T666C | -- | | | | | | | |
| E170F | T242S | V603G | -- | | | | | | | |
| E170F | T242S | S312Y | F611A | P661F | T666C | -- | | | | | | | |
| N369Y | G372A | -- | | | | | | | |
| S312Y | G372A | V603G | F611A | T666C | -- | | | | | | | |
| Q226Y | T242S | S312Y | N369Y | T666C | -- | | | | | | | |
| Q226Y | T242S | N369Y | P661F | -- | | | | | | | |
| Q226Y | T242S | V603G | -- | | | | | | | |
| E170F | S312Y | G372A | V603G | T666C | wt | | | | | | | |

TABLE 5-2-continued

Performance of Combinatorial BGL variants

| Variant | Gluc | Heat | HPLC | PASC | PCS | G2 | CNPG | CC |
|---|---|---|---|---|---|---|---|---|
| E170F | T242S | N369Y | G372A | V603G | F611A | -- | | | | | | | |
| E170F | Q226Y | T242S | S312Y | V603G | F611A | -- | | | | | | | |
| E170F | Q226Y | N369Y | F611A | -- | | | | | | | |
| E170F | Q226Y | T242S | F611A | P661F | -- | | | | | | | |
| E170F | Q226Y | T242S | G372A | V603G | + | | | | | | | |
| T242S | N369Y | G372A | T666C | -- | | | | | | | |
| E170F | Q226Y | T242S | S312Y | V603G | F611A | P661F | -- | | | | | | | |
| E170F | Q226Y | N369Y | V603G | F611A | -- | | | | | | | |
| E170F | S312Y | V603G | F611A | T666C | -- | | | | | | | |
| E170F | Q226Y | S312Y | G372A | T666C | | | | | | | | |
| E170F | S312Y | G372A | V603G | P661F | T666C | wt | | | | | | | |
| Q226Y | N369Y | G372A | V603G | P661F | -- | | | | | | | |
| T242S | S312Y | N369Y | V603G | F611A | P661F | T666C | -- | | | | | | | |
| S312Y | N369Y | V603G | T666C | -- | | | | | | | |
| E170F | T242S | N369Y | T666C | wt | | | | | | | |
| Q226Y | F611A | T666C | -- | | | | | | | |
| T242S | S312Y | N369Y | G372A | V603G | F611A | -- | -- | | | | | | |
| Q226Y | T242S | N369Y | G372A | F611A | T666C | -- | | | | | | | |
| T242S | S312Y | N369Y | G372A | V603G | P661F | | | | | | | | |
| E170F | Q226Y | F611A | T666C | -- | | | | | | | |
| S312Y | P661F | -- | | | | | | | |
| E170F | T242S | V603G | F611A | -- | | | | | | | |
| T242S | S312Y | N369Y | F611A | -- | | | | | | | |
| E170F | Q226Y | T242S | S312Y | G372A | V603G | F611A | P661F | T666C | wt | | | | | | | |
| E170F | V603G | + | ++ | -- | wt | ++ | wt | wt | + |
| Q226Y | S312Y | V603G | F611A | P661F | -- | -- | | | | | | | |
| E170F | T242S | N369Y | G372A | V603G | T666C | ++++ | -- | | | -- | + | -- | |
| E170F | T242S | F611A | +++ | -- | | | -- | - | -- | |
| E170F | Q226Y | N369Y | V603G | T666C | +++ | -- | | | - | ++ | -- | |
| E170F | Q226Y | T242S | S312Y | V603G | F611A | T666C | -- | -- | | | | | | |
| E170F | G372A | F611A | P661F | -- | -- | | | | | | | |
| E170F | T242S | S312Y | N369Y | G372A | ++++ | -- | | | | | | | |
| E170F | Q226Y | T242S | N369Y | T666C | - | -- | | | -- | + | -- | |
| Q226Y | T242S | G372A | F611A | -- | -- | | | | | | | |
| Q226Y | T242S | N369Y | G372A | V603G | P661F | T666C | wt | -- | | | | | | | |
| Q226Y | G372A | V603G | T666C | -- | -- | | | +++ | + | wt | |
| E170F | Q226Y | S312Y | G372A | V603G | F611A | T666C | -- | -- | | | | | | |
| E170F | Q226Y | T242S | S312Y | N369Y | G372A | V603G | +++ | -- | | | | | | |
| Q226Y | T242S | S312Y | N369Y | V603G | -- | -- | | | -- | +++ | -- | |
| E170F | Q226Y | T242S | V603G | F611A | T666C | -- | -- | | | | | | |
| E170F | Q226Y | S312Y | N369Y | G372A | V603G | T666C | -- | -- | | | | | | |
| E170F | Q226Y | T242S | V603G | F611A | ++ | -- | | | | | | | |
| E170F | T242S | S312Y | G372A | F611A | P661F | T666C | -- | -- | | | | | | |
| E170F | S312Y | V603G | F611A | P661F | -- | -- | | | | | | | |
| N369Y | V603G | P661F | -- | -- | | | | | | | |

TABLE 5-2-continued

Performance of Combinatorial BGL variants

| Variant | Gluc | Heat | HPLC | PASC | PCS | G2 | CNPG | CC |
|---|---|---|---|---|---|---|---|---|
| E170F | Q226Y | T242S | S312Y | N369Y | G372A | F611A | T666C | ++ | -- | | | | | | |
| E170F | Q226Y | V603G | P661F | -- | -- | | | | | | |
| T242S | S312Y | N369Y | G372A | F611A | P661F | -- | -- | | | | | | |
| S312Y | F611A | P661F | -- | -- | | | | | | |
| E170F | Q226Y | S312Y | G372A | F611A | T666C | -- | -- | | | | | | |
| Q226Y | S312Y | G372A | F611A | - | -- | | | | | | |
| E170F | Q226Y | P661F | +++ | -- | | | | | | |
| E170F | V603G | P661F | T666C | ++ | -- | | | | | | |
| Q226Y | S312Y | N369Y | G372A | V603G | F611A | T666C | -- | -- | | | | | | |
| E170F | Q226Y | G372A | F611A | P661F | | | | | | | | |
| E170F | T242S | S312Y | V603G | P661F | T666C | -- | -- | | | | | | |
| E170F | Q226Y | T242S | S312Y | N369Y | G372A | -- | -- | | | | | | |
| E170F | Q226Y | T242S | S312Y | N369Y | F611A | P661F | -- | -- | | | | | | |
| E170F | G372A | V603G | F611A | P661F | T666C | + | -- | | | | | | |
| E170F | Q226Y | S312Y | G372A | V603G | F611A | P661F | -- | -- | | | | | | |
| Q226Y | S312Y | G372A | V603G | F611A | T666C | -- | -- | | | | | | |
| E170F | T242S | N369Y | V603G | F611A | -- | -- | | | | | | |
| Q226Y | T242S | S312Y | V603G | F611A | P661F | T666C | + | -- | | | | | | |
| T242S | S312Y | N369Y | G372A | F611A | T666C | -- | -- | | -- | +++ | -- | |
| Q226Y | G372A | F611A | P661F | T666C | -- | -- | | | | | | |
| E170F | Q226Y | S312Y | ++ | -- | | -- | ++++ | -- | |
| T242S | S312Y | wt | -- | | +++ | wt | -- | |
| E170F | Q226Y | T242S | N369Y | V603G | F611A | P661F | T666C | -- | -- | | | | | | |
| Q226Y | T242S | S312Y | N369Y | G372A | F611A | -- | -- | | | | | | |
| E170F | S312Y | G372A | F611A | P661F | -- | -- | | | | | | |
| E170F | Q226Y | T242S | S312Y | G372A | F611A | T666C | -- | -- | | | | | | |
| E170F | Q226Y | T242S | G372A | V603G | P661F | T666C | ++ | | | | | | | |
| E170F | Q226Y | T242S | V603G | T666C | wt | | | | | | | |
| Q226Y | T242S | V603G | P661F | T666C | -- | | | | | | | |
| E170F | T242S | S312Y | G372A | T666C | ++ | | | | | | | |
| E170F | Q226Y | T242S | V603G | P661F | T666C | + | | | | | | | |
| Q226Y | T242S | G372A | V603G | F611A | -- | | | | | | | |
| S312Y | N369Y | G372A | V603G | P661F | -- | | | | | | | |
| E170F | T242S | V603G | T666C | wt | | | | | | | |
| E170F | Q226Y | T242S | S312Y | G372A | P661F | -- | | | | | | | |
| E170F | S312Y | G372A | V603G | F611A | P661F | T666C | wt | | | | | | | |
| E170F | T242S | N369Y | G372A | F611A | T666C | wt | | | | | | | |
| Q226Y | S312Y | G372A | F611P | P661F | T666C | -- | | | | | | | |
| E170F | Q226Y | T242S | S312Y | V603G | T666C | -- | | | | | | | |
| E170F | Q226Y | T242S | wt | | | | | | | | |
| Q226Y | S312Y | N369Y | G372A | T666C | -- | | | | | | | |
| Q226Y | T242S | V603G | F611A | T666C | -- | | | | | | | |
| S312Y | G372A | P661F | -- | | | | | | | | |

TABLE 5-2-continued

| Performance of Combinatorial BGL variants | | | | | | | | |
|---|---|---|---|---|---|---|---|---|
| Variant | Gluc | Heat | HPLC | PASC | PCS | G2 | CNPG | CC |
| V603G \| P661F \| T666C | -- | | | | | | | |
| E170F \| S312Y \| N369Y \| G372A \| V603G \| P661F | + | | | | | | | |
| E170F \| Q226Y \| S312Y \| G372A \| V603G \| P661F \| T666C | ++++ | | | | | | | |
| Q226Y \| S312Y \| G372A | -- | | | | | | | |
| T242S \| S312Y \| V603G \| F611A | -- | | | | | | | |
| E170F \| Q226Y \| S312Y \| N369Y \| G372A \| F611A | + | | | | | | | |
| Q226Y | -- | | | | | | | |
| Q226Y \| N369Y \| V603G \| P661F \| T666C | -- | | | | | | | |
| E170F \| G372A | + | | | | | | | |
| S312Y \| N369Y \| G372A \| V603G | wt | | | | | | | |
| T242S \| S312Y \| G372A | -- | | | | | | | |
| T242S \| N369Y \| G372A \| F611A \| T666C | -- | | | | | | | |
| E170F \| S312Y \| N369Y \| T666C | - | | | | | | | |
| E170F \| F611P | - | | | | | | | |
| Q226Y \| T242S \| S312Y \| G372A \| V603G | -- | | | | | | | |
| Q226Y \| T242S \| N369Y \| G372A \| V603G \| F611A \| P661F | - | | | | | | | |
| E170F \| Q226Y \| T242S \| S312Y \| G372A \| V603G | -- | | | | | | | |
| Q226Y \| G372A \| F611A \| P661F | -- | | | | | | | |
| T242S \| S312Y \| G372A \| V603G \| F611A \| P661F \| T666C | -- | | | | | | | |
| Q226Y \| V603G \| T666C | -- | | | | | | | |
| T242S \| S312Y \| F611A | -- | | | | | | | |
| E170F \| Q226Y \| T242S \| N369Y \| G372A \| P661F | + | | | | | | | |
| Q226Y \| T242S \| S312Y \| P661F | -- | | | | | | | |
| E170F \| T242S \| N369Y \| F611A \| P661F | -- | | | | | | | |
| Q226Y \| T242S \| N369Y \| G372A \| V603G | -- | | | | | | | |
| E170F \| T242S \| G372A \| P661F | wt | | | | | | | |
| E170F \| S312Y \| V603G \| P661F | wt | | | | | | | |
| E170F \| T242S \| S312Y \| V603G | -- | | | | | | | |
| E170F \| T242S \| N369Y \| V603G \| T666C | wt | | | | | | | |
| T242S | -- | | | | | | | |
| E170F \| T242S \| S312Y \| G372A \| F611P \| P661F \| T666C | -- | | | | | | | |
| T242S \| P661F | -- | | | | | | | |
| E170F \| T242S \| S312Y | wt | | | | | | | |
| E170F \| N369Y \| G372A \| T666C | wt | | | | | | | |
| Q226Y \| S312Y \| V603G \| F611A | ++++ | | | | | | | |
| Q226Y \| T242S \| S312Y \| G372A \| V603G \| F611A \| T666C | wt | | | | | | | |
| N369Y \| V603G \| F611A \| P661F | + | | | | | | | |
| S312Y \| T666C | -- | | | | | | | |
| E170F \| T242S \| N369Y \| G372A \| T666C | wt | | | | | | | |
| Q226Y \| T242S \| N369Y \| G372A \| V603G \| F611A \| T666C | -- | | | | | | | |
| S312Y \| P661F \| T666C | + | | | | | | | |
| E170F \| Q226Y \| T242S \| S312Y \| F611A \| P661F \| T666C | -- | | | | | | | |
| F611A \| T666C | -- | | | | | | | |
| E170F \| V603G \| F611A \| T666C | -- | | | | | | | |
| N369Y \| G372A \| V603G \| T666C | -- | | | | | | | |
| E170F \| S312Y \| N369Y \| G372A \| F611A \| P661F | -- | | | | | | | |
| T242S \| N369Y \| F611A \| P661F | -- | | | | | | | |
| Q226Y \| S312Y \| G372A \| P661F | -- | | | | | | | |
| Q226Y \| T242S \| S312Y \| F611A \| P661F \| T666C | +++ | | | | | | | |
| E170F \| T242S \| G372A \| F611A \| P661F \| T666C | -- | | | | | | | |
| E170F \| T242S \| G372A | -- | | | | | | | |
| Q226Y \| G372A \| P661F \| T666C | -- | | | | | | | |
| E170F \| T242S \| S312Y \| G372A \| V603G \| F611A \| P661F \| T666C | -- | | | | | | | |

TABLE 5-2-continued

| Performance of Combinatorial BGL variants | | | | | | | | |
|---|---|---|---|---|---|---|---|---|
| Variant | Gluc | Heat | HPLC | PASC | PCS | G2 | CNPG | CC |
| E170F \| T242S \| S312Y \| N369Y \| G372A \| V603G \| F611A \| T666C | −− | | | | | | | |
| Q226Y \| T242S \| V603G \| T666C G372A \| T666C | −− | | | | | | | |
| E170F \| Q226Y \| T242S \| S312Y \| N369Y \| G372A \| V603G \| F611A \| P661F \| T666C | wt | | | | | | | |
| E170F \| Q226Y \| T242S \| N369Y \| G372A \| V603G \| F611A \| P661F | wt | | | | | | | |
| Q226Y \| T242S \| S312Y \| N369Y \| G372A \| P661F \| T666C | −− | | | | | | | |
| E170F \| Q226Y \| S312Y \| N369Y \| G372A | +++ | | | | | | | |
| T242S \| S312Y \| N369Y \| G372A \| F611A | −− | | | | | | | |
| E170F \| T242S \| G372A \| P661F \| T666C | +++ | | | | | | | |
| E170F \| N369Y \| G372A \| V603G \| F611A \| P661F \| T666C | ++ | | | | | | | |
| E170F \| Q226Y \| T242S \| S312Y \| N369Y \| G372A \| T666C | −− | | | | | | | |
| Q226Y \| T242S \| T666C | −− | | | | | | | |
| E170F \| Q226Y \| G372A \| V603G \| P661F \| T666C | −− | | | | | | | |
| Q226Y \| T242S \| S312Y \| V603G | −− | | | | | | | |
| E170F | −− | | | | | | | |
| E170F \| T242S \| S312Y \| F611A | −− | | | | | | | |
| E170F \| Q226Y \| T242S \| S312Y \| N369Y \| V603G \| F611A \| P661F | − | | | | | | | |
| N369Y \| G372A \| F611A \| T666C | wt | | | | | | | |
| Q226Y \| T242S \| S312Y \| N369Y \| V603G \| T666C | ++ | | | | | | | |
| E170F \| Q226Y \| S312Y \| V603G | −− | | | | | | | |
| Q226Y \| T242S \| S312Y \| N369Y \| G372A \| V603G \| F611A | + | | | | | | | |
| E170F \| S312Y \| P661F | −− | | | | | | | |
| N369Y \| G372A \| V603G \| F611A \| T666C | ++ | | | | | | | |
| Q226Y \| S312Y \| N369Y \| G372A \| F611A | −− | | | | | | | |
| S312Y \| N369Y \| G372A \| V603G \| T666C | −− | | | | | | | |
| E170F \| Q226Y \| S312Y \| N369Y \| G372A \| P661F \| T666C | −− | | | | | | | |
| E170F \| S312Y \| N369Y \| V603G \| F611A \| T666C | −− | | | | | | | |
| E170F \| Q226Y \| N369Y \| P661F \| T666C | −− | | | | | | | |
| S312Y \| N369Y \| V603G \| F611A \| P661F \| T666C | −− | | | | | | | |
| T666C | −− | | | | | | | |
| Q226Y \| F611A | ++++ | | | | | | | |
| Q226Y \| T242S \| S312Y \| N369Y \| G372A \| F611A \| P661F \| T666C | ++ | | | | | | | |
| Q226Y \| N369Y \| V603G \| F611A \| P661F | −− | | | | | | | |
| N369Y | −− | | | | | | | |
| Q226Y \| S312Y \| V603G \| P661F \| T666C | −− | | | | | | | |
| N369Y \| F611A \| P661F | −− | | | | | | | |
| Q226Y \| S312Y \| N369Y \| G372A \| P661F \| T666C | − | | | | | | | |
| E170F \| T242S \| T666C | −− | | | | | | | |
| Q226Y \| N369Y \| G372A \| T666C | wt | | | | | | | |
| E170F \| Q226Y \| T242S \| S312Y \| G372A \| F611A \| P661F \| T666C | ++ | | | | | | | |
| E170F \| G372A \| P661F \| T666C | wt | | | | | | | |
| Q226Y \| T242S \| N369Y \| G372A \| F611A \| P661F | −− | | | | | | | |
| E170F \| S312Y \| N369Y | wt | | | | | | | |
| Q226Y \| T242S \| G372A \| V603G \| T666C | ++ | | | | | | | |
| E170F \| T242S \| G372A \| V603G \| F611A \| P661F \| T666C | ++++ | | | | | | | |

TABLE 5-2-continued

Performance of Combinatorial BGL variants

| Variant | Gluc | Heat | HPLC | PASC | PCS | G2 | CNPG | CC |
|---|---|---|---|---|---|---|---|---|
| Q226Y | T242S | N369Y | -- | | | | | | | |
| T242S | S312Y | G372A | F611A | T666C | -- | | | | | | | |
| G372A | F611A | T666C | | | | | | | | |
| E170F | T242S | S312Y | G372A | F611A | P661F | -- | | | | | | | |
| E170F | Q226Y | T242S | P661F | - | | | | | | | |
| S312Y | N369Y | F611A | -- | | | | | | | |
| E170F | Q226Y | T242S | N369Y | G372A | V603G | P661F | wt | | | | | | | |
| E170F | T242S | N369Y | G372A | F611A | P661F | T666C | -- | | | | | | | |
| Q226Y | S312Y | G372A | F611A | T666C | | | | | | | | |
| Q226Y | T242S | G372A | T666C | -- | | | | | | | |
| S312Y | G372A | T666C | wt | | | | | | | |
| E170F | Q226Y | T242S | S312Y | V603G | -- | | | | | | | |
| E170F | T242S | G372A | T666C | -- | | | | | | | |
| E170F | Q226Y | G372A | F611A | wt | | | | | | | |
| Q226Y | T242S | S312Y | V603G | F611A | T666C | -- | | | | | | | |
| E170F | Q226Y | S312Y | N369Y | -- | | | | | | | |
| T242S | S312Y | G372A | V603G | -- | | | | | | | |
| E170F | Q226Y | V603G | T666C | -- | | | | | | | |
| E170F | S312Y | V603G | T666C | -- | | | | | | | |
| E170F | Q226Y | T242S | N369Y | F611A | -- | | | | | | | |
| E170F | Q226Y | N369Y | G372A | V603G | F611A | -- | | | | | | | |
| E170F | Q226Y | T242S | G372A | V603G | F611A | -- | | | | | | | |
| S312Y | N369Y | V603G | -- | | | | | | | |
| E170F | G372A | V603G | T666C | wt | | | | | | | |
| E170F | Q226Y | T242S | F611A | T666C | -- | | | | | | | |
| E170F | Q226Y | S312Y | N369Y | F611A | -- | | | | | | | |
| E170F | G372A | T666C | + | | | | | | | |
| N369Y | V603G | -- | | | | | | | |
| G372A | V603G | F611A | P661F | | | | | | | | |
| T242S | N369Y | T666C | -- | | | | | | | |
| E170F | T242S | N369Y | G372A | V603G | F611A | T666C | wt | | | | | | | |
| S312Y | G372A | -- | | | | | | | |
| E170F | T242S | S312Y | N369Y | F611A | P661F | ++++ | | | | | | | |
| E170F | Q226Y | T242S | S312Y | G372A | V603G | P661F | T666C | wt | - | -- | ++ | + | +++ | +++ | + |
| E170F | Q226Y | N369Y | G372A | +++ | +++ | ++ | wt | -- | wt | - | wt |
| Q226Y | T242S | G372A | P661F | +++ | ++ | wt | wt | wt | wt | wt | wt |
| T242S | T666C | wt | wt | -- | ++ | ++ | +++ | +++ | ++ |
| E170F | Q226Y | N369Y | G372A | P661F | ++ | wt | wt | ++ | ++ | ++ | +++ | wt |
| T242S | N369Y | P661F | - | +++ | ++ | wt | - | wt | wt | wt |
| Q226Y | T666C | - | wt | -- | ++ | +++ | +++ | +++ | + |
| Q216E | T282I | S312D | S692K | ++ | ++ | ++ | wt | wt | wt | wt | wt |
| Q216K | T282K | S312D | A622K | S692L | wt | wt | + | wt | wt | wt | wt | + |
| Q216I | T282K | S312K | A622K | ++++ | +++ | -- | wt | wt | wt | wt | wt |
| Q216E | T282K | S692L | wt | wt | - | wt | wt | wt | wt | wt |
| Q216E | S312K | S692K | wt | wt | wt | ++ | ++ | +++ | +++ | + |
| D178K | A338K | S474D | G662L | - | wt | -- | wt | ++ | wt | wt | wt |
| N264L | A338I | S474R | G662D | ++ | wt | -- | wt | ++ | wt | - | + |
| D178N | N264K | A338D | S474R | G662K | wt | wt | -- | wt | ++ | wt | - | + |
| D178I | N264D | Q303I | A338K | G662L | wt | + | -- | wt | wt | wt | ++ | wt |
| D178I | Q303E | A338I | + | wt | -- | wt | wt | wt | wt | + |
| P176L | Q226W | K320S | G662F | -- | -- | -- | | | | | |
| P176L | Q226W | K320S | V522Y | G662F | -- | -- | -- | | | | | |
| P176L | Q226W | K320Y | R363E | -- | ++++ | -- | wt | + | + | ++ | wt |
| P176L | G662F | -- | -- | -- | + | ++ | ++ | ++ | ++ |
| P176L | Q316T | K320Y | V522Y | -- | wt | -- | | | | | |
| Q226W | R363E | V522Y | wt | -- | -- | -- | -- | -- | -- | wt |

TABLE 5-2-continued

Performance of Combinatorial BGL variants

| Variant | Gluc | Heat | HPLC | PASC | PCS | G2 | CNPG | CC |
|---|---|---|---|---|---|---|---|---|
| Q226W \| Q316T \| R363E | -- | -- | -- | - | wt | wt | + | wt |
| P176L \| Q226W \| Q316T \| K320Y \| R363E | -- | -- | -- | ++ | + | ++ | ++ | ++ |
| P176L \| Q226W \| Q316T \| K320S \| V522Y \| G662C | -- | -- | -- | ++ | wt | ++ | ++ | ++ |
| Q316T \| K320Y \| V522Y | wt | + | +++ | wt | wt | + | wt | wt |
| Q316T \| K320S \| G662F | wt | -- | -- | wt | wt | wt | wt | wt |
| R363E \| V522Y \| G662F | - | -- | -- | ++ | wt | ++ | + | ++ |
| Q226W \| K320S \| V522Y \| G662F | wt | -- | -- | wt | - | wt | wt | wt |
| Q316T \| K320Y \| R363E | ++ | -- | -- | | | | | |
| P176L \| Q316T \| G662C | ++++ | ++++ | -- | | | | | |
| Q316T \| K320Y \| R363E \| V522Y \| G662F | ++ | -- | -- | + | wt | wt | -- | ++ |
| Q226W \| K320Y \| G662C | -- | ++++ | -- | | | | | |
| P176L \| Q226W \| K320S \| G662C | -- | -- | -- | | | | | |
| K320Y \| G662C | - | -- | -- | | | | | |
| Q316T \| K320S \| V522Y \| G662F | -- | -- | -- | + | wt | + | - | ++ |
| P176L \| Q226W \| K320S \| R363E \| G662F | -- | -- | -- | +++ | ++ | +++ | + | +++ |
| Q316T \| K320Y \| G662F | + | -- | -- | -- | -- | -- | -- | ++ |
| Q226W \| K320S \| R363E | wt | -- | wt | wt | wt | wt | wt | wt |
| P176L \| Q226W \| K320Y \| R363E \| V522Y \| G662C | wt | -- | -- | | | | | |
| P176L \| Q226W \| Q316T \| K320Y \| V522Y | - | -- | -- | +++ | ++ | +++ | ++ | ++ |
| Q226W \| K320Y | wt | - | -- | + | - | wt | -- | + |
| P176L \| V522Y | -- | -- | -- | + | -- | wt | -- | + |
| Q226W \| K320Y \| V522Y | -- | -- | -- | +++ | wt | +++ | -- | +++ |
| P176L \| Q316T \| K320S \| R363E \| G662F | ++++ | ++++ | -- | wt | ++ | +++ | -- | + |
| Q226W \| Q316T \| K320S \| G662C | wt | -- | -- | | | | | |
| P176L \| Q226W \| K320Y \| R363E \| V522Y | -- | -- | -- | ++ | + | ++ | ++ | ++ |
| Q226W \| K320Y \| R363E | -- | -- | -- | +++ | ++ | +++ | ++ | +++ |
| Q226W \| Q316T \| V522Y \| G662F | +++ | + | -- | | | | | |
| Q316T \| K320Y \| R363E \| G662F | wt | -- | -- | +++ | + | +++ | - | ++ |
| P176L \| Q226W \| Q316T \| K320S \| R363E \| G662F | -- | -- | -- | | | | | |
| P176L \| Q226W \| Q316T \| R363E \| G662C | wt | -- | -- | | | | | |
| Q226W \| Q316T \| K320Y \| R363E \| G662F | wt | -- | -- | | | | | |
| Q316T \| K320S \| V522Y | - | -- | -- | + | wt | + | wt | + |
| P176L \| Q226W \| G547A \| G662C | +++ | + | -- | ++ | + | ++ | + | ++ |
| Q316T \| K320S \| R363E \| G662F | wt | -- | -- | wt | wt | wt | wt | wt |
| R363E \| G662C | wt | -- | -- | + | wt | wt | wt | ++ |
| P176L \| Q226W \| R363E \| V522Y | -- | -- | -- | wt | - | wt | -- | ++ |
| Q226W \| Q316T \| R363E \| V522Y \| G662F | -- | -- | -- | +++ | ++ | ++++ | ++ | +++ |
| P176L \| G662C | +++ | -- | -- | | | | | |
| P176L \| K320S \| V522Y \| G662C | - | + | -- | ++ | wt | ++ | wt | ++ |
| Q226W \| K320S \| R363E \| V522Y \| G662F | - | -- | -- | ++ | wt | ++ | -- | +++ |
| P176L \| K320S \| R363E \| G662C | - | -- | -- | ++ | ++ | +++ | +++ | + |
| R363E \| G547A \| G662C | wt | -- | -- | ++ | ++ | ++ | +++ | + |
| Q316T \| V522Y \| G662F | wt | -- | -- | wt | wt | wt | wt | + |
| G662C | ++++ | ++++ | -- | | | | | |
| Q226W \| G662C | -- | -- | -- | wt | - | wt | -- | + |
| Q226W \| K320Y \| R363E \| G662F | | | | | | | | |
| P176L \| Q226W \| R363E | - | -- | -- | -- | -- | -- | -- | ++ |
| Q226W \| K320S \| G662C | wt | -- | -- | ++ | + | ++ | ++ | + |
| P176L \| Q316T \| K320Y \| V522Y \| G547A \| G662F | - | -- | wt | wt | wt | + | + | wt |
| P176L \| Q226W \| Q316T \| K320Y \| R363E \| G662F | -- | -- | -- | + | ++ | ++ | + | ++ |
| P176L \| Q226W \| K320S \| V522Y | wt | -- | -- | wt | wt | wt | wt | + |
| P176L \| Q226W \| Q316T \| K320S \| G662F | -- | -- | -- | + | ++ | ++ | -- | ++ |
| Q226W \| K320S \| R363E \| G662C | -- | +++ | -- | | | | | |
| P176L \| Q316T | ++++ | ++++ | -- | | | | | |
| P176L \| Q316T \| K320S \| R363E \| V522Y \| G662C | -- | -- | -- | ++ | +++ | ++++ | -- | ++ |
| Q226W \| Q316T \| R363E \| G662F | - | -- | -- | wt | wt | wt | -- | ++ |
| K320Y \| R363E \| G662C | wt | -- | -- | ++ | +++ | ++++ | ++++ | ++ |
| K51A \| T242H \| D329A | wt | + | + | wt | wt | wt | wt | wt |
| D329A \| A347Y \| R542N | wt | + | + | wt | wt | wt | wt | wt |

TABLE 5-2-continued

Performance of Combinatorial BGL variants

| Variant | Gluc | Heat | HPLC | PASC | PCS | G2 | CNPG | CC |
|---|---|---|---|---|---|---|---|---|
| A347Y \| R542N | +++ | ++ | wt | wt | wt | wt | wt | wt |
| A347Y \| R542K | − | + | wt | wt | wt | wt | wt | wt |
| K51A \| A347Y \| R542N \| R645K | wt | wt | ++ | wt | wt | wt | wt | wt |
| K51A \| T242H \| D329A \| R542N | wt | wt | −− | wt | − | wt | wt | wt |
| K51A \| T242H \| D329A \| A347Y \| R542N \| R645G | wt | −− | −− | wt | wt | wt | ++ | + |
| D329A \| A347Y | wt | wt | −− | wt | wt | wt | + | wt |
| E170F \| G372A | | | +++ | −− | −− | −− | | |
| T242S \| N369L | | | wt | wt | wt | + | | |
| D215S \| S312Y | | | ++ | + | wt | + | | |
| N263T \| G372A | | | wt | wt | wt | + | | |
| N263T \| E170F | | | wt | wt | wt | − | | |
| D215S \| S548W | | | + | wt | wt | wt | | |
| N263T \| E170F \| G372A | | | ++++ | −− | −− | −− | | |
| N369T \| G372A | | | − | wt | wt | wt | | |
| Q226Y \| V603G \| F611A | | | ++++ | −− | −− | −− | | |
| E170F \| S312Y \| N369Y | | | −− | ++ | wt | +++ | | |
| D215S \| 263S \| S312Y \| K498F \| R586V | | | ++++ | −− | −− | −− | | |

++++ PI > 2
+++ 2 > PI > 1.5
++ 1.5 > PI > 1.2
+ 1.2 > PI > 1.1
wt 1.1 > P I > 0.9
− 0.9 > PI > 0.8
−− 0.8 > PI
blank Not tested The results of combinatorial substitutions were further analyzed to determine those variants that had at least two, three, four, five, or six (or more) improved activities over wild type BGL1. Variants possessing these multiple improved activities are shown below in Table 5-3 to Table 5-6.

TABLE 5-3

Variants Comprising Combination of Substitutions with At Least Two Improved Activities HPLC + PCS
L167W|D225Q
T242S|S312Y
D178K|A338K|S474D|G662L
Heat + G2
K345E|N369E|K428N|P661L
Q316T|K320Y|V522Y
Inh + G2
E170F|T242S|N369Y|G372A|
V603G|T666C
E170F|Q226Y|N369Y|V603G|
T666C
E170F|Q226Y|S312Y
PASC + CC
L167W|D177M|D564V|Q684R
L167W|D225Q|D564V
D177M|D225Q|D564T|Q626F|
Q684N
L167W|Q626F
D225Q|D564V|Q626F|Q684R
D177M|D225Q|D564V|Q684R
Q226W|K320Y
P176L|V522Y
R363E|G662C
PASC + G2
L167W|D177M|D225Q|Q626F|
Q684G
L167W|D177M|D564V|Q684G
D215S|S312Y
E170F|S312Y|N369Y
Heat + CC
N263C|K345E|N369E|P661L Inh + Heat
L167W|D225Q|Q626F|Q684D
L167W|D225Q|Q684N
L167W|D225Q|D564T|Q626F|Q684C
Q626F|Q684D
N264M|R265P|N369I|D370W
R179V|N238F|D370W
R179V|N238F|K656R
R179V|N264M|D370W
R179V|N238F|R265M
R179V|R265P|D370W|K656R
R179V|N238W|N264M|R265M|N369I
R179V|N369I|D370W|K656R
R179V|N264M|R265P|K656R
R179V|R265M|N369I
R179V|N264M|R265M|D370W|K656R
R179V|N264M|R265M|N369I
R179V|N238W|N264M
N238W|N264M|R265M|D370W
R179V|N238W|R265P|D370W
R179V|N238W|N264M|D370W|K656R
N264M|R265P
R265P|D370W (+G662F)
R179V|N264M|R265P|N369I|D370W
R265M|N369I
R179V|R265M|D370W
N238W|N264M|R265P
R179V|N238W|N264M|R265P
N264M|N369I
N238F|R265M|N369I
N263C|K345E|N369E|G372A|K428N|
P661E|S683W TABLE 5-3-continued Variants Comprising Combination of Substitutions with At Least Two Improved Activities Inh + CC
D178I|Q303E|A338I
Q316T|K320Y|G662F
N263C|K345E|N369T|G372A|K428N|
P661E|S683W
N263C|K345E|N369E|G372A
N263C|P661L|S683W
N263C|K345E|N369T|G372A|K428N
K345E|G372A|K428N|P661E
E170F|Q226Y|N369Y|G372A
Q226Y|T242S|G372A|P661F
Q216E|T282I|S312D|S692K
Q216I|T282K|S312K|A622K
P176L|Q316T|G662C
Q226W|Q316T|V522Y|G662F
P176L|Q316T
A347Y|R542N

TABLE 5-4

Variants Comprising Combination of Substitutions with At Least Three Improved Activities PASC + G2 + CC
L167W|D225Q|Q626F|Q684R
L167W|D564T|Q626F
P176L|Q226W|Q316T|K320S|V522Y|
G662C
R363E|V522Y|G662F
Q316T|K320S|V522Y|G662F
Q226W|K320Y|V522Y
Q316T|K320S|V522Y
Q226W|K320S|R363E|V522Y|G662F
HPLC + PCS + CC
D177M|D225Q|D564V|Q684G
D178N|N264K|A338D|S474R|G662K
HPLC + PCS + G2

Inh + PASC + CC
L167W|D177M|D564T|Q626F|
Q684N
L167W|Q626F|Q684D
L167W|D177M|D564T|Q684R
L167W|D177M|D225Q|Q684D
R179V|R265P|N369I
Q316T|K320Y|R363E|V522Y|
G662F
Inh + HPLC + PCS
D177M|D564T|Q626F|Q684A
Heat + HPLC + PCS
K345E|N369T|G372A|K428N|
P661L|S683W TABLE 5-4-continued Variants Comprising Combination of Substitutions with At Least Three Improved Activities

| | |
|---|---|
| K428N\|S683W | Inh + PASC + G2 |
| K345E\|K428N\|S683W | L167W\|D177M\|D225Q\|D564V |
| Q226Y\|G372A\|V603G\|T666C | |
| Inh + Heat + CC | |
| N238F\|N264M\|R265M\|N369I | |

TABLE 5-5

Variants Comprising Combination of Substitutions with At Least Four Improved Activities

| | |
|---|---|
| HPLC + PASC + PCS + CC | Inh + HPLC + PSC + CC |
| L167W\|D177M\|Q626F | N238W\|R265P\|K656R |
| L167W\|D177M\|D225Q\|D564V\|Q684G | N264M\|R265P (+G662F) |
| D177M\|D225Q\|D564T\|Q684N | N264L\|A338I\|S474R\|G662D |
| D177M\|Q626F\|Q684R | HPLC + PASC + PCS + G2 |
| Inh + Heat + HPLC + PCS | D177M\|D225Q\|D564T\|Q684A |
| L167W\|D225Q\|D564V\|Q626F\|Q684N | D177M\|D225Q\|D564V\|Q626F\|Q684N |
| Inh + PASC + G2 + CC | Inh + HPLC + PASC + PCS |
| L167W\|D177M\|Q626F\|Q684G | R265M\|K560S |
| L167W\|D177M\|D564V\|Q626F\|Q684A | HPLC + PCS + G2 + CC |
| Heat + PASC + G2 + CC | K345E\|N369E\|G372A\|P661E |
| P176L\|K320S\|V522Y\|G662C | N369T\|P661L\|S683W |
| Heat + HPLC + PCS + G2 | |
| N369T\|G372A\|P661L\|S683W | |
| P176L\|Q226W\|K320Y\|R363E | |

TABLE 5-6

Variants wi with Combination of Substitutions with At Least Five, Six, or Seven Improved Activities

| | |
|---|---|
| HPLC + PASC + PCS + G2 + CC | Heat + HPLC + PCS + G2 + CC |
| K345E\|N369T\|G372A\|P661E\|S683W | K345E\|N369E\|P661L |
| K320S\|R363E | |
| E170F\|Q226Y\|T242S\|S312Y\|G372A\|V603G\|P661F\|T666C | Inh + HPLC + PASC + PCS + G2 |
| T242S\|T666C | L167W\|D177M\|D546T\|Q626F\|Q684G |
| Q226Y\|T666C | |
| Q216E\|S312K\|S692K | E170F\|Q226Y\|N369Y\|G372A\|P661F |
| P176L\|G662F | |
| P176L\|Q226W\|Q316T\|K320Y\|R363E | Inh + Heat + PASC + G2 + CC |
| P176L\|Q226W\|K320S\|R363E\|G662F | |
| P176L\|Q226W\|Q316T\|K320Y\|V522Y | L167W\|D177M\|D564T\|Q684N |
| P176L\|Q226W\|K320Y\|R363E\|V552Y | Inh + Heat + HPLC + PCS + CC |
| Q226W\|K320Y\|R363E | |
| Q316T\|K320Y\|R363E\|G662F | E170F\|V603G |
| Q226W\|Q316T\|R363E\|V522Y\|G662F | Inh + Heat + HPLC + PASC + PCS + G2 + CC |
| P176L\|K320S\|R363E\|G662C | |
| R363E\|G547A\|G662C | N263C\|N369T |
| Q226W\|K320S\|G662C | N369T\|G372A\|K428N\|S683W |
| P176L\|Q226W\|Q316T\|K320Y\|R363E\|G662F | N263C\|G372A |
| | N263C\|K345E\|N369E\|G372A\|P661E |
| P176L\|Q226W\|Q316T\|K320S\|G662F | |
| P176L\|Q316T\|K320S\|R363E\|V522Y\|G662C | P176L\|Q226W\|G547A\|G662C |
| K320Y\|R363E\|G662C | Inh + Heat + HPLC + PASC + PCS + G2 |
| Heat + HPLC + PASC + PCS + G2 + CC | K345E\|N369E\|G372A\|S683W |
| | N369E\|S683W |
| K345E\|N369E\|P661E\|S683W | Inh + Heat + HPLC + PCS + G2 + CC |
| K345E\|P661E\|S683W | |
| N363C\|K345E\|N369E | G372A\|P661E\|S683W |
| N263C\|N369T\|P661E | P176L\|Q316T\|K320S\|R363E\|G662F |
| K345E\|N369E\|S683W | |
| N363C\|K345E\|N369T\|K428N | Inh + HPLC + PASC + PCS + G2 + CC |
| N263C\|N369E\|K428N\|P661E | |
| N263C\|N369T\|S683W | L167W\|D177M\|D225Q\|D564V\|Q626F\|Q684R |

Example 6

BGL1 Combinatorial Variants Exhibiting Reduced Glucose Inhibition

A number of BGL variants were selected and tested for their capacity to hydrolyze CNPG in the presence of glucose at a range of concentrations. A culture supernatant of a *H. jecorina* strain, producing wild type BGL1 or a BGL variant was diluted to a minimal CNPG activity of 20 mOD/min. The wild type BGL1 or the BGL variant supernatant was then mixed with various amounts of glucose, to a final glucose concentration of between 0 and 25 mM.

The assay was initiated by the addition of 1 mM CNPG in a 50 mM sodium acetate buffer, pH 5.0. Kinetic measurements were made by recording OD405 nm in a SpectraMax plate reader (Molecular devices) for 3 min.

IC50 values were measured using the formula $y=a/(1+x/b)$, wherein y represents the specific CNPG activity (in mOD/min), x represents the inhibitory substrate concentration (in mM glucose), a represents the maximum reaction rate (CNPG activity, in mOD/min), and b represents the inhibitor concentration at which the enzyme activity was reduced by half. To calculate reduction in inhibition, the IC50 value obtained for a given BGL variant was divided by the IC50 value obtained for the wild type BGL1.

TABLE 6-1

Performance Index of BGL variants In a Glucose Inhibition Activity Assay.

| BGL Variant | Reduction in Inhibition* |
|---|---|
| G372A | + |
| N263T | + |
| E170F\|G372A | + |
| E170F | + |
| N264M\|R265P\|G662F | + |
| N264M\|N369I | + |
| N263T\|G372A | + |
| R265M\|K560S | + |
| N264M\|N369I\|D370W | ++ |
| R179V\|R265P\|N369I | ++ |
| E170F\|S312Y\|N369Y | ++ |
| E170F\|N263T | +++ |
| R265P\|D370W\|G662F | +++ |
| N238W\|R265P\|K656R | +++ |
| N238F\|N264M\|R265M\|N369I | +++ |
| N238F | ++++ |
| E170F\|N263T\|G372A | ++++ |
| N238F\|R265M\|N369I | ++++ |

*'+', '++', '+++', and '++++' indicate a 1, 2- to 2-fold, 2- to 3-fold, 3- to 6-fold, 6- to 10-fold reduction in glucose inhibition, respectively, as compared to the glucose inhibition observed with the wild type BGL1.

Various modifications and variations of the present disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure which are understood by those skilled in the art are intended to be within the scope of the claims.

What is claimed is:

1. A beta-glucosidase 1 (BGL1) variant having at least 80% amino acid sequence identity to SEQ ID NO: 3 wherein the variant comprises a substitution corresponding to position Q226 in SEQ ID NO: 3 with W or Y, a substitution corresponding to N263 in SEQ ID NO: 3 with C, S, or T, a substitution corresponding to K345 in SEQ ID NO: 3 with E, a substitution corresponding to P661 in SEQ ID NO: 3 with E, F, L, I, or Q, or a substitution corresponding to G372 of SEQ ID NO: 3 with A.

2. The BGL1 variant of claim 1 wherein the variant comprises a substitution corresponding to G372 of SEQ ID NO: 3 with A.

3. A beta-glucosidase 1 (BGL1) variant having at least 80% amino acid sequence identity to SEQ ID NO: 3 wherein the BGL1 variant comprises a substitution corresponding to position Q226 in SEQ ID NO: 3 with W or Y, a substitution corresponding to N263 in SEQ ID NO: 3 of C, S, or T, a substitution corresponding to P661 in SEQ ID NO: 3 of F, L, or Q, a substitution corresponding to K345 in SEQ ID NO: 3 of E, a substitution corresponding to S683 in SEQ ID NO: 3 with W, or a substitution corresponding to G372 in SEQ ID NO: 3 with A.

4. A beta-glucosidase 1 (BGL1) variant having at least 80% amino acid sequence identity to SEQ ID NO: 3 wherein the BGL1 variant comprises a substitution corresponding to position Q226 in SEQ ID NO: 3 with W or Y, a substitution corresponding to N263 in SEQ ID NO: 3 of C or S, a substitution corresponding to P661 in SEQ ID NO: 3 of F, L, or Q, a substitution corresponding to S683 in SEQ ID NO: 3 with W, a substitution corresponding to K345 in SEQ ID NO: 3 with E or a substitution corresponding to G372 in SEQ ID NO: 3 with A.

5. A BGL1 variant according to claim 1 wherein the BGL1 variant comprises a substitution corresponding to N263 in SEQ ID NO: 3 with T.

6. A beta-glucosidase 1 (BGL1) variant having at least 80% amino acid sequence identity to SEQ ID NO: 3 wherein the BGL1 variant comprises a substitution corresponding to position Q226 in SEQ ID NO: 3 with W or Y, a substitution corresponding to N263 in SEQ ID NO: 3 of C or S, a substitution corresponding to P661 in SEQ ID NO: 3 of F, L, or Q, a substitution corresponding to K345 in SEQ ID NO: 3 of E, or a substitution corresponding to S683 in SEQ ID NO: 3 with W.

7. A composition comprising the BGL1 variant of claim 1.

8. The composition of claim 7 wherein the composition is enriched in the BGL1 variant.

9. An isolated nucleic acid encoding any one of the BGL1 variants of claim 1.

10. An expression vector comprising the nucleic acid of claim 9.

11. The expression vector of claim 10 wherein the isolated nucleic acid is operably linked to a regulatory sequence.

12. A host cell comprising the nucleic acid of claim 9.

13. A method for producing a BGL1 variant, comprising culturing the host cell of claim 12 in a culture medium under suitable conditions to produce the variant.

14. A method of converting biomass to sugars comprising contacting the biomass with a BGL1 variant of claim 1.

15. A composition comprising the BGL1 variant of claim 3.

16. The composition of claim 15 wherein the composition is enriched in the BGL1 variant.

17. A composition comprising the BGL1 variant of claim 4.

18. The composition of claim 17 wherein the composition is enriched in the BGL1 variant.

19. A composition comprising the BGL1 variant of claim 6.

20. The composition of claim 19 wherein the composition is enriched in the BGL1 variant.

* * * * *